US006977262B2

(12) United States Patent
Kohara et al.

(10) Patent No.: US 6,977,262 B2
(45) Date of Patent: Dec. 20, 2005

(54) DIHYDROPYRAZOLOPYRIDINE COMPOUNDS AND PHARMACEUTICAL USE THEREOF

(75) Inventors: Toshiyuki Kohara, Tokyo (JP); Kenji Fukunaga, Tokyo (JP); Masatake Fujimura, Tokyo (JP); Tokushi Hanano, Tokyo (JP); Hirotaka Okabe, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 10/631,847

(22) Filed: Aug. 1, 2003

(65) Prior Publication Data

US 2004/0052822 A1 Mar. 18, 2004

Related U.S. Application Data

(63) Continuation-in-part of application No. PCT/JP02/00829, filed on Feb. 1, 2002.

(30) Foreign Application Priority Data

| Feb. 2, 2001 | (JP) | 2001-026379 |
| Mar. 21, 2001 | (JP) | 2001-081238 |
| Sep. 28, 2001 | (JP) | 2001-304707 |
| Aug. 7, 2002 | (JP) | 2002-230581 |

(51) Int. Cl.$^7$ .................... A61K 31/437; C07D 471/04
(52) U.S. Cl. .................... 514/303; 546/120; 546/119; 544/127; 544/362; 514/234.2; 514/253
(58) Field of Search ............... 514/303, 234.2, 514/253; 546/120, 119; 544/127, 362

(56) References Cited

U.S. PATENT DOCUMENTS

3,790,576 A    2/1974   De Wald

FOREIGN PATENT DOCUMENTS

| EP | 0 107 619 | 5/1984 |
| EP | 0 114 273 | 8/1984 |
| EP | 0 157 260 | 10/1985 |
| EP | 0 327 500 | 8/1989 |
| EP | 0 355 234 | 2/1990 |
| GB | 2 146 326 | 4/1985 |
| WO | 92 03137 | 3/1992 |
| WO | 99 65897 | 12/1999 |
| WO | 01 66544 | 9/2001 |
| WO | 01 81345 | 11/2001 |

OTHER PUBLICATIONS

Jairo Quiroga et al., entitled "Synthesis of 5–cyano–4, dihydropyrazolo'3,4–b| pyridin–4–ones . . . ", Database CA 'Online! Chemical Abstracts Service, Columbus, Ohio, US.

Ikuo Adachi et al., entitled "Studies on dihydropyridines. Synthesis of 4, 7–dihydropyrazolo'3,4–bipridines with vasodilating and antihypertensive activities", Chemical and Pharmaceutical Bulletin., vol. 35, No. 8, pp. 3235–3252.

Reinhard Troschuetz, entitled "Synthesis of pyrido'2,3–dipyrimidines with a trimethoprim partial structure", Database CA 'Online! Chemical Abstracts Service, Columbus, Ohio, US.

F. Attaby, entitled "Reactions with cyanothioacetamide derivatives: synthesis of several new pyridine and annulated pyridine derivatives", Database Caplus 'Online! Chemical Abstracts Service, Columbus, Ohio, US.

Dyachenko et al., entitled "Synthesis and properties of N–methylmorpholinium–6–amino–3,5–dicyano–1, 4–dihydropyridine–4–spirocyclopentane–2–thiolate", Database Caplus 'Online! Chemical Abstracts Service, Columbus, Ohio, US.

Jairo Quiroga et al., entitled "Synthesis and structural analysis of 5–cyanodihydropyrazolo'3,4– bipyridines", Journal of Heterocyclic Chemistry (2001).

J. Quiroga et al., entitled "Regioselective synthesis of 4,7, 8,9–tetrahydro–2H–pyrazolo'3,4–biquinolin–5(6H)–ones. Mechanism and structural analysis". Tetrahedron, Elsevier Science Publishers, Amsterdam, NL, vol. 57, No. 32, Aug. 6, 2001.

M. Hoshi et al., "Regulation of mitochondrial pyruvate dehydrogenase activity by tau protein kinase I/glycogen synthase kinase 3β in brain", Proc. Natl. Acad. Sci., vol. 93, pp. 2719–2723, 1996.

S. R. D'Mello et al., "Lithium induces apoptosis in immature cerebellar granule cells but promotes survival of mature neurons", Experimental Cell Research, No. 211, pp. 332–338, 1994.

(Continued)

Primary Examiner—Charanjit S. Aulakh
(74) Attorney, Agent, or Firm—Wenderoth, Lind & Ponack, L.L.P.

(57) ABSTRACT

The present invention provides dihydropyrazolopyridine compounds represented by the formula (I):

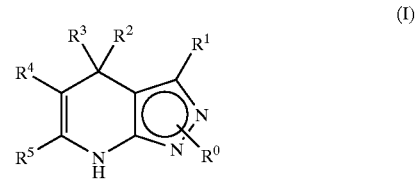

wherein each symbol is as defined in the specification, optically active forms thereof, and pharmaceutically acceptable salts thereof and hydrates thereof. The compounds of the present invention show a selective and strong inhibitory activity on glycogen synthase kinase-3 beta (GSK-3β), and are useful as medicaments for prevention and/or treatment of diabetes, diabetic complications and neurodegenerative diseases or as immunopotentiators.

31 Claims, 3 Drawing Sheets

OTHER PUBLICATIONS

C. Volonte et al., Neurosci. Letters, vol. 172, pp. 6–10, 1994.

S. Nonaka et al., "Neuroprotective effects of chronic lithium on focal cerebral ischemia in rats", NeuroReport, vol. 9, No. 9, pp. 2081–2084, 1998.

S. B. Maggirwar et al., "HIV–1 Tat–Mediated activation of glycogen synthase kinase–3β contributes to Tat–mediated neurotoxicity", Journal of Neurochemistry, vol. 73, No. 2, pp. 578–586, 1999.

V. Stambolic et al., "Lithium inhibits glycogen synthase kinase–3 activity and mimics wingless signalling in intact cells", Current Biology, vol. 6. No. 12, pp. 1664–1668, 1996.

P. S. Klein et al., "A molecular mechanism for the effect of lithium on development", Proc. Natl. Acad. Sci., vol. 93, pp. 8455–8459, 1996.

G. Chen et al., "The mood–stabilizing agent valproate inhibits the activity of glycogen synthase kinase–3", Journal of Neurochemistry, vol. 72, pp. 1327–1330, 1999.

S. Nonaka et al., "Chronic lithium treatment robustly protects neurons in the central nervous system against excitotoxity by inhibiting N–methyl–D–aspartate receptor–mediated calcium influx", Proc. Natl. Acad. Sci., vol. 95, pp. 2642–2647, 1998.

C. R. Beals et al., "Nuclear export of NF–ATc enhanced by glycogen synthase kinase–3", Science, vol. 275, pp. 1930–1933, 1997.

I. A. Graef et al., "L–type calcium channels and GSK–3 regulate the activity of NF–ATc4 in hippocampal neurons", Letters to Nature, vol. 401, pp. 703–708, 1999.

A. J. Zhu et al., "β–catenin signalling modulates proliferative potential of human epidermal keratinocytes independently of intercellular adhesion", Development, vol. 126, pp. 2285–2298, 1999.

S. T. Davis et al., "Prevention of chemotherapy–induced alopecia in rats by CDK inhibitors", Science, vol. 291, pp. 134–137, 2001.

T. T. Lee et al., "Overexpression of cellular activity and protein level of protein kinase F /GSK–3β correlates with human thyroid tumor cell dedifferentiation", Journal of Cellular Biochemistry, vol. 58, pp. 474–480, 1995.

K. P. Hoeflich et al., "Requirement for glycogen synthase kinase–3β in cell survival and NF–$_\kappa$B activation", Nature, vol. 406, pp. 86–90, 2000.

S. A. Milligan et al., "Inhibition of NF–kB with proteasome inhibitors enhances apoptosis in human lung adenocarcinoma cells in vitro", Anticancer Research, vol. 21, pp. 39–44, 2001.

R. Romieu–Mourez et al., "Roles of IKK kinase and protein kinase CK2 in activation of nuclear factor–kB in breast cancer", Cancer Research, vol. 61, pp. 3810–3818, 2001.

S. E. Nikoulina et al., "Potential role of glycogen synthase kinase–3 in skeletal muscle insulin resistance of type 2 diabetes", Diabetes, vol. 49, pp. 263–271, 2000.

R. V. Bhat et al., "Regulation and localization of tyrosine$^{218}$ phosphorylation of glycogen synthase kinase–3β in cellular and animal models of neuronal degeneration", Proc. Natl. Acad. Sci., vol. 97, pp. 11074–11079, 2000.

Mean ± S.E.,
**: $p<0.01$ vs Basal by Dunnett method (n=6)

Mean ± S.E.,
†† : p<0.01 vs Basal by t-test,
*:p<0.05, ** : p<0.01 vs Control by Dunnett method (n=6)

Mean±S.E.,
†:p<0.05 vs Basal by t-test,
*:p<0.05 vs Control by Dunnett method (n=3~5)

DIHYDROPYRAZOLOPYRIDINE COMPOUNDS AND PHARMACEUTICAL USE THEREOF

This application is a Continuation-in-Part of International Application No. PCT/JP02/00829 filed Feb. 1, 2002.

TECHNICAL FIELD OF THE INVENTION

The present invention relates to new compounds for medicaments, which have a glycogen synthase kinase-3 beta (GSK-3β)-inhibitory activity, and use thereof.

BACKGROUND OF THE INVENTION

It has been reported that glycogen synthase kinase-3 beta (GSK-3β), a protein kinase, is involved in the causes of various diseases as noted in the following.

Type-II diabetes is a disease in which the insulin reactivity of pancreatic β cells becomes low and glucose in blood increases. As a result, complications such as diabetic nephropathy, retinosis, heart disease and the like are induced. GSK-3β acts for inhibiting glycogen accumulation in peripheral tissues, lowering insulin response and increasing glucose in blood by phosphorylating glycogen synthase. Lithium having a GSK-3β-inhibitory activity actually lowers glucose in blood by a GSK-3β-inhibitory activity (Proc. Nat. Acad. Sci., 93, 8455 (1996)). Therefore, medicaments having a GSK-3β-inhibitory activity are considered to be a pharmaceutical agent effective for the improvement of Type II diabetes and complications thereof.

The developmental mechanism of Alzheimer's dementia has not yet been elucidated. However, it is considered that amyloid aggregation and neurofibril changes are closely related to the cause of the development. GSK-3β is involved in both the amyloid aggregation and the neurofibril changes as follows. (1) It binds with variant presenilin and increase production of insoluble amyloid (Proc. Nat. Acad. Sci., 95, 9637 (1998)). (2) It causes phosphorylation of the Tau protein, which causes neurofibril changes, and weakens the backbones of neurons to induce neuronal death (Neurosci. Lett., 128, 195 (1991)). In addition to the above, (3) the direct involvement of GSK-3β in nuronal death through inactivation of pyruvate dehydrogenase by phosphorylation to decrease the production amount of acetylcholine necessary for maintaining cell activity (Proc. Nat. Acad. Sci., 93, 2719 (1996)) has been reported.

In addition, the effectiveness for AIDS encephalopathia as a neurodegenerative disease other than Alzheimer's dementia has been suggested. Tat, which is a protein produced by HIV virus that causes AIDS, enhances GSK-3β activity in neurons to induce neuronal death (J. Neurochem., 73, 578 (1999)). From the above, GSK-3β inhibitors are considered to be medicaments effective for improving neurodegenerative diseases including Alzheimer's dementia.

Lithium and valproic acid, which have anti-manic-depressive activity, have a GSK-3β inhibitory activity (J. Neurochem., 72, 1327 (1999)). The relationship between anti-manic-depressive activity and GSK-3β inhibitory activity is unclear, but a suppressive activity on glutamic acid toxicity is considered to be partly responsible for maintaining neuronal activity (Proc. Nat. Acad. Sci., 95, 2642 (1998)). Based on the foregoing, GSK-3β inhibitors are considered to be medicaments effective for improving manic-depressive psychosis.

NF-AT, a transcription factor, is dephosphorylated by calcineurin to increase immunological responses (Science, 275, 1930 (1997)). GSK-3β acts for suppressing immunological function by conversely phosphorylating NF-AT. Therefore, GSK-3β inhibitors are considered to be medicaments effective for immunopotentiation.

Incidentally, JP-A-3-272189 (invention drawn to an improved synthesis method of mevalolacton intermediates), JP-A-2-275878 (therapeutic agents for hyperlipoproteinemia and atherosclerosis) and JP-A-1-272584 (therapeutic agents for hyperlipoproteinemia) disclose pyrazolo[3,4-b]pyridine compounds wherein the 6-position is either methyl, isopropyl or cyclopropyl. These publications do not disclose or suggest any action of these compounds on GSK-3β or the central nervous system.

The specifications of JP-A-59-65089, JP-A-59-118786, JP-A-60-56979, JP-A-60-197685 and the like disclose 6-methyl-4-substituted phenyl-4,7-dihydropyrazolo[3,4-b]pyridine-5-carboxylate compounds used for the treatment of cardiovascular diseases, and they are produced by similar methods. The present inventors reproduced the following reaction A according to the method described in JP-A-59-65089, but failed to obtain the compound of Example 14 (formula (IV) in the following) described therein. They confirmed that only the pyrazolo[1,5-a]pyrimidine derivative represented by the formula (V) could be produced. They measured IR, NMR and the melting point of the compound of the formula (V) and found them to be identical with IR, NMR and the melting point described in the specification of this publication. It is therefore concluded that an erroneous structural formula has been disclosed in these publications. In other words, 6-methyl-4-substituted phenyl-4,7-dihydropyrazolo[3,4-b]pyridine-5-carboxylate cannot be synthesized according to the methods described in these publications.

A

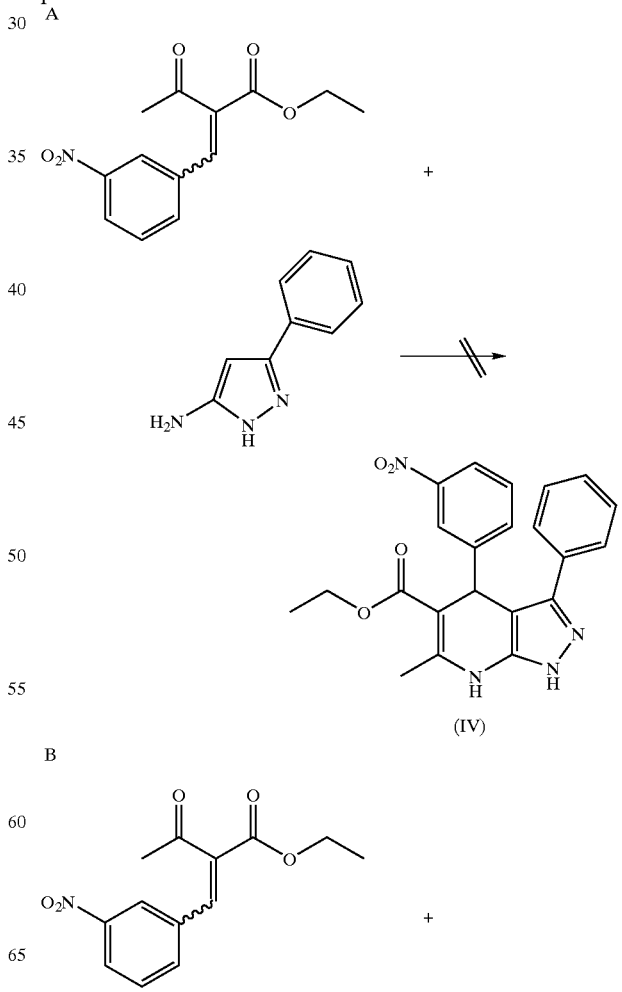

B

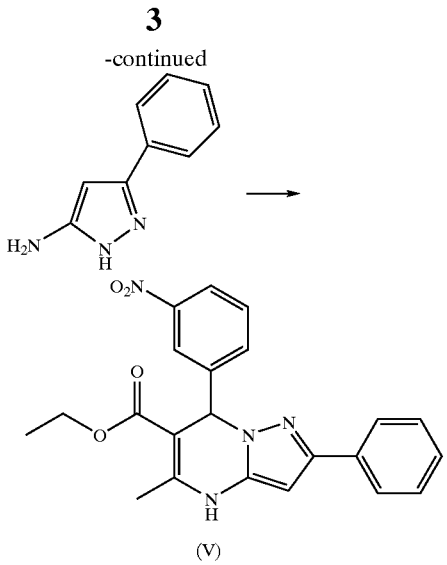

(V)

The compound of the above formula (IV) can be synthesized according to the method described in J. Chem. Soc., Perkin Trans. 1, 947 (1996), and this publication discloses methyl 4-(2-chlorophenyl)-6-methyl-4,7-dihydro-1H-pyrazolo[3,4-b]pyridine-5-carboxylate and the like.

SUMMARY OF THE INVENTION

An object of the present invention is to provide novel compounds having a selective and strong inhibitory activity against glycogen synthase kinase-3 beta (GSK-3β), and further, medicaments comprising them and pharmaceutical compositions comprising them.

The present inventors have intensively studied to achieve the above object, and have found that 4,7-dihydropyrazolo[3,4-b]pyridine derivatives have a selective and strong inhibitory activity on GSK-3β, which resulted in the completion of the present invention. That is, the present invention relates to medicaments comprising, as an active ingredient, dihydropyrazolopyridine compounds represented by the following formula (I), which have a GSK-3β-inhibitory activity and can be used as medicaments, optical isomers thereof, pharmaceutically acceptable salts thereof, or hydrates thereof.

The present invention provides the following.

[1] A dihydropyrazolopyridine compound of the formula (I):

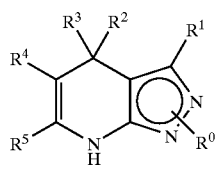

(I)

wherein $R^0$ is hydrogen, alkyl, aralkyl, acyl, cycloalkyl, formyl, haloalkyl, aminoalkyl, alkoxyalkyl, phenoxyalkyl, hydroxyalkyl, aminocarbonyl, alkylthiocarbonyl, carboxyalkyl, cycloalkoxyalkyl, alkylsulfinyl, alkylsulfonyl, phenylsulfonyl, phenylsulfinyl, mercaptoalkyl, alkylthioalkyl, acyloxyacetyl, acyloxyalkyl, phenyl optionally having substituent(s), aromatic heterocyclic group optionally having substituent(s), phenylalkyl optionally having substituent(s), or a group of the formula: —COOR$^8$ (wherein R$^8$ is hydrogen, alkyl, aryl optionally having substituent(s) or aralkyl optionally having substituent(s));

$R^1$ and $R^2$ are the same or different and each is hydrogen, alkyl, aralkyl, acyl, cycloalkyl, hydroxy, thiol, halogen, amino, formyl, carboxy, cyano, nitro, alkylthio, haloalkyl, aminoalkyl, acylamino, alkoxy, cycloalkoxy, phenoxy, phenylalkoxy, aminoalkoxy, alkoxyalkyl, phenoxyalkyl, hydroxyalkyl, alkoxycarbonyl, aminocarbonyl, alkylthiocarbonyl, carboxyalkyl, cycloalkoxyalkyl, phenylthio, alkylsulfinyl, alkylsulfonyl, phenylsulfonyl, mercaptoalkyl, alkylthioalkyl, phenyl optionally having substituent(s), aromatic heterocyclic group or. phenylalkyl;

$R^3$ is (1) alkyl or haloalkyl,
(2) cycloalkyl,
(3) phenyl optionally having substituent(s),
(4) aromatic heterocyclic group,
(5) a group derived from a benzene ring fused with a saturated or unsaturated 5 or 6 membered carbocyclic ring,
(6) a group derived from a benzene ring fused with a saturated or unsaturated 5 to 7 membered carbocyclic ring containing 1 to 3 heteroatom(s), or
(7) a group derived from a 5 to 7 membered saturated or unsaturated carbocyclic ring containing 1 to 3 heteroatom(s), which is fused with a benzene ring, wherein the groups of (2) to (7) may have one or more substituent(s), or a group selected from the groups represented by the following formulas (II) and (III):

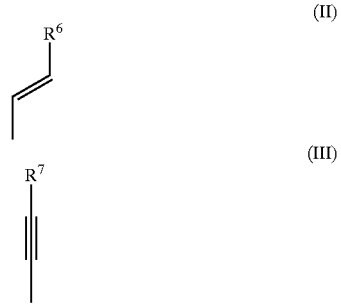

wherein R$^6$ and R$^7$ are each phenyl optionally having substituent(s) or an aromatic heterocyclic group, or R$^2$ and R$^3$ in conjunction form a ring optionally containing heteroatom(s), wherein the ring may be fused with a benzene ring optionally having substituent(s);

$R^4$ is alkoxycarbonyl, alkylcarbonyl, aminocarbonyl, hydrazinocarbonyl, alkylthiocarbonyl, formyl, carbamoyl, alkylthio, phenylthio, alkylsulfinyl, phenylsulfinyl, alkylsulfonyl, phenylsulfonyl, dialkylphosphinyl, dialkylphosphonyl, phenyl optionally having substituent(s), an aromatic heterocyclic group optionally having substituent(s), cyano or nitro; and $R^5$ is hydrogen, cyano, formyl, alkyl, cycloalkyl, alkoxyalkyl, phenoxyalkyl, dialkoxyalkyl, hydroxyalkyl, haloalkyl, carboxyalkyl, cycloalkoxyalkyl, phenylthio, alkylsulfinyl, alkylsulfonyl, phenylsulfonyl, mercaptoalkyl, alkylthioalkyl, alkoxycarbonylalkyl, alkoxycarbonylethenyl, aryl optionally having substituent(s), an aromatic heterocyclic group or phenylalkyl, or a group derived from a 5 to 7 membered saturated or unsaturated carbocyclic ring containing 1 to 3 heteroatom(s), which is fused with a benzene ring; or phenylaminoalkyl, acyl,
acylalkyl,
aminocarbonyl,
arylaminocarbonyl,
a saturated or unsaturated 4 to 7 membered heterocyclic ring optionally having substituent(s),
a saturated 3 to 7 membered carbocyclic ring having substituent(s),
alkyl substituted by a saturated or unsaturated 4 to 7 membered ring containing 1 or 2 nitrogen atom(s), which optionally has a substituent, or
a group of the formula: —$(CR^aR^b)_nNR^{11}R^{12}$ wherein n is an integer of 1 to 4, $R^a$ is hydrogen or alkyl, $R^b$ is hydrogen or alkyl, $R^{11}$ is hydrogen, alkyl, alkylsulfonyl, phenylsulfonyl, phenylalkylsulfonyl, alkylsulfinyl, phenylsulfinyl, phenylalkylsulfinyl, alkoxycarbonyl, phenoxycarbonyl, phenylalkoxycarbonyl, alkylcarbonyl, phenylcarbonyl or phenylalkylcarbonyl, and $R^{12}$ is hydrogen or alkyl, or $R^4$ and $R^5$ in conjunction may form a 5 or 6 membered ring optionally containing heteroatom(s), provided that when $R^0$, $R^1$ and $R^2$ are each hydrogen, $R^4$ is methoxycarbonyl and $R^5$ is methyl, then $R^3$ should not be phenyl, 2-chloropheny, 3-nitrophenyl, 4-carboxyphenyl or 4-methoxycarbonylphenyl, and when $R^5$ is alkyl, then $R^4$ is not alkoxycarbonyl, alkylsulfonyl, alkylsulfinyl, phenylsulfinyl, phenylsulfonyl, dialkylphosphinyl, dialkylphosphonyl, cyano or nitro, or an optically active form thereof, a pharmaceutically acceptable salt thereof or a hydrate thereof.

[2] The dihydropyrazolopyridine compound of the above-described [1], wherein $R^0$ is hydrogen, alkyl, acyl, cycloalkyl, formyl, haloalkyl, aminoalkyl, alkoxyalkyl, phenoxyalkyl, hydroxyalkyl, aminocarbonyl, alkylthiocarbonyl, carboxyalkyl, cycloalkoxyalkyl, alkylsulfinyl, alkylsulfonyl, phenylsulfonyl, mercaptoalkyl, alkylthioalkyl, acyloxyacetyl, acyloxyalkyl, phenyl optionally having substituent(s), aromatic heterocyclic group optionally having substituent(s), phenylalkyl optionally having substituent(s), or a group of the formula: —$COOR^8$ (wherein $R^8$ is hydrogen, alkyl, aryl optionally having substituent(s) or aralkyl optionally having substituent(s));

$R^1$ and $R^2$ are the same or different and each is hydrogen, alkyl, acyl, cycloalkyl, hydroxy, thiol, halogen, amino, formyl, carboxy, cyano, nitro, alkylthio, haloalkyl, aminoalkyl, acylamino, alkoxy, cycloalkoxy, phenoxy, phenylalkoxy, aminoalkoxy, alkoxyalkyl, phenoxyalkyl, hydroxyalkyl, alkoxycarbonyl, aminocarbonyl, alkylthiocarbonyl, carboxyalkyl, cycloalkoxyalkyl, phenylthio, alkylsulfinyl, alkylsulfonyl, phenylsulfonyl, mercaptoalkyl, alkylthioalkyl, phenyl optionally having substituent(s), aromatic heterocyclic group or phenylalkyl;

$R^3$ is
(1) alkyl or haloalkyl,
(2) cycloalkyl,
(3) phenyl optionally having substituent(s),
(4) aromatic heterocyclic group,
(5) a group derived from a benzene ring fused with a saturated or unsaturated 5 or 6 membered carbocyclic ring, (6) a group derived from a benzene ring fused with a saturated or unsaturated 5 to 7 membered carbocyclic ring containing 1 to 3 heteroatom(s), or
(7) a group derived from a 5 to 7 membered saturated or unsaturated carbocyclic ring containing 1 to 3 heteroatom(s), which is fused with a benzene ring, wherein the groups of (2) to (7) may have one or more substituent(s), or a group selected from the groups represented by the following formulas (II) and (III):

wherein $R^6$ and $R^7$ are each phenyl optionally having substituent(s) or an aromatic heterocyclic group, or $R^2$ and $R^3$ in conjunction form a ring optionally containing heteroatom(s), wherein the ring may be fused with a benzene ring optionally having substituent(s);

$R^4$ is alkoxycarbonyl, aminocarbonyl, hydrazinocarbonyl, alkylthiocarbonyl, formyl, carbamoyl, alkylthio, phenylthio, alkylsulfinyl, phenylsulfinyl, alkylsulfonyl, phenylsulfonyl, dialkylphosphinyl, dialkylphosphonyl, cyano or nitro; and $R^5$ is hydrogen, cyano, formyl, alkyl, cycloalkyl, alkoxyalkyl, phenoxyalkyl, dialkoxyalkyl, hydroxyalkyl, haloalkyl, carboxyalkyl, cycloalkoxyalkyl, phenylthio, alkylsulfinyl, alkylsulfonyl, phenylsulfonyl, mercaptoalkyl, alkylthioalkyl, alkoxycarbonylalkyl, alkoxycarbonylethenyl, aryl optionally having substituent(s), an aromatic heterocyclic group or phenylalkyl, or a group derived from a 5 to 7 membered saturated or unsaturated carbocyclic ring containing 1 to 3 heteroatom(s), which is fused with a benzene ring, or $R^4$ and $R^5$ in conjunction may form a 5 or 6 membered ring optionally containing heteroatom(s), provided that when $R^0$, $R^1$ and $R^2$ are each hydrogen, $R^4$ is methoxycarbonyl and $R^5$ is methyl, then $R^3$ should not be phenyl, 2-chloropheny, 3-nitrophenyl, 4-carboxyphenyl or 4-methoxycarbonylphenyl, or an optically active form thereof, a pharmaceutically acceptable salt thereof or a hydrate thereof.

[3] The dihydropyrazolopyridine compound of the above-described [2], wherein $R^5$ is alkyl having 2 to 8 carbon atoms, cycloalkyl, alkoxyalkyl, phenoxyalkyl, hydroxyalkyl, phenyl optionally having substituent(s), an aromatic heterocyclic group or phenylalkyl, or an optically active form thereof, a pharmaceutically acceptable salt thereof or a hydrate thereof.

[4] The dihydropyrazolopyridine compound of the above-described [2], wherein $R^1$ is hydrogen, alkyl, phenyl optionally having substituent(s), an aromatic heterocyclic group or phenylalkyl, or an optically active form thereof, a pharmaceutically acceptable salt thereof or a hydrate thereof.

[5] The dihydropyrazolopyridine compound of the above-described [2], wherein $R^2$ is hydrogen or alkyl, or an optically active form thereof, a pharmaceutically acceptable salt thereof or a hydrate thereof.

[6] The dihydropyrazolopyridine compound of the above-described [2], wherein $R^3$ is phenyl optionally having 1 to 3 substituent(s), naphthyl, 2,1,3-benzoxadiazol-4-yl or 3,4-dihydro-2H-benzopyran-8-yl, or an optically active form thereof, a pharmaceutically acceptable salt thereof or a hydrate thereof.

[7] The dihydropyrazolopyridine compound of the above-described [2], wherein $R^4$ is alkoxycarbonyl having 2 to 5 carbon atoms, cyano or nitro, or an optically active form thereof, a pharmaceutically acceptable salt thereof or a hydrate thereof.

[8] The dihydropyrazolopyridine compound of the above-described [2], wherein $R^5$ is alkyl having 2 to 4 carbon atoms, cyclopropyl, phenyl, thienyl or hydroxyalkyl, or an optically active form thereof, a pharmaceutically acceptable salt thereof or a hydrate thereof.

[9] The dihydropyrazolopyridine compound of the above-described [2], wherein $R^2$ and $R^3$ in conjunction form a ring containing sulfur atom and the ring is condensed with a benzene ring optionally having substituent(s), or an optically active form thereof, a pharmaceutically acceptable salt thereof or a hydrate thereof.

[10] The dihydropyrazolopyridine compound of the above-described [2], wherein $R^0$ is hydrogen or a group of the formula: —COOR$^8$ (wherein $R^8$ is alkyl, aryl optionally having substituent(s) or aralkyl optionally having substituent(s)), or an optically active form thereof, a pharmaceutically acceptable salt thereof or a hydrate thereof.

[11] The dihydropyrazolopyridine compound of the above-described [2], which is selected from the group consisting of

(32) ethyl 4,7-dihydro-4-(2-methoxyphenyl)-6-propyl-2H-pyrazolo[3,4-b]pyridine-5-carboxylate,

(47) ethyl 4-(2-chloro-3-trifluoromethylphenyl)-4,7-dihydro-6-propyl-2H-pyrazolo[3,4-b]pyridine-5-carboxylate,

(66) ethyl 4,7-dihydro-4-(naphthalen-1-yl)-6-propyl-2H-pyrazolo[3,4-b]pyridine-5-carboxylate,

(73) ethyl 4-(3,4-dihydro-2H-benzopyran-8-yl)-4,7-dihydro-6-propyl-2H-pyrazolo[3,4-b]pyridine-5-carboxylate,

(87) ethyl 4-(2-chlorophenyl)-4,7-dihydro-6-(thiophen-2-yl)-2H-pyrazolo[3,4-b]pyridine-5-carboxylate, (116) ethyl 4-(2,1,3-benzoxadiazol-4-yl)-4,7-dihydro-6-propyl-2H-pyrazolo[3,4-b]pyridine-5-carboxylate, (122) 4-(2,3-dichlorophenyl)-4,7-dihydro-5-nitro-6-propyl-2H-pyrazolo[3,4-b]pyridine, (140) 4-(2,1,3-benzoxadiazol-4-yl)-5-cyano-4,7-dihydro-6-propyl-2H-pyrazolo[3,4-b]pyridine, (147) 4-(2-bromo-3-cyanophenyl)-5-cyano-4,7-dihydro-6-phenyl-2H-pyrazolo[3,4-b]pyridine, (158) 4-(2,1,3-benzoxadiazol-4-yl)-5-cyano-4,7-dihydro-6-phenyl-2H-pyrazolo[3,4-b]pyridine, (171) 4-(2,1,3-benzoxadiazol-4-yl)-5-cyano-4,7-dihydro-6-(thiophen-2-yl)-2H-pyrazolo[3,4-b]pyridine, (182) ethyl 4-(2-bromo-3-nitrophenyl)-4,7-dihydro-6-propyl-2H-pyrazolo[3,4-b]pyridine-5-carboxylate, (183) ethyl 4-(2-bromo-3-cyanophenyl)-4,7-dihydro-6-propyl-2H-pyrazolo[3,4-b]pyridine-5-carboxylate, (189) 4-(2-bromo-3-nitrophenyl)-5-cyano-4,7-dihydro-6-propyl-2H-pyrazolo[3,4-b]pyridine, (205) ethyl 2-tert-butoxycarbonyl-4-(2-chlorophenyl)-4,7-dihydro-6-propyl-2H-pyrazolo[3,4-b]pyridine-5-carboxylate, (240) ethyl 4-(2,1,3-benzoxadiazol-4-yl)-6-ethyl-4,7-dihydro-2H-pyrazolo[3,4-b]pyridine-5-carboxylate, (257) 4-(2,1,3-benzoxadiazol-4-yl)-5-cyano-4,7-dihydro-6-hydroxymethyl-2H-pyrazolo[3,4-b]pyridine, (260) 4-(2-bromo-3-cyanophenyl)-5-cyano-4,7-dihydro-6-isopropyl-2H-pyrazol[3,4-b]pyridine, (264) 4-(2,1,3-benzoxadiazol-4-yl)-5-cyano-4,7-dihydro-6-isopropyl-2H-pyrazolo[3,4-b]pyridine, and (268) 4-(2-bromo-3-cyanophenyl)-5-cyano-6-cyclopropyl-4,7-dihydro-2H-pyrazolo[3,4-b]pyridine, a tautomer, an optically active form thereof, a pharmaceutically acceptable salt thereof or a hydrate thereof.

[12] The dihydropyrazolopyridine compound of the above-described [1], wherein $R^0$ is hydrogen, alkyl, aralkyl, acyl, cycloalkyl, formyl, haloalkyl, aminoalkyl, alkoxyalkyl, phenoxyalkyl, hydroxyalkyl, aminocarbonyl, alkylthiocarbonyl, carboxyalkyl, cycloalkoxyalkyl, alkylsulfinyl, alkylsulfonyl, phenylsulfonyl, phenylsulfinyl, mercaptoalkyl, alkylthioalkyl, acyloxyacetyl, acyloxyalkyl, phenyl optionally having substituent(s), aromatic heterocyclic group optionally having substituent(s), phenylalkyl optionally having substituent(s), or a group of the formula: —COOR$^8$ (wherein $R^8$ is hydrogen, alkyl, aryl optionally having substituent(s) or aralkyl optionally having substituent(s));

$R^1$ is hydrogen;

$R^2$ is hydrogen, alkyl, aralkyl, acyl, cycloalkyl, hydroxy, thiol, halogen, amino, formyl, carboxy, cyano, nitro, alkylthio, haloalkyl, aminoalkyl, acylamino, alkoxy, cycloalkoxy, phenoxy, phenylalkoxy, aminoalkoxy, alkoxyalkyl, phenoxyalkyl, hydroxyalkyl, alkoxycarbonyl, aminocarbonyl, alkylthiocarbonyl, carboxyalkyl, cycloalkoxyalkyl, phenylthio, alkylsulfinyl, alkylsulfonyl, phenylsulfonyl, mercaptoalkyl, alkylthioalkyl, phenyl optionally having substituent(s), aromatic heterocyclic group or phenylalkyl;

$R^3$ is (1) alkyl or haloalkyl, (2) cycloalkyl, (3) phenyl optionally having substituent(s), (4) aromatic heterocyclic group, (5) a group derived from a benzene ring fused with a saturated or unsaturated 5 or 6 membered carbocyclic ring, (6) a group derived from a benzene ring fused with a saturated or unsaturated 5 to 7 membered carbocyclic ring containing 1 to 3 heteroatom(s), or (7) a group derived from a 5 to 7 membered saturated. or unsaturated carbocyclic ring containing 1 to 3 heteroatom(s), which is fused with a benzene ring, wherein the groups of (2) to (7) may have one or more substituent(s), or a group selected from the groups represented by the following formulas (II) and (III):

(III)

wherein $R^6$ and $R^7$ are each phenyl optionally having substituent(s) or an aromatic heterocyclic group, or $R^2$ and $R^3$ in conjunction form a ring optionally containing heteroatom(s), wherein the ring may be fused with a benzene ring optionally having substituent(s);

$R^4$ is alkoxycarbonyl,
alkylcarbonyl,
alkylsulfonyl,
alkylsulfinyl,
phenylsulfinyl,
phenylsulfonyl,
dialkylphosphinyl,
dialkylphosphonyl,
phenyl optionally having substituent(s),
an aromatic heterocyclic group optionally having substituent(s),
cyano or
nitro; and $R^5$ is alkyl,
phenylaminoalkyl,
acyl,
acylalkyl,
aminocarbonyl,
arylaminocarbonyl,
a saturated or unsaturated 4 to 7 membered heterocyclic ring optionally having substituent(s),
a saturated 3 to 7 membered carbocyclic ring having substituent(s),
alkyl substituted by a saturated or unsaturated 4 to 7 membered ring containing 1 or 2 nitrogen atom(s), which optionally has a substituent, or
a group of the formula: —$(CR^aR^b)_n NR^{11}R^{12}$ wherein n is an integer of 1 to 4, $R^a$ is hydrogen or alkyl, $R^b$ is hydrogen or alkyl, $R^{11}$ is hydrogen, alkyl, alkylsulfonyl, phenylsulfonyl, phenylalkylsulfonyl, alkylsulfinyl, phenylsulfinyl, phenylalkylsulfinyl, alkoxycarbonyl, phenoxycarbonyl, phenylalkoxycarbonyl, alkylcarbonyl, phenylcarbonyl or phenylalkylcarbonyl, and $R^{12}$ is hydrogen or alkyl, provided that when $R^0$, $R^1$ and $R^2$ are each hydrogen, $R^4$ is methoxycarbonyl and $R^5$ is methyl, then $R^3$ should not be phenyl, 2-chlorophenyl, 3-nitrophenyl, 4-carboxyphenyl or 4-methoxycarbonylphenyl, and when $R^5$ is alkyl, then $R^4$ is not alkoxycarbonyl, alkylsulfonyl, alkylsulfinyl, phenylsulfinyl, phenylsulfonyl, dialkylphosphinyl, dialkylphosphonyl, cyano or nitro, or an optically active form thereof, or a pharmaceutically acceptable salt thereof.

[13] The dihydropyrazolopyridine compound of the above-described [12], wherein $R^4$ is alkoxycarbonyl, alkylcarbonyl, alkylsulfonyl, alkylsulfinyl, phenylsulfinyl, phenylsulfonyl, dialkylphosphinyl, dialkylphosphonyl, phenyl optionally having substituent(s), an aromatic heterocyclic group having substituent(s), cyano or nitro, and $R^5$ is alkyl, phenylaminoalkyl, acyl, acylalkyl, aminocarbonyl, arylaminocarbonyl, a saturated or unsaturated 4 to 7 membered heterocyclic ring optionally having substituent(s), a saturated 3 to 7 membered carbocyclic ring having substituent(s), alkyl substituted by a saturated or unsaturated 4 to 7 membered ring containing 1 or 2 nitrogen atom(s), which optionally has a substituent, or a group of the formula: —$(CH_2)_n NR^{11}R^{12}$ wherein n is an integer of 1 to 4, $R^{11}$ is hydrogen, alkyl, alkylsulfonyl, phenylsulfonyl, phenylalkylsulfonyl, alkylsulfinyl, phenylsulfinyl, phenylalkylsulfinyl, alkoxycarbonyl, phenoxycarbonyl, phenylalkoxycarbonyl, alkylcarbonyl, phenylcarbonyl or phenylalkylcarbonyl, and $R^{12}$ is hydrogen or alkyl, or an optically active form thereof, or a pharmaceutically acceptable salt thereof.

[14] The dihydropyrazolopyridine compound of the above-described [12] or [13], wherein $R^2$ is hydrogen or alkyl, or an optically active form thereof, or a pharmaceutically acceptable salt thereof.

[15] The dihydropyrazolopyridine compound of the above-described [12] or [13], wherein $R^3$ is phenyl optionally having 1 to 3 substituent(s), naphthyl, 2,1,3-benzoxadiazol-4-yl or 3,4-dihydro-2H-benzopyran-8-yl, or an optically active form thereof, or a pharmaceutically acceptable salt thereof.

[16] The dihydropyrazolopyridine compound of the above-described [12] or [13], wherein $R^4$ is alkoxycarbonyl having 2 to 5 carbon atoms, alkylcarbonyl having 2 to 5 carbon atoms, alkylsulfonyl having 1 to 4 carbon atoms, or alkylsulfinyl having 1 to 4 carbon atoms, or an optically active form thereof, or a pharmaceutically acceptable salt thereof.

[17] The dihydropyrazolopyridine compound of the above-described [12] or [13], wherein $R^5$ is a group of the formula: —$(CH_2)_n NR^{11}R^{12}$ wherein n is an integer of 1 to 4, $R^{11}$ is hydrogen, alkyl or alkoxycarbonyl and $R^{12}$ is hydrogen or alkyl, or an optically active form thereof, or a pharmaceutically acceptable salt thereof.

[18] The dihydropyrazolopyridine compound of the above-described [12] or [13], wherein $R^0$ is hydrogen or a group of the formula: —$COOR^8$ (wherein $R^8$ is alkyl, aryl optionally having substituent(s) or aralkyl optionally having substituent(s)), or an optically active form thereof, or a pharmaceutically acceptable salt thereof.

[19] The dihydropyrazolopyridine compound of the above-described [12] or [13], which is selected from the group consisting of (1002) 4-(2,1,3-benzoxadiazol-4-yl)-5-cyano-4,7-dihydro-6-(piperidin-4-yl)-2H-pyrazolo[3,4-b]pyridine,
(1003) 4-(2,1,3-benzoxadiazol-4-yl)-5-cyano-4,7-dihydro-6-(1-methylpiperidin-4-yl)-2H-pyrazolo[3,4-b]pyridine,
(1011) 4-(2,1,3-benzoxadiazol-4-yl)-5-cyano-4,7-dihydro-6-(4-methylmorpholin-2-yl)-2H-pyrazolo[3,4-b]pyridine,
(1014) 4-(2,1,3-benzoxadiazol-4-yl)-5-cyano-4,7-dihydro-6-(1-methyl-1,2,3,6-tetrahydropyridin-4-yl)-2H-pyrazolo[3,4-b]-pyridine,
(1023) 4-(2,1,3-benzoxadiazol-4-yl)-5-cyano-4,7-dihydro-6-(4-(N,N-dimethylamino)cyclohexyl)-2H-pyrazolo[3,4-b]pyridine,
(1027) 6-(1-acetyl-1,2,3,6-tetrahydropyridin-4-yl)-4-(2,1,3-benzoxadiazol-4-yl)-5-cyano-4,7-dihydro-2H-pyrazolo[3,4-b]-pyridine,
(1033) 4-(2,1,3-benzoxadiazol-4-yl)-5-cyano-4,7-dihydro-6-(1-ethylpiperidin-4-yl)-2H-pyrazolo[3,4-b]pyridine,
(1037) 4-(2-bromo-3-cyanophenyl)-5-cyano-4,7-dihydro-6-(piperidin-4-yl)-2H-pyrazolo[3,4-b]pyridine, (1038) 4-(2-bromo-3-cyanophenyl)-5-cyano-4,7-dihydro-6-(1-methylpiperidin-4-yl)-2H-pyrazolo[3,4-b]pyridine,
(1041) 4-(2-bromo-3-cyanophenyl)-5-cyano-4,7-dihydro-6-(1-methylpiperidin-3-yl)-2H-pyrazolo[3,4-b]pyridine,
(1046) 4-(2-bromo-3-cyanophenyl)-5-cyano-4,7-dihydro-6-(4-methylmorpholin-2-yl)-2H-pyrazolo[3,4-b]pyridine,
(1048) 4-(2-bromo-3-cyanophenyl)-5-cyano-4,7-dihydro-6-(1-methyl-1,2,3,6-tetrahydropyridin-4-yl)-2H-pyrazolo[3,4-b]-pyridine,
(1051) 6-(1-acetylpiperidin-4-yl)-4-(2-bromo-3-cyanophenyl)-5-cyano-4,7-dihydro-2H-pyrazolo[3,4-b]pyridine,
(1052) 6-(1-benzoylpiperidin-4-yl)-4-(2-bromo-3-cyanophenyl)-5-cyano-4,7-dihydro-2H-pyrazolo[3,4-b]pyridine,
(1053) 4-(2-bromo-3-cyanophenyl)-5-cyano-4,7-dihydro-6-(1-methanesulfonylpiperidin-4-yl)-2H-pyrazolo[3,4-b]pyridine,
(1059) 4-(2,1,3-benzoxadiazol-4-yl)-5-cyano-4,7-dihydro-6-(4-oxocyclohexan-1-yl)-2H-pyrazolo[3,4-b]pyridine,
(1062) 4-(2-bromo-3-cyanophenyl)-5-cyano-4,7-dihydro-6-(2-oxocyclohexan-1-yl)-2H-pyrazolo[3,4-b]pyridine,
(1063) 6-acetylmethyl-4-(2-bromo-3-cyanophenyl)-5-cyano-4,7-dihydro-2H-pyrazolo[3,4-b]pyridine,
(1073) 5-cyano-4,7-dihydro-4-(2,3-(methylenedioxy)phenyl)-6-(piperidin-4-yl)-2H-pyrazolo[3,4-b]pyridine,
(1075) 4-(2,1,3-benzoxadiazol-4-yl)-5-cyano-4,7-dihydro-2H-pyrazolo[3,4-b]pyridine-6-carboxylic acid phenylamide,
(1078) 4-(2-chlorophenyl)-5-cyano-4,7-dihydro-6-(4-phenyl-piperazin-1-yl)methyl-2H-pyrazolo[3,4-b]pyridine,
(1081) 6-acetyl-4-(2-bromo-3-cyanophenyl)-5-cyano-4,7-dihydro-2H-pyrazolo[3,4-b]pyridine,
(1082) 6-acetyl-4-(2,1,3-benzoxadiazol-4-yl)-5-cyano-4,7-dihydro-2H-pyrazolo[3,4-b]pyridine,
(1084) 4-(2-bromo-3-cyanophenyl)-5-(pyridin-2-yl)-4,7-dihydro-6-propyl-2H-pyrazolo[3,4-b]pyridine,
(1086) 4-(2-chlorophenyl)-5-cyano-4,7-dihydro-6-(pyrrolidin-3-yl)-2H-pyrazolo[3,4-b]pyridine, and
(1087) 4-(2,1,3-benzoxadiazol-4-yl)-5-(pyridin-2-yl)-4,7-dihydro-6-propyl-2H-pyrazolo[3,4-b]pyridine,
a tautomer thereof, an optically active form thereof, or a pharmaceutically acceptable salt thereof.

[20] A medicament comprising a dihydropyrazolopyridine compound of the above-described [1] or [2], an optically active form thereof, a pharmaceutically acceptable salt thereof or a hydrate thereof.

[21] A medicament comprising a dihydropyrazolopyridine compound of the above-described [12] or [13], an optically active form thereof, or a pharmaceutically acceptable salt thereof.

[22] A pharmaceutical composition comprising a dihydropyrazolopyridine compound of the above-described [1] or [2], an optically active form thereof, a pharmaceutically acceptable salt thereof or a hydrate thereof, and a pharmaceutically acceptable additive.

[23] A pharmaceutical composition comprising a dihydropyrazolopyridine compound of the above-described [12] or [13], an optically active form thereof, or a pharmaceutically acceptable salt thereof, and a pharmaceutically acceptable additive.

[24] A glycogen synthase kinase-3 beta inhibitor comprising a compound selected from the group consisting of a dihydropyrazolopyridine compound of the above-described [1] or [2], an optically active form thereof, a pharmaceutically acceptable salt thereof and a hydrate thereof.

[25] A glycogen synthase kinase-3 beta inhibitor comprising a compound selected from the group consisting of a dihydropyrazolopyridine compound of the above-described [12] or [13], an optically active form thereof and a pharmaceutically acceptable salt thereof.

[26] The medicament of the above-described [20] or [21], which is used for prevention and/or treatment of a disease caused by glycogen synthase kinase-3 beta hyperactivity.

[27] The medicament of the above-described [20] or [21], which is used for prevention and/or treatment of a neurodegenerative disease.

[28] The medicament of the above-described [27], wherein the disease is selected from the group consisting of Alzheimer's disease, ischemic cerebrovascular disorders, Down's syndrome, cerebral ischemia due to cerebral amyloid angiopathy, progressive supranuclear paralysis, subacute sclerosing panencephalitic Parkinsonism, postencephalitic Parkinsonism, boxer's encephalopathy, Parkinsonism dementia complex of Guam, Lewy body disease, Pick's disease, corticobasal degeneration, frontotemporal dementia, AIDS encephalopathy, Huntington's disease and manic-depressive psychosis.

[29] The medicament of the above-described [20] or [21], which is used for prevention and/or treatment of diabetes and diabetic complications.

[30] The medicament of the above-described [20] or [21], which is used as an immunopotentiator.

[31] The medicament of the above-described [20] or [21], which is used for prevention and/or treatment of alopecia, breast cancer, non-small cell lung carcinoma, thyroid cancer, T or B-cell lukemia or virus-induced tumors.

DETAILED DESCRIPTION OF THE INVENTION

Figure 1:
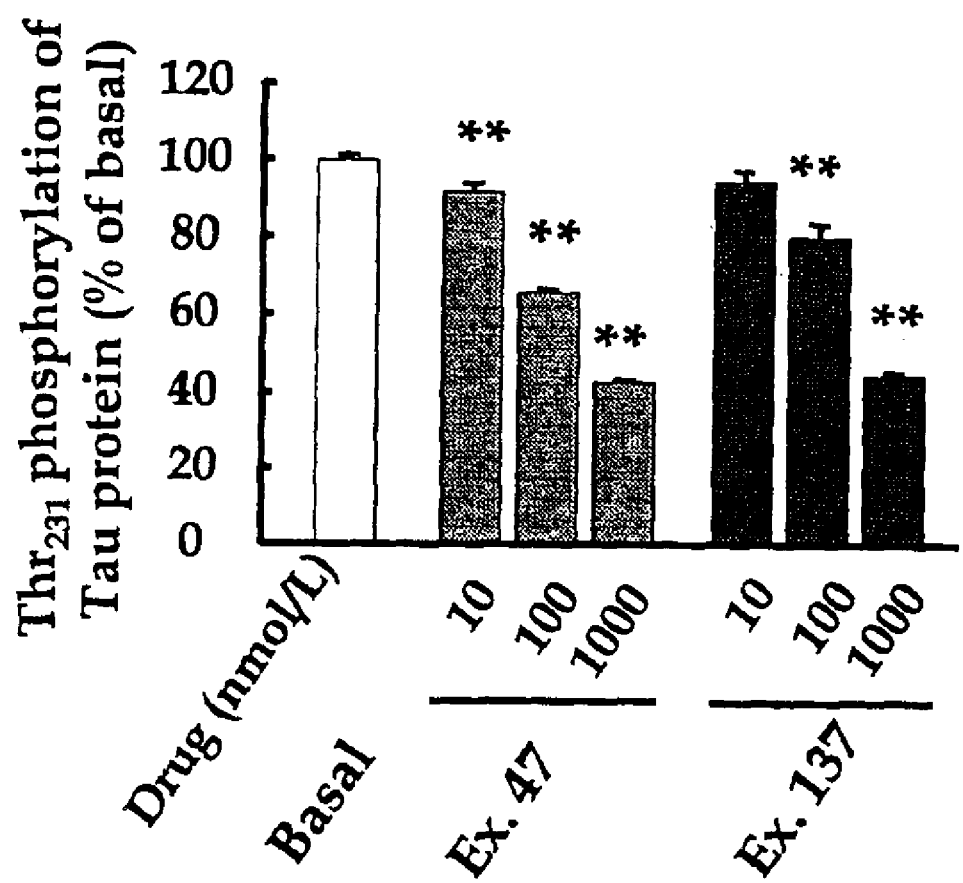
FIG. 1 shows the GSK-3β-inhibitory activity of the compounds of Example 47 and Example 137.

The formula (I) indicates the presence of tautomers represented by the following formulas (I-a) and (I-b), based on the positions of hydrogen atoms of the pyrazole ring. The present invention encompasses each isomer of the formulas (I-a) and (I-b), and a mixture of these isomers.

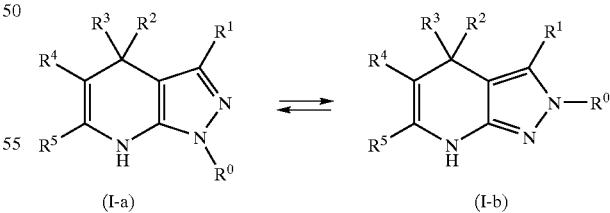

The compounds represented by the formula (I) in the present specification are described in detail in the following.

"Alkyl" means a linear or branched (hydro)carbon chain of 1 to 8 carbon atom(s), and includes methyl, ethyl, propyl, butyl, pentyl (i.e., amyl), hexyl, or a structural isomer thereof, such as isopropyl, isobutyl, sec-butyl, tert-butyl, isopentyl, neopentyl, tert-pentyl and the like, with a preference for alkyl having 1 to 4 carbon atom(s). The alkyl of $R^2$ is preferably alkyl having 1 to 4 carbon atoms. The alkyl of $R^5$ is preferably alkyl having 2 to 8 carbon atoms. The "alkyl having 2 to 8 carbon atoms" concretely includes ethyl, propyl, butyl, pentyl (i.e., amyl), hexyl, heptyl and octyl, or a structural isomer thereof, such as isopropyl, isobutyl, sec-butyl, tert-butyl, isopentyl, neopentyl, tert-pentyl and the like. Alkyl having 2 to 4 carbon atoms is more preferable, and propyl is particularly preferable.

"Acyl" means $C_2$–$C_{14}$ acyl, and includes "alkylcarbonyl" having 2 to 8 carbon atoms, such as acetyl, propionyl, butyryl, isobutyryl, valeryl, pivaloyl, hexanoyl, heptanoyl and the like, at $R^4$ preferably having 2 to 5 carbon atoms, and aromatic acyl having 7 to 12 carbon atoms including "$C_7$–$C_{12}$ arylcarbonyl" such as benzoyl, naphthoyl and the like and "$C_7$–$C_{12}$ aralkylcarbonyl" such as benzylcarbonyl, 2-phenylethylcarbonyl, 3-phenylpropylcarbonyl, cinnamoyl, and the like, and the like. The benzene and naphthalene rings may have 1 to 5 substituent(s) and substitution sites are not particularly limited.

"Acylalkyl" is acylalkyl consisting of the above $C_1$–$C_8$ alkyl and the above $C_2$–$C_{14}$ acyl, and includes, for example, acetylmethyl, propionylmethyl, butyrylmethyl, isobutyrylmethyl, valerylmethyl, pivaloylmethyl, 2-acetylethyl, 2-propionylethyl, 3-acetylpropyl and the like.

"Cycloalkyl" means a cyclic (hydro)carbon chain of 3 to 8 carbon atoms. Cycloalkyl concretely includes, for example, cyclopropyl, cyclobutyl, cyclopentyl, cyclohexyl, cycloheptyl and the like, with a preference for cycloalkyl having 3 to 6 carbon atoms. The cycloalkyl may have 1 to 5 substituent(s) and substitution sites are not particularly limited.

"Halogen" represents fluorine, chlorine, bromine or iodine.

"Amino" is primary amino, secondary or tertiary amino having the above alkyl (e.g., $C_1$–$C_8$ alkyl), and includes, for example, amino, mono- or di-$C_1$–$C_8$ alkyl-substituted amino such as methylamino, dimethylamino, ethylamino, diethylamino, propylamino, dipropylamino, butylamino, dibutylamino and the like, with a preference for tertiary amino containing alkyl having 1 to 4 carbon atom(s).

"Alkylthio" is a linear or branched alkylthio having 1 to 6 carbon atom(s), and includes, for example, methylthio, ethylthio, propylthio, butylthio, pentylthio (i.e., amylthio), hexylthio and structural isomers thereof, such as isopropylthio, isobutylthio, sec-butylthio, tert-butylthio, isopentylthio, neopentylthio, tert-pentylthio and the like, with a preference for alkylthio having 1 to 3 carbon atom(s).

"Phenylthio" means phenylthio optionally having 1 to 5 substituent(s) on the phenyl and substitution sites are not particularly limited.

"Haloalkyl" is the above alkyl (e.g., $C_1$–$C_8$ alkyl) substituted by 1 to 5 halogen(s), and represents fluoromethyl, chloromethyl, difluoromethyl, trifluoromethyl, 2,2,2-trifluoroethyl, 2,2,3,3,3-pentafluoropropyl and the like.

"Aminoalkyl" is the above-mentioned alkyl (e.g., $C_1$–$C_8$ alkyl) having the above amino, preferably primary amino, and includes, for example, aminomethyl, methylaminomethyl, dimethylaminomethyl, 2-aminoethyl, 3-aminopropyl, 4-aminobutyl, 2-methylaminoethyl, 2-dimethylaminoethyl, 2-ethylaminoethyl, 2-diethylaminoethyl and the like, with a preference for aminoalkyl containing alkyl having 1 to 4 carbon atom(s), and aminoalkyl containing alkyl having 1 to 4 carbon atom(s) having tertiary amino.

"Acylamino" is acylamino having the above acyl (e.g., $C_2$–$C_{14}$ acyl), and represents, for example, acetylamino, propionylamino, butyrylamino, valerylamino, pivaloylamino, benzoylamino, phenylacetylamino, phenylpropionylamino, phenylbutyrylamino and the like.

"Alkoxy" is alkoxy having the above alkyl (e.g., $C_1$–$C_8$ alkyl), and includes, for example, methoxy, ethoxy, propoxy, butoxy, pentyloxy (i.e., amyloxy), hexyloxy and structural isomers thereof, such as isopropoxy, isobutoxy, sec-butoxy, tert-butoxy, isopentyloxy, neopentyloxy, tert-pentyloxy and the like, with a preference for alkoxy having 1 to 4 carbon atom(s).

"Cycloalkoxy" is (cyclo)alkoxy having the above cycloalkyl (e.g., $C_3$–$C_8$ cycloalkyl), and includes, for example, cyclopropoxy, cyclobutoxy, cyclopentyloxy, cyclohexyloxy and the like, with a preference for cycloalkoxy having cycloalkyl having 3 to 6 carbon atoms.

"Phenoxy" means phenyloxy optionally having 1 to 5 substituent(s) on the phenyl and substitution sites are not particularly limited.

"Phenylalkoxy" is phenylalkoxy having the above alkoxy (e.g., $C_1$–$C_8$ alkoxy), and includes, for example, benzyloxy, 1-phenylethoxy, 2-phenylethoxy, 3-phenylpropoxy, 4-phenylbutoxy, 1-methyl-1-phenylethoxy, 1-methyl-2-phenylethoxy, 1-phenylpropoxy, 2-pheylpropoxy, 1-methyl-1-phenylpropoxy, 1-methyl-2-phenylpropoxy, 1-methyl-3-phenylpropoxy and the like, with a preference for phenylalkoxy containing alkoxy having 1 to 4 carbon atom(s)

The phenylalkoxy optionally has 1 to 5 substituent(s) on the phenyl and substitution sites are not particularly limited.

"Aminoalkoxy" is aminoalkoxy consisting of the above alkoxy (e.g., $C_1$–$C_8$ alkoxy) and amino, and includes, for example, aminomethoxy, methylaminomethoxy, dimethylaminomethoxy, 2-(dimethylamino)ethoxy, 3-(dimethylamino)propoxy, 4-(dimethylamino)butoxy and the like, with a preference for aminoalkoxy consisting of tertiary amino containing alkyl having 1 to 4 carbon atom(s), and alkoxy having 1 to 4 carbon atom(s).

"Alkoxyalkyl" is alkoxyalkyl consisting of the above alkoxy (e.g., $C_1$–$C_8$ alkoxy) and alkyl (e.g., $C_1$–$C_8$ alkyl), and includes, for example, methoxymethyl, ethoxymethyl, 2-methoxyethyl, propoxymethyl, isopropoxymethyl and the like, with a preference for alkoxyalkyl consisting of alkoxy having 1 to 4 carbon atom(s) and alkyl having 1 to 4 carbon atom(s).

"Phenoxyalkyl" is phenoxyalkyl containing of the above phenoxy and alkyl (e.g., $C_1$–$C_8$ alkyl), and includes, for example, phenoxymethyl, 2-phenoxyethyl, 3-phenoxypropyl and the like, with a preference for phenoxyalkyl containing alkyl having 1 to 4 carbon atom(s). The phenoxyalkyl optionally has 1 to 5 substituent(s) on the phenyl and substitution sites are not particularly limited.

"Dialkoxyalkyl" is dialkoxyalkyl consisting of the above alkyl and alkoxy, and includes, for example, dimethoxymethyl, diethoxymethyl, 2,2-dimethoxyethyl, 2,2-diethoxyethyl and the like, with a preference for dialkoxyalkyl consisting of alkoxy having 1 to 4 carbon atom(s) and alkyl having 1 to 4 carbon atom(s).

"Hydroxyalkyl" is hydroxyalkyl having the above alkyl (e.g., $C_1$–$C_8$ alkyl), and includes, for example, hydroxymethyl, 2-hydroxyethyl, 3-hydroxypropyl and the like, with a preference for hydroxyalkyl containing alkyl having 1 to 4 carbon atom(s).

"Alkoxycarbonyl" is alkoxycarbonyl having the above alkoxy (e.g., $C_1$–$C_8$ alkoxy), and includes, for example, methoxycarbonyl, ethoxycarbonyl, propoxycarbonyl, butoxycarbonyl, pentyloxycarbonyl, hexyloxycarbonyl and structural isomers thereof, such as isopropoxycarbonyl, isobutoxycarbonyl, sec-butoxycarbonyl, tert-butoxycarbonyl, isopentyloxycarbonyl, neopentyloxycarbonyl, tert-pentyloxycarbonyl and the like, with a preference for alkoxycarbonyl, in which the alkoxy moiety has 1 to 4 carbon atom(s). However, the alkoxycarbonyl of $R^4$ is preferably alkoxycarbonyl having 2 to 5 carbon atoms.

"Phenoxycarbonyl" is phenoxycarbonyl optionally having 1 to 5 substituent(s) on the phenyl and substitution sites are not particularly limited.

"Aminocarbonyl" is aminocarbonyl having the above amino (including mono- or di-$C_1$–$C_8$ alkyl-substituted amino), and includes, for example, aminocarbonyl (i.e., carbamoyl), methylaminocarbonyl, dimethylaminocarbonyl, ethylaminocarbonyl, diethylaminocarbonyl, propylaminocarbonyl, dipropylaminocarbonyl, phenylcarbamoyl, benzylcarbamoyl and the like, with a preference for tertiary-aminocarbonyl containing alkyl having 1 to 4 carbon atom(s).

"Alkylthiocarbonyl" is alkylthiocarbonyl having the above alkylthio (e.g., $C_1$–$C_6$ alkylthio), and includes, for example, methylthiocarbonyl, ethylthiocarbonyl, propylthiocarbonyl, butylthiocarbonyl and structural isomers thereof, such as isopropylthiocarbonyl, isobutylthiocarbonyl, sec-butylthiocarbonyl, tert-butylthiocarbonyl and the like, with a preference for alkylthiocarbonyl, in which the alkyl moiety has 1 to 3 carbon atoms.

"Carboxyalkyl" is carboxyalkyl having the above alkyl (e.g., $C_1$–$C_8$ alkyl), and includes, for example, carboxymethyl, carboxyethyl, carboxypropyl and the like, with a preference for carboxyalkyl containing alkyl having 1 to 4 carbon atom(s).

"Cycloalkoxyalkyl" is cycloalkoxyalkyl having the above cycloalkoxy and alkyl (e.g., cycloalkoxyalkyl consisting of the above $C_3$–$C_8$ cycloalkoxy and $C_1$–$C_8$ alkyl), and includes, for example, cyclopropoxymethyl, cyclopropoxyethyl, cyclobutoxymethyl, cyclopentyloxymethyl, cyclohexyloxymethyl and the like, with a preference for cycloalkoxyalkyl consisting of cycloalkoxy having 3 to 6 carbon atoms and alkyl having 1 to 4 carbon atom(s). The cycloalkoxyalkyl optionally has 1 to 3 substituent(s) on the cycloalkyl and substitution sites are not particularly limited.

"Alkylsulfinyl" is alkylsulfinyl having the above alkyl (e.g., $C_1$–$C_8$ alkyl), and includes, for example, methylsulfinyl, ethylsulfinyl, propylsulfinyl, isopropylsulfinyl and the like, with a preference for alkylsulfinyl containing alkyl having 1 to 5, preferably 1 to 4 carbon atom(s). The alkylsulfinyl of $R^4$ is preferably alkylsulfinyl having 1 to 4 carbon atoms.

"Phenylsulfinyl" means phenylsulfinyl optionally having 1 to 5 substituent(s) on the phenyl and substitution sites are not particularly limited.

"Alkylsulfonyl" is alkylsulfonyl having the above alkyl (e.g., $C_1$–$C_8$ alkyl), and includes, for example, methylsulfonyl, ethylsulfonyl, propylsulfonyl, isopropylsulfonyl and the like, with a preference for alkylsulfonyl containing alkyl having 1 to 5, preferably 1 to 4 carbon atom(s). The alkylsulfonyl of $R^4$ is preferably alkylsulfonyl having 1 to 4 carbon atoms.

"Phenylsulfonyl" means phenylsulfonyl optionally having 1 to 5 substituent(s) on the phenyl and substitution sites are not particularly limited.

"Mercaptoalkyl" is mercaptoalkyl having the above alkyl (e.g., $C_1$–$C_8$ alkyl), and includes, for example, mercaptomethyl, mercaptoethyl, mercaptopropyl and the like, with a preference for mercaptoalkyl containing alkyl having 1 to 4 carbon atom(s).

"Alkylthioalkyl" is alkylthioalkyl having the above alkylthio and alkyl (e.g., alkylthioalkyl consisting of the above $C_1$–$C_6$ alkylthio and $C_1$–$C_8$ alkyl), and includes, for example, methylthiomethyl, methylthioethyl, methylthiopropyl, ethylthiomethyl, ethylthioethyl, ethylthiopropyl and the like, with a preference for alkylthioalkyl consisting of alkylthio having 1 to 3 carbon atom(s) and alkyl having 1 to 4 carbon atom(s).

"Aryl" is aryl having 6 to 14 carbon atoms, and includes, for example, phenyl, 1-naphthyl, 2-naphthyl, 1-anthryl, 2-anthryl and the like. They may have 1 to 5 substituent(s) and substitution sites are not particularly limited.

"Aralkyl" is aralkyl wherein the above alkyl (e.g., $C_1$–$C_8$ alkyl) is substituted by the above aryl (e.g., $C_6$–$C_{14}$ aryl), and includes benzyl, 2-phenylethyl, 3-phenylpropyl, 1-naphthylmethyl, 2-naphthylmethyl and the like. These may have 1 to 5 substituent(s) on the aryl moiety and substitution sites are not particularly limited.

"Acyloxyacetyl" is acyloxyacetyl having the above acyl (e.g., $C_2$–$C_{14}$ acyl), and includes, for example, acetyloxyacetyl, propionyloxyacetyl, butyryloxyacetyl, benzoyloxyacetyl and the like.

"Acyloxyalkyl" is acyloxyalkyl having the above acyl (e.g., $C_2$–$C_{14}$ acyl) and alkyl (e.g., $C_1$–$C_8$ alkyl), and includes, for example, acetyloxymethyl, propionyloxymethyl, butyryloxymethyl, benzoyloxymethyl, 2-acetyloxyethyl, 2-propionyloxyethyl, 2-butyryloxyethyl, 2-benzoyloxyethyl and the like.

The substituent of the "phenyl optionally having substituent(s)" is exemplified by those mentioned for the "substituent" below, wherein the number of the substituent is generally 1 to 5, preferably 1 to 3, more preferably 3. Phenyl having 1 or 2 substituent(s) is particularly preferable and substitution sites are not particularly limited.

"Aromatic heterocyclic group" is, for example, a 5- or 6-membered aromatic heterocyclic group optionally containing 1 to 3 heteroatom(s) selected from the group consisting of nitrogen atom, oxygen atom and sulfur atom, and includes, for example, thiophenyl, furanyl, pyrrolyl, imidazolyl, pyrazolyl, thiazolyl, isothiazolyl, oxazolyl, isoxazolyl, pyridyl, pyridazinyl, pyrimidyl, pyrazinyl, oxadiazolyl (e.g., 1,3,4-oxadiazolyl, 1,2,4-oxadiazolyl, etc.), and the like. The aromatic heterocyclic group may have 1 to 6 substituent(s) and substitution sites are not particularly limited.

"Saturated or unsaturated 4 to 7 membered heterocyclic ring optionally having substituent(s)" includes the following groups and the like.

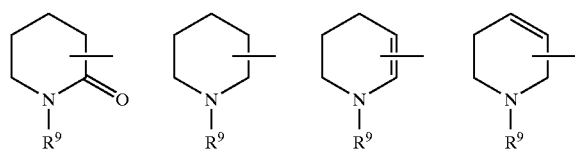

-continued

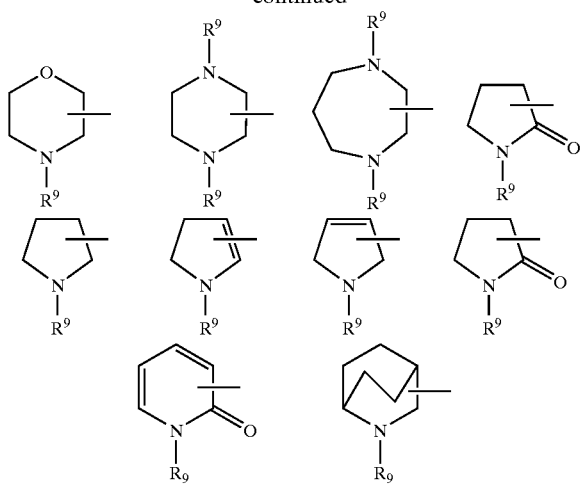

wherein R⁹ is each independently hydrogen, alkyl, acyl, aralkyl, cycloalkyl, formyl, haloalkyl, aminoalkyl, phenylalkyl, alkoxyalkyl, phenoxyalkyl, guanyl, hydroxyalkyl, aminocarbonyl, alkylthiocarbonyl, carboxyalkyl, alkoxycarbonyl, phenoxycarbonyl, alkylsulfinyl, alkylsulfonyl, phenylsulfonyl, mercaptoalkyl, alkylthioalkyl, acyloxyacetyl, acyloxyalkyl, aryl optionally having substituent(s), aromatic heterocyclic group optionally having substituent(s), or phenylalkyl optionally having substituent(s).

"Saturated 3 to 7 membered carbocyclic ring having substituent(s)" includes the following groups and the like.

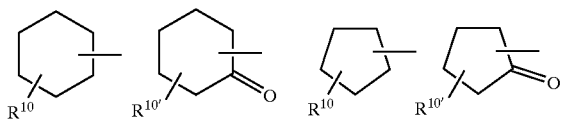

wherein $R^{10}$ is alkyl, acyl, aralkyl, cycloalkyl, formyl, haloalkyl, aminoalkyl, alkoxyalkyl, phenylalkyl, phenoxyalkyl, amino, hydroxyalkyl, aminocarbonyl, alkylthiocarbonyl, carboxyalkyl, alkylsulfinyl, alkylsulfonyl, phenylsulfonyl, mercaptoalkyl, alkylthioalkyl, acyloxyacetyl, acyloxyalkyl, aryl optionally having substituent(s), aromatic heterocyclic group optionally having substituent(s), or phenylalkyl optionally having substituent(s), and $R^{10'}$ is hydrogen, alkyl, acyl, aralkyl, cycloalkyl, formyl, haloalkyl, aminoalkyl, alkoxyalkyl, phenylalkyl, phenoxyalkyl, amino, hydroxyalkyl, aminocarbonyl, alkylthiocarbonyl, carboxyalkyl, alkylsulfinyl, alkylsulfonyl, phenylsulfonyl, mercaptoalkyl, alkylthioalkyl, acyloxyacetyl, acyloxyalkyl, aryl optionally having substituent(s), aromatic heterocyclic group optionally having substituent(s), or phenylalkyl optionally having substituent(s).

The substituent of the "aromatic heterocyclic group optionally having substituent(s)" is exemplified by those mentioned for the "substituent" below, wherein the number of the substituent is generally 1 to 6, preferably 1 to 5, more preferably 3, and substitution sites are not particularly limited.

"Phenylalkyl" is phenylalkyl having the above alkyl (e.g., phenylalkyl consisting of phenyl and the above $C_1$–$C_8$ alkyl), and includes, for example, benzyl, 2-phenylethyl, 3-phenylpropyl, 4-phenylbutyl, 1-phenylethyl, 1-methyl-2-phenylethyl, 1-phenylpropyl, 2-phenylpropyl, 1-methyl-1-phenylpropyl, 1-methyl-2-phenylpropyl, 1-methyl-3-phenylpropyl and the like, with a preference for phenylalkyl consisting of phenyl and alkyl having 1 to 4 carbon atom(s).

The kind and the number of the substituent of the "phenylalkyl optionally having substituent(s)" are the same as those for the above-mentioned "aromatic heterocyclic group" and substitution sites are not particularly limited.

"Alkoxycarbonylalkyl" is alkoxycarbonylalkyl having the above alkoxycarbonyl and alkyl, and includes, for example, methoxycarbonylmethyl, ethoxycarbonylmethyl, ethoxycarbonylmethyl, 2-ethoxycarbonylethyl, 3-ethoxycarbonylpropyl and the like.

"Alkoxycarbonylethenyl" is alkoxycarbonylethenyl having the above alkoxycarbonyl, and includes, for example, 2-methoxycarbonylethenyl, 2-ethoxycarbonylethenyl, 2-butoxycarbonylethenyl, 2-tert-butoxycarbonylethenyl and the like.

"Dialkylphosphinyl" is dialkylphosphinyl having the above alkyl (e.g., $C_1$–$C_8$ alkyl), and includes, for example, dimethylphosphinyl, diethylphosphinyl, dipropylphosphinyl and the like, with a preference for dialkylphosphinyl containing alkyl having 1 to 4 carbon atom(s).

"Dialkylphosphonyl" is dialkylphosphonyl having the above alkyl (e.g., $C_1$–$C_8$ alkyl), and includes, for example, dimethylphosphonyl, diethylphosphonyl, dipropylphosphonyl and the like, with a preference for dialkylphosphonyl containing alkyl having 1 to 4 carbon atom(s).

In the present specification, "substituent" includes alkyl, acyl, cycloalkyl, phenyl, aromatic heterocyclic group, phenylalkyl, hydroxy, carboxy, thiol, halogen, amino, formyl, carbamoyl, cyano, nitro, alkylthio, haloalkyl, aminoalkyl, acylamino, alkoxy, cycloalkoxy, phenoxy, phenylalkoxy, aminoalkoxy, alkoxyalkyl, phenoxyalkyl, hydroxyalkyl, alkoxycarbonyl, alkylsulfinyl, aminocarbonyl, alkylthiocarbonyl and the like.

"Ring optionally containing heteroatom(s)" is a 5 or 6 membered carbocyclic ring optionally containing 1 to 3 heteroatom(s) selected from the group consisting of nitrogen atom, oxygen atom and sulfur atom, with particular preference given to a ring containing sulfur atom. The ring may be substituted by one or more of the above substituents or oxo groups. The substitution site is not particularly limited. This ring is formed by $R^2$ and $R^3$ in the formula (I) together with the attached carbon atom. By forming this ring, a spiro ring is formed in the compound of the formula (I). The above ring can be fused with a benzene ring optionally having substituent(s) and substitution sites are not particularly limited. Such a ring includes, for example, 2,3-dihydrobenzo[b]thiophene, 2,3-dihydrobenzo[b]thiophen-1-oxide and the like.

"A group derived from a benzene ring fused with a saturated or unsaturated 5 or 6 membered carbocyclic ring" represents a group derived from naphthalene, 1,2-dihydronaphthalene, 1,2,3,4-tetrahydronaphthalene, indan and the like, with preference given to naphthalene (namely naphthyl) and particular preference given to 1-naphthyl. Of these, naphthyl such as naphthalen-1-yl and the like, and indanyl such as indan-4-yl and the like are preferable. The group may have 1 to 4 substituent(s) and substitution sites are not particularly limited.

"A group derived from a benzene ring fused with a saturated or unsaturated 5 to 7 membered carbocyclic ring containing 1 to 3 heteroatom(s)" includes the following groups and the like.

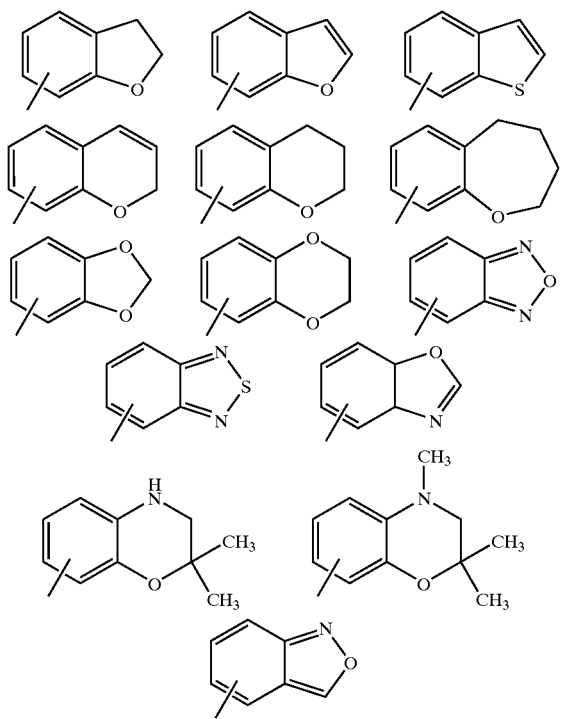

Of these, 2,1,3-benzoxadiazole, dihydrobenzo[b]furan, methylenedioxyphenyl and 3,4-dihydro-2H-benzopyrane are preferable, and 2,1,3-benzoxadiazol-4-yl, 2,3-dihydrobenzo-[b]furan-7-yl, 2,3-(methylenedioxy)phenyl and 3,4-dihydro-2H-benzopyran-8-yl are particularly preferable. The group may have 1 to 3 substituent(s) and substitution sites are not particularly limited.

Of these, 2,1,3-benzoxadiazole and 3,4-dihydro-2H-benzopyrane are preferable, and 2,1,3-benzoxadiazol-4-yl and 3,4-dihydro-2H-benzopyran-8-yl are particularly preferable.

"A group derived from a 5 to 7 membered saturated or unsaturated carbocyclic ring containing 1 to 3 heteroatom(s), which is fused with a benzene ring" includes the following groups and the like.

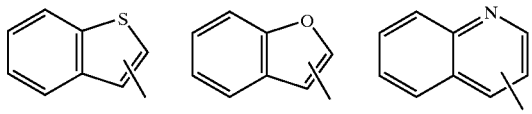

The group may have 1 to 5 substituent(s) and substitution sites are not particularly limited.

"Alkylcarbonylalkyl" is, for example, $C_1$–$C_4$ alkyl-carbonyl-$C_1$–$C_4$ alkyl, and includes, for example, methylcarbonylmethyl, ethylcarbonylmethyl, propylcarbonylmethyl, butylcarbonylmethyl and the like.

"Arylaminocarbonyl" is $C_6$–$C_{10}$ aryl-aminocarbonyl, and includes, for example, phenylaminocarbonyl, naphthylaminocarbonyl and the like. The arylaminocarbonyl optionally has 1 to 3 substituent(s) on the aryl and substitution sites are not particularly limited.

"Aralkylaminocarbonyl" is $C_7$–$C_{14}$ aralkyl-aminocarbonyl, and includes, for example, benzylaminocarbonyl and the like. The aralkylaminocarbonyl optionally has 1 to 3 substituent(s) on the aryl and substitution sites are not particularly limited.

"Alkyl substituted by a saturated or unsaturated 4 to 7 membered ring containing 1 or 2 nitrogen atom(s), which optionally has a substituent" means $C_1$–$C_8$ alkyl substituted by "a saturated or unsaturated 4 to 7 membered ring containing 1 or 2 nitrogen atom(s)", such as pyrrole, pyrroline, pyrazole, pyridine, piperidine, piperazine, homopiperadine or morpholine and the like, which optionally has a substituent such as $C_1$–$C_4$ alkyl, $C_6$–$C_{10}$ aryl such as phenyl, naphthyl and the like, and includes, for example, (4-phenylpiperazin-1-yl)methyl, 2-(4-phenylpiperazin-1-yl)ethyl, 3-(4-phenylpiperazin-1-yl)propyl, (4-(naphthalen-1-yl)piperazin-1-yl)methyl, 2-(4-(naphthalen-1-yl)piperazin-1-yl)ethyl, (4-methylhomopiperazin-1-yl)methyl and the like.

"Phenylaminoalkyl" is phenylamino-$C_1$–$C_4$ alkyl, and includes, for example, phenylaminomethyl, 2-phenylaminoethyl, 3-phenylaminopropyl, 4-phenylaminobutyl and the like. The phenylaminoalkyl optionally has 1 to 3 substituent(s) on the phenyl and substitution sites are not particularly limited.

"Phenylalkylcarbonyl" is phenyl-$C_1$–$C_4$ alkyl-carbonyl, and includes, for example, benzylcarbonyl, 2-phenylethylcarbonyl, 3-phenylpropylcarbonyl, 4-phenylbutylcarbonyl and the like. The phenylalkylcarbonyl optionally has 1 to 3 substituent(s) on the phenyl and substitution sites are not particularly limited.

"Alkyl" in the $R^{11}$ is $C_1$–$C_4$ alkyl, and includes, for examples, methyl, ethyl, propyl, isopropyl, butyl, iso-butyl, tert-butyl and the like.

"Alkylsulfonyl" in the $R^{11}$ is $C_1$–$C_4$ alkyl-sulfonyl, and includes, for example, methylsulfonyl, ethylsulfonyl, propylsulfonyl and the like.

"Phenylsulfonyl" in the $R^{11}$ is phenylsulfonyl optionally having 1 to 3 substituent(s) on the phenyl and substitution sites are not particularly limited.

"Phenylalkylsulfonyl" in the $R^{11}$ is phenyl-$C_1$–$C_4$ alkyl-sulfonyl, and includes, for example, benzylsulfonyl, 2-phenylethylsulfonyl, 3-phenylpropylsulfonyl, 4-phenylbutylsulfonyl and the like. The phenylalkylsulfonyl optionally has 1 to 3 substituent(s) on the phenyl and substitution sites are not particularly limited.

"Alkylsulfinyl" in the $R^{11}$ is $C_1$–$C_4$ alkyl-sulfinyl, and includes, for example, methylsulfinyl, ethylsulfinyl, propylsulfinyl and the like.

"Phenylsulfinyl" in the $R^{11}$ is phenylsulfinyl optionally having 1 to 3 substituent(s) on the phenyl and substitution sites are not particularly limited.

"Phenylalkylsulfinyl" in the $R^{11}$ is phenyl-$C_1$–$C_4$ alkyl-sulfinyl, and includes, for example, benzylsulfinyl, 2-phenylethylsulfinyl, 3-phenylpropylsulfinyl, 4-phenylbutylsulfinyl and the like. The phenylalkylsulfinyl optionally has 1 to 3 substituent(s) on the phenyl and substitution sites are not particularly limited.

"Alkoxycarbonyl" in the $R^{11}$ is $C_1$–$C_4$ alkoxy-carbonyl, and includes, for example, methoxycarbonyl, ethoxycarbonyl, propoxycarbonyl, tert-butoxycarbonyl and the like.

"Phenylalkoxycarbonyl" in the $R^{11}$ is phenyl-$C_1$–$C_4$ alkoxy-carbonyl, and includes, for example, benzyloxycarbonyl, 2-phenylethoxycarbonyl, 3-phenylpropoxycarbonyl, 4-phenylbutoxycarbonyl and the like. The phenylalkoxycarbonyl optionally has 1 to 3 substituent(s) on the phenyl and substitution sites are not particularly limited.

"Alkylcarbonyl" in the $R^{11}$ is $C_1$–$C_4$ alkyl-carbonyl and includes, for example, acetyl, propionyl, butylcarbonyl and the like.

"Phenylcarbonyl" in the $R^{11}$ is phenylcarbonyl optionally having 1 to 3 substituent(s) on the phenyl and substitution sites are not particularly limited.

"Phenylalkylcarbonyl" in the $R^{11}$ is phenyl-$C_1$–$C_4$ alkylcarbonyl, and includes, for example, benzylcarbonyl, 2-phenylethylcarbonyl, 3-phenylpropylcarbonyl, 4-phenylbutylcarbonyl and the like. The phenylalkylcarbonyl optionally has 1 to 3 substituent(s) on the phenyl and substitution sites are not particularly limited.

"Phenoxycarbonyl" in the $R^{11}$ means phenoxycarbonyl optionally having 1 to 3 substituent(s) on the phenyl and substitution sites are not particularly limited.

"Alkyl" in the $R^{12}$ is $C_1$–$C_4$ alkyl, and includes, for examples, methyl, ethyl, propyl, iso-propyl, butyl, iso-butyl, tert-butyl and the like.

The "5 or 6-membered ring optionally containing heteroatom(s)" is a 5 or 6 membered carbocyclic ring optionally containing 1 to 3 heteroatom(s) consisting of nitrogen atom, oxygen atom and sulfur atom. Examples thereof include furan, thiophene, pyrrole, oxazole, isoxazole, thiazole, isothiazole, imidazole, pyrazole, furazan, pyran, pyridine, pyridazine, pyrimidine, pyrazine, pyrroline, pyrrolidine, imidazoline and imidazolidine. Of these, furan, thiophene, pyrrole, oxazole, isoxazole, thiazole, isothiazole, furazan and pyridine are preferable.

The compounds represented by the formula (I) of the present invention can be converted to acid addition salts with pharmaceutically acceptable acids and such acid addition salts are also encompassed in the present invention. Such acid addition salts include, for example, salts with inorganic acids such as hydrochloric acid, hydrobromic acid, hydroiodic acid, sulfuric acid, nitric acid, phosphoric acid and the like, and salts with organic acids such as formic acid, acetic acid, trifluoroacetic acid, propionic acid, oxalic acid, malonic acid, succinic acid, fumaric acid, maleic acid, lactic acid, malic acid, citric acid, tartaric acid, methanesulfonic acid, benzenesulfonic acid, p-toluenesulfonic acid, glutamic acid and the like. Furthermore, the compounds of the present invention can form hydrates, solvates with ethanol and the like, and crystal polymorphs. When an asymmetric carbon atom exists, optical isomers and racemates thereof can be present, and all of these are encompassed in the present invention.

Of the compounds (I) of the present invention, a compound wherein $R^0$ is hydrogen can be synthesized as shown in the following according to the method described in J. Chem. Soc., Perkin Trans. 1, 947 (1996) and the like.

First Production Method

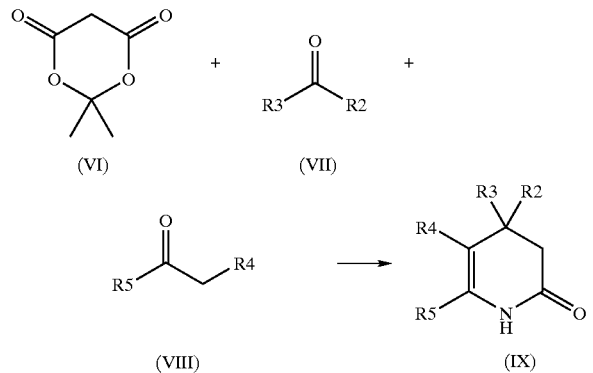

wherein $R^2$, $R^3$, $R^4$ and $R^5$ are as defined above.

Meldrum's acid of the formula (VI) and a carbonyl derivative of the formula (VII) are reacted with a carbonyl derivative of the formula (VIII), if desired, in the presence of ammonium acetate, to give an amide derivative of the formula (IX). The reaction is carried out in the presence of a carboxylic acid solvent inert to the reaction. As the solvent, formic acid, acetic acid, propionic acid, butyric acid, valeric acid and the like are generally used. The reaction is carried out at any temperature, for example, from 0° C. to 200° C., preferably from 60° C. to 100° C.

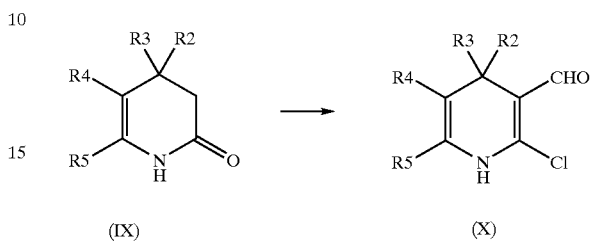

wherein $R^2$, $R^3$, $R^4$ and $R^5$ are as defined above.

The obtained amide derivative of the formula (IX) is reacted in the presence of dimethylformamide and phosphorus oxychloride to give a formyl derivative of the formula (X). The reaction is carried out in the presence of a solvent inert to the reaction. As the solvent, ether, tetrahydrofuran, dioxane, ethyl acetate, acetonitrile, benzene, toluene, chloroform, dichloromethane, dimethylformamide, dimethyl sulfoxide and the like are generally used. The reaction is carried out at any temperature, for example, from 0° C. to 200° C., preferably from 0° C. to 100° C., more preferably from 0° C. to 60° C. or 60° C. to 100° C.

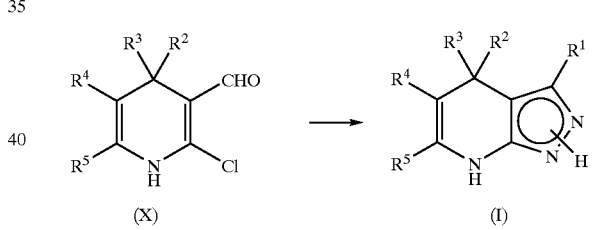

wherein $R^1$ (e.g., hydrogen), $R^2$, $R^3$, $R^4$ and $R^5$ are as defined above.

The compound (I) of the present invention can be produced by reacting the obtained formyl derivative of the formula (X) in the presence of hydrazine. The reaction is carried out in the presence of a solvent inert to the reaction. As the solvent, ether, tetrahydrofuran, dioxane, ethyl acetate, acetonitrile, benzene, toluene, chloroform, dichloromethane, dimethylformamide, dimethyl sulfoxide, pyridine, alcohol and the like are generally used. The reaction is carried out at any temperature, for example, from 0° C. to 200° C., preferably from 60° C. to 100° C.

The carbonyl derivative of the formula (VII), which is a starting material, can be synthesized according to the methods described in J. Org. Chem., 46, 783 (1981), Eur. J. Med. Chem., 31, 3 (1996) and Tetrahedron Lett., 24, 5023 (1983). The carbonyl derivative of the formula (VIII) can be synthesized according to the method described in Synthesis, 290 (1993).

Second Production Method

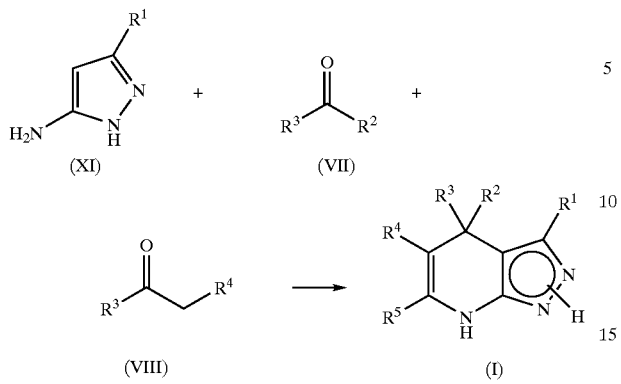

wherein $R^1$, $R^2$, $R^3$, $R^4$ and $R^5$ are as defined above.

The compounds (I) of the present invention can be produced by reacting aminopyrazole of the formula (XI) and a carbonyl derivative of the formula (VII) with a carbonyl derivative of the formula (VIII). The reaction is carried out in the presence of a solvent inert to the reaction. As the solvent, ether, tetrahydrofuran, dioxane, ethyl acetate, acetonitrile, benzene, toluene, chloroform, dichloromethane, dimethylformamide, dimethyl sulfoxide, alcohol and the like are generally used. The reaction is carried out at any temperature, for example, from 0° C. to 200° C., preferably from 60° C. to 100° C.

Of the compounds (I) of the present invention, a compound wherein $R^0$ is a substituent other than hydrogen can be synthesized as follows.

Third Production Method

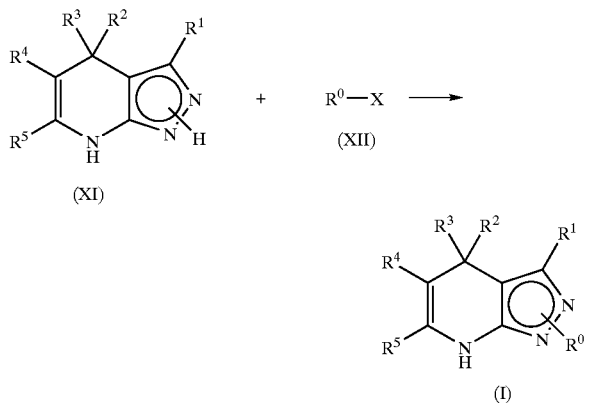

wherein $R^0$, $R^1$, $R^2$, $R^3$, $R^4$ and $R^5$ are as defined above, and X represents halogen, provided that $R^0$ is not hydrogen.

The compounds (I) of the present invention can be produced by reacting a dihydropyrazolopyridine derivative of the formula (XI) with halide of the formula (XII) in the presence of a base. Suitable base includes, for example, triethylamine, diisopropylethylamine, 4-dimethylaminopyridine and the like. The reaction is carried out in the presence of a solvent inert to the reaction. As the solvent, one without hydroxy group is generally used, such as tetrahydrofuran, ethyl acetate, benzene, toluene, chloroform, dichloromethane, dimethylformamide, dimethylimidazolidinone and the like. The reaction is carried out at any temperature, for example, from −10° C. to 200° C., preferably from 0° C. to 100° C.

Fourth Production Method

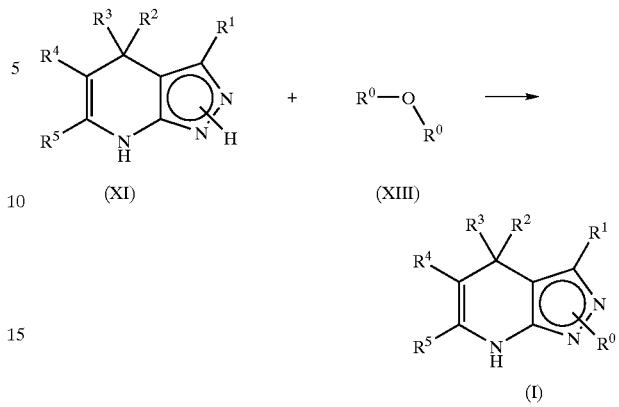

wherein $R^0$, $R^1$, $R^2$, $R^3$, $R^4$ and $R^5$ are as defined above, provided that $R^0$ is not hydrogen.

The compounds (I) of the present invention can be produced by reacting a dihydropyrazolopyridine derivative of the formula (XI) with anhydride of the formula (XIII) such as acetic anhydride or the like in the presence of a base. Suitable base includes, for example, triethylamine, pyridine, 4-dimethylaminopyridine and the like. The reaction is carried out in the presence of a solvent inert to the reaction. As the solvent, one without hydroxy group is generally used, such as tetrahydrofuran, ethyl acetate, benzene, toluene, chloroform, dichloromethane, dimethylformamide, dimethylimidazolidinone, pyridine and the like. The reaction is carried out at any temperature, for example, from −10° C. to 200° C., preferably from 0° C. to 100° C.

Those skilled in the art should understand that the above production methods can be modified corresponding to the desired compounds.

The compound (I) of the present invention thus produced can be isolated and purified as a free compound or a salt thereof. Isolation and purification is carried out by a conventional chemical process such as extraction, concentration, evaporation, crystallization, filtration, recrystallization, various kinds of chromatography and the like. When the purified product thus obtained is a racemate, a desired optically active compound can be separated by, for example, fractional recrystallization with optically active acid, or passing through a column packed with optically active carrier. The present invention also encompasses optically active compounds.

The compounds of the present invention obtained by the above methods have a weak inhibitory activity on kinases other than GSK-3β such as CaM kinase II, MAP kinase, Casein kinase, PKA, PKC and ROCK, but have a strong inhibitory activity on GSK-3β. Therefore, the compounds of the present invention have a GSK-3β-selective inhibitory activity and can be medicaments with small side-effect for diabetes, diabetic complications, neurodegenerative diseases (Alzheimer's disease, ischemic cerebrovascular disorders, Down's syndrome, cerebral ischemia due to cerebral amyloid angiopathy, progressive supranuclear paralysis, subacute sclerosing panencephalitic Parkinsonism, postencephalitic Parkinsonism, boxer's encephalopathy, Parkinsonism dementia complex of Guam, Lewy body disease, Pick's disease, corticobasal degeneration, frontotemporal dementia, AIDS encephalopathy, Huntington's disease, manic-depressive psychosis and the like), alopecia, breast cancer, non-small cell lung carcinoma, thyroid cancer, T or B-cell leukemia, and several virus-induced tumors. In addition, the compounds of the present invention are useful as immunopotentiators.

Formulations comprising the compounds of the present invention or salts thereof as an active ingredient are prepared using carriers, excipients and other additives conventionally used for formulation. The carrier and excipient for formulation may be a solid or liquid, and include, for example, lactose, magnesium stearate, starch such as corn starch and the like, talc, gelatin, agar, pectin, gum Arabic, olive oil, sesame oil, cacao butter, ethylene glycol and other conventionally used substances. Administration may be oral administration of tablet, pill, capsule, granule, powder, solution and the like, or parenteral administration by injection (intravenous injection, intramuscular injection and the like), suppository, transdermal agent and the like. While the dose is appropriately determined on each case in consideration of symptom, age and sex of the administration subject, and the like, it is generally 1–1,000 mg, preferably 50–200 mg per day for an adult person, which is orally administered once to several times a day, or 1–500 mg per day for an adult person, which is intravenously administered once to several times a day, or continuously administered intravenously for 1 to 24 hours a day.

As solid compositions for oral administration according to the present invention, tablet, powder, granule and the like are used. In such a solid composition, one or more active substances are mixed with at least one inert diluent, such as lactose, mannitol, glucose, hydroxypropylcellulose, microcrystalline cellulose, starch, polyvinylpyrrolidone, metasilicic acid and magnesium aluminate. The composition may contain, according to a conventional method, inert additives other than diluent, for example, a lubricant such as magnesium stearate, a disintegrator such as cellulose and calcium glycolate, a stabilizer such as lactose and a solubilizer such as glutamic acid and aspartic acid. Tablet and pill may be coated with a gastric or enteric coating film of, for example, sucrose, gelatin, hydroxypropylcellulose and the like. Liquid compositions for oral administration include pharmaceutically acceptable emulsion, solution, suspension, syrup, elixir and the like, and contain an inert diluent generally used, such as purified water and ethanol. This composition may contain an adjuvant such as wetting agent and suspending agent, a sweetener, a flavor, an aromatic and an antiseptic, in addition to the inert diluent. Injections for parenteral administration contain sterile aqueous or non-aqueous solution, suspension and emulsion. The aqueous solution and suspension include, for example, propylene glycol, polyethylene glycol, vegetable oil such as olive oil, alcohols such as ethanol, polysorbate 80 and the like. Such a composition may contain adjuvants such as antiseptic, wetting agent, emulsifier, dispersant, stabilizer and solubilizer. These are sterilized by, for example, filtration through a bacteria-retaining filter, addition of an antimicrobial agent, irradiation of ultraviolet ray and the like. Alternatively, a sterile solid composition may be prepared and used upon dissolution in sterile water or sterile solvent for injection prior to use.

EXAMPLE

The present invention is described in detail in the following, based on Examples, Formulation Examples and Experimental Examples. The scope of the present invention is not limited to these examples.

Example 1

Ethyl 4-(2-chlorophenyl)-4,7-dihydro-6-methyl-2H-pyrazolo[3,4-b]pyridine-5-carboxylate A solution of 2-chlorobenzaldehyde (1.7 g), 3-aminopyrazole (1.0 g) and ethyl acetoacetate (1.6 g) in acetonitrile (20 mL) was heated under reflux overnight. The reaction mixture was cooled to room temperature and the solvent was evaporated under reduced pressure to give an oil. The oil was purified by silica gel column chromatography (eluent:hexane-ethyl acetate (8:2)) to give the title compound (850 mg) as colorless crystals.

Melting Point (MP): 217–221° C.

Anal. Calcd. for: $C_{16}H_{16}N_3O_2Cl$: C, 60.47; H, 5.08; N, 13.22. Found: C, 60.15; H, 5.07; N, 13.53.

MS (EI): 317(M+).

$^1$H-NMR (400 MHz, DMSO-$d_6$) δ (ppm): 1.00 (3H, t, J=6.8 Hz), 2.25 (3H, s), 3.72–3.82 (2H, m), 5.57 (1H, s), 7.07–7.12 (2H, m), 7.18 (1H, d, J=7.3 Hz), 7.26 (1H, s), 7.34 (1H, d, J=7.9 Hz), 9.53 (1H, br.s), 11.98 (1H, br.s).

IR (KBr): ν=3393, 3267, 1670, 1589, 1518, 1278, 1217 cm$^{-1}$.

Example 2

Ethyl 4,7-dihydro-4-(2-methoxyphenyl)-6-methyl-2H-pyrazolo[3,4-b]pyridine-5-carboxylate The title compound was prepared from 2-methoxybenzaldehyde, 3-aminopyrazole and ethyl acetoacetate in the same manner as in Example 1.

MP: 196–200° C.

Anal. Calcd. for: $C_{17}H_{19}N_3O1/5H_2O$: C, 64.42; H, 6.17; N, 13.26. Found: C, 64.08; H, 6.05; N, 13.68.

MS (EI): 313 (M$^+$).

$^1$H-NMR (400 MHz, DMSO-$d_6$) δ (ppm): 1.00 (3H, t, J=6.8 Hz), 2.81 (3H, s), 3.72 (3H, s), 3.87 (2H, q, J=6.8 Hz), 5.54 (1H, s), 6.80 (1H, dd, J=7.3 Hz and 7.4 Hz), 6.90 (1H, d, J=7.8 Hz), 7.04 (1H, d, J=7.4 Hz), 7.13–7.15 (2H, m), 9.99 (1H, br.s), 11.98 (1H, br.s).

IR (KBr): ν=3362, 3267, 3204, 3090, 1662, 1589, 1516, 1275, 1097 cm$^{-1}$.

Example 3

Ethyl 4,7-dihydro-6-methyl-4-(2-trifluoromethylphenyl)-2H-pyrazolo[3,4-b]pyridine-5-carboxylate The title compound was prepared from 2-trifluoromethylbenzaldehyde, 3-aminopyrazole and ethyl acetoacetate in the same manner as in Example 1.

MP: 259–262° C.

Anal. Calcd. for: $C_{17}H_{16}F_3N_3O_21/5H_2O$: C, 57.53; H, 4.66; N, 11.84. Found: C, 57.56; H, 4.68; N, 11.86.

MS (EI): 352 (M$^+$+1).

$^1$H-NMR (400 MHz, DMSO-$d_6$) δ (ppm): 0.74 (3H, t, J=6.9 Hz), 2.40 (3H, s), 3.68–3.81 (2H, m), 5.42 (1H, s), 7.00 (1H, s), 7.28 (1H, dd, J=7.3 Hz and 7.4 Hz), 7.33 (1H, d, J=7.2 Hz), 7.51 (1H, dd, J=7.3 Hz and 7.4 Hz), 7.60 (1H, d, J=7.8 Hz), 9.58 (1H, br.s), 12.00 (1H, br.s).

IR (KBr): ν=3277, 3209, 3094, 1668, 1593, 1514, 1313, 1213, 1153, 1097, 765 cm$^{-1}$.

Example 4

Methyl 4-(2-chlorophenyl)-4,7-dihydro-6-methyl-2H-pyrazolo[3,4-b]pyridine-5-carboxylate The title compound was prepared from 2-chlorobenzaldehyde, 3-aminopyrazole and methyl acetoacetate in the same manner as in Example 1.

MP: 235° C.

Anal. Calcd. for: $C_{15}H_{14}ClN_3O_2 \cdot 2/5H_2O$: C, 57.94; H, 4.80; N, 13.51. Found: C, 58.03; H, 4.55; N, 13.43.

MS (EI): 303 (M$^+$).

$^1$H-NMR (400 MHz, DMSO-d$_6$) δ (ppm): 2.40 (3H, s), 3.34 (3H, s), 5.55 (1H, s), 7.09–7.11 (2H, m), 7.18 (1H, dd, J=7.3 Hz and 7.4 Hz), 7.29 (1H, s), 7.34 (1H, d, J=7.3 Hz), 9.57 (1H, br.s), 12.00 (1H, br.s).

Example 5 t-Butyl 4-(2-chlorophenyl)-4,7-dihydro-6-methyl-2H-pyrazolo[3,4-b]pyridine-5-carboxylate The title compound was prepared from 2-chlorobenzaldehyde, 3-aminopyrazole and t-butyl acetoacetate in the same manner as in Example 1.

MP: 207° C.

Anal. Calcd. for: $C_{18}H_{20}ClN_3O_2$: C, 62.52; H, 5.83; N, 12.15. Found: C, 62.51; H, 5.79; N, 12.17.

MS (EI): 345 (M$^+$).

$^1$H-NMR (400 MHz, DMSO-d$_6$) δ (ppm): 1.07 (9H, s), 2.36 (3H, s), 5.50 (1H, s), 7.11–7.15 (2H, m), 7.20 (1H, d, J=7.3 Hz), 7.25 (1H, s), 7.37 (1H, d, J=7.3 Hz), 9.35 (1H, br.s), 11.93 (1H, br.s).

Example 6

Isopropyl 4-(2-fluorophenyl)-4,7-dihydro-6-methyl-2H-pyrazolo[3,4-b]pyridine-5-carboxylate The title compound was prepared from 2-fluorobenzaldehyde, 3-aminopyrazole and isopropyl acetoacetate in the same manner as in Example 1.

MP: 218–220° C.

$^1$H-NMR (400 MHz, DMSO-d$_6$) δ (ppm): 0.66 (3H, d, J=6.3 Hz), 1.02 (3H, d, J=6.3 Hz), 2.37 (3H, s), 4.66 (1H, q, J=6.3 Hz), 5.40 (1H, s), 7.01–7.14 (4H, m), 7.19 (1H, s), 9.46 (1H, br.s), 11.97 (1H, br.s).

Example 7

Benzyl 4-(2-chlorophenyl)-4,7-dihydro-6-methyl-2H-pyrazolo[3,4-b]pyridine-5-carboxylate The title compound was prepared from 2-chlorobenzaldehyde, 3-aminopyrazole and benzyl acetoacetate in the same manner as in Example 1.

MP: 234° C.

Anal. Calcd. for: $C_{21}H_{18}ClN_3O_2$: C, 66.40; H, 4.78; N, 11.06. Found: C, 66.16; H, 4.86; N, 10.92.

MS (EI): 379 (M$^+$).

$^1$H-NMR (400 MHz, DMSO-d$_6$) δ (ppm): 2.43 (3H, s), 4.81 (1H, d, J=12.6 Hz), 4.92 (1H, d, J=12.6 Hz), 5.62 (1H, s), 6.86–6.88 (2H, m), 7.13–7.18 (6H, m), 7.31–7.34 (2H, m), 9.65 (1H, br.s), 12.01 (1H, br.s).

Example 8

4-(2-Chlorophenyl)-5-dimethylaminocarbonyl-4,7-dihydro-6-methyl-2H-pyrazolo[3,4-b]pyridine The title compound was prepared from 2-chlorobenzaldehyde, 3-aminopyrazole and N,N-dimethylacetamide in the same manner as in Example 1.

MP: 229° C.

Anal. Calcd. for: $C_{16}H_{17}ClN_4O \cdot 1/2H_2O$: C, 58.99; H, 5.57; N, 17.20. Found: C, 58.90; H, 5.46; N, 16.84.

MS (EI): 316 (M$^+$).

$^1$H-NMR (400 MHz, DMSO-d$_6$) δ (ppm): 1.77 (3H, s), 2.72 (6H, s), 5.39 (1H, s), 7.10–7.22 (4H, m), 7.30 (1H, d, J=7.3 Hz), 8.40 (1H, br.s), 11.83 (1H, br.s).

Example 9

4-(2-Chlorophenyl)-5-hydrazinocarbonyl-4,7-dihydro-6-methyl-2H-pyrazolo[3,4-b]pyridine To a solution of 4-(2-chlorophenyl)-4,7-dihydro-5-dimethylaminocarbonyl-6-methyl-2H-pyrazolo[3,4-b]pyridine (200 mg) in acetonitrile (200 mL) was added hydrazine (200 mg) and the mixture was heated under reflux overnight. The reaction mixture was cooled to room temperature, and the precipitated crystals were collected by filtration and washed with ethyl acetate to give the title compound as colorless crystals (150 mg).

MP: 220° C.

Anal. Calcd. for: $C_{14}H_{14}ClN_5O \cdot 3/10H_2O$: C, 54.39; H, 4.76; N, 22.65. Found: C, 54.36; H, 4.56; N, 22.65.

MS (EI): 303 (M$^+$).

$^1$H-NMR (400 MHz, DMSO-d$_6$) δ (ppm): 1.85 (3H, s), 3.20–3.80 (3H, br.s), 5.15 (1H, s), 6.81 (1H, s), 7.16–7.028 (3H, m), 7.34 (1H, d, J=7.3 Hz), 10.05–11.07 (2H, brs).

Example 10

4-(2-Fluorophenyl)-4,7-dihydro-6-methyl-5-isopropylthiocarbonyl-2H-pyrazolo[3,4-b]pyridine The title compound was prepared from 2-fluorobenzaldehyde, 3-aminopyrazole and acetoacetic acid isopropyl thioester in the same manner as in Example 1.

MP: 192–194° C.

$^1$H-NMR (400 MHz, DMSO-d$_6$) δ (ppm): 1.03 (3H, d, J=6.9 Hz), 1.15 (3H, d, J=6.9 Hz), 2.43 (3H, s), 3.35 (1H, q, J=6.9 Hz), 5.55 (1H, s), 7.04–7.15 (4H, m), 7.33 (1H, s), 9.81 (1H, br.s), 12.11 (1H, br.s).

Example 11

4,7-Dihydro-6-methyl-5-nitro-4-(2-trifluoromethylphenyl)-2H-pyrazolo[3,4-b]pyridine The title compound was prepared from 2-trifluoromethylbenzaldehyde, 3-aminopyrazole and 1-nitropropan-2-one in the same manner as in Example 1.

MP: 257–258° C.

$^1$H-NMR (400 MHz, DMSO-d$_6$) δ (ppm): 2.65 (3H, s), 5.75 (1H, s), 7.19 (1H, s), 7.30–7.35 (2H, m), 7.51 (1H, dd, J=7.3 Hz and 7.8 Hz), 7.66 (1H, d, J=7.8 Hz), 10.87 (1H, br.s), 12.45 (1H, br.s).

Example 12

Ethyl 4,7-dihydro-4-phenyl-6-trifluoromethyl-2H-pyrazolo[3,4-b]pyridine-5-carboxylate The title compound was prepared from benzaldehyde, 3-aminopyrazole and ethyl trifluoroacetoacetate in the same manner as in Example 1.

MP: 110–115° C.

Anal. Calcd. for: $C_{16}H_{14}N_3O_2F_3 \cdot 1/2H_2O$: C, 55.49; H, 4.37; N, 12.13. Found: C, 55.84; H, 4.70; N, 11.89.

MS (EI): 337 (M$^+$).

¹H-NMR (400 MHz, DMSO-$d_6$) δ (ppm): 0.84 (3H, t, J=6.9 Hz), 3.90 (2H, q, J=6.8 Hz), 5.54 (1H, s), 7.13–7.17 (3H, m), 7.24–7.28 (3H, m), 9.78 (1H, br.s), 12.20 (1H, br.s).
IR (KBr): ν=3375, 3175, 3067, 1707, 1606, 1533, 1278, 1206, 1197, 1167 cm$^{-1}$.

Example 13

Ethyl 4-(2-fluorophenyl)-4,7-dihydro-6-trifluoromethyl-2H-pyrazolo[3,4-b]pyridine-5-carboxylate The title compound was prepared from 2-fluorobenzaldehyde, 3-aminopyrazole and ethyl trifluoroacetoacetate in the same manner as in Example 1.
MP: 119–120° C.
Anal. Calcd. for: $C_{16}H_{13}F_4N_3O_2$: C, 54.09; H, 3.69; N, 11.84. Found: C, 53.84; H, 3.57; N, 11.79.
MS (EI): 356 (M$^+$+1).
¹H-NMR (400 MHz, DMSO-$d_6$) δ (ppm): 0.94 (3H, t, J=6.8 Hz), 3.89 (2H, q, J=6.8 Hz), 5.46 (1H, s), 7.11–7.20 (4H, m), 7.28–7.30 (1H, m), 9.92 (1H, br.s), 12.27 (1H, br.s).
IR (KBr): ν=3290, 3178, 3069, 1703, 1608, 1537, 1280, 1232, 1174, 1138, 756 cm$^{-1}$.

Example 14

Ethyl 4-(2-chlorophenyl)-4,7-dihydro-6-trifluoromethyl-2H-pyrazolo[3,4-b]pyridine-5-carboxylate maleate The title compound was prepared from 2-chlorobenzaldehyde, 3-aminopyrazole and ethyl trifluoroacetoacetate in the same manner as in Example 1.
MP: 171–172° C.
MS (EI): 371 (M$^+$).
¹H-NMR (400 MHz, DMSO-$d_6$) δ (ppm): 0.91 (3H, t, J=7.3 Hz), 3.50 (3H, br.s), 3.87 (2H, q, J=6.8 Hz), 5.66 (1H, s), 6.26 (2H, s), 7.15–7.18 (2H, m), 7.27 (1H, d, J=7.8 Hz), 7.30 (1H, s), 7.40 (1H, d, J=7.8 Hz), 9.65 (1H, br.s).
IR (KBr): ν=3297, 2935, 1730, 1624, 1550, 1479, 1186 cm$^{-1}$.

Example 15

Ethyl 4,7-dihydro-4-(2-methoxyphenyl)-6-trifluoromethyl-2H-pyrazolo[3,4-b]pyridine-5-carboxylate The title compound was prepared from 2-methoxybenzaldehyde, 3-aminopyrazole and ethyl trifluoroacetoacetate in the same manner as in Example 1.
MP: 144–146° C.
Anal. Calcd. for: $C_{17}H_{16}F_3N_3O_3$: C, 55.59; H, 4.39; N, 11.44. Found: C, 55.55; H, 4.38; N, 11.43.
MS (EI): 367 (M$^+$).
¹H-NMR (400 MHz, DMSO-$d_6$) δ (ppm): 0.94 (3H, t, J=6.8 Hz), 3.83 (3H, s), 3.89 (2H, q, J=6.8 Hz), 5.51 (1H, s), 6.84 (1H, dd, J=7.3 Hz and 7.4 Hz), 6.94–6.97 (2H, m), 7.13 (1H, dd, J=7.3 Hz and 7.4 Hz), 7.20 (1H, s), 9.70 (1H, br.s), 12.13 (1H, br.s).
IR (KBr): ν=3431, 3173, 3067, 2993, 2924, 1689, 1610, 1527, 1286, 1226, 1145 cm$^{-1}$.

Example 16

Ethyl 4,7-dihydro-6-trifluoromethyl-4-(2-trifluoromethylphenyl)-2H-pyrazolo[3,4-b]pyridine-5-carboxylate The title compound was prepared from 2-trifluoromethylbenzaldehyde, 3-aminopyrazole and ethyl trifluoroacetoacetate in the same manner as in Example 1.
MP: 182–186° C.
Anal. Calcd. for: $C_{17}H_{13}N_3O_2F_6$: C, 50.38; H, 3.23; N, 10.37. Found: C, 50.21; H, 3.15; N, 10.39.
MS (FAB): 406 (M$^+$+1).
¹-NMR (400 MHz, DMSO-$d_6$) δ (ppm): 0.83 (3H, t, J=6.8 Hz), 3.83 (2H, q, J=6.8 Hz), 5.49 (1H, s), 7.08 (1H, s), 7.35–7.39 (2H, m), 7.62 (1H, dd, J=7.3 Hz and 7.4 Hz), 7.66 (1H, d, J=7.8 Hz), 9.97 (1H, br.s), 12.30 (1H, br.s).
IR (KBr): ν=3339, 3177, 3067, 1711, 1608, 1537, 1313, 1280, 1182, 1141 cm$^{-1}$.

Example 17

Ethyl 4-(3-chlorophenyl)-4,7-dihydro-6-trifluoromethyl-2H-pyrazolo[3,4-b]pyridine-5-carboxylate The title compound was prepared from 3-chlorobenzaldehyde, 3-aminopyrazole and ethyl trifluoroacetoacetate in the same manner as in Example 1.
MP: 144–145° C.
Anal. Calcd. for: $C_{16}H_{13}N_3O_2F_3Cl$: C, 51.69; H, 3.52; N, 11.30. Found: C, 51.33; H, 3.74; N, 11.10.
MS (EI): 371 (M$^+$).
¹H-NMR (400 MHz, DMSO-$d_6$) δ (ppm): 0.98 (3H, t, J=6.8 Hz), 3.92 (2H, q, J=6.8 Hz), 5.21 (1H, s), 7.11 (1H, d, J=7.8 Hz), 7.17 (1H, s), 7.23 (1H, d, J=8.7 Hz), 7.29–7.33 (2H, m), 9.92 (1H, br.s), 12.30 (1H, br.s).
IR (KBr): ν=3321, 3178, 3070, 1703, 1610, 1535, 1278, 1224, 1184, 1145 cm$^{-1}$.

Example 18

Ethyl 4-(4-chlorophenyl)-4,7-dihydro-6-trifluoromethyl-2H-pyrazolo[3,4-b]pyridine-5-carboxylate The title compound was prepared from 4-chlorobenzaldehyde, 3-aminopyrazole and ethyl trifluoroacetoacetate in the same manner as in Example 1.
MP: 176–178° C.
Anal. Calcd. for: $C_{16}H_{13}F_3N_3O_2Cl$: C, 51.69; H, 3.52; N, 11.30. Found: C, 51.91; H, 3.77; N, 11.08.
MS (EI): 371 (M$^+$).
¹H-NMR (400 MHZ, DMSO-$d_6$) δ (ppm): 0.98 (3H, t, J=6.8 Hz), 3.90 (2H, q, J=7.3 Hz), 5.92 (1H, s), 7.16 (2H, d, J=8.2 Hz), 7.27 (1H, s), 7.31 (2H, d, J=8.2 Hz), 9.87 (1H, br.s), 12.27 (1H, br.s).
IR (KBr): ν=3476, 3368, 3178, 3078, 1714, 1695, 1606, 1537, 1278, 1172, 1134 cm$^{-1}$.

Example 19

Ethyl 4,7-dihydro-4-(4-methoxyphenyl)-6-trifluoromethyl-2H-pyrazolo[3,4-b]pyridine-5-carboxylate The title compound was prepared from 4-methoxybenzaldehyde, 3-aminopyrazole and ethyl trifluoroacetoacetate in the same manner as in Example 1.
MP: 159–161° C.
Anal. Calcd. for: $C_{17}H_{16}FN_3O_3$: C, 55.59; H, 4.39; N, 11.44. Found: C, 55.49; H, 4.54; N, 11.33.
MS (EI): 367 (M$^+$).
¹H-NMR (400 MHz, DMSO-$d_6$) δ (ppm): 0.99 (3H, t, J=7.3 Hz), 3.68 (3H, s), 3.89 (2H, q, J=7.3 Hz), 5.12 (1H, s), 6.82 (2H, d, J=8.7 Hz), 7.03 (2H, d, J=8.7 Hz), 7.22–7.24 (1H, m), 9.71 (1H, br.s), 12.19 (1H, br.s).

IR (KBr): ν=3323, 3231, 3173, 3067, 1699, 1610, 1535, 1510, 1302, 1248, 1184, 1145 $cm^{-1}$.

Example 20

Ethyl 4-(4-ethoxycarbonylphenyl)-4,7-dihydro-6-trifluoromethyl-2H-pyrazolo[3,4-b]pyridine-5-carboxylate The title compound was prepared from 4-ethoxycarbonylbenzaldehyde, 3-aminopyrazole and ethyl trifluoroacetoacetate in the same manner as in Example 1.

MP: 157–160° C.

Anal. Calcd. for: $C_{19}H_{18}F_3N_3O_4$: C, 55.75; H, 4.43; N, 10.26. Found: C, 55.68; H, 4.39; N, 10.43.

MS (FAB): 410 ($M^++1$).

$^1$H-NMR (400 MHz, DMSO-$d_6$) δ (ppm): 0.96 (3H, t, J=6.9 Hz), 1.28 (3H, t, J=7.3 Hz), 3.89 (2H, q, J=6.8 Hz), 4.27 (2H, q, J=7.3 Hz), 5.28 (1H, s), 7.27 (1H, s), 7.29 (2H, d, J=8.3 Hz), 7.87 (2H, d, J=8.2 Hz), 9.92 (1H, br.s), 12.28 (1H, br.s).

IR (KBr): ν=3393, 3188, 3082, 1692, 1612, 1539, 1284 $cm^{-1}$.

Example 21

Ethyl 4-(2-chlorophenyl)-4,7-dihydro-3-methyl-6-trifluoromethyl-2H-pyrazolo[3,4-b]pyridine-5-carboxylate The title compound was prepared from 2-chlorobenzaldehyde, 3-amino-5-methylpyrazole and ethyl trifluoroacetoacetate in the same manner as in Example 1.

MP: 165–168° C.

MS (EI): 385 ($M^+$).

$^1$H-NMR (400 MHz, DMSO-$d_6$) δ (ppm): 0.94 (3H, t, J=7.3 Hz), 1.81 (3H, s), 3.85 (2H, q, J=6.8 Hz), 5.54 (1H, s), 7.17–7.20 (2H, m), 7.27 (1H, dd, J=7.3 Hz and 7.4 Hz), 7.36 (1H, d, J=8.3 Hz), 9.79 (1H, br.s), 11.96 (1H, br.s).

IR (KBr): ν=3263, 3194, 3080, 1668, 1591, 1520, 1286, 1232, 1149, 1095, 1062 $cm^{-1}$.

Example 22

Ethyl 4,7-dihydro-4-(thiophen-2-yl)-6-trifluoromethyl-2H-pyrazolo[3,4-b]pyridine-5-carboxylate The title compound was prepared from thiophene-2-aldehyde, 3-aminopyrazole and ethyl trifluoroacetoacetate in the same manner as in Example 1.

MP: 157–161° C.

Anal. Calcd. for: $C_{14}H_{12}F_3N_3O_2S$: C, 49.27; H, 2.95; N, 12.31. Found: C, 49.10; H, 3.28; N, 12.13.

MS (EI): 343 ($M^+$).

$^1$H-NMR (400 MHz, DMSO-$d_6$) δ (ppm): 1.08 (3H, t, J=7.4 Hz), 4.00 (2H, q, J=7.4 Hz), 5.52 (1H, s), 6.76 (1H, d, J=2.9 Hz), 6.87 (1H, dd, J=2.9 Hz and 5.4 Hz), 7.30 (1H, d, J=5.4 Hz), 7.43 (1H, s), 9.96 (1H, br.s), 12.35 (1H, br.s).

IR (KBr): δ=3350, 3240, 3180, 1693, 1612, 1535, 1396, 1371, 1304, 1153, 1093, 1057, 694 $cm^{-1}$.

Example 23

Ethyl 4,7-dihydro-4-(thiophen-3-yl)-6-trifluoromethyl-2H-pyrazolo[3,4-b]pyridine-5-carboxylate The title compound was prepared from thiophene-3-aldehyde, 3-aminopyrazole and ethyl trifluoroacetoacetate in the same manner as in Example 1.

MP: 140–145° C.

Anal. Calcd. for: $Cl_4H_{12}F_3N_3O_2S$: C, 49.27; H, 2.95; N, 12.31. Found: C, 49.65; H, 2.64; N, 12.19.

MS (EI): 343 ($M^+$).

$^1$H-NMR (400 MHz, DMSO-$d_6$) δ (ppm): 1.03 (3H, t, J=7.3 Hz), 3.96 (2H, q, J=7.3 Hz), 5.30 (1H, s), 6.87 (1H, d, J=4.8 Hz), 7.05 (1H, s), 7.35 (1H, s), 7.39 (1H, dd, J=2.9 Hz and 4.8 Hz), 9.76 (1H, br.s), 12.25 (1H, br.s).

IR (KBr): ν=3356, 3182, 2982, 2932, 1689, 1614, 1537, 1304, 1224, 1153 $cm^{-1}$.

Example 24

Ethyl 4,7-dihydro-4-(1-naphthyl)-6-trifluoromethyl-2H-pyrazolo[3,4-b]pyridine-5-carboxylate The title compound was prepared from naphthalene-1-aldehyde, 3-aminopyrazole and ethyl trifluoroacetoacetate in the same manner as in Example 1.

MP: 119–120° C.

Anal. Calcd. for: $C_{20}H_{16}F_3N_3O_2 \cdot 1/2H_2O$: C, 60.45; H, 4.57; N, 10.57. Found: C, 60.20; H, 4.77; N, 10.39.

MS (FAB): 388 ($M^++1$).

$^1$H-NMR (400 MHz, DMSO-$d_6$) δ (ppm): 0.69 (3H, t, J=6.8 Hz), 3.73 (2H, q, J=6.8 Hz), 6.04 (1H, s), 7.09 (1H, s), 7.26 (1H, d, J=6.8 Hz), 7.41 (1H, dd, J=7.3 Hz and 7.4 Hz), 7.52–7.58 (2H, m), 7.75 (1H, d, J=8.3 Hz), 7.92 (1H, dd, J=7.3 Hz and 7.4 Hz), 8.33 (1H, s), 9.87 (1H, br.s), 12.14 (1H, br.s).

IR (KBr): ν=3173, 1670, 1606, 1138, 1095 $cm^{-1}$.

Example 25

Ethyl 4,7-dihydro-4-phenyl-6-propyl-2H-pyrazolo[3,4-b]pyridine-5-carboxylate maleate A solution of benzaldehyde (1.6 g), 3-aminopyrazole (1.0 g) and ethyl 3-ketohexanoate (1.9 g) in acetonitrile (20 mL) was heated under reflux overnight. The reaction mixture was cooled to room temperature, and the solvent was evaporated under reduced pressure to give an oil. The oil was purified by silica gel column chromatography (eluent:hexane-ethyl acetate (8:2)) to give the title compound (720 mg) as colorless crystals.

MP: 139–141° C.

Anal. Calcd. for: $C_{18}H_{21}N_3O_2 \cdot C_4H_4O_4 \cdot 1/2H_2O$: C, 60.54; H, 6.00; N, 9.63. Found: C, 60.16; H, 5.60; N, 10.01.

MS (EI): 311 ($M^+$).

$^1$H-NMR (400 MHz, DMSO-$d_6$) δ (ppm): 0.94–0.95 (6H, m), 1.62 (2H, q, J=7.8 Hz), 2.66–2.77 (2H, m), 3.50 (3H, br.s), 3.83 (2H, q, J=6.8 Hz), 5.10 (1H, s), 6.25 (2H, s), 7.05–7.20 (6H, m), 9.37 (1H, br.s).

IR (KBr): ν=3337, 3042, 1699, 1593, 1467, 1539, 1361, 1203 $cm^{-1}$

Example 26

Ethyl 4-(2-fluorophenyl)-4,7-dihydro-6-propyl-2H-pyrazolo[3,4-b]pyridine-5-carboxylate The title compound was prepared from 2-fluorobenzaldehyde, 3-aminopyrazole and ethyl 3-ketohexanoate in the same manner as in Example 25.

MP: 192–194° C.

Anal. Calcd. for: $C_{18}H_{20}FN_3O_2 \cdot 1/2H_2O$: C, 63.89; H, 6.26; N, 12.42. Found: C, 63.85; H, 6.01; N, 12.36.

MS (EI): 329 ($M^+$).

¹H-NMR (400 MHz, DMSO-d₆) δ (ppm): 0.93 (3H, t, J=7.3 Hz), 0.97 (3H, t, J=7.3 Hz), 1.62–1.68 (2H, m), 2.71–2.83 (2H, m), 3.82 (2H, q, J=7.3 Hz), 5.43 (1H, s), 7.05–7.11 (4H, m), 7.21 (1H, s), 9.48 (1H, br.s), 11.97 (1H, br.s).

IR (KBr): ν=3265, 3198, 2964, 1591, 1514, 1224, 1209, 1093 cm⁻¹.

Example 27

Ethyl 4-(2-chlorophenyl)-4,7-dihydro-6-propyl-2H-pyrazolo[3,4-b]pyridine-5-carboxylate The title compound was prepared from 2-chlorobenzaldehyde, 3-aminopyrazole and ethyl 3-ketohexanoate in the same manner as in Example 25.

MP: 202–205° C.

Anal. Calcd. for: $C_{18}H_{20}ClN_3O_2$: C, 62.52; H, 5.83; N, 12.15. Found: C, 62.28; H, 5.76; N, 12.37.

MS (FAB): 346 (M⁺+1).

¹H-NMR (400 MHz, DMSO-d₆) δ (ppm): 0.85 (3H, t, J=6.8 Hz), 0.95 (3H, t, J=7.3 Hz), 1.62–1.68 (2H, m), 2.67–2.87 (2H, m), 3.78 (2H, q, J=6.8 Hz), 5.58 (1H, s), 7.07–7.11 (2H, m), 7.18 (1H, dd, J=7.3 Hz and 7.4 Hz), 7.25 (1H, s), 7.34 (1H, d, J=7.8 Hz), 9.49 (1H, br.s), 11.97 (1H, br.s).

IR (KBr): ν=3263, 3209, 3194, 3080, 1668, 1591, 1520, 1286, 1232, 1149, 1062, 750 cm⁻¹.

Example 28

Methyl 4-(2-chlorophenyl)-4,7-dihydro-6-propyl-2H-pyrazolo[3,4-b]pyridine-5-carboxylate The title compound was prepared from 2-chlorobenzaldehyde, 3-aminopyrazole and methyl 3-ketohexanoate in the same manner as in Example 25.

MP: 203–207° C.

Anal. Calcd. for: $C_{17}H_{18}ClN_3O_2 \cdot 1/5H_2O$: C, 60.88; H, 5.53; N, 12.53. Found: C, 60.73; H, 5.36; N, 12.14.

MS (EI): 331 (M⁺).

¹H-NMR (400 MHz, DMSO-d₆) δ (ppm): 0.97 (3H, t, J=7.3 Hz), 1.64–1.66 (2H, m), 2.72–2.83 (2H, m), 3.31 (3H, s), 5.57 (1H, s), 7.10 (1H, d, J=7.3 Hz), 7.09–7.11 (1H, m), 7.17–7.18 (1H, m), 7.27 (1H, s), 7.34 (1H, d, J=7.8 Hz), 9.54 (1H, br.s), 11.97 (1H, br.s).

IR (KBr): ν=3260, 3190, 1672, 1591, 1516, 1232 cm⁻¹.

Example 29

Ethyl 4-(2-bromophenyl)-4,7-dihydro-6-propyl-2H-pyrazolo[3,4-b]pyridine-5-carboxylate The title compound was prepared from 2-bromobenzaldehyde, 3-aminopyrazole and ethyl 3-ketohexanoate in the same manner as in Example 25.

MP: 223° C.

Anal. Calcd. for: $C_{18}H_{20}BrN_3O_2$: C, 55.40; H, 5.17; N, 10.77. Found: C, 55.08; H, 5.14; N, 10.85.

MS (EI): 390 (M⁺).

¹H-NMR (400 MHz, DMSO-d₆) δ (ppm): 0.86 (3H, t, J=7.3 Hz), 0.97 (3H, t, J=7.3 Hz), 1.63–1.69 (2H, m), 2.71–2.74 (1H, m), 2.80–2.83 (1H, m), 3.77 (2H, q, J=7.3 Hz), 5.67 (1H, s), 7.00 (1H, dd, J=7.3 Hz and 7.4 Hz), 7.10 (1H, d, J=7.3 Hz), 7.22 (1H, dd, J=7.3 Hz and 7.4 Hz), 7.28 (1H, s), 7.51 (1H, d, J=7.3 Hz), 9.50 (1H, br.s), 11.97 (1H, br.s).

Example 30

Ethyl 4,7-dihydro-4-(2-methylphenyl)-6-propyl-2H-pyrazolo[3,4-b]pyridine-5-carboxylate The title compound was prepared from 2-methylbenzaldehyde, 3-aminopyrazole and ethyl 3-ketohexanoate in the same manner as in Example 25.

MP: 178° C.

Anal. Calcd. for: $C_{19}H_{23}N_3O_2$: C, 70.13; H, 7.12; N, 12.91. Found: C, 70.12; H, 7.35; N, 12.99.

MS (EI): 325 (M⁺).

¹H-NMR (400 MHz, DMSO-d₆) δ (ppm): 0.83 (3H, t, J=7.3 Hz), 0.96 (3H, t, J=7.3 Hz), 1.62–1.66 (2H, m), 2.44 (3H, s), 2.64–2.66 (1H, m), 2.76–2.79 (1H, m), 3.77 (2H, q, J=7.3 Hz), 5.31 (1H, s), 6.93 (1H, d, J=7.3 Hz), 6.99–7.05 (3H, m), 7.18 (1H, s), 9.34 (1H, br.s), 11.87 (1H, br.s).

Example 31

Ethyl 4,7-dihydro-6-propyl-4-(2-trifluoromethylphenyl)-2H-pyrazolo[3,4-b]pyridine-5-carboxylate The title compound was prepared from 2-trifluoromethylbenzaldehyde, 3-aminopyrazole and ethyl 3-ketohexanoate in the same manner as in Example 25.

MP: 198–202° C.

Anal. Calcd. for: $C_{19}H_{20}F_3N_3O_2 \cdot 1/2H_2O$: C, 58.76; H, 5.45; N, 10.81. Found: C, 58.82; H, 5.92; N, 10.62.

MS (EI): 379 (M⁺).

¹H-NMR (400 MHz, DMSO-d₆) δ (ppm): 0.76 (3H, t, J=7.3 Hz), 0.98 (3H, t, J=7.3 Hz), 1.64–1.68 (2H, m), 2.76–2.79 (2H, m), 3.80 (2H, q, J=7.3 Hz), 5.44 (1H, s), 7.00 (1H, s), 7.27–7.30 (1H, m), 7.33 (1H, d, J=7.8 Hz), 7.53 (1H, dd, J=7.3 Hz and 7.4 Hz), 7.61 (1H, d, J=7.3 Hz), 9.54 (1H, br.s), 11.99 (1H, br.s).

IR (KBr): ν=3265, 3198, 2964, 1591, 1514, 1224, 1209, 1093 cm⁻¹.

Example 32

Ethyl 4,7-dihydro-4-(2-methoxyphenyl)-6-propyl-2H-pyrazolo[3,4-b]pyridine-5-carboxylate The title compound was prepared from 2-methoxybenzaldehyde, 3-aminopyrazole and ethyl 3-ketohexanoate in the same manner as in Example 25.

MP: 169° C.

Anal. Calcd. for: $C_{19}H_{23}N_3O_3$: C, 66.84; H, 6.79; N, 12.31. Found: C, 66.58; H, 6.50; N, 12.34.

MS (EI): 341 (M⁺).

¹H-NMR (400 MHz, DMSO-d₆) δ (ppm): 0.85 (3H, t, J=7.3 Hz), 0.97 (3H, t, J=7.3 Hz), 1.66–1.68 (2H, m), 2.66–2.70 (1H, m), 2.81–2.88 (1H, m), 3.80 (2H, q, J=7.3 Hz), 3.85 (3H, s), 5.47 (1H, s), 6.76 (1H, dd, J=7.3 Hz and 7.4 Hz), 6.89–6.94 (2H, m), 7.04 (1H, dd, J=7.3 Hz and 7.4 Hz), 7.14 (1H, s), 9.29 (1H, br.s), 11.82 (1H, br.s).

Example 33

Ethyl 4-(2-ethoxyphenyl)-4,7-dihydro-6-propyl-2H-pyrazolo[3,4-b]pyridine-5-carboxylate The title compound was prepared from 2-ethoxybenzaldehyde, 3-aminopyrazole and ethyl 3-ketohexanoate in the same manner as in Example 25.

MP: 203° C.

Anal. Calcd. for: $C_{20}H_{25}N_3O_3$: C, 67.58; H, 7.09; N, 11.82. Found: C, 67.48; H, 7.06; N, 11.81.

MS (EI): 355 (M$^+$).

$^1$H-NMR (400 MHz, DMSO-d$_6$) δ (ppm): 0.85 (3H, t, J=7.3 Hz), 0.97 (3H, t, J=7.3 Hz), 1.41 (3H, t, J=7.3 Hz), 1.64–1.67 (2H, m), 2.68–2.71 (1H, m), 2.78–2.81 (1H, m), 3.79 (2H, q, J=7.3 Hz), 4.03–4.05 (1H, m), 4.10–4.12 (1H, m), 5.48 (1H, s), 6.74 (1H, dd, J=7.3 Hz and 7.4 Hz), 6.87 (1H, d, J=7.3 Hz), 6.94 (1H, d, J=7.3 Hz), 7.01 (1H, dd, J=7.3 Hz and 7.4 Hz), 7.14 (1H, s), 9.28 (1H, br.s), 11.79 (1H, br.s).

Example 34

Ethyl 4,7-dihydro-4-(2-propoxyphenyl)-6-propyl-2H-pyrazolo[3,4-b]pyridine-5-carboxylate The title compound was prepared from 2-propoxybenzaldehyde, 3-aminopyrazole and ethyl 3-ketohexanoate in the same manner as in Example 25.

MP: 205° C.

Anal. Calcd. for: $C_{21}H_{27}N_3O_3$: C, 68.27; H, 7.37; N, 11.37. Found: C, 68.05; H, 7.39; N, 11.35.

MS (EI): 369 (M$^+$).

$^1$H-NMR (400 MHz, DMSO-d$_6$) δ (ppm): 0.84 (3H, t, J=7.3 Hz), 0.97 (3H, t, J=7.3 Hz), 1.05 (3H, t, J=7.3 Hz), 1.64–1.67 (2H, m), 1.81–1.84 (2H, m), 2.70–2.73 (1H, m), 2.78–2.82 (1H, m), 3.77 (2H, q, J=7.3 Hz), 3.92 (1H, q, J=7.3 Hz), 4.07 (1H, q, J=7.3 Hz), 5.52 (1H, s), 6.75 (1H, dd, J=7.3 Hz and 7.4 Hz), 6.88 (1H, d, J=7.3 Hz), 6.94 (1H, d, J=7.3 Hz), 7.01 (1H, dd, J=7.3 Hz and 7.4 Hz), 7.11 (1H, s), 9.28 (1H, br.s), 11.79 (1H, br.s).

Example 35

Ethyl 4,7-dihydro-4-(2-isopropyloxyphenyl)-6-propyl-2H-pyrazolo[3,4-b]pyridine-5-carboxylate The title compound was prepared from 2-isopropyloxybenzaldehyde, 3-aminopyrazole and ethyl 3-ketohexanoate in the same manner as in Example 25.

MP: 210° C.

Anal. Calcd. for: $C_{21}H_{27}N_3O_3$: C, 68.27; H, 7.37; N, 11.37. Found: C, 67.93; H, 7.39; N, 11.32.

MS (EI): 369 (M$^+$).

$^1$H-NMR (400 MHz, DMSO-d$_6$) δ (ppm): 0.84 (3H, t, J=7.3 Hz), 0.97 (3H, t, J=7.3 Hz), 1.25 (3H, d, J=6.8 Hz), 1.39 (3H, d, J=6.8 Hz), 1.64–1.69 (2H, m), 2.68–2.72 (1H, m), 2.78–2.82 (1H, m), 3.77 (2H, q, J=7.3 Hz), 4.64–4.67 (1H, m), 5.45 (1H, s), 6.73 (1H, dd, J=7.3 Hz and 7.4 Hz), 6.89–6.90 (3H, m), 7.15 (1H, s), 9.27 (1H, br.s), 11.77 (1H, br.s).

Example 36

Ethyl 4-(2-butoxyphenyl)-4,7-dihydro-6-propyl-2H-pyrazolo[3,4-b]pyridine-5-carboxylate The title compound was prepared from 2-butoxybenzaldehyde, 3-aminopyrazole and ethyl 3-ketohexanoate in the same manner as in Example 25.

MP: 171° C.

Anal. Calcd. for: $C_{22}H_{29}N_3O_3$: C, 68.90; H, 7.62; N, 10.96. Found: C, 68.66; H, 7.63; N, 10.89.

MS (EI): 383 (M$^+$).

$^1$H-NMR (400 MHz, DMSO-d$_6$) δ (ppm): 0.84 (3H, t, J=7.3 Hz), 0.95–0.99 (6H, m), 1.52–1.80 (6H, m), 2.69–2.71 (1H, m), 1.76–1.80 (1H, m), 3.77 (2H, q, J=7.3 Hz), 3.95–3.98 (1H, m), 4.07–4.10 (1H, m), 5.51 (1H, s), 6.74 (1H, dd, J=7.3 Hz and 7.4 Hz), 6.88–6.94 (2H, m), 7.01 (1H, dd, J=7.3 Hz and 7.4 Hz), 7.10 (1H, s), 9.28 (1H, br.s), 11.79 (1H, br.s).

Example 37

Ethyl 4-(2-cyclopentyloxyphenyl)-4,7-dihydro-6-propyl-2H-pyrazolo[3,4-b]pyridine-5-carboxylate The title compound was prepared from 2-cyclopentyloxybenzaldehyde, 3-aminopyrazole and ethyl 3-ketohexanoate in the same manner as in Example 25.

MP: 195° C.

Anal. Calcd. for: $C_{23}H_{29}N_3O_3$: C, 69.85; H, 7.39; N, 10.62. Found: C, 69.63; H, 7.28; N, 10.61.

MS (EI): 395 (M$^+$).

$^1$H-NMR (400 MHz, DMSO-d$_6$) δ (ppm): 0.83 (3H, t, J=7.3 Hz), 0.97 (3H, t, J=7.3 Hz), 1.65–1.98 (8H, m), 2.66–2.78 (2H, m), 3.76 (2H, q, J=7.3 Hz), 4.89–4.93 (1H, m), 5.43 (1H, s), 6.72 (1H, dd, J=7.3 Hz and 7.4 Hz), 6.88–6.93 (2H, m), 7.00 (1H, dd, J=7.3 Hz and 7.4 Hz), 7.10 (1H, s), 9.28 (1H, br.s), 11.77 (1H, br.s)

Example 38

Ethyl 4-(2-benzyloxyphenyl)-4,7-dihydro-6-propyl-2H-pyrazolo[3,4-b]pyridine-5-carboxylate The title compound was prepared from 2-benzyloxybenzaldehyde, 3-aminopyrazole and ethyl 3-ketohexanoate in the same manner as in Example 25.

MP: 128° C.

Anal. Calcd. for: $C_{25}H_{27}N_3O_3$: C, 71.92; H, 6.52; N, 10.06. Found: C, 71.66; H, 6.73; N, 9.85.

MS (EI): 417 (M$^+$).

$^1$H-NMR (400 MHz, DMSO-d$_6$) δ (ppm): 0.84 (3H, t, J=7.3 Hz), 0.97 (3H, t, J=7.3 Hz), 1.64–1.67 (2H, m), 2.70–2.73 (1H, m), 2.80–2.83 (1H, m), 3.80 (2H, q, J=7.3 Hz), 5.20 (2H, d, J=30 Hz), 5.60 (1H, s), 6.78 (1H, dd, J=7.3 Hz and 7.4 Hz), 6.96–7.03 (3H, m), 7.08 (1H, s), 7.35 (1H, dd, J=7.3 Hz and 7.4 Hz), 7.40–7.43 (2H, m), 7.52–7.55 (2H, m), 9.30 (1H, br.s), 11.79 (1H, br.s).

Example 39

Ethyl 4,7-dihydro-4-(2-methylthiophenyl)-6-propyl-2H-pyrazolo[3,4-b]pyridine-5-carboxylate A solution of 2-methylthiobenzaldehyde (20 g), Meldrum's acid (19 g), ethyl 3-ketohexanoate (21 g) and ammonium acetate (11 g) in acetic acid (130 mL) was heated under reflux overnight. The reaction mixture was cooled to room temperature, and the solvent was evaporated under reduced pressure to give colorless crystals (9.7 g). To a solution of dimethylformamide (1.3 g) in chloroform (5 mL) were added phosphorus oxychloride (1.7 mL) and a solution of the obtained colorless crystals (1.5 g) in chloroform (10 mL) under ice-cooling, and the mixture was stirred overnight. Under ice-cooling, an aqueous sodium acetate (18.5 g) solution was added and the mixture was stirred for one hour. The reaction mixture was extracted with chloroform and the solvent was evaporated under reduced pressure to give an oil. The obtained oil was purified by silica gel column chromatography (eluent:hexane-ethyl acetate (8:2))

to give colorless crystals (0.9 g). To a solution of the obtained colorless crystals (0.9 g) in pyridine (10 mL) was added hydrazine (0.27 g) and the mixture was stirred with heating for 3 hours. The reaction mixture was cooled to room temperature, and the solvent was evaporated under reduced pressure to give an oil. The oil was purified by silica gel column chromatography (eluent:hexane-ethyl acetate (1:1)) to give the title compound (230 mg) as colorless crystals.

MP: 198° C.

Anal. Calcd. for: $C_{19}H_{23}N_3O_2S$: C, 63.84; H, 6.49; N, 11.75. Found: C, 63.56; H, 6.45; N, 11.64.

MS (EI): 357 (M$^+$).

$^1$H-NMR (400 MHz, DMSO-d$_6$) δ (ppm): 0.82 (3H, t, J=7.3 Hz), 0.96 (3H, t, J=7.3 Hz), 1.62–1.68 (2H, m), 2.48 (3H, s), 2.67–2.71 (1H, m), 2.79–2.83 (1H, m), 3.74 (2H, q, J=7.3 Hz), 5.54 (1H, s), 6.99–7.06 (3H, m), 7.22–7.25 (2H, m), 9.38 (1H, br.s), 11.86 (1H, br.s).

Example 40

Ethyl 4,7-dihydro-4-(2-methylsulfinylphenyl)-6-propyl-2H-pyrazolo[3,4-b]pyridine-5-carboxylate To a solution of ethyl 4,7-dihydro-4-(2-methylthio)-6-propyl-2H-pyrazolo[3,4-b]pyridine-5-carboxylate (100 mg) in tetrahydrofuran (3.0 mL) was added metachloroperbenzoic acid (60 mg) and the mixture was stirred at −78° C. for 30 minutes. An aqueous sodium thiosulfate solution was added, and the mixture was extracted with chloroform. The solvent was evaporated under reduced pressure to give colorless crystals. By recrystallization from ethyl acetate, the title compound (50 mg) was obtained as colorless crystals.

MP: 216° C.

Anal. Calcd. for: $C_{19}H_{23}N_3O_3S$: C, 61.10; H, 6.21; N, 11.25. Found: C, 61.32; H, 6.18; N, 10.99.

MS (EI): 373 (M$^+$).

$^1$H-NMR (400 MHz, DMSO-d$_6$) δ (ppm): 0.91 (3H, t, J=7.3 Hz), 0.97 (3H, t, J=7.3 Hz), 1.64–1.68 (2H, m), 2.69–2.72 (1H, m), 2.72 (3H, s), 2.76–2.79 (1H, m), 3.90 (2H, q, J=7.3 Hz), 5.36 (1H, s), 7.15 (1H, dd, J=7.3 Hz and 7.4 Hz), 7.20 (1H, s), 7.37–7.39 (2H, m), 7.85 (1H, dd, J=7.3 Hz and 7.4 Hz), 9.59 (1H, br.s), 12.04 (1H, br.s).

Example 41

Ethyl 4,7-dihydro-4-(2-nitrophenyl)-6-propyl-2H-pyrazolo[3,4-b]pyridine-5-carboxylate The title compound was prepared from 2-nitrobenzaldehyde and ethyl 3-ketohexanoate in the same manner as in Example 39.

MP: 218° C.

Anal. Calcd. for: $C_{18}H_{20}N_4O_4$: C, 60.66; H, 5.66; N, 15.72. Found: C, 60.25; H, 5.65; N, 15.44.

MS (EI): 356 (M$^+$).

$^1$H-NMR (400 MHz, DMSO-d$_6$) δ (ppm): 0.80 (3H, t, J=7.3 Hz), 0.95 (3H, t, J=7.3 Hz), 1.59–1.64 (2H, m), 2.69–2.73 (1H, m), 2.77–2.80 (1H, m), 3.72 (2H, q, J=7.3 Hz), 5.45 (1H, s), 7.28–7.33 (3H, m), 7.56 (1H, dd, J=7.3 Hz and 7.4 Hz), 7.76 (1H, d, J=7.3 Hz), 9.64 (1H, br.s), 10.07 (1H, br.s).

Example 42

Ethyl 4-(2-cyanophenyl)-4,7-dihydro-6-propyl-2H-pyrazolo[3,4-b]pyridine-5-carboxylate The title compound was prepared from 2-cyanobenzaldehyde and ethyl 3-ketohexanoate in the same manner as in Example 39.

MP: 211° C.

Anal. Calcd. for: $C_{19}H_{20}N_4O_2$: C, 67.84; H, 5.99; N, 16.66. Found: C, 67.49; H, 6.14; N, 16.23.

MS (EI): 336 (M$^+$).

$^1$H-NMR (400 MHz, DMSO-d$_6$) δ (ppm): 0.89 (3H, t, J=7.3 Hz), 0.94 (3H, t, J=7.3 Hz), 1.61–1.67 (2H, m), 2.71–2.73 (1H, m), 2.79–2.82 (1H, m), 3.80 (2H, q, J=7.3 Hz), 5.48 (1H, s), 7.21–7.29 (2H, m), 7.28 (1H, dd, J=7.3 Hz and 7.4 Hz), 7.55 (1H, dd, J=7.3 Hz and 7.4 Hz), 7.70 (1H, d, J=7.3 Hz), 9.63 (1H, br.s), 12.07 (1H, br.s).

Example 43

Ethyl 4-(2,3-difluorophenyl)-4,7-dihydro-6-propyl-2H-pyrazolo[3,4-b]pyridine-5-carboxylate The title compound was prepared from 2,3-difluorobenzaldehyde, 3-aminopyrazole and ethyl 3-ketohexanoate in the same manner as in Example 25.

MP: 207° C.

Anal. Calcd. for: $C_{18}H_{19}F_2N_3O_2 \cdot 1/5H_2O$: C, 61.60; H, 5.57; N, 11.97. Found: C, 61.41; H, 5.56; N, 11.59.

MS (EI): 347 (M$^+$).

$^1$H-NMR (400 MHz, DMSO-d$_6$) δ (ppm): 0.90–0.97 (6H, m), 1.60–1.66 (2H, m), 2.68–2.71 (1H, m), 2.79–2.82 (1H, m), 3.83 (2H, q, J=7.3 Hz), 5.45 (1H, s), 6.87 (1H, dd, J=7.3 Hz and 7.4 Hz), 7.03–7.13 (2H, m), 7.76 (1H, s), 9.55 (1H, br.s), 12.03 (1H, br.s).

Example 44

Ethyl 4-(2,3-dichlorophenyl)-4,7-dihydro-6-propyl-2H-pyrazolo[3,4-b]pyridine-5-carboxylate The title compound was prepared from 2,3-dichlorobenzaldehyde, 3-aminopyrazole and ethyl 3-ketohexanoate in the same manner as in Example 25.

MP: 220° C.

Anal. Calcd. for: $C_{18}H_{19}Cl_2N_3O_2$: C, 56.85; H, 5.04; N, 11.05. Found: C, 56.35; H, 5.00; N, 11.01.

MS (EI): 380 (M$^+$).

$^1$H-NMR (400 MHz, DMSO-d$_6$) δ (ppm): 0.88 (3H, t, J=7.3 Hz), 0.99 (3H, t, J=7.3 Hz), 1.66–1.69 (2H, m), 2.74–2.77 (1H, m), 2.82–2.86 (1H, m), 3.81 (2H, q, J=7.3 Hz), 5.66 (1H, s), 7.10 (1H, d, J=7.3 Hz), 7.24 (1H, dd, J=7.3 Hz and 7.4 Hz), 7.31 (1H, s), 7.38 (1H, d, J=7.3 Hz), 9.59 (1H, br.s), 12.04 (1H, br.s).

Example 45

Ethyl 4-(3-fluoro-2-methylphenyl)-4,7-dihydro-6-propyl-2H-pyrazolo[3,4-b]pyridine-5-carboxylate The title compound was prepared from 3-fluoro-2-methylbenzaldehyde, 3-aminopyrazole and ethyl 3-ketohexanoate in the same manner as in Example 25.

MP: 159–162° C.

Anal. Calcd. for: $C_{19}H_{22}FN_3O_3 \cdot 3/10H_2O$: C, 65.42; H, 6.53; N, 12.05. Found: C, 65.56; H, 6.29; N, 12.40.

MS (EI): 343 (M$^+$).

$^1$H-NMR (400 MHz, DMSO-d$_6$) δ (ppm): 0.89 (3H, t, J=7.3 Hz), 0.97 (3H, t, J=7.3 Hz), 1.64 (2H, m), 2.36 (3H, s), 2.67–2.84 (2H, m), 3.80 (2H, q, J=7.3 Hz), 5.35 (1H, s), 6.86 (2H, d, J=8.8 Hz), 7.07 (1H, dd, J=7.3 Hz and 7.4 Hz), 7.23 (1H, s), 9.42 (1H, br.s), 11.94 (1H, br.s).

IR (KBr): ν=3265, 3193, 2966, 2934, 1668, 1591, 1520, 1466, 1240 cm$^{-1}$.

Example 46

Ethyl 4-(2,3-dimethoxyphenyl)-4,7-dihydro-6-propyl-2H-pyrazolo[3,4-b]pyridine-5-carboxylate The title compound was prepared from 2,3-dimethoxybenzaldehyde, 3-aminopyrazole and ethyl 3-ketohexanoate in the same manner as in Example 25.

MP: 205–206° C.

Anal. Calcd. for: $C_{20}H_{25}N_3O_4$: C, 64.67; H, 6.78; N, 11.31. Found: C, 64.76; H, 6.81; N, 11.15.

MS (EI): 371 (M$^+$).

$^1$H-NMR (400 MHz, DMSO-d$_6$) δ (ppm): 0.90 (3H, t, J=7.4 Hz), 0.98 (3H, t, J=7.3 Hz), 1.66–1.68 (2H, m), 2.68–2.70 (1H, m), 2.80–2.83 (1H, m), 3.77 (3H, s), 3.80 (3H, s), 3.80–3.85 (2H, m), 5.44 (1H, s), 6.58 (1H, d, J=7.3 Hz), 6.76 (1H, d, J=6.8 Hz), 6.88 (1H, dd, J=7.3 Hz and 7.4 Hz), 7.11 (1H, s), 9.32 (1H, br.s), 11.83 (1H, br.s).

Example 47

Ethyl 4-(2-chloro-3-trifluoromethylphenyl)-4,7-dihydro-6-propyl-2H-pyrazolo[3,4-b]pyridine-5-carboxylate The title compound was prepared from 2-chloro-3-trifluoromethylbenzaldehyde, 3-aminopyrazole and ethyl 3-ketohexanoate in the same manner as in Example 25.

MP: 236–238° C.

Anal. Calcd. for: $C_{19}H_{19}ClF_3N_3O_2$: C, 55.15; H, 4.63; N, 10.15. Found: C, 55.07; H, 4.55; N, 10.13.

MS (EI): 413 (M$^+$).

$^1$H-NMR (400 MHz, DMSO-d$_6$) δ (ppm): 0.82 (3H, t, J=7.3 Hz), 0.97 (3H, t, J=7.3 Hz), 1.65 (2H, m), 2.70–2.90 (2H, m), 3.65–3.85 (2H, m), 5.72 (1H, s), 7.29 (1H, s), 7.41–7.42 (2H, m), 7.59–7.61 (1H, m), 9.62 (1H, br.s), 12.05 (1H, br.s).

Example 48

Ethyl 4-(2-chloro-4-fluorophenyl)-4,7-dihydro-6-propyl-2H-pyrazolo[3,4-b]pyridine-5-carboxylate The title compound was prepared from 2-chloro-4-fluorobenzaldehyde, 3-aminopyrazole and ethyl 3-ketohexanoate in the same manner as in Example 25.

MS (EI): 363 (M$^+$).

$^1$H-NMR (400 MHz, DMSO-d$_6$) δ (ppm): 0.88 (3H, t, J=7.3 Hz), 0.96 (3H, t, J=7.3 Hz), 1.62–1.67 (2H, m), 2.66–2.80 (2H, m), 3.77 (2H, q, J=7.3 Hz), 5.54 (1H, s), 7.08–7.13 (2H, m), 7.25 (1H, s), 7.32 (1H, dd, J=2.5 Hz and 8.8 Hz), 9.53 (1H, br.s), 11.99 (1H, br.s).

Example 49

Ethyl 4-(2,5-difluorophenyl)-4,7-dihydro-6-propyl-2H-pyrazolo[3,4-b]pyridine-5-carboxylate The title compound was prepared from 2,5-difluorobenzaldehyde, 3-aminopyrazole and ethyl 3-ketohexanoate in the same manner as in Example 25.

MP: 168–169° C.

MS (EI): 347 (M$^+$).

$^1$H-NMR (400 MHz, DMSO-d$_6$) δ (ppm): 0.92–0.99 (6H, m), 1.62–1.68 (2H, m), 2.67–2.71 (1H, m), 2.85–2.88 (1H, m), 3.80–3.91 (2H, m), 4.03 (1H, q, J=6.8 Hz), 5.40 (1H, s), 6.77–6.80 (1H, m), 6.98–7.00 (1H, m), 7.12–7.16 (1H, m), 7.26 (1H, s), 9.59 (1H, br.s), 12.06 (1H, br.s).

Example 50

Ethyl 4-(2,5-dichlorophenyl)-4,7-dihydro-6-propyl-2H-pyrazolo[3,4-b]pyridine-5-carboxylate The title compound was prepared from 2,5-dichlorobenzaldehyde, 3-aminopyrazole and ethyl 3-ketohexanoate in the same manner as in Example 25.

MP: 162° C.

Anal. Calcd. for: $C_{18}H_{19}Cl_2N_3O_2 \cdot 1/2H_2O$: C, 55.54; H, 5.18; N, 10.79. Found: C, 55.50; H, 5.50; N, 11.17.

MS (EI): 380 (M$^+$).

$^1$H-NMR (400 MHz, DMSO-d$_6$) δ (ppm): 0.89 (3H, t, J=7.3 Hz), 0.98 (3H, t, J=7.3 Hz), 1.62–1.66 (2H, m), 2.64–2.67 (1H, m), 2.86–2.90 (1H, m), 3.81 (2H, q, J=7.3 Hz), 5.55 (1H, s), 7.04 (1H, s), 7.18 (1H, d, J=7.3 Hz), 7.28 (1H, s), 7.41 (1H, d, J=7.3 Hz), 9.61 (1H, br.s), 12.06 (1H, br.s).

Example 51

Ethyl 4-(5-fluoro-2-methoxyphenyl)-4,7-dihydro-6-propyl-2H-pyrazolo[3,4-b]pyridine-5-carboxylate The title compound was prepared from 5-fluoro-2-methoxybenzaldehyde, 3-aminopyrazole and ethyl 3-ketohexanoate in the same manner as in Example 25.

MP: 164–167° C.

Anal. Calcd. for: $C_{19}H_{22}FN_3O_3$: C, 63.50; H, 6.17; N, 11.69. Found: C, 63.24; H, 6.09; N, 11.70.

MS (EI): 359 (M$^+$).

$^1$H-NMR (400 MHz, DMSO-d$_6$) δ (ppm): 0.87 (3H, t, J=7.3 Hz), 0.98 (3H, t, J=7.3 Hz), 1.64–1.69 (2H, m), 2.62–2.91 (2H, m), 3.79 (2H, q, J=7.3 Hz), 3.85 (3H, s), 5.44 (1H, s), 6.33 (1H, dd, J=3.0 Hz and 7.8 Hz), 6.83–6.91 (2H, m), 7.17 (1H, s), 9.41 (1H, br.s), 11.89 (1H, br.s).

IR (KBr): ν=3252, 2955, 1657, 1510, 1232, 1074 cm$^{-1}$.

Example 52

Ethyl 4-(2-chloro-5-methoxyphenyl)-4,7-dihydro-6-propyl-2H-pyrazolo[3,4-b]pyridine-5-carboxylate The title compound was prepared from 2-chloro-5-methoxybenzaldehyde, 3-aminopyrazole and ethyl 3-ketohexanoate in the same manner as in Example 25.

MP: 182° C.

Anal. Calcd. for: $C_{19}H_{22}ClN_3O_3$: C, 60.72; H, 5.90; N, 11.18. Found: C, 60.58; H, 5.88; N, 11.07.

MS (EI): 375 (M$^+$)

$^1$H-NMR (400 MHz, DMSO-d$_6$) δ (ppm): 0.88 (3H, t, J=7.3 Hz), 0.99 (3H, t, J=7.3 Hz), 1.64–1.69 (2H, m), 2.64–2.67 (1H, m), 2.87–2.90 (1H, m), 3.79 (2H, q, J=7.3 Hz), 3.86 (3H, s), 5.44 (1H, s), 6.85 (1H, d, J=7.3 Hz), 6.94 (1H, d, J=7.3 Hz), 7.10 (1H, dd, J=2.9 Hz and 7.3 Hz), 7.17 (1H, s), 9.43 (1H, br.s), 11.91 (1H, br.s).

Example 53

Ethyl 4-(2,5-dimethoxyphenyl)-4,7-dihydro-6-propyl-2H-pyrazolo[3,4-b]pyridine-5-carboxylate The title compound was prepared from 2,5-dimethoxybenzaldehyde, 3-aminopyrazole and ethyl 3-ketohexanoate in the same manner as in Example 25.

MP: 169–170° C.

MS (EI): 371 (M$^+$).

¹H-NMR (400 MHz, DMSO-d$_6$) δ (ppm): 0.88 (3H, t, J=7.3 Hz), 0.98 (3H, t, J=7.3 Hz), 1.68–1.70 (2H, m), 2.49–2.54 (1H, m), 2.94–2.97 (1H, m), 3.57 (3H, s), 3.79–3.83 (2H, m), 3.80 (3H, s), 4.02 (1H, q, J=7.3 Hz), 5.43 (1H, s), 6.49 (1H, d, J=2.9 Hz), 6.59 (1H, dd, J=2.9 Hz and 8.8 Hz), 6.82 (1H, d, J=8.8 Hz), 7.14 (1H, s), 9.32 (1H, br.s), 11.83 (1H, br.s).

Example 54

Ethyl 4-(2,6-difluorophenyl)-4,7-dihydro-6-propyl-2H-pyrazolo[3,4-b]pyridine-5-carboxylate The title compound was prepared from 2,6-difluorobenzaldehyde, 3-aminopyrazole and ethyl 3-ketohexanoate in the same manner as in Example 25.

MP: 185° C.

Anal. Calcd. for: $C_{18}H_{19}F_2N_3O_2 \cdot 1/2H_2O$: C, 60.67; H, 5.66; N, 11.79. Found: C, 60.68; H, 5.46; N, 11.61.

MS (EI): 347 (M$^+$).

¹H-NMR (400 MHz, DMSO-d$_6$) δ (ppm): 0.90–0.97 (6H, m), 1.54–1.58 (2H, m), 2.51–2.54 (1H, m), 2.76–2.81 (1H, m), 3.82 (2H, q, J=7.3 Hz), 5.53 (1H, s), 6.90 (2H, dd, J=7.3 Hz and 7.3 Hz), 7.16 (1H, d, J=7.3 Hz), 7.20 (1H, s), 9.50 (1H, br.s), 11.96 (1H, br.s).

Example 55

Ethyl 4-(2,6-dichlorophenyl)-4,7-dihydro-6-propyl-2H-pyrazolo[3,4-b]pyridine-5-carboxylate The title compound was prepared from 2,6-dichlorobenzaldehyde and ethyl 3-ketohexanoate in the same manner as in Example 39.

MP: 202° C.

Anal. Calcd. for: $C_{18}H_{19}Cl_2N_3O_2 \cdot 3/10H_2O$: C, 56.06; H, 5.12; N, 10.90. Found: C, 56.28; H, 5.46; N, 10.78.

MS (EI): 380 (M$^+$).

¹H-NMR (400 MHz, DMSO-d$_6$) δ (ppm): 0.83 (3H, t, J=7.3 Hz), 0.92 (3H, t, J=7.3 Hz), 1.57–1.62 (2H, m), 2.47–2.51 (1H, m), 2.77–2.80 (1H, m), 3.74 (2H, q, J=7.3 Hz), 6.03 (1H, s), 7.05 (1H, s), 7.13 (1H, dd, J=7.3 Hz and 7.4 Hz), 7.22 (1H, d, J=7.3 Hz), 7.39 (1H, d, J=7.3 Hz), 9.53 (1H, br.s), 11.93 (1H, br.s).

Example 56

Ethyl 4-(2-chloro-6-fluorophenyl)-4,7-dihydro-6-propyl-2H-pyrazolo[3,4-b]pyridine-5-carboxylate The title compound was prepared from 2-chloro-6-fluorobenzaldehyde, 3-aminopyrazole and ethyl 3-ketohexanoate in the same manner as in Example 25.

MP: 180–183° C.

MS (EI): 363 (M$^+$).

¹H-NMR (400 MHz, DMSO-d$_6$) δ (ppm): 0.92 (3H, t, J=6.9 Hz), 0.94 (3H, t, J=7.3 Hz), 1.56–1.61 (2H, m), 2.50–2.85 (2H, m), 3.80 (2H, q, J=7.3 Hz), 5.75 (1H, s), 7.01–7.17 (4H, m), 9.52 (1H, br.s), 11.97 (1H, br.s).

IR (KBr): ν=3265, 1591, 1518, 1456, 1228, 1097 cm$^{-1}$.

Example 57

Ethyl 4,7-dihydro-6-propyl-4-(pyridin-3-yl)-2H-pyrazolo[3,4-b]pyridine-5-carboxylate dihydrocloride The title compound was prepared from pyridine-3-aldehyde and ethyl 3-ketohexanoate in the same manner as in Example 39.

MP: 251° C.

Anal. Calcd. for: $C_{17}H_{20}N_4O_2 \cdot 2HCl$: C, 52.99; H, 5.76; N, 14.54. Found: C, 52.99; H, 5.67; N, 14.44.

MS (EI): 312 (M$^+$).

¹H-NMR (400 MHz, DMSO-d$_6$) δ (ppm): 0.91 (3H, t, J=7.3 Hz), 1.09 (3H, t, J=7.3 Hz), 1.52–1.61 (2H, m), 2.66–2.71 (2H, m), 3.93–4.00 (2H, m), 5.24 (1H, s), 7.90 (1H, dd, J=7.3 Hz and 7.4 Hz), 8.31–8.35 (2H, m), 8.66–8.69 (2H, m), 10.35 (1H, br.s).

Example 58

Ethyl 4,7-dihydro-6-propyl-4-(pyridin-4-yl)-2H-pyrazolo[3,4-b]pyridine-5-carboxylate dihydrocloride The title compound was prepared from pyridine-4-aldehyde and ethyl 3-ketohexanoate in the same manner as in Example 39.

MP: 266° C.

Anal. Calcd. for: $C_{17}H_{20}N_4O_2 \cdot 2HCl$: C, 52.99; H, 5.76; N, 14.54. Found: C, 52.63; H, 5.65; N, 14.69.

MS (EI): 312 (M$^+$).

¹H-NMR (400 MHz, DMSO-d$_6$) δ (ppm): 0.91 (3H, t, J=7.3 Hz), 1.12 (3H, t, J=7.3 Hz), 1.52–1.59 (2H, m), 2.64–2.72 (2H, m), 4.01 (2H, q, J=7.3 Hz), 5.30 (1H, s), 7.76 (2H, d, J=6.4 Hz), 8.66 (1H, s), 8.72 (2H, d, J=6.4 Hz), 10.39 (1H, br.s).

Example 59

Ethyl 4-(furan-2-yl)-4,7-dihydro-6-propyl-2H-pyrazolo[3,4-b]pyridine-5-carboxylate maleate The title compound was prepared from furan-2-aldehyde, 3-aminopyrazole and ethyl 3-ketohexanoate in the same manner as in Example 25.

MP: 108–111° C.

MS (EI): 301 (M$^+$).

¹H-NMR (400 MHz, DMSO-d$_6$) δ (ppm): 0.92 (3H, t, J=7.3 Hz), 1.05 (3H, t, J=6.8 Hz), 1.58 (2H, q, J=7.3 Hz), 2.66–2.72 (2H, m), 3.50 (3H, br.s), 3.94 (2H, q, J=6.8 Hz), 5.21 (1H, s), 5.78 (1H, d, J=2.9 Hz), 6.23 (1H, s), 6.24 (2H, s), 7.75 (1H, s), 7.38 (1H, s), 9.42 (1H, br.s).

IR (KBr): ν=3207, 2962, 1703, 1479, 1348, 1205, 1076, 866 cm$^{-1}$.

Example 60

Ethyl 4-(furan-3-yl)-4,7-dihydro-4-(furan-3-yl)-6-propyl-2H-pyrazolo[3,4-b]pyridine-5-carboxylate maleate The title compound was prepared from furan-3-aldehyde, 3-aminopyrazole and ethyl 3-ketohexanoate in the same manner as in Example 25.

MP: 121–123° C.

Anal. Calcd. for: $C_{16}H_{19}N_3O_3 \cdot C_4H_4O_4$: C, 57.54; H, 5.55; N, 10.07. Found: C, 57.14; H, 5.55; N, 10.37.

MS (EI): 301 (M$^+$).

¹H-NMR (400 MHz, DMSO-d$_6$) δ (ppm): 0.90 (3H, t, J=7.3 Hz), 1.08 (3H, t, J=7.4 Hz), 1.55–1.57 (2H, m), 2.62–2.70 (2H, m), 3.36 (1H, br.s), 3.50 (2H, br.s), 3.97 (2H, q, J=7.3 Hz), 5.06 (1H, s), 6.16 (1H, s), 6.24 (2H, s), 7.13 (1H, s), 7.35 (1H, s), 7.40 (1H, s), 9.31 (1H, br.s).

IR (KBr): ν=3350, 2972, 1591, 1467, 1361, 1203, 1089 cm$^{-1}$.

Example 61

Ethyl 4,7-dihydro-4-(2-methylfuran-3-yl)-6-propyl-2H-pyrazolo[3,4-b]pyridine-5-carboxylate The title compound was prepared from 2-methylfuran-3-aldehyde, 3-aminopyrazole and ethyl 3-ketohexanoate in the same manner as in Example 25.

MP: 123–125° C.

Anal. Calcd. for: $C_{17}H_{21}N_3O_3 \cdot 2/5H_2O$: C, 63.30; H, 6.81; N, 13.03. Found: C, 63.51; H, 6.64; N, 12.96.

MS (EI): 315 (M$^+$).

$^1$H-NMR (400 MHz, DMSO-d$_6$) δ (ppm): 0.93 (3H, t, J=7.3 Hz), 1.08 (3H, t, J=7.3 Hz), 1.58–1.60 (2H, m), 2.20 (3H, s), 2.55–2.75 (2H, m), 3.92 (2H, q, J=7.3 Hz), 4.99 (1H, s), 5.96 (1H, s), 7.21 (2H, s), 9.26 (1H, br.s), 11.91 (1H, br.s).

IR (KBr): ν=3265, 3198, 2964, 1591, 1514, 1224, 1209, 1093 cm$^{-1}$.

Example 62

Ethyl 4,7-dihydro-6-propyl-4-(thiophen-2-yl)-2H-pyrazolo[3,4-b]pyridine-5-carboxylate maleate The title compound was prepared from thiophene-2-aldehyde, 3-aminopyrazole and ethyl 3-ketohexanoate in the same manner as in Example 25.

MP: 129–131° C.

Anal. Calcd. for: $C_{16}H_{19}N_3O_2S \cdot C_4H_4O_4 \cdot 1/4H_2O$: C, 54.85; H, 5.41; N, 9.59. Found: C, 54.59; H, 5.22; N, 9.97.

MS (EI): 317 (M$^+$).

$^1$H-NMR (400 MHz, DMSO-d$_6$) δ (ppm): 0.92 (3H, t, J=7.4 Hz), 1.06 (3H, t, J=7.3 Hz), 1.58–1.60 (2H, m), 2.72–2.74 (2H, m), 3.50 (3H, br.s), 3.94 (2H, q, J=7.4 Hz), 5.44 (1H, s), 6.25 (2H, s), 6.69 (1H, s), 6.81 (1H, d), 7.15 (1H, d), 7.37 (1H, s), 9.50 (1H, br.s).

Example 63

Ethyl 4,7-dihydro-4-(3-methylthiophen-2-yl)-6-propyl-2H-pyrazolo[3,4-b]pyridine-5-carboxylate The title compound was prepared from 3-methylthiophene-2-aldehyde, 3-aminopyrazole and ethyl 3-ketohexanoate in the same manner as in Example 25.

MP: 125° C.

Anal. Calcd. for: $C_{17}H_{21}N_3O_2S \cdot H_2O$: C, 58.43; H, 6.63; N, 12.02. Found: C, 58.59; H, 6.33; N, 12.12.

MS (EI): 331 (M$^+$).

$^1$H-NMR (400 MHz, DMSO-d$_6$) δ (ppm): 0.96 (3H, t, J=7.4 Hz), 0.98 (3H, t, J=7.3 Hz), 1.60–1.63 (2H, m), 2.22 (3H, s), 2.83–2.90 (2H, m), 3.88 (2H, q, J=7.3 Hz), 5.42 (1H, s), 6.68 (1H, d, J=4.9 Hz), 7.02 (1H, d, J=5.4 Hz), 7.29 (1H, s), 9.45 (1H, br.s), 11.98 (1H, br.s).

IR (KBr): ν=3267, 3196, 2968, 1664, 1510, 1267, 1201, 1091 cm$^{-1}$.

Example 64

Ethyl 4-(5-chlorothiophen-2-yl)-4,7-dihydro-6-propyl-2H-pyrazolo[3,4-b]pyridine-5-carboxylate maleate The title compound was prepared from 5-chlorothiophene-2-aldehyde, 3-aminopyrazole and ethyl 3-ketohexanoate in the same manner as in Example 25.

MP: 129–131° C.

Anal. Calcd. for: $C_{16}H_{18}N_3O_2SC_4H_4O_4$: C, 51.33; H, 4.74; N, 8.98. Found: C, 51.34; H, 4.54; N, 9.03.

MS (EI): 351 (M$^+$).

$^1$H-NMR (400 MHz, DMSO-d$_6$) δ (ppm): 0.92 (3H, t, J=7.3 Hz), 1.10 (3H, t, J=6.9 Hz), 1.59–1.61 (2H, m), 2.57–2.82 (2H, m), 3.50 (2H, br.s), 3.38 (1H, s), 3.98 (2H, q, J=6.9 Hz), 5.36 (1H, s), 6.25 (2H, s), 6.53 (1H, d, J=3.9 Hz), 6.80 (1H, d, J=3.4 Hz), 7.42 (1H, s), 9.60 (1H, br.s).

IR (KBr): ν323205, 2964, 2629, 1618, 1471, 1363, 1205, 1080, 889, 652 cm$^{-1}$.

Example 65

Ethyl 4,7-dihydro-6-propyl-4-(thiophen-3-yl)-2H-pyrazolo[3,4-b]pyridine-5-carboxylate maleate The title compound was prepared from thiophene-3-aldehyde, 3-aminopyrazole and ethyl 3-ketohexanoate in the same manner as in Example 25.

MP: 141–143° C.

Anal. Calcd. for: $C_{16}H_{19}N_3O_2SC_4H_4O_4$: C, 54.42; H, 5.35; N, 9.69. Found: C, 54.17; H, 5.23; N, 9.66.

MS (EI): 317 (M$^+$).

$^1$H-NMR (400 MHz, DMSO-d$_6$) δ (ppm): 0.92 (3H, t, J=7.3 Hz), 1.03 (3H, t, J=6.8 Hz), 1.59–1.61 (2H, m), 2.60–2.78 (2H, m), 3.50 (2H, br.s), 3.91 (2H, q, J=6.8 Hz), 5.22 (2H, s), 6.26 (2H, s), 6.84–6.88 (2H, m), 7.29 (1H, dd, J=3.0 Hz and 4.9 Hz), 7.33 (1H, s), 12.0 (1H, br.s).

IR (KBr): ν=3346, 2980, 2611, 1697, 1467, 1361, 1205, 1087 cm$^{-1}$.

Example 66

Ethyl 4,7-dihydro-4-(naphthalen-1-yl)-6-propyl-2H-pyrazolo[3,4-b]pyridine-5-carboxylate The title compound was prepared from naphthalene-1-aldehyde, 3-aminopyrazole and ethyl 3-ketohexanoate in the same manner as in Example 25.

MP: 182° C.

Anal. Calcd. for: $C_{22}H_{23}N_3O_2$: C, 73.11; H, 6.41; N, 11.63. Found: C, 72.95; H, 6.47; N, 11.40.

MS (EI): 361 (M$^+$).

$^1$H-NMR (400 MHz, DMSO-d$_6$) δ (ppm): 0.62 (3H, t, J=7.3 Hz), 1.00 (3H, t, J=7.3 Hz), 1.69–1.73 (2H, m), 2.73–2.76 (1H, m), 2.84–2.87 (1H, m), 3.67 (2H, q, J=7.3 Hz), 5.95 (1H, s), 7.03 (1H, s), 7.23 (1H, d, J=7.3 Hz), 7.36 (1H, dd, J=7.3 Hz and 7.4 Hz), 7.49 (1H, dd, J=7.3 Hz and 7.4 Hz), 7.57 (1H, dd, J=7.3 Hz and 7.4 Hz), 7.65 (1H, d, J=7.3 Hz), 7.88 (1H, d, J=7.3 Hz), 8.40 (1H, d, J=7.3 Hz), 9.45 (1H, br.s), 11.82 (1H, br.s).

Example 67

Ethyl 4,7-dihydro-4-(naphthalen-2-yl)-6-propyl-2H-pyrazolo[3,4-b]pyridine-5-carboxylate maleate The title compound was prepared from naphthalene-2-aldehyde, 3-aminopyrazole and ethyl 3-ketohexanoate in the same manner as in Example 25.

MP: 136–138° C.

Anal. Calcd. for: $C_{22}H_{23}N_3O_2C_4H_4O_4 \cdot 1/4H_2O$: C, 64.79; H, 5.75; N, 8.72. Found: C, 64.86; H, 5.57; N, 8.99.

MS (EI): 361 (M$^+$).

$^1$H-NMR (400 MHz, DMSO-d$_6$) δ (ppm): 0.92–0.98 (6H, m), 1.64–1.68 (2H, m), 2.72–2.80 (2H, m), 3.50 (2H, br.s), 3.80 (2H, q, J=7.3 Hz), 5.27 (1H, s), 6.25 (2H, s), 7.23 (1H, s), 7.31 (1H, d, J=8.3 Hz), 7.41–7.43 (2H, m), 7.57 (1H, s), 7.73–7.77 (2H, m), 9.47 (1H, br.s).

IR (KBr): ν=3202, 2962, 1701, 1464, 1359, 1222 cm$^{-1}$.

Example 68

Ethyl 4,7-dihydro-4-(2-methoxynaphthalen-1-yl)-6-propyl-2H-pyrazolo[3,4-b]pyridine-5-carboxylate The title compound was prepared from 2-methoxynaphthalene-1-aldehyde, 3-aminopyrazole and ethyl 3-ketohexanoate in the same manner as in Example 25.

MP: 188–191° C.

Anal. Calcd. for: $C_{23}H_{25}N_3O_3$2/5$H_2O$: C, 69.29; H, 6.52; N, 10.54. Found: C, 69.35; H, 6.62; N, 10.21.

MS (EI): 391 (M$^+$).

$^1$H-NMR (400 MHz, DMSO-d$_6$) δ (ppm): 0.71 (3H, t, J=7.3 Hz), 0.95 (3H, t, J=7.3 Hz), 1.62–1.63 (2H, m), 2.49–2.86 (2H, m), 3.61 (2H, q, J=7.3 Hz), 3.97 (3H, s), 6.27 (1H, s), 6.89 (1H, s), 7.16–7.51 (3H, m), 7.71–7.77 (2H, m), 7.98 (1H, s), 9.43 (1H, br.s), 11.77 (1H, br.s).

IR (KBr): ν=3258, 1655, 1593, 1082 cm$^{-1}$.

Example 69

Ethyl 4-(2,3-dihydobenzo[b]furan-7-yl)-4,7-dihydro-6-propyl-2H-pyrazolo[3,4-b]pyridine-5-carboxylate The title compound was prepared from 2,3-dihydobenzo[b]furan-7-aldehyde, 3-aminopyrazole and ethyl 3-ketohexanoate in the same manner as in Example 25.

MP: 194–196° C.

Anal. Calcd. for: $C_{20}H_{23}N_3O_3$: C, 67.97; H, 6.56; N, 11.89. Found: C, 67.97; H, 6.68; N, 11.77.

MS (EI): 353 (M$^+$).

$^1$H-NMR (400 MHz, DMSO-d$_6$) δ (ppm): 0.92 (3H, t, J=7.4 Hz), 0.97 (3H, t, J=7.3 Hz), 1.66 (2H, m), 2.67–2.70 (1H, m), 2.82–2.84 (1H, m), 3.15 (2H, t, J=8.8 Hz), 3.83–3.86 (2H, m), 4.55–4.58 (2H, m), 5.29 (1H, s), 6.64 (1H, dd, J=7.3 Hz and 7.4 Hz), 6.72 (1H, d, J=6.9 Hz), 6.93 (1H, dd, J=7.3 Hz and 7.4 Hz), 7.20 (1H, s), 9.32 (1H, br.s), 11.86 (1H, br.s).

Example 70

Ethyl 4-(5-bromo-2,3-dihydobenzo[b]furan-7-yl)-4,7-dihydro-6-propyl-2H-pyrazolo[3,4-b]pyridine-5-carboxylate The title compound was prepared from 5-bromo-2,3-dihydobenzo[b]furan-7-aldehyde, 3-aminopyrazole and ethyl 3-ketohexanoate in the same manner as in Example 25.

MP: 200–210° C.

Anal. Calcd. for: $C_{20}H_{22}BrN_3O_3$: C, 55.57; H, 5.13; N, 9.72. Found: C, 55.23; H, 5.09; N, 9.89.

MS (EI): 432 (M$^+$).

$^1$H-NMR (400 MHz, DMSO-d$_6$) δ (ppm): 0.93–0.98 (6H, m), 1.64 (2H, q, J=7.3 Hz), 2.63 (1H, m), 2.88–2.90 (1H, m), 3.16 (2H, t, J=8.3 Hz), 3.85–3.87 (2H, m), 4.57–4.60 (2H, m), 5.23 (1H, s), 6.78 (1H, s), 7.11 (1H, s), 7.22 (1H, s), 9.44 (1H, br.s), 11.94 (1H, br.s)

Example 71

Ethyl 4-(5-chloro-2,3-dihydo-2-methylbenzo[b]furan-7-yl)-4,7-dihydro-6-propyl-2H-pyrazolo[3,4-b]pyridine-5-carboxylate maleate The title compound was prepared from 5-chloro-2,3-dihydo-2-methylbenzo[b]furan-7-aldehyde, 3-aminopyrazole and ethyl 3-ketohexanoate in the same manner as in Example 25.

MP: 155–158° C.

Anal. Calcd. for: $C_{21}H_{24}N_3O_3C_4H_4O_4$: C, 57.95; H, 5.45; N, 8.11. Found: C, 57.57; H, 5.28; N, 8.47.

MS (EI): 401 (M$^+$).

$^1$H-NMR (400 MHz, DMSO-d$_6$) δ (ppm): 0.94 (6H, t, J=6.8 Hz), 1.03 (3H, d, J=6.3 Hz), 1.65 (2H, m), 2.40–2.73 (2H, m), 2.87 (1H, m), 3.29 (1H, m), 3.50 (3H, br.s), 3.84 (2H, q, J=6.8 Hz), 5.05 (1H, m), 5.23 (1H, s), 6.25 (2H, s), 6.64 (1H, s), 6.95 (1H, s), 7.20 (1H, d, J=4.4 Hz), 9.43 (1H, br.s).

IR (KBr): ν=3207, 2976, 1589, 1462, 1201, 1082 cm$^{-1}$.

Example 72

Ethyl 4-(2H-1-benzopyran-8-yl)-4,7-dihydro-6-propyl-2H-pyrazolo[3,4-b]pyridine-5-carboxylate The title compound was prepared from 2H-1-benzopyran-8-aldehyde and ethyl 3-ketohexanoate in the same manner as in Example 39.

MP: 194° C.

Anal. Calcd. for: $C_{21}H_{23}N_3O_3$: C, 69.02; H, 6.34; N, 11.50. Found: C, 68.60; H, 6.43; N, 11.25.

MS (EI): 194 (M$^+$).

$^1$H-NMR (400 MHz, DMSO-d$_6$) δ (ppm): 0.90 (3H, t, J=7.3 Hz), 0.96 (3H, t, J=7.3 Hz), 1.64–1.68 (2H, m), 2.62–2.66 (1H, m), 2.80–2.84 (1H, m), 3.81 (2H, q, J=7.3 Hz), 4.85 (2H, dd, J=2.0 Hz and 9.8 Hz), 5.39 (1H, s), 5.89 (1H, d, J=9.8 Hz), 6.46 (1H, d, J=9.8 Hz), 6.67–6.80 (3H, m), 7.18 (1H, s), 9.31 (1H, br.s), 11.86 (1H, br.s).

Example 73

Ethyl 4-(3,4-dihydro-2H-benzopyran-8-yl)-4,7-dihydro-6-propyl-2H-pyrazolo[3,4-b]pyridine-5-carboxylate The title compound was prepared from 3,4-dihydro-2H-benzopyran-8-aldehyde and ethyl 3-ketohexanoate in the same manner as in Example 39.

MP: 208° C.

Anal. Calcd. for: $C_{21}H_{25}N_3O_3$1/2$H_2O$: C, 67.01; H, 6.96; N, 11.16. Found: C, 67.41; H, 6.84; N, 10.93.

MS (EI): 367 (M$^+$).

$^1$H-NMR (400 MHz, DMSO-d$_6$) δ (ppm): 0.89 (3H, t, J=7.3 Hz), 0.97 (3H, t, J=7.3 Hz), 1.63–1.68 (2H, m), 1.92–1.96 (2H, m), 2.67–2.82 (4H, m), 3.80 (2H, q, J=7.3 Hz), 4.22–4.26 (2H, m), 5.41 (1H, s), 6.61 (1H, dd, J=7.3 Hz and 7.4 Hz), 6.71–6.75 (2H, m), 7.17 (1H, s), 9.25 (1H, br.s), 11.80 (1H, br.s).

Example 74

Ethyl 4,7-dihydro-6-propyl-4-(quinolin-4-yl)-2H-pyrazolo[3,4-b]pyridine-5-carboxylate The title compound was prepared from quinoline-4-aldehyde and ethyl 3-ketohexanoate in the same manner as in Example 39.

MP: 198° C.

Anal. Calcd. for: $C_{21}H_{22}N_4O_2$2/5$H_2O$: C, 68.24; H, 6.22; N, 15.16. Found: C, 68.39; H, 6.04; N, 14.83.

MS (EI): 362 (M$^+$).

$^1$H-NMR (400 MHz, DMSO-d$_6$) δ (ppm): 0.61 (3H, t, J=7.3 Hz), 1.02 (3H, t, J=7.3 Hz), 1.68–1.72 (2H, m), 2.76–2.78 (1H, m), 2.86–2.89 (1H, m), 3.66–3.68 (2H, m), 5.97 (1H, s), 7.07 (1H, s), 7.17 (1H, d, J=4.4 Hz), 7.65 (1H, dd, J=7.3 Hz and 7.4 Hz), 7.74 (1H, dd, J=7.3 Hz and 7.4 Hz), 7.99 (1H, d, J=7.3 Hz), 8.48 (1H, d, J=7.8 Hz), 8.73 (1H, d, J=4.4 Hz), 9.61 (1H, br.s), 11.94 (1H, br.s)

Example 75

Ethyl 4-(benzo[b]thiophen-3-yl)-4,7-dihydro-6-propyl-2H-pyrazolo[3,4-b]pyridine-5-carboxylate The title compound was prepared from benzo[b]thiophene-3-aldehyde and ethyl 3-ketohexanoate in the same manner as in Example 39.

MP: 222° C.

Anal. Calcd. for: $C_{20}H_{21}N_3O_2S$: C, 65.37; H, 5.76; N, 11.44. Found: C, 65.11; H, 5.31; N, 11.83.

MS (EI): 238 (M$^+$).

$^1$H-NMR (400 MHz, DMSO-d$_6$) δ (ppm): 0.64 (3H, t, J=7.3 Hz), 1.20 (3H, t, J=7.3 Hz), 1.56–1.58 (2H, m), 2.66–2.78 (2H, m), 4.11 (2H, q, J=7.3 Hz), 4.89 (1H, s), 7.42–7.50 (2H, m), 7.55 (1H, s), 7.61 (1H, s), 7.96–8.01 (2H, m), 10.32 (1H, br.s), 12.13 (1H, br.s).

Example 76

Ethyl 4-(2,1,3-benzoxadiazol-4-yl)-4,7-dihydro-6-propyl-2H-pyrazolo[3,4-b]pyridine-5-carboxylate The title compound was prepared from 2,1,3-benzoxadiazole-4-aldehyde, 3-aminopyrazole and ethyl 3-ketohexanoate in the same manner as in Example 39.

MP: 207° C.

Anal. Calcd. for: $C_{18}H_{19}N_5O_3$: C, 61.18; H, 5.42; N, 19.82. Found: C, 61.06; H, 5.50; N, 19.66.

MS (EI): 353 (M$^+$).

$^1$H-NMR (400 MHz, DMSO-d$_6$) δ (ppm): 0.77 (3H, t, J=7.3 Hz), 0.97 (3H, t, J=7.3 Hz), 2.72–2.77 (1H, m), 2.82–2.86 (1H, m), 3.79 (2H, q, J=7.3 Hz), 5.68 (1H, s), 7.11 (1H, d, J=7.3 Hz), 7.22 (1H, s), 7.51 (1H, dd, J=7.3 Hz and 7.4 Hz), 7.78 (1H, d, J=7.3 Hz), 9.66 (1H, br.s), 12.01 (1H, br.s).

Example 77

Ethyl 4-(1,3-benzdioxazol-4-yl)-4,7-dihydro-6-propyl-2H-pyrazolo[3,4-b]pyridine-5-carboxylate The title compound was prepared from 1,3-benzdioxazole-4-aldehyde, 3-aminopyrazole and ethyl 3-ketohexanoate in the same manner as in Example 25.

MP: 203–207° C.

Anal. Calcd. for: $C_{19}H_{21}N_3O_4 1/10H_2O$: C, 63.89; H, 5.98; N, 11.76. Found: C, 63.72; H, 5.86; N, 12.01.

MS (EI): 355 (M$^+$).

$^1$H-NMR (400 MHz, DMSO-d$_6$) δ (ppm): 0.94 (3H, t, J=7.3 Hz), 0.96 (3H, t, J=7.4 Hz), 1.61–1.67 (2H, m), 2.64–2.82 (2H, m), 3.80–3.88 (2H, m), 5.28 (1H, s), 5.99 (1H, s), 6.00 (1H, d, J=9.7 Hz), 6.50 (1H, d, J=5.9 Hz), 6.65 (1H, s), 6.65–6.69 (1H, m), 7.25 (1H, s), 9.40 (1H, br.s), 11.94 (1H, br.s).

IR (KBr): ν=3265, 3188, 2962, 1662, 1587, 1514, 1462, 1253, 1215, 1066 cm$^{-1}$.

Example 78

Ethyl 4-(6-chloro-3,4-dihydro-2,2-dimethyl-2H-1,4-benzoxazin-8-yl)-4,7-dihydro-6-propyl-2H-pyrazolo[3,4-b]pyridine-5-carboxylate maleate The title compound was prepared from 6-chloro-3,4-dihydro-2,2-dimethyl-2H-1,4-benzoxazine-8-aldehyde, 3-aminopyrazole and ethyl 3-ketohexanoate in the same manner as in Example 25.

MS (EI): 430 (M$^+$).

$^1$H-NMR (400 MHz, DMSO-d$_6$) δ (ppm): 0.92 (3H, t, J=7.4 Hz), 0.96 (3H, t, J=7.3 Hz), 1.18 (3H, s), 1.32 (3H, s), 1.62–1.64 (2H, m), 2.66–2.82 (2H, m), 2.99 (2H, s), 3.80 (2H, t, J=7.3 Hz), 5.32 (1H, s), 6.01 (2H, s), 6.14 (1H, s), 6.32 (1H, s), 7.14 (1H, s), 9.31 (1H, br.s), 11.82 (1H, br.s).

IR (KBr): ν=3281, 2974, 1672, 1599, 1520, 1207, 1155, 1091 cm$^{-1}$.

Example 79

Ethyl 4-(6-chloro-3,4-dihydro-2,2,4-trimethyl-1,4-benzoxazin-8-yl)-4,7-dihydro-6-propyl-2H-pyrazolo[3,4-b]pyridine-5-carboxylate maleate The title compound was prepared from 6-chloro-3,4-dihydro-2,2,4-trimethyl-2H-1,4-benzoxazine-8-aldehyde, 3-aminopyrazole and ethyl 3-ketohexanoate in the same manner as in Example 25.

MS (EI): 444 (M$^+$).

$^1$H-NMR (400 MHz, DMSO-d$_6$) δ (ppm): 0.91 (3H, t, J=7.3 Hz), 0.96 (3H, t, J=7.3 Hz), 1.20 (6H, s), 1.35 (3H, s), 1.63–1.65 (2H, m), 2.83 (2H, s), 3.00 (2H, q, J=7.3 Hz), 5.34 (1H, s), 6.26 (2H, s), 6.43 (1H, d, J=2.5 Hz), 7.13 (1H, s), 9.33 (1H, s), 11.82 (1H, br.s).

IR (KBr): ν=3273, 2974, 1666, 1597, 1518, 1458, 1259, 1211 cm$^{-1}$.

Example 80

Ethyl 4-(2,3-dihydro-1,4-benzodioxin-6-yl)-4,7-dihydro-6-propyl-2H-pyrazolo[3,4-b]pyridine-5-carboxylate maleate The title compound was prepared from 2,3-dihydro-1,4-benzodioxin-6-aldehyde, 3-aminopyrazole and ethyl 3-ketohexanoate in the same manner as in Example 25.

MP: 147–149° C.

Anal. Calcd. for: $C_{20}H_{23}N_3O_4 C_4H_4O_4$: C, 59.37; H, 5.60; N, 8.66. Found: C, 59.12; H, 5.63; N, 8.57.

MS (EI): 369 (M$^+$).

$^1$H-NMR (400 MHz, DMSO-d$_6$) δ (ppm): 0.93 (3H, t, J=7.3 Hz), 1.02 (3H, t, J=6.8 Hz), 1.60 (2H, q, J=7.3 Hz), 2.64–2.68 (2H, m), 3.50 (2H, br.s), 3.86 (2H, q, J=7.3 Hz), 4.14 (4H, s), 4.99 (1H, s), 6.26 (2H, s), 6.54 (1H, s), 6.57 (1H, d, J=7.8 Hz), 6.65 (1H, d, J=7.8 Hz), 7.21 (1H, s), 11.97 (1H, br.s).

IR (KBr): ν=3211, 2694, 2878, 2658, 1697, 1506, 1466, 1363, 1302, 1082 cm$^{-1}$.

Example 81

Ethyl 4-(benzo[b]furan-2-yl)-4,7-dihydro-6-propyl-2H-pyrazolo[3,4-b]pyridine-5-carboxylate maleate The title compound was prepared from benzo[b]furan-2-aldehyde, 3-aminopyrazole and ethyl 3-ketohexanoate in the same manner as in Example 25.

MP: 123–125° C.

Anal. Calcd. for: $C_{20}H_{21}N_3O_3 C_4H_4O_4 1/2H_2O$: C, 61.19; H, 5.43; N, 8.92. Found: C, 61.02; H, 5.41; N, 9.27.

MS (EI): 351 (M$^+$).

$^1$H-NMR (400 MHz, DMSO-d$_6$) δ (ppm): 0.96 (3H, t, J=7.3 Hz), 1.02 (3H, t, J=6.8 Hz), 1.63 (2H, q, J=7.3 Hz), 2.73–2.76 (2H, m), 3.50 (3H, br.s), 3.93 (2H, q, J=7.3 Hz), 5.36 (1H, s), 6.24 (2H, s), 6.43 (1H, s), 7.10–7.21 (2H, m), 7.41–7.48 (3H, m), 9.51 (1H, br.s).

IR (KBr): ν=3190, 3080, 2962, 1705, 1581, 1454, 1359, 1195, 883 cm$^{-1}$.

Example 82

Ethyl 4-(2-chlorophenyl)-6-ethyl-4,7-dihydro-2H-pyrazolo[3,4-b]pyridine-5-carboxylate The title compound was prepared from 2-chlorobenzaldehyde, 3-aminopyrazole and ethyl 3-ketopentanoate in the same manner as in Example 1.

MP: 213° C.

Anal. Calcd. for: $C_{17}H_{18}ClN_3O_2$: C, 61.54; H, 5.47; N, 12.66. Found: C, 61.54; H, 5.46; N, 12.68.

MS (EI): 331 (M$^+$).

$^1$H-NMR (400 MHz, DMSO-d$_6$) δ (ppm): 0.85 (3H, t, J=7.3 Hz), 1.21 (3H, t, J=7.3 Hz), 2.78–2.84 (2H, m), 3.78 (2H, q, J=7.3 Hz), 5.58 (1H, s), 7.07–7.12 (2H, m), 7.18 (1H, dd, J=7.3 Hz and 7.4 Hz), 7.25 (1H, s), 7.34 (1H, d, J=7.3 Hz), 9.52 (1H, br.s), 11.97 (1H, br.s)

Example 83

Ethyl 6-butyl-4-(2-chlorophenyl)-4,7-dihydro-2H-pyrazolo[3,4-b]pyridine-5-carboxylate The title compound was prepared from 2-chlorobenzaldehyde, 3-aminopyrazole and ethyl 3-ketoheptanoate in the same manner as in Example 1.

MP: 209° C.

Anal. Calcd. for: $C_{19}H_{22}ClN_3O_2 1/5H_2O$: C, 62.79; H, 6.21; N, 11.56. Found: C, 62.78; H, 6.11; N, 11.45.

MS (EI): 359 (M$^+$).

$^1$H-NMR (400 MHz, DMSO-d$_6$) δ (ppm): 0.85 (3H, t, J=7.3 Hz), 0.92 (3H, t, J=7.3 Hz), 1.36–1.42 (2H, m), 1.60–1.64 (2H, m), 2.72–2.76 (1H, m), 2.83–2.86 (1H, m), 3.78 (2H, q, J=7.3 Hz), 5.58 (1H, s), 7.07–7.11 (2H, m), 7.18 (1H, dd, J=7.3 Hz and 7.4 Hz), 7.24 (1H, s), 7.34 (1H, d, J=7.3 Hz), 9.49 (1H, br.s), 11.96 (1H, br.s).

Example 84

Methyl 4-(2-chlorophenyl)-4,7-dihydro-6-methoxymethyl-2H-pyrazolo[3,4-b]pyridine-5-carboxylate The title compound was prepared from 2-chlorobenzaldehyde, 3-aminopyrazole and methyl 4-methoxyacetoacetate in the same manner as in Example 1.

MP: 160° C.

Anal. Calcd. for: $C_{16}H_{16}ClN_3O_3$: C, 57.33; H, 4.83; N, 12.59. Found: C, 57.53; H, 4.86; N, 12.58.

MS (EI): 333 (M$^+$).

$^1$H-NMR (400 MHz, DMSO-d$_6$) δ (ppm): 3.36 (3H, s), 3.38 (3H, s), 4.67 (2H, s), 5.58 (1H, s), 7.08–7.13 (2H, m), 7.19 (1H, dd, J=7.3 Hz and 7.4 Hz), 7.32–7.36 (2H, m), 9.14 (1H, br.s), 12.08 (1H, br.s).

Example 85

Ethyl 4-(2-chlorophenyl)-4,7-dihydro-6-phenyl-2H-pyrazolo[3,4-b]pyridine-5-carboxylate The title compound was prepared from 2-chlorobenzaldehyde, 3-aminopyrazole and ethyl benzoylacetoacetate in the same manner as in Example 1.

MP: 214° C.

Anal. Calcd. for: $C_{21}H_{18}ClN_3O_2 3/10H_2O$: C, 65.47; H, 4.87; N, 10.91. Found: C, 65.29; H, 4.73; N, 10.93.

MS (EI): 379 (M$^+$).

$^1$H-NMR (400 MHz, DMSO-d$_6$) δ (ppm): 0.57 (3H, t, J=7.3 Hz), 3.52 (2H, q, J=7.3 Hz), 5.65 (1H, s), 7.14 (1H, dd, J=7.3 Hz and 7.4 Hz), 7.27 (1H, dd, J=7.3 Hz and 7.4 Hz), 7.37–7.40 (8H, m), 9.53 (1H, br.s), 12.04 (1H, br.s).

Example 86

Ethyl 4-(2-chlorophenyl)-4,7-dihydro-6-(4-methoxyphenyl)-2H-pyrazolo[3,4-b]pyridine-5-carboxylate The title compound was prepared from 2-chlorobenzaldehyde, 3-aminopyrazole and ethyl (4-methoxybenzoyl)acetate in the same manner as in Example 1.

MP: 211° C.

Anal. Calcd. for: $C_{22}H_{20}ClN_3O_3$: C, 64.47; H, 4.92; N, 10.25. Found: C, 64.30; H, 5.00; N, 10.24.

MS (EI): 409 (M$^+$).

$^1$H-NMR (400 MHz, DMSO-d$_6$) δ (ppm): 0.64 (3H, t, J=7.3 Hz), 3.56 (2H, q, J=7.3 Hz), 3.79 (3H, s), 5.63 (1H, s), 6.95 (2H, d, J=7.3 Hz), 7.13 (1H, dd, J=7.3 Hz and 7.4 Hz), 7.24–7.38 (6H, m), 9.45 (1H, br.s), 12.03 (1H, br.s).

Example 87

Ethyl 4-(2-chlorophenyl)-4,7-dihydro-6-(thiophen-2-yl)-2H-pyrazolo[3,4-b]pyridine-5-carboxylate The title compound was prepared from 2-chlorobenzaldehyde, 3-aminopyrazole and ethyl (thiophen-2-carbonyl) acetate in the same manner as in Example 1.

MP: 200° C.

Anal. Calcd. for: $C_{19}H_{16}ClN_3O_2S$: C, 59.14; H, 4.18; N, 10.89. Found: C, 59.04; H, 4.31; N, 11.14.

MS (EI): 385 (M$^+$).

$^1$H-NMR (400 MHz, DMSO-d$_6$) δ (ppm): 1.02 (3H, t, J=7.3 Hz), 4.04 (2H, q, J=7.3 Hz), 5.16 (1H, s), 6.58 (1H, d, J=7.3 Hz), 7.18–7.70 (7H, m), 9.60 (1H, br.s), 12.74 (1H, br.s).

Example 88

Ethyl 6-benzyl-4-(2-chlorophenyl)-4,7-dihydro-2H-pyrazolo[3,4-b]pyridine-5-carboxylate The title compound was prepared from 2-chlorobenzaldehyde, 3-aminopyrazole and ethyl 4-phenylacetoacetate in the same manner as in Example 1.

MP: 247° C.

Anal. Calcd. for: $C_{22}H_{20}ClN_3O_2$ 1/5 $H_2O$: C, 66.48; H, 5.17; N, 10.57. Found: C, 66.30; H, 5.17; N, 10.37.

MS (EI): 393 (M$^+$).

$^1$H-NMR (400 MHz, DMSO-d$_6$) δ (ppm): 0.81 (3H, t, J=7.3 Hz), 3.76 (2H, q, J=7.3 Hz), 4.25 (2H, s), 5.65 (1H, s), 7.06–7.41 (10H, m), 9.68 (1H, br.s), 12.01 (1H, br.s).

Example 89

Ethyl 6-ethyl-4,7-dihydro-4-(2-methoxyphenyl)-2H-pyrazolo[3,4-b]pyridine-5-carboxylate The title compound was prepared from 2-methoxybenzaldehyde, 3-aminopyrazole and ethyl 3-ketopentanoate in the same manner as in Example 1.

MP: 169° C.

Anal. Calcd. for: $C_{18}H_{21}N_3O_3 3/10H_2O$: C, 64.97; H, 6.54; N, 12.63. Found: C, 64.86; H, 6.84; N, 12.33.

MS (EI): 327 (M$^+$).

$^1$H-NMR (400 MHz, DMSO-d$_6$) δ (ppm): 0.85 (3H, t, J=7.3 Hz), 1.18 (3H, t, J=7.3 Hz), 2.73–2.76 (1H, m), 2.81–2.85 (1H, m), 3.74 (2H, q, J=7.3 Hz), 3.85 (3H, s), 5.46 (1H, s), 6.76 (1H, dd, J=7.3 Hz and 7.4 Hz), 6.89–6.94 (2H, m), 7.04 (1H, dd, J=7.3 Hz and 7.4 Hz), 7.14 (1H, s), 9.32 (1H, br.s), 11.82 (1H, br.s).

Example 90

Ethyl 6-butyl-4,7-dihydro-4-(2-methoxyphenyl)-2H-pyrazolo[3,4-b]pyridine-5-carboxylate The title compound was prepared from 2-methoxybenzaldehyde, 3-aminopyrazole and ethyl 3-ketoheptanoate in the same manner as in Example 1.

MP: 190° C.

Anal. Calcd. for: $C_{20}H_{25}N_3O_3 1/2H_2O$: C, 65.91; H, 7.19; N, 11.53. Found: C, 65.92; H, 7.07; N, 11.88.

MS (EI): 355 (M$^+$).

$^1$H-NMR (400 MHz, DMSO-d$_6$) δ (ppm): 0.85 (3H, t, J=7.3 Hz), 0.93 (3H, t, J=7.3 Hz), 1.38–1.44 (2H, m), 1.59–1.64 (2H, m), 2.64–2.68 (1H, m), 2.85–2.90 (1H, m), 3.81 (2H, q, J=7.3 Hz), 3.85 (3H, s), 5.47 (1H, s), 6.76 (1H, dd, J=7.3 Hz and 7.4 Hz), 6.89–6.94 (2H, m), 7.04 (1H, dd, J=7.3 Hz and 7.4 Hz), 7.14 (1H, s), 9.29 (1H, br.s), 11.82 (1H, br.s).

Example 91

Methyl 4,7-dihydro-6-methoxymethyl-4-(2-methoxyphenyl)-2H-pyrazolo[3,4-b]pyridine-5-carboxylate The title compound was prepared from 2-methoxybenzaldehyde, 3-aminopyrazole and methyl 4-methoxyacetoacetate in the same manner as in Example 1.

MP: 186° C.

Anal. Calcd. for: $C_{17}H_{19}N_3O_4 1/5H_2O$: C, 61.32; H, 5.87; N, 12.62. Found: C, 61.34; H, 5.84; N, 12.52.

MS (EI): 329 (M$^+$).

$^1$H-NMR (400 MHz, DMSO-d$_6$) δ (ppm): 3.36 (3H, s), 3.38 (3H, s), 3.86 (3H, s), 4.68 (2H, s), 5.46 (1H, s), 6.77 (1H, dd, J=7.3 Hz and 7.4 Hz), 6.90–6.94 (2H, m), 7.06 (1H, dd, J=7.3 Hz and 7.4 Hz), 7.22 (1H, s), 8.94 (1H, br.s), 11.94 (1H, br.s).

Example 92

Ethyl 4,7-dihydro-4-(2-methoxyphenyl)-6-phenyl-2H-pyrazolo[3,4-b]pyridine-5-carboxylate The title compound was prepared from 2-methoxybenzaldehyde, 3-aminopyrazole and ethyl benzoylacetate in the same manner as in Example 1.

MP: 195° C.

Anal. Calcd. for: $C_{22}H_{21}N_3O_3$: C, 70.38; H, 5.64; N, 11.19. Found: C, 70.41; H, 5.71; N, 11.27.

MS (EI): 375 (M$^+$).

$^1$H-NMR (400 MHz, DMSO-d$_6$) δ (ppm): 0.55 (3H, t, J=7.3 Hz), 3.53 (2H, q, J=7.3 Hz), 3.88 (3H, s), 5.52 (1H, s), 6.84 (1H, dd, J=7.3 Hz and 7.4 Hz), 6.94 (1H, d, J=7.3 Hz), 7.09 (1H, dd, J=7.3 Hz and 7.4 Hz), 7.18 (1H, d, J=7.3 Hz), 7.23 (1H, s), 7.37–7.40 (5H, m), 9.33 (1H, br.s), 1.90 (1H, br.s).

Example 93

4-(2-Chlorophenyl)-4,7-dihydro-5-nitro-6-propyl-2H-pyrazolo[3,4-b]pyridine

To an aqueous solution (50 mL) of nitromethane (50 g) was added an aqueous solution (50 mL) of n-butylaldehyde (59 g), and the mixture was stirred with heating at 60° C. for 6 hours. The reaction mixture was allowed to cool to ambient temperature, and extracted with ethyl acetate. The solvent was evaporated under reduced pressure to give a brown oil (58 g). To a mixed solution of the obtained oil (50 g) in water (50 mL) and acetone (50 mL) was added sodium chromate (70 g). Under ice-cooling, concentrated sulfuric acid (46 mL) was added dropwise and the mixture was stirred for 5 hours. Ice-water (200 mL) was added and the mixture was extracted with ethyl acetate. The solvent was evaporated under reduced pressure and the residue was purified by silica gel column chromatography (eluent:hexane-ethyl acetate (10:1)) to give 1-nitropentan-2-one (40 g) as a brown oil. A solution of 2-chlorobenzaldehyde (1.8 g), 3-aminopyrazole (1.0 g) and 1-nitropentan-2-one (1.4 g) in acetonitrile (20 mL) was heated under reflux overnight. The reaction mixture was cooled to room temperature, and the solvent was evaporated under reduced pressure to give an oil. The obtained oil was purified by silica gel column chromatography (eluent:hexane-ethyl acetate (8:2)) to give the title compound (680 mg) as yellow crystals.

MP: 228° C.

Anal. Calcd. for: $C_{15}H_{15}ClN_4O_2$: C, 56.52; H, 4.74; N, 17.58. Found: C, 56.26; H, 4.91; N, 17.64.

MS (EI): 318 (M$^+$).

$^1$H-NMR (400 MHz, DMSO-d$_6$) δ (ppm): 1.02 (3H, t, J=7.3 Hz), 1.70–1.73 (2H, m), 2.89–2.91 (1H, m), 2.99–3.02 (1H, m), 5.90 (1H, s), 7.09–7.21 (3H, m), 7.39 (1H, d, J=7.3 Hz), 7.44 (1H, s), 10.84 (1H, br.s), 12.43 (1H, br.s).

Example 94

4-(2-Chlorophenyl)-5-cyano-4,7-dihydro-6-propyl-2H-pyrazolo[3,4-b]pyridine

To a solution of acetonitrile (4.8 g) in THF (150 mL) was added n-BuLi (67 mmol) at −78° C. Further, methyl butanoate (10 g) was added and the mixture was stirred for one hour. After acidification with hydrochloric acid, the mixture was extracted with ethyl acetate. The solvent was evaporated under reduced pressure and the residue was purified by silica gel column chromatography (eluent:hexane-ethyl acetate (10:1)) to give 1-cyanopentan-2-one (5.5 g) as a colorless oil. A solution of 2-chlorobenzaldehyde (1.9 g), 3-aminopyrazole (1.0 g) and 1-cyanopentan-2-one (1.6 g) in acetonitrile (20 mL) was heated under reflux overnight. The reaction mixture was cooled to room temperature, and the precipitated crystals were collected by filtration to give the title compound (1.3 g) as colorless crystals.

MP: 248° C.

Anal. Calcd. for: $C_{16}H_{15}ClN_4$: C, 64.32; H, 5.06; N, 18.75. Found: C, 64.49; H, 5.18; N, 18.81.

MS (EI): 298 (M$^+$).

$^1$H-NMR (400 MHz, DMSO-d$_6$) δ (ppm): 0.95 (3H, t, J=7.3 Hz), 1.64–1.70 (2H, m), 2.38–2.42 (2H, m), 5.36 (1H, s), 7.23–7.26 (3H, m), 7.32 (1H, dd, J=7.3 Hz and 7.4 Hz), 7.42 (1H, d, J=7.3 Hz), 9.83 (1H, br.s), 12.15 (1H, br.s).

Example 95

4-(2-Chlorophenyl)-5-cyano-4,7-dihydro-6-(4-methoxyphenyl)-2H-pyrazolo[3,4-b]pyridine To a solution of acetonitrile (76 g) in DMSO (100 mL) was added methyl p-anisate (100 g) and the mixture was stirred with heating at 60° C. for one hour. The reaction mixture was allowed to cool, and cold water (500 mL) was added dropwise. The mixture was acidified with hydrochloric acid and the precipitated crystals were collected by filtration. The obtained crystals were extracted with ethyl acetate and the solvent was evaporated under reduced pressure. The residue was recrystallized from ethyl acetate to give benzoylacetonitrile (60 g) as colorless crystals. A solution of 2-chlorobenzaldehyde (1.7 g), 3-aminopyrazole (1.0 g) and benzoylacetonitrile (1.8 g) in acetonitrile (20 mL) was heated under reflux overnight. The reaction mixture was cooled to room temperature, and the precipitated crystals were collected by filtration to give the title compound (2.63 g) as colorless crystals.

MP: 124° C.

Anal. Calcd. for: $C_{20}H_{15}ClN_4O8/5H_2O$: C, 61.34; H, 4.68; N, 14.31. Found: C, 61.32; H, 4.88; N, 14.31.

MS (EI): 362 (M$^+$).

$^1$H-NMR (400 MHz, DMSO-d$_6$) δ (ppm): 3.81 (3H, s), 5.48 (1H, s), 7.04 (2H, d, J=7.3 Hz), 7.26 (1H, dd, J=7.3 Hz and 7.4 Hz), 7.32 (1H, s), 7.35–7.39 (4H, m), 7.45 (1H, d, J=7.3 Hz), 9.99 (1H, br.s), 12.22 (1H, br.s).

Example 96

4-(2-Chlorophenyl)-2,4,7,8-tetrahydrofurano[3,4-b]pyrazolo[4,3-e]pyridin-5-one

The title compound was prepared from 2-chlorobenzaldehyde, 3-aminopyrazole and ethyl 4-chloroacetoacetate in the same manner as in Example 1.

MP: >270° C.

Anal. Calcd. for: $C_{14}H_{10}ClN_3O_2 2/5H_2O$: C, 57.02; H, 3.69; N, 14.25. Found: C, 57.13; H, 3.39; N, 14.38.

MS (FAB): 288 (M$^+$+1)

$^1$H-NMR (400 MHz, DMSO-d$_6$) δ (ppm): 4.91 (2H, dd, J=5.6 Hz and 26.6 Hz), 5.34 (1H, s), 7.15–7.24 (3H, m), 7.34 (1H, s), 7.41 (1H, d, J=6.8 Hz), 10.31 (1H, br.s), 12.20 (1H, br.s).

IR (KBr): ν=3167, 2966, 1722, 1637, 1608, 1510, 1026 cm$^{-1}$.

Example 97

5'-Ethoxycarbonyl-4',7'-dihydro-6'-propyl-spiro[benzo[b]thiophene-3(2H),4'-2'H-pyrazolo[3,4-b]pyridine]-5-oxide A solution of 2-methylthiobenzaldehyde (62 g), Meldrum's acid (58.7 g), ethyl 3-ketohexanoate (64.4 g) and ammonium acetate (40 g) in acetic acid (400 mL) was heated under reflux overnight. After the solution was cooled to room temperature, the solvent was evaporated under reduced pressure to give colorless crystals (40.2 g). To a solution of dimethylformamide (26.3 g) in chloroform (100 mL) were added, under ice-cooling, phosphorus oxychloride (33.6 mL) and a solution of the obtained colorless crystals (30 g) in chloroform (200 mL), and the mixture was stirred overnight. Under ice-cooling, an aqueous sodium acetate (370 g) solution was added and the mixture was stirred for one hour. The reaction mixture was extracted with chloroform and the solvent was evaporated under reduced pressure to give an oil. The oil was purified by silica gel column chromatography (eluent:hexane-ethyl acetate (8:2)) to give colorless crystals. To a solution of the obtained crystals in acetone (500 mL) was added diammonium cerium nitrate (42 g) and the mixture was stirred for 30 minutes. The solvent was evaporated under reduced pressure and the residue was extracted with ethyl acetate. The solvent was evaporated under reduced pressure to give colorless crystals. To a solution of the obtained colorless crystals in tetrahydrofuran (500 mL) was added metachloroperbenzoic acid (12 g) at −78° C. and the mixture was stirred for 30 minutes. An aqueous sodium thiosulfate solution was added, and the mixture was extracted with chloroform. The solvent was evaporated under reduced pressure to give colorless crystals. By recrystallization from ethyl acetate, colorless crystals (15 g) were obtained. To a solution of the obtained colorless crystals in tetrahydrofuran (100 mL) was added lithium diisopropylamide (2.5 eq.) at −78° C. Immediately thereafter, methanol and an aqueous ammonium chloride solution were added. The mixture was extracted with chloroform and the solvent was evaporated under reduced pressure to give an oil. To a solution of the obtained oil in pyridine (50 mL) was added hydrazine (4.2 g) and the mixture was stirred with heating for 2 hours. The reaction mixture was cooled to room temperature, and the solvent was evaporated under reduced pressure to give an oil. The oil was purified by silica gel column chromatography (eluent:hexane-ethyl acetate (1:1)) to give title compound (0.8 g) as colorless crystals.

MP: 246° C.

Anal. Calcd. for: $C_{19}H_{21}N_3O_3S$: C, 61.44; H, 5.70; N, 11.31. Found: C, 61.58; H, 5.81; N, 11.16.

MS (EI): 371 (M$^+$).

$^1$H-NMR (400 MHz, DMSO-d$_6$) δ (ppm): 0.70 (3H, t, J=7.3 Hz), 0.96 (3H, t, J=7.3 Hz), 1.63–1.68 (2H, m), 2.67–2.76 (2H, m), 3.07 (1H, d, J=14.9 Hz), 3.64 (2H, q, J=7.3 Hz), 4.00 (1H, d, J=14.9 Hz), 7.05–7.09 (2H, m), 7.40 (1H, dd, J=7.3 Hz and 7.4 Hz), 7.50 (1H, dd, J=7.3 Hz and 7.4 Hz), 7.81 (1H, d, J=7.3 Hz), 9.83 (1H, br.s), 12.11 (1H, br.s).

Example 98

Ethyl 4,7-dihydro-4-(2-hydroxyphenyl)-6-propyl-2H-pyrazolo[3,4-b]pyridine-5-carboxylate A solution of 2-methoxybenzaldehyde (15 g), Meldrum's acid (16 g), ethyl 3-ketohexanoate (17.4 g) and ammonium acetate (9.4 g) in acetic acid (110 mL) was heated under reflux overnight. The reaction mixture was cooled to room temperature, and the solvent was evaporated under reduced pressure to give colorless crystals (8.0 g). To a solution of the obtained colorless crystals (5.2 g) in dichloromethane (150 mL) were added ethanedithiol (20 mL) and aluminum chloride (32 g), and the mixture was stirred for 2 hours. After neutralization with 1N aqueous sodium hydroxide solution, the mixture was extracted with chloroform. The solvent was evaporated under reduced pressure to give an oil. The obtained oil was purified by silica gel column chromatography (eluent:hexane-ethyl acetate (8:2)) to give colorless crystals (2.0 g). To a solution of dimethylformamide (1.9 g) in chloroform (10 mL) were added phosphorus oxychloride (2.5 mL) and a solution of the obtained crystals in chloroform (20 mL) under ice-cooling, and the mixture was stirred overnight. Under ice-cooling, an aqueous sodium acetate (27 g) solution was added and the mixture was stirred for one hour. The mixture was extracted with chloroform and the solvent was evaporated under reduced pressure to give an oil. The obtained oil was purified by silica gel column chromatography (eluent:hexane-ethyl acetate (8:2)) to give a colorless oil (1.4 g). To a solution of the obtained oil in pyridine (10 mL) was added hydrazine (0.7 g), and the mixture was stirred with heating for 2 hours. The reaction mixture was cooled to room temperature, and the solvent was evaporated under reduced pressure to give an oil. The obtained oil was purified by silica gel column chromatography (eluent:hexane-ethyl acetate (1:1)) to give the title compound (0.2 g) as colorless crystals.

MP: 177° C.

Anal. Calcd. for: $C_{18}H_{21}N_{33}$: C, 66.04; H, 6.47; N, 12.84. Found: C, 65.96; H, 6.21; N, 12.66.

MS (EI): 327 (M$^+$).

$^1$H-NMR (400 MHz, DMSO-d$_6$) δ (ppm): 0.80 (3H, t, J=7.3 Hz), 0.96 (3H, t, J=7.3 Hz), 1.56–1.59 (2H, m), 2.70–2.80 (2H, m), 3.76 (2H, q, J=7.3 Hz), 5.50 (1H, s), 7.28–7.33 (3H, m), 7.63 (1H, dd, J=7.3 Hz and 7.4 Hz), 7.76 (1H, d, J=7.3 Hz), 9.64 (1H, br.s), 9.68 (1H, br.s), 10.12 (1H, br.s).

Example 99

Ethyl 4-(2-aminophenyl)-4,7-dihydro-6-propyl-2H-pyrazolo[3,4-b]pyridine-5-carboxylate To a solution of ethyl 4,7-dihydro-4-(2-nitrophenyl)-6-propyl-2H-pyrazolo[3,4-b]pyridine-5-carboxylate (1.68 g) in methanol (30 mL) was added 5% palladium-carbon (500 mg), and the mixture was stirred under 10 atm for 3 hours. After removing palladium-carbon by Celite filtration, the solvent was evaporated under reduced pressure to give an oil. The obtained oil was purified by silica gel column chromatography (eluent:hexane-ethyl acetate (1:1)) to give the title compound (120 mg) as colorless crystals.

MP: 179° C.

Anal. Calcd. for: $C_{18}H_{22}N_4O_2$: C, 66.24; H, 6.79; N, 17.17. Found: C, 65.96; H, 6.62; N, 17.16.

MS (EI): 326 (M$^+$).

$^1$H-NMR (400 MHz, DMSO-d$_6$) δ (ppm): 0.82 (3H, t, J=7.3 Hz), 0.98 (3H, t, J=7.3 Hz), 1.58–1.64 (2H, m), 2.72–2.78 (2H, m), 3.78 (2H, q, J=7.3 Hz), 5.52 (1H, s), 6.35–6.38 (2H, br.s), 7.28–7.36 (3H, m), 7.58 (1H, dd, J=7.3 Hz and 7.4 Hz), 7.78 (1H, d, J=7.3 Hz), 9.58 (1H, br.s), 11.48 (1H, br.s).

Example 100

Ethyl 4-(2-ethylphenyl)-4,7-dihydro-6-propyl-1H-pyrazolo[3,4-b]pyridine-5-carboxylate The title compound was prepared from 2-ethylbenzaldehyde, 3-aminopyrazole and ethyl 3-ketohexanoate in the same manner as in Example 25.

MP: 186° C.

Anal. Calcd. for: $C_{20}H_{25}N_3O_2 1/5H_2O$: C, 70.03; H, 7.46; N, 12.25. Found: C, 69.91; H, 7.53; N, 11.98.

MS (EI): 339 (M$^+$).

$^1$H-NMR (400 MHz, DMSO-d$_6$) δ (ppm): 0.86 (3H, t, J=7.3 Hz), 0.94 (3H, t, J=7.3 Hz), 1.24 (3H, t, J=7.3 Hz), 1.64 (2H, q, J=7.3 Hz), 2.64–2.68 (1H, m), 2.77–2.86 (3H, m), 3.78 (2H, q, J=7.3 Hz), 5.34 (1H, s), 6.98–7.01 (3H, m), 7.07–7.10 (2H, m), 9.34 (1H, s), 11.89 (1H, s).

Example 101

Ethyl 4,7-dihydro-6-propyl-4-(2-propylphenyl)-1H-pyrazolo[3,4-b]pyridine-5-carboxylate The title compound was prepared from 2-propylbenzaldehyde, 3-aminopyrazole and ethyl 3-ketohexanoate in the same manner as in Example 25.

MP: 197° C.

Anal. Calcd. for: $C_{21}H_{27}N_3O_2$: C, 71.36; H, 7.70; N, 11.89. Found: C, 71.07; H, 7.73; N, 11.84.

MS (EI): 353 (M$^+$).

$^1$H-NMR (400 MHz, DMSO-d$_6$) δ (ppm): 0.87 (3H, t, J=7.3 Hz), 0.94–1.00 (6H, m), 1.64 (2H, q, J=7.3 Hz), 2.68–2.80 (4H, m), 3.79 (2H, q, J=7.3 Hz), 5.33 (1H, s), 6.98–7.06 (5H, m), 9.34 (1H, s), 11.88 (1H, s).

Example 102

Ethyl 4-(2-butylphenyl)-4,7-dihydro-6-propyl-1H-pyrazolo[3,4-b]pyridine-5-carboxylate The title compound was prepared from 2-butylbenzaldehyde, 3-aminopyrazole and ethyl 3-ketohexanoate in the same manner as in Example 25.

MP: 175° C.

Anal. Calcd. for: $C_{22}H_{29}N_3O_2$: C, 71.90; H, 7.95; N, 11.43. Found: C, 71.50; H, 7.94; N, 11.36.

MS (EI): 367 (M$^+$).

$^1$H-NMR (400 MHz, DMSO-d$_6$) δ (ppm): 0.87 (3H, t, J=7.3 Hz), 0.92–0.97 (6H, m), 1.40 (2H, q, J=7.3 Hz), 1.60–1.66 (4H, m), 2.70–2.82 (4H, m), 3.80 (2H, q, J=7.3 Hz), 5.33 (1H, s), 6.97–7.06 (5H, m), 9.34 (1H, s), 11.88 (1H, s).

Example 103

Ethyl 4,7-dihydro-4-(indan-4-yl)-6-propyl-2H-pyrazolo[3,4-b]pyridine-5-carboxylate The title compound was prepared from indan-4-aldehyde, 3-aminopyrazole and ethyl 3-ketohexanoate in the same manner as in Example 1.

MP: 181–183° C.

Anal. Calcd. for: $C_{21}H_{25}N_3O_2$: C, 71.77; H, 7.17; N, 11.96. Found: C, 71.66; H, 7.14; N, 11.88.

MS (EI): 351 (M$^+$).

$^1$H-NMR (400 MHz, DMSO-d$_6$) δ (ppm): 0.90 (3H, t, J=7.3 Hz), 0.90 (3H, t, J=7.3 Hz), 1.62 (2H, m), 1.80–2.10 (2H, m), 2.52–3.10 (6H, m), 3.77 (2H, q, J=7.3 Hz), 5.17 (1H, s), 6.81 (1H, d, J=6.8 Hz), 6.91–6.96 (2H, m), 7.14 (1H, s), 9.33 (1H, br.s), 11.87 (1H, br.s).

Example 104

Ethyl 4,7-dihydro-6-propyl-4-(1,2,3,4-tetrahydronaphthalen-5-yl)-2H-pyrazolo[3,4-b]pyridine-5-carboxylate

Example 105

Ethyl 4-(benzo[b]furan-7-yl)-4,7-dihydro-6-propyl-2H-pyrazolo[3,4-b]pyridine-5-carboxylate

Example 106

Ethyl 4-(benzo[b]thiophen-7-yl)-4,7-dihydro-6-propyl-2H-pyrazolo[3,4-b]pyridine-5-carboxylate The title compound was prepared from benzo[b]thiophene-7-aldehyde, 3-aminopyrazole and ethyl 3-ketohexanoate in the same manner as in Example 25.

MP: 166° C.

Anal. Calcd. for: $C_{20}H_{21}N_3O_2S2H_2O$: C, 59.53; H, 6.25; N, 10.41. Found: C, 59.77; H, 6.46; N, 9.95.

MS (EI): 367 (M$^+$).

$^1$H-NMR (400 MHz, DMSO-d$_6$) δ (ppm): 0.74 (3,t, J=7.3 Hz), 0.97 (3H, t, J=7.3 Hz), 1.65–1.69 (2H, m), 2.70–2.80 (2H, m), 3.71 (2H, q, J=7.3 Hz), 5.48 (1H, s), 7.11–7.13 (2H, m), 7.26 (1H, dd, J=7.4 Hz and 7.5 Hz), 7.39 (1H, d, J=5.4 Hz), 7.63 (1H, d, J=7.3 Hz), 7.68 (1H, d, J=5.4 Hz), 9.57 (1H, s), 11.91 (1H, s).

Example 107

5'-Ethoxycarbonyl-4',7'-dihydro-6'-propyl-spiro [benzo[b]thiophene-3(2H),4'-2'H-pyrazolo[3,4-b] pyridine]

To a solution of 5'-ethoxycarbonyl-4',7'-dihydro-6'-propyl-spiro[benzo[b]thiophene-3(2H),4'-2'H-pyrazolo[3,4-b]pyridine]-1-oxide (100 mg) in carbon tetrachloride (20 mL) was added trimethylsilane iodide (0.1 g), and the mixture was stirred with heating for 30 minutes. The reaction mixture was allowed to cool to ambient temperature, and the mixture was extracted with chloroform. The solvent was evaporated under reduced pressure to give an oil. The obtained oil was purified by silica gel column chromatography (eluent:hexane-ethyl acetate (8:2)) to give the title compound (20 mg) as colorless crystals.

MP: 147° C.

Anal. Calcd. for: $C_{19}H_{21}N_3O_2S$: C, 64.20; H, 5.95; N, 11.82. Found: C, 64.18; H, 6.14; N, 11.56.

MS (EI): 355 (M$^+$).

$^1$H-NMR (400 MHz, DMSO-d$_6$) δ (ppm): 0.73 (3H, t, J=7.3 Hz), 0.95 (3H, t, J=7.3 Hz), 1.64–1.67 (2H, m), 2.56–2.64 (2H, m), 3.03 (1H, d, J=10.2 Hz), 3.72 (2H, q, J=7.3 Hz), 4.03 (1H, d, J=10.2 Hz), 6.69 (1H, d, J=7.3 Hz), 6.91 (1H, dd, J=7.3 Hz and 7.4 Hz), 7.03 (1H, dd, J=7.3 Hz and 7.4 Hz), 7.08 (1H, s), 7.15 (1H, d, J=7.3 Hz), 9.65 (1H, br.s), 11.96 (1H, br.s).

Example 108

Ethyl 4,7-dihydro-4-methyl-4-phenyl-6-propyl-2H-pyrazolo[3,4-b]pyridine-5-carboxylate To a solution of 5'-ethoxycarbonyl-4',7'-dihydro-6'-propyl-spiro[benzo[b]thiophene-3(2H),4'-2'H-pyrazolo[3,4-b]pyridin]-1-oxide (100 mg) in tetrahydrofuran (10 mL) were added disodium hydrogenphosphate (1.2 g) and methanol (5 mL) under ice-cooling, and 10% sodium amalgam (3.0 g) was added. The mixture was stirred for 5 hours, filtered through Celite and extracted with chloroform. The solvent was evaporated under reduced pressure to give an oil. The obtained oil was purified by silica gel column chromatography (eluent:hexane-ethyl acetate (8:2)) to give the title compound (80 mg) as colorless crystals.

MP: 207° C.

Anal. Calcd. for: $C_9H_{23}N_3O_2$: C, 70.13; H, 7.12; N, 12.91. Found: C, 69.89; H, 7.18; N, 12.99.

MS (EI): 325 (M$^+$).

$^1$H-NMR (400 MHz, DMSO-d$_6$) δ (ppm): 0.71 (3H, t, J=7.3 Hz), 0.96 (3H, t, J=7.3 Hz), 1.64–1.68 (2H, m), 2.28 (3H, s), 2.48–2.56 (2H, m), 3.71 (2H, q, J=7.3 Hz), 6.73–7.01 (5H, m), 7.10 (1H, s), 9.71 (1H, br.s), 11.87 (1H, br.s).

Example 109

Ethyl 4,7-dihydro-6-propyl-4-(2,3,5-trichlorophenyl)-pyrazolo[3,4-b]pyridine-5-carboxylate The title compound was prepared from 2,3,5-trichlorobenzaldehyde, 3-aminopyrazole and ethyl 3-ketohexanoate in the same manner as in Example 25.

MP: 218–220° C. (decomposition).

Anal. Calcd. for: $C_{18}H_{18}Cl_3N_3O_2$: C, 52.13; H, 4.37; N, 10.13. Found: C, 51.76; H, 4.37; N, 10.07.

MS (EI): 414 (M$^+$).

$^1$H-NMR (400 MHz, DMSO-d$_6$) δ (ppm): 0.89 (3H, t, J=6.9 Hz), 0.97 (3H, t, J=7.3 Hz), 1.62–1.67 (2H, m), 2.65–2.71 (1H, m), 2.85–2.92 (1H, m), 3.76–3.88 (2H, m), 5.62 (1H, s), 7.03 (1H, d, J=1.6 Hz), 7.33 (1H, s), 7.59 (1H, d, J=2.4 Hz), 9.69 (1H, s), 12.12 (1H, s).

Example 110

Ethyl 4,7-dihydro-6-propyl-4-(2,3,4,5-tetrahydrobenzo[b]oxepin-9-yl)-2H-pyrazolo[3,4-b] pyridine-5-carboxylate

Example 111

Ethyl 4-(3-chloro-2-methylphenyl)-4,7-dihydro-6-propyl-2H-pyrazolo[3,4-b]pyridine-5-carboxylate The title compound was prepared from 3-chloro-2-methylbenzaldehyde, 3-aminopyrazole and ethyl 3-ketohexanoate in the same manner as in Example 1.

MP: 185° C.

Anal. Calcd. for: $C_{19}H_{22}ClN_3O_2$: C, 63.42; H, 6.16; N, 11.68. Found: C, 63.37; H, 6.12; N, 11.65.

MS (EI): 359 (M$^+$).

$^1$H-NMR (400 MHz, DMSO-d$_6$) δ (ppm): 0.87 (3H, t, J=7.3 Hz), 0.95 (3H, t, J=7.3 Hz), 1.60–1.66 (2H, m), 2.67–2.69 (1H, m), 2.74–2.78 (1H, m), 3.78 (2H, q, J=7.3 Hz), 5.39 (1H, s), 6.95 (1H, d, J=7.3 Hz), 7.04 (1H, dd, J=7.3 Hz and 7.4 Hz), 7.12 (1H, d, J=7.3 Hz), 7.24 (1H, s), 9.44 (1H, br.s), 11.94 (1H, br.s).

Example 112

Ethyl 4-(2,1,3-benzothiadiazol-4-yl)-4,7-dihydro-6-propyl-2H-pyrazolo[3,4-b]pyridine-5-carboxylate The title compound was prepared from 2,1,3-benzothiadiazole-4-aldehyde, 3-aminopyrazole and ethyl 3-ketohexanoate in the same manner as in Example 25.

MP: 180° C.

Anal. Calcd. for: $C_{18}H_{19}N_5O_2S$: C, 8.52; H, 5.18; N, 18.96. Found: C, 58.51; H, 5.19; N, 18.81.

MS (EI): 369 (M$^+$).

$^1$H-NMR (400 MHz, DMSO-d$_6$) δ (ppm): 0.62 (3H, t, J=7.3 Hz), 1.00 (3H, t, J=7.3 Hz), 1.68–1.72 (2H, m), 2.76–2.89 (2H, m), 3.72 (2H, q, J=7.3Hz), 6.02 (1H, s), 7.16 (1H, s), 7.20 (1H, d, J=7.3 Hz), 7.60 (1H, dd, J=7.3 Hz and 7.4 Hz), 7.83 (1H, d, J=7.3 Hz), 9.55 (1H, s), 11.89 (1H, s).

Example 113

Ethyl 4-(2,1,3-benzoxadiazol-4-yl)-4,7-dihydro-6-methyl-2H-pyrazolo[3,4-b]pyridine-5-carboxylate The title compound was prepared from 2,1,3-benzoxadiazole-4-aldehyde, 3-aminopyrazole and ethyl acetoacetate in the same manner as in Example 25.

MP: 228° C.

Anal. Calcd. for: $C_{16}H_{15}N_5O_3$: C, 59.07; H, 4.65; N, 21.53. Found: C, 58.85; H, 4.75; N, 21.17.

MS (EI): 325 (M$^+$).

$^1$H-NMR (400 MHz, DMSO-d$_6$) δ (ppm): 0.75 (3H, t, J=7.3 Hz), 2.42 (3H, s), 3.79 (2H, q, J=7.3 Hz), 5.67 (1H, s), 7.14 (1H, d, J=6.6 Hz), 7.23 (1H, s), 7.49 (1H, dd, J=9.0 Hz and 6.6 Hz), 7.78 (1H, d, J=9.0 Hz), 9.69 (1H, s), 12.02 (1H, s).

Example 114

Ethyl 4-(2,1,3-benzoxadiazol-4-yl)-4,7-dihydro-6-phenyl-2H-pyrazolo[3,4-b]pyridine-5-carboxylate The title compound was prepared from 2,1,3-benzoxadiazole-4-aldehyde, 3-aminopyrazole and ethyl benzoylacetate in the same manner as in Example 1.

MP: 190° C.

Anal. Calcd. for: $C_{21}H_{17}N_5O_3$: C, 65.11; H, 4.42; N, 18.08. Found: C, 64.99; H, 4.59; N, 18.06.

MS (EI): 387 (M$^+$).

$^1$H-NMR (400 MHz, DMSO-d$_6$) δ (ppm): 0.54 (3H, t, J=7.3 Hz), 3.56 (2H, q, J=7.3 Hz), 5.68 (1H, s), 7.24 (1H, s), 7.26–7.42 (6H, m), 7.72 (1H, dd, J=7.3 Hz and 7.2 Hz), 7.94 (1H, d, J=7.3 Hz), 9.71 (1H, s), 12.08 (1H, s).

Example 115

Ethyl 4-(2,3-dichlorophenyl)-4,7-dihydro-6-phenyl-2H-pyrazolo[3,4-b]pyridine-5-carboxylate The title compound was prepared from 2,3-dichlorobenzaldehyde, 3-aminopyrazole and ethyl benzoylacetate in the same manner as in Example 1.

MP: 214° C.

Anal. Calcd. for: $C_{21}H_{17}N_5O_3$: C, 65.11; H, 4.42; N, 18.08. Found: C, 64.85; H, 4.48; N, 17.92.

MS (EI): 387 (M$^+$).

$^1$H-NMR (400 MHz, DMSO-d$_6$) δ (ppm): 0.57 (3H, t, J=7.3 Hz), 3.52 (2H, q, J=7.3 Hz), 5.70 (1H, s), 7.30–7.40 (9H, m), 9.61 (1H, s), 12.12 (1H, s).

Example 116

(+)Ethyl 4-(2,1,3-benzoxadiazol-4-yl)-4,7-dihydro-6-propyl-2H-pyrazolo[3,4-b]pyridine-5-carboxylate The compound described in Example 76 was separated using a semi-preparative column for optical resolution (CHIRALPAK AS, 1.0 cm×25 cm, eluent n-hexane/2-propanol/diethylamine=90/10/0.1, flow rate 2.0 mL/min, UV 254 nm, retention time 40 minutes, DAICEL CHEMICAL INDUSTRIES, LTD.) to give the title compound as colorless crystals.

MP: 159° C.

MS (EI): 353 (M$^+$).

Specific rotation: [a]$_D$=+260° (EtOH, c=0.5).

Example 117

(−)Ethyl 4-(2,1,3-benzoxadiazol-4-yl)-4,7-dihydro-6-propyl-2H-pyrazolo[3,4-b]pyridine-5-carboxylate The compound described in Example 76 was separated using a semi-preparative column for optical resolution (CHIRALPAK AS, 1.0 cm×25 cm, eluent n-hexane/2-propanol/diethylamine=90/10/0.1, flow rate 2.0 mL/min, UV 254 nm, retention time 55 minutes, DAICEL CHEMICAL INDUSTRIES, LTD.) to give the title compound as colorless crystals.

MP: 160° C.

MS (EI): 353 (M$^+$).

Specific rotation: [a]$_D$=−277° (EtOH, c=0.5).

Example 118

4-(2-Bromophenyl)-4,7-dihydro-5-nitro-6-propyl-2H-pyrazolo[3,4-b]pyridine

The title compound was prepared from n-butylaldehyde, 2-bromobenzaldehyde and 3-aminopyrazole in the same manner as in Example 93.

MP: 226° C.

Anal. Calcd. for: $C_{15}H_{15}BrN_4O_2$: C, 49.60; H, 4.16; N, 15.43. Found: C, 49.57; H, 4.28; N, 14.96.

MS (EI): 363 (M$^+$).

$^1$H-NMR (400 MHz, DMSO-d$_6$) δ (ppm): 1.02 (3H, t, J=7.3 Hz), 1.72–1.76 (2H, m), 2.85–3.05 (2H, m), 5.89 (1H, s), 7.07–7.1 (2H, m), 7.25 (1H, dd, J=7.5 Hz and 7.4 Hz), 7.47 (1H, s), 7.56 (1H, d, J=7.3 Hz), 10.84 (1H, s), 12.43 (1H, s).

Example 119

4,7-Dihydro-4-(2-methoxyphenyl)-5-nitro-6-propyl-2H-pyrazolo[3,4-b]pyridine

The title compound was prepared from n-butylaldehyde, 2-methoxybenzaldehyde and 3-aminopyrazole in the same manner as in Example 93.

MP: 223° C.

Anal. Calcd. for: $C_{16}H_{18}N_4O_3$: C, 61.13; H, 5.77; N, 17.82. Found: C, 61.01; H, 5.87; N, 17.92.

MS (EI): 314 (M$^+$).

$^1$H-NMR (400 MHz, DMSO-d$_6$) δ (ppm): 1.03 (3H, t, J=7.3 Hz), 1.72–1.78 (2H, m), 2.82–3.04 (2H, m), 3.86 (3H, s), 5.76 (1H, s), 6.78 (1H, dd, J=7.5 Hz and 7.4 Hz), 6.90 (1H, d, J=7.3 Hz), 6.95 (1H, d, J=7.3 Hz), 7.10 (1H, dd, J=7.5 Hz and 7.4 Hz), 7.33 (1H, s), 10.68 (1H, s), 12.29 (1H, s).

Example 120

4,7-Dihydro-4-(2-methylthiophenyl)-5-nitro-6-propyl-2H-pyrazolo[3,4-b]pyridine

The title compound was prepared from n-butylaldehyde, 2-methylthiobenzaldehyde and 3-aminopyrazole in the same manner as in Example 93.

MP: 211° C.

Anal. Calcd. for: $C_{16}H_{18}N_4O_2S$: C, 58.16; H, 5.49; N, 16.96. Found: C, 57.94; H, 5.47; N, 16.53.

MS (EI): 330 (M$^+$).

$^1$H-NMR (400 MHz, DMSO-d$_6$) δ (ppm): 1.02 (3H, t, J=7.3z), 1.71–1.76 (2H, m), 2.8–3.00 (2H, m), 5.89 (1H, s), 6.98 (1H, d, J=7.3 Hz), 7.03 (1H, dd, J=7.5 Hz and 7.4 Hz), 7.13 (1H, dd, J=7.5 Hz and 7.4 Hz), 7.28 (1H, d, J=7.3 Hz), 7.41 (1H, s), 10.74 (1H, s), 12.34 (1H, s).

Example 121

4,7-Dihydro-5-nitro-4-(2-nitrophenyl)-6-propyl-2H-pyrazolo[3,4-b]pyridine

The title compound was prepared from n-butylaldehyde, 2-nitrobenzaldehyde and 3-aminopyrazole in the same manner as in Example 93.

MP: 204° C.

Anal. Calcd. for: $C_{15}H_{15}N_5O_4$: C, 54.71; H, 4.59; N, 21.27. Found: C, 54.50; H, 4.77; N, 21.32.

MS (EI): 329 (M$^+$).

¹H-NMR (400 MHz, DMSO-d₆) δ (ppm): 1.01 (3H, t, J=7.3 Hz), 1.69–1.74 (2H, m), 2.85–2.99 (2H, m), 5.67 (1H, s), 6.94 (1H, d, J=7.3 Hz), 6.98–7.03 (2H, m), 7.09 (1H, d, J=7.3 Hz), 7.38 (1H, s), 10.69 (1H, s), 12.34 (1H, s).

Example 122

4-(2,3-Dichlorophenyl)-4,7-dihydro-5-nitro-6-propyl-2H-pyrazolo[3,4-b]pyridine

The title compound was prepared from n-butylaldehyde, 2,3-dichlorobenzaldehyde and 3-aminopyrazole in the same manner as in Example 93.

MP: 239° C.

Anal. Calcd. for: $C_{15}H_{14}Cl_2N_4O_2$: C, 51.01; H, 4.00; N, 15.86. Found: C, 50.70; H, 4.06; N, 15.60.

MS (EI): 353 (M⁺).

¹H-NMR (400 MHz, DMSO-d₆) δ (ppm): 1.02 (3H, t, J=7.3 Hz), 1.70–1.74 (2H, m), 2.89–2.92 (1H, m), 2.96–3.02 (1H, m), 5.96 (1H, s), 7.09 (1H, d, J=7.3 Hz), 7.24 (1H, dd, J=7.5 Hz and 7.4 Hz), 7.43 (1H, d, J=7.3 Hz), 7.49 (1H, s), 10.98 (1H, s), 12.49 (1H, s).

Example 123

4,7-Dihydro-4-(naphthalen-1-yl)-5-nitro-6-propyl-2H-pyrazolo[3,4-b]pyridine

The title compound was prepared from n-butylaldehyde, naphthalen-1-aldehyde and 3-aminopyrazole in the same manner as in Example 93.

MP: 226° C.

Anal. Calcd. for: $C_{19}H_{18}N_4O_2$: C, 68.25; H, 5.43; N, 16.76. Found: C, 68.29; H, 5.20; N, 16.67.

MS (EI): 334 (M⁺).

¹H-NMR (400 MHz, DMSO-d₆) δ (ppm): 1.06 (3H, t, J=7.3 Hz), 1.76–1.82 (2H, m), 2.95–3.06 (2H, m), 6.33 (1H, s), 7.18–7.22 (2H, m), 7.36 (1H, dd, J=7.5 Hz and 7.4 Hz), 7.54 (1H, dd, J=7.5 Hz and 7.4 Hz), 7.60 (1H, dd, J=7.5 Hz and 7.4 Hz), 7.71 (1H, d, J=7.3 Hz), 7.92 (1H, d, J=7.3 Hz), 8.46 (1H, d, J=7.3 Hz), 10.80 (1H, s), 12.29 (1H, s).

Example 124

4,7-Dihydro-4-(3,4-dihydro-2H-benzopyran-8-yl)-5-nitro-6-propyl-2H-pyrazolo[3,4-b]pyridine The title compound was prepared from n-butylaldehyde, 3,4-dihydro-2H-benzopyran-8-aldehyde and 3-aminopyrazole in the same manner as in Example 93.

MP: 234° C.

Anal. Calcd. for: $C_{13}H_{20}N_4O_3$: C, 63.52; H, 5.92; N, 16.46. Found: C, 63.22; H, 5.94; N, 16.44.

MS (EI): 340 (M⁺).

¹H-NMR (400 MHz, DMSO-d₆) δ (ppm): 1.02 (3H, t, J=7.3 Hz), 1.71–1.77 (2H, m), 1.92–1.95 (2H, m), 2.69–2.73 (2H, m), 2.85–3.02 (2H, m), 4.23–4.28 (2, m), 5.71 (1H, s), 6.61–6.67 (2H, m), 6.80 (1H, d, J=7.3 Hz), 7.37 (1H, s), 10.64 (1H, s), 12.28 (1H, s).

Example 125

4-(2,3-Dichlorophenyl)-4,7-dihydro-6-methyl-5-nitro-2H-pyrazolo[3,4-b]pyridine

The title compound was prepared from acetaldehyde, 2,3-dichlorobenzaldehyde and 3-aminopyrazole in the same manner as in Example 93.

MP: >270° C.

Anal. Calcd. for: $C_{13}H_{10}Cl_2N_4O_2$: C, 48.02; H, 3.10; N, 17.23. Found: C, 48.05; H, 3.12; N, 17.24.

MS (EI): 325 (M⁺).

¹H-NMR (400 MHz, DMSO-d₆) δ (ppm): 2.66 (3H, s), 5.94 (1H, s), 7.13 (1H, d, J=7.2 Hz), 7.22 (1H, dd, J=7.3 Hz and 7.2 Hz), 7.42 (1H, d, J=7.3 Hz), 7.50 (1H, s), 10.94 (1H, s), 12.49 (1H, s).

Example 126

4-(2,3-Dichlorophenyl)-6-ethyl-4,7-dihydro-5-nitro-2H-pyrazolo[3,4-b]pyridine

The title compound was prepared from propionaldehyde, 2,3-dichlorobenzaldehyde and 3-aminopyrazole in the same manner as in Example 93.

MP: 250° C.

Anal. Calcd. for: $C_{14}H_{12}Cl_2N_4O_2$: C, 49.58; H, 3.57; N, 16.52. Found: C, 49.54; H, 3.62; N, 16.73.

MS (EI): 339 (M⁺).

¹H-NMR (400 MHz, DMSO-d₆) δ (ppm): 1.29 (3H, t, J=7.3 Hz), 2.98–3.01 (2H, m), 5.94 (1H, s), 7.10 (1H, d, J=7.3 Hz), 7.24 (1H, dd, J=7.3 Hz and 7.2 Hz), 7.42 (1H, d, J=7.2 Hz), 7.49 (1H, s), 10.93 (1H, s), 12.49 (1H, s).

Example 127

6-Butyl-4-(2,3-dichlorophenyl)-4,7-dihydro-5-nitro-2H-pyrazolo[3,4-b]pyridine

The title compound was prepared from pentylaldehyde, 2,3-dichlorobenzaldehyde and 3-aminopyrazole in the same manner as in Example 93.

MP: 220° C.

Anal. Calcd. for: $C_{16}H_{16}Cl_2N_4O_2$: C, 52.33; H, 4.39; N, 15.26. Found: C, 52.64; H, 4.61; N, 14.51.

MS (EI): 367 (M⁺).

¹H-NMR (400 MHz, DMSO-d₆) δ (ppm): 0.94 (3H, t, J=7.3 Hz), 1.41–1.46 (2H, m), 1.63–1.68 (2H, m), 2.94–3.04 (2H, m), 5.95 (1H, s), 7.08 (1H, d, J=7.2 Hz), 7.23 (1H, dd, J=7.3 Hz and 7.2 Hz), 7.42 (1H, d, J=7.2 Hz), 7.48 (1H, s), 10.97 (1H, s), 12.28 (1H, s).

Example 128

4-(2-Bromophenyl)-5-cyano-4,7-dihydro-6-propyl-2H-pyrazolo[3,4-b]pyridine

The title compound was prepared from methyl butanoate, 2-bromobenzaldehyde and 3-aminopyrazole in the same manner as in Example 94.

MP: 237° C.

Anal. Calcd. for: $C_{16}H_{15}BrN_4$: C, 55.99; H, 4.41; N, 16.32. Found: C, 55.97; H, 4.45; N, 16.40.

MS (EI): 343 (M⁺).

¹H-NMR (400 MHz, DMSO-d₆) δ (ppm): 0.95 (3H, t, J=7.3 Hz), 1.64–1.70 (2, m), 2.40–2.44 (2H, m), 5.35 (1H, s), 7.15 (1H, dd, J=7.5 Hz and 7.4 Hz), 7.22 (1H, d, J=7.3 Hz), 7.27 (1H, s), 7.36 (1H, dd, J=7.5 Hz and 7.4 Hz), 7.59 (1H, d, J=7.3 Hz), 9.84 (1H, s), 12.16 (1H, s).

Example 129

5-Cyano-4,7-dihydro-4-(2-methoxyphenyl)-6-propyl-2H-pyrazolo[3,4-b]pyridine

The title compound was prepared from methyl butanoate, 2-methoxybenzaldehyde and 3-aminopyrazole in the same manner as in Example 94.

MP: 203° C.

Anal. Calcd. for: $C_{17}H_{18}N_4O$: C, 69.37; H, 6.16; N, 19.03. Found: C, 69.34; H, 6.25; N, 19.01.

MS (EI): 294 (M+).

$^1$H-NMR (400 MHz, DMSO-$d_6$) δ (ppm): 0.96 (3H, t, J=7.3 Hz), 1.65–1.70 (2H, m), 2.38–2.43 (2H, m), 3.83 (3H, s), 5.22 (1H, s), 6.89 (1H, dd, J=7.5 Hz and 7.4 Hz), 6.99 (1H, d, J=7.3 Hz), 7.05 (1H, d, J=7.3 Hz), 7.15–7.18 (2H, m), 9.65 (1H, s), 12.02 (1H, s).

Example 130

5-Cyano-4,7-dihydro-4-(2-methylthiophenyl)-6-propyl-2H-pyrazolo[3,4-b]pyridine

The title compound was prepared from methyl butanoate, 2-methylthiobenzaldehyde and 3-aminopyrazole in the same manner as in Example 94.

MP: 216° C.

Anal. Calcd. for: $C_{17}H_{18}N_4S$: C, 65.78; H, 5.84; N, 18.05. Found: C, 65.68; H, 5.81; N, 17.83.

MS (EI): 310 (M+).

$^1$H-NMR (400 MHz, DMSO-$d_6$) δ (ppm): 0.96 (3H, t, J=7.3 Hz), 1.65–1.70 (2H, m), 2.40–2.46 (2H, m), 2.48 (3H, s), 5.34 (1H, s), 7.13–7.21 (4H, m), 7.30 (1H, d, J=7.3 Hz), 9.75 (1H, s), 12.07 (1H, s).

Example 131

5-Cyano-4,7-dihydro-4-(2-methylphenyl)-6-propyl-2H-pyrazolo[3,4-b]pyridine

The title compound was prepared from methyl butanoate, 2-methylbenzaldehyde and 3-aminopyrazole in the same manner as in Example 94.

MP: 230° C.

Anal. Calcd. for: $C_{17}H_{18}N_4$: C, 73.35; H, 6.52; N, 20.13. Found: C, 73.44; H, 6.61; N, 20.13.

MS (EI): 278 (M+).

$^1$H-NMR (400 MHz, DMSO-$d_6$) δ (ppm): 0.93 (3H, t, J=7.3 Hz), 1.65–1.67 (2H, m), 2.32 (3H, s), 2.35–2.41 (2H, m), 5.13 (1H, s), 7.06–7.16 (5H, m), 9.69 (1H, s), 12.07 (1H, s).

Example 132

5-Cyano-4,7-dihydro-4-(2-nitrophenyl)-6-propyl-2H-pyrazolo[3,4-b]pyridine

The title compound was prepared from methyl butanoate, 2-nitrobenzaldehyde and 3-aminopyrazole in the same manner as in Example 94.

MP: 216° C.

Anal. Calcd. for: $C_{16}H_{15}N_5O_2$: C, 62.13; H, 4.89; N, 22.64. Found: C, 62.16; H, 4.93; N, 22.57.

MS (EI): 309 (M+).

$^1$H-NMR (400 MHz, DMSO-$d_6$) δ (ppm): 0.94 (3H, t, J=7.3 Hz), 1.64–1.69 (2H, m), 2.36–2.42 (2H, m), 5.38 (1H, s), 7.27 (1H, s), 7.42–7.49 (2H, m), 7.70 (1H, dd, J=7.5 Hz and 7.4 Hz), 7.89 (1H, d, J=7.3 Hz), 9.91 (1H, s), 12.21 (1H, s).

Example 133

5-Cyano-4-(2-cyanophenyl)-4,7-dihydro-6-propyl-2H-pyrazolo[3,4-b]pyridine

The title compound was prepared from methyl butanoate, 2-cyanobenzaldehyde and 3-aminopyrazole in the same manner as in Example 94.

MP: 218° C.

Anal. Calcd. for: $C_{17}H_{15}N_5$: C, 70.57; H, 5.23; N, 24.21. Found: C, 70.54; H, 5.30; N, 24.07.

MS (EI): 289 (M+).

$^1$H-NMR (400 MHz, DMSO-$d_6$) δ (ppm): 0.94 (3H, t, J=7.3 Hz), 1.63–1.68 (2H, m), 2.36–2.40 (2H, m), 5.23 (1H, s), 7.26 (1H, s), 7.38 (1H, d, J=7.3 Hz), 7.43 (1H, dd, J=7.5 Hz and 7.4 Hz), 7.69 (1H, dd, J=7.5 Hz and 7.4 Hz), 7.80 (1H, d, J=7.3 Hz), 9.94 (1H, s), 12.22 (1H, s).

Example 134

5-Cyano-4-(2,3-dichlorophenyl)-4,7-dihydro-6-propyl-2H-pyrazolo[3,4-b]pyridine

The title compound was prepared from methyl butanoate, 2,3-dichlorobenzaldehyde and 3-aminopyrazole in the same manner as in Example 94.

MP: 242° C.

Anal. Calcd. for: $C_{16}H_{14}Cl_2N_4 1/5H_2O$: C, 57.05; H, 4.31; N, 16.63. Found: C, 57.23; H, 4.49; N, 16.25.

MS (EI): 333 (M+).

$^1$H-NMR (400 MHz, DMSO-$d_6$) δ (ppm): 0.94 (3H, t, J=7.3 Hz), 1.62–1.68 (2H, m), 2.40–2.46 (2H, m), 5.44 (1H, s), 7.22 (1H, d, J=7.3 Hz), 7.30 (1H, s), 7.35 (1H, dd, J=7.5 Hz and 7.4 Hz), 7.51 (1H, d, J=7.3 Hz), 9.89 (1H, s), 12.19 (1H, s).

Example 135

5-Cyano-4,7-dihydro-4-(naphthalen-1-yl)-6-propyl-2H-pyrazolo[3,4-b]pyridine

The title compound was prepared from methyl butanoate, naphthalene-1-aldehyde and 3-aminopyrazole in the same manner as in Example 94.

MP: 263° C.

Anal. Calcd. for: $C_{20}H_{18}N_4$: C, 76.41; H, 5.77; N, 17.82. Found: C, 76.05; H, 5.85; N, 17.73.

MS (EI): 314 (M+).

$^1$H-NMR (400 MHz, DMSO-$d_6$) δ (ppm): 0.97 (3H, t, J=7.3 Hz), 1.68–1.73 (2H, m), 2.44–2.48 (2H, m), 5.71 (1H, s), 7.04 (1H, s), 7.39–7.46 (4H, m), 7.81 (1H, d, J=7.3 Hz), 7.94 (1H, d, J=7.3 Hz), 9.83 (1H, s), 12.02 (1H, s).

Example 136

5-Cyano-4-(3,4-dihydro-2H-benzopyran-8-yl)-4,7-dihydro-6-propyl-2H-pyrazolo[3,4-b]pyridine The title compound was prepared from methyl butanoate, 3,4-dihydro-2H-benzopyran-8-aldehyde and 3-aminopyrazole in the same manner as in Example 94.

MP: 230° C.

Anal. Calcd. for: $C_{19}H_{20}N_4O$: C, 71.23; H, 6.29; N, 17.49. Found: C, 71.20; H, 6.48; N, 17.55.

MS (EI): 320 (M+).

$^1$H-NMR (400 MHz, DMSO-$d_6$) δ (ppm): 0.95 (3H, t, J=7.3 Hz), 1.64–1.70 (2H, m), 1.92–1.95 (2H, m), 2.38–2.43 (2H, m), 2.72–2.76 (2H, m), 4.16–4.27 (2H, m), 5.16 (1H, s), 6.74 (1H, dd, J=7.5 Hz and 7.4 Hz), 6.83–6.88 (2H, m), 7.20 (1H, s), 9.62 (1H, s), 12.01 (1H, s).

Example 137

4-(2,1,3-Benzoxadiazol-4-yl)-5-cyano-4,7-dihydro-6-propyl-2H-pyrazolo[3,4-b]pyridine The title compound was prepared from methyl butanoate, 2,1,3-benzothiadiazole-4-aldehyde and 3-aminopyrazole in the same manner as in Example 94.

MP: 194° C.

Anal. Calcd. for: $C_{16}H_{14}N_6O$: C, 62.73; H, 4.61; N, 27.44. Found: C, 62.52; H, 4.78; N, 27.19.

MS (EI): 306 (M$^+$).

$^1$H-NMR (400 MHz, DMSO-d$_6$) δ (ppm): 0.92 (3H, t, J=7.3 Hz), 1.63–1.68 (2H, m), 2.38–2.43 (2H, m), 5.40 (1H, s), 7.25 (1H, s), 7.40 (1H, d, J=7.3 Hz), 7.58 (1H, dd, J=7.5 Hz and 7.4 Hz), 7.92 (1H, d, J=7.3z), 9.93 (1H, s), 12.13 (1H, s).

Example 138

4-(2,1,3-Benzothiadiazol-4-yl)-5-cyano-4,7-dihydro-6-propyl-2H-pyrazolo[3,4-b]pyridine The title compound was prepared from methyl butanoate, 2,1,3-benzothiadiazol-4-aldehyde and 3-aminopyrazole in the same manner as in Example 94.

MP: 195° C.

Anal. Calcd. for: $C_{16}H_{14}N_6S$: C, 59.61; H, 4.38; N, 26.07. Found: C, 59.33; H, 4.48; N, 25.76.

MS (EI): 322 (M$^+$).

$^1$H-NMR (400 MHz, DMSO-d$_6$) δ (ppm): 0.98 (3H, t, J=7.3 Hz), 1.68–1.74 (2H, m), 2.45–2.50 (2H, m), 5.72 (1H, s), 7.19 (1H, s), 7.43 (1H, d, J=7.3 Hz), 7.72 (1H, dd, J=7.5 Hz and 7.4 Hz), 7.97 (1H, d, J=7.3 Hz), 9.87 (1H, s), 12.06 (1H, s).

Example 139

5-Cyano-4,7-dihydro-4-(2-methylbenzoxazol-4-yl)-6-propyl-2H-pyrazolo[3,4-b]pyridine The title compound was prepared from methyl butanoate, 2-methylbenzoxazole-4-aldehyde and 3-aminopyrazole in the same manner as in Example 94.

MP: 208° C.

Anal. Calcd. for: $C_{18}H_{17}N_5O1/5H_2O$: C, 66.94; H, 5.43; N, 21.68. Found: C, 66.85; H, 5.52; N, 22.09.

MS (EI): 319 (M$^+$).

$^1$H-NMR (400 MHz, DMSO-d$_6$) δ (ppm): 0.97 (3H, t, J=7.3 Hz), 1.67–1.72 (2H, m), 2.40–2.45 (2H, m), 2.63 (3H, s), 5.51 (1H, s), 7.06 (1H, d, J=7.3 Hz), 7.16 (1H, s), 7.29 (1H, dd, J=7.3 Hz and 7.2 Hz), 7.47 (1H, d, J=7.3 Hz), 9.77 (1H, s), 12.06 (1H, s).

Example 140

R(−) 4-(2,1,3-Benzoxadiazol-4-yl)-5-cyano-4,7-dihydro-6-propyl-2H-pyrazolo[3,4-b]pyridine To a solution of the compound described in Example 137 (64.5 g) in THF (1000 mL) was added (−)camphorsulfonic acid (49 g) at room temperature and the mixture was stirred for 1 hour. The solvent was evaporated under reduced pressure to give an oil. The obtained oil was recrystallized from acetonitrile twice to give colorless crystals (11 g). To a solution of the obtained colorless crystals in methanol (50 mL) was added water (50 mL). The mixture was neutralized with a saturated aqueous sodium hydrogencarbonate solution and extracted with ethyl acetate. The solvent was evaporated under reduced pressure. The residual methanol solution was added dropwise to water (1000 mL) and the crystals were collected by filtration to give the title compound (11 g) as pale-yellow crystals. (CHIRALPAK AS, 0.25 cm×25 cm, eluent n-hexane/2-propanol/diethylamine=80/20/0.1, flow rate 1.5 mL/min, UV 254 nm, retention time 10 minutes, DAICEL CHEMICAL INDUSTRIES, LTD.)

MP: 170° C.

MS (EI): 306 (M$^+$).

Specific rotation: $[a]_D$=−80° (EtOH, c=1.0).

Example 141

S(+) 4-(2,1,3-Benzoxadiazol-4-yl)-5-cyano-4,7-dihydro-6-propyl-2H-pyrazolo[3,4-b]pyridine To a solution of the compound (54 g), which was recovered from the mother liquor obtained in Example 140, in THF (600 mL) was added (+)camphorsulfonic acid (41 g) at room temperature and the mixture was stirred for 1 hour. The solvent was evaporated under reduced pressure to give an oil. The obtained oil was recrystallized from acetonitrile twice to give colorless crystals (12 g). To a solution of the obtained colorless crystals in methanol (50 mL) was added water (50 mL) The mixture was neutralized with a saturated aqueous sodium hydrogencarbonate solution and extracted with ethyl acetate. The solvent was evaporated under reduced pressure and the residual methanol solution was added dropwise to water (1000 mL). The crystals were collected by filtration to give the title compound (11 g) as pale-yellow crystals. (CHIRALPAK AS, 0.25 cm×25 cm, eluent n-hexane/2-propanol/diethylamine=80/20/0.1, flow rate 1.5 mL/min, UV 254 nm, retention time 13 minutes, DAICEL CHEMICAL INDUSTRIES, LTD.)

MP: 170° C.

MS (EI): 306 (M$^+$).

Specific rotation: $[a]_D$=+82° (EtOH, c=1.0).

Example 142

4-(2-Chlorophenyl)-5-cyano-4,7-dihydro-6-phenyl-2H-pyrazolo[3,4-b]pyridine

The title compound was prepared from methyl benzoate, 2-chlorobenzaldehyde and 3-aminopyrazole in the same manner as in Example 95.

MP: 158° C.

Anal. Calcd. for: $C_{19}H_{13}ClN_4H_2O$: C, 65.05; H, 4.31; N, 15.97. Found: C, 65.35; H, 4.19; N, 16.21.

MS (EI): 332 (M$^+$).

$^1$H-NMR (400 MHz, DMSO-d$_6$) δ (ppm): 5.51 (1H, s), 7.25–7.51 (8H, m), 7.59–7.61 (2H, m), 10.07 (1H, s), 12.24 (1H, s).

Example 143

5-Cyano-4,7-dihydro-4-(2-methylthiophenyl)-6-phenyl-2H-pyrazolo[3,4-b]pyridine

The title compound was prepared from methyl benzoate, 2-methylthiobenzaldehyde and 3-aminopyrazole in the same manner as in Example 95.

MP: 146° C.

Anal. Calcd. for: $C_{20}H_{16}N_4S4/5H_2O$: C, 66.94; H, 4.94; N, 15.61. Found: C, 66.85; H, 4.81; N, 15.65.

MS (EI): 344 (M$^+$).

$^1$H-NMR (400 MHz, DMSO-d$_6$) δ (ppm): 2.48 (3H, s), 5.48 (1H, s), 7.19–7.33 (5H, m), 7.48–7.50 (3H, m), 7.59–7.61 (2H, m), 9.99 (1H, s), 12.16 (1H, s).

Example 144

5-Cyano-4-(2-cyanophenyl)-4,7-dihydro-6-phenyl-2H-pyrazolo[3,4-b]pyridine

The title compound was prepared from methyl benzoate, 2-cyanobenzaldehyde and 3-aminopyrazole in the same manner as in Example 95.

MP: 148° C.

Anal. Calcd. for: $C_{20}H_{13}N_5 \cdot 3/5H_2O$: C, 71.89; H, 4.28; N, 20.96. Found: C, 71.89; H, 4.33; N, 20.91.

MS (EI): 323 (M$^+$).

$^1$H-NMR (400 MHz, DMSO-d$_6$) δ (ppm): 5.38 (1H, s), 7.31 (1H, s), 7.44–7.59 (7H, m), 7.70 (1H, dd, J=7.3 Hz and 7.2 Hz), 7.83 (1H, d, J=7.3 Hz), 10.21 (1H, s), 12.31 (1H, s).

Example 145

5-Cyano-4-(2,3-dichlorophenyl)-4,7-dihydro-6-phenyl-2H-pyrazolo[3,4-b]pyridine

The title compound was prepared from methyl benzoate, 2,3-dichlorobenzaldehyde and 3-aminopyrazole in the same manner as in Example 95.

MP: 162° C.

Anal. Calcd. for: $C_{19}H_{12}Cl_2N_4$: C, 62.14; H, 3.29; N, 15.26. Found: C, 61.57; H, 3.93; N, 17.19.

MS (EI): 367 (M$^+$).

$^1$H-NMR (400 MHz, DMSO-d$_6$) δ (ppm): 5.59 (1H, s), 7.37–7.42 (3H, m), 7.48–7.55 (4H, m), 7.59–7.62 (2H, m), 10.14 (1H, s), 12.28 (1H, s).

Example 146

5-Cyano-4,7-dihydro-4-(naphthalen-1-yl)-6-phenyl-2H-pyrazolo[3,4-b]pyridine

The title compound was prepared from methyl benzoate, naphthalene-1-benzaldehyde and 3-aminopyrazole in the same manner as in Example 95.

MP: 174° C.

Anal. Calcd. for: $C_{23}H_{16}N_4$: C, 79.29; H, 4.63; N, 16.08. Found: C, 79.50; H, 4.85; N, 16.58.

MS (EI): 348 (M$^+$).

$^1$H-NMR (400 MHz, DMSO-d$_6$) δ (ppm): 5.87 (1H, s), 7.12 (1H, s), 7.50–7.63 (9H, m), 7.82 (1H, d, J=7.3 Hz), 7.96 (1H, d, J=7.3 Hz), 8.34 (1H, d, J=7.3 Hz), 10.09 (1H, s), 12.12 (1H, s).

Example 147

4-(2-Bromo-3-cyanophenyl)-5-cyano-4,7-dihydro-6-phenyl-2H-pyrazolo[3,4-b]pyridine The title compound was prepared from methyl benzoate, 2-bromo-3-cyanobenzaldehyde and 3-aminopyrazole in the same manner as in Example 95.

MP: >270° C.

Anal. Calcd. for: $C_{20}H_{12}BrN_5$: C, 59.72; H, 3.01; N, 17.41. Found: C, 59.53; H, 3.17; N, 17.30.

MS (EI): 402 (M$^+$).

$^1$H-NMR (400 MHz, DMSO-d$_6$) δ (ppm): 5.63 (1H, s), 7.39 (1H, s), 7.49–7.51 (3H, m), 7.60–7.63 (3H, m), 7.75 (1H, d, J=7.3 Hz), 7.85 (1H, d, J=7.3 Hz), 10.21 (1H, s), 12.33 (1H, s).

Example 148

5-Cyano-4-(3,4-dihydro-2H-benzopyran-8-yl)-4,7-dihydro-6-phenyl-2H-pyrazolo[3,4-b]pyridine The title compound was prepared from methyl benzoate, 3,4-dihydro-2H-benzopyran-8-benzaldehyde and 3-aminopyrazole in the same manner as in Example 95.

MP: 255° C.

Anal. Calcd. for: $C_{22}H_{18}N_4O$: C, 74.56; H, 5.12; N, 15.81. Found: C, 74.27; H, 5.11; N, 15.82.

MS (EI): 354 (M$^+$).

$^1$H-NMR (400 MHz, DMSO-d$_6$) δ (ppm): 1.94–1.97 (2H, m), 2.75–2.78 (2H, m), 4.20–4.30 (2H, m), 5.30 (1H, s), 6.80 (1H, dd, J=7.3 Hz and 7.2 Hz), 6.91 (1H, d, J=7.3 Hz), 7.02 (1H, d, J=7.3 Hz), 7.28 (1H, s), 7.49–7.51 (3H, m), 7.60–7.63 (2H, m), 9.88 (1H, s), 12.11 (1H, s).

Example 149

5-Cyano-4-(2,3-difluorophenyl)-4,7-dihydro-6-phenyl-2H-pyrazolo[3,4-b]pyridine

The title compound was prepared from methyl benzoate, 2,3-difluorobenzaldehyde and 3-aminopyrazole in the same manner as in Example 95.

MP: 165° C.

Anal. Calcd. for: $C_{19}H_{12}F_2N_4 \cdot 3/5H_2O$: C, 66.12; H, 3.86; N, 16.23. Found: C, 65.87; H, 3.81; N, 16.46.

MS (EI): 334 (M$^+$).

$^1$H-NMR (400 MHz, DMSO-d$_6$) δ (ppm): 5.40 (1H, s), 7.16–7.38 (4H, m), 7.48–7.50 (3H, m), 7.57–7.59 (2H, m), 10.11 (1H, s), 12.30 (1H, s).

Example 150

5-Cyano-4,7-dihydro-4-(2-methoxyphenyl)-6-phenyl-2H-pyrazolo[3,4-b]pyridine

The title compound was prepared from methyl benzoate, 2-methoxybenzaldehyde and 3-aminopyrazole in the same manner as in Example 95.

MP: 206° C.

Anal. Calcd. for: $C_{20}H_{16}N_4O$: C, 73.15; H, 4.91; N, 17.06. Found: C, 73.23; H, 5.14; N, 17.19.

MS (EI): 328 (M$^+$).

$^1$H-NMR (400 MHz, DMSO-d$_6$) δ (ppm): 3.86 (3H, s), 5.36 (1H, s), 6.94 (1H, dd, J=7.3 Hz and 7.2 Hz), 7.02 (1H, d, J=7.3 Hz), 7.19–7.25 (3H, m), 7.48–7.51 (3H, m), 7.60–7.63 (2H, m), 9.91 (1H, s), 12.12 (1H, s)

Example 151

5-Cyano-4,7-dihydro-4,6-bis-(2-methoxyphenyl)-2H-pyrazolo[3,4-b]pyridine

The title compound was prepared from methyl o-anisate, 2-methoxybenzaldehyde and 3-aminopyrazole in the same manner as in Example 95.

MP: 220° C.

Anal. Calcd. for: $C_{21}H_{18}N_4O_2$: C, 70.38; H, 5.06; N, 15.63. Found: C, 69.97; H, 5.13; N, 16.15.

MS (EI): 358 (M$^+$).

$^1$H-NMR (400 MHz, DMSO-d$_6$) δ (ppm): 3.86 (3H, s), 3.88 (3H, s), 5.32 (1H, s), 6.95–7.06 (3H, m), 7.14–7.25 (3H, m), 7.37 (1H, d, J=7.3 Hz), 7.45 (1H, dd, J=7.3 Hz and 7.2 Hz), 9.74 (1H, s), 12.05 (1H, s).

Example 152

5-Cyano-4,7-dihydro-4-(2-methoxyphenyl)-6-(3-methoxyphenyl)-2H-pyrazolo[3,4-b]pyridine The title compound was prepared from methyl m-anisate, 2-methoxybenzaldehyde and 3-aminopyrazole in the same manner as in Example 95.

MP: 192° C.

Anal. Calcd. for: $C_{21}H_{18}N_4O_2$: C, 70.38; H, 5.06; N, 15.63. Found: C, 69.97; H, 5.09; N, 15.54.

MS (EI): 358 (M$^+$).

$^1$H-NMR (400 MHz, DMSO-d$_6$) δ (ppm): 3.81 (3H, s), 3.86 (3H, s), 5.35 (1H, s), 6.95 (1H, dd, J=7.3 Hz and 7.2 Hz), 7.01 (1H, d, J=7.3 Hz), 7.07 (1H, d, J=7.3 Hz), 7.14 (1H, s), 7.18–7.23 (5H, m), 7.41 (1H, dd, J=7.3 Hz and 7.2 Hz), 9.88 (1H, s), 12.12 (1H, s).

Example 153

5-Cyano-4,7-dihydro-4-(2-methoxyphenyl)-6-(4-methoxyphenyl)-2H-pyrazolo[3,4-b]pyridine The title compound was prepared from methyl p-anisate, 2-methoxybenzaldehyde and 3-aminopyrazole in the same manner as in Example 95.

MP: 149° C.

Anal. Calcd. for: $C_{21}H_{18}N_4O_2 \cdot 1/2H_2O$: C, 68.65; H, 5.21; N, 15.25. Found: C, 68.67; H, 4.99; N, 15.35.

MS (EI): 358 (M$^+$).

$^1$H-NMR (400 MHz, DMSO-d$_6$) δ (ppm): 3.81 (3H, s), 3.86 (3H, s), 5.33 (1H, s), 6.94 (1H, dd, J=7.3 Hz and 7.2 Hz), 7.01–7.05 (3H, m), 7.18–7.24 (3H, m), 7.56 (2H, d, J=7.2 Hz), 9.82 (1H, s), 12.10 (1H, s).

Example 154

5-Cyano-4,7-dihydro-4-(2-nitrophenyl)-6-phenyl-2H-pyrazolo[3,4-b]pyridine

The title compound was prepared from methyl benzoate, 2-nitrobenzaldehyde and 3-aminopyrazole in the same manner as in Example 95.

MP: 221° C.

Anal. Calcd. for: $C_{19}H_{13}N_5O_2$: C, 66.47; H, 3.82; N, 20.40. Found: C, 66.48; H, 4.08; N, 20.41.

MS (EI): 343 (M$^+$).

$^1$H-NMR (400 MHz, DMSO-d$_6$) δ (ppm): 5.54 (1H, s), 7.34 (1H, s), 7.49–7.52 (4H, m), 7.59–7.64 (3H, m), 7.74 (1H, dd, J=7.3 Hz and 7.2 Hz), 7.91 (1H, d, J=7.3 Hz), 10.16 (1H, s), 12.30 (1H, s).

Example 155

5-Cyano-4,7-dihydro-6-(2-methoxyphenyl)-4-(2-nitrophenyl)-2H-pyrazolo[3,4-b]pyridine The title compound was prepared from methyl o-anisate, 2-nitrobenzaldehyde and 3-aminopyrazole in the same manner as in Example 95.

MP: 207° C.

Anal. Calcd. for: $C_{20}H_{15}N_5O_3$: C, 64.34; H, 4.05; N, 18.76. Found: C, 64.03; H, 4.21; N, 18.68.

MS (EI): 373 (M$^+$).

$^1$H-NMR (400 MHz, DMSO-d$_6$) δ (ppm): 3.85 (3H, s), 5.50 (1H, s), 7.03 (1H, dd, J=7.3 Hz and 7.2 Hz), 7.14 (1H, d, J=7.3 Hz), 7.33 (1H, s), 7.37 (1H, d, J=7.3 Hz), 7.44–7.52 (2H, m), 7.74–7.80 (2H, m), 7.92 (1H, d, J=7.3 Hz), 10.02 (1H, s), 12.25 (1H, s).

Example 156

5-Cyano-4,7-dihydro-6-(3-methoxyphenyl)-4-(2-nitrophenyl)-2H-pyrazolo[3,4-b]pyridine The title compound was prepared from methyl m-anisate, 2-nitrobenzaldehyde and 3-aminopyrazole in the same manner as in Example 95.

MP: 220° C.

Anal. Calcd. for: $C_{20}H_{15}N_5O_3$: C, 64.34; H, 4.05; N, 18.76. Found: C, 63.92; H, 4.14; N, 18.74.

MS (EI): 373 (M$^+$).

$^1$H-NMR (400 MHz, DMSO-d$_6$) δ (ppm): 381 (3H, s), 5.53 (1H, s), 7.07 (1H, d, J=7.3 Hz), 7.14–7.18 (2H, m), 7.33 (1H, s), 7.40 (1H, dd, J=7.3 Hz and 7.2 Hz), 7.50 (1H, dd, J=7.3 Hz and 7.2 Hz), 7.63 (1H, d, J=7.3 Hz), 7.74 (1H, dd, J=7.3 Hz 7.2 Hz), 7.91 (1H, d, J=7.3 Hz), 10.13 (1H, s), 12.30 (1H, s).

Example 157

5-Cyano-4,7-dihydro-6-(4-methoxyphenyl)-4-(2-nitrophenyl)-2H-pyrazolo[3,4-b]pyridine The title compound was prepared from methyl p-anisate, 2-nitrobenzaldehyde and 3-aminopyrazole in the same manner as in Example 95.

MP: 215° C.

Anal. Calcd. for: $C_{20}H_{15}N_5O_3$: C, 64.34; H, 4.05; N, 18.76. Found: C, 64.13; H, 4.12; N, 18.69.

MS (EI): 373 (M$^+$).

$^1$H-NMR (400 MHz, DMSO-d$_6$) δ (ppm): 3.81 (3H, s), 5.51 (1H, s), 7.03 (2H, d, J=7.3 Hz), 7.33 (1H, s), 7.47–7.55 (3H, m), 7.61 (1H, d), 7.74 (1H, dd, J=7.3 Hz and 7.2 Hz), 7.91 (1H, d, J=7.3 Hz), 10.07 (1H, s), 12.28 (1H, s).

Example 158

4-(2,1,3-Benzoxadiazol-4-yl)-5-cyano-4,7-dihydro-6-phenyl-2H-pyrazolo[3,4-b]pyridine The title compound was prepared from methyl benzoate, 2,1,3-benzoxadiazole-4-aldehyde and 3-aminopyrazole in the same manner as in Example 95.

MP: 231° C.

Anal. Calcd. for: $C_{19}H_{12}N_6O$: C, 67.05; H, 3.55; N, 24.69. Found: C, 66.76; H, 3.90; N, 24.71.

MS (EI): 340 (M$^+$).

$^1$H-NMR (400 MHz, DMSO-d$_6$) δ (ppm): 5.55 (1H, s), 7.33 (1H, s), 7.50–7.64 (7H, m), 7.95 (1H, d, J=7.3 Hz), 10.20 (1H, s), 12.23 (1H, s).

Example 159

4-(2,1,3-Benzoxadiazol-4-yl)-5-cyano-4,7-dihydro-6-(2-methoxyphenyl)-2H-pyrazolo[3,4-b]pyridine The title compound was prepared from methyl o-anisate, 2,1,3-benzoxadiazole-4-aldehyde and 3-aminopyrazole in the same manner as in Example 95.

MP: 180° C.

Anal. Calcd. for: $C_{20}H_{14}N_6O_2$: C, 64.86; H, 3.81; N, 22.69. Found: C, 64.11; H, 3.98; N, 22.34.

MS (EI): 370 (M$^+$).

$^1$H-NMR (400 MHz, DMSO-d$_6$) δ (ppm): 3.84 (3H, s), 5.56 (1H, s), 7.03 (1H, dd, J=7.3 Hz and 7.2 Hz), 7.14 (1H, d, J=6.8 Hz), 7.33–7.35 (2H, m), 7.45 (1H, dd, J=7.3 Hz and 7.2 Hz), 7.54 (1H, d, J=7.3 Hz), 7.65 (1H, dd, J=8.8 Hz and 6.8 Hz), 7.94 (1H, d, J=8.8 Hz), 10.04 (1H, s), 12.18 (1H, s)

Example 160

4-(2,1,3-Benzoxadiazol-4-yl)-5-cyano-4,7-dihydro-6-(3-methoxyphenyl)-2H-pyrazolo[3,4-b]pyridine The title compound was prepared from methyl m-anisate, 2,1,3-benzoxadiazole-4-aldehyde and 3-aminopyrazole in the same manner as in Example 95.

MP: 198° C.

Anal. Calcd. for: $C_{20}H_{14}N_6O_2·4/5H_2O$: C, 62.43; H, 4.09; N, 21.84. Found: C, 62.60; H, 3.99; N, 22.15.

MS (EI): 370 (M$^+$).

$^1$H-NMR (400 MHz, DMSO-d$_6$) δ (ppm): 3.80 (3H, s), 5.55 (1H, s), 7.06–7.17 (3H, m), 7.33 (1H, s), 7.40 (1H, dd, J=7.3 Hz), 7.52 (1H, d, J=6.6 Hz), 7.62 (1H, dd, J=8.8 Hz and 6.8 Hz), 7.95 (1H, d, J=6.8 Hz), 10.18 (1H, s), 12.24 (1H, s).

Example 161

4-(2,1,3-Benzoxadiazol-4-yl)-5-cyano-4,7-dihydro-6-(4-methoxyphenyl)-2H-pyrazolo[3,4-b]pyridine The title compound was prepared from methyl p-anisate, 2,1,3-benzoxadiazole-4-aldehyde and 3-aminopyrazole in the same manner as in Example 95.

MP: 244° C.

Anal. Calcd. for: $C_{20}H_{14}N_6O_2$: C, 64.86; H, 3.81; N, 22.69. Found: C, 64.77; H, 3.91; N, 22.49.

MS (EI): 370 (M$^+$).

$^1$H-NMR (400 MHz, DMSO-d$_6$) δ (ppm): 3.80 (3H, s), 5.53 (1H, s), 7.02 (2H, d, J=7.3 Hz), 7.32 (1H, s), 7.50–7.53 (3H, m), 7.61 (1H, dd, J=8.8 Hz and 6.8 Hz), 7.94 (1H, d, J=8.8 Hz), 10.11 (1H, s), 12.21 (1H, s)

Example 162

4-(2,1,3-Benzothiadiazol-4-yl)-5-cyano-4,7-dihydro-6-phenyl-2H-pyrazolo[3,4-b]pyridine The title compound was prepared from methyl benzoate, 2,1,3-benzothiadiazole-4-aldehyde and 3-aminopyrazole in the same manner as in Example 95.

MP: 258° C.

MS (EI): 356 (M$^+$).

$^1$H-NMR (400 MHz, DMSO-d$_6$) δ (ppm): 5.85 (1H, s), 7.27 (1H, s), 7.51–7.52 (3H, m), 7.61–7.67 (3H, m), 7.76 (1H, dd, J=8.8 Hz and 6.8 Hz), 8.00 (1H, d, J=8.8 Hz), 10.13 (1H, s), 12.16 (1H, s).

Example 163

4-(2,1,3-Benzothiadiazol-4-yl)-5-cyano-4,7-dihydro-6-(2-methoxyphenyl)-2H-pyrazolo[3,4-b]pyridine The title compound was prepared from methyl o-anisate, 2,1,3-benzothiadiazole-4-aldehyde and 3-aminopyrazole in the same manner as in Example 95.

MP: 231° C.

Anal. Calcd. for: $C_{20}H_{14}N_6OS·3/10H_2O$: C, 61.30; H, 3.76; N, 21.45. Found: C, 61.24; H, 3.74; N, 22.09.

MS (EI): 386 (M$^+$).

$^1$H-NMR (400 MHz, DMSO-d$_6$) δ (ppm): 3.89 (3H, s), 5.85 (1H, s), 706 (1H, dd, J=7.6 Hz and 7.3 Hz), 7.17 (1H, d, J=8.3 Hz), 7.28 (1H, s), 7.43–7.49 (2H, m), 7.69 (1H, d, J=6.8 Hz), 7.80 (1H, dd, J=8.8 Hz and 6.8 Hz), 7.99 (1H, d, J=8.8 Hz), 9.97 (1H, s), 12.11 (1H, s).

Example 164

4-(2,1,3-Benzothiadiazol-4-yl)-5-cyano-4,7-dihydro-6-(3-methoxyphenyl)-2H-pyrazolo[3,4-b]pyridine The title compound was prepared from methyl m-anisate, 2,1,3-benzothiadiazole-4-aldehyde and 3-aminopyrazole in the same manner as in Example 95.

MP: 220° C.

Anal. Calcd. for: $C_{20}H_{14}N_6OS$: C, 62.16; H, 3.65; N, 21.75. Found: C, 61.98; H, 3.70; N, 21.66.

MS (EI): 386 (M$^+$).

$^1$H-NMR (400 MHz, DMSO-d$_6$) δ (ppm): 3.82 (3H, s), 5.85 (1H, s), 7.08 (1H, d, J=8.3 Hz), 7.19 (1H, s), 7.23–7.27 (2H, m), 7.42 (1H, dd, J=7.8 Hz and 7.2 Hz), 7.61 (1H, d, J=6.6 Hz), 7.75 (1H, dd, J=8.8 Hz and 6.8 Hz), 7.99 (1H, d, J=8.1 Hz), 10.10 (1H, s), 12.16 (1H, s).

Example 165

4-(2,1,3-Benzothiadiazol-4-yl)-5-cyano-4,7-dihydro-6-(4-methoxyphenyl)-2H-pyrazolo[3,4-b]pyridine The title compound was prepared from methyl p-anisate, 2,1,3-benzothiadiazole-4-aldehyde and 3-aminopyrazole in the same manner as in Example 95.

MP: 238° C.

MS (EI): 386 (M$^+$).

$^1$H-NMR (400 MHz, DMSO-d$_6$) δ (ppm): 3.81 (3H, s), 5.83 (1H, s), 7.04 (2H, d, J=8.8 Hz), 7.26 (1H, s), 7.73–7.77 (3H, m), 7.75 (1H, dd, J=8.8 Hz and 6.8 Hz), 7.99 (1H, d, J=8.8 Hz), 10.04 (1H, s), 12.14 (1H, s).

Example 166

4-(2,1,3-Benzoxadiazol-4-yl)-5-cyano-4,7-dihydro-6-(pyridin-4-yl)-2H-pyrazolo[3,4-b]pyridine The title compound was prepared from methyl isonicotinate, 2,1,3-benzoxadiazole-4-aldehyde and 3-aminopyrazole in the same manner as in Example 95.

MP: 236° C.

MS (EI): 341 (M$^+$).

$^1$H-NMR (400 MHz, DMSO-d$_6$) δ (ppm): 5.58 (1H, s), 7.35 (1H, s), 7.54–7.64 (4H, m), 7.96 (1H, d, J=8.1 Hz), 8.72 (2H, d, J=5.9 Hz), 10.40 (1H, s), 12.29 (1H, s).

Example 167

4-(2,1,3-Benzoxadiazol-4-yl)-5-cyano-4,7-dihydro-6-(4-pyridin-3-yl)-2H-pyrazolo[3,4-b]pyridine The title compound was prepared from methyl nicotinate, 2,1,3-benzoxadiazole-4-aldehyde and 3-aminopyrazole in the same manner as in Example 95.

MP: 216° C.

Anal. Calcd. for: $C_{18}H_{11}N_7O·1/5H_2O$: C, 62.68; H, 3.33; N, 28.43. Found: C, 62.73; H, 3.43; N, 28.30.

MS (EI): 341 (M$^+$).

$^1$H-NMR (400 MHz, DMSO-d$_6$) δ (ppm): 5.59 (1H, s), 7.35 (1H, s), 7.52–7.63 (3H, m), 7.95–8.00 (2H, m), 8.69 (1H, d, J=4.9 Hz), 8.76 (1H, s), 10.39 (1H, s), 12.28 (1H, s).

Example 168

4-(2,1,3-Benzoxadiazol-4-yl)-5-cyano-4,7-dihydro-6-(4-pyridin-2-yl)-2H-pyrazolo[3,4-b]pyridine The title compound was prepared from methyl picolinate, 2,1,3-benzoxadiazole-4-aldehyde and 3-aminopyrazole in the same manner as in Example 95.

MP: 188° C.

MS (EI): 341 (M$^+$).

$^1$H-NMR (400 MHz, DMSO-d$_6$) δ (ppm): 5.59 (1H, s), 7.34 (1H, s), 7.51–7.53 (2H, m), 7.63 (1H, dd, J=9.0 Hz and 6.6 Hz), 7.75 (1H, d, J=6.6 Hz), 7.95–7.97 (2H, m), 8.69 (1H, d, J=5.4 Hz), 10.20 (1H, s), 12.26 (1H, s).

Example 169

4-(2,1,3-Benzoxadiazol-4-yl)-5-cyano-4,7-dihydro-6-(naphthalen-1-yl)-2H-pyrazolo[3,4-b]pyridine The title compound was prepared from methyl 1-naphthoate, 2,1,3-benzoxadiazole-4-aldehyde and 3-aminopyrazole in the same manner as in Example 95.

MP: 213° C.

Anal. Calcd. for: $C_{23}H_{14}N_6O$: C, 70.76; H, 3.61; N, 21.53. Found: C, 70.33; H, 3.74; N, 21.23.

MS (EI): 390 ($M^+$).

$^1$H-NMR (400 MHz, DMSO-$d_6$) δ (ppm): 5.65 (1H, s), 7.35–7.66 (7H, m), 7.96–8.21 (4H, m), 10.35 (1H, s), 12.23 (1H, s).

Example 170

4-(2,1,3-Benzoxadiazol-4-yl)-5-cyano-6-(furan-2-yl)-4,7-dihydro-2H-pyrazolo[3,4-b]pyridine The title compound was prepared from methyl furan-2-carboxylate, 2,1,3-benzoxadiazole-4-aldehyde and 3-aminopyrazole in the same manner as in Example 95.

MP: 241° C.

Anal. Calcd. for: $C_{17}H_{10}N_6O_2$: C, 61.82; H, 3.05; N, 25.44. Found: C, 61.72; H, 3.19; N, 25.34.

MS (EI): 330 ($M^+$).

$^1$H-NMR (400 MHz, DMSO-$d_6$) δ (ppm): 5.54 (1H, s), 6.69 (1H, s), 7.22 (1H, d, J=3.4 Hz), 7.32 (1H, s), 7.48 (1H, d, J=6.3 Hz), 7.61 (1H, dd, J=9.0 Hz and 6.3 Hz), 7.89 (1H, s), 7.94 (1H, d, J=9.0 Hz), 10.17 (1H, s), 12.26 (1H, s).

Example 171

4-(2,1,3-Benzoxadiazol-4-yl)-5-cyano-4,7-dihydro-6-(thiophen-2-yl)-2H-pyrazolo[3,4-b]pyridine The title compound was prepared from methyl thiophene-2-carboxylate, 2,1,3-benzoxadiazole-4-aldehyde and 3-aminopyrazole in the same manner as in Example 95.

MP: 230° C.

Anal. Calcd. for: $C_{17}H_{10}N_6OS$: C, 58.95; H, 2.91; N, 24.26. Found: C, 58.71; H, 3.08; N, 24.03.

MS (EI): 346 ($M^+$).

$^1$H-NMR (400 MHz, DMSO-$d_6$) δ (ppm): 5.54 (1H, s), 7.17 (1H, dd, J=4.9 Hz and 4.8 Hz), 7.33 (1H, s), 7.49 (1H, d, J=6.6 Hz), 7.58–7.64 (2H, m), 7.77 (1H, d, J=4.9 Hz), 7.95 (1H, d, J=9.0 Hz), 10.21 (1H, s), 12.27 (1H, s).

Example 172

4-(2,1,3-Benzoxadiazol-4-yl)-5-cyano-4,7-dihydro-6-(naphthalen-2-yl)-2H-pyrazolo[3,4-b]pyridine The title compound was prepared from methyl 2-naphthoate, 2,1,3-benzoxadiazole-4-aldehyde and 3-aminopyrazole in the same manner as in Example 95.

MP: 228° C.

Anal. Calcd. for: $C_{23}H_{14}N_6O$: C, 70.76; H, 3.61; N, 21.53. Found: C, 70.66; H, 3.81; N, 20.94.

MS (EI): 390 ($M^+$).

$^1$H-NMR (400 MHz, DMSO-$d_6$) δ (ppm): 5.48 (1H, s), 7.24 (1H, s), 7.44–7.55 (5H, m), 7.85–7.92 (4H, m), 8.05 (1H, s), 10.21 (1H, s), 12.14 (1H, s).

Example 173

4-(2,1,3-Benzoxadiazol-4-yl)-5-cyano-6-(furan-2-yl)-4,7-dihydro-2H-pyrazolo[3,4-b]pyridine The title compound was prepared from methyl furan-3-carboxylate, 2,1,3-benzoxadiazole-4-aldehyde and 3-aminopyrazole in the same manner as in Example 95.

MP: 237° C.

Anal. Calcd. for: $C_{17}H_{10}N_6O_2$: C, 61.82; H, 3.05; N, 25.44. Found: C, 61.59; H, 3.27; N, 25.01.

MS (EI): 330 ($M^+$).

$^1$H-NMR (400 MHz, DMSO-$d_6$) δ (ppm): 5.52 (1H, s), 6.93 (1H, d, J=1.0 Hz), 7.31 (1H, s), 7.48 (1H, d, J=6.6 Hz), 7.60 (1H, dd, J=9.0 Hz and 6.6 Hz), 7.80 (1H, dd, J=1.0 Hz), 7.94 (1H, d, J=9.0 Hz), 8.24 (1H, s), 10.07 (1H, s), 12.25 (1H, s).

Example 174

4-(2,1,3-Benzoxadiazol-4-yl)-5-cyano-4,7-dihydro-6-(thiophen-3-yl)-2H-pyrazolo[3,4-b]pyridine The title compound was prepared from methyl thiophene-3-carboxylate, 2,1,3-benzoxadiazole-4-aldehyde and 3-aminopyrazole in the same manner as in Example 95.

MP: 242° C.

Anal. Calcd. for: $C_{17}H_{10}N_6OS$: C, 58.95; H, 2.91; N, 24.26. Found: C, 58.52; H, 3.15; N, 23.92.

MS (EI): 346 ($M^+$).

$^1$H-NMR (400 MHz, DMSO-$d_6$) δ (ppm): 5.54 (1H, s), 7.32 (1H, s), 7.42 (1H, d, J=5.1 Hz), 7.50 (1H, d, J=6.6 Hz), 7.61–7.66 (2H, m), 7.94 (1H, d, J=9.0 Hz), 8.00 (1H, s), 10.13 (1H, s), 12.24 (1H, s).

Example 175

6-(Benzo[b]furan-2-yl)-4-(2,1,3-benzoxadiazol-4-yl)-5-cyano-4,7-dihydro-2H-pyrazolo[3,4-b]pyridine The title compound was prepared from methyl benzo[b]furan-2-carboxylate, 2,1,3-benzoxadiazole-4-aldehyde and 3-aminopyrazole in the same manner as in Example 95.

MP: >270° C.

Anal. Calcd. for: $C_{21}H_{12}N_6O_2$: C, 66.31; H, 3.18; N, 22.09. Found: C, 66.26; H, 3.34; N, 21.53.

MS (EI): 380 ($M^+$).

$^1$H-NMR (400 MHz, DMSO-$d_6$) δ (ppm): 5.62 (1H, s), 7.31–7.36 (2H, m), 7.45 (1H, dd, J=9.0 Hz and 6.7 Hz), 7.53 (1H, d, J=6.7 Hz), 7.61–7.65 (3H, m), 7.77 (1H, d, J=7.3 Hz), 7.96 (1H, d, J=9.0 Hz), 10.44 (1H, s), 12.33 (1H, s).

Example 176

4-(2,1,3-Benzoxadiazol-4-yl)-5-cyano-4,7-dihydro-6-methyl-2H-pyrazolo[3,4-b]pyridine The title compound was prepared from ethyl acetate, 2,1,3-benzoxadiazole-4-aldehyde and 3-aminopyrazole in the same manner as in Example 94.

MP: 212° C.

Anal. Calcd. for: $C_{14}H_{10}N_6O3/5H_2O$: C, 58.17; H, 3.91; N, 29.07. Found: C, 58.45; H, 4.08; N, 28.61.

MS (EI): 278 ($M^+$).

$^1$H-NMR (400 MHz, DMSO-$d_6$) δ (ppm): 2.14 (3H, s), 5.40 (1H, s), 7.25 (1H, s), 7.40 (1H, d, J=6.6 Hz), 7.59 (1H, dd, J=9.0 Hz 6.6 Hz), 7.92 (1H, d, J=9.0 Hz), 9.98 (1H, s), 12.13 (1H, s).

Example 177

4-(2,1,3-Benzoxadiazol-4-yl)-6-butyl-5-cyano-4,7-dihydro-2H-pyrazolo[3,4-b]pyridine The title compound was prepared from methyl pentanoate, 2,1,3-benzoxadiazole-4-aldehyde and 3-aminopyrazole in the same manner as in Example 94.

MP: 200° C.

Anal. Calcd. for: $C_{17}H_{16}N_6O$: C, 63.74; H, 5.03; N, 26.23. Found: C, 63.85; H, 5.01; N, 26.26.

MS (EI): 320 (M$^+$).

$^1$H-NMR (400 MHz, DMSO-d$_6$) δ (ppm): 0.88 (3H, t, J=7.3 Hz), 1.30–1.39 (2H, m), 1.57–1.65 (2H, m), 2.06–2.40 (2H, m), 5.39 (1H, s), 7.25 (1H, s), 7.39 (1H, d, J=6.6 Hz), 7.59 (1H, dd, J=9.0 Hz and 6.6 Hz), 7.91 (1H, d, J=9.0 Hz), 9.94 (1H, s), 12.13 (1H, s).

Example 178

Ethyl 4-(2-chloro-3-methylphenyl)-4,7-dihydro-6-propyl-2H-pyrazolo[3,4-b]pyridine-5-carboxylate A suspension of 2-chloro-m-xylene (15 ml), N-bromosuccinimide (23.3 g) and benzoyl peroxide (200 mg) in carbon tetrachloride (150 ml) was heated under reflux for 6 hours. The insoluble material was filtered off and the filtrate was concentrated under reduced pressure. The obtained residue was purified by silica gel column chromatography (eluent:hexane) to give 2-bromomethyl-1-chloro-6-methylbenzene (16.0 g) as a colorless oil. 2-Bromomethyl-1-chloro-6-methylbenzene (25.4 g) and hexamethylenetetramine (32.4 g) were dissolved in acetic acid-water (1:1, 10 ml) and the mixture was heated under reflux for 5 hours. To the reaction mixture was added concentrated hydrochloric acid (40 ml) and the mixture was heated under reflux for 1 hour. The reaction mixture was extracted with ethyl acetate. The extract was washed with an aqueous sodium hydrogencarbonate solution and a saturated aqueous sodium chloride solution, and dried over anhydrous magnesium sulfate. The solvent was evaporated to give 2-chloro-3-methylbenzaldehyde (19.4 g) as a yellow oil. Subsequently, the title compound was prepared from 2-chloro-3-methylbenzaldehyde, 3-aminopyrazole and ethyl 3-ketohexanoate in the same manner as in Example 25.

MP: 198–200° C.

Anal. Calcd. for: $C_{19}H_{22}ClN_3O_2$: C, 63.42; H, 6.16; N, 11.68. Found: C, 63.19; H, 6.14; N, 11.71.

MS (EI): 359 (M$^+$).

$^1$H-NMR (400 MHz, DMSO-d$_6$) δ (ppm): 0.85 (3H, t, J=7.3 Hz), 0.97 (3H, t, J=7.3 Hz), 1.65 (2H, m), 2.33 (3H, s), 2.68–2.71 (1H, m), 2.79–2.84 (1H, m), 3.72–3.82 (2H, m), 5.63 (1H, s), 6.93–6.96 (1H, m), 7.05–7.07 (2H, m), 7.24 (1H, s), 9.46 (1H, s), 11.94 (1H, s).

Example 179

Ethyl 4-(2-chloro-3-nitrophenyl)-4,7-dihydro-6-propyl-2H-pyrazolo[3,4-b]pyridine-5-carboxylate To a solution of 2-chloro-3-nitrobenzoic acid (5.0 g) in THF (50 ml) was added borane-tetrahydrofuran complex (1M THF solution, 30 ml) under ice-cooling and the mixture was stirred at room temperature for 24 hours. To the reaction mixture was added a saturated aqueous sodium hydrogencarbonate solution and the mixture was extracted with ethyl acetate. The extract was washed with water and a saturated aqueous sodium chloride solution, and dried over anhydrous magnesium sulfate. The solvent was evaporated to give a pale-yellow solid (3.7 g). The obtained pale-yellow solid (1.6. g) and manganese dioxide (1.7 g) were heated under reflux in toluene for 4.5 hours. The insoluble material was filtered off and the filtrate was concentrated under reduced pressure. The obtained residue was purified by silica gel column chromatography (eluent:hexane-ethyl acetate (4:1)) to give 2-chloro-3-nitrobenzaldehyde (1.3 g) as a pale-yellow solid. Subsequently, the title compound was prepared from 2-chloro-3-nitrobenzaldehyde, 3-aminopyrazole and ethyl 3-ketohexanoate in the same manner as in Example 25.

MS (EI): 390 (M$^+$).

$^1$H-NMR (400 MHz, DMSO-d$_6$) δ (ppm): 0.85 (3H, t, J=6.8 Hz), 0.97 (3H, t, J=7.3 Hz), 1.64–1.68 (2H, m), 2.70–2.85 (2H, m), 3.73–386 (2H, m), 5.67 (1H, s), 7.31 (1H, s), 7.39–7.47 (2H, m), 7.73 (1H, dd, J=1.5, 7.8 Hz), 9.67 (1H, s), 12.10 (1H, s).

Example 180

Ethyl 4-(2-chloro-3-cyanophenyl)-4,7-dihydro-6-propyl-2H-pyrazolo[3,4-b]pyridine-5-carboxylate To a solution of 2-chloro-3-methylbenzaldehyde (19.4 g) in ethanol (45 ml) was added an aqueous hydroxylamine hydrochloride (9.7 g) solution (12 ml), and an aqueous sodium hydroxide (6.9 g) solution (10 ml) was added. The mixture was stirred at room temperature for 1.5 hours. Water (500 ml) was added and the precipitated crystals were collected by filtration. The obtained white crystals (16.1 g) were dissolved in acetic anhydride (50 ml) and the mixture was heated under reflux for 2.5 hours. The reaction mixture was concentrated under reduced pressure and the obtained residue was purified by silica gel column chromatography (eluent:hexane-ethyl acetate (5:1)) to give 2-cyano-6-methylchlorobenzene (10.9 g) as a white solid. A suspension of 2-cyano-6-methylchlorobenzene (10.9 g), N-bromosuccinimide (12.8 g) and benzoyl peroxide (523 mg) in carbon tetrachloride (100 ml) was heated under reflux for 3.5 hours. The insoluble material was filtered off and the filtrate was concentrated under reduced pressure. The obtained residue was purified by silica gel column chromatography (eluent:hexane-ethyl acetate (20:1)) to give 2-chloro-3-cyanobenzaldehyde (12.8 g) as a colorless oil. Subsequently, the title compound was prepared from 2-chloro-3-cyanobenzaldehyde, 3-aminopyrazole and ethyl 3-ketohexanoate in the same manner as in Example 25.

MP: 213–215° C.

Anal. Calcd. for: $C_{19}H_{19}ClN_4O_2$: C, 61.54; H, 5.16; N, 15.11. Found: C, 61.25; H, 5.36; N, 14.71.

MS (EI): 370 (M$^+$).

$^1$H-NMR (400 MHz, DMSO-d$_6$) δ (ppm): 0.86 (3H, t, J=6.9 Hz), 0.96 (3H, t, J=7.3 Hz), 1.65 (2H, m), 2.70–2.80 (2H, m), 3.73–3.81 (2H, m), 5.63 (1H, s), 7.31 (1H, s), 7.42–7.44 (2H, m), 7.72 (1H, dd, J=3.0, 6.4 Hz), 9.65 (1H, s), 12.08 (1H, s).

IR (KBr): ν=3344, 3292, 2985, 2954, 2242, 1652 cm$^{-1}$.

Example 181

Ethyl 4-(2,3-dibromophenyl)-4,7-dihydro-6-propyl-2H-pyrazolo[3,4-b]pyridine-5-carboxylate A suspension of 2-bromo-3-nitrotoluene (5.0 g), iron (3.9 g) and ammonium chloride (3.7 g) in ethanol (50 ml)-water (17 ml) was heated under reflux for 2 hours. The insoluble matter was filtered off. To the filtrate was added ethyl acetate (100 ml) and the mixture was washed with water and a saturated aqueous sodium chloride solution, and dried over anhydrous magnesium sulfate. The solvent was evaporated and the obtained residue was purified by silica gel column chromatography (eluent:hexane-ethyl acetate (5:1)) to give a pale-yellow oil (4.8 g). The obtained pale-yellow oil (4.8 g) was dissolved in 47% hydrobromic acid (50 ml). Under ice-cooling, an aqueous sodium nitrite (1.6 g) solution (18 ml) was added and the mixture was stirred under ice-cooling for 30 minutes. The reaction mixture was added dropwise to a solution of cuprous bromide (2.0 g) in 47% hydrobromic acid (20 ml) over 30 minutes and the mixture was stirred at 60° C. for 4.5 hours. To the reaction mixture was added water (100 ml) and the mixture was extracted with ethyl acetate. The extract was washed with water and a saturated aqueous sodium hydrogencarbonate solution, and dried over anhydrous magnesium sulfate. The solvent was evaporated and the obtained residue was purified by silica gel column chromatography (eluent:hexane-ethyl acetate (9:1)) to give 2,3-dibromotoluene (2.6 g) as a brown oil. A suspension of 2,3-dibromotoluene (2.6 g), N-bromosuccinimide (1.85 g) and benzoyl peroxide (50 mg) in carbon tetrachloride (30 ml) was heated under reflux for 2 hours. The insoluble material was filtered off and the filtrate was concentrated under reduced pressure. The obtained residue was purified by silica gel column chromatography (eluent:hexane) to give a colorless oil (1.1 g). To a solution of the obtained colorless oil (1.1 g) in dimethyl sulfoxide (8.6 ml)-methylene chloride (2 ml) was added trimethylamine-N-oxide (1.0 g) under ice-cooling and the mixture was stirred at room temperature for 1 hour. The reaction mixture was poured into water (50 ml) and the mixture was extracted with ethyl acetate. The extract was washed with 5% hydrochloric acid, a saturated aqueous sodium hydrogencarbonate solution and a saturated aqueous sodium chloride solution, and dried over anhydrous magnesium sulfate. The solvent was evaporated to give 2,3-dibromobenzaldehyde (0.5 g) as a brown oil. Then the title compound was prepared from 2,3-dibromobenzaldehyde, 3-aminopyrazole and ethyl 3-ketohexanoate in the same manner as in Example 25.

MP: 180–183° C. (decomposition).

MS (EI): 469 (M$^+$).

$^1$H-NMR (400 MHz, DMSO-d$_6$) δ (ppm): 0.86 (3H, t, J=7.3 Hz), 0.96 (3H, t, J=7.3 Hz), 1.65 (2H, m), 2.70–2.80 (2H, m), 3.72–3.83 (2H, m), 5.67 (1H, s), 7.07 (1H, d, J=5.8 Hz), 7.18 (1H, dd, J=5.8, 7.8 Hz), 7.48 (1H, d, J=7.8 Hz), 9.57 (1H, s), 12.02 (1H, s)

IR (KBr): ν=3344, 3292, 2985, 2954, 2242, 1652 cm$^{-1}$.

Example 182

Ethyl 4-(2-bromo-3-nitrophenyl)-4,7-dihydro-6-propyl-2H-pyrazolo[3,4-b]pyridine-5-carboxylate 1/2H$_2$O A suspension of 2-bromo-3-nitrotoluene (5.1 g), N-bromosuccinimide (4.2 g) and benzoyl peroxide (229 mg) in carbon tetrachloride (50 ml) was heated under reflux for 3 hours. The insoluble material was filtered off and the filtrate was concentrated under reduced pressure. The obtained residue was purified by silica gel column chromatography (eluent:hexane-ethyl acetate (10:1)) to give a yellow solid (5.4 g). The obtained yellow solid (5.4 g) and hexamethylenetetramine (5.1 g) were dissolved in acetic acid-water (1:1, 16 ml) and the mixture was heated under reflux for 2 hours. To the reaction mixture was added concentrated hydrochloric acid (6 ml) and the mixture was heated under reflux for 15 minutes. The reaction mixture was extracted with ethyl acetate. The extract was washed with water, an aqueous sodium hydrogencarbonate solution and a saturated aqueous sodium chloride solution and dried over anhydrous magnesium sulfate. The solvent was evaporated, and the obtained residue was purified by silica gel column chromatography (eluent:hexane-ethyl acetate (5:1)) and crystallized (hexane-ethyl acetate (5:1)) to give 2-bromo-3-nitrobenzaldehyde (1.2 g) as yellow crystals. Subsequently, the title compound was prepared from 2-bromo-3-nitrobenzaldehyde, 3-aminopyrazole and ethyl 3-ketohexanoate in the same manner as in Example 25.

MP: 213–215° C.

Anal. Calcd. for: C$_{18}$H$_{19}$BrN$_4$O$_4$1/2H$_2$O: C, 48.66; H, 4.54; N, 12.61. Found: C, 48.34; H, 4.20; N, 13.04.

MS (EI): 435 (M$^+$).

$^1$H-NMR (400 MHz, DMSO-d$_6$) δ (ppm): 0.87 (3H, t, J=7.3 Hz), 0.97 (3H, t, J=7.3 Hz), 1.63–1.68 (2H, m), 2.77–2.81 (2H, m), 3.72–3.85 (2H, m), 5.68 (1H, s), 7.33–7.36 (2H, m), 7.47 (1H, dd, J=7.8, 7.8 Hz), 7.66 (1H, d, J=7.8 Hz), 9.67 (1H, s), 12.09 (1H, s).

Example 183

Ethyl 4-(2-bromo-3-cyanophenyl)-4,7-dihydro-6-propyl-2H-pyrazolo[3,4-b]pyridine-5-carboxylate The title compound was prepared from 2-bromo-m-xylene, 3-aminopyrazole and ethyl 3-ketohexanoate in the same manner as in Example 180.

MP: 210–212° C. (decomposition).

Anal. Calcd. for: C$_{19}$H$_{19}$BrN$_4$O$_2$: C, 54.95; H, 4.61; N, 13.49. Found: C, 54.98; H, 4.94; N, 13.11.

MS (EI): 415 (M$^+$).

$^1$H-NMR (400 MHz, DMSO-d$_6$) δ (ppm): 0.85 (3H, t, J=6.8 Hz), 0.97 (3H, t, J=7.3 Hz), 1.62–1.68 (2H, m), 2.75–2.80 (2H, m), 3.72–3.83 (2H, m), 5.63 (1H, s), 7.32 (1H, s), 7.39–7.48 (2H, m), 7.68 (1H, dd, J=1.9, 7.3 Hz), 9.65 (1H, s), 12.07 (1H, s).

Example 184

4-(2-Chloro-3-cyanophenyl)-5-cyano-4,7-dihydro-6-propyl-2H-pyrazolo[3,4-b]pyridine The title compound was prepared from methyl butanoate, 2-chloro-3-cyanobenzaldehyde and 3-aminopyrazole in the same manner as in Example 94.

MP: >250° C.

Anal. Calcd. for: C$_{17}$H$_{14}$Cl$_3$N$_5$: C, 63.06; H, 4.36; N, 21.63. Found: C, 63.10; H, 4.42; N, 21.61.

MS (EI): 323 (M$^+$).

$^1$H-NMR (400 MHz, DMSO-d$_6$) δ (ppm): 0.94 (3H, t, J=7.3 Hz), 1.61–1.71 (2H, m), 2.35–2.49 (2H, m), 5.47 (1H, s), 7.32 (1H, s), 7.52–7.59 (2H, m), 7.87 (1H, dd, J=2.0, 7.3 Hz), 9.95 (1H, s), 12.24 (1H, s).

Example 185

4-(2-Chloro-3-nitrophenyl)-5-cyano-4,7-dihydro-6-propyl-2H-pyrazolo[3,4-b]pyridine The title compound was prepared from methyl butanoate, 2-chloro-3-nitrobenzaldehyde and 3-aminopyrazole in the same manner as in Example 94.

MP: 234–235° C.

Anal. Calcd. for: C$_{16}$H$_{14}$ClN$_5$O$_2$: C, 55.90; H, 4.10; N, 20.37. Found: C, 55.93; H, 4.34; N, 20.72.

MS (EI): 343 (M$^+$).

¹H-NMR (400 MHz, DMSO-d$_6$) δ (ppm): 0.94 (3H, t, J=7.3 Hz), 1.64–20 1.69 (2H, m), 2.37–2.45 (2H, m), 5.52 (1H, s), 7.34 (1H, s), 7.54–7.60 (2H, m), 7.89 (1H, dd, J=2.0, 6.9 Hz), 9.97 (1H, s), 12.25 (1H, s).

Example 186

4-(2-Bromo-3-cyanophenyl)-5-cyano-4,7-dihydro-6-propyl-2H-pyrazolo[3,4-b]pyridine 1/5H$_2$O The title compound was prepared from methyl butanoate, 2-bromo-3-cyanobenzaldehyde and 3-aminopyrazole in the same manner as in Example 94.

MP: 275–279° C. (decomposition).

Anal. Calcd. for: C$_{17}$H$_{14}$BrN$_5$1/5H$_2$O: C, 55.05; H, 3.89; N, 18.88. Found: C, 54.98; H, 3.91; N, 18.81.

MS (EI): 368 (M$^+$).

¹H-NMR (400 MHz, DMSO-d$_6$) δ (ppm): 0.94 (3H, t, J=7.3 Hz), 1.64–1.69 (2H, m), 2.38–2.43 (2H, m), 5.47 (1H, s), 7.33 (1H, s), 7.54–7.60 (2H, m), 7.83 (1H, dd, J=2.0, 7.4 Hz), 9.95 (1H, s), 12.24 (1H, s).

Example 187

(+)Ethyl 4-(3,4-dihydro-2H-benzopyran-8-yl)-4,7-dihydro-6-propyl-2H-pyrazolo[3,4-b]pyridine-5-carboxylate To a solution of the compound (1.94 g) described in Example 73 in acetonitrile (15 ml) was added (–)-10-camphorsulfonic acid (1.23 g) at 50° C. and the mixture was stirred under ice-cooling for 30 minutes. The precipitated crystals were collected by filtration and recrystallized (ethanol-ethyl acetate (2:1), 30 ml) to give white crystals (0.81 g). The obtained white crystals were suspended in water and a saturated aqueous sodium hydrogencarbonate solution was added. The mixture was extracted with ethyl acetate and the extract was washed with water and a saturated aqueous sodium chloride solution, and dried over anhydrous magnesium sulfate. The solvent was evaporated to give a colorless transparent oil. The obtained colorless transparent oil was crystallized from ethyl acetate to give the title compound (470 mg) as white crystals.

MP: 159–161° C.

Anal. Calcd. for: C$_{21}$H$_{25}$N$_3$O$_3$: C, 68.64; H, 6.86; N, 11.44. Found: C, 68.37; H, 6.86; N, 11.26.

Specific rotation: [α]$_D$=+200° (EtOH, c=0.5).

MS (EI): 367 (M$^+$).

¹H-NMR (400 MHz, DMSO-d$_6$) δ (ppm): 0.91 (3H, t, J=6.8 Hz), 0.98 (3H, t, J=7.3 Hz), 1.60–1.70 (2H, m), 1.90–2.00 (2H, m), 2.67–2.82 (4H, m), 3.81 (2H, m), 4.25 (2H, m), 5.42 (1H, s), 6.62 (1H, dd, J=7.4, 7.8 Hz), 6.72–6.76 (2H, m), 7.18 (1H, s), 9.26 (1H, s), 11.81 (1H, s).

Example 188

(–)Ethyl 4-(3,4-dihydro-2H-benzopyran-8-yl)-4,7-dihydro-6-propyl-2H-pyrazolo[3,4-b]pyridine-5-carboxylate The filtrate obtained by filtering off the (–)-10-camphorsulfonate salt in Example 187 was concentrated under reduced pressure and suspended in water. To the suspension was added a saturated aqueous sodium hydrogencarbonate solution and the mixture was extracted with ethyl acetate. The extract was washed with a saturated aqueous sodium chloride solution and dried over anhydrous magnesium sulfate. The solvent was evaporated and the obtained residue was crystallized from ethyl acetate to give white crystals (780 mg). By the same process as in Example 187 using the obtained white crystals and (+)-10-camphorsulfonic acid, the title compound (150 mg) was obtained as white crystals.

MP: 160–161° C.

Anal. Calcd. for: C$_{21}$H$_{25}$N$_3$O$_3$: C, 68.64; H, 6.86; N, 11.44. Found: C, 68.49; H, 6.81; N, 11.42.

Specific rotation: [α]$_D$=–202° (EtOH, c=0.5)

MS (EI): 367 (M$^+$).

¹H-NMR (400 MHz, DMSO-d$_6$) δ (ppm): 0.91 (3H, t, J=6.8 Hz), 0.98 (3H, t, J=7.3 Hz), 1.60–1.70 (2H, m), 1.90–2.00 (2H, m), 2.67–2.82 (4H, m), 3.81 (2H, m), 4.25 (2H, m), 5.42 (1H, s), 6.62 (1H, dd, J=7.4, 7.8 Hz), 6.72–6.76 (2H, m), 7.18 (1H, s), 9.26 (1H, s), 11.81 (1H, s).

Example 189

4-(2-Bromo-3-nitrophenyl)-5-cyano-4,7-dihydro-6-propyl-2H-pyrazolo[3,4-b]pyridine The title compound was prepared from methyl butanoate, 2-bromo-3-nitrobenzaldehyde and 3-aminopyrazole in the same manner as in Example 94.

MP: 250–255° C. (decomposition).

Anal. Calcd. for: C$_{16}$H$_{14}$BrN$_5$O$_2$: C, 49.50; H, 3.63; N, 18.04. Found: C, 49.37; H, 3.76; N, 18.02.

MS (EI): 388 (M$^+$).

¹H-NMR (400 MHz, DMSO-d$_6$) δ (ppm): 0.95 (3H, t, J=7.6 Hz), 1.64–1.70 (2H, m), 2.39–2.44 (2H, m), 5.53 (1H, s), 7.34 (1H, s), 7.49 (1H, d, J=7.8 Hz), 7.60 (1H, dd, J=7.8, 8.0 Hz), 7.82 (1H, d, J=8.0 Hz), 9.97 (1H, s), 12.25 (1H, s).

Example 190

Ethyl 4,7-dihydro-4-(2-methoxy-3-methylphenyl)-6-propyl-2H-pyrazolo[3,4-b]pyridine-5-carboxylate A suspension of 2,6-dimethylphenol (19.5 g), iodomethane (31 ml) and potassium carbonate (33.2 g) in dimethylformamide (200 ml) was stirred at 60° C. for 10 hours. The reaction mixture was poured into water (300 ml) and the mixture was extracted with ethyl acetate. The extract was washed with a saturated aqueous sodium chloride solution and dried over anhydrous magnesium sulfate. The solvent was evaporated and the obtained residue was purified by silica gel column chromatography (eluent:hexane) to give 2-methoxy-m-xylene (12 g) as a colorless oil. A suspension of 2-methoxy-m-xylene (5.1 g), N-bromosuccinimide (4.2 g) and bezoyl peroxide (229 mg) in carbon tetrachloride (50 ml) was heated under reflux for 3 hours. The insoluble material was filtered off and the filtrate was concentrated under reduced pressure. The obtained residue was purified by silica gel column chromatography (eluent:hexane-ethyl acetate (10:1)) to give a yellow solid (5.4 g). The obtained yellow solid (5.4 g) and hexamethylenetetramine (5.1 g) were dissolved in acetic acid-water (1:1, 16 ml) and the mixture was heated under reflux for 2 hours. To the reaction mixture was added concentrated hydrochloric acid (6 ml) and the mixture was heated under reflux for 15 minutes. The reaction mixture was extracted with ethyl acetate. The extract was washed with water, an aqueous sodium hydrogencarbonate solution and a saturated aqueous sodium chloride solution, and dried over anhydrous magnesium sulfate. The solvent was evaporated and the obtained residue was purified by silica gel column chromatography (eluent: hexane-ethyl acetate (5:1)) and crystallized (hexane-ethyl acetate (5:1)) to give 2-methoxy-3-methylbenzaldehyde (1.2 g) as yellow crystals. Subsequently, the title compound was prepared from 2-methoxy-3-methylbenzaldehyde, 3-aminopyrazole and ethyl 3-ketohexanoate in the same manner as in Example 25.

MP: 220–222° C.

Anal. Calcd. for: $C_{20}H_{25}N_3O_3$: C, 67.58; H, 7.09; N, 11.82. Found: C, 67.47; H, 7.02; N, 11.91.

MS (EI): 355 (M$^+$).

$^1$H-NMR (400 MHz, DMSO-d$_6$) δ (ppm): 0.89 (3H, t, J=7.0 Hz), 0.97 (3H, t, J=7.3 Hz), 1.60–1.70 (2H, m), 2.23 (3H, s), 2.66–2.85 (2H, m), 3.81 (3H, s), 3.81–3.85 (2H, m), 5.43 (1H, s), 6.82–6.91 (3H, m), 7.13 (1H, s), 9.31 (1H, s), 11.82 (1H, s).

Example 191

Ethyl 4-(3-cyano-2-methoxyphenyl)-4,7-dihydro-6-propyl-2H-pyrazolo[3,4-b]pyridine-5-carboxylate The title compound was prepared from 2-methoxy-3-methylbenzaldehyde, 3-aminopyrazole and ethyl 3-ketohexanoate in the same manner as in Example 180.

MP: 220–222° C.

Anal. Calcd. for: $C_{20}H_{22}N_4O_3$: C, 65.56; H, 6.05; N, 15.29. Found: C, 65.20; H, 6.10; N, 15.23.

MS (EI): 366 (M$^+$).

$^1$H-NMR (400 MHz, DMSO-d$_6$) δ (ppm): 0.89 (3H, t, J=7.1 Hz), 0.96 (3H, t, J=7.3 Hz), 1.60–1.70 (2H, m), 2.70–2.80 (2H, m), 3.75–3.90 (2H, m), 4.02 (3H, s), 5.46 (1H, s), 7.14–7.19 (2H, m), 7.32 (1H, d, J=6.1 Hz), 7.53 (1H, d, J=7.8 Hz), 9.51 (1H, s), 11.97 (1H, s).

Example 192

5-Cyano-6-ethyl-4,7-dihydro-4-(2-nitrophenyl)-2H-pyrazolo[3,4-b]pyridine

The title compound was prepared from methyl propionate, 2-nitrobenzaldehyde and 3-aminopyrazole in the same manner as in Example 94.

MP: 228–230° C. (decomposition).

Anal. Calcd. for: $C_{15}H_{13}N_5O_2$: C, 61.01; H, 4.44; N, 23.72. Found: C, 60.72; H, 4.51; N, 23.78.

MS (EI): 295 (M$^+$).

$^1$H-NMR (400 MHz, DMSO-d$_6$) δ (ppm): 1.21 (3H, t, J=7.4 Hz), 2.42–2.49 (2H, m), 5.37 (1H, s), 7.27 (1H, s), 7.43–7.49 (2H, m), 7.70 (1H, dd, J=7.6, 8.0 Hz), 7.89 (1H, d, J=8.0 Hz), 9.94 (1H, s), 12.21 (1H, s).

Example 193

5-Cyano-4-(2,3-dichlorophenyl)-6-ethyl-4,7-dihydro-2H-pyrazolo[3,4-b]pyridine

The title compound was prepared from methyl propionate, 2,3-dichlorobenzaldehyde, 3-aminopyrazole and 1-cyanobutan-2-one in the same manner as in Example 94.

MP: >300° C.

Anal. Calcd. for: $C_{15}H_{12}Cl_2N_4$: C, 56.44; H, 3.79; N, 17.55. Found: C, 56.33; H, 3.86; N, 17.67.

MS (EI): 319 (M$^+$).

$^1$H-NMR (400 MHz, DMSO-d$_6$) δ (ppm): 1.21 (3H, t, J=7.6 Hz), 2.38–2.49 (2H, m), 5.43 (1H, s), 7.23 (1H, d, J=6.8 Hz), 7.31–7.37 (2H, m), 7.51 (1H, dd, J=1.7, 8.1 Hz), 9.92 (1H, s), 12.19 (1H, s).

Example 194

5-Cyano-6-ethyl-4,7-dihydro-4-(2-methoxyphenyl)-2H-pyrazolo[3,4-b]pyridine

The title compound was prepared from methyl propionate, 2-methoxybenzaldehyde and 3-aminopyrazole in the same manner as in Example 94.

MP: 230–232° C.

Anal. Calcd. for: $C_{16}H_{16}N_4O$: C, 68.55; H, 5.75; N, 19.99. Found: C, 68.16; H, 5.97; N, 20.39.

MS (EI): 280 (M$^+$).

$^1$H-NMR (400 MHz, DMSO-d$_6$) δ (ppm): 1.22 (3H, t, J=7.6 Hz), 2.42–2.49 (2H, m), 3.84 (3H, s), 5.21 (1H, s), 6.86–6.91 (1H, m), 6.99 (1H, d, J=8.3 Hz), 7.05 (1H, d, J=7.6 Hz), 7.15–7.19 (2H, m), 9.68 (1H, s), 12.02 (1H, s).

Example 195

4-(2-Chloro-3-cyanophenyl)-5-cyano-6-ethyl-4,7-dihydro-2H-pyrazolo[3,4-b]pyridine The title compound was prepared from methyl propionate, 2-chloro-3-cyanobenzaldehyde and 3-aminopyrazole in the same manner as in Example 94.

MP: >300° C.

Anal. Calcd. for: $C_{16}H_{12}ClN_5$: C, 62.04; H, 3.90; N, 22.61. Found: C, 61.74; H, 4.14; N, 22.93.

MS (EI): 309 (M$^+$).

$^1$H-NMR (400 MHz, DMSO-d$_6$) δ (ppm): 1.21 (3H, t, J=7.6 Hz), 2.42–2.49 (2H, m), 5.45 (1H, s), 7.33 (1H, s), 7.52–7.60 (2H, m), 7.87 (1H, dd, J=2.0, 7.3 Hz), 9.97 (1H, s), 12.23 (1H, s).

Example 196

4-(2,1,3-Benzoxazol-4-yl)-5-cyano-6-ethyl-4,7-dihydro-2H-pyrazolo[3,4-b]pyridine The title compound was prepared from methyl propionate, 2,1,3-benzoxazole-4-aldehyde and 3-aminopyrazole in the same manner as in Example 94.

MP: 206–208° C. (decomposition).

Anal. Calcd. for: $C_{15}H_{12}N_6O$: C, 61.64; H, 4.14; N, 28.75. Found: C, 61.43; H, 4.41; N, 28.85.

MS (EI): 292 (M$^+$).

$^1$H-NMR (400 MHz, DMSO-d$_6$) δ (ppm): 1.20 (3H, t, J=7.6 Hz), 2.40–2.50 (2H, m), 5.40 (1H, s), 7.26 (1H, s), 7.40 (1H, d, J=6.6 Hz), 7.58 (1H, dd, J=6.6, 9.0 Hz), 7.92 (1H, d, J=9.0 Hz), 9.97 (1H, s), 12.14 (1H, s).

Example 197

4-(2-Chlorophenyl)-5-cyano-6-ethyl-4,7-dihydro-2H-pyrazolo[3,4-b]pyridine

The title compound was prepared from methyl propionate, 2-chlorobenzaldehyde and 3-aminopyrazole in the same manner as in Example 94.

MP: >300° C.

Anal. Calcd. for: $C_{15}H_{13}ClN_4$: C, 63.27; H, 4.60; N, 19.68. Found: C, 63.14; H, 4.69; N, 19.67.

MS (EI): 284 (M$^+$).

$^1$H-NMR (400 MHz, DMSO-d$_6$) δ (ppm): 1.21 (3H, t, J=7.6 Hz), 2.42–2.49 (2H, m), 5.35 (1H, s), 7.22–7.26 (3H, m), 7.30–7.34 (1H, m), 7.42 (1H, d, J=7.8 Hz), 9.85 (1H, s), 12.15 (1H, s).

Example 198

4-(2-Bromo-3-cyanophenyl)-5-cyano-6-ethyl-4,7-dihydro-2H-pyrazolo[3,4-b]pyridine The title compound was prepared from methyl propionate, 2-bromo-3-cyanobenzaldehyde and 3-aminopyrazole in the same manner as in Example 94.

MP: >300° C.

Anal. Calcd. for: $C_{16}H_{12}BrN_5$: C, 54.25; H, 3.41; N, 19.77. Found: C, 54.13; H, 3.56; N, 19.98.

MS (EI): 354 (M$^+$).

$^1$H-NMR (400 MHz, DMSO-d$_6$) δ (ppm): 1.21 (3H, t, J=7.6 Hz), 2.43 (2H, m), 5.46 (1H, s), 7.33 (1H, s), 7.56–7.60 (2H, m), 7.82–7.84 (1H, m), 9.98 (1H, s), 12.24 (1H, s).

Example 199

4-(2-Bromophenyl)-5-cyano-6-ethyl-4,7-dihydro-2H-pyrazolo[3,4-b]pyridine

The title compound was prepared from methyl propionate, 2-bromobenzaldehyde and 3-aminopyrazole in the same manner as in Example 94.

MP: 250–253° C. (decomposition).

Anal. Calcd. for: $C_{15}H_{13}BrN_4$: C, 54.73; H, 3.98; N, 17.02. Found: C, 54.28; H, 3.96; N, 16.94.

MS (EI): 329 (M$^+$).

$^1$H-NMR (400 MHz, DMSO-d$_6$) δ (ppm): 1.21 (3H, t, J=7.6 Hz), 2.42–2.45 (2H, m), 5.34 (1H, s), 7.16 (1H, dd, J=7.5, 7.6 Hz), 7.22 (1H, d, J=6.6 Hz), 7.27 (1H, s), 7.36 (1H, dd, J=6.3, 7.3 Hz), 7.59 (1H, d, J=6.8 Hz), 9.86 (1H, s), 12.15 (1H, s).

Example 200

Ethyl 4-(2-chlorophenyl)-6-cyano-4,7-dihydro-2H-pyrazolo[3,4-b]pyridine-5-carboxylate 1/4 hydrate A solution of 1,1'-carbonylbis-1H-imidazole (22.5 g), ethanol (8.1 ml) and toluene (100 ml) was stirred at room temperature for 1.5 hours. To the reaction mixture was added ice-water (100 ml) and the mixture was extracted with ethyl acetate. The extract was washed with a saturated-aqueous sodium chloride solution and dried over anhydrous magnesium sulfate. The solvent was evaporated and the obtained residue was purified by silica gel column chromatography (eluent:hexane-ethyl acetate (1:1)) to give a colorless oil (19.3 g). A solution of the obtained residue (19.3 g) and pyruvic aldehyde dimethyl acetal (11.1 ml) in toluene (50 ml) was added dropwise to a suspension of sodium hydride (8.44 g) in toluene (250 ml) under reflux with heating over 15 minutes, and the mixture was heated under reflux for 1.5 hours. To the reaction mixture was added a 10% aqueous citric acid solution (610 ml) and the mixture was extracted with ethyl acetate. The extract was washed with a saturated aqueous sodium chloride solution and dried over anhydrous magnesium sulfate. The solvent was evaporated and the obtained residue was purified by silica gel column chromatography (eluent:hexane-ethyl acetate (5:1)) to give ethyl 4,4-dimethoxy-3-oxobutanoate (15.1 g) as a colorless oil. Subsequently, ethyl 4-(2-chlorophenyl)-6-dimethoxymethyl-4,7-dihydro-2H-pyrazolo[3,4-b]pyridine-5-carboxylate was obtained as a yellow solid from 2-chlorobenzaldehyde, 3-aminopyrazole and ethyl 4,4-dimethoxy-2-oxobutanoate in the same manner as in Example 1. To a solution of ethyl 4-(2-chlorophenyl)-6-dimethoxymethyl-4,7-dihydro-2H-pyrazolo[3,4-b]pyridine-5-carboxylate (463 mg) in tetrahydrofuran (5 ml) was added 1N hydrochloric acid (10 ml) and the mixture was stirred at room temperature for 6 hours. To the reaction mixture was added a saturated aqueous sodium hydrogencarbonate solution and the mixture was extracted with ethyl acetate. The extract was washed with a saturated aqueous sodium chloride solution and dried over anhydrous magnesium sulfate. The solvent was evaporated and the obtained residue was purified by silica gel column chromatography (eluent:hexane-ethyl acetate (1:1)) to give ethyl 4-(2-chlorophenyl)-6-formyl-4,7-dihydro-2H-pyrazolo[3,4-b]pyridine-5-carboxylate (290 mg) as a yellow solid. A solution of ethyl 4-(2-chlorophenyl)-6-formyl-4,7-dihydro-2H-pyrazolo[3,4-b]pyridine-5-carboxylate (290 mg) and hydroxylamine-O-sulfonic acid (128.5 mg) in water (10 ml)-ethanol (10 ml) was stirred at 80° C. for 2 hours. To the reaction mixture was added a saturated aqueous sodium hydrogencarbonate solution and the mixture was extracted with ethyl acetate. The extract was washed with a saturated aqueous sodium chloride solution and dried over anhydrous magnesium sulfate. The solvent was evaporated and the obtained residue was purified by silica gel column chromatography (eluent:hexane-ethyl acetate (1:1)) and crystallized from ethanol-ethyl acetate to give the title compound (53 mg) as yellow crystals.

MP: 275–278° C. (decomposition).

Anal. Calcd. for: $C_{16}H_{13}ClN_4O_2 \cdot 1/4H_2O$: C, 57.66; H, 4.08; N, 16.81. Found: C, 57.54; H, 4.06; N, 16.66.

MS (EI): 328 (M$^+$).

$^1$H-NMR (400 MHz, DMSO-d$_6$) δ (ppm): 0.93 (3H, t, J=7.1 Hz), 3.91 (2H, m), 5.67 (1H, s), 7.15–7.19 (2H, m), 7.25 (1H, dd, J=7.3, 8.3 Hz), 7.33 (1H, s), 7.39 (1H, d, J=8.3 Hz), 10.81 (1H, s), 12.34 (1H, s).

Example 201

4-(2-Chloro-3-trifluoromethylphenyl)-5-cyano-4,7-dihydro-6-propyl-2H-pyrazolo[3,4-b]pyridine The title compound was prepared from methyl butanoate, 2-chloro-3-trifluoromethylbenzaldehyde and 3-aminopyrazole in the same manner as in Example 94.

MP: >250° C.

Anal. Calcd. for: $C_{17}H_{14}ClF_3N_4$: C, 55.67; H, 3.85; N, 15.28. Found: C, 55.81; H, 3.97; N, 15.44.

MS (EI): 366 (M$^+$).

$^1$H-NMR (400 MHz, DMSO-d$_6$) δ (ppm): 0.95 (3H, t, J=7.3 Hz), 1.64–1.70 (2H, m), 2.40–2.43 (2H, m), 5.55 (1H, s), 7.31 (1H, s), 7.54–7.56 (2H, m), 7.74 (1H, dd, J=3.6, 5.6 Hz), 9.93 (1H, s), 12.22 (1H, s).

Example 202

4-(2-Chloro-3-trifluoromethylphenyl)-5-cyano-4,7-dihydro-6-phenyl-2H-pyrazolo[3,4-b]pyridine The title compound was prepared from benzoic acid, 2-chloro-3-trifluoromethylbenzaldehyde and 3-aminopyrazole in the same manner as in Example 95.

MP: >250° C.

Anal. Calcd. for: $C_{20}H_{12}ClF_3N_4$: C, 59.94; H, 3.02; N, 13.98. Found: C, 59.74; H, 3.18; N, 13.95.

MS (EI): 400 (M$^+$).

$^1$H-NMR (400 MHz, DMSO-d$_6$) δ (ppm): 570 (1H, s), 7.39 (1H, s), 7.49–7.51 (3H, m), 7.57–7.62 (3H, m), 7.75–7.79 (2H, m), 10.18 (1H, s), 12.31 (1H, s).

Example 203

4-(2-Chlorophenyl)-5-cyano-4,7-dihydro-6-isopropyl-2H-pyrazolo[3,4-b]pyridine

The title compound was prepared from methyl isobutyrate, 2-chlorobenzaldehyde and 3-aminopyrazole in the same manner as in Example 94.

MP: >250° C.

Anal. Calcd. for: $C_{16}H_{15}ClN_4$: C, 64.32; H, 5.06; N, 18.75. Found: C, 64.18; H, 5.12; N, 18.84.

MS (EI): 298 (M$^+$).

$^1$H-NMR (400 MHz, DMSO-d$_6$) δ (ppm): 1.23 (3H, d, J=6.8 Hz), 1.27 (3H, d, J=6.8 Hz), 3.06 (1H, m), 5.34 (1H, s), 7.22–7.26 (3H, m), 7.30–7.34 (1H, m), 7.42 (1H, d, J=7.1 Hz), 9.63 (1H, s), 12.16 (1H, s).

Example 204

Ethyl 1-tert-butoxycarbonyl-4-(2-chlorophenyl)-4,7-dihydro-6-propyl-1H-pyrazolo[3,4-b]pyridine-5-carboxylate To a solution of the compound (1.2 g) described in Example 27 and dimethylaminopyridine (128 mg) in THF (40 ml) was added di-tert-butyldicarbonate (830 mg) and the mixture was stirred at room temperature for one day. The solvent was evaporated under reduced pressure and the title compound (102 mg) was obtained as colorless crystals by silica gel column chromatography (eluent:hexane-ethyl acetate (3:1)).

MP: 112–116° C.

Anal. Calcd. for: $C_{23}H_{28}ClN_3O_4$: C, 61.95; H, 6.33; N, 9.42. Found: C, 61.84; H, 6.33; N, 9.34.

MS (EI): 445 (M$^+$).

$^1$H-NMR (400 MHz, DMSO-d$_6$) δ (ppm): 0.87 (3H, t, J=6.9 Hz), 0.98 (3H, t, J=7.3 Hz), 1.56 (9H, s), 1.62–1.72 (2H, m), 2.80–2.92 (2H, m), 3.85 (2H, q, J=6.9 Hz), 5.56 (1H, s), 7.14–7.17 (2H, m), 7.23 (1H, dd, J=7.3 and 7.8 Hz), 7.30 (1H, s), 7.39 (1H, d, J=7.4 Hz), 8.75 (1H, s).

Example 205

Ethyl 2-tert-butoxycarbonyl-4-(2-chlorophenyl)-4,7-dihydro-6-propyl-2H-pyrazolo[3,4-b]pyridine-5-carboxylate Through the column of silica gel column chromatography used in Example 204 was further flowed hexane-ethyl acetate (3:1) as an eluent, the title compound (300 mg) was obtained as colorless crystals.

MP: 144–147° C.

Anal. Calcd. for: $C_{23}H_{28}ClN_3O_4$: C, 61.95; H, 6.33; N, 9.42. Found: C, 61.93; H, 6.35; N, 9.40.

MS (EI): 445 (M$^+$).

$^1$H-NMR (400 MHz, DMSO-d$_6$) δ (ppm): 0.85 (3H, t, J=6.9 Hz), 0.97 (3H, t, J=7.3 Hz), 1.49 (9H, s), 1.63–1.69 (2H, m), 2.66–2.85 (2H, m), 3.80 (2H, q, J=6.9 Hz), 5.57 (1H, s), 7.10–7.15 (1H, m), 7.17 (1H, ddd, J=1.5, 7.3 and 7.8 Hz), 7.23 (1H, dd, J=6.4 and 7.3 Hz), 7.41 (1H, d, J=7.2 Hz), 7.67 (1H, s), 10.01 (1H, s).

Example 206

Ethyl 4-(2-chlorophenyl)-4,7-dihydro-1-methoxycarbonyl-6-propyl-1H-pyrazolo[3,4-b]pyridine-5-carboxylate The title compound was obtained as a colorless amorphous solid from ethyl 4-(2-chlorophenyl)-4,7-dihydro-6-propyl-1H-pyrazolo[3,4-b]pyridine-5-carboxylate, dimethylaminopyridine and methyl chloroformate in the same manner as in Example 204.

MS (EI): 403 (M$^+$).

IR (KBr): ν=3422, 1736, 1699, 1531, 1450, 1232, 1086 cm$^{-1}$.

$^1$H-NMR (400 MHz, DMSO-d$_6$) δ (ppm): 0.87 (3H, t, J=7.1 Hz), 0.97 (3H, t, J=7.3 Hz), 1.60–1.66 (2H, m), 2.86–2.89 (2H, m), 3.83 (2H, q, J=7.1 Hz), 3.94 (3H, s), 5.55 (1H, s), 7.13–7.38 (4H, m), 7.35 (1H, s), 8.67 (1H, s)

Example 207

Ethyl 4-(2-chlorophenyl)-4,7-dihydro-2-methoxycarbonyl-6-propyl-2H-pyrazolo[3,4-b]pyridine-5-carboxylate Through the column of silica gel column chromatography used in Example 206 was further flowed hexane-ethyl acetate (3:1) as an eluent, the title compound was obtained as colorless crystals.

MP: 141–143° C.

MS (EI): 403 (M$^+$).

IR (KBr): ν=3290, 1774, 1695, 1633, 1597, 1523, 1444, 1364, 1307, 1209 cm$^{-1}$.

$^1$H-NMR (400 MHz, DMSO-d$_6$) δ (ppm): 0.86 (3H, t, J=7.1 Hz), 0.95 (3H, t, J=7.3 Hz), 1.64–1.70 (2H, m), 2.71–2.85 (2H, m), 3.78 (2H, q, J=7.1 Hz), 3.85 (1H, s), 5.57 (1H, s), 7.10–7.24 (3H, m), 7.42 (1H, d, J=1.4 Hz), 7.72 (1H, s), 9.94 (1H, s).

Example 208

Ethyl 1-benzyloxycarbonyl-4-(2-chlorophenyl)-4,7-dihydro-6-propyl-1H-pyrazolo[3,4-b]pyridine-5-carboxylate The title compound was obtained as colorless crystals from ethyl 4-(2-chlorophenyl)-4,7-dihydro-6-propyl-1H-pyrazolo[3,4-b]pyridine-5-carboxylate, dimethylaminopyridine and benzyl chloroformate in the same manner as in Example 204.

MP: 80° C.

Anal. Calcd. for: $C_{26}H_{26}ClN_3O_4$: C, 65.07; H, 5.46; N, 8.75. Found: C, 65.24; H, 5.71; N, 8.50.

MS (EI): 479 (M$^+$).

IR (KBr): ν=3344, 1745, 1701, 1527, 1451, 1226, 1084, 1060 cm$^{-1}$.

$^1$H-NMR (400 MHz, DMSO-d$_6$) δ (ppm): 0.88 (3H, t, J=7.0 Hz), 0.94 (3H, t, J=7.3 Hz), 1.56–1.62 (2H, m), 2.81–2.88 (2H, m), 3.82 (2H, q, J=7.0 Hz), 5.41 (2H, s), 5.55 (1H, s), 7.13–7.24 (3H, m), 7.36 (1H, s), 7.37 (6H, m), 8.62 (1H, s).

Example 209

Ethyl 2-benzyloxycarbonyl-4-(2-chlorophenyl)-4,7-dihydro-6-propyl-2H-pyrazolo[3,4-b]pyridine-5-carboxylate Further elution using the column of silica gel column chromatography in Example 208 and hexane-ethyl acetate (3:1) as an eluent, the title compound was obtained as a colorless amorphous solid.

MS (EI): 479 (M$^+$).

IR (KBr): ν=3294, 1759, 1697, 1601, 1383, 1363, 1300, 1201 cm$^{-1}$.

¹H-NMR (400 MHz, DMSO-d₆) δ (ppm): 0.85 (3H, t, J=7.0 Hz), 0.95 (3H, t, J=7.3 Hz), 1.61–1.67 (2H, m), 2.72–2.82 (2H, m), 3.79 (2H, q, J=7.0 Hz), 5.30 (2H, s), 5.56 (1H, s), 7.09–7.41 (9H, m), 7.73 (1H, s), 9.95 (1H, s).

Example 210

Ethyl 1-benzoyl-4-(2-chlorophenyl)-4,7-dihydro-6-propyl-1H-pyrazolo[3,4-b]pyridine-5-carboxylate The title compound was obtained as colorless crystals from ethyl 4-(2-chlorophenyl)-4,7-dihydro-6-propyl-1H-pyrazolo[3,4-b]pyridine-5-carboxylate, dimethylaminopyridine and benzoyl chloride in the same manner as in Example 204.

MP: 115° C.

Anal. Calcd. for: $C_{25}H_{24}ClN_3O_3$: C, 66.74; H, 5.38; N, 9.34. Found: C, 66.58; H, 5.41; N, 9.28.

MS (EI): 449 (M⁺).

IR (KBr): ν=3414, 1680, 1641, 1516, 1095 cm⁻¹.

¹H-NMR (400 MHz, DMSO-d₆) δ (ppm): 0.90 (3H, t, J=6.3 Hz), 1.00 (3H, t, J=7.3 Hz), 1.65–1.71 (2H, m), 2.90–2.93 (2H, m), 3.85 (2H, q, J=7.3 Hz), 5.63 (1H, s), 7.16–7.22 (2H, m), 7.29 (1H, d, J=7.3 Hz), 7.40 (1H, d, J=7.8 Hz), 7.46 (1H, s), 7.50–7.54 (2H, m), 7.65 (1H, dd, J=6.3 and 7.8 Hz), 7.98 (1H, d, J=6.3 Hz), 9.10 (1H, s).

Example 211

Ethyl 2-benzoyl-4-(2-chlorophenyl)-4,7-dihydro-6-propyl-2H-pyrazolo[3,4-b]pyridine-5-carboxylate Through the column of silica gel column chromatography used in Example 210 was further flowed hexane-ethyl acetate (3:1) as an eluent, the title compound was obtained as a colorless amorphous solid.

MP: 119–121° C.

Anal. Calcd. for: $C_{25}H_{24}ClN_3O_3$: C, 66.74; H, 5.38; N, 9.34. Found: C, 66.58; H, 5.43; N, 9.30.

MS (EI): 479 (M⁺).

IR (KBr): ν=3406, 1670, 1628, 1601, 1481, 1348, 1084 cm⁻¹.

¹H-NMR (400 MHz, DMSO-d₆) δ (ppm): 0.87 (3H, t, J=6.8 Hz), 0.97 (3H, t, J=7.3 Hz), 1.65–1.67 (2H, m), 2.74–2.83 (2H, m), 3.82 (2H, q, J=7.3 Hz), 5.65 (1H, s), 7.13–7.26 (3H, m), 7.44 (1H, d, J=7.8 Hz), 7.47–7.51 (2H, m), 7.60 (1H, dd, J=7.3 and 7.3 Hz), 7.91 (2H, d, J=7.8), 8.00 (1H, s), 10.06 (1H, s).

Example 212

Ethyl 1-benzylcarbonyl-4-(2-chlorophenyl)-4,7-dihydro-6-propyl-1H-pyrazolo[3,4-b]pyridine-5-carboxylate The title compound was obtained as a colorless amorphous solid from ethyl 4-(2-chlorophenyl)-4,7-dihydro-6-propyl-1H-pyrazolo[3,4-b]pyridine-5-carboxylate, dimethylaminopyridine and phenylacetyl chloride in the same manner as in Example 204.

¹H-NMR (400 MHz, DMSO-d₆) δ (ppm): 0.89 (3H, t, J=6.8 Hz), 0.94 (3H, t, J=7.3 Hz), 1.60–1.61 (2H, m), 2.84–2.86 (2H, m), 3.82 (2H, q, J=6.8 Hz), 4.47 (2H, s), 5.59 (1H, s), 7.20–9.44 (10H, m), 8.90 (1H, s).

Example 213

Ethyl 2-benzylcarbonyl-4-(2-chlorophenyl)-4,7-dihydro-6-propyl-2H-pyrazolo[3,4-b]pyridine-5-carboxylate Through the column of silica gel column chromatography used in Example 212 was further flowed hexane-ethyl acetate (3:1) as an eluent, the title compound was obtained as a colorless amorphous solid.

MS (EI): 463 (M⁺).

IR (KBr): ν=3308, 1699, 1628, 1630, 1599, 1523 cm⁻¹.

¹H-NMR (400 MHz, DMSO-d₆) δ (ppm): 0.87 (3H, t, J=6.8 Hz), 0.98 (3H, t, J=7.3 Hz), 1.65–1.71 (2H, m), 2.77–2.84 (2H, m), 3.83 (2H, q, J=6.8 Hz), 4.25 (2H, s), 5.60 (1H, s), 7.11–7.31 (8H, m), 7.41 (1H, d, J=7.8 Hz), 7.84 (1H, s), 10.30 (1H, s).

Example 214

Ethyl 4-(2-chlorophenyl)-4,7-dihydro-1-phenylcarbamoyl-6-propyl-1H-pyrazolo[3,4-b]pyridine-5-carboxylate The title compound was obtained as a colorless amorphous solid from ethyl 4-(2-chlorophenyl)-4,7-dihydro-6-propyl-1H-pyrazolo[3,4-b]pyridine-5-carboxylate, dimethylaminopyridine and phenyl isocyanate in the same manner as in Example 204.

MS (EI): 464 (M⁺).

IR (KBr): ν=3310, 1699, 1597, 1518, 1448, 1369, 1228, 1194, 1093 cm⁻¹.

¹H-NMR (400 MHz, DMSO-d₆) δ (ppm): 0.98 (3H, t, J=7.1 Hz), 0.97 (3H, t, J=7.3 Hz), 1.96 (2H, m), 2.87 (2H, m), 3.83 (2H, q, J=7.1 Hz), 5.61 (1H, s), 7.11–7.69 (8H, m), 7.67 (2H, d, J=7.8 Hz), 8.86 (1H, s), 10.31 (1H, s).

Example 215

Ethyl 4-(2-chlorophenyl)-4,7-dihydro-2-phenylcarbamoyl-6-propyl-2H-pyrazolo[3,4-b]pyridine-5-carboxylate Through the column of silica gel column chromatography used in Example 214 was further flowed hexane-ethyl acetate (3:1) as an eluent, the title compound was obtained as colorless crystals.

MP: 145–147° C.

Anal. Calcd. for: $C_{25}H_{25}ClN_4O_3$: C, 64.58; H, 5.42; N, 12.05. Found: C, 64.10; H, 5.41; N, 12.30.

MS (EI): 464 (M⁺).

IR (KBr): ν=3341, 1697, 1653, 1630, 1597, 1520, 1367, 1197, 1093 cm⁻¹.

¹H-NMR (400 MHz, DMSO-d₆) δ (ppm): 0.88 (3H, t, J=7.0 Hz), 0.97 (3H, t, J=7.3 Hz), 1.68 (2H, m), 2.80–2.92 (2H, m), 3.82 (2H, q, J=7.0 Hz), 5.62 (1H, s), 7.10–7.20 (3H, m), 7.22 (1H, dd, J=7.1 and 7.1 Hz), 7.31–7.33 (2H, m), 7.41 (1H, d, J=7.1 Hz), 7.58–7.60 (2H, m), 7.85 (1H, s), 9.67 (1H, s), 9.83 (1H, s).

Example 216

Ethyl 1-benzylcarbamoyl-4-(2-chlorophenyl)-4,7-dihydro-6-propyl-1H-pyrazolo[3,4-b]pyridine-5-carboxylate The title compound was obtained as a colorless amorphous solid from ethyl 4-(2-chlorophenyl)-4,7-dihydro-6-propyl-1H-pyrazolo[3,4-b]pyridine-5-carboxylate, dimethylaminopyridine and benzyl isocyanate in the same manner as in Example 204.

MS (EI): 478 (M⁺).

IR (KBr): ν=3402, 1699, 1637, 1525, 1226, 1091 cm⁻¹.

¹H-NMR (400 MHz, DMSO-d₆) δ (ppm): 0.88 (3H, t, J=7.0 Hz), 0.96 (3H, t, J=7.3 Hz), 1.61–1.63 (2H, m), 2.83

(2H, m), 3.82 (2H, q, J=7.0 Hz), 4.37 (2H, d), 5.58 (1H, s), 7.11–7.31 (9H, m), 7.38 (1H, d, J=7.8 Hz), 8.74 (1H, s), 9.01 (1H, s).

Example 217

Ethyl 4-(2-chlorophenyl)-4,7-dihydro-1-phenoxycarbonyl-6-propyl-1H-pyrazolo[3,4-b]pyridine-5-carboxylate The title compound was obtained as a colorless amorphous solid from ethyl 4-(2-chlorophenyl)-4,7-dihydro-6-propyl-1H-pyrazolo[3,4-b]pyridine-5-carboxylate, dimethylaminopyridine and phenyl chloroformate in the same manner as in Example 204.

MS (EI): 465 (M$^+$).

IR (KBr): ν=3339, 1728, 1633, 1525, 1371, 1302, 1224, 1091 cm$^{-1}$.

$^1$H-NMR (400 MHz, DMSO-d$_6$) δ (ppm): 0.83 (3H, t, J=7.1 Hz), 0.96 (3H, t, J=7.3 Hz), 1.70 (2H, m), 2.94 (2H, m), 3.82 (2H, q, J=7.1 Hz), 5.62 (1H, s), 7.12–7.53 (9H, m), 8.26 (1H, s), 9.30 (1H, s).

Example 218

Ethyl 4-(2-chlorophenyl)-4,7-dihydro-2-phenoxycarbonyl-6-propyl-2H-pyrazolo[3,4-b]pyridine-5-carboxylate Through the column of silica gel column chromatography used in Example 217 was further flowed hexane-ethyl acetate (3:1) as an eluent, the title compound was obtained as colorless crystals.

MP: 156–157° C.

Anal. Calcd. for: C$_{25}$H$_{24}$ClN$_3$O$_4$: C, 64.44; H, 5.19; N, 9.02. Found: C, 64.42; H, 5.31; N, 9.04.

MS (EI): 465 (M$^+$).

IR (KBr): ν=3325, 1765, 1685, 1597, 1525, 1373, 1205, 1099 cm$^{-1}$.

$^1$H-NMR (400 MHz, DMSO-d$_6$) δ (ppm): 0.87 (3H, t, J=7.1 Hz), 1.00 (3H, t, J=7.3 Hz), 1.67–1.69 (2H, m), 2.76–2.85 (2H, m), 3.82 (2H, q, J=7.1 Hz), 5.61 (1H, s), 7.15 (1H, dd, J=1.7 and 6.8 Hz), 7.15 (1H, dd, J=1.7 and 6.8 Hz), 7.17 (1H, dd, J=2.0 and 7.6 Hz), 7.24 (1H, dd, J=1.3 and 7.4 Hz), 7.27–7.31 (3H, m), 7.41–7.45 (3H, m), 7.89 (1H, s), 10.01 (1H, s).

Example 219

Ethyl 4-(2-chlorophenyl)-1-ethoxycarbonyl-4,7-dihydro-6-propyl-1H-pyrazolo[3,4-b]pyridine-5-carboxylate The title compound was obtained as colorless crystals from ethyl 4-(2-chlorophenyl)-4,7-dihydro-6-propyl-1H-pyrazolo[3,4-b]pyridine-5-carboxylate, dimethylaminopyridine and ethyl chloroformate in the same manner as in Example 204.

MP: 88–89° C.

Anal. Calcd. for: C$_{21}$H$_{24}$ClN$_3$O$_4$: C, 60.36; H, 5.79; N, 10.06. Found: C, 60.24; H, 5.72; N, 10.05.

MS (EI): 417 (M$^+$).

IR (KBr): ν=3422, 1734, 1705, 1647, 1591, 1531, 1228, 1086, 1062 cm$^{-1}$.

$^1$H-NMR (400 MHz, DMSO-d$_6$) δ (ppm): 0.87 (3H, t, J=7.1 Hz), 0.96 (3H, t, J=7.3 Hz), 1.31 (3H, t, J=7.1 Hz), 1.61–1.66 (2H, m), 2.83–2.92 (2H, m), 3.83 (2H, q, J=7.1 Hz), 4.41 (2H, q, J=7.1 Hz), 5.55 (1H, s), 7.13–7.16 (2H, m), 7.25 (1H, dd, J=7.0 and 7.6 Hz), 7.34 (1H, s), 7.38 (1H, d, J=7.6 Hz), 8.65 (1H, s).

Example 220

Ethyl 4-(2-chlorophenyl)-2-ethoxycarbonyl-4,7-dihydro-6-propyl-2H-pyrazolo[3,4-b]pyridine-5-carboxylate Through the column of silica gel column chromatography used in Example 219 was further flowed hexane-ethyl acetate (3:1) as an eluent, the title compound was obtained as a colorless amorphous solid.

MS (EI): 417 (M$^+$).

IR (KBr): ν=3325, 1765, 1685, 1631, 1597, 1525, 1373, 1205, 1099 cm$^{-1}$.

$^1$H-NMR (400 MHz, DMSO-d$_6$) δ (ppm): 0.87 (3H, t, J=7.1 Hz), 0.97 (3H, t, J=7.3 Hz), 1.26 (3H, t, J=7.0 Hz), 1.63–1.69 (2H, m), 2.74–2.81 (2H, m), 3.81 (2H, q, J=7.1 Hz), 4.29 (2H, q, J=7.0 Hz), 5.57 (1H, s), 7.12 (1H, dd, J=6.3 and 7.5 Hz), 7.17 (1H, d, J=7.8 Hz), 7.23 (1H, dd, J=6.3 and 7.4 Hz), 7.40 (1H, d, J=7.8 Hz), 7.71 (1H, s), 9.96 (1H, s).

Example 221

Ethyl 4-(2-chlorophenyl)-4,7-dihydro-1-propoxycarbonyl-6-propyl-1H-pyrazolo[3,4-b]pyridine-5-carboxylate The title compound was obtained as colorless crystals from ethyl 4-(2-chlorophenyl)-4,7-dihydro-6-propyl-1H-pyrazolo[3,4-b]pyridine-5-carboxylate, dimethylaminopyridine and propyl chloroformate in the same manner as in Example 204.

MP: 66–68° C.

MS (EI): 431 (M$^+$).

IR (KBr): ν=3356, 1738, 1695, 1527, 1282, 1084 cm$^{-1}$.

$^1$H-NMR (400 MHz, DMSO-d$_6$) δ (ppm): 0.88 (3H, t, J=7.0 Hz), 0.92 (3H, t, J=7.3 Hz), 0.97 (3H, t, J=7.3 Hz), 1.62–1.67 (2H, m), 1.70–1.75 (2H, m), 2.85–2.92 (2H, m), 3.83 (2H, q, J=7.0 Hz), 4.32 (2H, t, J=6.5 Hz), 5.57 (1H, s), 7.14–7.18 (2H, m), 7.26 (1H, dd, J=6.3 and 7.6 Hz), 7.35 (1H, s), 7.39 (1H, d, J=7.8 Hz) 9.10 (1H, s).

Example 222

Ethyl 4-(2-chlorophenyl)-4,7-dihydro-2-propoxycarbonyl-6-propyl-2H-pyrazolo[3,4-b]pyridine-5-carboxylate Through the column of silica gel column chromatography used in Example 221 was further flowed hexane-ethyl acetate (3:1) as an eluent, the title compound was obtained as colorless crystals.

MP: 59° C.

Anal. Calcd. for: C$_{22}$H$_{26}$ClN$_3$O$_4$: C, 61.18; H, 6.07; N, 9.73. Found: C, 60.81; H, 5.98; N, 9.74.

MS (EI): 431 (M$^+$).

IR (KBr): ν=3296, 1761, 1697, 1633, 1599, 1523, 1365, 1218, 1089 cm$^{-1}$.

$^1$H-NMR (400 MHz, DMSO-d$_6$) δ (ppm): 0.87 (3H, t, J=7.1 Hz), 0.89 (3H, t, J=7.5 Hz), 0.97 (3H, t, J=7.3 Hz), 1.63–1.69 (4H, m), 2.74–2.81 (2H, m), 3.81 (2H, q, J=7.1 Hz), 4.21 (2H, t, J=6.6 Hz), 5.58 (1H, s), 7.12 (1H, dd, J=1.8 and 7.6 Hz), 7.17 (1H, ddd, J=1.9, 7.3 and 7.6 Hz), 7.22 (1H, ddd, J=1.2, 7.3 and 7.6 Hz), 7.41 (1H, dd, J=1.2 and 7.8 Hz), 7.72 (1H, s), 9.99 (1H, s).

Example 223

Ethyl 4-(2-chlorophenyl)-4,7-dihydro-2-isobutylyl-6-propyl-2H-pyrazolo[3,4-b]pyridine-5-carboxylate The title compound was obtained as a colorless amorphous solid from ethyl 4-(2-chlorophenyl)-4,7-dihydro-6-propyl-1H-pyrazolo[3,4-b]pyridine-5-carboxylate, dimethylaminopyridine and isobutyryl chloride in the same manner as in Example 204.

$^1$H-NMR (400 MHz, DMSO-$d_6$) δ (ppm): 0.84 (3H, t, J=7.0 Hz), 0.96 (3H, t, J=7.3 Hz), 1.10 (3H, d, J=6.9 Hz), 1.14 (3H, d, J=6.8 Hz), 1.64–1.70 (2H, m), 2.75–2.83 (2H, m), 3.53 (1H, q, J=7.0 Hz), 3.83 (2H, t, J=6.9 Hz), 5.59 (1H, s), 7.12 (1H, s), 7.16 (1H, dd, J=5.8 and 7.8 Hz), 7.24 (1H, dd, J=6.3 and 7.5 Hz), 7.41 (1H, s), 7.81 (1H, s), 10.05 (1H, s).

Example 224

Ethyl 1-acetyl-4-(2-chlorophenyl)-4,7-dihydro-6-propyl-1H-pyrazolo[3,4-b]pyridine-5-carboxylate The title compound was obtained as colorless crystals from ethyl 4-(2-chlorophenyl)-4,7-dihydro-6-propyl-1H-pyrazolo[3,4-b]pyridine-5-carboxylate, dimethylaminopyridine and acetyl chloride in the same manner as in Example 204.

MP: 75–76° C.

Anal. Calcd. for: $C_{20}H_{22}ClN_3O_3$: C, 61.93; H, 5.72; N, 10.83. Found: C, 61.77; H, 5.78; N, 10.90.

MS (EI): 387 (M$^+$).

$^1$H-NMR (400 MHz, DMSO-$d_6$) δ (ppm): 0.89 (3H, t, J=7.3 Hz), 0.97 (3H, t, J=7.3 Hz), 1.60–1.66 (2H, m), 2.66 (3H, s), 2.85–2.90 (2H, m), 3.81 (2H, q, J=7.3 Hz), 5.57 (1H, s), 7.14–7.18 (2H, m), 7.26 (1H, dd, J=7.3 and 7.6 Hz), 7.38 (1H, s), 7.39 (1H, d, J=8.1 Hz), 8.90 (1H, s).

Example 225

Ethyl 2-acetyl-4-(2-chlorophenyl)-4,7-dihydro-6-propyl-2H-pyrazolo[3,4-b]pyridine-5-carboxylate Through the column of silica gel column chromatography used in Example 224 was further flowed hexane-ethyl acetate (3:1) as an eluent, the title compound was obtained as a colorless amorphous solid.

MS (EI): 387 (M$^+$).

IR (KBr): ν=3306, 1699, 1633, 1601, 1523, 1371, 1197, 1086 cm$^{-1}$.

$^1$H-NMR (400 MHz, DMSO-$d_6$) δ (ppm): 0.87 (3H, t, J=7.0 Hz), 0.96 (3H, t, J=7.3 Hz), 1.66 (2H, m), 2.44 (3H, s), 2.65–2.85 (2H, m), 3.80 (2H, q, J=7.0 Hz), 5.58 (1H, s), 7.09–7.22 (3H, m), 7.40 (1H, d, J=7.9 Hz), 7.80 (1H, s), 10.0 (1H, s).

Example 226

Ethyl 1-butoxycarbonyl-4-(2-chlorophenyl)-4,7-dihydro-6-propyl-1H-pyrazolo[3,4-b]pyridine-5-carboxylate The title compound was obtained as a colorless amorphous solid from ethyl 4-(2-chlorophenyl)-4,7-dihydro-6-propyl-1H-pyrazolo[3,4-b]pyridine-5-carboxylate, dimethylaminopyridine and butyl chloroformate in the same manner as in Example 204.

MS (EI): 445 (M$^+$).

$^1$H-NMR (400 MHz, DMSO-$d_6$) δ (ppm): 0.87 (3H, t, J=7.3 Hz), 0.88 (3H, t, J=7.1 Hz), 1.33–1.38 (2H, m), 1.60–1.69 (4H, m), 2.85–2.87 (2H, m), 3.82 (2H, q, J=7.3 Hz), 4.36 (2H, t, J=6.5 Hz), 5.55 (1H, s), 7.13–7.17 (2H, m), 7.25 (1H, dd, J=6.4 and 6.5 Hz), 7.34 (1H, s), 7.37 (1H, d, J=7.5 Hz), 8.61 (1H, s).

Example 227

Ethyl 2-butoxycarbonyl-4-(2-chlorophenyl)-4,7-dihydro-6-propyl-2H-pyrazolo[3,4-b]pyridine-5-carboxylate Through the column of silica gel column chromatography used in Example 226 was further flowed hexane-ethyl acetate (3:1) as an eluent, the title compound was obtained as a colorless amorphous solid.

MS (EI): 445 (M$^+$).

$^1$H-NMR (400 MHz, DMSO-$d_6$) δ (ppm): 0.86 (3H, t, J=7.3 Hz), 0.87 (3H, t, J=7.3 Hz), 0.96 (3H, t, J=7.3 Hz), 1.31–1.32 (2H, m), 1.61 (4H, m), 2.73–2.80 (2H, m), 3.80 (2H, q, J=7.3 Hz), 4.24 (2H, t, J=6.5 Hz), 5.57 (1H, s), 7.09–7.22 (3H, m), 7.39 (1H, d, J=7.8 Hz), 7.70 (1H, s), 9.98 (1H, s).

Example 228

Ethyl 4-(2-chlorophenyl)-1-cinnamoyl-4,7-dihydro-6-propyl-1H-pyrazolo[3,4-b]pyridine-5-carboxylate The title compound was obtained as a colorless amorphous solid from ethyl 4-(2-chlorophenyl)-4,7-dihydro-6-propyl-1H-pyrazolo[3,4-b]pyridine-5-carboxylate, dimethylaminopyridine and cinnamoyl chloride in the same manner as in Example 204.

MP: 131–134° C.

Anal. Calcd. for: $C_{27}H_{26}ClN_3O_3$: C, 68.13; H, 5.51; N, 8.83. Found: C, 68.04; H, 5.58; N, 8.75.

MS (EI): 475 (M$^+$).

IR (KBr): ν=3396, 1687, 1624, 1521, 1394, 1207, 1087 cm$^{-1}$.

$^1$H-NMR (400 MHz, DMSO-$d_6$) δ (ppm): 0.89 (3H, t, J=7.0 Hz), 0.98 (3H, t, J=7.1 Hz), 1.62–1.68 (2H, m), 2.89–2.91 (2H, m), 3.84 (2H, q, J=7.0 Hz), 5.60 (1H, s), 7.16 (1H, dd, J=7.4 and 7.8 Hz), 7.18 (1H, d, J=6.3 Hz), 7.26 (1H, dd, J=6.3 and 7.4 Hz), 7.39 (1H, d, J=7.8 Hz), 7.45 (1H, s), 7.46 (3H, m), 7.67 (1H, d, J=6.1 Hz), 7.69–7.76 (2H, m), 7.91 (1H, d, J=7.4 Hz), 9.01 (1H, s).

Example 229

Ethyl 4-(2-chlorophenyl)-1-cinnamoyl-4,7-dihydro-6-propyl-2H-pyrazolo[3,4-b]pyridine-5-carboxylate Through the column of silica gel column chromatography-used in Example 228 was further flowed hexane-ethyl acetate (3:1) as an eluent, the title compound was obtained as colorless crystals.

MS (EI): 475 (M$^+$).

IR (KBr): ν=3304, 1695, 1674, 1601, 1521, 1365, 1168, 1095 cm$^{-1}$.

$^1$H-NMR (400 MHz, DMSO-$d_6$) δ (ppm): 0.86 (3H, t, J=7.0 Hz), 0.98 (3H, t, J=7.3 Hz), 1.65–1.70 (2H, m), 2.76–2.87 (2H, m), 3.82 (2H, q, J=7.0 Hz), 5.62 (1H, s), 7.12–7.18 (2H, m), 7.24 (1H, dd, J=7.3 and 7.3 Hz), 7.42 (1H, d, J=7.8 Hz), 7.45–7.46 (3H, m), 7.60 (1H, d, J=6.1 Hz), 7.62–7.70 (2H, m), 7.86 (1H, d, J=6.1 Hz), 7.85 (1H, s), 10.09 (1H, s).

Example 230

Ethyl 4-(2-chlorophenyl)-4,7-dihydro-3-methyl-6-propyl-2H-pyrazolo[3,4-b]pyridine-5-carboxylate The title compound was obtained as colorless crystals from 2-ethylbenzaldehyde, 3-amino-5-methylpyrazol and ethyl 3-ketohexanoate in the same manner as in Example 25.

MP: 164–165° C.

MS (EI): 359 (M$^+$).

$^1$H-NMR (400 MHz, DMSO-d$_6$) δ (ppm): 0.94 (3H, t, J=7.0 Hz), 1.02 (3H, t, J=7.3 Hz), 1.61 (2H, m), 1.89 (3H, s), 2.60–2.85 (2H, m), 3.80 (2H, q, J=7.0 Hz), 5.44 (1H, s), 7.00–7.30 (4H, m), 9.39 (1H, s), 11.66 (1H, s).

Example 231

Ethyl 4-(2-chlorophenyl)-4,7-dihydro-2-methyl-6-propyl-2H-pyrazolo[3,4-b]pyridine-5-carboxylate A solution of ethyl 3-ketohexanoate (7.5 g), 2-chlorobenzaldehyde (6.6 g), piperidine (1.2 g) and acetic acid (2.25 g) in benzene (50 ml) was heated under reflux for 5 hours, and the reaction mixture was dehydrated using a Dean-Stark condenser. The solvent was evaporated under reduced pressure, and the residue was purified by silica gel column chromatography using an eluent (hexane-ethyl acetate (3:1)) to give ethyl 2-(2-chlorophenyl)methylen-3-oxohexanoate ((E)/(Z)=1:1 mixture) as a yellow oil. A solution of ethyl 2-(2-chlorophenyl)methylene-3-oxohexanoate ((E)/(Z)=1:1 mixture, 2.8 g), 3-amino-1-methylpyrazole (0.25 g) and p-toluenesulfonic acid (25 mg) in toluene (5 mL) and dimethylsulfoxide (0.5 mL) was heated under reflux for one day. The solvent was evaporated under reduced pressure, and the mixture was extracted with ethyl acetate (10 mL) and washed with a saturated aqueous sodium chloride solution. The organic layer was dried over anhydrous sodium sulfate and the solvent was evaporated under reduced pressure to give an oil. The obtained oil was purified by silica gel column chromatography (eluent (ethyl acetate-methanol (10:1))) to give the title compound as colorless crystals.

MP: 150–151° C.

MS (EI): 359 (M$^+$).

$^1$H-NMR (400 MHz, DMSO-d$_6$) δ (ppm): 0.83 (3H, t, J=7.0 Hz), 0.96 (3H, t, J=6.5 Hz), 1.65 (2H, m), 2.67–2.85 (2H, m), 3.58 (3H, s), 3.77 (2H, q, J=7.0 Hz), 5.55 (1H, s), 7.07–7.11 (2H, m), 7.19 (1H, dd, J=7.4 and 7.8 Hz), 7.24 (1H, d, J=8.3 Hz), 9.45 (1H, s).

Example 232

Ethyl 4-(2-chlorophenyl)-4,7-dihydro-1-methyl-6-propyl-1H-pyrazolo[3,4-b]pyridine-5-carboxylate The title compound was obtained as a colorless amorphous solid from ethyl 2-(2-chlorophenyl)methylen-3-oxohexanoate ((E)/(Z)=1:1 mixture), 3-amino-2-methylpyrazole and p-toluenesulfonic acid.

MS (EI): 359 (M$^+$).

$^1$H-NMR (400 MHz, DMSO-d$_6$) δ (ppm): 0.84 (3H, t, J=7.0 Hz), 1.00 (3H, t, J=7.1 Hz), 1.67–1.69 (2H, m), 2.70–2.88 (2H, m), 3.65 (3H, s), 3.80 (2H, q, J=7.0 Hz), 5.55 (1H, s), 6.96 (1H, s), 7.08–7.12 (2H, m), 7.20 (1H, dd, J=6.8 and 7.8 Hz), 7.35 (1H, d, J=7.8 Hz), 9.31 (1H, s).

Example 233

Ethyl 4,7-dihydro-1-methyl-4-(naphthalen-1-yl)-6-propyl-1H-pyrazolo[3,4-b]pyridine-5-carboxylate A solution of ethyl 3-ketohexanoate (6.6 g), 1-naphthaldehyde (7.34 g), piperidine (1.2 g) and acetic acid (2.25 g) in benzene (50 mL) was heated under reflux for 3 hours and the reaction mixture was dehydrated using a Dean-Stark condenser. The solvent was evaporated and the residue was purified by silica gel column chromatography using an eluent (hexane-ethyl acetate (3:1)) to give ethyl 2-(naphthalen-1-yl)methylene-3-oxohexanoate ((E)/(Z)=1:1 mixture) as a yellow oil. The title compound was obtained as a colorless amorphous solid from ethyl 2-(naphthalen-1-yl)methylene-3-oxohexanoate ((E)/(Z)=1:1 mixture), 3-amino-2-methylpyrazole and p-toluenesulfonic acid.

MS (EI): 375 (M$^+$).

$^1$H-NMR (400 MHz, DMSO-d$_6$) δ (ppm): 0.60 (3H, t, J=6.9 Hz), 1.03 (3H, t, J=6.9 Hz), 1.74 (2H, m), 2.78–2.85 (2H, m), 3.65 (3H, s), 3.68 (2H, q, J=6.9 Hz), 5.94 (1H, s), 6.76 (1H, s), 7.20 (1H, d, J=7.3 Hz), 7.37 (1H, dd, J=7.4 and 7.8 Hz), 7.50 (1H, dd, J=6.9 and 7.8 Hz), 7.58 (1H, m), 7.67 (1H, d, J=8.3 Hz), 7.88 (1H, d, J=8.3 Hz), 8.42 (1H, d, J=8.8 Hz), 9.26 (1H, s).

Example 234

Ethyl 4-(3-chlorophenyl)-4,7-dihydro-6-propyl-2H-pyrazolo[3,4-b]pyridine-5-carboxylate The title compound was obtained as colorless crystals from 3-chlorobenzaldehyde, 3-aminopyrazole and ethyl 3-ketohexanoate in the same manner as in Example 25.

MP: 140–143° C.

Anal. Calcd. for: C$_{18}$H$_{20}$ClN$_3$O$_2$2/5H$_2$O: C, 61.24; H, 5.94; N, 11.90. Found: C, 61.50; H, 5.94; N, 11.99.

MS (EI): 345 (M$^+$).

IR (KBr): ν=3263, 1736, 1666, 1591, 1514, 1275, 1222, 1207, 1087 cm$^{-1}$.

$^1$H-NMR (400 MHz, DMSO-d$_6$) δ (ppm): 0.95 (3H, t, J=7.0 Hz), 1.04 (3H, t, J=7.1 Hz), 1.58–1.63 (2H, m), 2.63–2.81 (2H, m), 3.86 (2H, q, J=7.0 Hz), 5.11 (1H, s), 7.08 (1H, d, J=7.8 Hz), 7.12 (2H, m), 7.21 (1H, d, J=8.3 Hz), 7.26 (1H, s), 9.84 (1H, s), 11.99 (1H, s).

Example 235

Ethyl 4-(4-chlorophenyl)-4,7-dihydro-6-propyl-2H-pyrazolo[3,4-b]pyridine-5-carboxylate The title compound was obtained as colorless crystals from 4-chlorobenzaldehyde, 3-aminopyrazole and ethyl 3-ketohexanoate in the same manner as in Example 25.

MP: 159–161° C.

Anal. Calcd. for: C$_{18}$H$_{20}$ClN$_3$O$_2$1/5H$_2$O: C, 61.87; H, 5.88; N, 12.03. Found: C, 61.92; H, 6.23; N, 11.95.

MS (EI): 345 (M$^+$).

IR (KBr): ν=3263, 1730, 1662, 1593, 1516, 1207, 1091 cm$^{-1}$.

$^1$H-NMR (400 MHz, DMSO-d$_6$) δ (ppm): 0.92 (3H, t, J=7.0 Hz), 0.95 (3H, t, J=7.3 Hz), 1.60 (2H, m), 2.64–2.80 (2H, m), 3.84 (2H, q, J=7.0 Hz), 5.10 (1H, s), 7.13 (2H, d, J=7.3 Hz), 7.22 (1H, s), 7.25 (2H, d, J=7.3 Hz), 9.45 (1H, s), 11.96 (1H, s).

Example 236

Ethyl 4,7-dihydro-4-(4-methyl-1H-imidazol-5-yl)-6-propyl-2H-pyrazolo[3,4-b]pyridine-5-carboxylate The title compound was obtained as colorless crystals from 4-methyl-5-imidazolecarboxaldehyde, 3-aminopyrazole and ethyl 3-ketohexanoate in the same manner as in Example 25.

MP: 219–220° C.

Anal. Calcd. for: $C_{16}H_{21}N_5O_2 1/2H_2O$: C, 59.61; H, 6.25; N, 21.72. Found: C, 59.34; H, 6.48; N, 22.06.

MS (EI): 315 (M+).

IR (KBr): ν=3113, 2980, 1687, 1620, 1568, 1244, 1159 cm$^{-1}$.

$^1$H-NMR (400 MHz, DMSO-d$_6$) δ (ppm): 0.94 (3H, t, J=7.3 Hz), 1.08 (3H, t, J=7.0 Hz), 1.58–1.59 (2H, m), 2.21 (3H, s), 2.58–2.79 (2H, m), 3.97 (2H, q, J=7.3 Hz), 5.50 (1H, s), 6.14 (1H, s), 7.14 (1H, s), 7.19 (1H, s), 9.78 (1H, s), 11.53 (1H, s).

Example 237

Ethyl 4,7-dihydro-4-(1-methyl-1H-imidazol-2-yl)-6-propyl-2H-pyrazolo[3,4-b]pyridine-5-carboxylate The title compound was obtained as colorless crystals from 1-methyl-2-imidazolecarboxaldehyde, 3-aminopyrazole and ethyl 3-ketohexanoate in the same manner as in Example 25.

MP: 209° C.

Anal. Calcd. for: $C_{16}H_{21}N_5O_2 3/5H_2O$: C, 59.28; H, 6.28; N, 21.60. Found: C, 59.00; H, 6.52; N, 21.55.

MS (EI): 315 (M+).

IR (KBr): ν=3254, 3184, 3080, 1685, 1593, 1518, 1278, 1207, 1078 cm$^{-1}$.

$^1$H-NMR (400 MHz, DMSO-d$_6$) δ (ppm): 0.91 (3H, t, J=6.8 Hz), 0.93 (3H, t, J=7.3 Hz), 1.55–1.61 (2H, m), 2.57–2.80 (2H, m), 3.44 (3H, s), 3.87 (2H, q, J=6.8 Hz), 5.29 (1H, s), 6.56 (1H, s), 6.84 (1H, s), 7.27 (1H, s), 9.38 (1H, s), 11.97 (1H, s).

Example 238

Ethyl 4,7-dihydro-4-(1H-imidazol-5-yl)-6-propyl-2H-pyrazolo[3,4-b]pyridine-5-carboxylate The title compound was obtained as colorless crystals from 3-imidazolecarboxyaldehyde, 3-aminopyrazole and ethyl 3-ketohexanoate in the same manner as in Example 25.

MP: 200° C.

Anal. Calcd. for: $C_{15}H_{17}N_5O_2 1/2H_2O$: C, 58.43; H, 5.88; N, 22.71. Found: C, 58.53; H, 6.25; N, 22.93.

MS (EI): 301 (M+).

IR (KBr): ν=3217, 1655, 1585, 1506, 1226, 1205, 1084 cm$^{-1}$.

$^1$H-NMR (400 MHz, DMSO-d$_6$) δ (ppm): 0.92 (3H, t, J=7.3 Hz), 1.01 (3H, t, J=7.3 Hz), 1.57–1.59 (2H, m), 2.59–2.74 (2H, m), 3.90 (2H, q, J=7.3 Hz), 5.12 (1H, s), 6.35 (1H, s), 7.35 (1H, s), 7.38 (1H, s), 9.21 (1H, s), 11.91 (1H, s).

Example 239

Ethyl 4-(2,1,3-benzoxadiazol-4-yl)-6-butyl-4,7-dihydro-2H-pyrazolo[3,4-b]pyridine-5-carboxylate The title compound was prepared from 2,1,3-benzoxadiazole-4-aldehyde, 3-aminopyrazole and ethyl 3-ketoheptanoate in the same manner as in Example 1.

MP: 213° C.

Anal. Calcd. for: $C_{19}H_{21}N_5O_3$: C, 62.11; H, 5.76; N, 19.06. Found: C, 62.08; H, 5.75; N, 18.95.

MS (EI): 367 (M+).

$^1$H-NMR (400 MHz, DMSO-d$_6$) δ (ppm): 0.77 (3H, t, J=7.3 Hz), 0.92 (3H, t, J=7.3 Hz), 1.32–1.40 (2H, m), 1.60–1.64 (2H, m), 2.76–2.86 (2H, m), 3.76–3.82 (2H, m), 5.68 (1H, s), 7.11 (1H, d, J=6.6 Hz), 7.22 (1H, s), 7.51 (1H, dd, J=9.0 Hz and 6.6 Hz), 7.77 (1H, d, J=9.0 Hz), 9.65 (1H, s), 12.00 (1H, s).

Example 240

Ethyl 4-(2,1,3-benzoxadiazol-4-yl)-6-ethyl-4,7-dihydro-2H-pyrazolo[3,4-b]pyridine-5-carboxylate The title compound was prepared from 2,1,3-benzoxadiazole-4-aldehyde, 3-aminopyrazole and ethyl 3-ketopentanoate in the same manner as in Example 1.

MP: 196° C.

Anal. Calcd. for: $C_{17}H_{17}N_5O_3$: C, 60.17; H, 5.05; N, 20.64. Found: C, 60.09; H, 5.15; N, 20.41.

MS (EI): 339 (M+).

$^1$H-NMR (400 MHz, DMSO-d$_6$) δ (ppm): 0.75 (3H, t, J=7.3 Hz), 1.21 (3H, t, J=7.3 Hz), 2.83 (2H, q, J=7.3 Hz), 3.73–3.84 (2H, m), 5.68 (1H, s), 7.12 (1H, d, J=6.6 Hz), 7.22 (1H, s), 7.50 (1H, dd, J=9.0 Hz and 6.6 Hz), 7.77 (1H, d, J=9.0 Hz), 9.68 (1H, s), 12.01 (1H, s).

Example 241

4-(2-Chlorophenyl)-5-cyano-4,7-dihydro-6-(thiophen-2-yl)-2H-pyrazolo[3,4-b]pyridine The title compound was prepared from methyl thiophene-2-carboxylate, 2-chlorobenzaldehyde and 3-aminopyrazole in the same manner as in Example 95.

MP: 174° C.

Anal. Calcd. for: $C_{17}H_{11}ClN_4S 1/10H_2O$: C, 59.94; H, 3.31; N, 16.45. Found: C, 59.82; H, 3.48; N, 16.93.

MS (EI): 338 (M+).

$^1$H-NMR (400 MHz, DMSO-d$_6$) δ (ppm): 5.50 (1H, s), 7.18 (1H, dd, J=7.3 Hz and 7.2 Hz), 7.24–7.35 (4H, m), 7.45 (1H, d, J=7.8 Hz), 7.60 (1H, d, J=3.6 Hz), 7.77 (1H, d, J=3.9 Hz), 10.08 (1H, s), 12.29 (1H, s)

Example 242

5-Cyano-4,7-dihydro-4-(2-methoxyphenyl)-6-(thiophen-2-yl)-2H-pyrazolo[3,4-b]pyridine The title compound was prepared from methyl thiophene-2-carboxylate, 2-methoxybenzaldehyde and 3-aminopyrazole in the same manner as in Example 95.

MP: 215° C.

Anal. Calcd. for: $C_{18}H_{14}N_4OS$: C, 64.65; H, 4.22; N, 16.75. Found: C, 64.66; H, 4.32; N, 17.02.

MS (EI): 334 (M+).

$^1$H-NMR (400 MHz, DMSO-d$_6$) δ (ppm): 3.85 (3H, s), 5.34 (1H, s), 6.93 (1H, dd, J=7.3 Hz and 7.2 Hz), 7.01 (1H, d, J=7.3 Hz), 7.14–7.25 (4H, m), 7.60 (1H, d, J=3.6 Hz), 7.77 (1H, d, J=5.1 Hz), 9.91 (1H, s), 12.17 (1H, s).

Example 243

5-Cyano-4,7-dihydro-4-(2-methylthiophenyl)-6-(thiophen-2-yl)-2H-pyrazolo[3,4-b]pyridine The title compound was prepared from methyl thiophene-2-carboxylate, 2-methylthiobenzaldehyde and 3-aminopyrazole in the same manner as in Example 95.

MP: 222° C.

Anal. Calcd. for: $C_{18}H_{14}N_4S_2 2/5H_2O$: C, 60.44; H, 4.17; N, 15.66. Found: C, 60.58; H, 4.44; N, 15.35.

MS (EI): 350 (M+).

¹H-NMR (400 MHz, DMSO-d$_6$) δ (ppm): 2.49 (3H, s), 5.48 (1H, s), 7.17–7.28 (5H, m), 7.33 (1H, d, J=7.3 Hz), 7.60 (1H, d, J=3.7 Hz), 7.77 (1H, d, J=3.9 Hz), 10.01 (1H, s), 12.22 (1H, s).

Example 244

5-Cyano-4,7-dihydro-4-(2-nitrophenyl)-6-(thiophen-2-yl)-2H-pyrazolo[3,4-b]pyridine The title compound was prepared from methyl thiophene-2-carboxylate, 2-nitrobenzaldehyde and 3-aminopyrazole in the same manner as in Example 95.

MP: 165° C.

Anal. Calcd. for: C$_{17}$H$_{11}$N$_5$O$_2$S: C, 58.44; H, 3.17; N, 20.05. Found: C, 58.15; H, 3.42; N, 20.38.

MS (EI): 349 (M⁺).

¹H-NMR (400 MHz, DMSO-d$_6$) δ (ppm): 5.54 (1H, s), 7.18 (1H, dd, J=7.3 Hz and 7.2 Hz), 7.34 (1H, s), 7.48–7.55 (2H, m), 7.60 (1H, d, J=3.7 Hz), 7.72–7.79 (2H, m), 7.92 (1H, d, J=8.1 Hz), 10.16 (1H, s), 12.35 (1H, s).

Example 245

4-(2,1,3-Benzothiadiazol-4-yl)-5-cyano-4,7-dihydro-6-(thiophen-2-yl)-2H-pyrazolo[3,4-b]pyridine The title compound was prepared from methyl thiophene-2-carboxylate, 2,1,3-benzothiadiazol-4-aldehyde and 3-aminopyrazole in the same manner as in Example 95.

MP: 254° C.

Anal. Calcd. for: C$_{17}$H$_{10}$N$_6$S$_2$: C, 56.34; H, 2.78; N, 23.19. Found: C, 56.01; H, 2.91; N, 23.19.

MS (EI): 362 (M⁺).

¹H-NMR (400 MHz, DMSO-d$_6$) δ (ppm): 5.84 (1H, s), 7.19 (1H, dd, J=4.4 Hz and 4.3 Hz), 7.28 (1H, s), 7.55 (1H, d, J=6.8 Hz), 7.65 (1H, d, J=3.7 Hz), 7.72–7.79 (2H, m), 7.99 (1H, d, J=8.8 Hz), 10.14 (1H, s), 12.21 (1H, s).

Example 246

5-Cyano-4,7-dihydro-4-(naphthalen-1-yl)-6-(thiophen-2-yl)-2H-pyrazolo[3,4-b]pyridine The title compound was prepared from methyl thiophene-2-carboxylate, naphthalene-1-aldehyde and 3-aminopyrazole in the same manner as in Example 95.

MP: 214° C.

Anal. Calcd. for: C$_{21}$H$_{14}$N$_4$S: C, 71.16; H, 3.98; N, 15.81. Found: C, 70.75; H, 3.96; N, 15.85.

MS (EI): 354 (M⁺).

¹H-NMR (400 MHz, DMSO-d$_6$) δ (ppm): 5.87 (1H, s), 7.13 (1H, s), 7.18 (1H, dd, J=4.6 Hz and 3.9 Hz), 7.45–7.54 (4H, m), 7.62 (1H, d, J=3.9 Hz), 7.78 (1H, d, J=4.9 Hz), 7.83 (1H, d, J=8.1 Hz), 7.95 (1H, d, J=9.3 Hz), 8.31 (1H, d, J=7.3 Hz), 10.09 (1H, s), 12.17 (1H, s).

Example 247

5-Cyano-4-(2,3-dichlorophenyl)-4,7-dihydro-6-(thiophen-2-yl)-2H-pyrazolo[3,4-b]pyridine The title compound was prepared from methyl thiophene-2-carboxylate, 2,3-dichlorobenzaldehyde and 3-aminopyrazole in the same manner as in Example 95.

MP: 232° C.

Anal. Calcd. for: C$_{17}$H$_{10}$Cl$_2$N$_4$S1/10H$_2$O: C, 54.44; H, 2.74; N, 14.94. Found: C, 54.08; H, 2.90; N, 15.29.

MS (EI): 373 (M⁺).

¹H-NMR (400 MHz, DMSO-d$_6$) δ (ppm): 5.58 (1H, s), 7.18 (1H, dd, J=7.3 Hz and 7.2 Hz), 7.32–7.41 (3H, m), 7.54 (1H, dd, J=7.3 Hz and 1.5 Hz), 7.60 (1H, d, J=3.7 Hz), 7.78 (1H, d, J=4.9 Hz), 10.14 (1H, s), 12.32 (1H, s).

Example 248

5-Cyano-4,7-dihydro-4-(2-methylphenyl)-6-phenyl-2H-pyrazolo[3,4-b]pyridine

The title compound was prepared from methyl benzoate, 2-methylbenzaldehyde and 3-aminopyrazole in the same manner as in Example 95.

MP: 246° C.

Anal. Calcd. for: C$_{20}$H$_{16}$N$_4$1.0H$_2$O: C, 72.71; H, 5.49; N, 16.96. Found: C, 72.50; H, 5.26; N, 17.20.

MS (EI): 312 (M⁺).

¹H-NMR (400 MHz, DMSO-d$_6$) δ (ppm): 2.38 (3H, s), 5.29 (1H, s), 7.11–7.23 (5H, m), 7.47–7.49 (3H, m), 7.55–7.58 (2H, m), 9.94 (1H, s), 12.17 (1H, s).

Example 249

5-Cyano-4,7-dihydro-4-(2-methylphenyl)-6-(thiophen-2-yl)-2H-pyrazolo[3,4-b]pyridine The title compound was prepared from methyl thiophene-2-carboxylate, 2-methylbenzaldehyde and 3-aminopyrazole in the same manner as in Example 95.

MP: 276° C.

Anal. Calcd. for: C$_{18}$H$_{14}$N$_4$S: C, 67.90; H, 4.43; N, 17.60. Found: C, 67.93; H, 4.54; N, 17.64.

MS (EI): 318 (M⁺).

¹H-NMR (400 MHz, DMSO-d$_6$) δ (ppm): 2.36 (3H, s), 5.28 (1H, s), 7.11–7.18 (5H, m), 7.24 (1H, s), 7.55 (1H, dd, J=3.7 Hz and 1.0 Hz), 7.74 (1H, dd, J=5.9 Hz and 1.0 Hz), 9.95 (1H, s), 12.22 (1H, s).

Example 250

4-(2-Chlorophenyl)-5-cyano-6-dimethoxymethyl-4,7-dihydro-2H-pyrazolo[3,4-b]pyridine The title compound was prepared from methyl dimethoxyacetate, 2-chlorobenzaldehyde and 3-aminopyrazole in the same manner as in Example 94.

¹H-NMR (400 MHz, DMSO-d$_6$) δ (ppm): 3.39 (6H, s), 5.18 (1H, s), 5.43 (1H, s), 7.23–7.27 (3H, m), 7.32–7.35 (1H, m), 7.44 (1H, d, J=7.8 Hz), 9.65 (1H, s), 12.21 (1H, s).

Example 251

4-(2-Chlorophenyl)-5-cyano-6-formyl-4,7-dihydro-2H-pyrazolo[3,4-b]pyridine 4-(2-Chlorophenyl)-5-cyano-6-dimethoxymethyl-4,7-dihydro-2H-pyrazolo[3,4-b]pyridine (4.4 g) was added to trifluoroacetic acid (20 ml) under ice-cooling and the mixture was stirred at room temperature for 2.5 hours. The reaction mixture was concentrated under reduced pressure and crystallized from ethyl acetate (50 ml) to give the title compound (1.9 g) as yellow crystals.

¹H-NMR (400 MHz, DMSO-d$_6$) δ (ppm): 5.63 (1H, s), 7.27–7.46 (5H, m), 7.48 (1H, d, J=7.1 Hz), 9.73 (1H, s), 10.17 (1H, s), 12.34 (1H, s).

Example 252

4-(2-Chlorophenyl)-5-cyano-4,7-dihydro-6-hydroxymethyl-2H-pyrazolo[3,4-b]pyridine To a suspension of 4-(2-chlorophenyl)-5-cyano-6-formyl-4,7-dihydro-2H-pyrazolo[3,4-b]pyridine (400 mg) in methanol (10 ml) was added sodium borohydride (53 mg) under ice-cooling and the mixture was stirred at the same temperature for 30 minutes. 10% Hydrochloric acid was added to the reaction mixture, and a saturated sodium hydrogencarbonate solution was added. The precipitated crystals were collected by filtration and washed with ethanol to give the title compound (295 mg) as yellow crystals.

MP: 205–210° C. (decomposition).
Anal. Calcd. for: $C_{14}H_{11}ClN_4O1/4H_2O$: C, 57.74; H, 3.98; N, 19.24. Found: C, 57.38; H, 3.93; N, 18.94.
MS (EI): 286 (M$^+$).
$^1$H-NMR (400 MHz, DMSO-d$_6$) δ (ppm): 4.29 (2H, d, J=5.6 Hz), 5.38 (1H, s), 5.49 (1H, t, J=5.6 Hz), 7.22–7.34 (4H, m), 7.43 (1H, d, J=8.0 Hz), 9.60 (1H, s), 12.17 (1H, s).

Example 253

4-(2-Chlorophenyl)-5-cyano-4,7-dihydro-6-(trans-2-ethoxycarbonylethenyl)-2H-pyrazolo[3,4-b]pyridine To a suspension of sodium hydride (94 mg) in dimethoxyethane (10 ml) was added ethyl diethylphosphonoacetate (528 mg) and the mixture was stirred at room temperature for 15 minutes. Under ice-cooling, 4-(2-chlorophenyl)-5-cyano-6-formyl-4,7-dihydro-2H-pyrazolo[3,4-b]pyridine (670 mg) was added to the mixture, and the mixture was stirred at the same temperature for 1 hour. Water was added to the reaction mixture and the mixture was extracted with ethyl acetate. The extract was washed with a saturated aqueous sodium chloride solution and dried over anhydrous magnesium sulfate. The solvent was evaporated and the obtained residue was purified by silica gel column chromatography (eluent:hexane-ethyl acetate (1:1)) to give the title compound (560 mg) as yellow crystals.

MP: 240–243° C. (decomposition).
Anal. Calcd. for: $C_{18}H_{15}ClN_4O_21/2H_2O$: C, 59.43; H, 4.43; N, 15.40. Found: C, 59.53; H, 4.26; N, 15.31.
MS (EI): 354 (M$^+$).
$^1$H-NMR (400 MHz, DMSO-d$_6$) δ (ppm): 1.25 (3H, d, J=7.1 Hz), 4.21 (2H, q, J=7.1 Hz), 5.52 (1H, s), 6.93 (1H, d, J=15.9 Hz), 7.27–7.46 (6H, m), 10.09 (1H, s), 12.31 (1H, s).

Example 254

4-(2-Chlorophenyl)-5-cyano-6-(2-ethoxycarbonylethyl)-4,7-dihydro-2H-pyrazolo[3,4-b]pyridine A suspension of 4-(2-chlorophenyl)-5-cyano-4,7-dihydro-6-(trans-2-ethoxycarbonylethenyl)-2H-pyrazolo[3,4-b]pyridine (260 mg) and 5% palladium on carbon (110 mg) in ethanol was subjected to catalytic hydrogenation at room temperature for 5 hours. The reaction mixture was filtered through Celite and the filtrate was concentrated under reduced pressure. The obtained residue was purified by silica gel column chromatography (eluent:hexane-ethyl acetate (1:1)) to give a yellow solid. The yellow solid was crystallized from ethyl acetate-diisopropyl ether to give the title compound (160 mg) as pale-yellow crystals.

MP: 172–174° C.
MS (EI): 356 (M$^+$).

$^1$H-NMR (400 MHz, DMSO-d$_6$) δ (ppm): 1.18 (3H, t, J=7.3 Hz), 2.60–2.80 (4H, m), 4.08 (2H, q, J=7.3 Hz), 5.35 (1H, s), 7.20–7.31 (4H, m), 7.42 (1H, d, J=8.0 Hz), 9.84 (1H, s), 12.16 (1H, s).

Example 255

4-(2,1,3-Benzoxadiazol-4-yl)-5-cyano-6-dimethoxymethyl-4,7-dihydro-2H-pyrazolo[3,4-b]pyridine The title compound was prepared from methyl dimethoxyacetate, 2,1,3-benzoxadiazole-4-aldehyde and 3-aminopyrazole in the same manner as in Example 94.

$^1$H-NMR (400 MHz, DMSO-d$_6$) δ (ppm): 3.35 (3H, s), 3.38 (3H, s), 5.16 (1H, s), 5.47 (1H, s), 7.26 (1H, s), 7.42 (1H, d, J=6.6 Hz), 7.60 (1H, dd, J=6.6, 8.5 Hz), 7.94 (1H, d, J=8.5 Hz), 9.77 (1H, s), 12.19 (1H, s).

Example 256

4-(2,1,3-Benzoxadiazol-4-yl)-5-cyano-6-formyl-4,7-dihydro-2H-pyrazolo[3,4-b]pyridine The title compound was prepared from 4-(2,1,3-benzoxadiazol-4-yl)-5-cyano-6-dimethoxymethyl-4,7-dihydro-2H-pyrazolo[3,4-b]pyridine in the same manner as in Example 251.

$^1$H-NMR (400 MHz, DMSO-d$_6$) δ (ppm): 5.71 (1H, s), 7.33 (1H, s), 7.56 (1H, d, J=6.6 Hz), 7.62 (1H, dd, J=6.6, 8.8 Hz), 7.98 (1H, d, J=8.8 Hz), 9.73 (1H, s), 10.32 (1H, s), 12.32 (1H, s).

Example 257

4-(2,1,3-Benzoxadiazol-4-yl)-5-cyano-4,7-dihydro-6-hydroxymethyl-2H-pyrazolo[3,4-b]pyridine The title compound was prepared from 4-(2,1,3-benzoxadiazol-4-yl)-5-cyano-6-formyl-4,7-dihydro-2H-pyrazolo[3,4-b]pyridine in the same manner as in Example 252.

MP: 215–220° C. (decomposition).
Anal. Calcd. for: $C_{14}H_{10}N_6O_21/2H_2O$: C, 55.44; H, 3.66; N, 27.71. Found: C, 55.32; H, 3.68; N, 27.31.
MS (EI): 294 (M$^+$).
$^1$H-NMR (400 MHz, DMSO-d$_6$) δ (ppm): 4.30 (2H, s), 5.45 (1H, s), 5.52 (1H, brs), 7.27 (1H, s), 7.42 (1H, d, J=6.6 Hz), 7.59 (1H, dd, J=6.6, 9.0 Hz), 7.93 (1H, d, J=9.0 Hz), 9.71 (1H, s), 12.16 (1H, s)

Example 258

4-(2,1,3-Benzoxadiazol-4-yl)-5-cyano-4,7-dihydro-6-(trans-2-ethoxycarbonylethenyl)-2H-pyrazolo[3,4-b]pyridine The title compound was prepared from 4-(2,1,3-benzoxadiazol-4-yl)-5-cyano-6-formyl-4,7-dihydro-2H-pyrazolo[3,4-b]pyridine in the same manner as in Example 253.

$^1$H-NMR (400 MHz, DMSO-d$_6$) δ (ppm): 1.24 (3H, d, J=7.1 Hz), 4.21 (2H, q, J=7.1 Hz), 5.59 (1H, s), 6.96 (1H, d, J=16.1 Hz), 7.32 (1H, s), 7.39 (1H, d, J=16.1 Hz), 7.50 (1H, m), 7.59 (1H, m), 7.96 (1H, d, J=8.3 Hz), 10.21 (1H, s), 12.29 (1H, s).

Example 259

4-(2,1,3-Benzoxadiazol-4-yl)-5-cyano-6-(2-ethoxycarbonylethyl)-4,7-dihydro-2H-pyrazolo[3,4-b]pyridine The title compound was prepared from 4-(2,1,3-benzoxadiazol-4-yl)-5-cyano-4,7-dihydro-6-(trans-2- ethoxycarbonylethenyl)-2H-pyrazolo[3,4-b]pyridine in the same manner as in Example 254.

MS (EI): 364 (M+).

$^1$H-NMR (400 MHz, DMSO-d$_6$) δ (ppm): 1.18 (3H, t, J=7.1 Hz), 2.66–2.80 (4H, m), 4.08 (2H, q, J=7.1 Hz), 5.40 (1H, s), 7.26 (1H, s), 7.42 (1H, d, J=6.6 Hz), 7.58 (1H, dd, J=6.6, 9.0 Hz), 7.92 (1H, d, J=9.0 Hz), 9.96 (1H, s), 12.16 (1H, s).

Example 260

4-(2-Bromo-3-cyanophenyl)-5-cyano-4,7-dihydro-6-isopropyl-2H-pyrazolo[3,4-b]pyridine The title compound was prepared from methyl isobutyrate, 2-bromo-3-cyanobenzaldehyde and 3-aminopyrazole in the same manner as in Example 94.

MP: >250° C.

Anal. Calcd. for: C$_{17}$H$_{14}$BrN$_5$: C, 55.45; H, 3.83; N, 19.02. Found: C, 55.30; H, 3.91; N, 18.98.

MS (EI): 368 (M+).

$^1$H-NMR (400 MHz, DMSO-d$_6$) δ (ppm): 1.23 (3H, d, J=6.8 Hz), 1.27 (3H, d, J=6.8 Hz), 3.03 (1H, m), 5.45 (1H, s), 7.33 (1H, s), 7.55–7.82 (2H, m), 7.83 (1H, dd, J=2.0, 7.1 Hz), 9.76 (1H, s), 12.25 (1H, s).

Example 261

4-(2-Bromophenyl)-5-cyano-4,7-dihydro-6-isopropyl-2H-pyrazolo[3,4-b]pyridine acetonitrile The title compound was prepared from methyl isobutyrate, 2-bromobenzaldehyde and 3-aminopyrazole in the same manner as in Example 94.

MP: >250° C.

Anal. Calcd. for: C$_{16}$H$_{15}$BrN$_4$C$_2$H$_3$N: C, 56.26; H, 4.72; N, 18.22. Found: C, 56.05; H, 4.56; N, 17.09.

MS (EI): 343 (M+).

$^1$H-NMR (400 MHz, DMSO-d$_6$) δ (ppm): 1.24 (3H, d, J=7.1 Hz), 1.27 (3H, d, J=7.1 Hz), 2.06 (3H, s), 3.06 (1H, m), 5.23 (1H, s), 7.13–7.18 (1H, m), 7.22 (1H, d, J=7.6 Hz), 7.27 (1H, s), 7.36 (1H, dd, J=1.2, 7.6 Hz), 7.59 (1H, dd, J=1.2, 8.0 Hz), 9.64 (1H, s), 12.17 (1H, s).

Example 262

5-Cyano-4,7-dihydro-6-isopropyl-4-(2-nitrophenyl)-2H-pyrazolo[3,4-b]pyridine

The title compound was prepared from methyl isobutyrate, 2-nitrobenzaldehyde and 3-aminopyrazole in the same manner as in Example 94.

MP: 224° C.

MS (EI): 309 (M+).

$^1$H-NMR (400 MHz, DMSO-d$_6$) δ (ppm): 1.23 (3H, d, J=7.1 Hz), 1.28 (3H, d, J=7.1 Hz), 3.03 (1H, m), 5.36 (1H, s), 7.27 (1H, s), 7.43–7.49 (2H, m), 7.70 (1H, dd, J=1.2, 8.8 Hz), 7.89 (1H, dd, J=1.2, 8.3 Hz), 9.71 (1H, s), 12.23 (1H, s).

Example 263

5-Cyano-4-(2,3-dichlorophenyl)-4,7-dihydro-6-isopropyl-2H-pyrazolo[3,4-b]pyridine The title compound was prepared from methyl isobutyrate, 2,3-dichlorobenzaldehyde and 3-aminopyrazole in the same manner as in Example 94.

MP: >250° C.

Anal. Calcd. for: C$_{16}$H$_{14}$C$_{12}$N$_4$: C, 57.67; H, 4.23; N, 16.89. Found: C, 57.74; H, 4.27; N, 16.89.

MS (EI): 333 (M+).

$^1$H-NMR (400 MHz, DMSO-d$_6$) δ (ppm): 1.23 (3H, d, J=7.1 Hz), 1.27 (3H, d, J=7.1 Hz), 3.04 (1H, m), 5.42 (1H, s), 7.23 (1H, d, J=7.6 Hz), 7.31 (1H, s), 7.35 (1H, dd, J=7.6, 7.8 Hz), 7.51 (1H, dd, J=1.5, 7.8 Hz), 9.70 (1H, s), 12.21 (1H, s).

Example 264

4-(2,1,3-Benzoxadiazol-4-yl)-5-cyano-4,7-dihydro-6-isopropyl-2H-pyrazolo[3,4-b]pyridine The title compound was prepared from methyl isobutyrate, 2,1,3-benzoxadiazole-4-aldehyde and 3-aminopyrazole in the same manner as in Example 94.

MP: 222–223° C. (decomposition).

Anal. Calcd. for: C$_{16}$H$_{14}$N$_6$O: C, 62.71; H, 4.61; N, 27.44. Found: C, 62.71; H, 4.65; N, 27.45.

MS (EI): 306 (M+).

$^1$H-NMR (400 MHz, DMSO-d$_6$) δ (ppm): 1.24 (3H, d, J=7.1 Hz), 1.25 (3H, d, J=7.1 Hz), 3.03 (1H, m), 5.39 (1H, s), 7.26 (1H, s), 7.40 (1H, d, J=6.6 Hz), 7.58 (1H, dd, J=6.6, 8.8 Hz), 7.92 (1H, d, J=8.8 Hz), 9.74 (1H, s), 12.15 (1H, s).

Example 265

5-Cyano-4,7-dihydro-6-isopropyl-4-(2-methoxyphenyl)-2H-pyrazolo[3,4-b]pyridine

The title compound was prepared from methyl isobutyrate, 2-methoxybenzaldehyde and 3-aminopyrazole in the same manner as in Example 94.

MP: >250° C.

Anal. Calcd. for: C$_{17}$H$_{18}$N$_4$O: C, 69.37; H, 6.16; N, 19.03. Found: C, 69.13; H, 6.21; N, 19.54.

MS (EI): 294 (M+).

$^1$H-NMR (400 MHz, DMSO-d$_6$) δ (ppm): 1.23 (3H, d, J=7.1 Hz), 1.28 (3H, d, J=7.1 Hz), 3.09 (1H, m), 3.83 (3H, s), 5.19 (1H, s), 6.90 (1H, dd, J=7.4, 7.6 Hz), 6.99 (1H, d, J=7.6 Hz), 7.05 (1H, dd, J=1.7, 7.4 Hz), 7.15–7.19 (2H, m), 9.47 (1H, s), 12.04 (1H, s), Example 266

4-(2-Chlorophenyl)-5-cyano-6-cyclopropyl-4,7-dihydro-2H-pyrazolo[3,4-b]pyridine

The title compound was prepared from methyl cyclopropanecarboxylate, 2-chlorobenzaldehyde and 3-aminopyrazole in the same manner as in Example 94.

MP: >250° C.

Anal. Calcd. for: C$_{16}$H$_{13}$ClN$_4$: C, 64.76; H, 4.42; N, 18.88. Found: C, 64.71; H, 4.50; N, 19.05.

MS (EI): 296 (M+).

$^1$H-NMR (400 MHz, DMSO-d$_6$) δ (ppm): 0.89–0.93 (2H, m), 1.00–1.15 (2H, m), 2.01 (1H, m), 5.35 (1H, s), 7.22–7.26 (3H, m), 7.31–7.34 (1H, m), 7.42 (1H, d, J=7.8 Hz), 9.14 (1H, s), 12.16 (1H, s).

Example 267

4-(2-Bromophenyl)-5-cyano-6-cyclopropyl-4,7-dihydro-2H-pyrazolo[3,4-b]pyridine

The title compound was prepared from methyl cyclopropanecarboxylate, 2-bromobenzaldehyde and 3-aminopyrazole in the same manner as in Example 94.

MP: >250° C.

Anal. Calcd. for: $C_{16}H_{13}BrN_4$: C, 56.32; H, 3.84; N, 16.42. Found: C, 56.18; H, 3.90; N, 16.48.

MS (EI): 341 (M$^+$).

$^1$H-NMR (400 MHz, DMSO-d$_6$) δ (ppm): 0.90–0.93 (2H, m), 1.00–1.15 (2H, m), 2.01 (1H, m), 5.34 (1H, s), 7.13–7.22 (2H, m), 7.27 (1H, s), 7.34–7.38 (1H, m), 7.59 (1H, d, J=6.8 Hz), 9.15 (1H, s), 12.16 (1H, s).

Example 268

4-(2-Bromo-3-cyanophenyl)-5-cyano-6-cyclopropyl-4,7-dihydro-2H-pyrazolo[3,4-b]pyridine 1/4 acetonitrile The title compound was prepared from methyl cyclopropanecarboxylate, 2-bromo-3-cyanobenzaldehyde and 3-aminopyrazole in the same manner as in Example 94.

MP: >250° C.

Anal. Calcd. for: $C_{17}H_{12}BrN_5H_2O1/4CH_3CN$: C, 53.28; H, 3.77; N, 18.64. Found: C, 53.28; H, 3.72; N, 18.81.

MS (EI): 366 (M$^+$).

$^1$H-NMR (400 MHz, DMSO-d$_6$) δ (ppm): 0.90–0.93 (2H, m), 1.03–1.08 (2H, m), 1.96–2.00 (1H, m), 5.45 (1H, s), 7.32 (1H, s), 7.54–7.60 (2H, m), 7.83 (1H, dd, J=1.7, 7.1 Hz), 9.27 (1H, s), 12.25 (1H, s).

Example 269

4-(2,1,3-Benzoxadiazol-4-yl)-5-cyano-6-cyclopropyl-4,7-dihydro-2H-pyrazolo[3,4-b]pyridine The title compound was prepared from methyl cyclopropanecarboxylate, 2,1,3-benzoxadiazole-4-aldehyde and 3-aminopyrazole in the same manner as in Example 94.

MP: 200–201° C. (decomposition).

Anal. Calcd. for: $C_{16}H_{12}N_6O H_2O$: C, 59.62; H, 4.38; N, 26.07. Found: C, 59.93; H, 4.05; N, 26.19.

MS (EI): 304 (M$^+$).

$^1$H-NMR (400 MHz, DMSO-d$_6$) δ (ppm): 0.88–0.93 (2H, m), 1.01–1.12 (2H, m), 1.99 (1H, m), 5.39 (1H, s), 7.25 (1H, s), 7.40 (1H, d, J=6.6 Hz), 7.59 (1H, dd, J=6.6, 9.0 Hz), 7.92 (1H, d, J=9.0 Hz), 9.26 (1H, s), 12.15 (1H, s).

Example 270

4-(2-Methoxyphenyl)-5-cyano-6-cyclopropyl-4,7-dihydro-2H-pyrazolo[3,4-b]pyridine 1/4 acetonitrile The title compound was prepared from methyl cyclopropanecarboxylate, 2-methoxybenzaldehyde and 3-aminopyrazole in the same manner as in Example 94.

MP: 241–243° C.

Anal. Calcd. for: $C_{17}H_{16}N_4O1/4CH_3CN$: C, 69.46; H, 5.58; N, 19.67. Found: C, 69.35; H, 5.56; N, 19.64.

MS (EI): 292 (M$^+$).

$^1$H-NMR (400 MHz, DMSO-d$_6$) δ (ppm): 0.90–0.92 (2H, m), 0.99–1.10 (2H, m), 2.01–2.06 (1H, m), 3.84 (3H, s), 5.21 (1H, s), 6.90 (1H, dd, J=7.3, 7.6 Hz), 6.98–7.05 (2H, m), 7.15–7.19 (2H, m), 8.97 (1H, s), 12.04 (1H, s)

Example 271

5-Cyano-6-cyclopropyl-4-(2,3-dichlorophenyl)-4,7-dihydro-2H-pyrazolo[3,4-b]pyridine 1/4 acetonitrile The title compound was prepared from methyl cyclopropanecarboxylate, 2,3-dichlorobenzaldehyde and 3-aminopyrazole in the same manner as in Example 94.

MP: >250° C.

Anal. Calcd. for: $C_{16}H_{12}Cl_2N_41/4CH_3CN$: C, 58.04; H, 3.76; N, 17.43. Found: C, 57.87; H, 3.79; N, 17.44.

MS (EI): 331 (M$^+$).

$^1$H-NMR (400 MHz, DMSO-d$_6$) δ (ppm): 0.90–0.93 (2H, m), 1.03–1.08 (2H, m), 1.98–2.03 (1H, m), 5.43 (1H, s), 7.22 (1H, d, J=7.8 Hz), 7.31 (1H, s), 7.35 (1H, t, J=7.8 Hz), 7.51 (1H, dd, J=1.5, 7.8 Hz), 9.21 (1H, s), 12.20 (1H, s).

Example 272

5-Cyano-6-cyclopropyl-4,7-dihydro-4-(2-nitrophenyl)-2H-pyrazolo[3,4-b]pyridine

The title compound was prepared from methyl cyclopropanecarboxylate, 2-nitrobenzaldehyde and 3-aminopyrazole in the same manner as in Example 94.

MP: 236–238° C. (decomposition).

Anal. Calcd. for: $C_{16}H_{13}N_5O_2$: C, 62.53; H, 4.26; N, 22.79. Found: C, 62.54; H, 4.29; N, 22.85.

MS (EI): 307 (M$^+$).

$^1$H-NMR (400 MHz, DMSO-d$_6$) δ (ppm): 0.90–0.93 (2H, m), 1.01–1.09 (2H, m), 1.99 (1H, m), 5.37 ($^1$H, s), 7.27 (1H, s), 7.42–7.49 (2H, m), 7.70 (1H, dd, J=7.5, 7.6 Hz), 7.90 (1H, d, J=8.1 Hz), 9.23 (1H, s), 12.22 (1H, s).

Example 273

Ethyl 4-(2-chlorophenyl)-6-dimethoxymethyl-4,7-dihydro-2H-pyrazolo[3,4-b]pyridine-5-carboxylate The title compound was prepared from 2-chlorobenzaldehyde, 3-aminopyrazole and ethyl 4,4-dimethoxy-3-oxobutanoate in the same manner as in Example 1.

$^1$H-NMR (400 MHz, DMSO-d$_6$) δ (ppm): 0.87 (3H, t, J=7.1 Hz), 3.35 (3H, s), 3.46 (3H, s), 3.82 (2H, m), 5.64 (1H, s), 6.11 (1H, s), 7.10–7.14 (2H, m), 7.20–7.24 (1H, m), 7.27 (1H, s), 7.36 (1H, d, J=8.3 Hz), 8.94 (1H, s), 12.05 (1H, s).

Example 274

Ethyl 4-(2-chlorophenyl)-6-formyl-4,7-dihydro-2H-pyrazolo[3,4-b]pyridine-5-carboxylate To a solution of ethyl 4-(2-chlorophenyl)-6-dimethoxymethyl-4,7-dihydro-2H-pyrazolo[3,4-b]pyridine-5-carboxylate (463 mg) in tetrahydrofuran (5 ml) was added 1 N hydrochloric acid (10 ml) and the mixture was stirred at room temperature for 6 hours. To the reaction mixture was added a saturated aqueous sodium hydrogencarbonate solution and the mixture was extracted with ethyl acetate. The extract was washed with a saturated aqueous sodium chloride solution and dried over anhydrous magnesium sulfate. The solvent was evaporated and the obtained residue was purified by silica gel column chromatography (eluent:hexane-ethyl acetate (1:1)) to give the title compound (290 mg) as a yellow solid.

$^1$H-NMR (400 MHz, DMSO-d$_6$) δ (ppm): 0.89 (3H, t, J=7.3 Hz), 3.91 (2H, m), 5.70 (1H, s), 7.14–7.24 (3H, m), 7.31 (1H, s), 7.40 (1H, d, J=7.8 Hz), 9.64 (1H, s), 10.23 (1H, s), 12.19 (1H, s).

Example 275

Ethyl 4-(2-chlorophenyl)-4,7-dihydro-6-isopropyl-2H-pyrazolo[3,4-b]pyridine-5-carboxylate 2-Chlorobenzaldehyde (1.41 g), 3-aminopyrazole (0.83 g) and ethyl isobutyrylacetate (1.58 g) were stirred in acetic acid (10 ml) at 80° C. for 2 hours. Under ice-cooling, a saturated aqueous sodium hydrogencarbonate solution was added to the reaction mixture. The insoluble material was filtered off, and the mixture was extracted with ethyl acetate. The extract was washed with a saturated aqueous sodium chloride solution and dried over anhydrous magnesium sulfate. The extract was concentrated under reduced pressure and the obtained residue was purified by silica gel column chromatography (eluent:hexane-ethyl acetate (1:1)). The purified product was crystallized from hexane-ethyl acetate to give the title compound (115 mg) as white crystals.

MP: 211–213° C.

$^1$H-NMR (400 MHz, DMSO-$d_6$) δ (ppm): 0.85 (3H, t, J=7.1 Hz), 1.16 (3H, m), 1.28 (3H, d, J=7.1 Hz), 3.76 (2H, m), 4.35 (1H, m), 5.59 (1H, s), 7.07–7.13 (2H, m), 7.18–7.22 (1H, m), 7.24 (1H, s), 7.35 (1H, dd, J=1.2, 8.1 Hz), 9.14 (1H, s), 11.97 (1H, s).

Example 276

Ethyl 4-(2-bromophenyl)-4,7-dihydro-6-isopropyl-2H-pyrazolo[3,4-b]pyridine-5-carboxylate The title compound was prepared from 2-bromobenzaldehyde, 3-aminopyrazole and ethyl isobutyrylacetate in the same manner as in Example 275.

MP: 214–215° C.

$^1$H-NMR (400 MHz, DMSO-$d_6$) δ (ppm): 0.84 (3H, t, J=6.8 Hz), 1.16 (3H, m), 1.28 (3H, d, J=6.8 Hz), 3.76 (2H, m), 4.35 (1H, m), 5.56 (1H, s), 7.07–7.13 (2H, m), 7.02 (1H, dd, J=7.3, 7.8 Hz), 7.11 (1H, d, J=6.4 Hz), 7.24 (1H, dd, J=7.4, 7.8 Hz), 7.28 (1H, s), 7.52 (1H, d, J=7.8 Hz), 9.15 (1H, s), 11.98 (1H, s).

Example 277

Ethyl 4-(2-chlorophenyl)-6-cyclopropyl-4,7-dihydro-2H-pyrazolo[3,4-b]pyridine-5-carboxylate To a solution of 2-oxazolydone (20.8 g) in tetrahydrofuran (750 ml) was added n-butyllithium (1.56 M hexane solution, 153 ml) at −78° C. and the mixture was stirred at the same temperature for 30 minutes. To the reaction mixture was added a solution of cyclopropanecarbonyl chloride (25 g) in tetrahydrofuran (50 ml) at −78° C. over 30 minutes. The mixture was stirred for 14 hours while gradually raising the temperature to room temperature. The reaction mixture was poured into ice-water and the mixture was extracted with ethyl acetate. The extract was washed with a saturated aqueous sodium chloride solution and dried over anhydrous magnesium sulfate. The extract was concentrated under reduced pressure and the obtained residue was purified by silica gel column chromatography (eluent:hexane-ethyl acetate (1:1)) to give white crystals (26 g). A mixture of the obtained white crystals (10 g), ethyl bromoacetate (21.5 ml) and zinc powder (25.3 g) in tetrahydrofuran (300 ml) was ultrasonicated for 2 hours and heated under reflux for 2 hours. To the reaction mixture was added 10% hydrochloric acid and the insoluble material was filtered off through Celite. The filtrate was extracted with ethyl acetate, and the extract was washed with a saturated aqueous sodium chloride solution and dried over anhydrous magnesium sulfate. The extract was concentrated under reduced pressure and the obtained residue was purified by silica gel column chromatography (eluent:hexane-ethyl acetate (1:1)) to give ethyl 3-cyclopropyl-3-oxopropionate (5.7 g) as a yellow oil. Subsequently, the title compound was prepared from 2-chlorobenzaldehyde, 3-aminopyrazole and ethyl 3-cyclopropyl-3-oxopropionate in the same manner as in Example 275.

MP: 190–192° C.

$^1$H-NMR (400 MHz, DMSO-$d_6$) δ (ppm): 0.83–0.93 (4H, m), 1.10 (1H, m), 3.14 (1H, m), 3.80 (2H, m), 5.60 (21H, s), 7.08–7.12 (2H, m), 7.18–7.22 (1H, m), 7.25 (1H, s), 7.34 (1H, d, J=8.3 Hz), 8.62 (1H, s), 11.99 (1H, s).

Example 278

4-(2-Bromo-3-cyanophenyl)-5-cyano-4,7-dihydro-6-(thiophen-2-yl)-2H-pyrazolo[3,4-b]pyridine The title compound was prepared from methyl thiophene-2-carboxylate, 2-bromo-3-cyanobenzaldehyde and 3-aminopyrazole in the same manner as in Example 95.

MP: >280° C.

Anal. Calcd. for: $C_{18}H_{10}BrN_5S$: C, 52.95; H, 2.47; N, 17.15. Found: C, 52.72; H, 2.69; N, 17.21.

MS (EI): 408 (M$^+$).

$^1$H-NMR (400 MHz, DMSO-$d_6$) δ (ppm): 5.62 (1H, s), 7.18 (1H, dd, J=5.1 Hz and 3.7 Hz), 7.40 (1H, s), 7.59–7.67 (3H, m), 7.79 (1H, d, J=3.9 Hz), 7.86 (1H, dd, J=7.6 Hz and 2.0 Hz), 10.20 (1H, s), 12.37 (1H, s).

Example 279

4-(2-Chlorophenyl)-5-cyano-4,7-dihydro-3-methyl-6-propyl-2H-pyrazolo[3,4-b]pyridine The title compound was prepared from methyl butanoate 2-chlorobenzaldehyde and 3-amino-5-methylpyrazole in the same manner as in Example 94.

MP: 260° C.

$^1$H-NMR (400 MHz, DMSO-$d_6$) δ (ppm): 0.91 (3H, t, J=7.3 Hz), 1.60–1.65 (2H, m), 1.71 (3H, s), 2.33 (2H, q, J=7.3 Hz), 5.27 (1H, s), 7.20–7.24 (2H, m), 7.31 (1H, dd, J=7.3 Hz and 7.2 Hz), 7.39 (1H, d, J=7.3 Hz), 9.68 (1H, s), 11.83 (1H, s)

Example 280

4-(2-Chlorophenyl)-5-cyano-4,7-dihydro-3-phenyl-6-propyl-2H-pyrazolo[3,4-b]pyridine The title compound was prepared from methyl butanoate 2-chlorobenzaldehyde and 3-amino-5-phenylpyrazole in the same manner as in Example 94.

MP: 262° C.

$^1$H-NMR (400 MHz, DMSO-$d_6$) δ (ppm): 0.89 (3H, t, J=7.3 Hz), 1.61–1.63 (2H, m), 2.36 (2H, q, J=7.3 Hz), 5.61 (1H, s), 7.09–7.34 (9H, m), 9.89 (1H, s), 12.62 (1H, s)

Example 281

1-tert-Butoxycarbonyl-4-(2-chlorophenyl)-5-cyano-4,7-dihydro-6-propyl-1 H-pyrazolo[3,4-b]pyridine The title compound was obtained as a colorless amorphous solid from 4-(2-chlorophenyl)-5-cyano-4,7-dihydro-6-propyl-2H-pyrazolo[3,4-b]pyridine, dimethylaminopyridine and di-tert-butyl dicarbonate in the same manner as in Example 204.

MP: 98–102° C.

MS (EI): 398 (M$^+$).

IR (KBr): ν=3391, 2199, 1723, 1643, 1529, 1394, 1149 cm$^{-1}$.

¹H-NMR (400 MHz, DMSO-d₆) δ (ppm): 0.95 (3H, t, J=7.3 Hz), 1.57 (3H, s), 1.60–1.67 (2H, m), 2.53–2.61 (2H, m), 5.38 (1H, s), 7.25–7.31 (3H, m), 7.35 (1H, ddd, J=1.4, 7.3 and 7.8 Hz), 7.45 (1H, d, J=8.1 Hz), 9.20 (1H, s).

Example 282

2-tert-Butoxycarbonyl-4-(2-chlorophenyl)-5-cyano-4,7-dihydro-6-propyl-2H-pyrazolo[3,4-b]pyridine Through the column of silica gel column chromatography used in Example 281 was further flowed hexane-ethyl acetate (3:1) as an eluent, the title compound was obtained as colorless crystals.

MP: 175° C. (decomposition).

Anal. Calcd. for: $C_{21}H_{23}ClN_4O_2$: C, 63.23; H, 5.81; N, 14.05. Found: C, 62.91; H, 5.80; N, 13.82.

MS (EI): 398 (M⁺).

IR (KBr): ν=3329, 2197, 1747, 1612, 1523, 1369, 1311, 1151, 949 cm⁻¹.

¹H-NMR (400 MHz, DMSO-d₆) δ (ppm): 0.93 (3H, t, J=7.4 Hz), 1.65 (2H, q, J=7.3 Hz), 2.40–2.44 (2H, m), 2.48 (9H, s), 5.32 (1H, s), 7.27–7.36 (3H, m), 7.45 (1H, d, J=7.8 Hz), 7.68 (1H, s), 10.32 (1H, s).

Example 283

4-(2-Chlorophenyl)-5-cyano-4,7-dihydro-1-phenylcarbamoyl-6-propyl-1 H-pyrazolo[3,4-b]pyridine The title compound was obtained as a colorless amorphous solid from 4-(2-chlorophenyl)-5-cyano-4,7-dihydro-6-propyl-2H-pyrazolo[3,4-b]pyridine, dimethylaminopyridine and phenyl isocyanate in the same manner as in Example 204.

MP: 138–140° C.

Anal. Calcd. for: $C_{23}H_{20}ClN_5O1/4H_2O$: C, 654; H, 4.89; N, 16.58. Found: C, 65.20; H, 5.05; N, 16.17.

MS (EI): 417 (M⁺).

IR (KBr): ν=3387, 3294, 2202, 1712, 1537 cm⁻¹.

¹H-NMR (400 MHz, DMSO-d₆) δ (ppm): 0.95 (3H, t, J=7.3 Hz), 1.63 (2H, q, J=7.4 Hz), 2.58 (2H, m), 5.43 (1H, s), 7.13 (1H, dd, J=7.4 and 7.5 Hz), 7.24–7.36 (6H, m), 7.46 (1H, d, J=7.8 Hz), 7.69 (2H, d, J=7.8 Hz), 9.46 (1H, s), 10.38 (1H, s).

Example 284

4-(2-Chlorophenyl)-5-cyano-4,7-dihydro-2-phenylcarbamoyl-6-propyl-2H-pyrazolo[3,4-b]pyridine Through the column of silica gel column chromatography used in Example 283 was further flowed hexane-ethyl acetate (3:1) as an eluent, the title compound was obtained as a colorless oil.

MP: 167–171° C.

MS (EI): 417 (M⁺).

IR (KBr): ν=3215, 2204, 1732, 1631, 1523, 1375 cm⁻¹.

¹H-NMR (400 MHz, DMSO-d₆) δ (ppm): 0.97 (3H, t, J=7.4 Hz), 1.65 (2H, q, J=7.3 Hz), 2.48 (2H, m), 5.39 (1H, s), 6.95 (1H, dd, J=7.3 and 7.3 Hz), 7.11 (2H, dd, J=7.3 and 7.6 Hz), 7.24–7.49 (4H, m), 7.61 (2H, d, J=7.8 Hz), 7.88 (1H, s), 8.63 (1H, s), 9.77 (1H, s), 10.17 (1H, s).

Example 285

2-Acetoxyacetyl-4-(2-chlorophenyl)-5-cyano-4,7-dihydro-6-propyl-2H-pyrazolo[3,4-b]pyridine The title compound was obtained as colorless crystals from 4-(2-chlorophenyl)-5-cyano-4,7-dihydro-6-propyl-2H-pyrazolo[3,4-b]pyridine, dimethylaminopyridine and acetoxyacetyl chloride in the same manner as in Example 204.

MP: 149–150° C.

Anal. Calcd. for: $C_{20}H_{19}ClN_4O_3$: C, 60.23; H, 4.80; N, 14.05. Found: C, 60.17; H, 4.83; N, 13.90.

MS (EI): 398 (M⁺).

IR (KBr): ν=3281, 3238, 2197, 1745, 1630, 1608, 1523, 1385, 1344, 1236, 1172 cm⁻¹.

¹H-NMR (400 MHz, DMSO-d₆) δ (ppm): 0.95 (3H, t, J=7.3 Hz), 1.64–1.70 (2H, m), 2.44 (2H, q, J=7.3 Hz), 3.33 (3H, s), 5.26 (2H, s), 5.37 (1H, s), 7.29–7.35 (3H, m), 7.46 (1H, d, J=7.8 Hz), 7.86 (1H, s), 10.45 (1H, s).

Example 286

Ethyl 1-acetoxyacetyl-4-(2-chlorophenyl)-4,7-dihydro-6-propyl-1H-pyrazolo[3,4-b]pyridine-5-carboxylate The title compound was obtained as colorless crystals from ethyl 4-(2-chlorophenyl)-4,7-dihydro-6-propyl-2H-pyrazolo[3,4-b]pyridine-5-carboxylate, dimethylaminopyridine and acetoxyacetyl chloride in the same manner as in Example 204.

MP: 130–131° C.

Anal. Calcd. for: $C_{22}H_{24}ClN_3O_5$: C, 59.26; H, 5.43; N, 9.42. Found: C, 59.17; H, 5.39; N, 9.31.

MS (EI): 445 (M⁺).

IR (KBr): ν=3337, 1732, 1529, 1390, 1246, 1086 cm⁻¹.

¹H-NMR (400 MHz, DMSO-d₆) δ (ppm): 0.88 (3H, t, J=7.0 Hz), 0.97 (3H, t, J=7.3 Hz), 1.64–1.70 (2H, m), 2.76–2.82 (2H, m), 3.31 (3H, s), 3.85 (2H, q, J=7.0 Hz), 5.27 (2H, dd, J=3.0 and 9.8 Hz), 5.60 (1H, s), 7.10–7.25 (3H, m), 7.41 (1H, dd, J=1.4 and 8.0 Hz), 7.82 (1H, s), 10.1 (1H, s).

Example 287

Ethyl 1-benzylcarbonyl-4-(2-chlorophenyl)-4,7-dihydro-6-propyl-1 H-pyrazolo[3,4-b]pyridine-5-carboxylate The title compound was obtained as colorless crystals from ethyl 4-(2-chlorophenyl)-4,7-dihydro-6-propyl-2H-pyrazolo[3,4-b]pyridine-5-carboxylate, dimethylaminopyridine and phenylacetyl chloride in the same manner as in Example 204.

MS (EI): 463 (M⁺).

IR (KBr): ν=3418, 1701, 1521, 1392, 1228 cm⁻¹.

¹H-NMR (400 MHz, DMSO-d₆) δ (ppm): 0.88 (3H, t, J=7.0 Hz), 0.93 (3H, t, J=7.3 Hz), 1.57–1.62 (2H, m), 2.80–2.87 (2H, m), 3.82 (2H, q, J=7.0 Hz), 4.33 (2H, s), 5.57 (1H, s), 7.15 (1H, dd, J=7.4 and 7.8 Hz), 7.18–7.31 (7H, m), 7.39 (1H, d, J=7.8 Hz), 7.44 (1H, s), 8.94 (1H, s).

Example 288

4-(2,1,3-Benzoxadiazol-4-yl)-2-tert-butoxycarbonyl-5-cyano-4,7-dihydro-6-propyl-2H-pyrazolo[3,4-b]pyridine The title compound was obtained as colorless crystals from 4-(2,1,3-benzoxadiazol-4-yl)-5-cyano-4,7-dihydro-6-propyl-1 H-pyrazolo[3,4-b]pyridine, dimethylaminopyridine and tert-butyldicarbonate in the same manner as in Example 204.

MP: 168–170° C.

Anal. Calcd. for: $C_{21}H_{22}N_6O_3$: C, 62.06; H, 5.46; N, 20.68. Found: C, 61.92; H, 5.44; N, 20.52.

MS (EI): 406 (M$^+$).

$^1$H-NMR (400 MHz, DMSO-d$_6$) δ (ppm): 0.89 (3H, t, J=7.3 Hz), 1.47 (9H, s), 1.65 (2H, m), 2.40 (2H, m), 5.39 (1H, s), 7.49 (1H, d, J=6.3 Hz), 7.60 (1H, dd, J=6.6 and 9.0 Hz), 7.79 (1H, s), 7.96 (1H, d, J=6.6 Hz), 10.43 (1H, s).

Example 289

4-(2,1,3-Benzoxadiazol-4-yl)-5-cyano-4,7-dihydro-1-phenylcarbamoyl-6-propyl-2H-pyrazolo[3,4-b]pyridine The title compound was obtained as colorless crystals from 4-(2,1,3-benzoxadiazol-4-yl)-5-cyano-4,7-dihydro-6-propyl-2H-pyrazolo[3,4-b]pyridine, dimethylaminopyridine and phenyl isocyanate in the same manner as in Example 204.

MP: 138–140° C.

Anal. Calcd. for: $C_{23}H_{19}N_7O_2$: C, 64.93; H, 4.50; N, 23.05. Found: C, 65.07; H, 5.05; N, 21.24.

MS (EI): 425 (M$^+$).

$^1$H-NMR (400 MHz, DMSO-d$_6$) δ (ppm): 0.91 (3H, t, J=7.3 Hz), 1.62 (2H, m), 2.58 (2H, m), 5.47 (1H, s), 7.13 (1H, dd, J=6.3 and 6.6 Hz), 7.32–7.39 (3H, m), 7.49 (1H, d, J=6.5 Hz), 7.61–7.91 (3H, m), 7.98 (1H, d, J=9.1 Hz), 9.54 (1H, s), 10.34 (1H, s).

The compounds of the above-described Examples are as follows.

Example 1

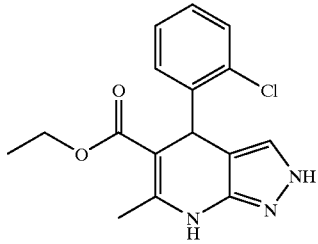

Example 2

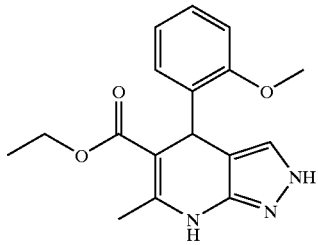

Example 3

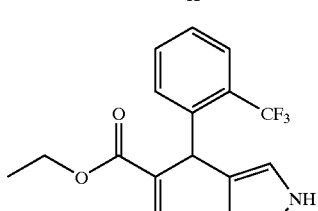
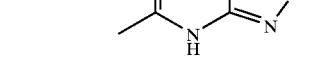

Example 4

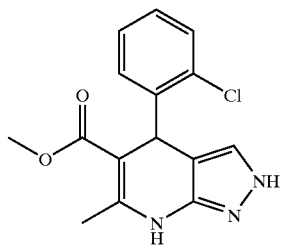

Example 5

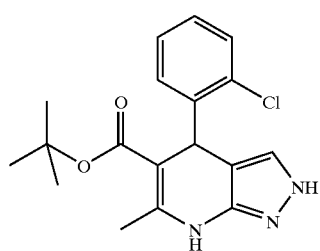

Example 6

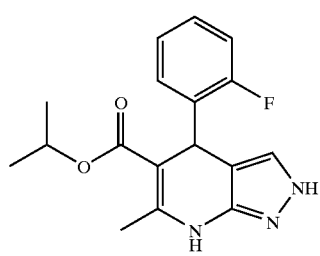

Example 7

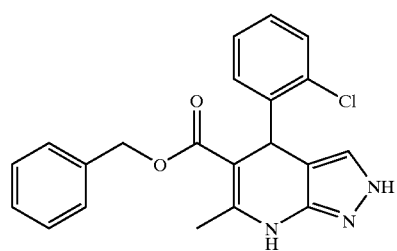

Example 8

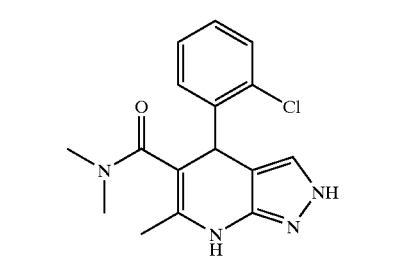

Example 9
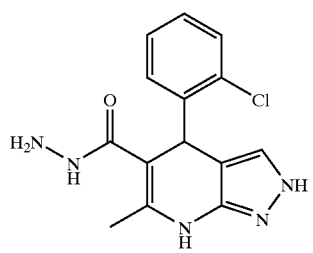
Example 10
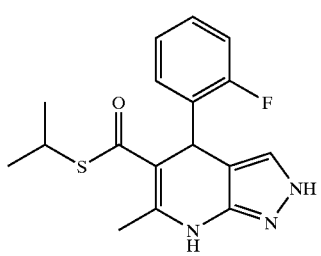
Example 11
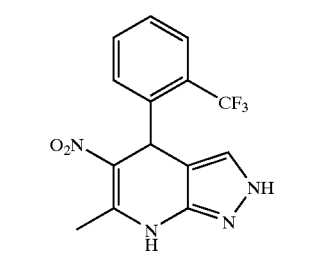
Example 12
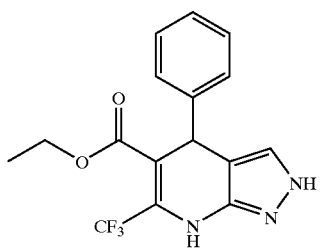
Example 13
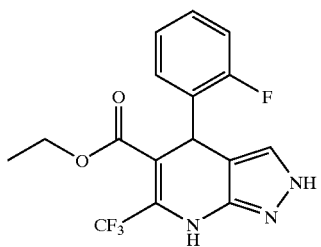
Example 14
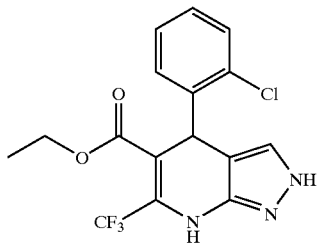
Example 15
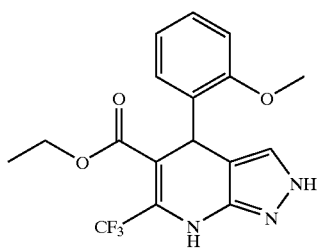
Example 16
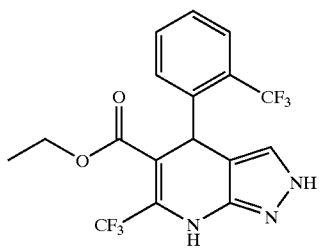
Example 17
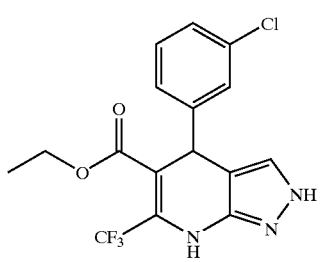
Example 18
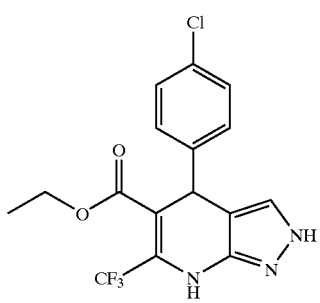
Example 19
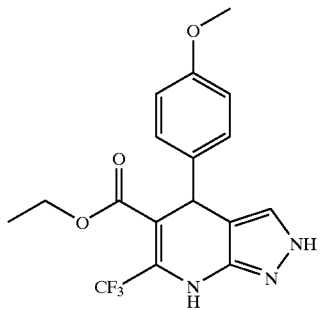

Example 20

Example 21

Example 22

Example 23

Example 24

Example 25

Example 26

Example 27

Example 28

Example 29

Example 30

Example 31

-continued
Example 32
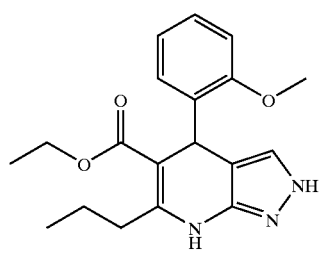
Example 33
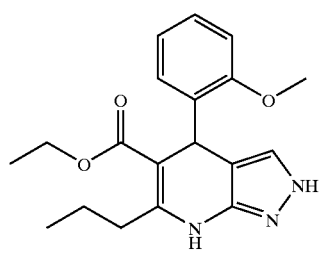
Example 34
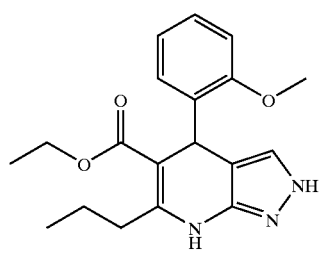
Example 35
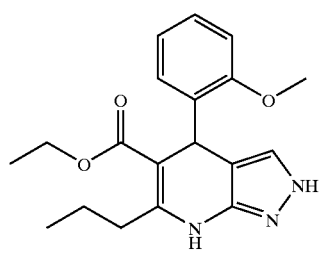
Example 36
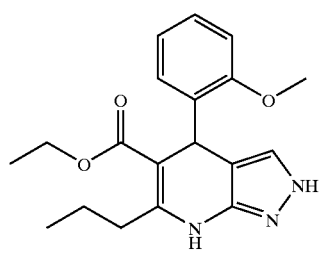
Example 37
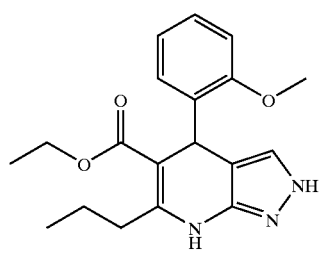
-continued
Example 38
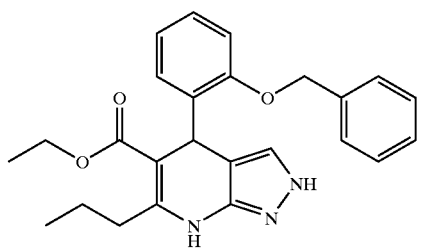
Example 39
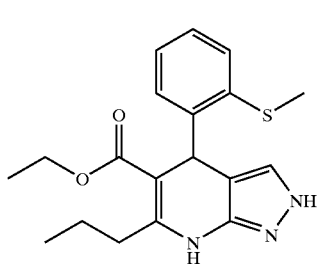
Example 40
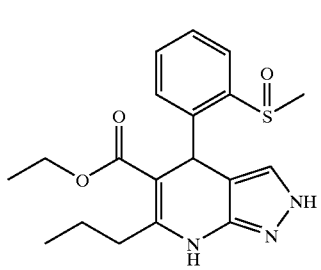
Example 41
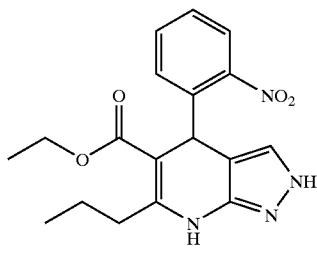
Example 42
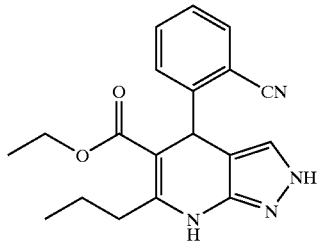
Example 43
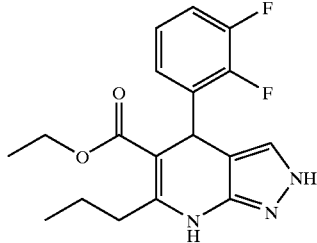

Example 44
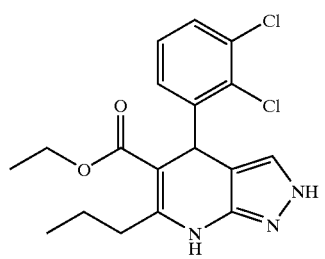
Example 45
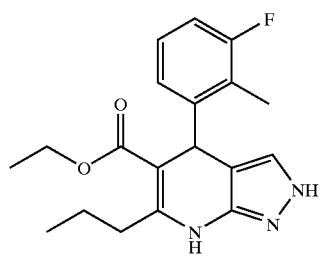
Example 46
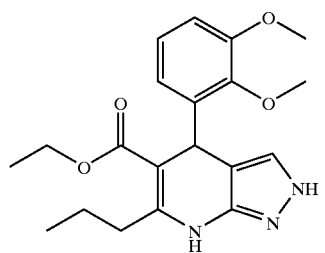
Example 47
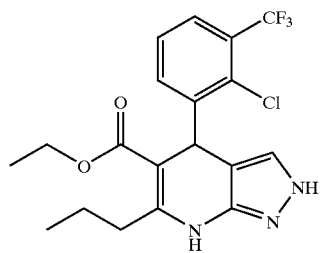
Example 48
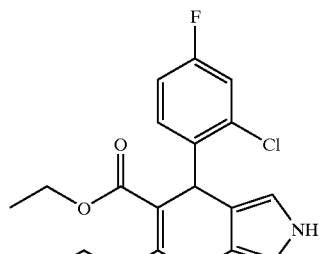
Example 49
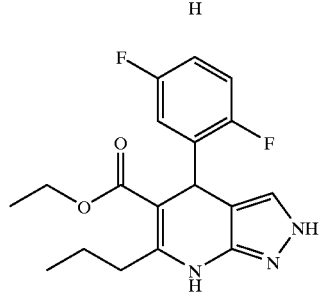
Example 50
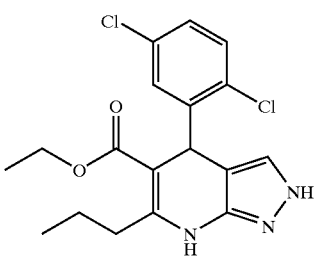
Example 51
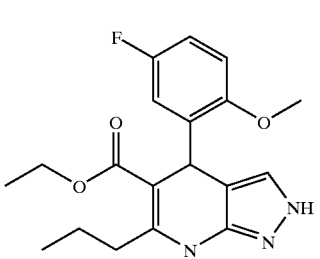
Example 52
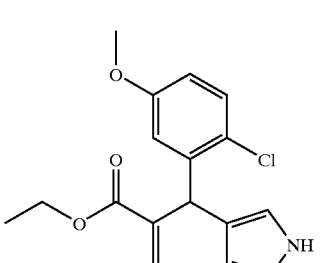
Example 53
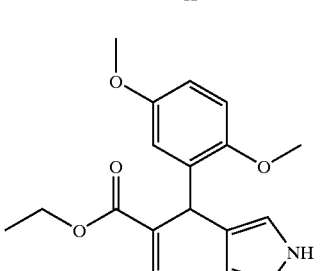
Example 54
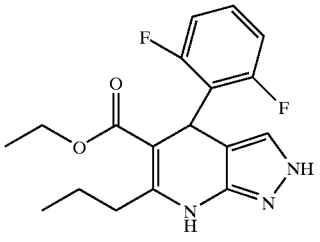
Example 55
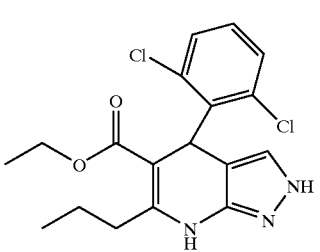

Example 56
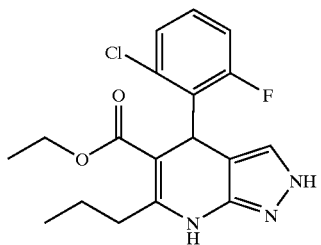
Example 57
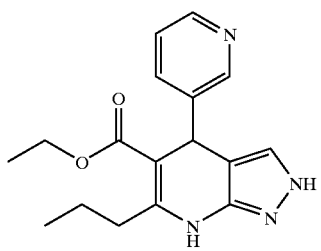
Example 58
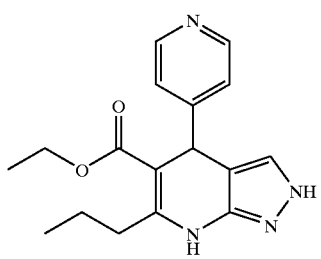
Example 59
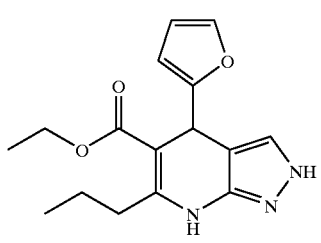
Example 60
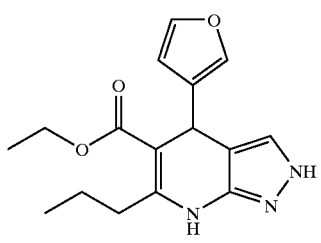
Example 61
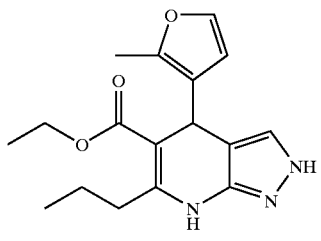
Example 62
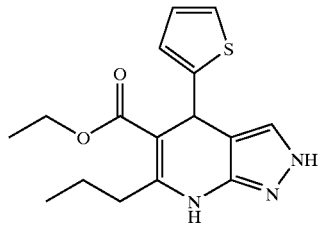
Example 63
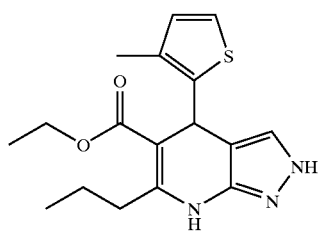
Example 64
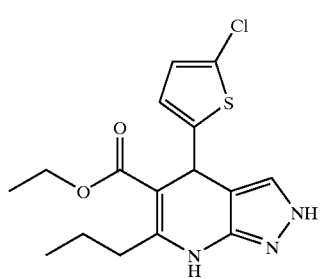
Example 65
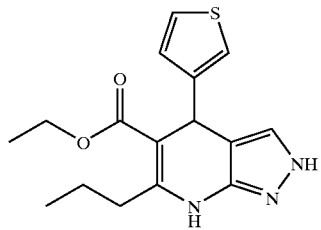
Example 66
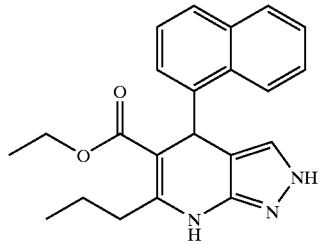
Example 67
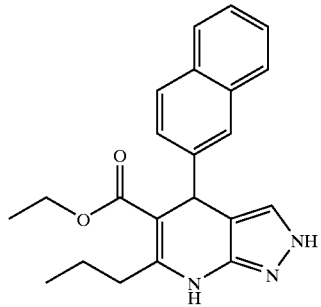

-continued
Example 68
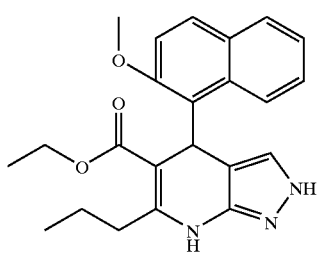
Example 69
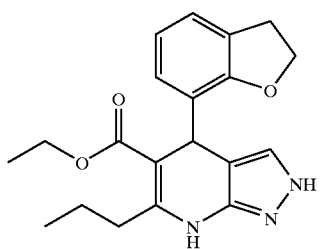
Example 70
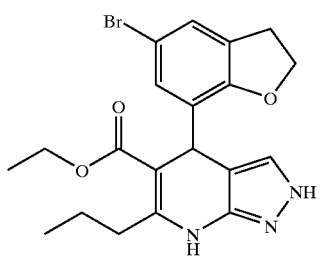
Example 71
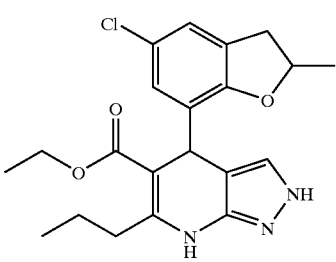
Example 72
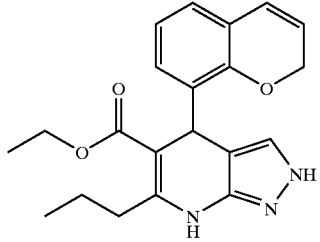
Example 73
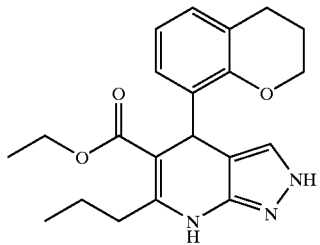
-continued
Example 74
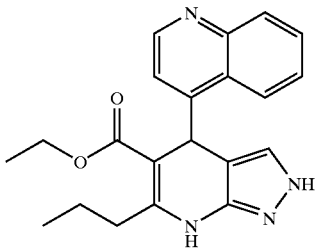
Example 75
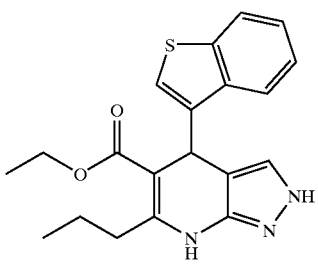
Example 76
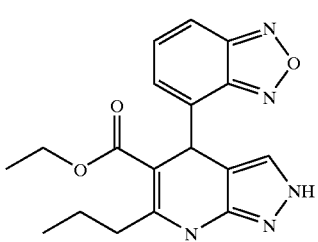
Example 77
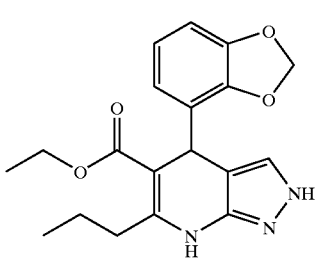
Example 78
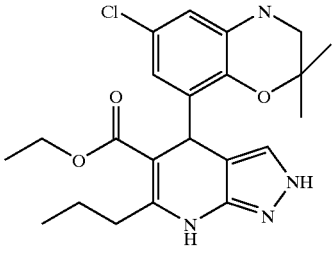
Example 79
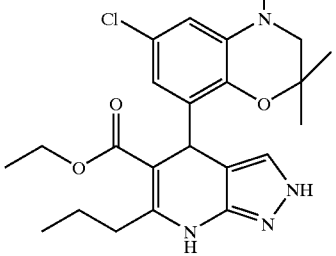

Example 80
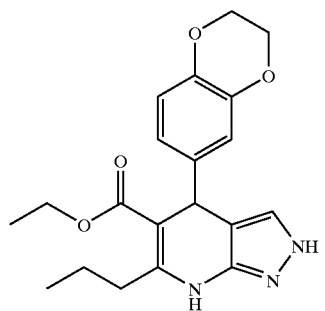
Example 81
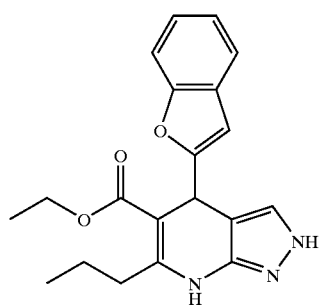
Example 82
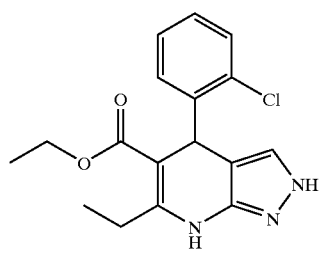
Example 83
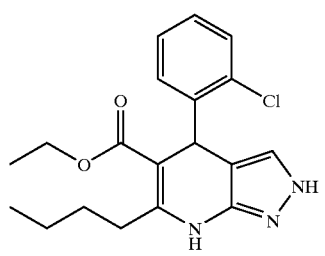
Example 84
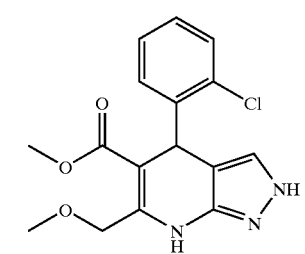
Example 85
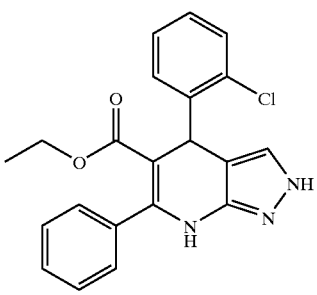
Example 86
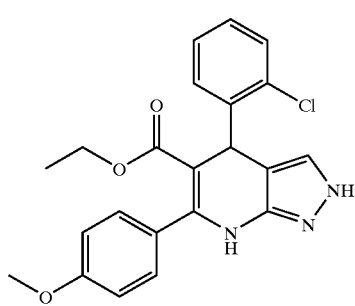
Example 87
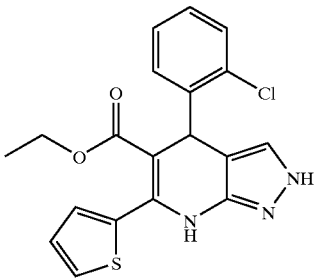
Example 88
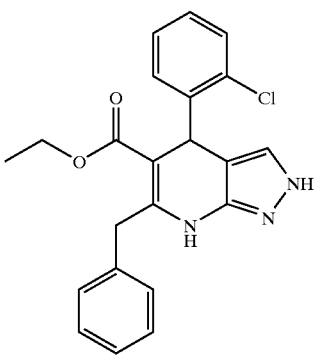
Example 89
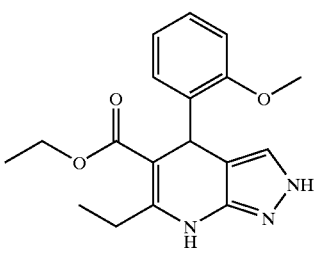

Example 90
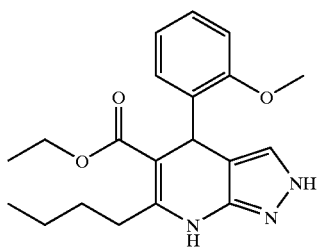
Example 91
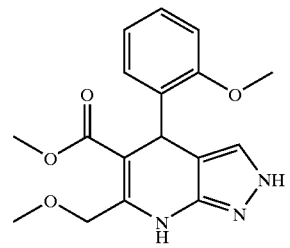
Example 92
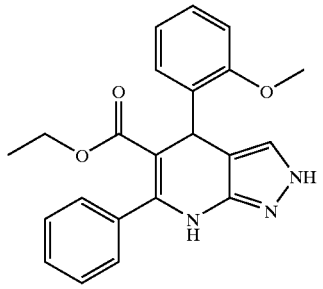
Example 93
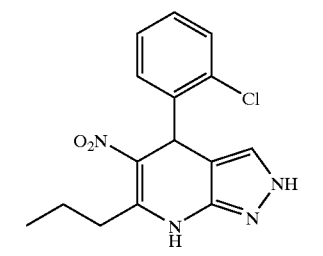
Example 94
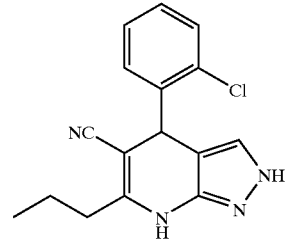
Example 95
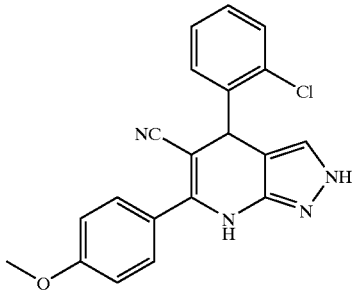
Example 96
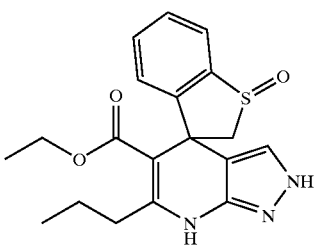
Example 97
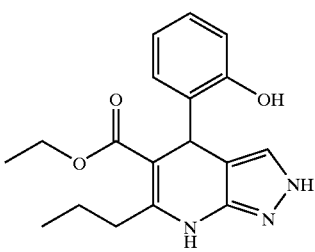
Example 98
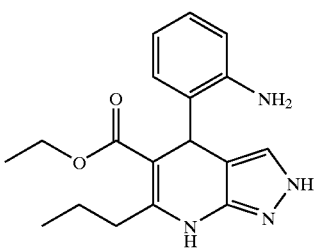
Example 99
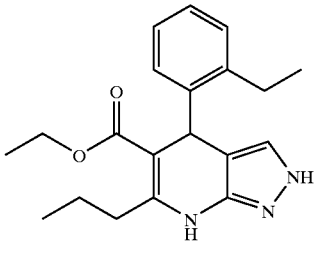
Example 100
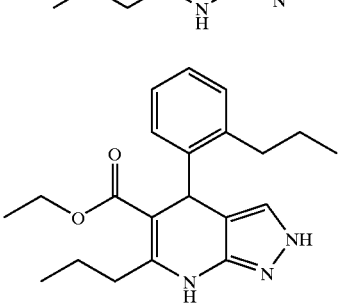
Example 101
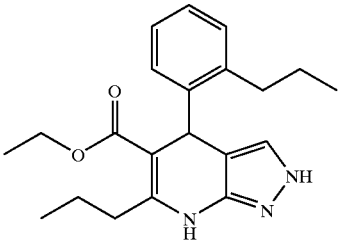

Example 102
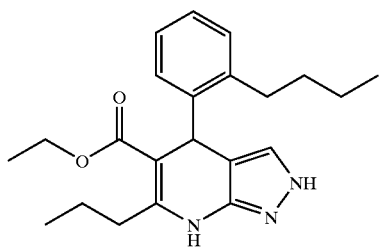
Example 103
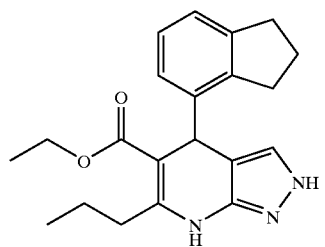
Example 104
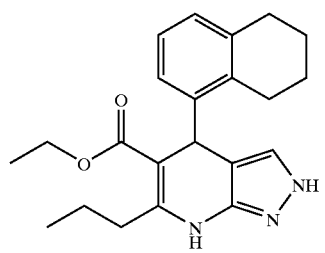
Example 105
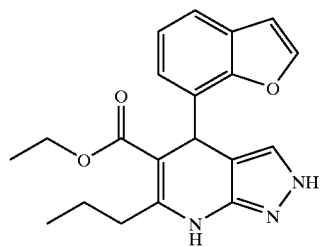
Example 106
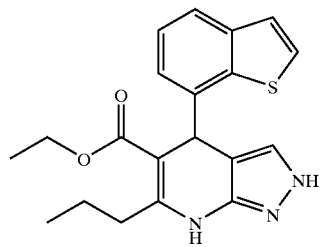
Example 107
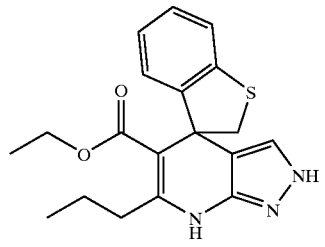
Example 108
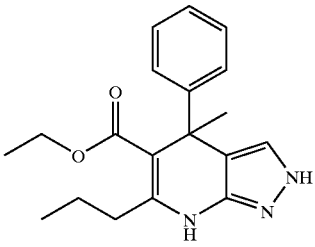
Example 109
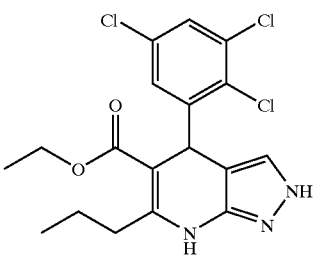
Example 110
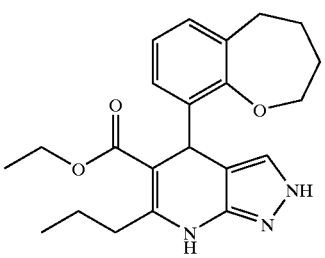
Example 111
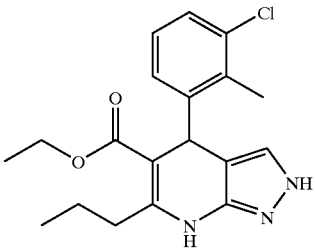
Example 112
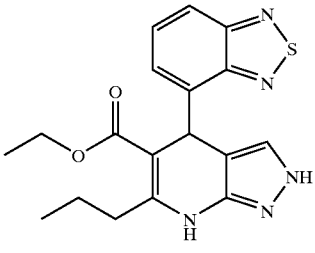
Example 113
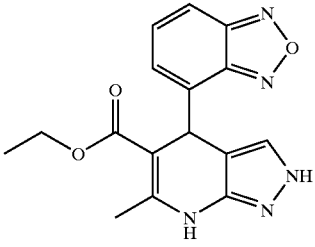

Example 114
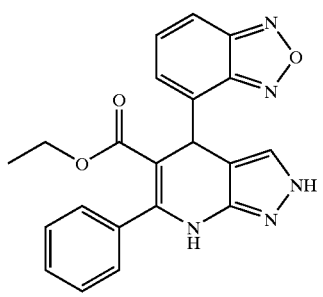
Example 115
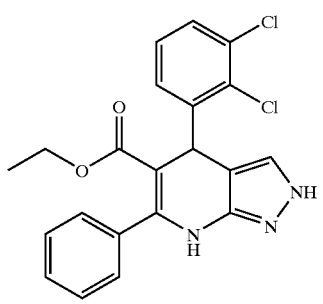
Example 116
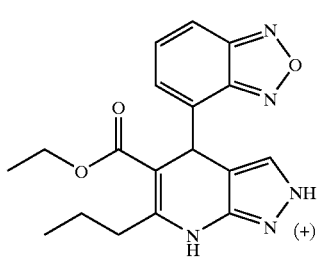
Example 117
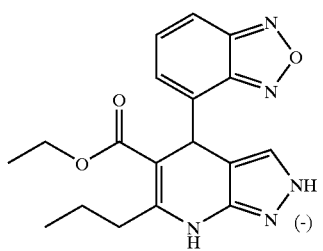
Example 118
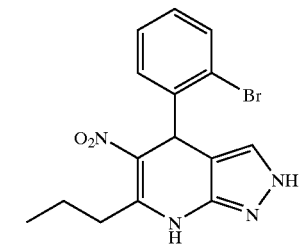
Example 119
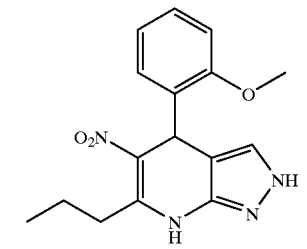
Example 120
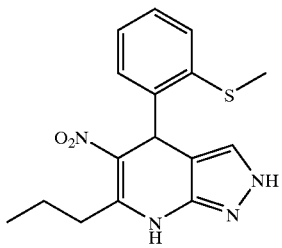
Example 121
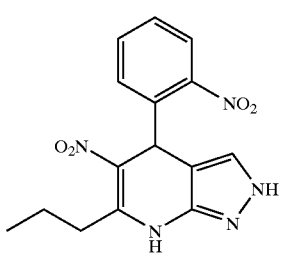
Example 122
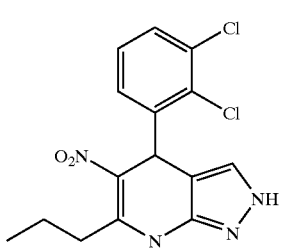
Example 123
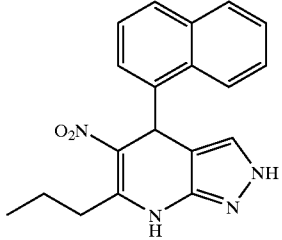
Example 124
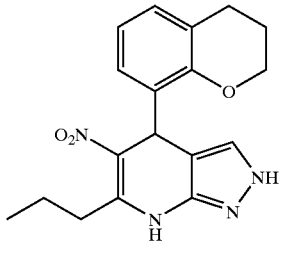
Example 125
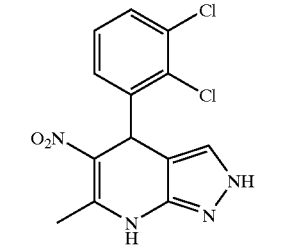

Example 126
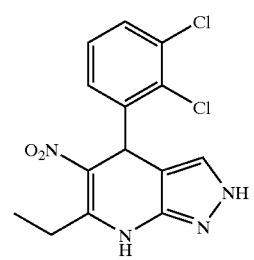
Example 127
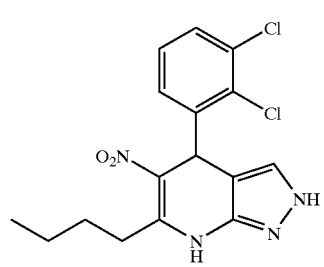
Example 128
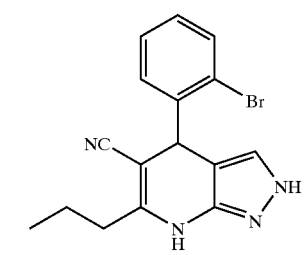
Example 129
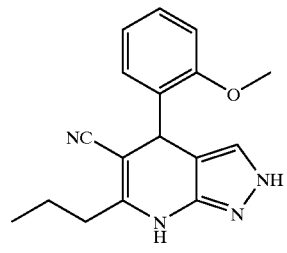
Example 130
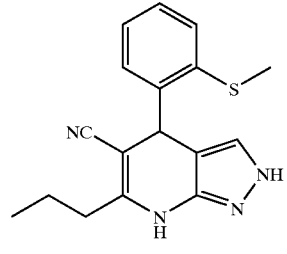
Example 131
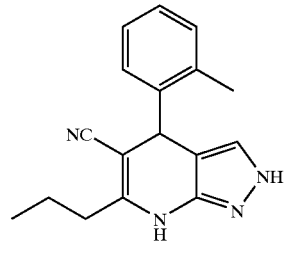
Example 132
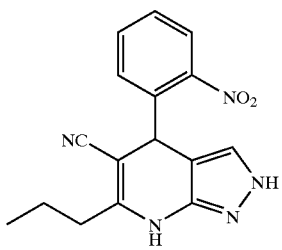
Example 133
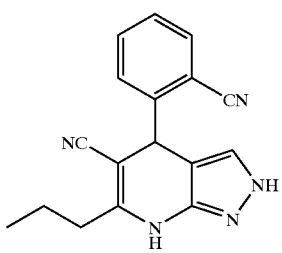
Example 134
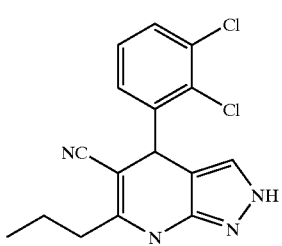
Example 135
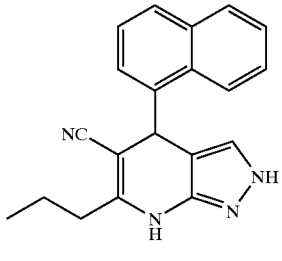
Example 136
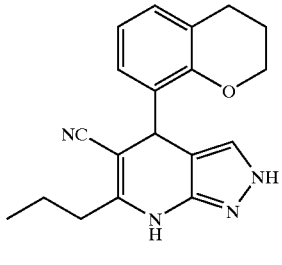
Example 137
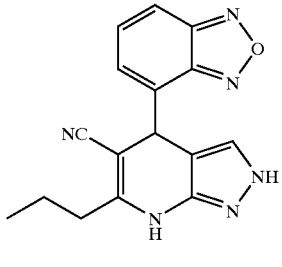

Example 138
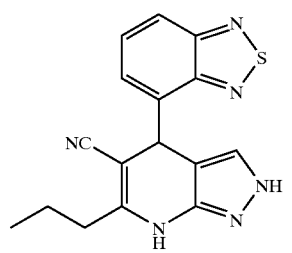
Example 139
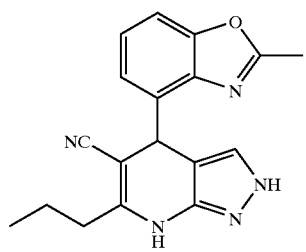
Example 140
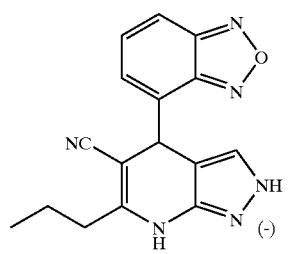 (−)
Example 141
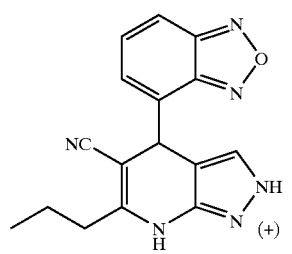 (+)
Example 142
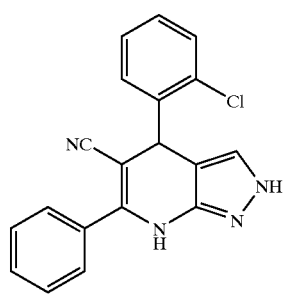
Example 143
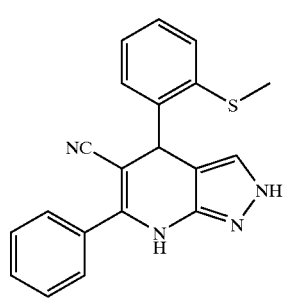
Example 144
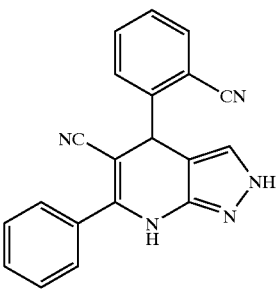
Example 145
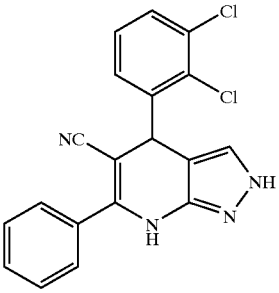
Example 146
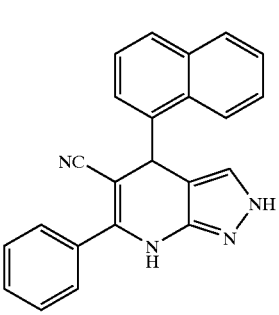
Example 147
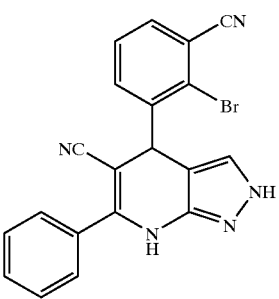
Example 148
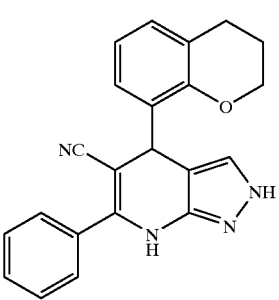

Example 149
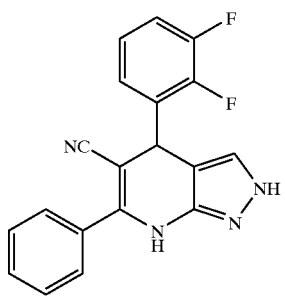
Example 150
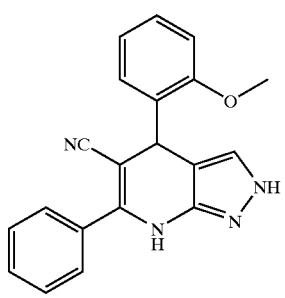
Example 151
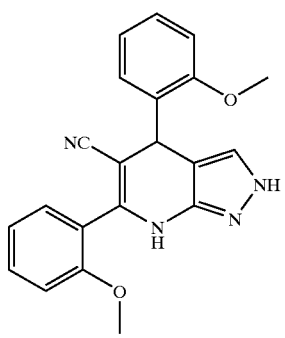
Example 152
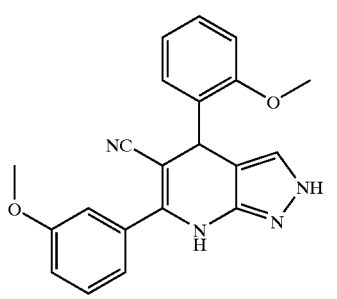
Example 153
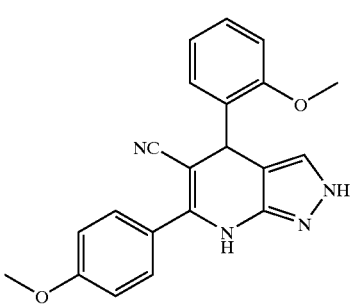
Example 154
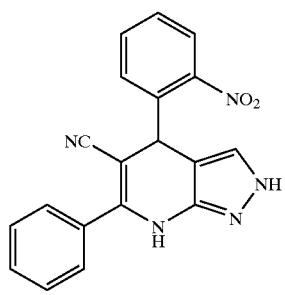
Example 155
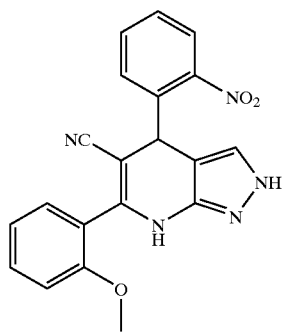
Example 156
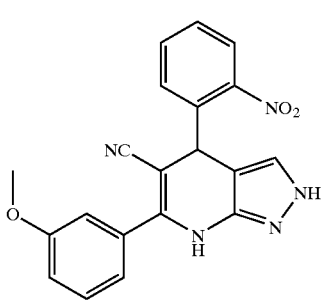
Example 157
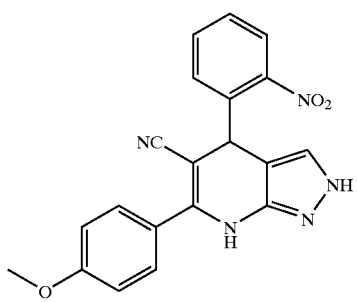
Example 158
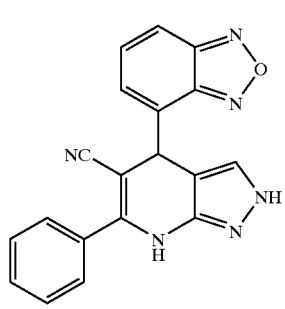

Example 159
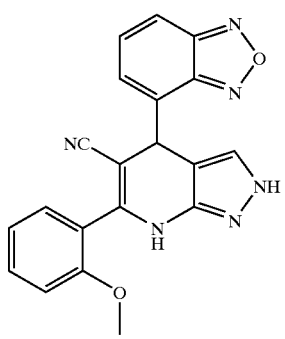
Example 160
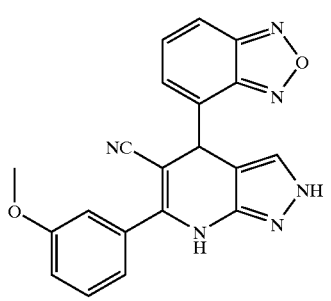
Example 161
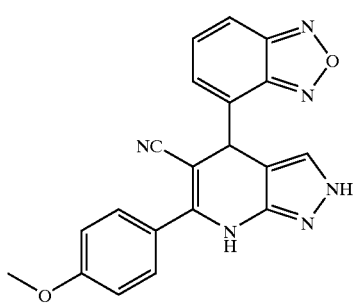
Example 162
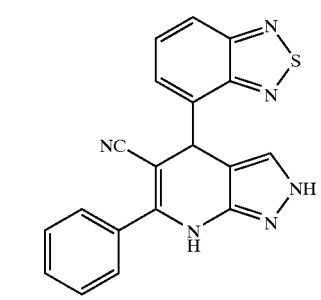
Example 163
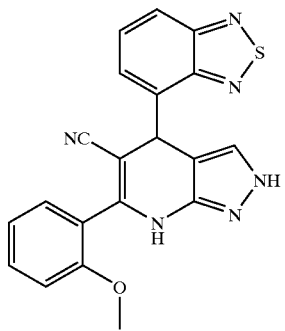
Example 164
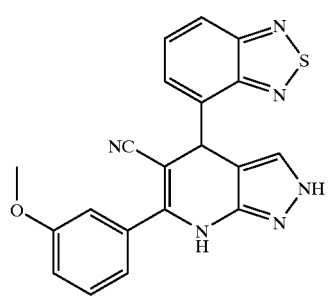
Example 165
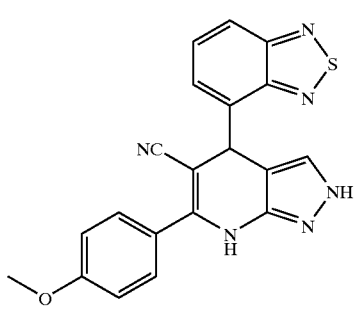
Example 166
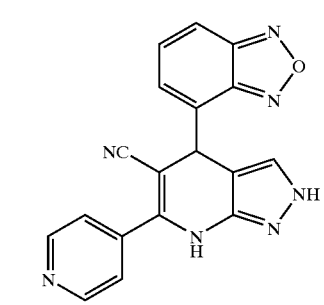
Example 167
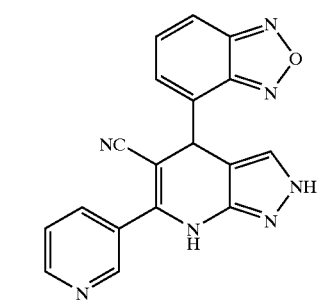
Example 168
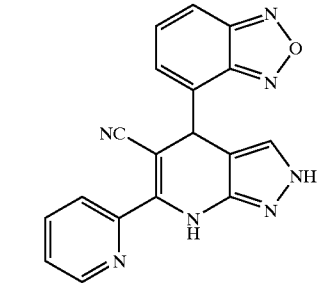

Example 169
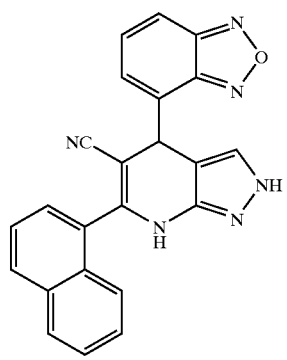
Example 170
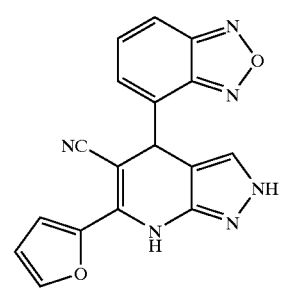
Example 171
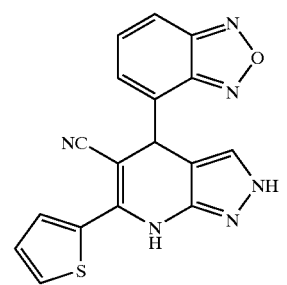
Example 172
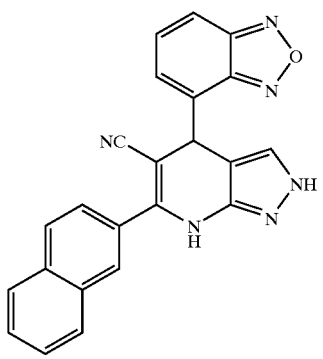
Example 173
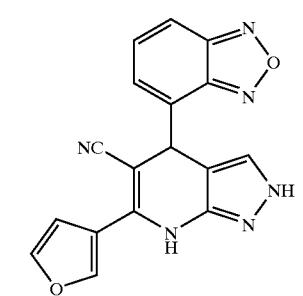
Example 174
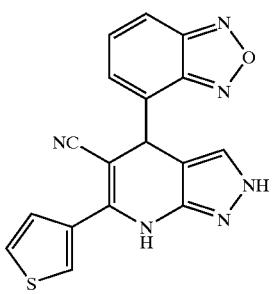
Example 175
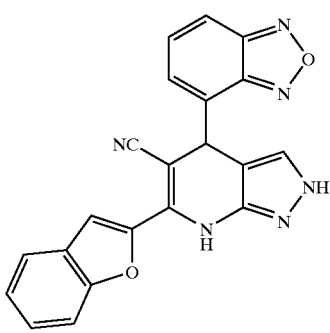
Example 176
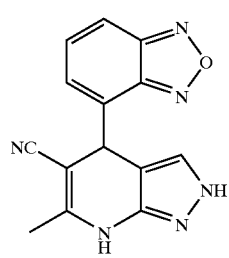
Example 177
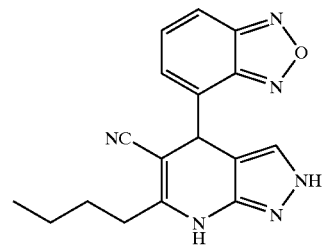
Example 178
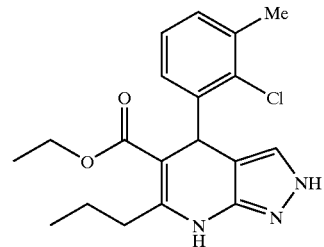
Example 179
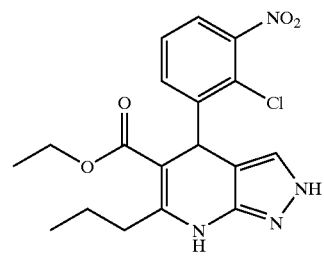

Example 180
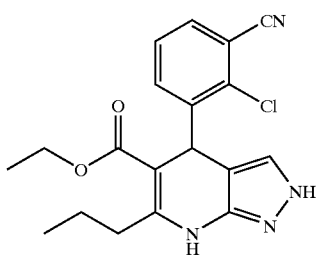
Example 181
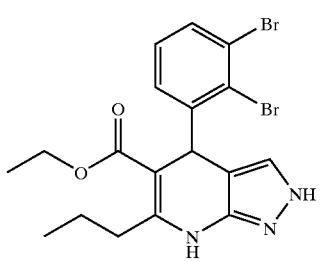
Example 182
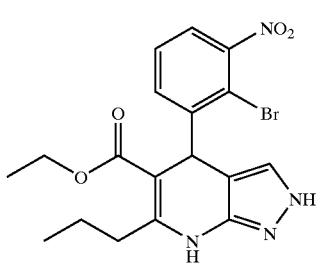
Example 183
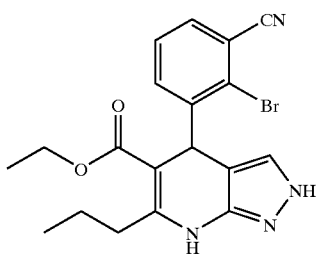
Example 184
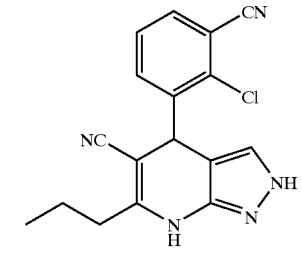
Example 185
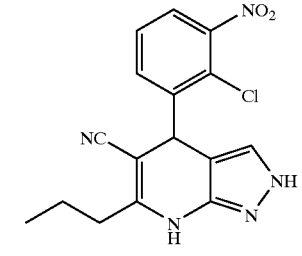
Example 186
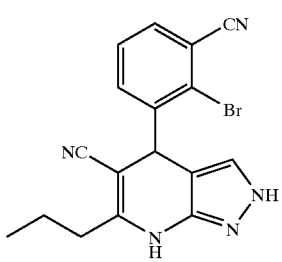
Example 187
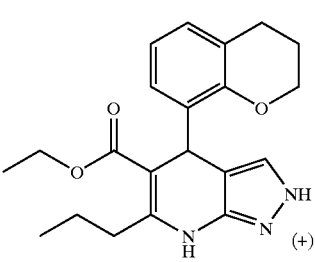
Example 188
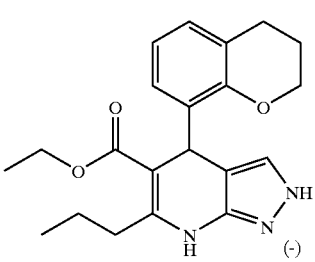
Example 189
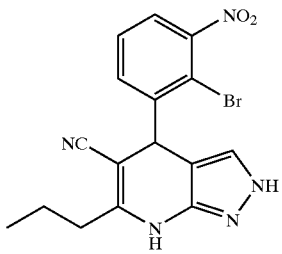
Example 190
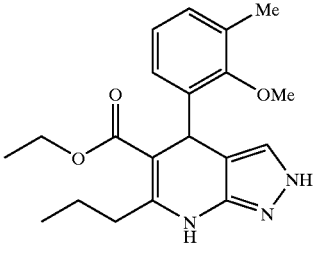
Example 191
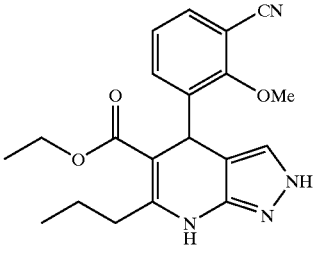

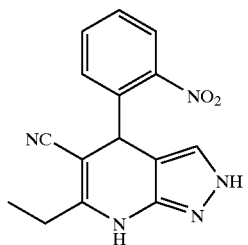
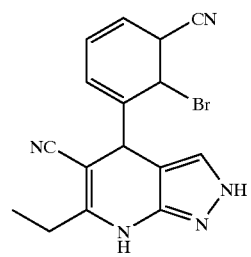

Example 204
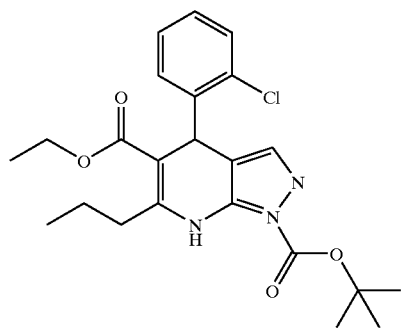
Example 205
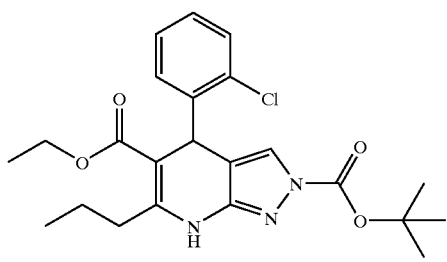
Example 206
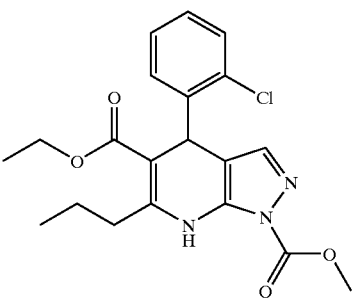
Example 207
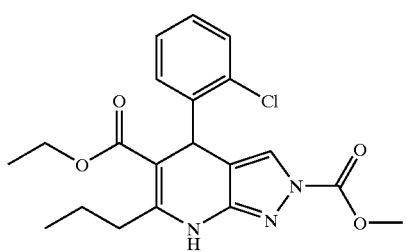
Example 208
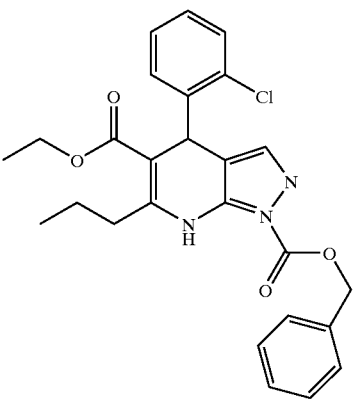
Example 209
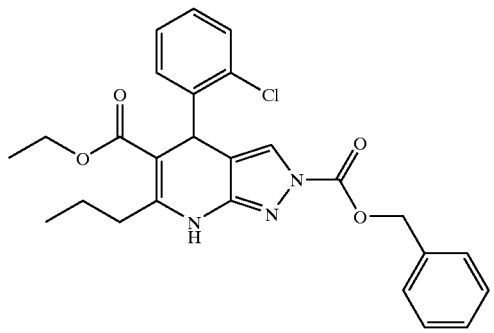
Example 210
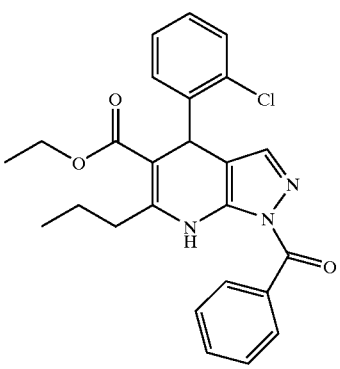
Example 211
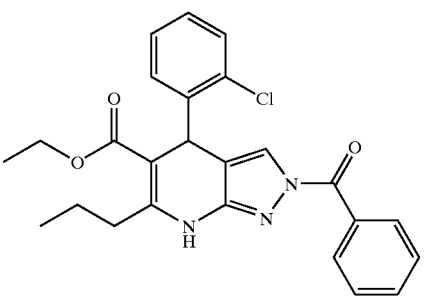
Example 212
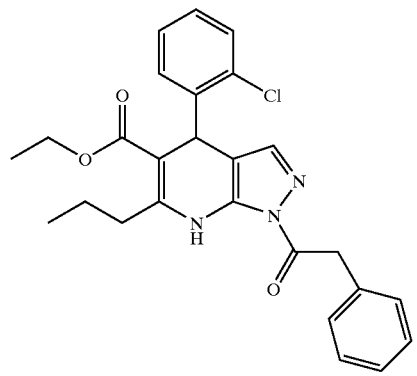

Example 213
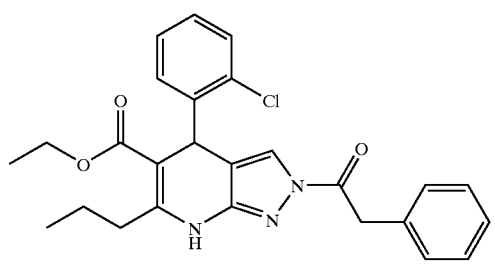
Example 214
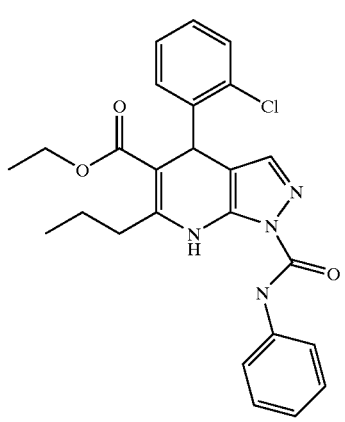
Example 215
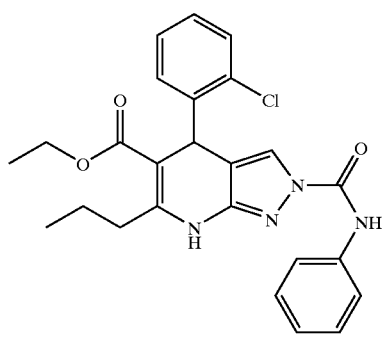
Example 216
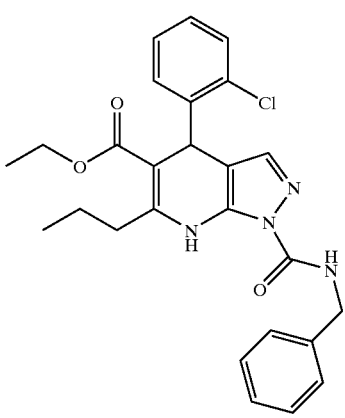
Example 217
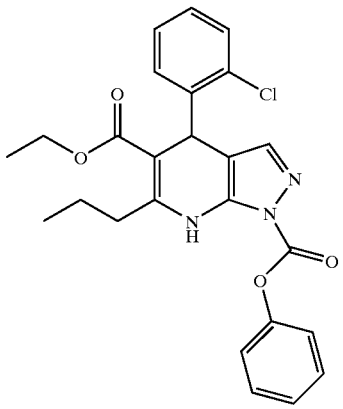
Example 218
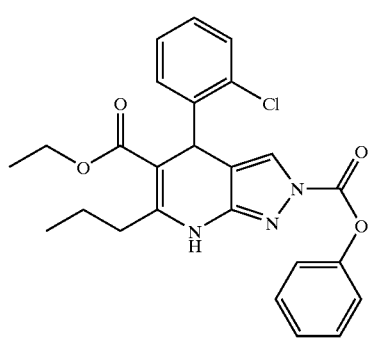
Example 219
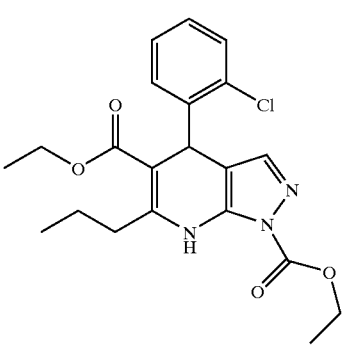
Example 220
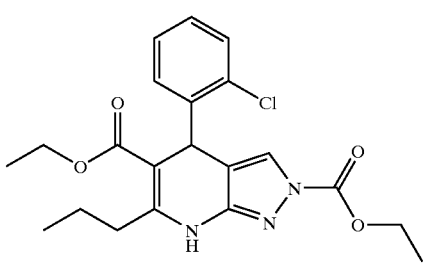

Example 221
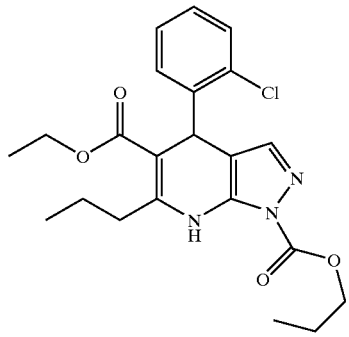
Example 222
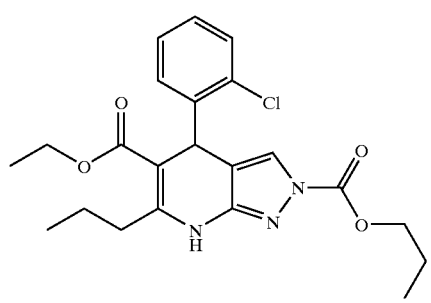
Example 223
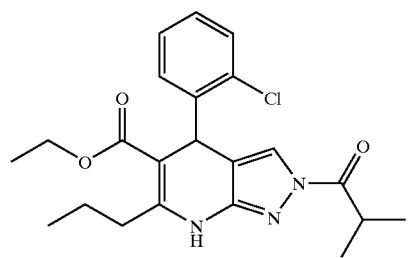
Example 224
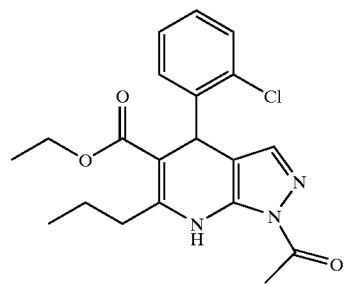
Example 225
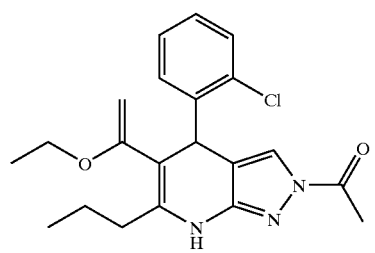
Example 226
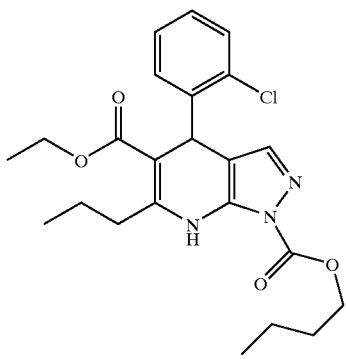
Example 227
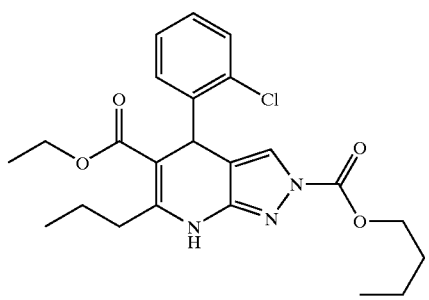
Example 228
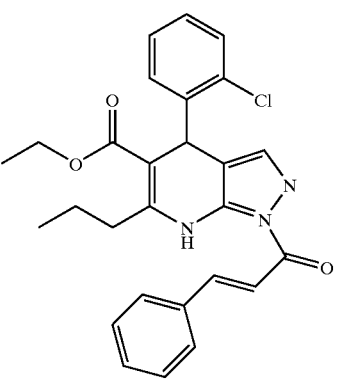
Example 229
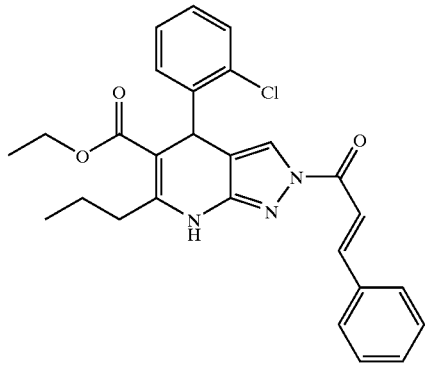
Example 230
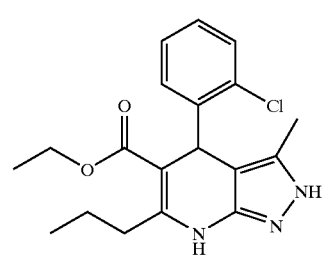

Example 231
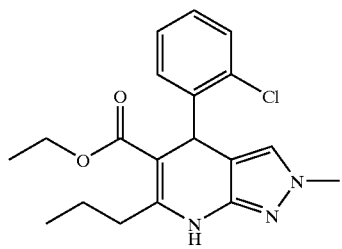
Example 232
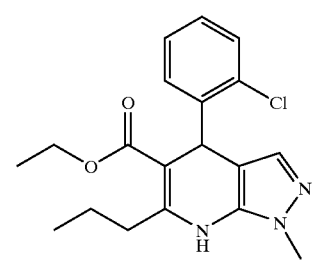
Example 233
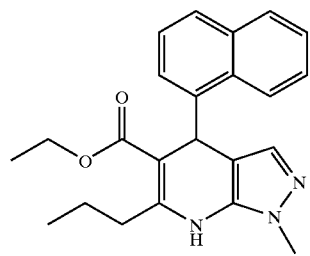
Example 234
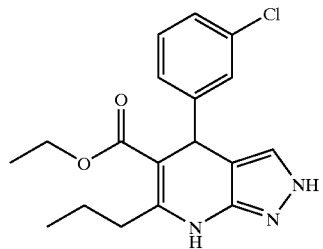
Example 235
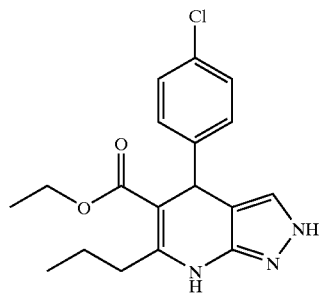
Example 236
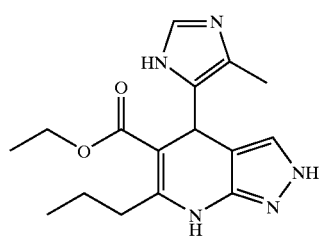
Example 237
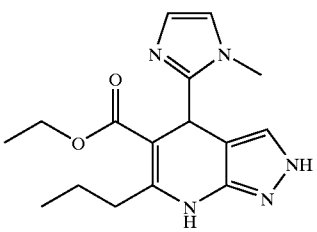
Example 238
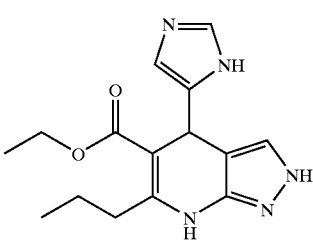
Example 239
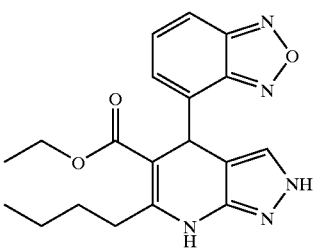
Example 240
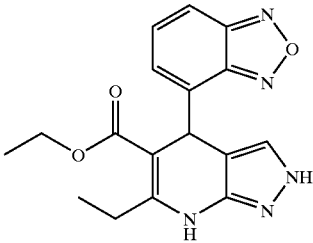
Example 241
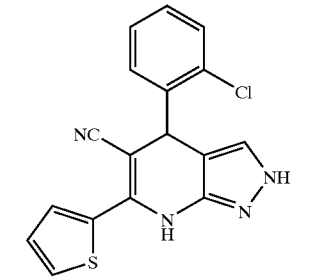
Example 242
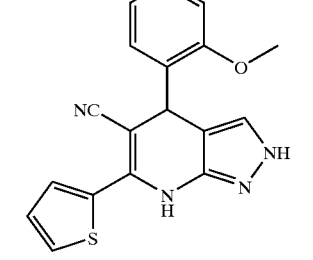

Example 243
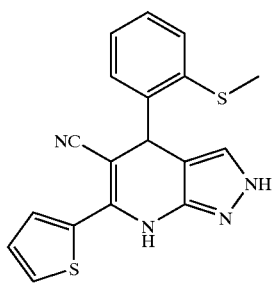
Example 244
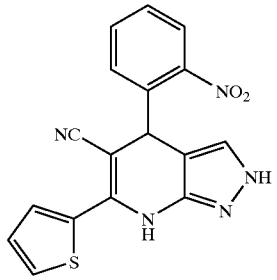
Example 245
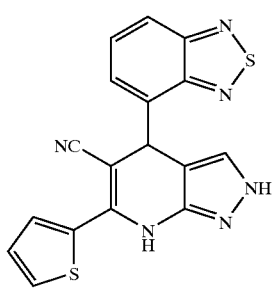
Example 246
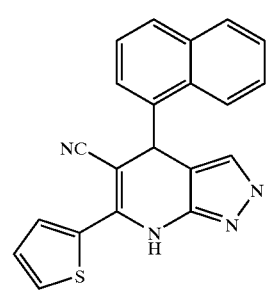
Example 247
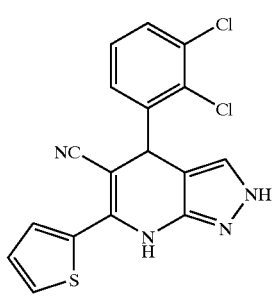
Example 248
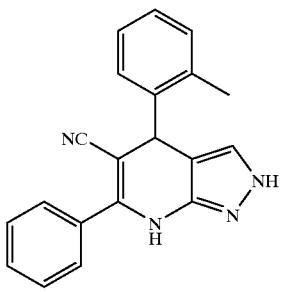
Example 249
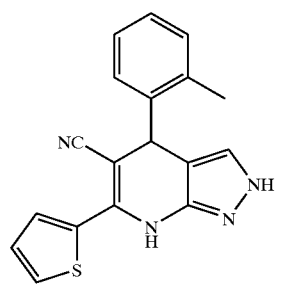
Example 250
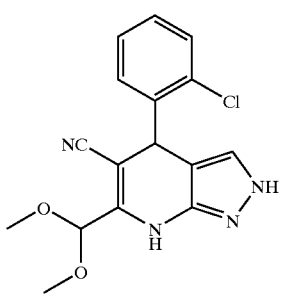
Example 251
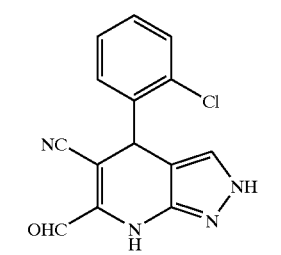
Example 252
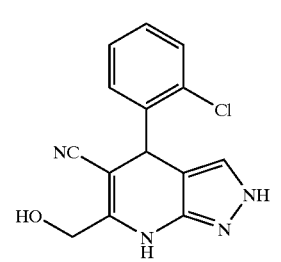
Example 253
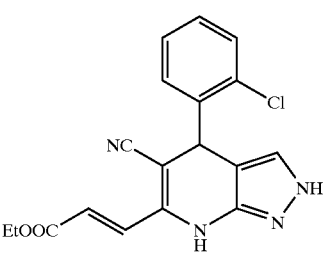

Example 254
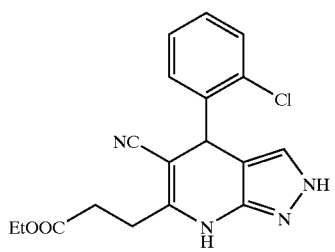
Example 255
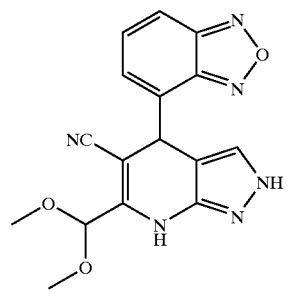
Example 256
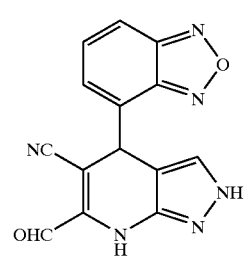
Example 257
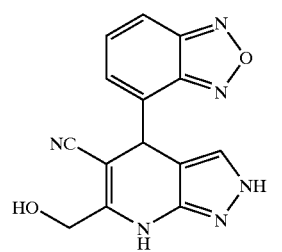
Example 258
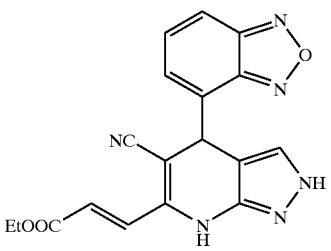
Example 259
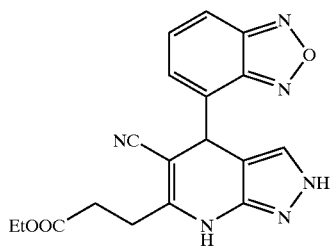
Example 260
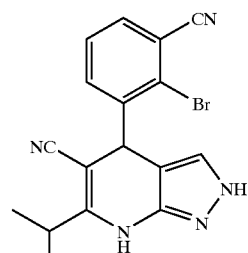
Example 261
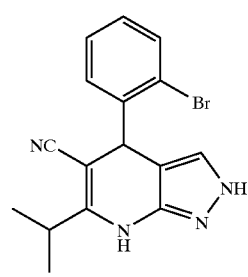
Example 262
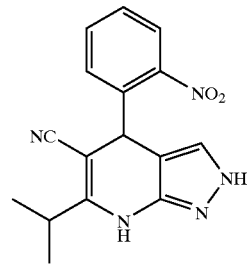
Example 263
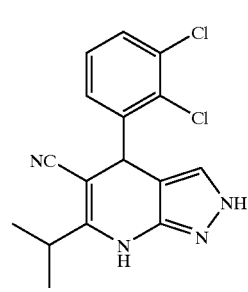
Example 264
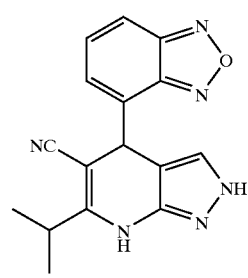
Example 265
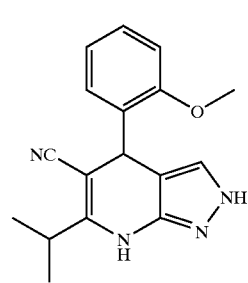

-continued
Example 266
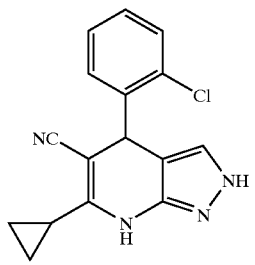
Example 267
Example 268
Example 269
Example 270
Example 271
-continued
Example 272
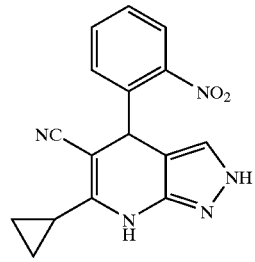
Example 273
Example 274
Example 275
Example 276
Example 277

Example 278
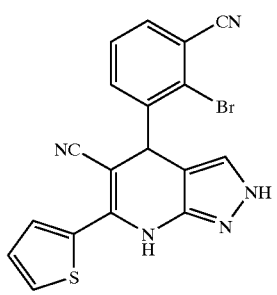
Example 279
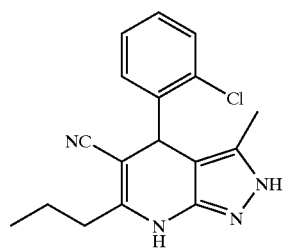
Example 280
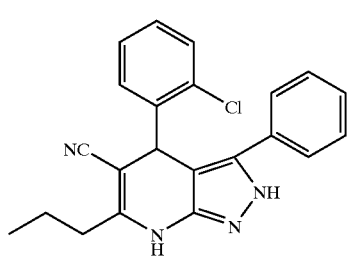
Example 281
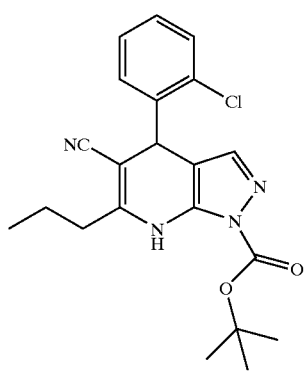
Example 282
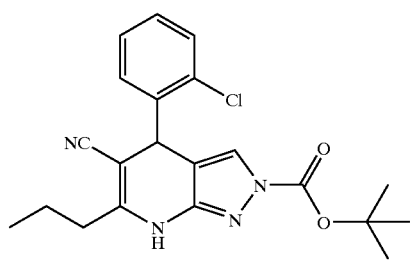
Example 283
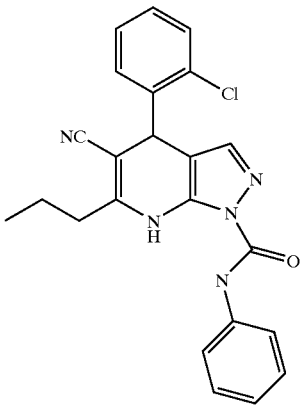
Example 284
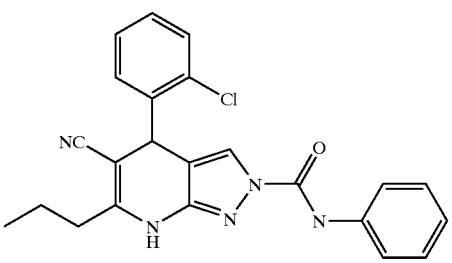
Example 285
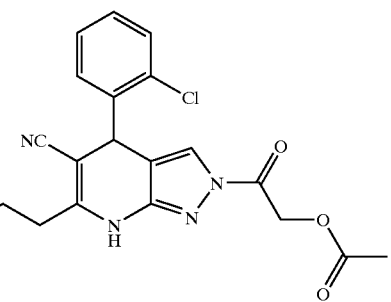
Example 286
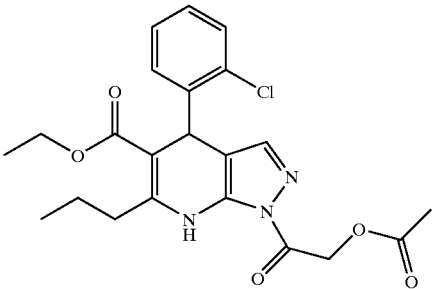

Example 287

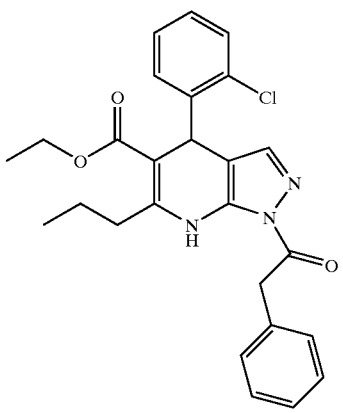

Example 288

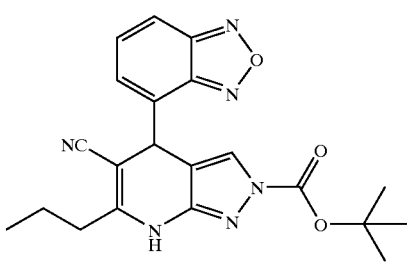

Example 289

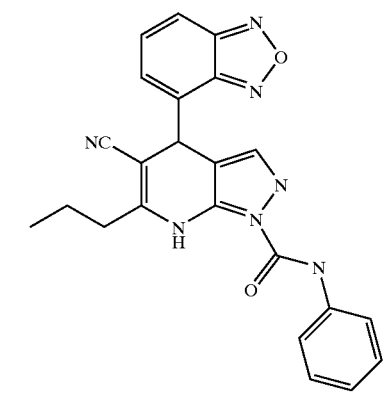

Example 290

4-(2-Chlorophenyl)-5-cyano-4,7-dihydro-3-(4-methoxyphenyl)-6-propyl-2H-pyrazolo[3,4-b]pyridine To a solution of acetonitrile (15 g) in DMSO (25 mL) was added methyl p-anisate (25 g) and the mixture was stirred with heating at 60° C. for 1 hour. The reaction mixture was allowed to cool and cold water (100 mL) was added dropwise. The mixture was acidified with hydrochloric acid and the precipitated crystals were collected by filtration. The obtained crystals were extracted with ethyl acetate and the solvent was evaporated under reduced pressure. The residue was recrystallized from ethyl acetate to give 4-methoxybenzoylacetonitrile (21 g) as colorless crystals. To a solution of the obtained crystals in toluene was added hydrazine monohydrate (13 g) and the mixture was heated under reflux for 3 hours. The mixture was cooled and the precipitated crystals were collected by filtration to give 5-amino-3-(4-methoxyphenyl)pyrazole (22 g). Subsequently, the title compound was prepared from methyl butyrate, 2-chlorobenzaldehyde and 5-amino-3-(4-methoxyphenyl)pyrazole in the same manner as in Example 94.

MP: 284° C.

Anal. Calcd. for: $C_{23}H_{21}ClN_4O$: C, 68.23; H, 5.23; N, 13.84. Found: C, 68.17; H, 5.29; N, 13.86.

MS (EI): 404 (M$^+$).

$^1$H-NMR (400 MHz, DMSO-d$_6$) δ (ppm): 0.89 (3H, t, J=7.3 Hz), 1.58–1.63 (2H, m), 2.32–2.38 (2H, m), 3.70 (3H, s), 5.56 (1H, s), 6.81 (2H, d, J=7.2 Hz), 7.09–7.12 (2H, m), 7.17 (1H, dd, J=7.3 Hz and 7.2 Hz), 7.24–7.30 (3H, m), 9.85 (1H, brs), 12.46 (1H, brs).

Example 291

4-(2,1,3-Benzoxadiazol-4-yl)-6-(2-bromothiophen-5-yl)-5-cyano-4,7-dihydro-2H-pyrazolo[3,4-b]pyridine The title compound was prepared from methyl 5-bromothiophene-2-carboxylate, 2,1,3-benzoxadiazole-4-aldehyde and 3-aminopyrazole in the same manner as in Example 95.

MP: 208° C.

Anal. Calcd. for: $C_{17}H_9BrN_6OS$: C, 48.01; H, 2.13; N, 19.76. Found: C, 47.94; H, 2.36; N, 19.78.

MS (EI): 425 (M$^+$).

$^1$H-NMR (400 MHz, DMSO-d$_6$) δ (ppm): 5.54 (1H, s), 7.32–7.34 (2H, m), 7.42 (1H, d, J=3.9 Hz), 7.50 (1H, d, J=6.6 Hz), 7.61 (1H, dd, J=9.0 Hz), 7.95 (1H, d, J=9.0 Hz), 10.32 (1H, brs), 12.32 (1H, brs).

Example 292

4-(2,1,3-Benzoxadiazol-4-yl)-5-cyano-4,7-dihydro-6-(3-methylthiophen-2-yl)-2H-pyrazolo[3,4-b]pyridine The title compound was prepared from methyl 3-methylthiophene-2-carboxylate, 2,1,3-benzoxadiazole-4-aldehyde and 3-aminopyrazole in the same manner as in Example 95.

MP: 202° C.

Anal. Calcd. for: $C_{18}H_{12}N_6OS$: C, 59.99; H, 3.36; N, 23.32. Found: C, 59.89; H, 3.53; N, 23.06.

MS (EI): 360 (M$^+$).

$^1$H-NMR (400 MHz, DMSO-d$_6$) δ (ppm): 2.17 (3H, s), 5.54 (1H, s), 6.96 (1H, d, J=5.1 Hz), 7.32 (1H, s), 7.49 (1H, d, J=6.6 Hz), 7.60–7.64 (2H, m), 7.96 (1H, d, J=9.0 Hz), 10.19 (1H, brs), 12.25 (1H, brs).

Example 293

4-(2,1,3-Benzoxadiazol-4-yl)-5-cyano-4,7-dihydro-6-(1-methoxymethylindol-3-yl)-2H-pyrazolo[3,4-b]pyridine The title compound was prepared from methyl 1-methoxymethylindol-3-carboxylate, 2,1,3-benzoxadiazole-4-aldehyde and 3-aminopyrazole in the same manner as in Example 95.

MP: 200° C.

MS (EI): 423 (M$^+$).

$^1$H-NMR (400 MHz, DMSO-d$_6$) δ (ppm): 3.19 (3H, s), 5.55–5.63 (3H, m), 7.15 (1H, dd, J=7.3 Hz and 7.2 Hz), 7.25 (1H, dd, J=7.3 Hz and 7.2 Hz), 7.34 (1H, s), 7.54 (1H, d, J=7.3 Hz), 7.60–7.66 (3H, m), 7.93–7.97 (2H, m), 10.12 (1H, brs), 12.22 (1H, brs).

Example 294

4-(2-Chlorophenyl)-5-cyano-4,7-dihydro-6-propyl-3-(thiophen-2-yl)-2H-pyrazolo[3,4-b]pyridine The title compound was prepared from methyl thiophene-2-carboxylate, methyl butyrate and 2-chlorobenzaldehyde in the same manner as in Example 290.

MP: 256° C.

Anal. Calcd. for: $C_{20}H_{17}ClN_4S$: C, 63.07; H, 4.50; N, 14.71. Found: C, 62.98; H, 4.52; N, 14.68.

MS (EI): 380 (M$^+$).

$^1$H-NMR (400 MHz, DMSO-d$_6$) δ (ppm): 0.86 (3H, t, J=7.3 Hz), 1.56–1.62 (2H, m), 2.31–2.36 (2H, m), 5.46 (1H, s), 7.00–7.24 (5H, m), 7.36 (1H, d, J=7.3 Hz), 7.50 (1H, d, J=4.9 Hz), 9.95 (1H, brs), 12.74 (1H, brs)

Example 295

4-(2-Chlorophenyl)-5-cyano-4,7-dihydro-3-(furan-2-yl)-6-propyl-2H-pyrazolo[3,4-b]pyridine The title compound was prepared from methyl furan-2-carboxylate, methyl butyrate and 2-chlorobenzaldehyde in the same manner as in Example 290.

MP: 253° C.

Anal. Calcd. for: $C_{20}H_{17}ClN_4O$: C, 65.84; H, 4.70; N, 15.36. Found: C, 65.81; H, 4.84; N, 15.49.

MS (EI): 364 (M$^+$).

$^1$H-NMR (400 MHz, DMSO-d$_6$) δ (ppm): 0.88 (3H, t, J=7.3 Hz), 1.58–1.63 (2H, m), 2.32–2.36 (2H, m), 5.48 (1H, s), 6.31 (1H, d, J=3.2 Hz), 6.45 (1H, d, J=1.5 Hz), 7.14–7.23 (3H, m), 7.36 (1H, d, J=7.3 Hz), 7.59 (1H, s), 9.93 (1H, brs), 12.76 (1H, brs).

Example 296

4-(2-Chlorophenyl)-5-cyano-4,7-dihydro-3-(2-methoxyphenyl)-6-propyl-2H-pyrazolo[3,4-b]pyridine The title compound was prepared from methyl 2-methoxybezoate, methyl butyrate and 2-chlorobenzaldehyde in the same manner as in Example 290.

MP: >270° C.

Anal. Calcd. for: $C_{23}H_{21}ClN_4O$: C, 68.23; H, 5.23; N, 13.84. Found: C, 68.23; H, 5.31; N, 13.87.

MS (EI): 404 (M$^+$).

$^1$H-NMR (400 MHz, DMSO-d$_6$) δ (ppm): 0.90 (3H, t, J=7.3 Hz), 1.60–1.65 (2H, m), 2.32–2.36 (2H, m), 3.70 (3H, s), 5.41 (1H, s), 6.76 (1H, dd, J=7.3 Hz and 7.2 Hz), 6.90–6.94 (2H, m), 6.98–7.04 (2H, m), 7.08–7.15 (2H, m), 7.22 (1H, dd, J=7.3 Hz and 7.2 Hz), 9.83 (1H, brs), 12.21 (1H, brs).

Example 297

4-(2-Chlorophenyl)-5-cyano-4,7-dihydro-3-(3-methoxyphenyl)-6-propyl-2H-pyrazolo[3,4-b]pyridine The title compound was prepared from methyl 3-methoxybenzoate, methyl butyrate and 2-chlorobenzaldehyde in the same manner as in Example 290.

MP: 239° C.

Anal. Calcd. for: $C_{23}H_{21}ClN_4O$: C, 68.23; H, 5.23; N, 13.84. Found: C, 68.16; H, 5.31; N, 13.80.

MS (EI): 404 (M$^+$).

$^1$H-NMR (400 MHz, DMSO-d$_6$) δ (ppm): 0.88 (3H, t, J=7.3 Hz), 1.58–1.63 (2H, m), 2.31–2.36 (2H, m), 3.68 (3H, s), 6.78 (1H, d, J=7.3 Hz), 6.87–6.89 (2H, m), 7.11–7.20 (4H, m), 7.29 (1H, d, J=7.3 Hz), 9.92 (1H, brs), 12.64 (1H, brs).

Example 298

4-(2,1,3-Benzoxadiazol-4-yl)-6-(2-chlorothiophen-5-yl)-5-cyano-4,7-dihydro-2H-pyrazolo[3,4-b]pyridine The title compound was prepared from methyl 5-chlorothiophene-2-carboxylate, 2,1,3-benzoxadiazole-4-aldehyde and 3-aminopyrazole in the same manner as in Example 95.

MP: 210° C.

Anal. Calcd. for: $C_{17}H_9ClN_6OS$: C, 53.62; H, 2.38; N, 22.07. Found: C, 53.51; H, 2.67; N, 22.13.

MS (EI): 380 (M$^+$).

$^1$H-NMR (400 MHz, DMSO-d$_6$) δ (ppm): 5.54 (1H, s), 7.23 (1H, d, J=3.9 Hz), 7.33 (1H, s), 7.46 (1H, d, J=3.9 Hz), 7.50 (1H, d, J=6.6 Hz), 7.60 (1H, dd, J=9.0 Hz and 6.6 Hz), 7.95 (1H, d, J=9.0 Hz), 10.31 (1H, brs), 12.30 (1H, brs).

Example 299

4-(2,1,3-Benzoxadiazol-4-yl)-5-cyano-4,7-dihydro-6-(2-methylthiophen-5-yl)-2H-pyrazolo[3,4-b]pyridine The title compound was prepared from methyl 5-methylthiophene-2-carboxylate, 2,1,3-benzoxadiazole-4-aldehyde and 3-aminopyrazole in the same manner as in Example 95.

MP: 192° C.

MS (EI): 360 (M$^+$).

$^1$H-NMR (400 MHz, DMSO-d$_6$) δ (ppm): 2.50 (3H, s), 5.52 (1H, s), 6.87 (1H, d, J=3.6 Hz), 7.32 (1H, s), 7.40 (1H, d, J=3.7 Hz), 7.48 (1H, d, J=6.6 Hz), 7.61 (1H, dd, J=9.0 Hz and 6.6 Hz), 7.95 (1H, d, J=9.0 Hz), 10.12 (1H, brs), 12.26 (1H, brs).

Example 300

4-(2-Chlorophenyl)-5-cyano-4,7-dihydro-3-(naphthalen-1-yl)-6-propyl-2H-pyrazolo[3,4-b]pyridine The title compound was prepared from methyl naphthalene-1-carboxylate, methyl butyrate and 2-chlorobenzaldehyde in the same manner as in Example 290.

MP: 254° C.

Anal. Calcd. for: $C_{26}H_{21}ClN_4$: C, 73.49; H, 4.98; N, 13.19. Found: C, 73.81; H, 5.05; N, 13.08.

MS (EI): 424 (M$^+$).

$^1$H-NMR (400 MHz, DMSO-d$_6$) δ (ppm): 0.95 (3H, t, J=7.3 Hz), 1.64–1.70 (2H, m), 2.46–2.49 (2H, m), 5.25 (1H, s), 6.88–7.02 (5H, m), 7.31 (1H, dd, J=7.3 Hz and 7.2 Hz), 7.42–7.47 (3H, m), 7.83–7.88 (2H, m), 9.95 (1H, brs), 12.46 (1H, brs).

Example 301

4-(2-Chlorophenyl)-5-cyano-4,7-dihydro-3-(naphthalen-2-yl)-6-propyl-2H-pyrazolo[3,4-b]pyridine The title compound was prepared from methyl naphthalene-2-carboxylate, methyl butyrate and 2-chlorobenzaldehyde in the same manner as in Example 290.

MP: >270° C.

Anal. Calcd. for: $C_{26}H_{21}ClN_4$: C, 73.49; H, 4.98; N, 13.19. Found: C, 73.23; H, 5.01; N, 13.26.

MS (EI): 424 (M$^+$).

$^1$H-NMR (400 MHz, DMSO-d$_6$) δ (ppm): 0.91 (3H, t, J=7.3 Hz), 1.61–1.66 (2H, m), 2.31–2.41 (2H, m), 5.76 (1H, s), 7.05 (1H, dd, J=7.3 Hz and 7.2 Hz), 7.12–7.16 (2H, m), 7.28 (1H, d, J=7.3 Hz), 7.45–7.52 (2H, m), 7.57 (1H, d, J=7.3 Hz), 7.77–7.84 (4H, m), 9.94 (1H, brs), 12.79 (1H, brs)

Example 302

4-(2-Chlorophenyl)-5-cyano-4,7-dihydro-3,6-dipropyl-2H-pyrazolo[3,4-b]pyridine

To a solution of acetonitrile (4.8 g) in THF (150 mL) was added n-BuLi (67 mmol) at −78° C. Methyl butyrate (10 g) was added and the mixture was stirred for 1 hour. The reaction mixture was acidified with hydrochloric acid and extracted with ethyl acetate. The solvent was evaporated under reduced pressure and the residue was purified by silica gel column chromatography (eluent:hexane-ethyl acetate (10:1)) to give 1-cyanopentan-2-one (5.5 g) as a colorless oil. To a solution of the obtained colorless oil in toluene was added hydrazine monohydrate (5.0 g) and the mixture was heated under reflux for 3 hours. The mixture was cooled and the solvent was evaporated under reduced pressure. The reaction mixture was purified by silica gel column chromatography (eluent: chloroform-methanol (10:1)) to give 5-amino-3-propylpyrazole (5.0 g). A solution of 2-chloroaldehyde (1.7 g), 5-amino-3-propylpyrazole (1.5 g) and 1-cyanopentan-2-one (1.6 g) in acetonitrile (20 mL) was heated under reflux overnight. The mixture was cooled to room temperature and the precipitated crystals were collected by filtration to give the title compound (2.1 g) as colorless crystals.

MP: 237° C.

Anal. Calcd. for: $C_{19}H_{21}ClN_4$: C, 66.95; H, 6.21; N, 16.44. Found: C, 66.98; H, 6.26; N, 16.41.

MS (EI): 340 (M$^+$).

$^1$ H-NMR (400 MHz, DMSO-d$_6$) δ (ppm): 0.57 (3H, t, J=7.3 Hz), 0.91 (3H, t, J=7.3 Hz), 1.02–1.07 (2H, m), 1.59–1.65 (2H, m), 2.01–2.12 (2H, m), 2.30–2.38 (2H, m), 5.28 (1H, s), 7.20–7.23 (2H, m), 7.30 (1H, dd, J=7.3 Hz and 7.2 Hz), 7.38 (1H, d, J=7.3 Hz), 9.70 (1H, brs), 11.85 (1H, brs).

Example 303

4-(2-Chlorophenyl)-5-cyano-4,7-dihydro-3-hydroxy-6-propyl-2H-pyrazolo[3,4-b]pyridine The title compound was prepared from methyl butyrate, 2-chlorobenzaldehyde and 3-amino-5-hydroxypyrazole in the same manner as in Example 94.

MS (EI): 314 (M$^+$).

$^1$H-NMR (400 MHz, DMSO-d$_6$) δ (ppm): 0.89 (3H, t, J=7.3 Hz), 1.56–1.60 (2H, m), 2.26–2.38 (2H, m), 5.11 (1H, s), 7.14–7.21 (3H, m), 7.27 (1H, dd, J=7.3 Hz and 7.2 Hz), 7.34 (1H, d, J=7.3 Hz), 9.64 (1H, brs), 10.45 (1H, brs).

Example 304

3-Butyl-4-(2-chlorophenyl)-5-cyano-4,7-dihydro-6-propyl-2H-pyrazolo[3,4-b]pyridine The title compound was prepared from methyl pentanoate, methyl butyrate and 2-chlorobenzaldehyde in the same manner as in Example 302.

MP: 212° C.

Anal. Calcd. for: $C_{20}H_{23}ClN_4$: C, 67.69; H, 6.53; N, 15.79. Found: C, 67.58; H, 6.46; N, 15.75.

MS (EI): 354 (M$^+$).

$^1$H-NMR (400 MHz, DMSO-d$_6$) δ (ppm): 0.64 (3H, t, J=7.3 Hz), 0.89–0.98 (6H, m), 1.10–1.14 (1H, m), 1.59–1.64 (2H, m), 2.05–2.16 (2H, m), 2.31–2.35 (2H, m), 5.28 (1H, s), 7.20–7.24 (2H, m), 7.29 (1H, dd, J=7.3 Hz and 7.2 Hz), 7.38 (1H, d, J=7.3 Hz), 9.70 (1H, brs), 11.85 (1H, brs).

Example 305

4-(2,1,3-Benzoxadiazol-4-yl)-6-(benzothiophen-2-yl)-5-cyano-4,7-dihydro-2H-pyrazolo[3,4-b]pyridine The title compound was prepared from methyl benzothiophene-2-carboxylate, 2,1,3-benzoxadiazole-4-aldehyde and 3-aminopyrazole in the same manner as in Example 95.

MP: 220° C.

Anal. Calcd. for: $C_{21}H_{12}N_6OS$: C, 63.62; H, 3.05; N, 21.20. Found: C, 63.58; H, 3.29; N, 21.09.

MS (EI): 396 (M$^+$).

$^1$H-NMR (400 MHz, DMSO-d$_6$) δ (ppm): 5.60 (1H, s), 7.36 (1H, s), 7.44–7.46 (2H, m), 7.54 (1H, d, J=6.3 Hz), 7.64 (1H, dd, J=9.0 Hz and 6.6 Hz), 7.88 (1H, s), 7.94–7.98 (2H, m), 8.05 (1H, d, J=9.0 Hz), 10.40 (1H, brs), 12.31 (1H, brs)

Example 306

4-(2-Chlorophenyl)-5-cyano-6-cyclohexyl-4,7-dihydro-2H-pyrazolo[3,4-b]pyridine

The title compound was prepared from methyl cyclohexanecarboxylate, 2-chlorobenzaldehyde and 3-aminopyrazole in the same manner as in Example 94.

MP: 163° C.

Anal. Calcd. for: $C_{19}H_{19}ClN_4 \cdot 1/2H_2O$: C, 65.61; H, 5.80; N, 16.11. Found: C, 65.40; H, 5.77; N, 15.86.

MS (EI): 338 (M$^+$).

$^1$H-NMR (400 MHz, DMSO-d$_6$) δ (ppm): 1.16–1.30 (3H, m), 1.66–1.85 (7H, m), 2.66–2.72 (1H, m), 5.33 (1H, s), 7.21–7.25 (3H, m), 7.32 (1H, dd, J=7.3 Hz and 7.2 Hz), 7.41 (1H, d, J=7.3 Hz), 9.60 (1H, brs), 12.15 (1H, brs).

Example 307

6-t-Butyl-4-(2-chlorophenyl)-5-cyano-4,7-dihydro-2H-pyrazolo[3,4-b]pyridine

The title compound was prepared from methyl pivalate, 2-chlorobenzaldehyde and 3-aminopyrazole in the same manner as in Example 94.

MP: 198° C.

Anal. Calcd. for: $C_{17}H_{17}ClN_4$: C, 65.28; H, 5.48; N, 17.91. Found: C, 64.98; H, 5.47; N, 17.78.

MS (EI): 312 (M$^+$).

$^1$H-NMR (400 MHz, DMSO-d$_6$) δ (ppm): 1.41 (9H, s), 5.33 (1H, s), 7.21–7.33 (4H, m), 7.41 (1H, d, J=7.3 Hz), 8.88 (1H, brs), 12.20 (1H, brs).

Example 308

4-(2-Chlorophenyl)-5-cyano-3-cyclopropyl-4,7-dihydro-6-propyl-2H-pyrazolo[3,4-b]pyridine The title compound was prepared from methyl cyclopropanecarboxylate, methyl butyrate and 2-chlorobenzaldehyde in the same manner as in Example 302.

MP: 270° C.

Anal. Calcd. for: $C_{19}H_{19}ClN_4$: C, 67.35; H, 5.65; N, 16.54. Found: C, 67.34; H, 5.66; N, 16.62.

MS (EI): 338 ($M^+$).

$^1$H-NMR (400 MHz, DMSO-$d_6$) δ (ppm): 0.22–0.25 (1H, m), 0.41–0.44 (1H, m), 0.50–0.54 (1H, m), 0.62–0.66 (1H, m), 0.90 (3H, t, J=7.3 Hz), 1.25–1.29 (1H, m), 1.58–1.63 (2H, m), 2.31–2.36 (2H, m), 5.33 (1H, s), 7.18–7.23 (2H, m), 7.30 (1H, dd, J=7.3 Hz and 7.2 Hz), 7.38 (1H, d, J=7.3 Hz), 9.69 (1H, brs), 11.73 (1H, brs).

Example 309

4-(2-Chlorophenyl)-5-cyano-4,7-dihydro-3-ethyl-6-propyl-2H-pyrazolo[3,4-b]pyridine The title compound was prepared from methyl propionate, methyl butyrate and 2-chlorobenzaldehyde in the same manner as in Example 302.

MP: 269° C.

Anal. Calcd. for: $C_{18}H_{19}ClN_4$: C, 66.15; H, 5.86; N, 17.14. Found: C, 66.27; H, 5.86; N, 17.25.

MS (EI): 326 ($M^+$).

$^1$H-NMR (400 MHz, DMSO-$d_6$) δ (ppm): 0.72 (3H, t, J=7.3 Hz), 0.91 (3H, t, J=7.3 Hz), 1.59–1.64 (2H, m), 2.09–2.11 (2H, m), 2.31–2.40 (2H, m), 5.29 (1H, s), 7.20–7.24 (2H, m), 7.30 (1H, dd, J=7.3 Hz and 7.2 Hz), 7.38 (1H, d, J=7.3 Hz), 9.70 (1H, brs), 11.86 (1H, brs).

Example 310

3-t-Butyl-4-(2-chlorophenyl)-5-cyano-4,7-dihydro-6-propyl-2H-pyrazolo[3,4-b]pyridine The title compound was prepared from methyl pivalate, methyl butyrate and 2-chlorobenzaldehyde in the same manner as in Example 302.

MP: >270° C.

Anal. Calcd. for: $C_{20}H_{23}ClN_4$: C, 67.69; H, 6.53; N, 15.79. Found: C, 67.55; H, 6.56; N, 15.66.

MS (EI): 354 ($M^+$).

$^1$H-NMR (400 MHz, DMSO-$d_6$) δ (ppm): 0.84 (3H, t, J=7.3 Hz), 0.95 (9H, s), 1.53–1.59 (2H, m), 2.26–2.30 (2H, m), 5.39 (1H, s), 6.97 (1H, d, J=7.3 Hz), 7.20 (1H, dd, J=7.3 Hz and 7.2 Hz), 7.27 (1H, dd, J=7.3 Hz and 7.2 Hz), 7.38 (1H, d, J=7.3 Hz), 9.73 (1H, brs), 11.87 (1H, brs).

Example 311

4-(2-Chlorophenyl)-5-cyano-3-cyclohexyl-4,7-dihydro-6-propyl-2H-pyrazolo[3,4-b]pyridine The title compound was prepared from methyl cyclohexanecarboxylate, methyl butyrate and 2-chlorobenzaldehyde in the same manner as in Example 302.

MP: >270° C.

Anal. Calcd. for: $C_{22}H_{25}ClN_4$: C, 69.37; H, 6.62; N, 14.71. Found: C, 69.17; H, 6.62; N, 14.91.

MS (EI): 380 ($M^+$).

$^1$H-NMR (400 MHz, DMSO-$d_6$) δ (ppm): 0.89–1.17 (9H, m), 1.47–1.64 (6H, m), 2.06–2.08 (1H, m), 2.31–2.38 (2H, m), 5.30 (1H, s), 7.19–7.23 (2H, m), 7.29 (1H, dd, J=7.3 Hz and 7.2 Hz), 7.38 (1H, d, J=7.3 Hz), 9.71 (1H, brs), 11.83 (1H, brs).

Example 312

4-(2-Chlorophenyl)-5-cyano-6-cycloheptyl-4,7-dihydro-2H-pyrazolo[3,4-b]pyridine

The title compound was prepared from methyl cycloheptanecarboxylate, 2-chlorobenzaldehyde and 3-aminopyrazole in the same manner as in Example 94.

MP: 146° C.

MS (EI): 352 ($M^+$).

$^1$H-NMR (400 MHz, DMSO-$d_6$) δ (ppm): 1.42–1.98 (12H, m), 2.78–2.81 (1H, m), 5.33 (1H, s), 7.21–7.24 (3H, m), 7.32 (1H, dd, J=7.3 Hz and 7.2 Hz), 7.41 (1H, d, J=7.3 Hz), 9.61 (1H, brs), 12.18 (1H, brs).

Example 313

4-(2-Chlorophenyl)-5-cyano-6-cyclobutyl-4,7-dihydro-2H-pyrazolo[3,4-b]pyridine

The title compound was prepared from methyl cyclobutanecarboxylate, 2-chlorobenzaldehyde and 3-aminopyrazole in the same manner as in Example 94.

MP: 188° C.

Anal. Calcd. for: $C_{17}H_{15}ClN_4$: C, 65.70; H, 4.86; N, 18.03. Found: C, 65.51; H, 5.21; N, 18.27.

MS (EI): 310 ($M^+$).

$^1$H-NMR (400 MHz, DMSO-$d_6$) δ (ppm): 1.72–1.77 (1H, m), 1.93–1.97 (1H, m), 2.09–2.12 (2H, m), 2.38–2.43 (2H, m), 2.58–2.61 (1H, m), 5.33 (1H, s), 7.20–7.32 (4H, m), 7.41 (1H, d, J=7.3 Hz), 9.72 (1H, brs), 12.18 (1H, brs).

Example 314

4-(2-Chlorophenyl)-5-cyano-3-cyclopentyl-4,7-dihydro-6-propyl-2H-pyrazolo[3,4-b]pyridine The title compound was prepared from methyl cyclopentanecarboxylate, methyl butyrate and 2-chlorobenzaldehyde in the same manner as in Example 302.

MP: >270° C.

Anal. Calcd. for: $C_{12}H_{23}ClN_4$: C, 68.75; H, 6.32; N, 15.27. Found: C, 68.56; H, 6.36; N, 15.22.

MS (EI): 366 ($M^+$).

$^1$H-NMR (400 MHz, DMSO-$d_6$) δ (ppm): 0.89 (3H, t, J=7.3 Hz), 1.31–1.74 (10H, m), 2.30–2.37 (2H, m), 2.52–2.54 (1H, m), 5.30 (1H, s), 7.17–7.22 (2H, m), 7.28 (1H, dd, J=7.3 Hz and 7.2 Hz), 7.37 (1H, d, J=7.3 Hz), 9.71 (1H, brs), 11.86 (1H, brs).

Example 315

4-(2-Chlorophenyl)-5-cyano-4,7-dihydro-6-propyl-3-isopropyl-2H-pyrazolo[3,4-b]pyridine The title compound was prepared from methyl 2-methylpropionate, methyl butyrate and 2-chlorobenzaldehyde in the same manner as in Example 302.

MP: >270° C.

Anal. Calcd. for: $C_{19}H_{21}ClN_4$: C, 66.95; H, 6.21; N, 16.44. Found: C, 66.90; H, 6.27; N, 16.44.

MS (EI): 340 ($M^+$).

$^1$ H-NMR (400 MHz, DMSO-$d_6$) δ (ppm): 0.67 (3H, d, J=7.2 Hz), 0.90 (3H, t, J=7.3 Hz), 0.95 (3H, d, J=7.3 Hz), 1.57–1.63 (2H, m), 2.30–2.35 (2H, m), 5.30 (1H, s), 7.19–7.23 (2H, m), 7.29 (1H, dd, J=7.3 Hz and 7.2 Hz), 7.38 (1H, d, J=7.3 Hz), 9.71 (1H, brs), 11.88 (1H, brs).

Example 316

4-(2-Chlorophenyl)-5-cyano-6-cyclopentyl-4,7-dihydro-2H-pyrazolo[3,4-b]pyridine

The title compound was prepared from methyl cyclopentanecarboxylate, 2-chlorobenzaldehyde and 3-aminopyrazole in the same manner as in Example 94.

MP: 225° C.

Anal. Calcd. for: $C_{18}H_{17}ClN_4 \cdot 1/5H_2O$: C, 65.83; H, 5.34; N, 17.06. Found: C, 66.02; H, 5.51; N, 16.62.

MS (EI): 324 (M$^+$).

$^1$H-NMR (400 MHz, DMSO-d$_6$) δ (ppm): 1.56–1.60 (2H, m), 1.78–1.87 (6H, m), 3.06–3.10 (1H, m), 5.34 (1H, s), 7.22–7.26 (3H, m), 7.32 (1H, dd, J=7.3 Hz and 7.2 Hz), 7.42 (1H, d, J=7.3 Hz), 9.61 (1H, brs), 12.16 (1H, brs).

Example 317

4-(2-Bromo-3-cyanophenyl)-5-cyano-6-cyclopentyl-4,7-dihydro-2H-pyrazolo[3,4-b]pyridine The title compound was prepared from methyl cyclopentanecarboxylate, 2-bromo-3-cyanobenzaldehyde and 3-aminopyrazole in the same manner as in Example 94.

MP: 247° C.

MS (EI): 394 (M$^+$).

$^1$H-NMR (400 MHz, DMSO-d$_6$) δ (ppm): 1.52–1.58 (2H, m), 1.75–1.82 (6H, m), 3.01–3.06 (1H, m), 5.46 (1H, s), 7.33 (1H, s), 7.54–7.58 (2H, m), 7.84 (1H, d, J=7.3 Hz), 9.73 (1H, brs), 12.25 (1H, brs).

Example 318

4-(2,1,3-Benzoxadiazol-4-yl)-5-cyano-6-cyclopentyl-4,7-dihydro-2H-pyrazolo[3,4-b]pyridine The title compound was prepared from methyl cyclopentanecarboxylate, 2,1,3-benzoxadiazole-4-aldehyde and 3-aminopyrazole in the same manner as in Example 94.

MP: 193° C.

Anal. Calcd. for: $C_{18}H_{16}N_6O$: C, 65.05; H, 4.85; N, 25.29. Found: C, 64.72; H, 4.98; N, 24.86.

MS (EI): 332 (M$^+$).

$^1$H-NMR (400 MHz, DMSO-d$_6$) δ (ppm): 1.55–1.58 (2H, m), 1.80–1.86 (6H, m), 3.06–3.09 (1H, m), 5.39 (1H, s), 7.26 (1H, s), 7.38 (1H, d, J=6.6 Hz), 7.60 (1H, dd, J=9.0 Hz and 6.6 Hz), 7.91 (1H, d, J=9.0 Hz), 9.72 (1H, brs), 12.15 (1H, brs).

Example 319

4-(2-Bromo-3-cyanophenyl)-6-t-butyl-5-cyano-4,7-dihydro-2H-pyrazolo[3,4-b]pyridine The title compound was prepared from methyl pivalate, 2-bromo-3-cyanobenzaldehyde and 3-aminopyrazole in the same manner as in Example 94.

MP: 251° C.

Anal. Calcd. for: $C_{18}H_{16}BrN_5 \cdot 1/2H_2O$: C, 55.25; H, 4.38; N, 17.90. Found: C, 55.55; H, 4.30; N, 18.14.

MS (EI): 382 (M$^+$).

$^1$H-NMR (400 MHz, DMSO-d$_6$) δ (ppm): 1.41 (9H, s), 5.46 (1H, s), 7.33 (1H, s), 7.54–7.60 (2H, m), 7.82 (1H, d, J=7.3 Hz), 9.00 (1H, brs), 12.29 (1H, brs)

Example 320

4-(2,1,3-Benzoxadiazol-4-yl)-6-t-butyl-5-cyano-4,7-dihydro-2H-pyrazolo[3,4-b]pyridine The title compound was prepared from methyl pivalate, 2,1,3-benzoxadiazole-4-aldehyde and 3-aminopyrazole in the same manner as in Example 94.

MP: 204° C.

Anal. Calcd. for: $C_{17}H_{16}N_6O \cdot 1/2H_2O$: C, 63.03; H, 5.10; N, 25.94. Found: C, 63.08; H, 5.08; N, 26.00.

MS (EI): 320 (M$^+$).

$^1$H-NMR (400 MHz, DMSO-d$_6$) δ (ppm): 1.40 (9H, s), 5.37 (1H, s), 7.26 (1H, s), 7.38 (1H, d, J=6.6 Hz), 7.59 (1H, dd, J=9.0 Hz and 6.6 Hz), 7.91 (1H, d, J=9.0 Hz), 9.02 (1H, brs), 12.20 (1H, brs).

Example 321

4-(2-Bromo-3-cyanophenyl)-5-cyano-6-cyclobutyl-4,7-dihydro-2H-pyrazolo[3,4-b]pyridine The title compound was prepared from methyl cyclobutanecarboxylate, 2-bromo-3-cyanobenzaldehyde and 3-aminopyrazole in the same manner as in Example 94.

MP: 278° C.

Anal. Calcd. for: $C_{18}H_{14}BrN_5$: C, 56.86; H, 3.71; N, 18.42. Found: C, 56.57; H, 3.79; N, 18.48.

MS (EI): 380 (M$^+$).

$^1$H-NMR (400 MHz, DMSO-d$_6$) δ (ppm): 1.71 (1H, m), 1.88–1.95 (1H, m), 5 2.06–2.13 (2H, m), 2.38–2.47 (2H, m), 3.56–3.60 (1H, m), 5.45 (1H, s), 7.33 (1H, s), 7.57–7.59 (2H, m), 7.82 (1H, d, J=7.3 Hz), 9.84 (1H, brs), 12.27 (1H, brs).

Example 322

4-(2,1,3-Benzoxadiazol-4-yl)-5-cyano-6-cyclobutyl-4,7-dihydro-2H-pyrazolo[3,4-b]pyridine The title compound was prepared from methyl cyclobutanecarboxylate, 2,1,3-benzoxadiazole-4-aldehyde and 3-aminopyrazole in the same manner as in Example 94.

MP: 194° C.

Anal. Calcd. for: $C_{17}H_{14}N_6O$: C, 64.14; H, 4.43; N, 26.40. Found: C, 64.08; H, 4.51; N, 26.26.

MS (EI): 318 (M$^+$).

$^1$ H-NMR (400 MHz, DMSO-d$_6$) δ (ppm): 1.72–1.76 (1 H, m), 1.90–1.97 (1H, m), 2.10–2.14 (2H, m), 2.39–2.46 (2H, m), 3.56–3.60 (1H, m), 5.38 (1H, s), 7.26 (1H, s), 7.37 (1H, d, J=6.6 Hz), 7.58 (1H, dd, J=9.0 Hz and 6.6 Hz), 7.91 (1H, d, J=9.0 Hz), 9.82 (1H, brs), 12.17 (1H, brs).

Example 323

4-(2,1,3-Benzoxadiazol-4-yl)-5-cyano-6-cyclohexyl-4,7-dihydro-2H-pyrazolo[3,4-b]pyridine The title compound was prepared from methyl cyclohexanecarboxylate, 2,1,3-benzoxadiazole-4-aldehyde and 3-aminopyrazole in the same manner as in Example 94.

MP: 210° C.

Anal. Calcd. for: $C_{19}H_{18}N_6O$: C, 65.88; H, 5.24; N, 24.26. Found: C, 65.88; H, 5.25; N, 24.19.

MS (EI): 346 (M$^+$).

$^1$ H-NMR (400 MHz, DMSO-d$_6$) δ (ppm): 1.21–1.26 (3H, m), 1.62–1.80 (7H, m), 2.66–2.70 (1H, m), 5.38 (1H, s), 7.25 (1H, s), 7.38 (1H, d, J=6.6 Hz), 7.59 (1H, dd, J=9.0 Hz and 6.6 Hz), 7.91 (1H, d, J=9.0 Hz), 9.72 (1H, brs), 12.15 (1H, brs).

Example 324

4-(2,1,3-Benzoxadiazol-4-yl)-5-cyano-6-cycloheptyl-4,7-dihydro-2H-pyrazolo[3,4-b]pyridine The title compound was prepared from methyl cycloheptanecarboxylate, 2,1,3-benzoxadiazole-4-aldehyde and 3-aminopyrazole in the same manner as in Example 94.

MP: 228° C.

Anal. Calcd. for: $C_{20}H_{20}N_6O$: C, 66.65; H, 5.59; N, 23.32. Found: C, 66.45; H, 5.70; N, 22.97.

MS (EI): 360 (M$^+$).

$^1$H-NMR (400 MHz, DMSO-d$_6$) δ (ppm): 1.38–1.98 (12H, m), 2.76–2.79 (1H, m), 5.37 (1H, s), 7.24 (1H, s), 7.38 (1H, d, J=6.6 Hz), 7.58 (1H, dd, J=9.0 Hz and 6.6 Hz), 7.91 (1H, d,=9.0 Hz), 9.72 (1H, brs), 12.13 (1H, brs).

Example 325

4-(2-Bromo-3-cyanophenyl)-5-cyano-6-cyclohexyl-4,7-dihydro-2H-pyrazolo[3,4-b]pyridine The title compound was prepared from methyl cyclohexanecarboxylate, 2-bromo-3-cyanobenzaldehyde and 3-aminopyrazole in the same manner as in Example 94.

MP: 193° C.

Anal. Calcd. for: $C_{20}H_{18}BrN_5 \cdot 1/2H_2O$: C, 57.56; H, 4.59; N, 16.78. Found: C, 57.25; H, 4.37; N, 16.56.

MS (EI): 408 (M$^+$).

$^1$H-NMR (400 MHz, DMSO-d$_6$) δ (ppm): 1.21–1.26 (3H, m), 1.66–1.80 (7H, m), 2.66–2.69 (1H, m), 5.45 (1H, s), 7.33 (1H, s), 7.55–7.60 (2H, m), 7.82 (1H, d, J=7.3 Hz), 9.73 (1H, brs), 12.24 (1H, brs).

Example 326

4-(2-Bromo-3-cyanophenyl)-5-cyano-6-cycloheptyl-4,7-dihydro-2H-pyrazolo[3,4-b]pyridine The title compound was prepared from methyl cycloheptanecarboxylate, 2-bromo-3-cyanobenzaldehyde and 3-aminopyrazole in the same manner as in Example 94.

MP: 252° C.

Anal. Calcd. for: $C_{21}H_{20}BrN_5 \cdot 1/2H_2O$: C, 58.48; H, 4.91; N, 16.24. Found: C, 58.53; H, 4.73; N, 16.19.

MS (EI): 422 (M$^+$).

$^1$H-NMR (400 MHz, DMSO-d$_6$) δ (ppm): 1.44–1.58 (12H, m), 2.76–2.79 (1H, m), 5.44 (1H, s), 7.31 (1H, s), 7.54–7.60 (2H, m), 7.83 (1H, d, J=7.3 Hz), 9.73 (1H, brs), 12.23 (1H, brs).

Example 327

5-Cyano-4,7-dihydro-6-propyl-4-(pyridin-3-yl)-2H-pyrazolo[3,4-b]pyridine

The title compound was prepared from methyl butyrate, pyridine-3-aldehyde and 3-aminopyrazole in the same manner as in Example 94.

MP: 201° C.

Anal. Calcd. for: $C_{15}H_{15}N_5$: C, 67.90; H, 5.70; N, 26.40. Found: C, 67.42; H, 5.74; N, 26.72.

MS (EI): 265 (M$^+$).

$^1$H-NMR (400 MHz, DMSO-d$_6$) δ (ppm): 0.92 (3H, t, J=7.3 Hz), 1.62–1.67 (2H, m), 2.36–2.39 (2H, m), 4.98 (1H, s), 7.27 (1H, s), 7.35 (1H, dd, J=7.3 Hz and 2.9 Hz), 7.54 (1H, d, J=7.3 Hz), 8.41–8.44 (2H, m), 9.81 (1H, brs), 12.18 (1H, brs).

Example 328

3-t-Butoxycarbonyloxy-4-(2-chlorophenyl)-5-cyano-4,7-dihydro-6-propyl-1 H-pyrazolo[3,4-b]pyridine To a solution of 4-(2-chlorophenyl)-5-cyano-4,7-dihydro-3-hydroxy-6-propyl-2H-pyrazolo[3,4-b]pyridine (12.5 g) in THF (400 mL) was added triethylamine (4.5 g), dimethylaminopyridine (0.5 g) and di-t-butylcarbonate (9.6 g) and the mixture was stirred for 3 hours. The mixture was extracted with ethyl acetate and the solvent was evaporated under reduced pressure. The residue was recrystallized from ethyl acetate to give the title compound (12 g) as colorless crystals.

MP: 182° C.

Anal. Calcd. for: $C_{21}H_{23}ClN_4O_3$: C, 60.79; H, 5.59; N, 13.50. Found: C, 60.60; H, 5.50; N, 13.44.

MS (EI): 414 (M$^+$).

$^1$H-NMR (400 MHz, DMSO-d$_6$) δ (ppm): 0.91 (3H, t, J=7.3 Hz), 1.54 (9H, s), 2.49–2.51 (2H, m), 5.18 (1H, s), 7.23–7.27 (2H, m), 7.32 (1H, dd, J=7.3 Hz and 7.2 Hz), 7.38 (1H, d, J=7.3 Hz), 9.15 (1H, brs), 10.99 (1H, brs).

Example 329

4-(2,1,3-Benzoxadiazol-4-yl)-5-cyano-6-(2,2-dimethoxyethyl)-4,7-dihydro-2H-pyrazolo[3,4-b]pyridine The title compound was prepared from methyl 3,3-dimethoxypropionate, 2,1,3-benzoxadiazole-4-aldehyde and 3-aminopyrazole in the same manner as in Example 94.

MP: 115° C.

Anal. Calcd. for: $C_{17}H_{16}N_6O_3 \cdot 1.0H_2O$: C, 55.13; H, 4.90; N, 22.69. Found: C, 55.30; H, 4.51; N, 22.99.

MS (EI): 352 (M$^+$).

$^1$H-NMR (400 MHz, DMSO-d$_6$) δ (ppm): 2.71 (2.75 (2H, m), 3.28 (3H, s), 3.31 (3H, s), 4.74 (1H, t, J=5.9 Hz), 5.43 (1H, s), 7.28 (1H, s), 7.40 (1H, d, J=6.6 Hz), 7.61 (1H, dd, J=9.0 Hz and 6.6 Hz), 7.92 (1H, d, J=9.0 Hz), 9.99 (1H, brs), 12.18 (1H, brs).

Example 330

4-(2-Chlorophenyl)-5-cyano-4,7-dihydro-3-(2,2-dimethoxyethyl)-6-propyl-2H-pyrazolo[3,4-b] pyridine The title compound was prepared from methyl 3,3-dimethoxypropionate, methyl butyrate and 2-chlorobenzaldehyde in the same manner as in Example 302.

MP: 180° C.

Anal. Calcd. for: $C_{20}H_{23}ClN_4O_2$: C, 62.09; H, 5.99; N, 14.48. Found: C, 62.35; H, 6.02; N, 14.50.

MS (EI): 386 (M$^+$).

$^1$H-NMR (400 MHz, DMSO-d$_6$) δ (ppm): 0.91 (3H, t, J=7.3 Hz), 1.59–1.64 (2H, m), 2.28–2.35 (4H, m), 3.00 (3H, s), 3.02 (3H, s), 3.81 (1H, t, J=7.3 Hz), 5.31 (1H, s), 7.24–7.31 (3H, m), 7.40 (1H, d, J=7.3 Hz), 9.75 (1H, brs), 11.92 (1H, brs).

Example 331

4-(2,1-Benzoisoxazol-4-yl)-5-cyano-4,7-dihydro-6-propyl-2H-pyrazolo[3,4-b]pyridine The title compound was prepared from methyl butyrate, 2,1-benzoisoxazole-4-aldehyde and 3-aminopyrazole in the same manner as in Example 94.

MP: 239° C.

MS (EI): 305 (M$^+$).

$^1$H-NMR (400 MHz, DMSO-d$_6$) δ (ppm): 0.91 (3H, t, J=7.3 Hz), 1.64–1.67 (2H, m), 2.40–2.43 (2H, m), 5.23 (1H, s), 6.91 (1H, d, J=6.6 Hz), 7.28 (1H, s), 7.36 (1H, dd, J=9.3 Hz and 6.6 Hz), 7.52 (1H, d, J=9.3 Hz), 9.37 (1H, s), 9.96 (1H, brs), 12.21 (1H, brs).

Example 332

4-(2,1-Benzoisoxazol-4-yl)-5-cyano-4,7-dihydro-6-isopropyl-2H-pyrazolo[3,4-b]pyridine The title compound was prepared from methyl isobutyrate, 2,1-benzoisoxazole-4-aldehyde and 3-aminopyrazole in the same manner as in Example 94.

MP: 245° C.

MS (EI): 305 ($M^+$).

$^1$H-NMR (400 MHz, DMSO-$d_6$) δ (ppm): 1.23–1.26 (6H, m), 3.03 (1H, t, J=5.9 Hz), 5.21 (1H, s), 6.92 (1H, d, J=6.6 Hz), 7.30 (1H, s), 7.37 (1H, dd, J=9.3 Hz and 6.6 Hz), 7.53 (1H, d, J=9.3 Hz), 9.34 (1H, s), 9.78 (1H, brs), 12.23 (1H, brs).

Example 333

4-(2,1-Benzoisoxazol-4-yl)-5-cyano-6-cyclopropyl-4,7-dihydro-2H-pyrazolo[3,4-b]pyridine The title compound was prepared from methyl cyclopropanecarboxylate, 2,1-benzoisoxazole-4-aldehyde and 3-aminopyrazole in the same manner as in Example 94.

MP: 248° C.

MS (EI): 303 ($M^+$).

$^1$H-NMR (400 MHz, DMSO-$d_6$) δ (ppm): 0.89–0.91 (2H, m), 1.05–1.08 (2H, m), 1.94–1.98 (2H, m), 5.20 (1H, s), 6.91 (1H, d, J=6.6 Hz), 7.28 (1H, s), 7.36 (1H, dd, J=9.3 Hz and 6.6 Hz), 7.52 (1H, d, J=9.3 Hz), 9.26 (1H, s), 9.36 (1H, brs), 12.22 (1H, brs).

Example 334

4-(2,1,3-Benzoxadiazol-4-yl)-5-cyano-6-(1-t-butoxycarbonylindol-3-yl)-4,7-dihydro-2H-pyrazolo[3,4-b]pyridine The title compound was prepared from methyl 1-t-butoxycarbonylindole-3-carboxylate, 2,1,3-benzoxadiazole-4-aldehyde and 3-aminopyrazole in the same manner as in Example 95.

MP: 202° C.

MS (EI): 479 ($M^+$).

$^1$H-NMR (400 MHz, DMSO-$d_6$) δ (ppm): 1.65 (9H, s), 5.60 (1H, s), 7.27–7.41 (3H, m), 7.54–7.58 (2H, m), 7.64 (1H, dd, J=7.3 Hz and 7.2 Hz), 7.97 (1H, d, J=7.3 Hz), 8.03 (1H, s), 8.10 (1H, d, J=7.3 Hz), 10.23 (1H, brs), 12.26 (1H, brs).

Example 335

4-(2,1,3-Benzoxadiazol-4-yl)-5-cyano-4,7-dihydro-6-(indol-3-yl)-2H-pyrazolo[3,4-b]pyridine (1-t-Butoxycarbonylindol-3-yl)-4,7-dihydro-2H-pyrazolo[3,4-b]pyridine (0.6 g) was added to trifluoroacetic acid (15 mL) under ice-cooling and the mixture was stirred for 3 hours. The solvent was evaporated under reduced pressure, and ethyl acetate and a saturated aqueous sodium hydrogencarbonate solution were added to neutralize the mixture. The mixture was extracted with ethyl acetate and the solvent was evaporated under reduced pressure. The residue was recrystallized from ethyl acetate to give the title compound (0.4 g) as colorless crystals.

MP: 238° C.

Anal. Calcd. for: $C_{21}H_{13}N_7O_3/5H_2O$: C, 64.64; H, 3.67; N, 25.13. Found: C, 64.77; H, 4.05; N, 25.59.

MS (EI): 379 ($M^+$).

$^1$H-NMR (400 MHz, DMSO-$d_6$) δ (ppm): 5.56 (1H, s), 7.08 (1H, dd, J=7.3 Hz and 7.2 Hz), 7.15 (1H, dd, J=7.3 Hz and 7.2 Hz), 7.44 (1H, s), 7.44–7.54 (3H, m), 7.65 (1H, dd, J=7.3 Hz and 7.2 Hz), 7.76 (1H, s), 7.95 (1H, d, J=7.3 Hz), 9.98 (1H, brs), 11.63 (1H, brs), 12.20 (1H, brs).

Example 336

4-(2-Chlorophenyl)-5-cyano-4,7-dihydro-3-dimethoxymethyl-6-propyl-2H-pyrazolo[3,4-b]pyridine The title compound was prepared from methyl dimethylacetate, methyl butyrate and 2-chlorobenzaldehyde in the same manner as in Example 302.

MP: 212° C.

Anal. Calcd. for: $C_{19}H_{21}ClN_4O_2$: C, 61.21; H, 5.68; N, 15.03. Found: C, 61.25; H, 5.69; N, 15.17.

MS (EI): 372 ($M^+$).

$^1$H-NMR (400 MHz, DMSO-$d_6$) δ (ppm): 0.88 (3H, t, J=7.3 Hz), 1.57–1.63 (2H, m), 2.28–2.35 (2H, m), 2.93 (6H, s), 4.93 (1H, s), 5.30 (1H, s), 7.10 (1H, d, J=7.3 Hz), 7.19 (1H, dd, J=7.3 Hz and 7.2 Hz), 7.25 (1H, dd, J=7.3 Hz and 7.2 Hz), 7.35 (1H, d, J=7.3 Hz), 9.80 (1H, brs), 12.29 (1H, brs).

Example 337

5-Cyano-4,7-dihydro-6-propyl-4-(pyridin-4-yl)-2H-pyrazolo[3,4-b]pyridine

The title compound was prepared from methyl butyrate, pyridine-4-aldehyde and 3-aminopyrazole in the same manner as in Example 94.

MP: 224° C.

Anal. Calcd. for: $C_{15}H_{15}N_5$: C, 67.90; H, 5.70; N, 26.40. Found: C, 67.90; H, 5.79; N, 26.31.

MS (EI): 265 ($M^+$).

$^1$H-NMR (400 MHz, DMSO-$d_6$) δ (ppm): 0.92 (3H, t, J=7.3 Hz), 1.62–1.67 (2H, m), 2.35–2.43 (2H, m), 4.95 (1H, s), 7.20 (2H, dd, J=4.6 Hz and 1.5 Hz), 7.29 (1H, s), 8.50 (2H, dd, J=4.6 Hz and 1.5 Hz), 9.84 (1H, brs), 12.20 (1H, brs).

Example 338

5-Cyano-4,7-dihydro-4-(3-methyl-2-nitrophenyl)-6-propyl-2H-pyrazolo[3,4-b]pyridine The title compound was prepared from methyl butyrate, 3-methyl-2-nitrobenzaldehyde and 3-aminopyrazole in the same manner as in Example 94.

MP: 250° C.

Anal. Calcd. for: $C_{17}H_{17}N_5O_2$: C, 63.15; H, 5.30; N, 21.66. Found: C, 62.89; H, 5.51; N, 22.11.

MS (EI): 323 ($M^+$).

$^1$H-NMR (400 MHz, DMSO-$d_6$) δ (ppm): 0.94 (3H, t, J=7.3 Hz), 1.63–1.68 (2H, m), 2.26 (3H, s), 2.36–2.42 (2H, m), 4.83 (1H, s), 7.17 (1H, s), 7.20 (1H, d, J=7.3 H), 7.32 (1H, d, J=7.3 Hz), 7.48 (1H, dd, J=7.3 Hz and 7.2 Hz), 9.91 (1H, brs), 12.22 (1H, brs).

Example 339

5-Cyano-4,7-dihydro-4-(3-methyl-2-nitrophenyl)-6-isopropyl-2H-pyrazolo[3,4-b]pyridine The title compound was prepared from methyl isobutyrate, 3-methyl-2-nitrobenzaldehyde and 3-aminopyrazole in the same manner as in Example 94.

MP: 261° C.

Anal. Calcd. for: $C_{17}H_{17}N_5O_2 \cdot 1/2H_2O$: C, 61.43; H, 5.46; N, 21.07. Found: C, 61.82; H, 5.32; N, 21.31.

MS (EI): 323 (M$^+$).

$^1$H-NMR (400 MHz, DMSO-d$_6$) δ (ppm): 1.21 (3H, d, J=7.2 Hz), 1.26 (3H, d, J=7.2 Hz), 2.25 (3H, s), 3.01 (1H, t, J=7.2 Hz), 4.84 (1H, s), 7.17 (1H, s), 7.22 (1H, d, J=7.3 Hz), 7.32 (1H, d, J=7.3 Hz), 7.48 (1H, dd, J=7.3 Hz and 7.2 Hz), 9.71 (1H, brs), 12.24 (1H, brs).

Example 340

5-Cyano-6-cyclopropyl-4,7-dihydro-4-(3-methyl-2-nitrophenyl)-2H-pyrazolo[3,4-b]pyridine The title compound was prepared from methyl cyclopropanecarboxylate, 3-methyl-2-nitrobenzaldehyde and 3-aminopyrazole in the same manner as in Example 94.

MP: 265° C.

Anal. Calcd. for: $C_{17}H_{15}N_5O_2$: C, 63.54; H, 4.71; N, 21.79. Found: C, 63.44; H, 4.85; N, 22.04.

MS (EI): 321 (M$^+$).

$^1$H-NMR (400 MHz, DMSO-d$_6$) δ (ppm): 0.90–1.07 (4H, m), 1.96–1.99 (1H, m), 2.26 (3H, s), 4.81 (1H, s), 7.17 (1H, s), 7.20 (1H, d, J=7.3 Hz), 7.32 (1H, d, J=7.3 Hz), 7.48 (1H, dd, J=7.3 Hz and 7.2 Hz), 9.23 (1H, brs), 12.23 (1H, brs).

Example 341

Ethyl 4-(2,1,3-benzoxazol-4-yl)-4,7-dihydro-6-(1-methylethyl)-2H-pyrazolo[3,4-b]pyridine-5-carboxylate 1/2 ethyl acetate The title compound was prepared from 2,1,3-benzoxazole-4-aldehyde, 3-aminopyrazole and ethyl isobutyrylacetate in the same manner as in Example 275.

MP: 190–193° C. (decomposition).

$^1$H-NMR (400 MHz, DMSO-d$_6$) δ (ppm): 0.73 (3H, t, J=7.1 Hz), 1.19 (3H, d, J=7.1 Hz), 1.29 (3H, d, J=7.1 Hz), 3.77 (2H, m), 4.37 (1H, m), 5.69 (1H, s), 7.12 (1H, d, J=6.6 Hz), 7.22 (1H, s), 7.51 (1H, dd, J=6.6, 9.0 Hz), 7.78 (1H, d, J=8.8 Hz), 9.31 (1H, brs), 12.02 (1H, brs).

Example 342

Ethyl 4-(2-nitrophenyl)-4,7-dihydro-6-(1-methylethyl)-2H-pyrazolo[3,4-b]pyridine-5-carboxylate The title compound was prepared from 2-nitrobenzaldehyde, 3-aminopyrazole and ethyl isobutyrylacetate in the same manner as in Example 275.

MP: 205–206° C.

$^1$H-NMR (400 MHz, DMSO-d$_6$) δ (ppm): 0.78 (3H, t, J=6.8 Hz), 1.15 (3H, d, J=7.1 Hz), 1.26 (3H, d, J=7.1 Hz), 3.71 (2H, m), 4.33 (1H, m), 5.44 (1H, s), 7.29–7.34 (3H, m), 7.58 (1H, m), 7.78 (1H, d, J=8.0 Hz), 9.33 (1H, brs), 12.11 (1H, brs).

Example 343

Ethyl 4-(2-methoxyphenyl)-4,7-dihydro-6-(1-methylethyl)-2H-pyrazolo[3,4-b]pyridine-5-carboxylate 1/2 ethyl acetate The title compound was prepared from 2-methoxybenzaldehyde, 3-aminopyrazole and ethyl isobutyrylacetate in the same manner as in Example 275.

MP: 179–180° C.

$^1$H-NMR (400 MHz, DMSO-d$_6$) δ (ppm): 0.81 (3H, t, J=7.1 Hz), 1.17 (3H, d, J=7.1 Hz), 1.27 (3H, d, J=7.1 Hz), 3.76 (2H, m), 3.85 (3H, s), 4.31 (1H, m), 5.46 (1H, s), 6.77 (1H, m), 6.89 (1H, d, J=8.0 Hz), 6.94 (1H, d, J=7.6 Hz), 7.04 (1H, m), 7.14 (1H, s), 8.98 (1H, brs), 11.86 (1H, brs)

Example 344

Ethyl 4-(2-bromophenyl)-4,7-dihydro-6-cyclopropyl-2H-pyrazolo[3,4-b]pyridine-5-carboxylate The title compound was prepared from cyclopropanecarbonyl chloride, 2-bromobenzaldehyde and 3-aminopyrazole in the same manner as in Example 277.

MP: 168–170° C.

$^1$H-NMR (400 MHz, DMSO-d$_6$) δ (ppm): 0.86 (3H, t, J=7.1 Hz), 0.87–0.90 (2H, m), 1.10–1.14 (2H, m), 3.16 (1H, m), 3.78 (2H, m), 5.57 (1H, s), 7.01 (1H, dd, J=5.8, 7.6 Hz), 7.09 (1H, d, J=7.8 Hz), 7.24 (1H, m), 7.29 (1H, s), 7.51 (1H, d, J=6.8 Hz), 8.65 (1H, brs), 12.01 (1H, brs).

Example 345

Ethyl 4-(2-bromo-3-cyanophenyl)-4,7-dihydro-6-cyclopropyl-2H-pyrazolo[3,4-b]pyridine-5-carboxylate The title compound was prepared from cyclopropanecarbonyl chloride, 2-bromo-3-cyanobenzaldehyde and 3-aminopyrazole in the same manner as in Example 277.

MP: 168–170° C.

$^1$H-NMR (400 MHz, DMSO-d$_6$) δ (ppm): 0.86 (3H, t, J=7.1 Hz), 0.88–1.00 (2H, m), 1.10–1.18 (2H, m), 3.14 (1H, m), 3.80 (2H, m), 5.64 (1H, s), 7.33 (1H, s), 7.34–7.49 (2H, m), 7.68 (1H, m), 8.77 (1H, brs), 12.10 (1H, brs).

Example 346

4-(2-Chlorophenyl)-5-cyano-7-methyl-6-propyl-4,7-dihydro-2H-pyrazolo[3,4-b]pyridine A solution of 3-aminopyrazole (3.0 g), di-t-butyl dicarbonate (17.3 g) and dimethylaminopyridine (1.3 g) in tetrahydrofuran (360 ml) was stirred at room temperature. The reaction mixture was concentrated under reduced pressure. The obtained residue was purified by silica gel column chromatography (eluent:hexane-ethyl acetate (10:1)) to give a mixture (7.9 g) of 1-(t-butoxycarbonyl)-3-(t-butoxycarbonylamino)pyrazole and 2-(t-butoxycarbonyl)-3-(t-butoxycarbonylamino)pyrazole as a white amorphous solid. To a suspension of the obtained white amorphous solid (7.9 g) and sodium hydride (1.1 g) in DMF (80 ml) was added methyl iodide (4.0 g) under ice-cooling and the mixture was stirred at room temperature for 1 hour. To the reaction mixture was added water under ice-cooling and the resulting mixture was extracted with ethyl acetate. The extract was washed with a saturated aqueous sodium chloride solution, dried over anhydrous magnesium sulfate, and concentrated under reduced pressure. The obtained residue was purified by silica gel column chromatography (eluent:hexane-ethyl acetate (10:1)) to give a white solid (5.3 g). The obtained white solid (5.3 g) was dissolved in methylene chloride (50 ml), and trifluoroacetic acid (7 ml) was added. The resulting mixture was stirred at room temperature for 20 hours. The reaction mixture was concentrated under reduced pressure and the obtained residue was purified by silica gel column chromatography (eluent:chloroform-methanol (10:1)) to give 3-methylaminopyrazole (1.54 g) as a colorless transparent oil. Subsequently, the title compound was prepared from methyl butyrate, 2-chlorobenzaldehyde and 3-methylaminopyrazole in the same manner as in Example 94.

MP: 170–171° C.

Anal. Calcd. for: $C_{17}H_{17}N_4Cl$: C, 65.28; H, 5.48; N, 17.91. Found: C, 65.14; H, 5.52; N, 17.72.

MS (EI): 312 (M$^+$).

$^1$H-NMR (400 MHz, DMSO-d$_6$) δ (ppm): 1.00 (3H, t, J=7.3 Hz), 1.68 (2H, m), 2.62 (2H, m), 3.36 (3H, s), 5.36 (1H, s), 7.22–7.26 (2H, m), 7.30–7.32 (2H, m), 7.42 (1H, d, J=8.1 Hz), 12.31 (1H, brs).

Example 347

4-(2,1,3-Benzoxazol-4-yl)-5-cyano-7-methyl-6-propyl-4,7-dihydro-2H-pyrazolo[3,4-b]pyridine The title compound was prepared from methyl butyrate, 2,1,3-benzoxazole-4-aldehyde and 3-methylaminopyrazole in the same manner as in Example 346.

MP: 198–200° C.

Anal. Calcd. for: $C_{17}H_{16}N_6O$: C, 63.74; H, 5.03; N, 26.23. Found: C, 63.78; H, 5.12; N, 26.47.

MS (EI): 320 (M$^+$).

$^1$H-NMR (400 MHz, DMSO-d$_6$) δ (ppm): 0.97 (3H, t, J=7.4 Hz), 1.61 (2H, m), 2.63 (2H, m), 3.41 (3H, s), 5.40 (1H, s), 7.32 (1H, s), 7.40 (1H, d, J=6.6 Hz), 7.59 (1H, dd, J=6.5, 6.6 Hz), 7.92 (1H, d, J=9.3 Hz), 12.30 (1H, brs).

Example 348

4-(2-Bromo-3-cyanophenyl)-5-cyano-7-methyl-6-propyl-4,7-dihydro-2H-pyrazolo[3,4-b]pyridine The title compound was prepared from methyl butyrate, 2-bromo-3-cyanobenzaldehyde and 3-methylaminopyrazole in the same manner as in Example 346.

MP: 218–220° C.

Anal. Calcd. for: $C_{18}H_{16}N_5Br$: C, 56.56; H, 4.22; N, 18.32. Found: C, 56.60; H, 4.41; N, 18.18.

MS (EI): 382 (M$^+$).

$^1$H-NMR (400 MHz, DMSO-d$_6$) δ (ppm): 1.00 (3H, t, J=7.3 Hz), 1.63 (2H, m), 2.62 (2H, m), 3.37 (3H, s), 5.47 (1H, s), 7.39 (1H, s), 7.56–7.58 (2H, m), 7.83 (1H, m), 12.41 (1H, brs).

Example 349

4-(2-Chlorophenyl)-5-cyano-4,7-dihydro-6-methyl-2H-pyrazolo[3,4-b]pyridine

The title compound was prepared from ethyl acetate, 2-chlorobenzaldehyde and 3-aminopyrazole in the same manner as in Example 94.

$^1$H-NMR (400 MHz, DMSO-d$_6$) δ (ppm): 2.14 (3H, s), 5.35 (1H, s), 7.21–7.33 (4H, m), 7.42 (1H, d, J=8.1 Hz), 9.87 (1H, brs), 12.15 (1H, brs).

Example 350

4-(2-Chlorophenyl)-5-cyano-4,7-dihydro-6-(morpholin-4-yl)methyl-2H-pyrazolo[3,4-b]pyridine dihydrochloride A solution of 4-(2-chlorophenyl)-5-cyano-4,7-dihydro-6-methyl-2H-pyrazolo[3,4-b]pyridine (22.9 g), di-t-butyl dicarbonate (19.4 g) and dimethylaminopyridine (0.5 g) in tetrahydrofuran (200 ml) was stirred at room temperature for 30 minutes. The reaction mixture was ice-cooled and the precipitated crystals were collected by filtration to give 2-(t-butoxycarbonyl)-4-(2-chlorophenyl)-5-cyano-4,7-dihydro-6-methyl-2H-pyrazolo[3,4-b]pyridine (21.8 g) as white crystals. 2-(t-Butoxycarbonyl)-4-(2-chlorophenyl)-5-cyano-4,7-dihydro-6-methyl-2H-pyrazolo[3,4-b]pyridine (5.0 g), N-bromosuccinimide (2.5 g) and azobisisobutyronitrile (66 mg) were suspended in benzene (50 ml) and the suspension was stirred for 1 hour. The reaction mixture was concentrated under reduced pressure, and the obtained residue was purified by silica gel column chromatography (eluent:hexane-ethyl acetate (2:1)) and crystallized from ethyl acetate to give 6-bromomethyl-2-(t-butoxycarbonyl)-4-(2-chlorophenyl)-5-cyano-4,7-dihydro-2H-pyrazolo[3,4-b]pyridine as white crystals. To a suspension of sodium hydride (32 mg) in DMF (10 ml) was added morpholine (70 μl) and the mixture was stirred at room temperature for 30 minutes. To the reaction mixture was added 6-bromomethyl-2-(t-butoxycarbonyl)-4-(2-chlorophenyl)-5-cyano-4,7-dihydro-2H-pyrazolo[3,4-b]pyridine (0.36 g) and the mixture was stirred under ice-cooling for 1 hour. To the reaction mixture was added water, and the precipitated crystals were collected by filtration and washed with hexane to give 2-(t-butoxycarbonyl)-4-(2-chlorophenyl)-5-cyano-4,7-dihydro-6-(morpholin-4-yl)methyl-2H-pyrazolo[3,4-b]pyridine (450 mg) as white crystals. A solution of 2-(t-butoxycarbonyl)-4-(2-chlorophenyl)-5-cyano-4,7-dihydro-6-(morpholin-4-yl)methyl-2H-pyrazolo[3,4-b]pyridine (440 mg) in trifluoroacetic acid (5 ml) was stirred at room temperature for 30 minutes. The reaction mixture was concentrated under reduced pressure and 4M hydrochloric acid-dioxane solution was added. The precipitated crystals were collected by filtration and washed with ethyl acetate to give the title compound (250 mg) as pale-yellow crystals.

MP: 210–214° C. (decomposition).

$^1$H-NMR (400 MHz, DMSO-d$_6$) δ (ppm): 3.20–3.40 (3H, m), 3.84–4.00 (3H, m), 4.17–4.40 (4H, m), 5.49 (1H, s), 7.26–7.37 (4H, s), 7.45 (1H, d, J=7.8 Hz), 10.22 (1H, brs), 11.05 (1H, brs), 12.33 (1H, brs).

Example 351

6-Benzyloxymethyl-4-(2-Chlorophenyl)-5-cyano-4,7-dihydro-2H-pyrazolo[3,4-b]pyridine The title compound was prepared from ethyl benzyloxyacetate, 2-chlorobenzaldehyde and 3-aminopyrazole in the same manner as in Example 94.

MP: 165–166° C.

$^1$H-NMR (400 MHz, DMSO-d$_6$) δ (ppm): 4.35 (2H, d, J=2.9 Hz), 4.57 (2H, s), 5.42 (1H, s), 7.24–7.45 (10H, m), 10.03 (1H, brs), 12.22 (1H, brs).

Example 352

4-(2-Chlorophenyl)-5-cyano-4,7-dihydro-6-(methylpiperazin-1-yl)methyl-2H-pyrazolo[3,4-b]pyridine dihydrochloride 4-(2-Chlorophenyl)-5-cyano-6-(t-butyldimethylsilyloxy)methyl-4,7-dihydro-2H-pyrazolo[3,4-b]pyridine was prepared from ethyl t-butyldimethylsilyloxyacetate, 2-chlorobenzaldehyde and 3-aminopyrazole in the same manner as in Example 94. To a solution of 4-(2-chlorophenyl)-5-cyano-6-(t-butyldimethylsilyloxy)methyl-4,7-dihydro-2H-pyrazolo[3,4-b]pyridine (10 g) in tetrahydrofuran (100 ml) was added a THF solution (24.9 ml) of 1.0 M tetrabutylammonium fluoride and the mixture was stirred at room temperature for 1 hour. To the reaction mixture was added ethyl acetate (200 ml), and the resulting mixture was washed with a saturated aqueous sodium chloride solution and dried over anhydrous magnesium sulfate. The solvent was evaporated and the obtained residue was crystallized from ethyl acetate to give 4-(2-chlorophenyl)-5-cyano-6-hydroxymethyl-4,7-dihydro-2H-pyrazolo[3,4-b]pyridine (5.46 g) as a white solid. To a solution of 4-(2-chlorophenyl)-5-cyano-6-hydroxymethyl-4,7-dihydro-2H-pyrazolo[3,4-b]pyridine (1.0 g) and carbon tetrabromide (1.27 g) in methylene chloride (35 ml) was added triphenylphosphine (1.0 g) under ice-cooling and the mixture was stirred under ice-cooling for 4 hours. The reaction mixture was concentrated under reduced pressure and the obtained residue was purified by silica gel column chromatography (eluent:hexane-ethyl acetate (1:1)) to give 4-(2-chlorophenyl)-5-cyano-6-bromomethyl-4,7-dihydro-2H-pyrazolo[3,4-b]pyridine (0.45 g) as a pale-yellow solid. To a suspension of sodium hydride (25 mg) in DMF (3 ml) was added 1-methylpiperazine (69 μl) and the mixture was stirred at room temperature for 30 minutes. To this reaction mixture was added a solution of 4-(2-chlorophenyl)-5-cyano-6-bromomethyl-4,7-dihydro-2H-pyrazolo[3,4-b]pyridine (200 mg) in DMF (3 ml) under ice-cooling and the mixture was stirred under ice-cooling for 1 hour. To the reaction mixture was added water and the mixture was extracted with ethyl acetate. The extract was washed with a saturated aqueous sodium chloride solution and dried over anhydrous magnesium sulfate. The solvent was evaporated and the obtained residue was purified by silica gel column chromatography (eluent:ethyl acetate-methanol (4:1)). The obtained oil was treated with hydrogen chloride-methanol to give the title compound (87 mg) as white crystals.

MP: 222–225° C. (decomposition).

$^1$H-NMR (400 MHz, DMSO-d$_6$) δ (ppm): 2.66–2.75 (2H, m), 2.75 (3H, s), 3.00–3.10 (4H, m), 3.41–3.55 (4H, m), 5.42 (1H, s), 7.24–7.36 (4H, m), 7.43 (1H, d, J=8.0 Hz), 9.77 (1H, brs), 12.17 (1H, brs).

Example 353

4-(2-Chlorophenyl)-5-cyano-4,7-dihydro-6-(piperidin-1-yl)methyl-2H-pyrazolo[3,4-b]pyridine Hydrochloride The title compound was prepared from 4-(2-chlorophenyl)-5-cyano-6-bromomethyl-4,7-dihydro-2H-pyrazolo[3,4-b]pyridine and piperidine in the same manner as in Example 352.

$^1$H-NMR (400 MHz, DMSO-d$_6$) δ (ppm): 1.43 (1H, m), 1.67–1.82 (5H, m), 3.05–3.25 (2H, m), 3.48 (2H, m), 4.10 (2H, m), 5.49 (1H, s), 7.26–7.35 (4H, m), 7.45 (1H, d, J=8.0 Hz), 10.28 (1H, brs), 10.59 (1H, brs).

Example 354

Ethyl 4-(2-nitrophenyl)-4,7-dihydro-6-cyclopropyl-2H-pyrazolo[3,4-b]pyridine-5-carboxylate The title compound was prepared from cyclopropanecarbonyl chloride, 2-nitrobenzaldehyde and 3-aminopyrazole in the same manner as in Example 277.

MP: 162–164° C. (decomposition).

$^1$H-NMR (400 MHz, DMSO-d$_6$) δ (ppm): 0.81 (3H, t, J=7.4 Hz), 0.85–0.95 (2H, m), 1.10–1.18 (2H, m), 3.12 (1H, m), 3.72 (2H, m), 5.46 (1H, s), 7.27–7.34 (3H, m), 7.58 (1H, m), 7.78 (1H, d, J=8.0 Hz), 8.78 (1H, brs), 12.12 (1H, brs).

Example 355

Ethyl 4-(2,1,3-benzoxazol-4-yl)-4,7-dihydro-6-cyclopropyl-2H-pyrazolo[3,4-b]pyridine-5-carboxylate The title compound was prepared from cyclopropanecarbonyl chloride, 2,1,3-benzoxazole-4-aldehyde and 3-aminopyrazole in the same manner as in Example 277.

MP: 109–111° C. (decomposition).

$^1$H-NMR (400 MHz, DMSO-d$_6$) δ (ppm): 0.76 (3H, t, J=6.8 Hz), 0.85–0.86 (2H, m), 1.14–1.18 (2H, m), 3.12 (1H, m), 3.80 (2H, m), 5.69 (1H, s), 7.13 (1H, d, J=6.6 Hz), 7.23 (1H, s), 7.51 (1H, m), 7.79 (1H, d, J=9.0 Hz), 8.83 (1H, brs), 12.05 (1H, brs).

Example 356

4-(2,1,3-Benzoxazol-4-yl)-5-cyano-4,7-dihydro-2-(phenylcarbamoyl)-6-propyl-2H-pyrazolo[3,4-b]pyridine The title compound was obtained as colorless crystals from 4-(2,1,3-benzoxadiazol-4-yl)-5-cyano-4,7-dihydro-6-propyl-2H-pyrazolo[3,4-b]pyridine, dimethylaminopyridine and phenylisocyanate in the same manner as in Example 204.

MS (EI): 425 (M$^+$).

$^1$H-NMR (400 MHz, DMSO-d$_6$) δ (ppm): 0.91 (3H, t, J=7.3 Hz), 1.64 (2H, m), 2.58 (2H, m), 5.44 (1H, s), 7.10 (1H, dd, J=6.3 and 7.6 Hz), 7.31–7.34 (2H, m), 7.52 (1H, d, J=6.6 Hz), 7.59–7.64 (3H, m), 7.95 (1H, s), 7.97 (1H, d, J=9.0 Hz), 9.83 (1H, brs), 10.30 (1H, brs).

Example 357

4-(2-Chlorophenyl)-5-cyano-4,7-dihydro-1-(4-pentenoyl)-6-propyl-1H-pyrazolo[3,4-b]pyridine The title compound was obtained as colorless crystals from 4-(2-chlorophenyl)-5-cyano-4,7-dihydro-6-propyl-2H-pyrazolo[3,4-b]pyridine, dimethylaminopyridine and 4-pentenoyl chloride in the same manner as in Example 204.

MP: 140° C.

Anal. Calcd. for: $C_{21}H_{21}ClN_4O$: C, 66.22; H, 5.62; N, 14.71. Found: C, 66.20; H, 5.60; N, 14.65.

MS (EI): 380 (M$^+$).

$^1$H-NMR (400 MHz, DMSO-d$_6$) δ (ppm): 0.95 (3H, t, J=7.3 Hz), 1.62 (2H, m), 2.39–2.58 (4H, m), 3.11 (2H, t, J=7.6 Hz), 4.98 (1H, d, J=7.1 Hz), 5.06 (1H, d, J=10.3 Hz), 5.40 (1H, s), 5.85 (1H, m), 7.27–7.37 (4H, m), 7.46 (1H, d, J=7.0 Hz), 9.58 (1H, brs).

Example 358

4-(2-Chlorophenyl)-5-cyano-4,7-dihydro-2-(4-pentenoyl)-6-propyl-2H-pyrazolo[3,4-b]pyridine The title compound was obtained as colorless crystals from 4-(2-chlorophenyl)-5-cyano-4,7-dihydro-6-propyl-2H-pyrazolo[3,4-b]pyridine, dimethylaminopyridine and 4-pentenoyl chloride in the same manner as in Example 204.

MP: 176–177° C.

Anal. Calcd. for: $C_{21}H_{21}ClN_4O$: C, 66.22; H, 5.56N, 14.71. Found: C, 66.15; H, 5.63; N, 14.55.

MS (EI): 380 (M$^+$).

$^1$H-NMR (400 MHz, DMSO-d$_6$) δ (ppm): 0.95 (3H, t, J=7.3 Hz), 1.67 (2H, m), 2.34–2.49 (4H, m), 3.00 (2H, t, J=7.6 Hz), 4.96 (1H, d, J=10.6 Hz), 5.02 (1H, d, J=27.1 Hz), 5.36 (1H, s), 5.82 (1H, m), 7.30–7.35 (3H, m), 7.46 (1H, d, J=7.8 Hz), 7.83 (1H, s), 10.39 (1H, brs).

Example 359

5-Cyano-4,7-dihydro-4-(6-methylpyridin-2-yl)-6-propyl-2H-pyrazolo[3,4-b]pyridine The title compound was prepared from methyl butyrate, 6-methylpyridine-2-aldehyde and 3-aminopyrazole in the same manner as in Example 94.

MP: 177–181° C.

Anal. Calcd. for: $C_{16}H_{17}N_5 \cdot 4/5H_2O$: C, 65.42; H, 6.38; N, 23.84. Found: C, 65.52; H, 6.31; N, 24.19.

MS (EI): 279 (M$^+$).

$^1$H-NMR (400 MHz, DMSO-d$_6$) δ (ppm): 0.95 (3H, t, J=7.6 Hz), 1.66 (2H, m), 2.41 (2H, m), 2.43 (3H, s), 4.94 (1H, s), 6.98 (1H, d, J=7.6 Hz), 7.06 (1H, d, J=7.5 Hz), 7.21 (1H, s), 7.62 (1H, dd, J=7.6 and 7.7 Hz), 9.71 (1H, brs), 12.09 (1H, brs).

Example 360

4-(5-Cyano-4,7-dihydro-6-propyl-2H-pyrazolo[3,4-b]pyridine)pyridine-N-oxide

The title compound was prepared from methyl butyrate, pyridine-4-aldehyde-N-oxide and 3-aminopyrazole in the same manner as in Example 94.

MP: 110–115° C.

Anal. Calcd. for: $C_{15}H_{15}N_5O$: C, 62.01; H, 6.18; N, 24.11. Found: C, 61.94; H, 5.85; N, 23.73.

MS (EI): 283 (M$^+$).

$^1$H-NMR (400 MHz, DMSO-d$_6$) δ (ppm): 0.91 (3H, t, J=7.3 Hz), 1.62 (2H, m), 2.36 (2H, m), 4.98 (1H, s), 7.18 (2H, d, J=6.6 Hz), 7.31 (1H, s), 8.14 (2H, d, J=6.3 Hz), 9.86 (1H, brs), 12.2 (1H, brs).

Example 361

5-Cyano-4,7-dihydro-4-(3-(4-morpholinomethyl)phenyl)-6-propyl-2H-pyrazolo[3,4-b]pyridine The title compound was prepared from methyl butyrate, 3-(4-morpholinomethyl)benzaldehyde and 3-aminopyrazole in the same manner as in Example 94.

MS (EI): 363 (M$^+$).

$^1$H-NMR (400 MHz, DMSO-d$_6$) δ (ppm): 0.92 (3H, t, J=7.3 Hz), 1.63 (2H, m), 2.30 (4H, m), 2.30 (2H, m), 3.40 (2H, s), 3.53 (4H, m), 4.86 (1H, s), 7.05 (1H, d, J=7.8 Hz), 7.10 (1H, d, J=7.6 Hz), 7.14 (1H, s), 7.19 (1H, s), 7.23 (1H, dd, J=7.5 and 7.6 Hz), 9.70 (1H, brs), 12.10 (1H, brs).

Example 362

4-(3-Bromophenyl)-5-cyano-4,7-dihydro-6-propyl-2H-pyrazolo[3,4-b]pyridine

The title compound was prepared from methyl butyrate, 3-bromobenzaldehyde and 3-aminopyrazole in the same manner as in Example 94.

MP: 202–205° C.

Anal. Calcd. for: $C_{16}H_{15}BrN_4$: C, 55.99; H, 4.41; N, 16.32. Found: C, 55.82; H, 4.46; N, 17.03.

MS (EI): 343 (M$^+$).

$^1$H-NMR (400 MHz, DMSO-d$_6$) δ (ppm): 0.91 (3H, t, J=7.3 Hz), 1.63 (2H, m), 2.37 (2H, m), 4.92 (1H, s), 7.18 (1H, d, J=7.9 Hz), 7.25 (1H, s), 7.28 (1H, d, J=7.8 Hz), 7.33 (1H, s), 7.39 (1H, d, J=8.3 Hz), 9.80 (1H, brs), 12.18 (1H, brs).

Example 363

5-Cyano-4,7-dihydro-4-(4-fluoro-2-chlorophenyl)-6-propyl-2H-pyrazolo[3,4-b]pyridine The title compound was prepared from methyl butyrate, 2-chloro-4-fluorobenzaldehyde and 3-aminopyrazole in the same manner as in Example 94.

MP: 209–212° C.

Anal. Calcd. for: $C_{16}H_{14}ClFN_4$: C, 60.67; H, 4.45; N, 17.69. Found: C, 60.48; H, 4.48; N, 17.87.

MS (EI): 316 (M$^+$).

$^1$H-NMR (400 MHz, DMSO-d$_6$) δ (ppm): 0.93 (3H, t, J=7.3 Hz), 1.64 (2H, m), 2.39 (2H, m), 5.33 (1H, s), 7.17–7.40 (3H, m), 7.41 (1H, dd, J=2.7 and 6.1 Hz), 9.85 (1H, brs), 12.17 (1H, brs).

Example 364

5-Cyano-4,7-dihydro-4-(3-(morpholin-4-yl)phenyl)-6-propyl-2H-pyrazolo[3,4-b]pyridine The title compound was prepared from methyl butyrate, 3-(morpholin-4-yl)benzaldehyde and 3-aminopyrazole in the same manner as in Example 94.

MP: 196–200° C.

Anal. Calcd. for: $C_{20}H_{23}N_5O$: C, 68.47; H, 6.63; N, 20.04. Found: C, 68.41; H, 6.77; N, 20.16.

MS (EI): 349 (M$^+$).

$^1$H-NMR (400 MHz, DMSO-d$_6$) δ (ppm): 0.92 (3H, t, J=7.3 Hz), 1.63 (2H, m), 2.32 (2H, m), 3.05 (4H, t, J=4.6 Hz), 7.71 (4H, t, J=4.6 Hz), 4.80 (1H, s), 6.59 (1H, d, J=7.5 Hz), 6.74 (1H, m), 6.76 (1H, s), 7.13 (1H, dd, J=7.8 and 7.8 Hz), 7.21 (1H, s), 9.67 (1H, brs), 12.02 (1H, brs).

Example 365

5-Cyano-4,7-dihydro-4-(3-(morpholin-4-yl)phenyl)-6-isopropyl-2H-pyrazolo[3,4-b]pyridine The title compound was prepared from methyl isobutyrate, 3-(morpholin-4-yl)benzaldehyde and 3-aminopyrazole in the same manner as in Example 94.

MP: 254–257° C.

Anal. Calcd. for: $C_{20}H_{23}N_5O$: C, 68.47; H, 6.63; N, 20.04. Found: C, 68.56; H, 6.73; N, 20.30.

MS (EI): 349 (M$^+$).

$^1$H-NMR (400 MHz, DMSO-d$_6$) δ (ppm): 1.20 (3H, d, J=7.0 Hz), 1.22 (3H, d, J=7.1 Hz), 3.02 (2H, m), 3.04 (4H, t, J=4.8 Hz), 3.70 (4H, t, J=4.8 Hz), 4.78 (1H, s), 6.59 (1H, d, J=7.6 Hz), 7.74 (1H, s), 7.13 (1H, dd, J=7.5 and 8.1 Hz), 7.22 (1H, s), 9.48 (1H, brs), 12.09 (1H, brs).

Example 366

5-Cyano-6-cyclopropyl-4,7-dihydro-4-(3-(morpholin-4-yl)phenyl)-2H-pyrazolo[3,4-b]pyridine The title compound was prepared from methyl cyclopropanecarboxylate, 3-(morpholin-4-yl)benzaldehyde and 3-aminopyrazole in the same manner as in Example 94.

MP: >260° C.

MS (EI): 347 (M$^+$).

¹H-NMR (400 MHz, DMSO-d₆) δ (ppm): 0.86 (4H, m), 1.93–1.98 (1H, m), 3.05 (4H, t, J=4.6 Hz), 3.70 (4H, t, J=4.6 Hz), 4.79 (1H, s), 6.56 (1H, d, J=7.5 Hz), 6.74 (1H, s), 6.77 (1H, s), 7.13 (1H, dd, J=7.8 and 7.8 Hz), 7.20 (1H, s), 8.98 (1H, brs), 12.09 (1H, brs).
The compounds of the above-described Examples are as follows.
Example 290
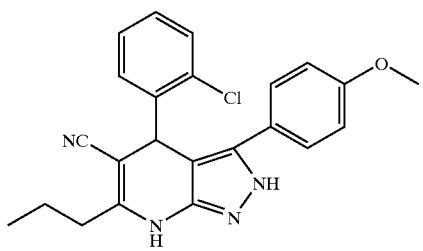
Example 291
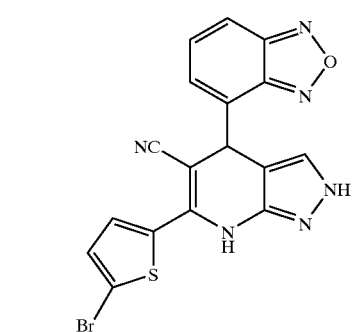
Example 292
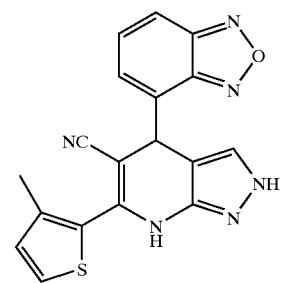
Example 293
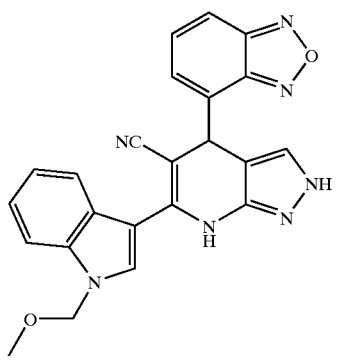
Example 294
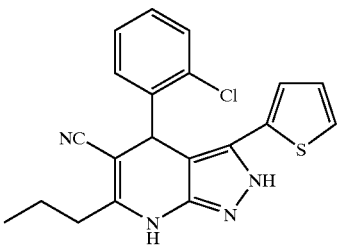
Example 295
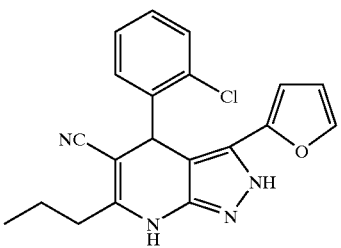
Example 296
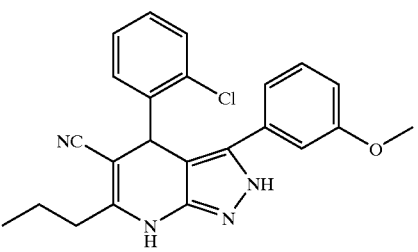
Example 297
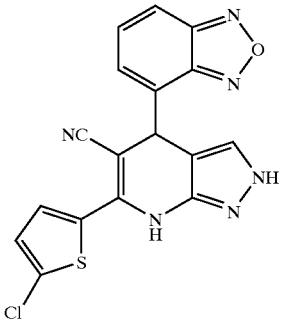
Example 298
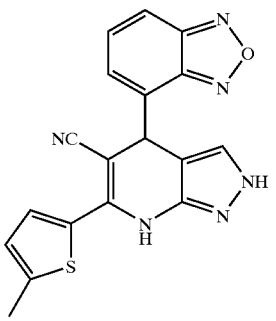
Example 299
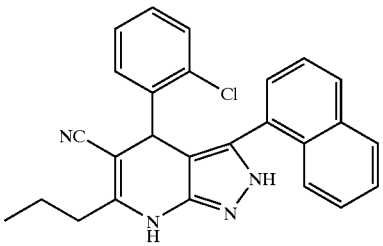
Example 300

Example 301
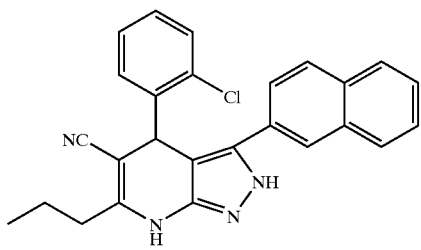
Example 302
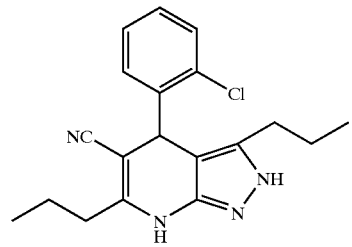
Example 303
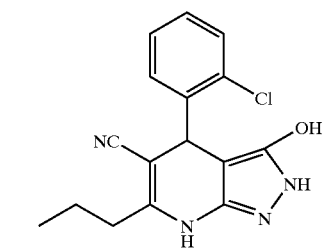
Example 304
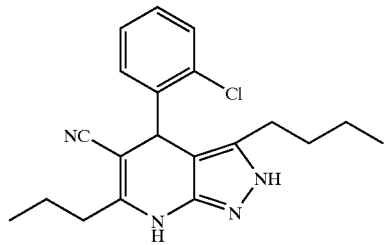
Example 305
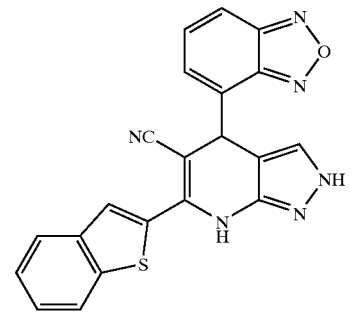
Example 306
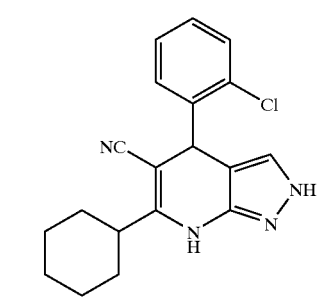
Example 307
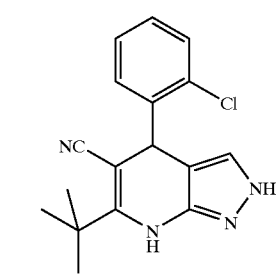
Example 308
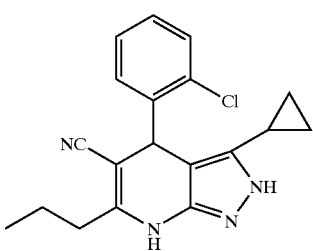
Example 309
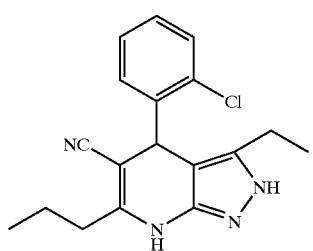
Example 310
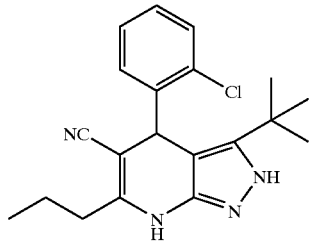
Example 311
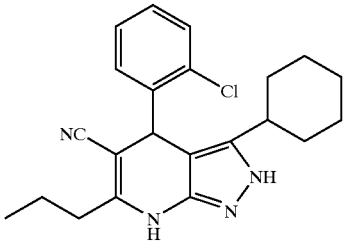
Example 312
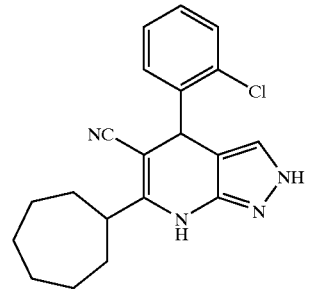

Example 313
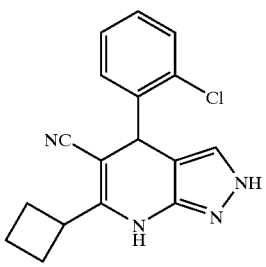
Example 314
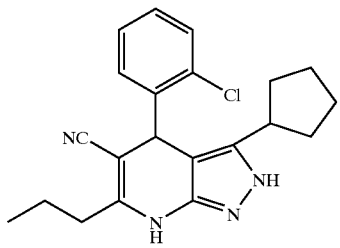
Example 315
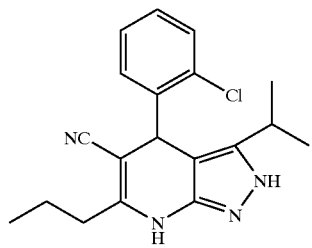
Example 316
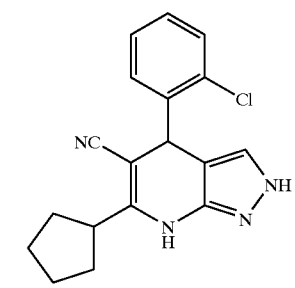
Example 317
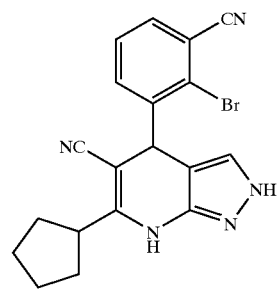
Example 318
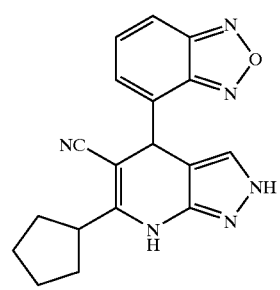
Example 319
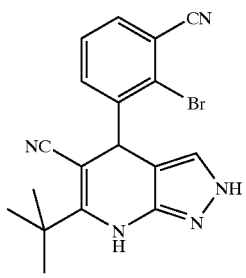
Example 320
Example 321
Example 322
Example 323

Example 324
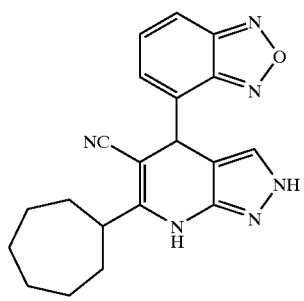
Example 325
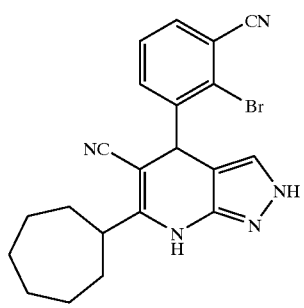
Example 326
Example 327
Example 328
Example 329
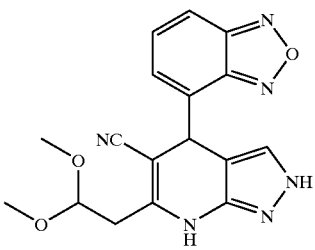
Example 330
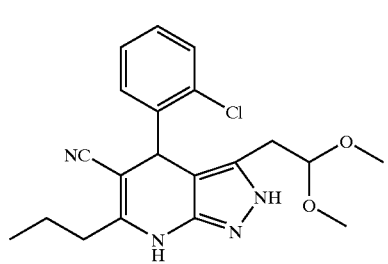
Example 331
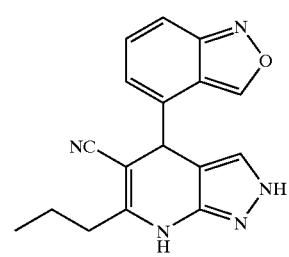
Example 332
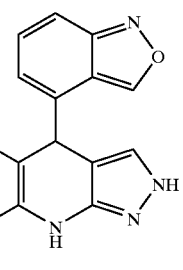
Example 333
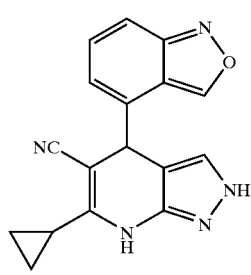

-continued
Example 334
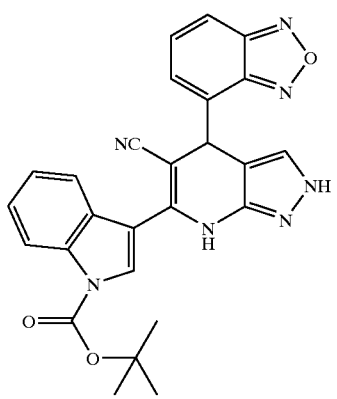
Example 335
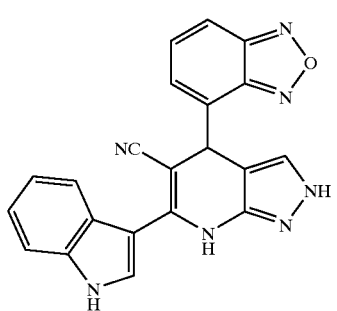
Example 336
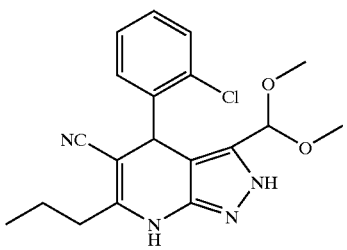
Example 337
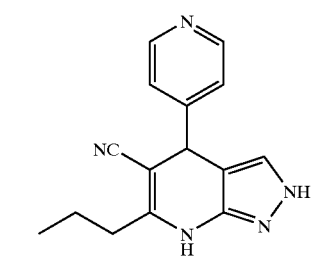
Example 338
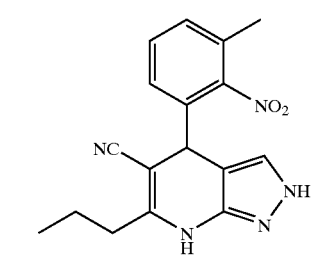
-continued
Example 339
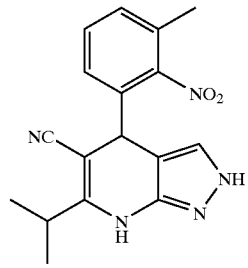
Example 340
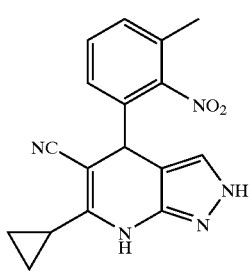
Example 341
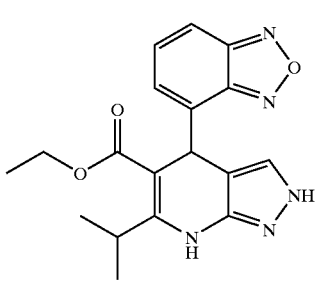
Example 342
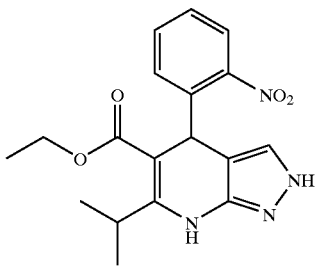
Example 343
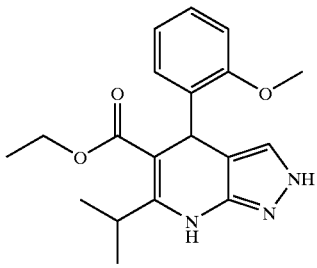
Example 344
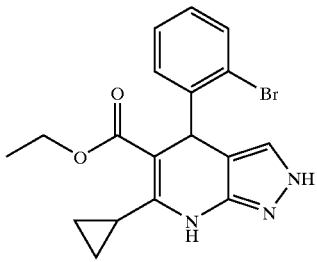

Example 345
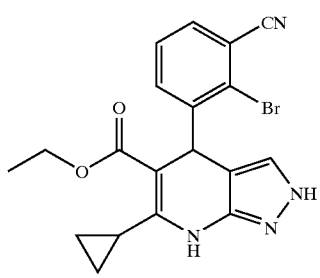
Example 346
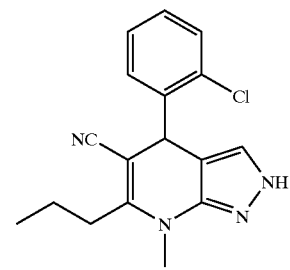
Example 347
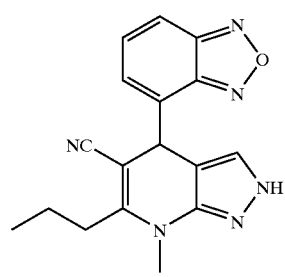
Example 348
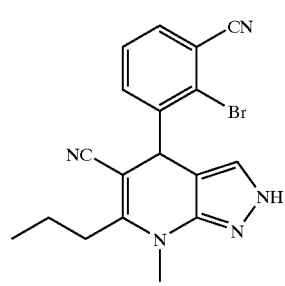
Example 349
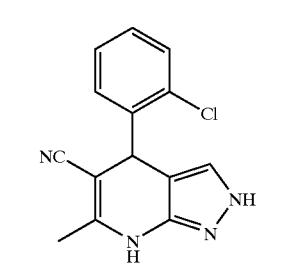
Example 350
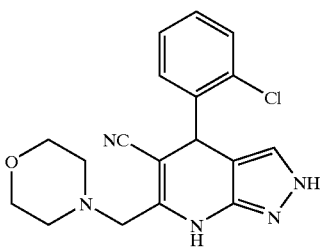
Example 351
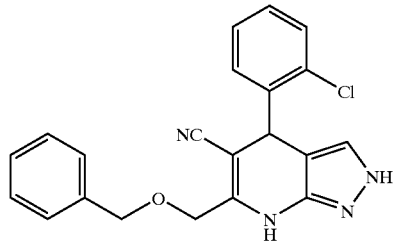
Example 352
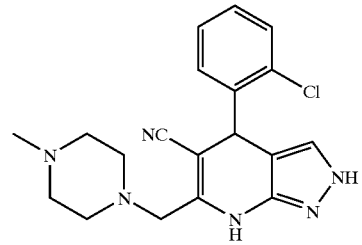
Example 353
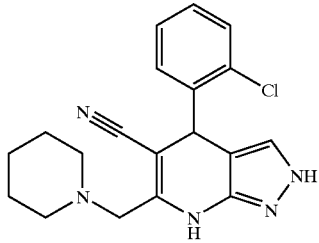
Example 354
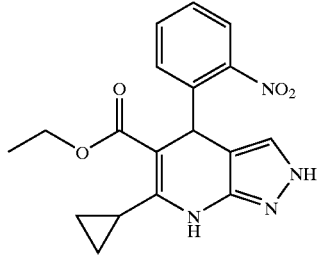
Example 355
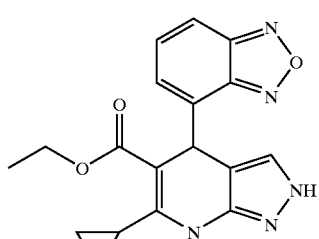
Example 356
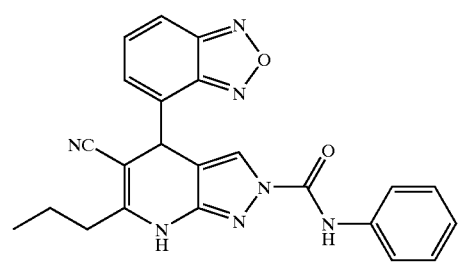

Example 357

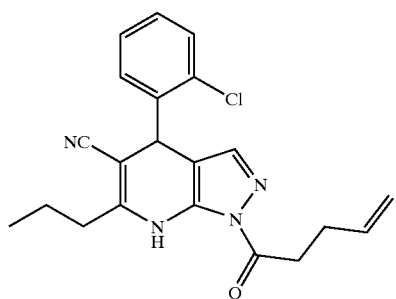

Example 358

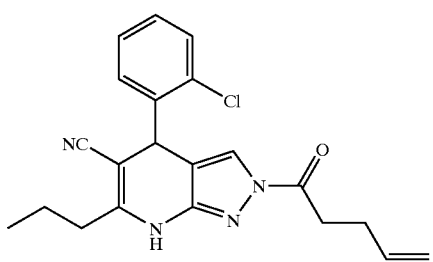

Example 359

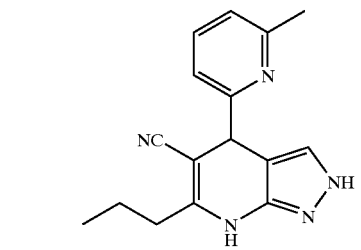

Example 360

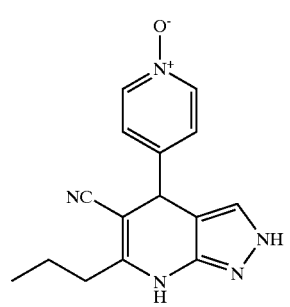

Example 361

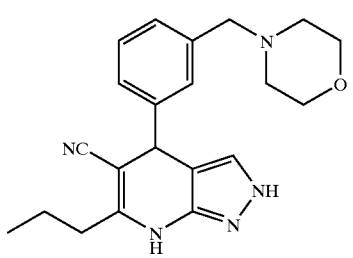

Example 362

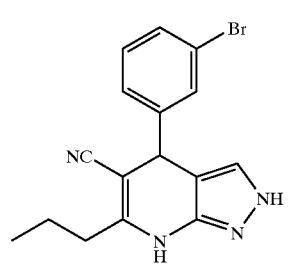

Example 363

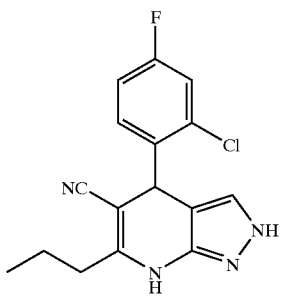

Example 364

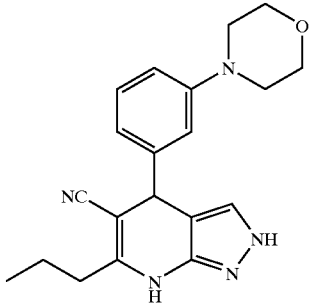

Example 365

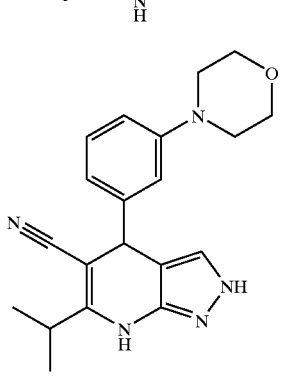

Example 366

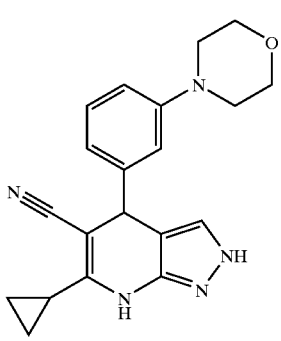

Example 1001

4-(2,1,3-Benzoxadiazol-4-yl)-6-(1-t-butoxycarbonylpiperidin-4-yl)-5-cyano-4,7-dihydro-2H-pyrazolo[3,4-b]pyridine To a solution of ethyl isonipecotate (10.0 g) in THF (200 mL) was added triethylamine (7.8 g), 4-dimethylaminopyridine (0.8 g) and di-tert-butyldicarbonate (15.3 g) at 0° C. and the mixture was stirred for an hour. The mixture was extracted with ethyl acetate and the solvent was evaporated under reduced pressure to give ethyl N-Boc-piperidine-4-carboxylate (16.3 g) as a colorless oil. To a solution of acetonitrile (3.2 g) in THF (300 mL) was added n-BuLi (44 mmol) at −78° C. and stirred for three hours. Further, ethyl N-Boc-piperidine-4-carboxylate (16.3 g) was added and the mixture was stirred for an hour. After acidification with hydrochloric acid, the mixture was extracted with ethyl acetate. The solvent was evaporated under reduced pressure and the residue was purified by silica gel column chromatography (eluent:hexane-ethyl acetate (5:1)) to give 1-(N-Boc-piperidin-4-yl)-2-cyanoethan-1-one (11.6 g) as a colorless oil. A solution of 2,1,3-benzoxadiazole-4-aldehyde (1.0 g), 3-aminopyrazole (0.6 g) and 2-(N-Boc-piperidin-4-yl)-1-cyanoethan-2-one (1.7 g) in acetonitrile (10 mL) was heated under reflux overnight. The reaction mixture was cooled to room temperature, and the precipitated crystals were collected by filtration to give the title compound (2.0 g) as colorless crystals.

MP: 226° C.

Anal. Calcd. For: $C_{23}H_{25}N_7O_3$: C, 61.73; H, 5.63; N, 21.97. Found: C, 61.45; H, 5.82; N, 21.61.

MS (EI): 447 ($M^+$).

$^1$H-NMR (400 MHz, DMSO-$d_6$) δ (ppm): 1.42 (9H, m), 1.59–1.62 (2H, m), 1.89–1.92 (2H, m), 2.62–2.86 (3H, m), 4.05–4.08 (2H, m), 5.40 (1H, s), 7.26 (1H, s), 7.41 (1H, d, J=6.6 Hz), 7.58 (1H, dd, J=9.0 Hz and 6.6 Hz), 7.92 (1H, d, J=9.0 Hz), 9.81 (1H, brs), 12.24 (1H, brs).

Example 1002

4-(2,1,3-Benzoxadiazol-4-yl)-5-cyano-4,7-dihydro-6-(piperidin-4-yl)-2H-pyrazolo[3,4-b]pyridine 4-(2,1,3-Benzoxadiazol-4-yl)-6-(1-t-butoxycarbonylpiperidin-4-yl)-5-cyano-4,7-dihydro-2H-pyrazolo[3,4-b]pyridine (1.7 g) was added to trifluoroacetic acid (20 mL) at 0° C. and the mixture was stirred for an hour. The solvent was evaporated under reduced pressure. After alkalification with sodium bicarbonate, the mixture was extracted with ethyl acetate. The solvent was evaporated under reduced pressure and the residue was washed with acetonitrile, and the precipitated crystals were collected by filtration to give the title compound (0.83 g) as yellow crystals.

MP: 216° C.

MS (EI): 348 ($M^+$).

$^1$H-NMR (400 MHz, DMSO-$d_6$) δ (ppm): 1.78–1.81 (2H, m), 2.07–2.11 (2H, m), 2.80–2.86 (3H, m), 3.27–3.30 (3H, m), 5.39 (1H, s), 7.27 (1H, s), 7.43 (1H, d, J=6.6 Hz), 7.58 (1H, dd, J=9.0 Hz and 6.6 Hz), 7.92 (1H, d, J=9.0 Hz), 9.86 (1H, brs), 12.24 (1H, brs).

Example 1003

4-(2,1,3-Benzoxadiazol-4-yl)-5-cyano-4,7-dihydro-6-(1-methylpiperidin-4-yl)-2H-pyrazolo[3,4-b]pyridine To a solution of 4-(2,1,3-Benzoxadiazol-4-yl)-5-cyano-4,7-dihydro-6-(piperidin-4-yl)-2H-pyrazolo[3,4-b]pyridine (0.7 g) in MeOH (200 mL) was added 37% formaldehyde (0.18 g), sodium cyanoborohydride (0.19 g) and acetic acid (0.36 g) at room temperature and the mixture was stirred overnight. After alkalification with sodium bicarbonate, the mixture was extracted with ethyl acetate. The solvent was evaporated under reduced pressure and the residue was washed with acetonitrile, and the precipitated crystals were collected by filtration to give the title compound (0.32 g) as yellow crystals.

MP: >270° C.

MS (EI): 361 ($M^+$).

$^1$H-NMR (400 MHz, DMSO-$d_6$) δ (ppm): 1.57–1.60 (2H, m), 1.82–1.88 (2H, m), 2.01–2.06 (2H, m), 2.15 (3H, s), 2.58–2.61 (1H, m), 2.85–2.88 (2H, m), 5.40 (1H, s), 7.26 (1H, s), 7.40 (1H, d, J=6.6 Hz), 7.58 (1H, dd, J=9.0 Hz and 6.6 Hz), 7.91 (1H, d, J=9.0 Hz), 9.76 (1H, brs), 12.17 (1H, brs).

Example 1004

4-(2,1,3-Benzoxadiazol-4-yl)-6-(1-t-butoxycarbonylpiperidin-3-yl)-5-cyano-4,7-dihydro-2H-pyrazolo[3,4-b]pyridine The title compound was prepared from ethyl nipecotate, 2,1,3-benzoxadiazole-4-aldehyde and 3-aminopyrazole in the same manner as in Example 1001.

MP: 229° C.

Anal. Calcd. For: $C_{23}H_{25}N_7O_3$: C, 61.73; H, 5.63; N, 21.97. Found: C, 61.56; H, 5.66; N, 21.67.

MS (EI): 447 ($M^+$).

$^1$H-NMR (400 MHz, DMSO-$d_6$) δ (ppm): 1.32–1.40 (2H, m), 1.39 (9H, s), 1.69–1.78 (2H, m), 2.69–2.76 (2H, m), 3.16–3.19 (1H, m), 3.92–3.95 (2H, m), 5.42 (1H, s), 7.28 (1H, s), 7.42 (1H, d, J=6.6 Hz), 7.58 (1H, dd, J=9.0 Hz and 6.6 Hz), 7.92 (1H, d, J=9.0 Hz), 9.87 (1H, brs), 12.21 (1H, brs).

Example 1005

4-(2,1,3-Benzoxadiazol-4-yl)-5-cyano-4,7-dihydro-6-(piperidin-3-yl)-2H-pyrazolo[3,4-b]pyridine The title compound was prepared from 4-(2,1,3-benzoxadiazol-4-yl)-6-(1-t-butoxycarbonylpiperidin-3-yl)-5-cyano-4,7-dihydro-2H-pyrazolo[3,4-b]pyridine in the same manner as in Example 1002.

MP: 202° C.

Anal. Calcd. For: $C_{18}H_{17}N_7O$: C, 62.24; H, 4.93; N, 28.23. Found: C, 61.97; H, 5.13; N, 27.89.

MS (EI): 347 ($M^+$).

$^1$H-NMR (400 MHz, DMSO-$d_6$) δ (ppm): 1.42–1.45 (1H, m), 1.72–1.88 (3H, m), 2.66–2.84 (5H, m), 2.94–3.02 (1H, m), 5.38 (1H, s), 7.26 (1H, s), 7.39 (1H, d, J=6.6 Hz), 7.58 (1H, dd, J=9.0 Hz and 6.6 Hz), 7.91 (1H, d, J=9.0 Hz), 10.39 (1H, brs), 12.17 (1H, brs).

Example 1006

4-(2,1,3-Benzoxadiazol-4-yl)-5-cyano-4,7-dihydro-6-(1-methylpiperidin-3-yl)-2H-pyrazolo[3,4-b]pyridine The title compound was prepared from 4-(2,1,3-benzoxadiazol-4-yl)-5-cyano-4,7-dihydro-6-(piperidin-3-yl)-2H-pyrazolo[3,4-b]pyridine in the same manner as in Example 1003.

MP: 228° C.

MS (EI): 361 ($M^+$).

$^1$H-NMR (400 MHz, DMSO-$d_6$) δ (ppm): 1.53–1.76 (4H, m), 2.21 (3H, s), 2.47–2.55 (4H, m), 2.93–2.96 (1H, m), 5.38 (1H, s), 7.27 (1H, s), 7.40 (1H, d, J=6.6 Hz), 7.59 (1H, dd, J=9.0 Hz and 6.6 Hz), 7.92 (1H, d, J=9.0 Hz), 10.16 (1H, brs), 12.20 (1H, brs).

Example 1007

4-(2,1,3-Benzoxadiazol-4-yl)-6-(1-t-butoxycarbonylpiperidin-2-yl)-5-cyano-4,7-dihydro-2H-pyrazolo[3,4-b]pyridine The title compound was prepared from ethyl pipecolinate, 2,1,3-benzoxadiazole-4-aldehyde and 3-aminopyrazole in the same manner as in Example 1001.

MS (EI): 447 ($M^+$).

¹H-NMR (400 MHz, DMSO-d₆) δ (ppm): 1.27 and 1.32 (9H, s), 1.42–1.97 (6H, m), 3.30–3.33 (1H, m), 3.53–3.61 (1H, m), 4.47–4.50 (1H, m), 5.37 and 5.39 (1H, s), 7.26 and 7.29 (1H, s), 7.38–7.44 (1H, m), 7.54–7.60 (1H, m), 7.90–7.93 (1H, m), 9.63 and 9.73 (1H, brs), 12.16 (1H, brs).

Example 1008

4-(2,1,3-Benzoxadiazol-4-yl)-5-cyano-4,7-dihydro-6-(piperidin-2-yl)-2H-pyrazolo[3,4-b]pyridine The title compound was prepared from 4-(2,1,3-benzoxadiazol-4-yl)-6-(1-t-butoxycarbonylpiperidin-2-yl)-5-cyano-4,7-dihydro-2H-pyrazolo[3,4-b]pyridine in the same manner as in Example 1002.

MS (EI): 347 (M⁺).

¹H-NMR (400 MHz, DMSO-d₆) δ (ppm): 1.27–1.88 (6H, m), 3.12–3.16 (1H, m), 4.12–4.15 (1H, m), 4.48–4.58 (1H, m), 5.64 and 5.66 (1H, s), 7.22–7.28 (1H, m), 7.45–7.52 (2H, m), 7.87–7.90 (1H, m), 8.26 (1H, br), 10.92 and 10.94 (1H, brs), 12.35 (1H, brs).

Example 1009

4-(2,1,3-Benzoxadiazol-4-yl)-6-(4-t-butoxycarbonylmorpholin-2-yl)-5-cyano-4,7-dihydro-2H-pyrazolo[3,4-b]pyridine The title compound was prepared from ethyl morpholine-2-carboxylate, 2,1,3-benzoxadiazole-4-aldehyde and 3-amino-pyrazole in the same manner as in Example 1001.

MS (EI): 449 (M⁺).

¹H-NMR (400 MHz, DMSO-d₆) δ (ppm): 1.36 and 1.40 (9H, s), 2.95–3.06 (2H, m), 3.50–3.52 (1H, m), 3.75–3.95 (3H, m), 4.34–4.40 (1H, m), 5.44 and 5.48 (1H, s), 7.26 and 7.30 (1H, s), 7.42–7.45 (1H, m), 7.57–7.62 (1H, m), 7.93–7.96 (1H, m), 9.84 and 9.92 (1H, brs), 12.23 (1H, brs).

Example 1010

4-(2,1,3-Benzoxadiazol-4-yl)-5-cyano-4,7-dihydro-6-(morpholin-2-yl)-2H-pyrazolo[3,4-b]pyridine The title compound was prepared from 4-(2,1,3-benzoxadiazol-4-yl)-6-(4-t-butoxycarbonylmorpholin-2-yl)-5-cyano-4,7-dihydro-2H-pyrazolo[3,4-b]pyridine in the same manner as in Example 1002.

MS (EI): 349 (M⁺).

¹H-NMR (400 MHz, DMSO-d₆) δ (ppm): 2.64–2.95 (4H, m), 3.53 (1H, br), 3.55–3.57 (1H, m), 3.82–3.85 (1H, m), 4.41–4.45 (1H, m), 5.43 and 5.44 (1H, s), 7.24 and 7.28 (1H, s), 7.38–7.41 (1H, m), 7.56–7.61 (1H, m), 7.91–7.94 (1H, m), 9.74 and 9.76 (1H, brs), 12.19 (1H, brs).

Example 1011

4-(2,1,3-Benzoxadiazol-4-yl)-5-cyano-4,7-dihydro-6-(4-methylmorpholin-2-yl)-2H-pyrazolo[3,4-b]pyridine The title compound was prepared from 4-(2,1,3-benzoxadiazol-4-yl)-5-cyano-4,7-dihydro-6-(morpholin-2-yl)-2H-pyrazolo[3,4-b]pyridine in the same manner as in Example 1003.

MP: 143° C.

MS (EI): 363 (M⁺).

¹H-NMR (400 MHz, DMSO-d₆) δ (ppm): 2.21 (3H, s), 2.19–2.30 (2H, m), 2.60–2.69 (2H, m), 3.60–3.62 (1H, m), 3.88–3.92 (1H, m), 4.48–4.50 (1H, m), 5.44 (1H, s), 7.28 (1H, s), 7.39 (1H, d, J=6.6 Hz), 7.58 (1H, dd, J=9.0 Hz and 6.6 Hz), 7.92 (1H, d, J=9.0 Hz), 9.80 (1H, brs), 12.20 (1H, brs).

Example 1012

4-(2,1,3-Benzoxadiazol-4-yl)-6-(1-t-butoxycarbonyl-1,2,3,6-tetrahydropyridin-4-yl)-5-cyano-4,7-dihydro-2H-pyrazolo[3,4-b]pyridine The title compound was prepared from ethyl 1,2,3,6-tetrahydropyridine-4-carboxylate, 2,1,3-benzoxadiazole-4-aldehyde and 3-aminopyrazole in the same manner as in Example 1001.

MP: 222° C.

MS (EI): 445 (M⁺).

¹H-NMR (400 MHz, DMSO-d₆) δ (ppm): 1.41 (9H, s), 2.35–2.39 (2H, m), 3.46–3.48 (2H, m), 3.90–3.92 (2H, m), 5.43 (1H, s), 6.06–6.09 (1H, m), 7.28 (1H, s), 7.45 (1H, d, J=6.6 Hz), 7.60 (1H, dd, J=9.0 Hz and 6.6 Hz), 7.93 (1H, d, J=9.0 Hz), 9.94 (1H, brs), 12.19 (1H, brs).

Example 1013

4-(2,1,3-Benzoxadiazol-4-yl)-5-cyano-4,7-dihydro-6-(1,2,3,6-tetrahydropyridin-4-yl)-2H-pyrazolo[3,4-b]pyridine The title compound was prepared from 4-(2,1,3-benzoxadiazol-4-yl)-6-(1-t-butoxycarbonyl-1,2,3,6-tetrahydropyridin-4-yl)-5-cyano-4,7-dihydro-2H-pyrazolo[3,4-b]pyridine in the same manner as in Example 1002.

MP: 180° C.

MS (EI): 345 (M⁺).

¹H-NMR (400 MHz, DMSO-d₆) δ (ppm): 2.26–2.32 (2H, m), 2.87–2.90 (2H, m), 3.30–3.36 (3H, m), 5.42 (1H, s), 6.09–6.10 (1H, m), 7.30 (1H, s), 7.43 (1H, d, J=6.6 Hz), 7.60 (1H, dd, J=9.0 Hz and 6.6 Hz), 7.92 (1H, d, J=9.0 Hz), 9.87 (1H, brs), 12.18 (1H, brs).

Example 1014

4-(2,1,3-Benzoxadiazol-4-yl)-5-cyano-4,7-dihydro-6-(1-methyl-1,2,3,6-tetrahydropyridin-4-yl)-2H-pyrazolo[3,4-b]pyridine The title compound was prepared from 4-(2,1,3-benzoxadiazol-4-yl)-5-cyano-4,7-dihydro-6-(1,2,3,6-tetrahydropyridin-4-yl)-2H-pyrazolo[3,4-b]pyridine in the same manner as in Example 1003.

MP: 218° C.

MS (EI): 359 (M⁺).

¹H-NMR (400 MHz, DMSO-d₆) δ (ppm): 2.24 (3H, s), 2.35–2.42 (2H, m), 2.91–2.93 (2H, m), 3.31–3.33 (2H, m), 5.42 (1H, s), 6.04–6.05 (1H, m), 7.27 (1H, s), 7.43 (1H, d, J=6.6 Hz), 7.59 (1H, dd, J=9.0 Hz and 6.6 Hz), 7.92 (1H, d, J=9.0 Hz), 9.87 (1H, brs), 12.17 (1H, brs).

Example 1015

4-(2,1,3-Benzoxadiazol-4-yl)-6-(2-(N-t-butoxycarbonyl-N-methylamino)ethyl)-5-cyano-4,7-dihydro-2H-pyrazolo[3,4-b]-pyridine To a solution of ethyl 3-aminopropionate hydrochloride (19 g) in THF (600 mL) was added triethylamine (44 mL), dimethylaminopyridine (1.5 g) and di-tert-butyldicarbonate (30 g) at 0° C. and the mixture was stirred at 40° C. for four hours. The mixture was extracted with ethyl acetate and the solvent was evaporated under reduced pressure to give ethyl N-Boc-3-aminopropionate (16.7 g) as a colorless oil. To a solution of ethyl N-Boc-3-aminopropionate (5.0 g) in THF (50 mL) was added t-BuOK (2.8 g) and methyl iodide (4.9 g) at 0° C. and the mixture was stirred at room temperature for an hour. The mixture was extracted with ethyl acetate and the solvent was evaporated under reduced pressure to give ethyl 3-(N-Boc-N-methylamino)propionate (4.3 g) as a colorless oil. Subsequently, the title compound was prepared from ethyl 3-(N-Boc-N-methylamino)propionate, 2,1,3-benzoxadiazole-4-aldehyde and 3-aminopyrazole in the same manner as in Example 1001.

MP: 240° C.

Anal. Calcd. For: $C_{21}H_{23}N_7O_3$: C, 59.85; H, 5.50; N, 23.26. Found: C, 59.69; H, 5.45; N, 23.22.

MS (EI): 421 (M$^+$).

$^1$H-NMR (400 MHz, DMSO-d$_6$) δ (ppm): 1.26 and 2.32 (9H, s), 2.62–2.63 (2H, m), 2.81 (3H, s), 3.48–3.55 (2H, m), 5.40 (1H, s), 7.27 (1H, s), 7.40 (1H, d, J=6.6 Hz), 7.57 (1H, dd, J=9.0 Hz and 6.6 Hz), 7.92 (1H, d, J=9.0 Hz), 10.07 (1H, brs), 12.15 (1H, brs).

Example 1016

4-(2,1,3-Benzoxadiazol-4-yl)-5-cyano-4,7-dihydro-6-(2-(N-methylamino)ethyl)-2H-pyrazolo[3,4-b]pyridine The title compound was prepared from 4-(2,1,3-benzoxadiazol-4-yl)-6-(2-(N-t-butoxycarbonyl-N-methylamino)ethyl)-5-cyano-4,7-dihydro-2H-pyrazolo[3,4-b]pyridine in the same manner as in Example 1002.

MP: 174° C.

MS (EI): 321 (M$^+$).

$^1$H-NMR (400 MHz, DMSO-d$_6$) δ (ppm): 2.29 (3H, s), 2.50–2.78 (4H, m), 3.31 (3H, br), 5.39 (1H, s), 7.24 (1H, s), 7.43 (1H, d, J=6.6 Hz), 7.58 (1H, dd, J=9.0 Hz and 6.6 Hz), 7.91 (1H, d, J=9.0 Hz).

Example 1017

4-(2,1,3-Benzoxadiazol-4-yl)-6-(2-(N-t-butoxycarbonyl-amino)ethyl)-5-cyano-4,7-dihydro-2H-pyrazolo[3,4-b]pyridine The title compound was prepared from ethyl 3-aminopropionate hydrochloride, 2,1,3-benzoxadiazole-4-aldehyde and 3-aminopyrazole in the same manner as in Example 1001.

MP: 231° C.

Anal. Calcd. For: $C_{20}H_{21}N_7O_3$: C, 58.96; H, 5.20; N, 24.06. Found: C, 58.81; H, 5.19; N, 23.82.

MS (EI): 407 (M$^+$).

$^1$H-NMR (400 MHz, DMSO-d$_6$) δ (ppm): 1.33 (9H, s), 2.55–2.60 (2H, m), 3.23–3.33 (2H, m), 5.41 (1H, s), 6.81 (1H, brs), 7.25 (1H, s), 7.44 (1H, d, J=6.6 Hz), 7.57 (1H, dd, J=9.0 Hz and 6.6 Hz), 7.92 (1H, d, J=9.0 Hz), 9.94 (1H, brs), 12.14 (1H, brs).

Example 1018

6-(2-Aminoethyl)-4-(2,1,3-benzoxadiazol-4-yl)-5-cyano-4,7-dihydro-2H-pyrazolo[3,4-b]pyridine The title compound was prepared from 4-(2,1,3-benzoxadiazol-4-yl)-6-(2-(N-t-butoxycarbonylamino)ethyl)-5-cyano-4,7-dihydro-2H-pyrazolo[3,4-b]pyridine in the same manner as in Example 1002.

MS (EI): 307 (M$^+$).

$^1$H-NMR (400 MHz, DMSO-d$_6$) δ (ppm): 2.50–2.54 (2H, m), 2.88 (2H, t, J=7.3 Hz), 3.35 (4H, br), 5.40 (1H, s), 7.25 (1H, s), 7.44 (1H, d, J=6.6 Hz), 7.58 (1H, dd, J=9.0 Hz and 6.6 Hz), 7.92 (1H, d, J=9.0 Hz).

Example 1019

4-(2,1,3-Benzoxadiazol-4-yl)-5-cyano-4,7-dihydro-6-(2-(N,N-dimethylamino)ethyl)-2H-pyrazolo[3,4-b]pyridine The title compound was prepared from 4-(2,1,3-benzoxadiazol-4-yl)-5-cyano-4,7-dihydro-6-(2-(N-methylamino)ethyl)-2H-pyrazolo[3,4-b]pyridine in the same manner as in Example 1003.

MP: 215° C.

MS (EI): 335 (M$^+$).

$^1$H-NMR (400 MHz, DMSO-d$_6$) δ (ppm): 2.19 (6H, s), 2.45–2.62 (4H, m), 5.41 (1H, s), 7.27 (1H, s), 7.43 (1H, d, J=6.6 Hz), 7.58 (1H, dd, J=9.0 Hz and 6.6 Hz), 7.92 (1H, d, J=9.0 Hz), 10.04 (1H, brs), 12.16 (1H, brs).

Example 1020

4-(2,1,3-Benzoxadiazol-4-yl)-6-((N-t-butoxycarbonyl-N-methylamino)methyl)-5-cyano-4,7-dihydro-2H-pyrazolo[3,4-b]-pyridine The title compound was prepared from glycine ethyl ester hydrochloride, 2,1,3-benzoxadiazole-4-aldehyde and 3-amino-pyrazole in the same manner as in Example 1015.

MP: 207° C.

Anal. Calcd. For: $C_{20}H_{21}N_7O_3$: C, 58.96; H, 5.20; N, 24.06. Found: C, 58.80; H, 5.12; N, 24.38.

MS (EI): 407 (M$^+$).

$^1$H-NMR (400 MHz, DMSO-d$_6$) δ (ppm): 1.33 and 1.39 (9H, s), 2.81 (3H, s), 4.13–4.20 (2H, m), 5.42 (1H, s), 7.29 (1H, s), 7.43 (1H, d, J=6.6 Hz), 7.58 (1H, dd, J=9.0 Hz and 6.6 Hz), 7.94 (1H, d, J=9.0 Hz), 9.33 (1H, brs), 12.15 (1H, brs).

Example 1021

4-(2,1,3-Benzoxadiazol-4-yl)-5-cyano-4,7-dihydro-6-((N-methylamino)methyl)-2H-pyrazolo[3,4-b]pyridine trifluoroacetate 4-(2,1,3-Benzoxadiazol-4-yl)-6-((N-t-butoxycarbonyl-N-methylamino)methyl)-5-cyano-4,7-dihydro-2H-pyrazolo[3,4-b]-pyridine (0.6 g) was added to trifluoroacetic acid (10 mL) at 0° C. and the mixture was stirred for an hour. The solvent was evaporated under reduced pressure and the residue was crystallized by ethanol, and the precipitated crystals were collected by filtration to give the title compound (0.1 g) as yellow crystals.

MP: 174° C.

MS (EI): 307 (M$^+$).

$^1$H-NMR (400 MHz, DMSO-d$_6$) δ (ppm): 3.10 (3H, s), 4.51–4.68 (2H, m), 7.24 (1H, d, J=6.6 Hz), 7.45 (1H, s), 7.52 (1H, dd, J=9.0 Hz and 6.6 Hz), 7.89 (1H, d, J=9.0 Hz), 8.08–8.20 (2H, br), 10.81 (1H, brs), 12.41 (1H, brs).

Example 1022

4-(2,1,3-Benzoxadiazol-4-yl)-5-cyano-4,7-dihydro-6-(4-(N-methylamino)cyclohexyl)-2H-pyrazolo[3,4-b]pyridine The title compound was prepared from ethyl 4-aminocyclo-hexanecarboxylate, 2,1,3-benzoxadiazole-4- aldehyde and 3-aminopyrazole in the same manner as in Example 1015, and Example 1002 followed.

MS (EI): 375 (M+).

¹H-NMR (400 MHz, DMSO-d₆) δ (ppm): 1.32–1.35 (2H, m), 1.81–2.12 (6H, m), 2.57 (3H, s), 2.65–2.69 (1H, m), 2.81–2.85 (1H, m), 5.39 (1H, s), 7.28 (1H, s), 7.41 (1H, d, J=6.6 Hz), 7.59 (1H, dd, J=9.0 Hz and 6.6 Hz), 7.92 (1H, d, J=9.0 Hz), 8.54 (1H, br), 9.79 (1H, brs), 12.22 (1H, brs).

Example 1023

4-(2,1,3-Benzoxadiazol-4-yl)-5-cyano-4,7-dihydro-6-(4-(N,N-dimethylamino)cyclohexyl)-2H-pyrazolo[3,4-b]pyridine The title compound was prepared from 4-(2,1,3-benzoxadiazol-4-yl)-5-cyano-4,7-dihydro-6-(4-(N-methylamino)-cyclohexyl)-2H-pyrazolo[3,4-b]pyridine in the same manner as in Example 1003.

MP: 241° C.

MS (EI): 389 (M+).

¹H-NMR (400 MHz, DMSO-d₆) δ (ppm): 1.15–2.02 (9H, m), 2.15 and 2.21 (6H, s), 2.62–2.76 (1H, m), 5.38 and 5.43 (1H, s), 7.26 (1H, s), 7.38–7.44 (1H, m), 7.56–7.62 (1H, m), 7.90–7.96 (1H, m), 9.74 (1H, brs), 12.18 (1H, brs).

Example 1024

4-(2,1,3-Benzoxadiazol-4-yl)-5-cyano-4,7-dihydro-6-(1-phenylpiperidin-4-yl)-2H-pyrazolo[3,4-b]pyridine To a solution of ethyl isonipecotate (8.9 g) in CH₂Cl₂ (500 mL) was added triphenyl bismus (25 g) and Copper(II) acetate (10.3 g) at room temperature, the mixture was stirred overnight. After filteration, the mixture was extracted with CH₂Cl₂. The solvent was evaporated under reduced pressure and the residue was purified by silica gel column chromatography (eluent:hexane-ethyl acetate (10:1)) to give ethyl 1-phenylpiperidine-4-carboxylate (8.6 g) as colorless crystals. To a solution of acetonitrile (1.9 g) in THF (200 mL) was added n-BuLi (41 mmol) at −78° C. Further, ethyl 1-phenylpiperidine-4-carboxylate (8.6 g) was added and the mixture was stirred for an hour. After acidification with hydrochloric acid, the mixture was extracted with ethyl acetate. The solvent was evaporated under reduced pressure and the residue was purified by silica gel column chromatography (eluent:hexane-ethyl acetate (10:1)) to give 1-(1-phenylpiperidin-4-yl)-2-cyanoethan-1-one (2.0 g) as colorless crystals. A solution of 2,1,3-benzoxadiazole-4-aldehyde (0.3 g), 3-aminopyrazole (0.2 g) and 1-(1-phenylpiperidin-4-yl)-2-cyanoethan-1-one (0.5 g) in acetonitrile (10 mL) was heated under reflux overnight. The reaction mixture was cooled to room temperature, and the precipitated crystals were collected by filtration to give the title compound (0.6 g) as colorless crystals.

MS (FAB): 424 (M++1).

¹H-NMR (400 MHz, DMSO-d₆) δ (ppm): 1.73–1.76 (2H, m), 2.14–2.18 (2H, m), 2.62–2.66 (2H, m), 2.81–2.84 (1H, m), 3.80–3.84 (2H, m), 5.41 (1H, s), 6.75 (1H, dd, J=7.3 Hz and 7.2 Hz), 6.94–6.96 (2H, m), 7.18–7.27 (3H, m), 7.42 (1H, d, J=6.6 Hz), 7.59 (1H, dd, J=9.0 Hz and 6.6 Hz), 7.92 (1H, d, J=9.0 Hz), 9.81 (1H, brs), 12.17 (1H, brs).

Example 1025

6-(1-Acetylpiperidin-4-yl)-4-(2,1,3-benzoxadiazol-4-yl)-5-cyano-4,7-dihydro-2H-pyrazolo[3,4-b]pyridine To a solution of ethyl isonipecotate (8.0 g) in THF (100 mL) was added triethylamine (5.7 g), dimethylaminopyridine (0.6 g) and acetyl chloride (4.4 g) at 0° C. and the mixture was stirred for an hour. The mixture was extracted with ethyl acetate and the solvent was evaporated under reduced pressure to give ethyl 1-acetylpiperidine-4-carboxylate (10 g) as a colorless oil. To a solution of acetonitrile (2.5 g) in THF (300 mL) was added n-BuLi (57 mmol) at −78° C. Further, ethyl 1-acetylpiperidine-4-carboxylate (10 g) was added and the mixture was stirred for an hour. After acidification with hydrochloric acid, the mixture was extracted with ethyl acetate. The solvent was evaporated under reduced pressure and the residue was purified by silica gel column chromatography (eluent:hexane-ethyl acetate (10:1)) to give 1-(1-acetylpiperidin-4-yl)-2-cyanoethan-1-one (7.5 g) as a colorless oil. A solution of 2,1,3-benzoxadiazole-4-aldehyde (0.3 g), 3-aminopyrazole (0.17 g) and 1-(1-acetylpiperidin-4-yl)-2-cyanoethan-1-one (0.4 g) in acetonitrile (10 mL) was heated under reflux overnight. The reaction mixture was cooled to room temperature, and the precipitated crystals were collected by filtration to give the title compound (0.49 g) as yellow crystals.

MP: 248° C.

MS (FAB): 340 (M++1).

¹H-NMR (400 MHz, DMSO-d₆) δ (ppm): 1.62–1.64 (2H, m), 1.82–1.84 (1H, m), 2.00–2.02 (4H, m), 2.49–2.50 (1H, m), 2.94–3.07 (2H, m), 3.89–3.92 (1H, m), 4.48–4.51 (1H, m), 5.40 (1H, s), 7.27 (1H, s), 7.42 (1H, d, J=6.6 Hz), 7.59 (1H, dd, J=9.0 Hz and 6.6 Hz), 7.92 (1H, d, J=9.0 Hz), 9.81 (1H, brs), 12.18 (1H, brs).

Example 1026

4-(2,1,3-Benzoxadiazol-4-yl)-6-(1-benzoylpiperidin-4-yl)-5-cyano-4,7-dihydro-2H-pyrazolo[3,4-b]pyridine The title compound was prepared from benzoylchloride, ethyl isonipecotate, 2,1,3-benzoxadiazole-4-aldehyde and 3-aminopyrazole in the same manner as in Example 1025.

MP: 228° C.

MS (FAB):452 (M++1).

¹H-NMR (400 MHz, DMSO-d₆) δ (ppm): 1.59–1.76 (2H, m), 2.04–2.08 (2H, m), 2.76–2.80 (1H, m), 3.01–3.09 (2H, m), 3.58–3.60 (1H, m), 4.60–4.63 (1H, m), 5.41 (1H, s), 7.28 (1H, s), 7.43–7.46 (6H, m), 7.56–7.59 (1H, m), 7.92 (1H, d, J=9.0 Hz), 9.90 (1H, brs), 12.21 (1H, brs).

Example 1027

6-(1-Acetyl-1,2,3,6-tetrahydropyridin-4-yl)-4-(2,1,3-benzoxadiazol-4-yl)-5-cyano-4,7-dihydro-2H-pyrazolo[3,4-b]-pyridine The title compound was prepared from acetyl chloride, ethyl 1,2,3,6-tetrahydropyridine-4-carboxylate, 2,1,3-benzoxadiazole-4-aldehyde and 3-aminopyrazole in the same manner as in Example 1025.

MP: 237° C.

MS (EI): 387 (M+).

¹H-NMR (400 MHz, DMSO-d₆) δ (ppm): 2.00 and 2.04 (3H, s), 2.46–2.49 (2H, m), 3.55–3.58 (2H, m), 4.00–4.06 (2H, m), 5.44 (1H, s), 6.10 (1H, s), 7.29 (1H, s), 7.45 (1H, d, J=6.6 Hz), 7.59 (1H, dd, J=9.0 Hz and 6.6 Hz), 7.93 (1H, d, J=9.0 Hz), 9.94 (1H, brs), 12.17 (1H, brs).

Example 1028

4-(2,1,3-Benzoxadiazol-4-yl)-5-cyano-4,7-dihydro-6-(1-(ethoxycarbonyl)piperidin-4-yl)-2H-pyrazolo[3,4-b]pyridine The title compound was prepared from ethyl chloroformate, ethyl isonipecotate, 2,1,3-benzoxadiazole-4- aldehyde and 3-aminopyrazole in the same manner as in Example. 1025.

MS (EI): 419 (M$^+$).

$^1$H-NMR (400 MHz, DMSO-d$_6$) δ (ppm): 1.19 (3H, t, J=7.3 Hz), 1.61–1.63 (2H, m), 1.90–1.94 (2H, m), 2.84–2.88 (3H, m), 4.02–4.07 (4H, m), 5.40 (1H, s), 7.26 (1H, s), 7.41 (1H, d, J=6.6 Hz), 7.58 (1H, dd, J=9.0 Hz and 6.6 Hz), 7.92 (1H, d, J=9.0 Hz), 9.80 (1H, brs), 12.17 (1H, brs).

Example 1029

4-(2,1,3-Benzoxadiazol-4-yl)-5-cyano-4,7-dihydro-6-(1-methanesulfonylpiperidin-4-yl)-2H-pyrazolo[3,4-b]pyridine The title compound was prepared from methanesulfonylchloride, ethyl isonipecotate 2,1,3-benzoxadiazole-4-aldehyde and 3-aminopyrazole in the same manner as in Example 1025.

MP: 243° C.

MS (EI): 425 (M$^+$).

$^1$H-NMR (400 MHz, DMSO-d$_6$) δ (ppm): 1.73–1.76 (2H, m), 2.04–2.08 (2H, m), 2.74–2.78 (3H, m), 2.88 (3H, s), 3.66–3.69 (2H, m), 5.41 (1H, s), 7.27 (1H, s), 7.42 (1H, d, J=6.6 Hz), 7.58 (1H, dd, J=9.0 Hz and 6.6 Hz), 7.93 (1H, d, J=9.0 Hz), 9.84 (1H, brs), 12.20 (1H, brs).

Example 1030

4-(2,1,3-Benzoxadiazol-4-yl)-5-cyano-4,7-dihydro-6-(1-(N,N-dimethylaminocarbonyl)piperidin-4-yl)-2H-pyrazolo[3,4-b]-pyridine The title compound was prepared from 1-chloro-N,N-dimethylformamide, ethyl isonipecotate, 2,1,3-benzoxadiazole-4-aldehyde and 3-aminopyrazole in the same manner as in Example 1025.

MS (EI): 418 (M$^+$).

$^1$H-NMR (400 MHz, DMSO-d$_6$) δ (ppm): 1.61–1.63 (2H, m), 2.00–2.06 (2H, m), 2.65–2.67 (2H, m), 2.75 (6H, s), 2.81–2.85 (1H, m), 3.64–3.67 (2H, m), 5.40 (1H, s), 7.27 (1H, s), 7.41 (1H, d, J=6.6 Hz), 7.59 (1H, dd, J=9.0 Hz and 6.6 Hz), 7.92 (1H, d, J=9.0 Hz), 9.86 (1H, brs), 12.18 (1H, brs).

Example 1031

4-(2,1,3-Benzoxadiazol-4-yl)-5-cyano-4,7-dihydro-6-(1-guanylpiperidin-4-yl)-2H-pyrazolo[3,4-b]pyridine To a solution of 4-(2,1,3-benzoxadiazol-4-yl)-5-cyano-4,7-dihydro-6-(piperidin-4-yl)-2H-pyrazolo[3,4-b]pyridine (1.5 g) in MeOH (30 mL) was added diisopropylethylamine (4.2 g), and 1H-pyrazole-1-carboxamidine hydrochloride (0.96 g) at room temperature and the mixture was stirred overnight. The precipitated crystals were collected by filtration to give the title compound (1.0 g) as yellow crystals.

MP: >270° C.

MS (EI): 389 (M$^+$).

$^1$H-NMR (400 MHz, DMSO-d$_6$) δ (ppm): 1.53–1.56 (2H, m), 1.86–1.91 (2H, m), 2.47–2.50 (2H, m), 2.71–2.77 (1H, m), 3.00–3.03 (2H, m), 3.32–3.36 (3H, br), 5.39 (1H, s), 7.26 (1H, s), 7.39 (1H, d, J=6.6 Hz), 7.59 (1H, dd, J=9.0 Hz and 6.6 Hz), 7.91 (1H, d, J=9.0 Hz), 9.79 (1H, brs), 12.21 (1H, brs).

Example 1032

6-(1-Acetylpiperidin-3-yl)-4-(2,1,3-benzoxadiazol-4-yl)-5-cyano-4,7-dihydro-2H-pyrazolo[3,4-b]pyridine The title compound was prepared from acetyl chloride, ethyl nipecotate, 2,1,3-benzoxadiazole-4-aldehyde and 3-aminopyrazole in the same manner as in Example 1025.

MP: 219° C.

Anal. Calcd. For: C$_{20}$H$_{19}$N$_7$O$_2$: C, 61.69; H, 4.92; N, 25.18. Found: C, 61.36; H, 4.90; N, 25.12.

MS (EI): 389 (M$^+$).

$^1$H-NMR (400 MHz, DMSO-d$_6$) δ (ppm): 1.25–1.49 (1H, m), 1.74–1.78 (2H, m), 2.00 (3H, s), 2.01–2.04 (1H, m), 2.49–2.98 (3H, m), 3.78–3.81 (1H, m), 4.37–4.40 (1H, m), 5.29 and 5.42 (1H, s), 7.28 (1H, s), 7.41–7.48 (1H, m), 7.58–7.62 (1H, m), 7.92–7.95 (1H, m), 9.90 (1H, brs), 12.21 (1H, brs)

Example 1033

4-(2,1,3-Benzoxadiazol-4-yl)-5-cyano-4,7-dihydro-6-(1-ethylpiperidin-4-yl)-2H-pyrazolo[3,4-b]pyridine The title compound was prepared from 4-(2,1,3-benzoxadiazol-4-yl)-5-cyano-4,7-dihydro-6-(piperidin-4-yl)-2H-pyrazolo[3,4-b]pyridine and acetaldehyde in the same manner as in Example 1003.

MP: 231° C.

MS (EI): 375 (M$^+$).

$^1$H-NMR (400 MHz, DMSO-d$_6$) δ (ppm): 0.99 (3H, t, J=7.3 Hz), 1.60–1.63 (2H, m), 1.85–1.88 (2H, m), 2.00–2.04 (2H, m), 2.31–2.34 (2H, m), 2.64–2.66 (1H, m), 2.97–3.00 (2H, m), 5.39 (1H, s), 7.26 (1H, s), 7.40 (1H, d, J=6.6 Hz), 7.58 (1H, dd, J=9.0 Hz and 6.6 Hz), 7.92 (1H, d, J=9.0 Hz), 9.75 (1H, brs), 12.18 (1H, brs).

Example 1034

4-(2,1,3-Benzoxadiazol-4-yl)-5-cyano-4,7-dihydro-6-(1-propylpiperidin-4-yl)-2H-pyrazolo[3,4-b]pyridine The title compound was prepared from 4-(2,1,3-Benzoxadiazol-4-yl)-5-cyano-4,7-dihydro-6-(piperidin-4-yl)-2H-pyrazolo[3,4-b]pyridine and propionaldehyde in the same manner as in Example 1003.

MP: 246° C.

Anal. Calcd. For: C$_{21}$H$_{23}$N$_7$O: C, 64.76; H, 5.95; N, 25.18. Found: C, 64.23; H, 5.87; N, 24.86.

MS (EI): 389 (M$^+$).

$^1$H-NMR (400 MHz, DMSO-d$_6$) δ (ppm): 0.84 (3H, t, J=7.3 Hz), 1.40–1.45 (2H, m), 1.59–1.62 (2H, m), 1.82–1.86 (2H, m), 2.00–2.05 (2H, m), 2.21 (2H, t, J=7.3 Hz), 2.62–2.65 (1H, m), 2.94–2.97 (2H, m), 5.39 (1H, s), 7.26 (1H, s), 7.40 (1H, d, J=6.6 Hz), 7.58 (1H, dd, J=9.0 Hz and 6.6 Hz), 7.91 (1H, d, J=9.0 Hz), 9.77 (1H, brs), 12.18 (1H, brs).

Example 1035

4-(2,1,3-Benzoxadiazol-4-yl)-5-cyano-4,7-dihydro-6-(1-iso-propylpiperidin-4-yl)-2H-pyrazolo[3,4-b]pyridine The title compound was prepared from 4-(2,1,3-benzoxadiazol-4-yl)-5-cyano-4,7-dihydro-6-(piperidin-4-yl)-2H-pyrazolo[3,4-b]pyridine and acetone in the same manner as in Example 1003.

MP: 260° C.

MS (EI): 389 (M$^+$).

$^1$H-NMR (400 MHz, DMSO-d$_6$) δ (ppm): 1.22 (6H, d, J=7.3 Hz), 1.82–3.42 (10H, m), 5.40 (1H, s), 7.27 (1H, s), 7.42 (1H, d, J=6.6 Hz), 7.59 (1H, dd, J=9.0 Hz and 6.6 Hz), 7.92 (1H, d, J=9.0 Hz), 9.66 (1H, brs), 12.22 (1H, brs).

Example 1036

4-(2-Bromo-3-cyanophenyl)-6-(1-t-butoxycarbonylpiperidin-4-yl)-5-cyano-4,7-dihydro-2H-pyrazolo[3,4-b]pyridine The title compound was prepared from ethyl isonipecotate, 2-bromo-3-cyanobenzaldehyde and 3-aminopyrazole in the same manner as in Example 1001.

MP: >270° C.

Anal. Calcd. For: $C_{24}H_{25}BrN_6O_2$: C, 56.59; H, 4.95; N, 16.50. Found: C, 56.47; H, 4.87; N, 16.52.

MS (EI): 509 (M$^+$).

$^1$H-NMR (400 MHz, DMSO-d$_6$) δ (ppm): 1.41 (9H, s), 1.59–1.66 (2H, m), 1.85–1.90 (2H, m), 2.65–2.82 (3H, m), 4.05–4.07 (2H, m), 5.47 (1H, s), 7.33 (1H, s), 7.56–7.60 (2H, m), 7.84 (1H, d, J=7.3 Hz), 9.81 (1H, brs), 12.26 (1H, brs).

Example 1037

4-(2-Bromo-3-cyanophenyl)-5-cyano-4,7-dihydro-6-(piperidin-4-yl)-2H-pyrazolo[3,4-b]pyridine The title compound was prepared from 4-(2-bromo-3-cyano-phenyl)-6-(1-t-butoxycarbonylpiperidin-4-yl)-5-cyano-4,7-dihydro-2H-pyrazolo[3,4-b]pyridine in the same manner as in Example 1002.

MP: >270° C.

MS (EI): 409 (M$^+$).

$^1$H-NMR (400 MHz, DMSO-d$_6$) δ (ppm): 1.53–1.56 (2H, m), 1.83–1.87 (2H, m), 2.46–2.50 (3H, m), 2.71–2.74 (1H, m), 3.00–3.04 (1H, m), 5.45 (1H, s), 7.32 (1H, s), 7.56–7.58 (2H, m), 7.81 (1H, d, J=7.3 Hz), 9.74 (1H, brs), 12.26 (1H, brs)

Example 1038

4-(2-Bromo-3-cyanophenyl)-5-cyano-4,7-dihydro-6-(1-methylpiperidin-4-yl)-2H-pyrazolo[3,4-b]pyridine The title compound was prepared from 4-(2-bromo-3-cyano-phenyl)-5-cyano-4,7-dihydro-6-(piperidin-4-yl)-2H-pyrazolo-[3,4-b]pyridine in the same manner as in Example 1003.

MP: >270° C.

MS (EI): 423 (M$^+$).

$^1$H-NMR (400 MHz, DMSO-d$_6$) δ (ppm): 1.65–1.71 (2H, m), 2.02–2.08 (3H, m), 2.29 (3H, s), 2.48–2.52 (1H, m), 1.66–1.69 (1H, m), 2.95–2.98 (2H, m), 5.50 (1H, s), 7.34 (1H, s), 7.55–7.57 (2H, m), 7.83 (1H, d, J=7.3 Hz), 9.83 (1H, brs), 12.32 (1H, brs).

Example 1039

4-(2-Bromo-3-cyanophenyl)-6-(1-t-butoxycarbonylpiperidin-3-yl)-5-cyano-4,7-dihydro-2H-pyrazolo[3,4-b]pyridine The title compound was prepared from ethyl nipecotate, 2-bromo-3-cyanobenzaldehyde and 3-aminopyrazole in the same manner as in Example 1001.

MP: 238° C.

Anal. Calcd. For: $C_{24}H_{25}BrN_6O_2$: C, 56.56; H, 4.95; N, 16.50. Found: C, 56.49; H, 4.85; N, 16.50.

MS (EI): 509 (M$^+$).

$^1$H-NMR (400 MHz, DMSO-d$_6$) δ (ppm): 1.37 and 1.39 (9H, s), 1.68–2.06 (4H, m), 2.65–2.75 (2H, m), 3.30–3.32 (1H, m), 3.94–3.97 (2H, m), 5.47 and 5.49 (1H, s), 7.34 (1H, s), 7.58–7.61 (2H, m), 7.82–7.86 (1H, m), 9.89 (1H, brs), 12.31 (1H, brs).

Example 1040

4-(2-Bromo-3-cyanophenyl)-5-cyano-4,7-dihydro-6-(piperidin-3-yl)-2H-pyrazolo[3,4-b]pyridine trifluoroacetate The title compound was prepared from 4-(2-bromo-3-cyano-phenyl)-6-(1-t-butoxycarbonylpiperidin-3-yl)-5-cyano-4,7-dihydro-2H-pyrazolo[3,4-b]pyridine in the same manner as in Example 1021.

MP: 225° C.

Anal. Calcd. For: $C_{19}H_{17}BrN_6CF_3COOH$: C, 48.20; H, 3.47; N, 16.06. Found: C, 47.98; H, 3.52; N, 15.97.

MS (EI): 409 (M$^+$).

$^1$H-NMR (400 MHz, DMSO-d$_6$) δ (ppm): 1.68–1.98 (4H, m), 2.65–2.68 (1H, m), 3.21–3.33 (4H, m), 5.50 (1H, s), 7.35 (1H, s), 7.55–7.66 (2H, m), 7.84–7.87 (1H, m), 8.54 (1H, br), 8.96 (1H, br), 9.96 (1H, brs), 12.36 (1H, br)

Example 1041

4-(2-Bromo-3-cyanophenyl)-5-cyano-4,7-dihydro-6-(1-methylpiperidin-3-yl)-2H-pyrazolo[3,4-b]pyridine The title compound was prepared from 4-(2-bromo-3-cyano-phenyl)-5-cyano-4,7-dihydro-6-(piperidin-3-yl)-2H-pyrazolo-[3,4-b]pyridine trifluoroacetate in the same manner as in Example 1003.

MP: 174° C.

MS (EI): 423 (M$^+$).

$^1$H-NMR (400 MHz, DMSO-d$_6$) δ (ppm): 1.54–1.78 (4H, m), 2.18–2.20 (1H, m), 2.20 (3H, s), 2.55–2.58 (2H, m), 2.94–2.96 (1H, m), 3.31–3.34 (1H, m), 5.47 (1H, s), 7.33 (1H, s), 7.57–7.58 (2H, m), 7.84 (1H, d, J=7.3 Hz), 10.06 (1H, brs), 12.29 (1H, brs).

Example 1042

4-(2-Bromo-3-cyanophenyl)-6-(1-t-butoxycarbonylpiperidin-2-yl)-5-cyano-4,7-dihydro-2H-pyrazolo[3,4-b]pyridine The title compound was prepared from ethyl pipecolinate, 2-bromo-3-cyanobenzaldehyde and 3-aminopyrazole in the same manner as in Example 1001.

MS (EI): 509 (M$^+$).

$^1$H-NMR (400 MHz, DMSO-d$_6$) δ (ppm): 1.35 (9H, s), 1.34–1.90 (6H, m), 3.48–3.52 (2H, m), 4.42–4.48 (1H, m), 5.43 and 5.46 (1H, s), 7.36–7.39 (1H, m), 7.53–7.57 (2H, m), 7.80–7.83 (1H, m), 9.68 and 9.82 (1H, brs), 12.26 (1H, brs).

Example 1043

4-(2-Bromo-3-cyanophenyl)-5-cyano-4,7-dihydro-6-(piperidin-2-yl)-2H-pyrazolo[3,4-b]pyridine trifluoroacetate The title compound was prepared from 4-(2-bromo-3-cyano-25 phenyl)-6-(1-t-butoxycarbonylpiperidin-2-yl)-5-cyano-4,7-dihydro-2H-pyrazolo[3,4-b]pyridine in the same manner as in Example 1021.

MP: 232° C.

MS (EI): 409 (M$^+$).

¹H-NMR (400 MHz, DMSO-d$_6$) δ (ppm): 1.27–1.98 (5H, m), 2.47–2.51 (2H, m), 3.12–3.18 (1H, m), 4.7–4.10 (1H, m), 4.50–4.57 (1H, m), 7.40–7.63 (3H, m), 7.79–7.82 (2H, m), 8.06 (1H, br), 10.93 (1H, brs), 12.41 (1H, brs).

Example 1044

4-(2-Bromo-3-cyanophenyl)-6-(4-t-butoxycarbonylmorpholin-2-yl)-5-cyano-4,7-dihydro-2H-pyrazolo[3,4-b]pyridine The title compound was prepared from ethyl morpholine-2-carboxylate, 2-bromo-3-cyanobenzaldehyde and 3-amino-pyrazole in the same manner as in Example 1001.

MP: 219° C.

MS (EI): 511 (M$^+$).

¹H-NMR (400 MHz, DMSO-d$_6$) δ (ppm): 1.40 (9H, s), 2.97–3.10 (2H, m), 3.47–3.53 (1H, m), 3.77–3.94 (3H, m), 4.37–4.39 (1H, m), 5.52 and 5.54 (1H, s), 7.34–7.36 (1H, m), 7.58–7.65 (2H, m), 7.94–7.96 (1H, m), 9.87 and 9.92 (1H, brs), 12.33 (1H, brs).

Example 1045

4-(2-Bromo-3-cyanophenyl)-5-cyano-4,7-dihydro-6-(morpholin-2-yl)-2H-pyrazolo[3,4-b]pyridine trifluoroacetate The title compound was prepared from 4-(2-bromo-3-cyano-phenyl)-6-(4-t-butoxycarbonylmorpholin-2-yl)-5-cyano-4,7-dihydro-2H-pyrazolo[3,4-b]pyridine in the same manner as in Example 1021.

MP: 236° C.

MS (EI): 411 (M$^+$).

¹H-NMR (400 MHz, DMSO-d$_6$) δ (ppm): 3.02–3.05 (1H, m), 3.24–3.33 (3H, m), 3.80–3.84 (1H, m), 4.08–4.11 (1H, m), 4.82–4.85 (1H, m), 5.55 (1H, s), 7.36 (1H, s), 7.55–7.62 (2H, m), 7.84–7.87 (1H, m), 9.14 (2H, br), 10.04–10.09 (1H, brs), 12.40 (1H, brs).

Example 1046

4-(2-Bromo-3-cyanophenyl)-5-cyano-4,7-dihydro-6-(4-methylmorpholin-2-yl)-2H-pyrazolo[3,4-b]pyridine The title compound was prepared from 4-(2-bromo-3-cyano-phenyl)-5-cyano-4,7-dihydro-6-(morpholin-2-yl)-2H-pyrazolo-[3,4-b]pyridine trifluoroacetate in the same manner as in Example 1003.

MP: 180° C.

MS (EI): 425 (M$^+$).

¹H-NMR (400 MHz, DMSO-d$_6$) δ (ppm): 2.18–2.20 (1H, m), 2.20 and 2.21 (3H, s), 2.26–2.29 (1H, m), 2.58–2.62 (1H, m), 2.75–2.78 (1H, m), 3.58–3.62 (1H, m), 3.88–3.91 (1H, m), 4.48–4.50 (1H, m), 5.51 (1H, s), 7.35 (1H, s), 7.56–7.61 (2H, m), 7.84–7.86 (1H, m), 9.81 and 9.84 (1H, brs), 12.31 (1H, brs).

Example 1047

4-(2-Bromo-3-cyanophenyl)-5-cyano-4,7-dihydro-6-(1,2,3,6-tetrahydropyridin-4-yl)-2H-pyrazolo[3,4-b]pyridine The title compound was prepared from ethyl 1,2,3,6-tetrahydropyridine-4-carboxylate, 2-bromo-3-cyanobenzaldehyde and 3-aminopyrazole in the same manner as in Example 1001, and Example 1002 followed.

MP: 226° C.

MS (EI): 407 (M$^+$).

¹H-NMR (400 MHz, DMSO-d$_6$) δ (ppm): 2.36–2.40 (2H, m), 2.95–2.98 (2H, m), 3.56–3.60 (3H, m), 5.51 (1H, s), 6.15 (1H, s), 7.34 (1H, s), 7.56–7.60 (2H, m), 7.84 (1H, d, J=7.3 Hz), 9.93 (1H, brs), 12.32 (1H, brs).

Example 1048

4-(2-Bromo-3-cyanophenyl)-5-cyano-4,7-dihydro-6-(1-methyl-1,2,3,6-tetrahydropyridin-4-yl)-2H-pyrazolo[3,4-b]pyridine The title compound was prepared from 4-(2-bromo-3-cyano-phenyl)-5-cyano-4,7-dihydro-6-(1,2,3,6-tetrahydropyridin-4-yl)-2H-pyrazolo[3,4-b]pyridine in the same manner as in Example 1003.

MP: 233° C.

MS (EI): 421 (M$^+$).

¹H-NMR (400 MHz, DMSO-d$_6$) δ (ppm): 2.31 (3H, s), 2.56–2.67 (4H, m), 3.00–3.03 (2H, m), 5.50 (1H, s), 6.10 (1H, s), 7.34 (1H, s), 7.58–7.60 (2H, m), 7.83 (1H, d, J=7.3 Hz), 9.91 (1H, brs), 12.29 (1H, brs).

Example 1049

4-(2-Bromo-3-cyanophenyl)-6-((N-t-butoxycarbonyl-N-methyl-amino)methyl)-5-cyano-4,7-dihydro-2H-pyrazolo[3,4-b]pyridine The title compound was prepared from glycine ethyl ester hydrochloride, 2-bromo-3-cyanobenzaldehyde and 3-amino-pyrazole in the same manner as in Example 1015.

MS (EI): 469 (M$^+$).

¹H-NMR (400 MHz, DMSO-d$_6$) δ (ppm): 1.39 (9H, s), 2.85 (3H, s), 4.15–4.18 (2H, m), 5.49 (1H, s), 7.37 (1H, s), 7.56–7.57 (2H, m), 7.83 (1H, d, J=7.3 Hz), 9.78–9.93 (1H, br), 12.31 (1H, brs).

Example 1050

4-(2-Bromo-3-cyanophenyl)-5-cyano-4,7-dihydro-6-((N-methyl-amino)methyl)-2H-pyrazolo[3,4-b]pyridine trifluoracetate The title compound was prepared from 4-(2-bromo-3-cyano-phenyl)-6-((N-t-butoxycarbonyl-N-methylamino)methyl)-5-cyano-4,7-dihydro-2H-pyrazolo[3,4-b]pyridine in the same manner as in Example 1021.

MP: 258° C.

MS (EI): 369 (M$^+$).

¹H-NMR (400 MHz, DMSO-d$_6$) δ (ppm): 3.10 (3H, s), 4.46–4.66 (2H, m), 5.50 (1H, s), 7.47–7.48 (2H, m), 7.65 (1H, s), 7.80–7.81 (2H, m), 8.09 (1H, br), 10.81 (1H, brs), 12.38 (1H, brs).

Example 1051

6-(1-Acetylpiperidin-4-yl)-4-(2-bromo-3-cyanophenyl)-5-cyano-4,7-dihydro-2H-pyrazolo[3,4-b]pyridine The title compound was prepared from acetyl chloride, ethyl isonipecotate, 2-bromo-3-cyanobenzaldehyde and 3-aminopyrazole in the same manner as in Example 1025.

MP: >280° C.

MS (EI): 451 (M$^+$).

¹H-NMR (400 MHz, DMSO-d$_6$) δ (ppm): 1.63–1.82 (3H, m), 1.98–2.00 (1H, m), 2.00 (3H, s), 2.49–2.51 (1H, m), 2.94–3.10 (2H, m), 3.89–3.91 (1H, m), 4.48–4.50 (1H, m), 5.47 (1H, s), 7.34 (1H, s), 7.56–7.58 (2H, m), 7.84 (1H, d, J=7.3 Hz), 9.81 (1H, brs), 12.27 (1H, brs).

Example 1052

6-(1-Benzoylpiperidin-4-yl)-4-(2-bromo-3-cyanophenyl)-5-cyano-4,7-dihydro-2H-pyrazolo[3,4-b]pyridine The title compound was prepared from benzoyl chloride, ethyl isonipecotate, 2-bromo-3-cyanobenzaldehyde and 3-aminopyrazole in the same manner as in Example 1025.

MP: >280° C.

MS (FAB):514 (M$^+$+1).

¹H-NMR (400 MHz, DMSO-d$_6$) δ (ppm): 1.64–2.04 (4H, m), 2.76–2.80 (1H, m), 3.05–3.10 (2H, m), 3.60–3.63 (1H, m), 4.62–4.65 (1H, m), 5.48 (1H, s), 7.34–7.58 (8H, m), 7.84 (1H, d, J=7.3 Hz), 9.90 (1H, brs), 12.31 (1H, brs).

Example 1053

4-(2-Bromo-3-cyanophenyl)-5-cyano-4,7-dihydro-6-(1-methanesulfonylpiperidin-4-yl)-2H-pyrazolo[3,4-b]pyridine The title compound was prepared from methanesulfonyl chloride, ethyl isonipecotate, 2-bromo-3-cyanobenzaldehyde and 3-aminopyrazole in the same manner as in Example 1025.

MP: >280° C.

MS (EI): 487 (M$^+$).

¹H-NMR (400 MHz, DMSO-d$_6$) δ (ppm): 1.75–2.07 (4H, m), 2.76–2.79 (2H, m), 2.89 (3H, s), 3.66–3.69 (2H, m), 5.48 (1H, s), 7.34 (1H, s), 7.56–7.58 (2H, m), 7.84 (1H, d, J=7.3 Hz), 9.84 (1H, brs), 12.30 (1H, brs).

Example 1054

6-(1-t-Butoxycarbonylpiperidin-4-yl)-4-(2-chlorophenyl)-5-cyano-4,7-dihydro-2H-pyrazolo[3,4-b]pyridine The title compound was prepared from ethyl isonipecotate, 2-chlorobenzaldehyde and 3-aminopyrazole in the same manner as in Example 1001.

MP: >280° C.

Anal. Calcd. For: C$_{23}$H$_{26}$ClN$_5$O$_2$: C, 62.79; H, 5.96; N, 15.92. Found: C, 62.81; H, 5.87; N, 16.01.

MS (EI): 439 (M$^+$).

¹H-NMR (400 MHz, DMSO-d$_6$) δ (ppm): 1.41 (9H, s), 1.58–1.67 (2H, m), 1.86–1.91 (2H, m), 2.84–2.90 (3H, m), 4.06–4.09 (2H, m), 5.35 (1H, s), 7.21–7.33 (4H, m), 7.42 (1H, d, J=7.3 Hz), 9.69 (1H, brs), 12.18 (1H, brs).

Example 1055

4-(2-Chlorophenyl)-5-cyano-4,7-dihydro-6-(piperidin-4-yl)-2H-pyrazolo[3,4-b]pyridine The title compound was prepared from 6-(1-t-butoxycarbonylpiperidin-4-yl)-4-(2-chlorophenyl)-5-cyano-4,7-dihydro-2H-pyrazolo[3,4-b]pyridine in the same manner as in Example 1002.

MP: 221° C.

MS (EI): 339 (M$^+$).

¹H-NMR (400 MHz, DMSO-d$_6$) δ (ppm): 1.84–1.92 (2H, m), 2.10–2.16 (2H, m), 2.96–3.00 (3H, m), 3.30–3.40 (2H, m), 5.36 (1H, s), 7.22–7.33 (4H, m), 7.42 (1H, d, J=7.2 Hz), 8.56 (1H, br), 9.76 (1H, brs), 12.26 (1H, brs).

Example 1056

4-(2-Chlorophenyl)-5-cyano-4,7-dihydro-6-(1-methylpiperidin-4-yl)-2H-pyrazolo[3,4-b]pyridine The title compound was prepared from 4-(2-chlorophenyl)-5-cyano-4,7-dihydro-6-(piperidin-4-yl)-2H-pyrazolo[3,4-b]-pyridine trifluoroacetate in the same manner as in Example 1003.

MP: >270° C.

Anal. Calcd. For: C$_{19}$H$_{20}$ClN$_5$: C, 64.49; H, 5.70; N, 19.79. Found: C, 64.71; H, 5.68; N, 19.59.

MS (EI): 353 (M$^+$).

¹H-NMR (400 MHz, DMSO-d$_6$) δ (ppm): 1.56–1.65 (2H, m), 1.84–1.90 (2H, m), 2.02–2.06 (2H, m), 2.16 (3H, s), 2.60–2.65 (1H, m), 2.85–2.88 (2H, m), 5.34 (1H, s), 7.21–7.33 (4H, m), 7.41 (1H, d, J=7.3 Hz), 9.63 (1H, brs), 12.17 (1H, brs).

Example 1057

2-Acetyl-6-(1-acetylpiperidin-4-yl)-4-(2-chlorophenyl)-5-cyano-4,7-dihydro-2H-pyrazolo[3,4-b]pyridine To a solution of 4-(2-chlorophenyl)-5-cyano-4,7-dihydro-6-(piperidin-4-yl)-2H-pyrazolo[3,4-b]pyridine (1.0 g) in pyridine (1.2 mL) was added acetic anhydride (0.42 mL) at room temperature and the mixture was stirred for two hours. The mixture was evaporated under reduced pressure and the residue was washed with methanol and the precipitated crystals were collected by filtration to give the title compound (0.6 g) as colorless crystals.

MS (EI): 423 (M$^+$).

¹H-NMR (400 MHz, DMSO-d$_6$) δ (ppm): 1.58–1.70 (2H, m), 1.91–1.96 (1H, m), 1.99–2.00 (1H, m), 2.02 (3H, s), 2.51 (3H, s), 2.55–2.58 (1H, m), 3.11–3.18 (2H, m), 3.91–3.94 (1H, m), 4.49–4.52 (1H, m), 5.37 (1H, s), 7.32–7.37 (3H, m), 7.48 (1H, d, J=7.3 Hz), 7.84 (1H, s), 10.24 (1H, brs).

Example 1058

4-(2,1,3-Benzoxadiazol-4-yl)-5-cyano-4,7-dihydro-6-(2-oxocyclohexan-1-yl)-2H-pyrazolo[3,4-b]pyridine To a solution of ethyl 2-cyclohexanonecarboxylate (25 g) in toluene (200 mL) was added ethyleneglycol (10.1 g) and p-toluenesulfonic acid (2.8 g) at room temperature and the mixture was heated under reflux with Dean-Stark apparatus for five hours. The reaction mixture was cooled to room temperature, the solvent was evaporated under reduced pressure and the residue was purified by silica gel column chromatography (eluent:hexane-ethyl acetate (10:1)) to give ethyl 1,4-dioxa-spiro[4,5]decane-6-carboxylate (31 g) as a colorless oil. To a solution of acetonitrile (7.2 g) in THF (700 mL) was added n-BuLi (160 mmol) at −78° C. Further, ethyl 1,4-dioxa-spiro[4,5]decane-6-carboxylate (31 g) was added and the mixture was stirred for an hour. After acidification with hydrochloric acid, the mixture was extracted with ethyl acetate. The solvent was evaporated under reduced pressure and the residue was purified by silica gel column chromatography (eluent:hexane-ethyl acetate (10:1)) to give 1-cyano-2-(1,4-dioxa-spiro[4,5]decan-6-yl)ethan-2-one (14.5 g) as a colorless oil. A solution of 2,1,3-benzoxadiazole-4-aldehyde (0.8 g), 3-aminopyrazole (0.5 g) and 1-cyano-2-(1,4-dioxa-spiro[4,5]-decan-6-yl)ethan-2-one (1.2 g) in acetonitrile (10 mL) was heated under reflux overnight. The reaction mixture was cooled to room temperature, and the precipitated crystals were collected by filtration to give 4-(2,1,3-benzoxadiazol-4-yl)-5-cyano-4,7-dihydro-6-(1,4-dioxa-spiro[4,5]decan-6-yl)-2H-pyrazolo[3,4-b]pyridine (1.3 g) as colorless crystals.

To a solution of 4-(2,1,3-Benzoxadiazol-4-yl)-5-cyano-4,7-dihydro-6-(1,4-dioxa-spiro[4,5]decan-6-yl)-2H-pyrazolo[3,4-b]pyridine (1.0 g) in methanol (30 mL) was added 4N HCl dioxane solution (6.0 mL) at room temperature and the mixture was heated at 60° C. for two hours. After alkalification with sodium bicarbonate, the mixture was extracted with chloroform. The solvent was evaporated under reduced pressure and the residue was purified by silica gel column chromatography (eluent:hexane-ethyl acetate (1:1)) to give the title compound (20 mg) as colorless crystals.

MP: >270° C.

MS (EI): 360 (M$^+$).

$^1$H-NMR (400 MHz, DMSO-d$_6$) δ (ppm): 1.74–1.80 (5H, m), 2.60–2.65 (3H, m), 3.31–3.35 (1H, m), 5.98 (1H, s), 6.92 (1H, d, J=6.6 Hz), 7.39 (1H, s), 7.47 (1H, dd, J=9.0 Hz and 6.6 Hz), 7.84 (1H, d, J=9.0 Hz), 9.33 (1H, brs), 12.15 (1H, brs).

Example 1059

4-(2,1,3-Benzoxadiazol-4-yl)-5-cyano-4,7-dihydro-6-(4-oxocyclohexan-1-yl)-2H-pyrazolo[3,4-b]pyridine The title compound was prepared from ethyl 4-cyclohexanonecarboxylate, 2,1,3-benzoxadiazole-4-aldehyde and 3-aminopyrazole in the same manner as in Example 1058.

MS (FAB):361 (M+1).

$^1$H-NMR (400 MHz, DMSO-d$_6$) δ (ppm): 1.96–2.12 (3H, m), 2.22–2.30 (3H, m), 2.48–2.51 (1H, m), 3.27–3.31 (2H, m), 5.42 (1H, s), 7.26 (1H, s), 7.38–7.46 (1H, m), 7.57–7.61 (1H, m), 7.88–7.95 (1H, m), 9.76 (1H, brs), 12.16 (1H, br).

Example 1060

4-(2,1,3-Benzoxadiazol-4-yl)-5-cyano-4,7-dihydro-6-(2-oxocyclopentan-1-yl)-2H-pyrazolo[3,4-b]pyridine The title compound was prepared from ethyl 2-cyclopentanonecarboxylate, 2,1,3-benzoxadiazole-4-aldehyde and 3-aminopyrazole in the same manner as in Example 1058.

MS (FAB):347 (M$^+$+1).

$^1$H-NMR (400 MHz, DMSO-d$_6$) δ (ppm): 1.60–1.63 (2H, m), 1.86–2.05 (2H, m), 2.31–2.34 (2H, m), 3.43–3.46 (1H, m), 5.47 (1H, s), 7.25 and 7.30 (1H, s), 7.39–7.46 (1H, m), 7.56–7.60 (1H, m), 7.91–7.94 (1H, m), 9.90 (1H, brs), 12.20 (1H, brs)

Example 1061

6-Acetylmethyl-4-(2,1,3-benzoxadiazol-4-yl)-5-cyano-4,7-dihydro-2H-pyrazolo[3,4-b]pyridine The title compound was prepared from ethyl acetoacetate, 2,1,3-benzoxadiazole-4-aldehyde and 3-aminopyrazole in the same manner as in Example 1058.

MP: 200° C.

MS (FAB):321 (M$^+$+1).

$^1$H-NMR (400 MHz, DMSO-d$_6$) δ (ppm): 2.22 (3H, s), 3.63–3.66 (2H, m), 5.48 (1H, s), 7.30 (1H, s), 7.47 (1H, d, J=6.6 Hz), 7.61 (1H, dd, J=9.0 Hz and 6.6 Hz), 7.94 (1H, d, J=9.0 Hz), 10.00 (1H, brs), 12.21 (1H, brs).

Example 1062

4-(2-Bromo-3-cyanophenyl)-5-cyano-4,7-dihydro-6-(2-oxocyclohexan-1-yl)-2H-pyrazolo[3,4-b]pyridine The title compound was prepared from ethyl 2-cyclohexanonecarboxylate, 2-bromo-3-cyanobenzaldehyde and 3-aminopyrazole in the same manner as in Example 1058.

MP: 273° C.

MS (EI): 422 (M$^+$).

$^1$H-NMR (400 MHz, DMSO-d$_6$) δ (ppm): 1.72–1.81 (5H, m), 2.59–2.65 (3H, m), 3.30–3.32 (1H, m), 5.91 (1H, s), 7.05 (1H, d, J=7.3 Hz), 7.40–7.43 (2H, m), 7.52 (1H, s), 7.74 (1H, d, J=7.3 Hz), 9.33 (1H, brs), 12.24 (1H, brs).

Example 1063

6-Acetylmethyl-4-(2-bromo-3-cyanophenyl)-5-cyano-4,7-dihydro-2H-pyrazolo[3,4-b]pyridine The title compound was prepared from ethyl acetoacetate, 2-bromo-3-cyanobenzaldehyde and 3-aminopyrazole in the same manner as in Example 1058.

MP: 230° C.

MS (EI): 382 (M$^+$).

$^1$H-NMR (400 MHz, DMSO-d$_6$) δ (ppm): 2.23 (3H, s), 3.60–3.67 (2H, m), 5.50 (1H, s), 7.39 (1H, s), 7.60 (1H, dd, J=7.3 Hz and 7.2 Hz), 7.70 (1H, d, J=7.3 Hz), 7.83 (1H, d, J=7.3 Hz), 9.97 (1H, brs), 12.29 (1H, brs).

Example 1064

4-(2-Chlorophenyl)-5-cyano-4,7-dihydro-6-(piperidin-4-yl)-2H-pyrazolo[3,4-b]pyridine hydrochloride 4-(2-Chlorophenyl)-5-cyano-4,7-dihydro-6-(1-t-butoxycarbonylpiperidin-4-yl)-2H-pyrazolo[3,4-b]pyridine (2.0 g) was added to 4N-HCl dioxane solution (20 mL) at 0° C. and the mixture was stirred for an hour. The solvent was evaporated under reduced pressure and the residue was washed by ethanol, and the precipitated crystals were collected by filtration to give the title compound (1.2 g) as yellow crystals.

MS (EI): 339 (M$^+$).

$^1$H-NMR (400 MHz, DMSO-d$_6$) δ (ppm): 1.83–1.90 (2H, m), 2.07–2.15 (2H, m), 2.94–2.97 (3H, m), 3.34–3.37 (2H, m), 5.36 (1H, s), 7.22–7.33 (4H, m), 7.42 (1H, d, J=7.3 Hz), 8.41 (1H, br), 9.17 (1H, br), 9.77 (1H, brs), 12.27 (1H, brs).

Example 1065

4-(2,1,3-Benzoxadiazol-4-yl)-5-cyano-4,7-dihydro-6-(piperidin-4-yl)-2H-pyrazolo[3,4-b]pyridine hydrochloride The title compound was prepared from 4-(2,1,3-benzoxadiazol-4-yl)-6-(1-t-butoxycarbonylpiperidin-4-yl)-5-cyano-4,7-dihydro-2H-pyrazolo[3,4-b]pyridine in the same manner as in Example 1064.

MP: >270° C.

Anal. Calcd. For: $C_{18}H_{17}N_7OHCl$: C, 56.09; H, 5.20; N, 24.10. Found: C, 55.80; H, 5.00; N, 23.80.

MS (EI): 347 (M$^+$).

$^1$H-NMR (400 MHz, DMSO-d$_6$) δ (ppm): 1.82–1.85 (2H, m), 2.14–2.20 (2H, m), 2.93–2.99 (3H, m), 3.34–3.36 (2H, m), 5.40 (1H, s), 7.27 (1H, s), 7.43 (1H, d, J=6.6 Hz), 7.58 (1H, dd, J=9.0 Hz and 6.6 Hz), 7.92 (1H, d, J=9.0 Hz), 8.44 (1H, br), 9.21 (1H, br), 9.87 (1H, brs), 12.25 (1H, brs).

Example 1066

4-(2-Bromo-3-cyanophenyl)-5-cyano-4,7-dihydro-6-(piperidin-4-yl)-2H-pyrazolo[3,4-b]pyridine Hydrochloride The title compound was prepared from 4-(2-bromo-3-cyanophenyl)-6-(1-t-butoxycarbonylpiperidin-4-yl)-5-cyano-4,7-dihydro-2H-pyrazolo[3,4-b]pyridine in the same manner as in Example 1064.

MP: >270° C.

MS (EI): 409 (M$^+$).

$^1$H-NMR (400 MHz, DMSO-d$_6$) δ (ppm): 1.84–1.92 (2H, m), 2.07–2.10 (2H, m), 2.92–2.98 (5H, m), 5.48 (1H, s), 7.34 (1H, s), 7.57–7.59 (2H, m), 7.84 (1H, dd, J=7.3 Hz and 7.2 Hz), 8.30 (1H, br), 9.04 (1H, br), 9.90 (1H, brs), 12.35 (1H, br).

Example 1067

4-(2-Bromo-3-cyanophenyl)-5-cyano-6-(1-t-butoxycarbonyl-pyrrolidin-2-yl)-4,7-dihydro-2H-pyrazolo[3,4-b]pyridine The title compound was prepared from ethyl 1-t-butoxycarbonylpyrrolidine-2-carboxylate, 2-bromo-3-cyanobenzaldehyde and 3-aminopyrazole in the same manner as in Example 1001.

MS (EI): 495 (M$^+$).

$^1$H-NMR (400 MHz, DMSO-d$_6$) δ (ppm): 1.47 (9H, s), 1.82–1.97 (4H, m), 2.31 (1H, m), 3.50 (1H, m), 4.53 (1H, m), 5.47 (1H, s), 7.51–7.91 (4H, m), 9.83 (1H, m), 12.26 (1H, s).

Example 1068

4-(2-Bromo-3-cyanophenyl)-5-cyano-6-(pyrrolidin-2-yl)-4,7-dihydro-2H-pyrazolo[3,4-b]pyridine The title compound was prepared from 4-(2-bromo-3-cyano-phenyl)-5-cyano-6-(1-t-butoxycarbonylpyrrolidin-2-yl)-4,7-dihydro-2H-pyrazolo[3,4-b]pyridine in the same manner as in Example 1002.

MP: >240° C.

MS (EI): 395 (M$^+$).

$^1$H-NMR (400 MHz, DMSO-d$_6$) δ (ppm): 1.39–1.55 (1H, m), 1.97 (2H, m), 2.30 (1H, m), 3.32 (2H, m), 4.10–4.28 (1H, m), 5.41 (1H, s), 6.52 (1H, s), 7.34–7.47 (2H, m), 7.70 (1H, dd, J=8.3 Hz and 9.0 Hz), 11.89 (1H, brs).

Example 1069

4-(2,1,3-Benzoxadiazol-4-yl)-6-(1-t-butoxycarbonylpyrrolidin-2-yl)-5-cyano-4,7-dihydro-2H-pyrazolo[3,4-b]pyridine The title compound was prepared from ethyl 1-t-butoxycarbonylpyrrolidine-2-carboxylate, 2,1,3-benzoxadiazole-4-aldehyde and $^3$-aminopyrazole in the same manner as in Example 1001.

MS (EI): 433 (M$^+$).

$^1$H-NMR (400 MHz, DMSO-d$_6$) δ (ppm): 1.40 (9H, s), 1.78–1.89 (4H, m), 2.11–2.31 (1H, m), 3.72 (1H, m), 4.53 (1H, m), 5.40 (1H, s), 7.26 (1H, s), 7.30–7.40 (1H, m), 7.58 (1H, dd, J=6.4 Hz and 9.6 Hz), 7.91 (1H, d, J=9.6 Hz), 9.86 (1H, s), 12.16 (1H, s).

Example 1070

4-(2,1,3-Benzoxadiazol-4-yl)-5-cyano-4,7-dihydro-6-(pyrrolidin-2-yl)-2H-pyrazolo[3,4-b]pyridine The title compound was prepared from 4-(2,1,3-benzoxadiazol-4-yl)-6-(1-t-butoxycarbonylpyrrolidin-2-yl)-5-cyano-4,7-dihydro-2H-pyrazolo[3,4-b]pyridine in the same manner as in Example 1002.

MP: >240° C.

MS (EI): 333 (M$^+$).

$^1$H-NMR (400 MHz, DMSO-d$_6$) δ (ppm): 1.41–1.46 (1H, m), 1.97–2.14 (4H, m), 3.72 (1H, m), 4.11–4.32 (1H, m), 5.52 (1H, s), 7.00 (1H, s), 7.26 (1H, s), 7.30–7.42 (1H, m), 7.58 (1H, dd, J=6.4 Hz and 9.6 Hz), 7.91 (1H, d, J=9.3 Hz), 11.87 (1H, s).

Example 1071

6-($^1$-t-Butoxycarbonylpyrrolidin-2-yl)-4-(2-chlorophenyl)-5-cyano-4,$^7$-dihydro-2H-pyrazolo[3,4-b]pyridine The title compound was prepared from ethyl 1-t-butoxycarbonylpyrrolidine-2-carboxylate, 2-chlorobenzaldehyde and 3-aminopyrazole in the same manner as in Example 1001.

MS (EI): 425 (M$^+$).

$^1$H-NMR (400 MHz, DMSO-d$_6$) δ (ppm): 1.36 (9H, s), 1.86 (4H, m), 2.32 (1H, m), 3.54 (1H, m), 4.57 (1H, m), 5.38 (1H, s), 7.23–7.27 (4H, m), 7.42 (1H, d, J=7.6 Hz), 9.68 (1H, s), 12.17 (1H, s).

Example 1072

6-(1-t-Butoxycarbonylpiperidin-4-yl)-5-cyano-4,7-dihydro-4-(2,3-(methylenedioxy)phenyl)-2H-pyrazolo[3,4-b]pyridine The title compound was prepared from ethyl 1-t-butoxycarbonylpiperidine-4-carboxylate, 2,3-(methylenedioxy)-benzaldehyde and $^3$-aminopyrazole in the same manner as in Example 1001.

MS (EI): 449 (M$^+$).

$^1$H-NMR (400 MHz, DMSO-d$_6$) δ (ppm): 1.39 (1H, m), 1.97–2.13 (2H, m), 2.00 (2H, m), 2.78–3.15 (2H, m), 3.31 (1H, m), 3.96 (2H, s), 5.03 (1H, d, J=9.5 Hz), 6.00–6.02 (1H, m), 6.64 (1H, d, J=2.9 Hz), 6.78 (1H, d, J=1.7 Hz), 7.29 (1H, s), 9.46 (1H, s), 12.18 (1H, s).

Example 1073

5-Cyano-4,7-dihydro-4-(2,3-(methylenedioxy)phenyl)-6-(piperidin-4-yl)-2H-pyrazolo[3,4-b]pyridine The title compound was prepared from 6-(1-t-butoxycarbonylpiperidin-4-yl)-5-cyano-4,7-dihydro-4-(2,3-(methylenedioxy)phenyl)-2H-pyrazolo[3,4-b]-pyridine in the same manner as in Example 1002.

MS (EI): 390 (M$^+$).

¹H-NMR (400 MHz, DMSO-d₆) δ (ppm): 1.27–1.88 (5H, m), 2.49–2.96 (5H, m), 5.02 (1H, s), 6.00–6.02 (2H, m), 6.66 (1H, m), 6.76 (2H, m), 7.27 (1H, s), 9.98 (1H, s), 12.14 (1H, s).

Example 1074

4-(2-Chlorophenyl)-5-cyano-4,7-dihydro-2H-pyrazolo[3,4-b]-pyridine-6-carboxylic acid phenylamide The title compound was prepared from N-phenyloxamic acid ethyl ester, 2-chlorobenzaldehyde and 3-aminopyrazole in the same manner as in Example 1001.

MS (EI): 375 (M⁺).

¹H-NMR (400 MHz, DMSO-d₆) δ (ppm): 5.50 (1H, s), 7.13 (1H, dd, J=7.1 Hz and 7.6 Hz), 7.25–7.46 (7H, m), 7.66 (2H, dd, J=8.3 Hz), 10.4 (1H, s), 10.76 (1H, s), 12.3 (1H, s).

Example 1075

4-(2,1,3-Benzoxadiazol-4-yl)-5-cyano-4,7-dihydro-2H-pyrazolo[3,4-b]pyridine-6-carboxylic acid phenylamide The title compound was prepared from N-phenyloxamic acid ethyl ester, 2,1,3-benzoxadiazole-4-aldehyde and 3-aminopyrazole in the same manner as in Example 1001.

MS (EI): 383 (M⁺).

¹H-NMR (400 MHz, DMSO-d₆) δ (ppm): 5.59 (1H, s), 7.11–7.15 (1H, dd, J=7.3 Hz and 7.6 Hz), 7.33–7.36 (3H, m), 7.51 (1H, d, J=6.6 Hz), 7.63–7.68 (3H, m), 7.96 (1H, d, J=9.0 Hz), 10.52 (1H, s), 10.76 (1H, s), 12.3 (1H, s).

Example 1076

4-(2-Chlorophenyl)-5-cyano-4,7-dihydro-6-[4-(naphthalen-1-yl)piperazin-1-yl]methyl-2H-pyrazolo[3,4-b]pyridine trihydrochloride 4-(2-Chlorophenyl)-5-cyano-6-(t-butyldimethylsilyl-oxy)methyl-4,7-dihydro-2H-pyrazolo[3,4-b]pyridine was prepared from ethyl t-butyldimethylsilyloxyacetate, 2-chlorobenzaldehyde and 3-aminopyrazole in the same manner as in Example 1001. To a solution of 4-(2-chlorophenyl)-5-cyano-6-(t-butyldimethylsilyloxy)methyl-4,7-dihydro-2H-pyrazolo[3,4-b]pyridine (20 g) in tetrahydrofuran (200 mL) was added a THF solution (49.9 mL) of 1.0 M tetrabutylammonium fluoride and the mixture was stirred at room temperature for 1 hour. To the reaction mixture was added ethyl acetate (800 mL), and the resulting mixture was washed with a saturated aqueous sodium chloride solution and dried over anhydrous magnesium sulfate. The solvent was evaporated and the obtained residue was crystallized from ethyl acetate to give 4-(2-chlorophenyl)-5-cyano-6-hydroxymethyl-4,7-dihydro-2H-pyrazolo[3,4-b]pyridine (12.7 g) as a white solid. To a solution of 4-(2-chlorophenyl)-5-cyano-6-hydroxymethyl-4,7-dihydro-2H-pyrazolo[3,4-b]pyridine (12.7 g) and carbon tetrabromide (15.4 g) in methylene chloride (340 mL) was added triphenylphosphine (12.2 g) in methylene chloride (100 mL) under ice-cooling and the mixture was stirred at room temperature for 13 hours. The reaction mixture was concentrated under reduced pressure and the obtained residue was purified by silica gel column chromatography (eluent:hexane-ethyl acetate (1:1)) to give 4-(2-chlorophenyl)-5-cyano-6-bromomethyl-4,7-dihydro-2H-pyrazolo[3,4-b]pyridine (3.84 g) as a pale-yellow solid. To a suspension of sodium hydride (60 mg) in DMF (10 mL) was added 1-(naphthalen-1-yl)piperazine (334 mg) and the mixture was stirred under ice-cooling for 30 minutes. To this reaction mixture was added a solution of 4-(2-chlorophenyl)-5-cyano-6-bromomethyl-4,7-dihydro-2H-pyrazolo[3,4-b]pyridine (500 mg) under ice-cooling and the mixture was stirred under ice-cooling for 6 hours. To the reaction mixture was added water and the mixture was extracted with ethyl acetate. The extract was washed with a saturated aqueous sodium chloride solution and dried over anhydrous magnesium sulfate. The solvent was evaporated and the obtained residue was purified by silica gel column chromatography (eluent:ethyl acetate-methanol (1:1)). The obtained oil was treated with hydrogen chloride-methanol to give the title compound (370 mg) as white crystals.

MP: 203–205° C (decomposition).

MS (EI): 481 (M⁺).

¹H-NMR (400 MHz, DMSO-d₆) δ (ppm): 3.31–3.70 (8H, m), 4.33 (2H, m), 4.85 (3H, m), 5.54 (1H, s), 7.19 (1H, d, J=7.3 Hz), 7.29–7.54 (8H, m), 7.67 (1H, d, J=8.1 Hz), 7.92 (1H, d, J=7.1 Hz), 8.15 (1H, d, J=7.3 Hz), 10.35 (1H, s), 11.28 (1H, brs).

Example 1077

4-(2-Chlorophenyl)-5-cyano-4,7-dihydro-6-(4-methyl-homopiperazin-1-yl)methyl-2H-pyrazolo[3,4-b]pyridine dihydrochloride The title compound was prepared from 4-(2-chlorophenyl)-5-cyano-6-bromomethyl-4,7-dihydro-2H-pyrazolo[3,4-b]pyridine and N-methylhomopiperazine in the same manner as in Example 1076.

MP: 204–206° C. (decomposition).

MS (EI): 382 (M⁺).

¹H-NMR (400 MHz, DMSO-d₆) δ (ppm): 2.22 (2H, m), 2.78 (3H, s), 3.24–4.11 (12H, m), 5.48 (1H, s), 7.14–7.35 (4H, m), 7.45 (1H, d, J=8.0 Hz), 10.17 (1H, brs), 11.51 (1H, brs).

Example 1078

4-(2-Chlorophenyl)-5-cyano-4,7-dihydro-6-(4-phenylpiperazin-1-yl)methyl-2H-pyrazolo[3,4-b]pyridine trihydrochloride The title compound was prepared from 4-(2-chlorophenyl)-5-cyano-6-bromomethyl-4,7-dihydro-2H-pyrazolo[3,4-b]pyridine and 1-phenylpiperazine in the same manner as in Example 1076.

MP: 217–220° C. (decomposition).

MS (EI): 430 (M⁺).

¹H-NMR (400 MHz, DMSO-d₆) δ (ppm): 3.20–4.00 (9H, m), 4.27 (2H, m), 5.51 (1H, s), 6.86 (1H, t, J=7.1 Hz), 7.01 (2H, d, J=8.0 Hz), 7.24–7.39 (6H, m), 7.45 (1H, d, J=9.9 Hz), 9.50 (1H, brs), 10.37 (1H, s), 11.40 (1H, brs).

Example 1079

4-(2-Chlorophenyl)-5-cyano-4,7-dihydro-6-phthalimidomethyl-2H-pyrazolo[3,4-b]pyridine To a solution of 4-(?-chlorophenyl)-5-cyano-6-bromomethyl-4,7-dihydro-2H-pyrazolo[3,4-b]pyridine (0.8 g) in DMF (10 mL) was added potassium phthalimide (445 mg) under ice-cooling and the mixture was stirred under ice-cooling for 4 hours. To the reaction mixture was added water and the mixture was extracted with ethyl acetate. The extract was washed with a saturated aqueous sodium chloride solution and dried over anhydrous magnesium sulfate. The solvent was evaporated and the obtained residue was purified by silica gel column chromatography (eluent:ethyl acetate-hexane (2:1)) to give the title compound (285 mg) as white crystals.

MP: >250° C.

MS (EI): 416 (M$^+$).

$^1$H-NMR (400 MHz, DMSO-d$_6$) δ (ppm): 4.66 (2H, d, J=2.4 Hz), 5.40 (1H, s), 7.24–7.45 (5H, m), 7.82–7.94 (4H, m), 10.04 (1H, s), 12.23 (1H, s).

Example 1080

6-Acetyl-4-(2-chlorophenyl)-5-cyano-4,7-dihydro-2H-pyrazolo[3,4-b]pyridine 4-(2-Chlorophenyl)-5-cyano-4,7-dihydro-6-(1,1-dimethoxyethyl)-2H-pyrazolo[3,4-b]pyridine was prepared from methyl 2,2-dimethoxypropionate, 2-chlorobenzaldehyde and 3-aminopyrazole in the same manner as in Example 1001. To a solution of 4-(2-chlorophenyl)-5-cyano-4,7-dihydro-6-(1,1-dimethoxyethyl)-2H-pyrazolo[3,4-b]pyridine (1.0 g) in dichloromethane (10 mL) was added a trifluoroacetic acid (10 mL) under ice-cooling and the mixture was stirred under ice-cooling for 1 hour. The solvent was evaporated and the obtained residue was crystallized from ethyl acetate to give the title compound (370 mg) as white crystals.

MP: 225–228° C. (decomposition).

MS (EI): 298 (M$^+$).

$^1$H-NMR (400 MHz, DMSO-d$_6$) δ (ppm): 2.56 (3H, s), 5.49 (1H, s), 7.25–7.36 (4H, m), 7.45 (1H, d, J=7.8 Hz), 10.12 (1H, s), 12.50 (1H, brs).

Example 1081

6-Acetyl-4-(2-bromo-3-cyanophenyl)-5-cyano-4,7-dihydro-2H-pyrazolo[3,4-b]pyridine The title compound was prepared from 2-bromo-3-cyanobenzaldehyde, 3-aminopyrazole and methyl 2,2-dimethoxypropionate in the same manner as in Example 1001.

MP: >230° C.

MS (EI): 368 (M$^+$).

$^1$H-NMR (400 MHz, DMSO-d$_6$) δ (ppm): 2.42 (3H, s), 5.54 (1H, s), 7.32 (1H, brs), 7.50–7.59 (2H, m), 7.80 (1H, dd, J=1.7 Hz and 7.3 Hz), 10.19 (1H, s), 12.39 (1H, brs).

Example 1082

6-Acetyl-4-(2,1,3-benzoxadiazol-4-yl)-5-cyano-4,7-dihydro-2H-pyrazolo[3,4-b]pyridine The title compound was prepared from 2,1,3-benzoxadiazole-4-aldehyde, 3-aminopyrazole and methyl 2,2-dimethoxypropionate in the same manner as in Example 1001.

MP: 230° C. (decomposition).

MS (EI): 306 (M$^+$).

$^1$H-NMR (400 MHz, DMSO-d$_6$) δ (ppm): 2.55 (3H, s), 5.54 (1H, s), 7.33 (1H, s), 7.49 (1H, d, J=6.6 Hz), 7.61 (1H, dd, J=6.6 Hz and 8.6 Hz), 7.96 (1H, d, J=9.2 Hz), 10.27 (1H, s), 12.36 (1H, brs).

Example 1083

6-(1-Benzyl-2-oxopyrrolidin-4-yl)-4-(2-chlorophenyl)-5-cyano-4,7-dihydro-2H-pyrazolo[3,4-b]pyridine The title compound was prepared from 2-chlorobenzaldehyde, 3-aminopyrazole and methyl 1-benzyl-2-oxopyrrolidine-4-carboxylate in the same manner as in Example 1001.

MP: >230° C.

Anal. Calcd. for: $C_{24}H_{20}ClN_5O$: C, 67.05; H, 4.69; N, 16.29. Found: C, 66.86; H, 4.56; N, 16.31.

MS (EI): 429 (M$^+$).

$^1$H-NMR (400 MHz, DMSO-d$_6$) δ (ppm): 2.60 (1H, dd, J=9.5 Hz and 16.4 Hz), 2.81 (1H, dd, J=10.5 Hz and 16.4 Hz), 3.39 (1H, m), 3.47 (1H, m), 4.42 (2H, m), 5.36 (1H, s), 7.23–7.43 (10H, m), 10.04 (1H, s), 12.21 (1H, s).

Example 1084

4-(2-Bromo-3-cyanophenyl)-5-(pyridin-2-yl)-4,7-dihydro-6-propyl-2H-pyrazolo[3,4-b]pyridine To a solution of 2-picoline (10 g) in THF (75 mL) was added n-BuLi (113 mmol) at −40° C. Further, methyl butanoate (15.8 mL) was added and the mixture was stirred for 1 hour, and the mixture quenched with water. The mixture was extracted with ethyl acetate. The solvent was evaporated under reduced pressure and the residue was purified by silica gel column chromatography (eluent:hexane-ethyl acetate (1:1)) to give 2-(2-oxopentanyl)pyridine (4.8 g) as a yellow oil. A solution of 2-bromo-3-cyanobenzaldehyde (1.5 g), Meldrum's acid (1.0 g), 2-(2-oxopentanyl)pyridine (1.2 g) and ammonium acetate (0.6 g) in acetic acid (7 mL) was heated under reflux for 11 hours. The reaction mixture was cooled to room temperature, and the solvent was evaporated under reduced pressure and the residue was purified by silica gel column chromatography (eluent: hexane-ethyl acetate (1:1)) and the obtained residue was crystallized from ethyl acetate to give colorless crystals (520 mg). To a solution of dimethylformamide (384 mg) in chloroform (5 mL) were added phosphorus oxychloride (805 mg) and a solution of the obtained crystals (520 mg) under ice-cooling, and the mixture was stirred overnight. Under ice-cooling, an aqueous sodium acetate (3.4 g) solution was added and the mixture was stirred for 1 hour. The mixture was extracted with ethyl acetate and the solvent was evaporated under reduced pressure to give oil. The obtained oil was purified by silica gel column chromatography (eluent: chloroform-methanol (9:1)) to give a yellow solid (530 mg). To a solution of the obtained solid in pyridine (10 mL) was added hydrazine (120 mg), and the mixture was stirred with heating for 4 hours. The reaction mixture was cooled to room temperature, and the solvent was evaporated under reduced pressure to give oil. To the obtained oil was added water and the mixture was extracted with ethyl acetate. The extract was washed a saturated aqueous sodium chloride solution, and dried over anhydrous magnesium sulfate. The solvent was evaporated and the obtained residue was crystallized from ethyl acetate to give the title compound (145 mg) as a pale-yellow crystal.

MP: 205–208° C. (decomposition).

Anal. Calcd. for: $C_{21}H_{18}BrN_5$: C, 60.01; H, 4.32; N, 16.66. Found: C, 59.83; H, 4.42; N, 16.26 .

MS (EI): 420 (M$^+$).

$^1$H-NMR (400 MHz, DMSO-d$_6$) δ (ppm): 0.83 (3H, t, J=7.6 Hz), 1.62 (2H, m), 2.24 (1H, m), 2.33 (1H, m), 5.93 (1H, s), 6.98 (1H, dd, J=4.9 Hz and 7.3 Hz), 7.05 (1H, d, J=7.8 Hz), 7.28 (1H, m), 7.39 (1H, m), 7.51–7.60 (3H, m), 8.36 (1H, d, J=3.6 Hz), 8.52 (1H, s), 11.84 (1H, s).

Example 1085

6-(1-tert-Butoxycarbonylpyrrolidin-3-yl)-4-(2-chlorophenyl)-5-cyano-4,7-dihydro-2H-pyrazolo[3,4-b]pyridine To a solution of methyl 1-benzyl-2-oxopyrrolidine-4-carboxylate (10.9 g) in THF (50 mL) was added 1.0 M borane in THF (84 mL) under ice-cooling and the mixture was refluxed for 1 hour. Decomposition of excess borane and boron complexes was effected by the dropwise addition of 30 mL of methanolic hydrogen chloride followed by refluxing for 1 hour. After removal of the solvents under reduced pressure another 30 mL of methanolic hydrogen chloride was added, and the mixture was refluxed an additional 1 hour. The solvents were again removed in vacuo and the residue was treated with saturated aqueous sodium hydrogencarbonate solution and dried over anhydrous magnesium sulfate. The solvent was evaporated and the obtained residue was purified by silica gel column chromatography (eluent:hexane-ethyl acetate (1:1)) to give methyl 1-benzyl-3-pyrrolidinecarboxylate (4.8 g) as a pale yellow oil. A suspension of methyl 1-benzyl-3-pyrrolidinecarboxylate (4.8 mg), 5% palladium on carbon (300 mg) and ammonium formate (2.8 g) in methanol (50 mL)-water (5 mL) was refluxed for 2 hours. The reaction mixture was filtered through Celite and the filtrate was concentrated under reduced pressure. The obtained residue was purified by silica gel column chromatography (eluent:chloroform-methanol (9:1)) to give methyl 3-pyrrolidinecarboxylate as a yellow oil. To a solution of methyl 3-pyrrolidinecarboxylate (1.7 g) in dichloromethane (20 mL) was added dimethylaminopyridine (161 mg) and di-tert-butyldicarbonate (3.4 g) at 0° C. and the mixture was stirred for 13 hours. The mixture was evaporated under reduced pressure and the obtained residue was purified by silica gel column chromatography (eluent:hexane-ethyl acetate (2:1)) to give methyl 1-tert-butoxycarbonyl-3-pyrrolidinecarboxylate (2.6 g) as a colorless oil. To a solution of acetonitrile (554 mg) in THF (30 mL) was added n-BuLi (12.4 mmol) at −78° C. Further, methyl 1-tert-butoxycarbonyl-3-pyrrolidinecarboxylate (2.6 g) in THF (10 mL) was added and the mixture was stirred for 10 hours and the reaction was quenched with water. The mixture was evaporated under reduced pressure and the residue was purified by silica gel column chromatography (eluent:hexane-ethyl acetate (2:1)) to give 1-(1-tert-butoxycarbonylpyrrolidin-3-yl)-2-cyanoethan-1-one (2.35 g) as a colorless oil. A solution of 2-chlorophenylaldehyde (1.4 g), 3-aminopyrazole (819 mg) and 1-(1-tert-butoxycarbonylpyrrolidin-3-yl)-2-cyanoethan-1-one (2.35 g) in acetonitrile (10 mL) was heated under reflux for 1.5 hours. The reaction mixture was cooled to room temperature, and the precipitated crystals were collected by filtration to give the title compound (2.18 g) as colorless crystals.

Anal. Calcd. For: $C_{22}H_{24}ClN_5O_2$: C, 62.04; H, 5.68; N, 16.44. Found: C, 61.94; H, 5.69; N, 16.45.

MS (EI): 425 (M$^+$).

$^1$H-NMR (400 MHz, DMSO-d$_6$) δ (ppm): 1.14 (9H, s), 2.07 (1H, m), 2.32 (1H, m), 3.29–3.58 (5H, m), 5.37 (1H, s), 7.22–7.34 (4H, m), 7.42 (1H, d, J=8.3 Hz), 9.78 (1H, s), 12.20 (1H, s).

Example 1086

4-(2-Chlorophenyl)-5-cyano-4,7-dihydro-6-(pyrrolidin-3-yl)-2H-pyrazolo[3,4-b]pyridine 6-(1-tert-Butoxycarbonylpyrrolidin-3-yl)-4-(2-chlorophenyl)-5-cyano-4,7-dihydro-2H-pyrazolo[3,4-b]pyridine (706 mg) was added to 4N-HCl dioxane solution (5 mL) at room temperature and the mixture was stirred for 2 hours. The solvent was evaporated under reduced pressure and the residue was washed by ethanol-ethyl acetate, and the precipitated crystals were collected by filtration to give the title compound (460 mg) as colorless crystals.

MP: 210–215° C. (decomposition).

MS (EI): 325 (M$^+$).

$^1$H-NMR (400 MHz, DMSO-d$_6$) δ (ppm): 2.24 (2H, m), 3.15 (1H, m), 3.26–3.55 (3H, m), 3.64 (1H, m), 5.34 (1H, s), 5.40 (1H, brs), 7.23–7.32 (4H, m), 7.43 (1H, d, J=7.3 Hz), 9.38 (1H, brs), 9.51 (1H, brs), 9.97 (1H, s).

Example 1087

4-(2,1,3-Benzoxadiazol-4-yl)-5-(pyridin-2-yl)-4,7-dihydro-6-propyl-2H-pyrazolo[3,4-b]pyridine The title compound was prepared from 2,1,3-benzoxadiazole-4-aldehyde, Meldrum's acid, 2-(2-oxopentanyl)pyridine and ammonium acetate in the same manner as in Example 1084.

MS (EI): 358 (M$^+$).

$^1$H-NMR (400 MHz, DMSO-d$_6$) δ (ppm): 0.84 (3H, t, J=7.3 Hz), 1.64 (2H, m), 2.27 (1H, m), 2.35 (1H, m), 5.96 (1H, s), 6.95 (1H, m), 7.11–7.18 (3H, m), 7.40 (1H, m), 7.51 (1H, m), 7.69 (1H, d, J=9.3 Hz), 8.35 (1H, m), 8.54 (1H, s), 11.78 (1H, brs).

Example 1088

6-(1-t-Butoxycarbonylpiperidin-4-yl)-5-cyano-4,7-dihydro-4-(indan-4-yl)-2H-pyrazolo[3,4-b]pyridine The title compound was prepared from ethyl isonipecotate, 4-indancarboxaldehyde and 3-aminopyrazole in the same manner as in Example 1001.

MS (EI): 445 (M$^+$).

$^1$H-NMR (400 MHz, DMSO-d$_6$) δ (ppm) 1.41 (9H, s), 1.56–1.59 (2H, m), 1.88–1.06 (4H, m), 2.58–2.83 (7H, m), 4.06 (2H, m), 4.96 (1H, s), 6.90 (1H, m), 7.04–7.07 (2H, m), 7.14 (1H, s), 9.55 (1H, s), 12.08 (1H, s)

Example 1089

6-(1-t-Butoxycarbonylpiperidin-4-yl)-5-cyano-4,7-dihydro-4-(2,3-dihydrobenzo[b]furan-7-yl)-2H-pyrazolo[3,4-b]pyridine The title compound was prepared from ethyl isonipecotate, 7-(2,3-dihydrobenzo[b]furan)carboxaldehyde and 3-aminopyrazole in the same manner as in Example 1001.

MS (EI): 445 (M$^+$).

$^1$H-NMR (400 MHz, DMSO-d$_6$) δ (ppm): 1.42 (9H, s), 1.57–1.66 (2H, m), 1.88 (4H, m), 2.73–2.90 (3H, m), 3.17 (2H, m), 4.09 (2H, m), 4.54 (2H, m), 5.01 (1H, s), 6.76 (1H, m), 6.84 (1H, d, J=7.1 Hz), 7.05 (1H, d, J=6.6 Hz), 7.22 (1H, s), 9.52 (1H, s), 12.0$^6$ (1H, s).

Example 1090

6-(1-t-Butoxycarbonylpiperidin-4-yl)-5-cyano-4,7-dihydro-4-(3, 4-dihydro-2H-benzopyran-8-yl)-2H-pyrazolo[3,4-b]pyridine The title compound was prepared from ethyl isonipecotate, 8-(3,4-dihydro-2H-benzopyrane)carboxaldehyde and 3-amino-pyrazole in the same manner as in Example 1001.

MS (EI): 461 (M$^+$).

$^1$H-NMR (400 MHz, DMSO-d$_6$) δ (ppm): 1.42 (9H, s), 1.58–1.69 (2H, m), 1.80–2.00 (4H, m), 2.73–2.95 (5H, m), 4.09 (2H, m), 4.22 (2H, m), 5.14 (1H, s), 6.74 (1H, m), 6.84–6.89 (2H, m), 7.21 (1H, s), 9.48 (1H, s), 12.03 (1H, s).

Example 1091

6-(1-t-Butoxycarbonylpiperidin-4-yl)-4-(2-chloro-3-trifluoromethylphenyl)-5-cyano-4,7-dihydro-2H-pyrazolo[3,4-b]pyridine The title compound was prepared from ethyl isonipecotate, 2–15 chloro-3-trifluoromethylbenzaldehyde and 3-aminopyrazole in the same manner as in Example 1001.

MS (EI): 461 (M$^+$).

$^1$H-NMR (400 MHz, DMSO-d$_6$) δ (ppm): 1.41 (9H, s), 1.62 (2H, m), 1.89 (2H, m), 2.60–2.90 (3H, m), 4.10 (2H, m), 5.54 (1H, s), 7.32 (1H, s), 7.52–7.56 (2H, m), 7.75 (1H, d, J=9.3 Hz), 9.79 (1H, s), 12.25 (1H, s).

Example 1092

5-Cyano-4,7-dihydro-4-(3,4-dihydro-2H-benzopyran-8-yl)-6-(piperidin-4-yl)-2H-pyrazolo[3,4-b]pyridine Hydrochloride The title compound was prepared from 6-(1-t-butoxy-25 carbonylpiperidin-4-yl)-5-cyano-4,7-dihydro-4-(3,4-dihydro-2H-benzopyran-8-yl)-2H-pyrazolo[3,4-b]pyridine in the same manner as in Example 1002.

MS (EI): 361 (M$^+$).

$^1$H-NMR (400 MHz, DMSO-d$_6$) δ (ppm): 1.83–1.98 (4H, m), 2.14 (2H, m), 2.74 (2H, m), 2.90–3.00 (3H, m), 4.22 (2H, m), 3.40–3.70 (5H, m), 4.16–4.27 (2H, m), 5.15 (1H, s), 6.74 (1H, m), 6.83–6.89 (2H, m), 7.22 (1H, s), 9.54 (1H, s)

Example 1093

5-Cyano-4,7-dihydro-4-(indan-4-yl)-6-(piperidin-4-yl)-2H-pyrazolo[3,4-b]pyridine Hydrochloride The title compound was prepared from 6-(1-t-butoxycarbonylpiperidin-4-yl)-5-cyano-4,7-dihydro-4-(indan-4-yl)-2H-pyrazolo[3,4-b]pyridine in the same manner as in Example 1002.

MS (EI): 345 (M$^+$).

$^1$H-NMR (400 MHz, DMSO-d$_6$) δ (ppm): 1.80–1.99 (4H, m), 2.14 (2H, m), 2.58 (1H, m), 2.82–2.95 (6H, m), 3.30–3.50 (2H, m), 4.97 (1H, s), 6.90 (1H, m), 7.04–7.09 (2H, m), 7.17 (1H, s), 8.37 (1H, m), 9.10 (1H, m), 9.62 (1H, s), 12.18 (1H, brs).

Example 1094

5-Cyano-4,7-dihydro-4-(indan-4-yl)-6-(1-methylpiperidin-4-yl)-2H-pyrazolo[3,4-b]pyridine The title compound was prepared from 5-cyano-4,7-dihydro-4-(indan-4-yl)-6-(piperidin-4-yl)-2H-pyrazolo[3,4-b]pyridine hydrochloride in the same manner as in Example 1003.

$^1$H-NMR (400 MHz, DMSO-d$_6$) δ (ppm): 1.56 (2H, m), 1.84–1.98 (6H, m), 2.15 (2H, m), 2.58 (1H, m), 2.80–3.00 (6H, m), 3.20–3.40 (2H, m), 4.95 (1H, s), 6.90 (1H, m), 7.05–7.07 (2H, m), 7.14 (1H, s), 9.54 (1H, brs), 12.10 (1H, brs).

Example 1095

5-Cyano-4,7-dihydro-4-(3,4-dihydro-2H-benzopyran-8-yl)-6-(1-methylpiperidin-4-yl)-2H-pyrazolo[3,4-b]pyridine Hydrochloride The title compound was prepared from 5-cyano-4,7-dihydro-4-(3,4-dihydro-2H-benzopyran-8-yl)-6-(piperidin-4-yl)-2H-pyrazolo[3,4-b]pyridine hydrochloride in the same manner as in Example 1003.

$^1$H-NMR (400 MHz, DMSO-d$_6$) δ (ppm): 1.90–2.00 (4H, m), 2.24 (2H, m), 2.73–2.75 (5H, m), 2.94–3.08 (3H, m), 3.40–3.48 (2H, m), 4.17–4.27 (2H, m), 5.15 (1H, s), 6.74 (1H, m), 6.84–6.89 (2H, m), 7.22 (1H, s), 9.58 (1H, s), 9.80 (1H, m), 12.15 (1H, s).

Example 1096

4-(2,1,3-Benzoxadiazol-4-yl)-5-cyano-4,7-dihydro-6-(1-methanesulfonylpiperidin-2-yl)-2H-pyrazolo[3,4-b]pyridine The title compound was prepared from methanesulfonylchloride, ethyl pipecolinate, 2,1,3-benzoxadiazole-4-aldehyde and 3-aminopyrazole in the same manner as in Example 1025.

MS (EI): 425 (M$^+$).

$^1$H-NMR (400 MHz, DMSO-d$_6$) δ (ppm): 1.20–2.07 (7H, m), 2.95 and 2.98 (3H, s), 2.98–3.17 (1H, m), 3.63–3.68 (1H, m), 5.40 and 5.52 (1H, s), 7.24 and 7.27 (1H, s), 7.41–7.63 (2H, m), 7.90–7.93 (1H, m), 9.80 and 9.82 (1H, brs), 12.16 (1H, brs).

Example 1097

4-(2,1,3-Benzoxadiazol-4-yl)-5-cyano-4,7-dihydro-6-(1-methylpiperidin-4-yl)-2H-pyrazolo[3,4-b] pyridine Hydrochloride The title compound was prepared from 4-(2,1,3-benzoxadiazol-4-yl)-5-cyano-4,7-dihydro-6-(1-methylpiperidin-4-yl)-2H-pyrazolo[3,4-b]pyridine in the same manner as in Example 1064.

MS (EI): 361 (M$^+$).

$^1$H-NMR (400 MHz, DMSO-d$_6$) δ (ppm): 1.86–1.90 (2H, m), 2.24–2.27 (2H, m), 2.48 (3H, s), 2.72–2.75 (2H, m), 2.94–2.98 (2H, m), 3.20–3.33 (1H, br), 3.44–3.47 (1H, m), 5.40 (1H, s), 7.28 (1H, s), 7.44 (1H, d, J=6.6 Hz), 7.59 (1H, dd, J=9.0 Hz and 6.6 Hz), 7.93 (1H, d, J=9.0 Hz), 9.92 (1H, brs), 12.26 (1H, brs).

Example 1098

4-(2,1,3-Benzoxadiazol-4-yl)-5-cyano-4,7-dihydro-6-(1,2-dihydro-1-methyl-2-oxo-pyridin-4-yl)-2H-pyrazolo[3,4-b]pyridine The title compound was prepared from 1,2-dihydro-1-methyl-2-oxo-pyridine-4-carboxylic acid ethyl ester, 2,1,3-benzoxadiazole-4-aldehyde and 3-aminopyrazole in the same manner as in Example 1001.

MS (EI): 371 (M$^+$).

$^1$H-NMR (400 MHz, DMSO-d$_6$) δ (ppm): 3.46 (3H, s), 5.42 (1H, s), 6.34 (1H, d, J=7.2 Hz), 6.56 (1H, s), 7.33 (1H, s), 7.52 (1H, d, J=7.2 Hz), 7.61 (1H, dd, J=9.0 Hz and 6.6 Hz), 7.80 (1H, d, J=6.6 Hz), 7.95 (1H, d, J=9.0 Hz), 10.33 (1H, brs), 12.29 (1H, brs).

Example 1099

4-(2,1,3-Benzoxadiazol-4-yl)-5-cyano-4,7-dihydro-6-(1,2,5,6-tetrahydropyridin-3-yl)-2H-pyrazolo[3,4-b]pyridine Hydrochloride The title compound was prepared from 1,2,3,4-tetrahydropyridine-3-carboxylic acid ethyl ester, 2,1,3- benzoxadiazole-4-aldehyde and 3-aminopyrazole in the same manner as in Examples 1001 and 1002.

MS (EI): 345 (M$^+$).

$^1$H-NMR (400 MHz, DMSO-d$_6$) δ (ppm): 2.42–2.44 (2H, m), 3.11–3.14 (2H, m), 3.84–3.87 (2H, m), 4.39 (1H, br), 5.46 (1H, s), 6.36 (1H, s), 7.30 (1H, s), 7.49 (1H, d, J=6.6 Hz), 7.56 (1H, dd, J=9.0 Hz and 6.6 Hz), 7.94 (1H, d, J=9.0 Hz), 9.39 (2H, br), 10.06 (1H, brs).

Example 1100

4-(2,1,3-Benzoxadiazol-4-yl)-5-cyano-4,7-dihydro-6-(1-methyl-1,4,5,6-tetrahydropyridin-3-yl)-2H-pyrazolo[3,4-b]pyridine The title compound was prepared from 4-(2,1,3-benzoxadiazol-4-yl)-5-cyano-4,7-dihydro-6-(1,4,5,6-tetrahydropyridin-3-yl)-20 2H-pyrazolo[3,4-b]pyridine in the same manner as in Example 1003.

MS (EI): 359 (M$^+$).

$^1$H-NMR (400 MHz, DMSO-d$_6$) δ (ppm): 2.18–2.20 (2H, m), 2.43–2.47 (2H, m), 3.02–3.11 (2H, m), 5.43 (1H, s), 6.11 (1H, s), 7.26 (1H, s), 7.43 (1H, d, J=6.6 Hz), 7.59 (1H, dd, J=9.0 Hz and 6.6 Hz), 7.92 (1H, d, J=9.0 Hz), 9.87 (1H, brs), 12.16 (1H, brs).

Example 1101

4-(2,1,3-Benzoxadiazol-4-yl)-5-cyano-4,7-dihydro-6-(1-(methylamino)ethyl)-2H-pyrazolo[3,4-b]pyridine 2 Hydrochloride The title compound was prepared from 2-methylglycine ethyl ester, 2,1,3-benzoxadiazole-4-aldehyde and 3-aminopyrazole in the same manner as in Examples 1015 and 1002.

MS (EI): 321 (M$^+$).

$^1$H-NMR (400 MHz, DMSO-d$_6$) δ (ppm): 1.56 (3H, d, J=6.8 Hz), 3.07 (3H, s), 4.59–4.68 (3H, m), 5.66 (1H, s), 7.29 (1H, d, J=6.6 Hz), 7.44 (1H, s), 7.52 (1H, dd, J=9.0 Hz and 6.6 Hz), 7.87 (1H, d, J=9.0 Hz), 8.22 (1H, br), 8.44 (1H, br), 10.95 (1H, brs).

Example 1102

4-(2-Bromo-3-cyanophenyl)-5-cyano-4,7-dihydro-6-(1,2-dihydro-1-methyl-2-oxo-pyridin-4-yl)-2H-pyrazolo[3,4-b]pyridine The title compound was prepared from 1,2-dihydro-1-methyl-2-oxo-pyridine-4-carboxylic acid ethyl ester, 2-bromo-3-cyanobenzaldehyde and 3-aminopyrazole in the same manner as in Example 1001.

MS (EI): 433 (M$^+$).

$^1$H-NMR (400 MHz, DMSO-d$_6$) δ (ppm): 3.46 (3H, s), 5.35 (1H, s), 6.37 (1H, d, J=7.2 Hz), 6.61 (1H, s), 7.38 (1H, s), 7.60 (1H, dd, J=7.3 Hz and 7.2 Hz), 7.72–7.86 (3H, m), 10.31 (1H, brs), 12.37 (1H, brs).

Example 1103

4-(2-Bromo-3-cyanophenyl)-5-cyano-4,7-dihydro-6-(4-(methylamino)cyclohexyl)-2H-pyrazolo[3,4-b]pyridine 2 Hydrochloride The title compound was prepared from 4-aminocyclohexanecarboxylic acid ethyl ester, 2-bromo-3-cyanobenzaldehyde and 3-aminopyrazole in the same manner as in Examples 1015 and 1002.

MS (EI): 436 (M$^+$).

$^1$H-NMR (400 MHz, DMSO-d$_6$) δ (ppm): 1.39 (2H, m), 1.80–1.90 (4H, m), 2.15–2.16 (2H, m), 2.84–2.86 (1H, m), 3.14–3.16 (1H, m), 4.20 (2H, br), 5.46 (1H, s), 7.33 (1H, s), 7.56–7.57 (2H, m), 7.82 (1H, d, J=7.3 Hz), 8.98 (2H, br), 9.80 (1H, brs).

Example 1104

4-(2-Bromo-3-cyanophenyl)-5-cyano-4,7-dihydro-6-(1,2,5,6-tetrahydropyridin-3-yl)-2H-pyrazolo[3,4-b]pyridine 2 hydrochloride The title compound was prepared from 1,2,5,6-tetrahydropyridine-3-carboxylic acid ethyl ester, 2-bromo-3-cyanobenzaldehyde and 3-aminopyrazole in the same manner as in Examples 1001 and 1002.

MS (EI): 407 (M$^+$).

$^1$H-NMR (400 MHz, DMSO-d$_6$) δ (ppm): 2.43–2.44 (2H, m), 3.13–3.15 (2H, m), 3.70–3.72 (2H, br), 3.86–3.88 (2H, m), 5.54 (1H, s), 6.41 (1H, s), 7.36 (1H, s), 7.58 (1H, dd, J=7.3 Hz and 7.2 Hz), 7.84 (1H, d, J=7.3 Hz), 7.86 (1H, d, J=7.3 Hz), 9.32 (2H, br), 10.03 (1H, brs).

Example 1105

4-(2-Bromo-3-cyanophenyl)-5-cyano-4,7-dihydro-6-(4-(dimethylamino)cyclohexyl)-2H-pyrazolo[3,4-b]pyridine The title compound was prepared from 4-(2-bromo-3-cyanophenyl)-5-cyano-4,7-dihydro-6-(4-(methylamino)cyclohexyl)-2H-pyrazolo[3,4-b]pyridine in the same manner as in Example 1003.

MS (EI): 450 (M$^+$).

$^1$H-NMR (400 MHz, DMSO-d$_6$) δ (ppm): 1.26–1.29 (2H, m), 1.76–1.93 (6H, m), 2.27 (6H, s), 2.34–2.36 (1H, m), 2.63–2.66 (1H, m), 5.45 (1H, s), 7.33 (1H, s), 7.56–7.60 (2H, m), 7.82 (1H, d, J=7.3 Hz), 9.74 (1H, brs), 12.27 (1H, s).

Example 1106

4-(2-Bromo-3-cyanophenyl)-5-cyano-4,7-dihydro-6-(1-methyl-1,4,5,6-tetrahydropyridin-3-yl)-2H-pyrazolo[3,4-b]pyridine The title compound was prepared from 4-(2-bromo-3-cyanophenyl)-5-cyano-4,7-dihydro-6-(1,4,5,6-tetrahydropyridin-3-yl)-2H-pyrazolo[3,4-b]pyridine in the same manner as in Example 1003.

MS (E I): 420 (M$^+$).

$^1$H-NMR (400 MHz, DMSO-d$_6$) δ (ppm): 2.21–2.22 (2H, m), 2.28 (3H, s), 2.48–2.49 (2H, m), 3.08–3.12 (2H, m), 5.49 (1H, s), 6.15 (1H, s), 7.33 (1H, s), 7.56–7.61 (2H, m), 7.84 (1H, dd, J=7.3 Hz and 7.2 Hz), 9.87 (1H, brs), 12.26 (1H, brs).

Example 1107

6-(exo-2-Azabicyclo[2,2,2]octan-6-yl)-4-(2,1,3-benzoxadiazol-4-yl)-5-cyano-4,7-dihydro-2H-pyrazolo[3,4-b]pyridine 2 Hydrochloride The title compound was prepared from exo-2-azabicyclo[2,2,2]octane-6-carboxylic acid. ethyl ester, 2,1,3-benzoxadiazole-4-aldehyde and 3-aminopyrazole in the same manner as in Examples 1001 and 1002.

MS (EI): 373 (M$^+$).

¹H-NMR (400 MHz, DMSO-d₆) δ (ppm): 1.53–1.55 (1H, m), 1.75–1.77 (1H, m), 1.89–2.06 (4H, m), 2.21–2.23 (1H, m), 3.07–3.10 (2H, m), 3.43–3.48 (4H, m), 5.39–5.43 (1H, s), 7.26–7.28 (1H, m), 7.44–7.47 (1H, m), 7.57–7.61 (1H, m), 7.93–7.95 (1H, m), 8.87–9.03 (1H, br), 9.46–9.52 (1H, br), 9.73 and 9.80 (1H, brs).

Example 1108

6-(endo-2-Azabicyclo[2,2,2]octan-6-yl)-4-(2,1,3-benzoxadiazol-4-yl)-5-cyano-4,7-dihydro-2H-pyrazolo[3,4-b]pyridine 2 Hydrochloride The title compound was prepared from endo-2-azabicyclo[2,2,2]octane-6-carboxylic acid ethyl ester, 2,1,3-benzoxadiazole-4-aldehyde and 3-aminopyrazole in the same manner as in Examples 1001 and 1002.

MS (EI): 373 (M⁺).

¹H-NMR (400 MHz, DMSO-d₆) δ (ppm): 1.67–1.73 (3H, m), 2.03–2.13 (4H, m), 3.04–3.06 (1H, m), 3.34–3.57 (5H, m), 5.49 (1H, s), 7.30 (1H, s), 7.50–7.51 (1H, m), 7.58–7.60 (1H, m), 7.92–7.94 (1H, m), 8.07 (1H, br), 9.79 (1H, br), 9.89 (1H, br).

Example 1109

4-(2,1,3-Benzoxadiazol-4-yl)-5-cyano-4,7-dihydro-6-(exo-2-methyl-2-azabicyclo[2,2,2]octan-6-yl)-2H-pyrazolo[3,4-b]pyridine The title compound was prepared from 6-(exo-2-azabicyclo[2,2,2]octan-6-yl)-4-(2,1,3-benzoxadiazol-4-yl)-5-cyano-4,7-dihydro-2H-pyrazolo[3,4-b]pyridine in the same manner as in Example 1003.

MS (EI): 387 (M⁺).

¹H-NMR (400 MHz, DMSO-d₆) δ (ppm): 1.43–1.44 (1H, m), 1.70–1.90 (5H, m), 2.11–2.13 (1H, m), 2.38–2.46 (4H, m), 3.00–3.02 (1H, m), 3.32–3.36 (2H, m), 5.38 and 5.40 (1H, s), 7.25–7.27 (1H, m), 7.38–7.42 (1H, m), 7.56–7.61 (1H, m), 7.90–7.93 (1H, m), 9.73 (1H, br), 12.23 (1H, br).

Example 1110

Ethyl 4-(2,1,3-benzoxadiazol-4-yl)-4,7-dihydro-6-(piperidin-4-yl)-2H-pyrazolo[3,4-b]pyridine-5-carboxylate 2 Hydrobromide A solution of 2,1,3-benzoxadiazole-4-aldehyde (3.0 g), Meldrum's acid (3.0 g), ethyl 3-keto-3-(1-benzylcarbonylpiperidin-4-yl)propionate (6.8 g) and ammonium acetate (1.8 g) in acetic acid (20 mL) was stirred under reflux for 12 hrs. The reaction mixture was cooled to room temperature, and the solvent was evaporated under reduced pressure to give colorless crystals (4.7 g). To a solution of dimethylformamide (2.7 g) in chloroform (10 mL) were added phosphorus oxychloride (3.4 mL) and a solution of the obtained colorless crystals (4.7 g) in chloroform (10 mL) under ice-cooling, and the mixture was stirred overnight. Under ice-cooling, an aqueous sodium acetate (37.8 g) solution was added and the mixture was stirred for one hour. The reaction mixture was extracted with chloroform and the solvent was evaporated under reduced pressure to give an oil. The obtained oil was purified by silica gel column chromatography (eluent:hexane-ethyl acetate (8:2)) to give colorless crystals. To a solution of the obtained colorless crystals in pyridine (20 mL) was added hydrazine (1.4 g) and the mixture was stirred with heating for 3 hours. The reaction mixture was cooled to room temperature, and the solvent was evaporated under reduced pressure to give an oil. The oil was purified by silica gel column chromatography (eluent:hexane-ethyl acetate (1:1)) to give the title compound (840 mg) as colorless crystals. To a solution of the obtained colorless crystals in acetic acid (10 mL) was added HBr-AcOH solution (10 mL) and the mixture was stirred for 3 hours. The solvent was evaporated under reduced pressure to give colorless crystals. The crystal was purified by recrystallization from EtOH to give the title compound (630 mg) as colorless crystals.

MS (EI): 394 (M⁺).

¹H-NMR (400 MHz, DMSO-d₆) δ (ppm): 0.77 (3H, t, J=7.3 Hz), 1.80–2.16 (4H, m), 2.90–2.93 (2H, m), 3.40–3.43 (2H, m), 3.80 (2H, q, J=7.3 Hz), 4.12–4.15 (1H, m), 4.50 (2H, br), 5.67 (1H, s), 7.17 (1H, d, J=6.6 Hz), 7.26 (1H, s), 7.51 (1H, dd, J=9.0 Hz and 6.6 Hz), 7.79 (1H, d, J=9.0 Hz), 8.10 (1H, br), 8.74 (1H, br), 9.38 (1H, brs).

Example 1111

4-(2,1,3-Benzoxadiazol-4-yl)-5-cyano-4,7-dihydro-6-(endo-2-methyl-2-azabicyclo[2,2,2]octan-6-yl)-2H-pyrazolo[3,4-b]pyridine The title compound was prepared from 6-(endo-2-azabicyclo[2,2,2]octan-6-yl)-4-(2,1,3-benzoxadiazol-4-yl)-5-cyano-4,7-dihydro-2H-pyrazolo[3,4-b]pyridine in the same manner as in Example 1003.

MS (EI): 387 (M⁺).

¹H-NMR (400 MHz, DMSO-d₆) δ (ppm): 1.43–1.47 (2H, m), 1.60–1.64 (2H, m), 1.81–1.82 (1H, m), 1.79–2.06 (2H, m), 2.24–2.26 (1H, m), 2.36 (3H, s), 2.76–2.80 (2H, m), 3.19–3.22 (1H, m), 5.43 (1H, s), 7.25 (1H, s), 7.42–7.46 (1H, m), 7.57–7.60 (1H, m), 7.90–7.94 (1H, m), 10.79 (1H, brs), 12.16 (1H, brs).

Example 1112

Ethyl 4-(2,1,3-benzoxadiazol-4-yl)-4,7-dihydro-6-(1-methylpiperidin-4-yl)-2H-pyrazolo[3,4-b]pyridine-5-carboxylate 2 Hydrochloride The title compound was prepared from ethyl 4-(2,1,3-benzoxadiazol-4-yl)-4,7-dihydro-6-(piperidin-4-yl)-2H-pyrazolo[3,4-b]pyridine-5-carboxylate in the same manner as in Example 1003.

MS (EI): 408 (M⁺).

¹H-NMR (400 MHz, DMSO-d₆) δ (ppm): 0.75 (3H, t, J=7.3 Hz), 1.55–1.56 (1H, m), 1.71–1.73 (1H, m), 1.87–2.06 (4H, m), 2.17 (3H, s), 2.84–2.87 (2H, m), 3.78 (2H, q, J=7.3 Hz), 3.93–3.96 (1H, m), 5.68 (1H, s), 7.12 (1H, d, J=6.6 Hz), 7.22 (1H, s), 7.49 (1H, dd, J=9.0 Hz and 6.6 Hz), 7.77 (1H, d, J=9.0 Hz), 9.32 (1H, brs), 12.06 (1H, brs).

Example 1113

4-(2-Bromophenyl)-5-cyano-4,7-dihydro-6-(piperidin-4-yl)-2H-pyrazolo[3,4-b]pyridine Hydrochloride The title compound was prepared from ethyl nipecotate, 2-bromobenzaldehyde and 3-aminopyrazole in the same manner as in Examples 1001 and 1002.

MS (EI): 383 (M⁺).

¹H-NMR (400 MHz, DMSO-d₆) δ (ppm): 1.85–1.93 (2H, m), 2.14–2.20 (2H, m), 2.94–2.98 (2H, m), 3.32–3.36 (3H, m), 5.36 (1H, s), 7.16 (1H, dd, J=7.3 Hz and 7.2 Hz), 7.23–7.27 (2H, m), 7.35 (1H, dd, J=7.3 Hz and 7.2 Hz), 7.59 (1H, d, J=7.3 Hz), 8.41 (1H, br), 9.14 (1H, br), 9.73 (1H, brs), 12.21 (1H, brs).

Example 1114

5-Cyano-4,7-dihydro-4-(2-methoxyphenyl)-6-(piperidin-4-yl)-2[1]H-pyrazolo[3,4-b]pyridine Hydrochloride The title compound was prepared from ethyl nipecotate, 2-methoxybenzaldehyde and 3-aminopyrazole in the same manner as in Examples 1001 and 1002.

MS (EI): 335 (M$^+$).

$^1$H-NMR (400 MHz, DMSO-d$_6$) δ (ppm): 1.87–1.95 (2H, m), 2.14–2.20 (2H, m), 2.94–3.03 (3H, m), 3.32–3.36 (2H, m), 3.82 (3H, s), 5.21 (1H, s), 6.88 (1H, dd, J=7.3 Hz and 7.2 Hz), 6.99 (1H, d, J=7.3 Hz), 7.05 (1H, d, J=7.3 Hz), 7.15–7.20 (2H, m), 8.44 (1H, br), 9.17 (1H, br), 9.53 (1H, brs), 12.11 (1H, brs).

Example 1115

5-Cyano-4-(2,3-dichlorophenyl)-4,7-dihydro-6-(piperidin-4-yl)-2H-pyrazolo[3,4-b]pyridine Hydrochloride The title compound was prepared from ethyl nipecotate, 2,3-dichlorobenzaldehyde and 3-aminopyrazole in the same manner as in Examples 1001 and 1002.

MS (EI): 373 (M$^+$).

$^1$H-NMR (400 MHz, DMSO-d$_6$) δ (ppm): 1.84–1.90 (2H, m), 2.16–2.20 (2H, m), 2.94–3.00 (3H, m), 3.32–3.38 (2H, m), 5.44 (1H, s), 7.24–7.36 (3H, m), 7.56 (1H, d, J=7.3 Hz), 8.52 (1H, br), 9.24 (1H, br), 9.79 (1H, brs), 12.29 (1H, brs).

Example 1116

4-(2-Bromophenyl)-5-cyano-4, -7-dihydro-6-(1-methylpiperidin-4-yl)-2H-pyrazolo[3,4-b]pyridine The title compound was prepared from 4-(2-bromophenyl)-5-cyano-4,7-dihydro-6-(piperidin-4-yl)-2H-pyrazolo[3,4-b]pyridine in the same manner as in Example 1003.

MS (EI): 397 (M$^+$).

$^1$H-NMR (400 MHz, DMSO-d$_6$) δ (ppm): 1.56–1.63 (2H, m), 1.85–1.90 (2H, m), 2.01–2.06 (2H, m), 2.17 (3H, s), 2.62–2.65 (1H, m), 2.87–2.89 (2H, m), 5.34 (1H, s), 7.14–7.26 (3H, m), 7.36 (1H, dd, J=7.3 Hz and 7.2 Hz), 7.60 (1H, d, J=7.3 Hz), 9.60 (1H, brs), 12.16 (1H, brs)

Example 1117

5-Cyano-4,7-dihydro-4-(2-methoxyphenyl)-6-(1-methylpiperidin-4-yl)-2H-pyrazolo[3,4-b]pyridine The title compound was prepared from 5-cyano-4,7-dihydro-4-(2-methoxyphenyl)-6-(piperidin-4-yl)-2H-pyrazolo[3,4-b]pyridine in the same manner as in Example 1003.

MS (EI): 349 (M$^+$).

$^1$H-NMR (400 MHz, DMSO-d$_6$) δ (ppm): 1.56–1.66 (2H, m), 1.86–1.92 (2H, m), 2.01–2.04 (2H, m), 2.17 (3H, s), 2.64–2.67 (1H, m), 2.86–2.88 (2H, m), 3.84 (3H, s), 5.20 (1H, s), 6.90 (1H, dd, J=7.3 Hz and 7.2 Hz), 6.98 (1H, d, J=7.3 Hz), 7.05 (1H, d, J=7.3 Hz), 7.16–7.19 (2H, m), 9.41 (1H, brs), 12.01 (1H, brs).

Example 1118

5-Cyano-4-(2,3-dichlorophenyl)-4,7-dihydro-6-(1-methylpiperidin-4-yl)-2H-pyrazolo[3,4-b]pyridine The title compound was prepared from 5-cyano-4-(2,3-dichlorophenyl)-4,7-dihydro-6-(piperidin-4-yl)-2H-pyrazolo[3,4-b]pyridine hydrochloride in the same manner as in Example 1003.

MS (EI): 387 (M$^+$).

$^1$H-NMR (400 MHz, DMSO-d$_6$) δ (ppm): 0.57–1.65 (2H, m), 1.85–1.90 (2H, m), 2.01–2.06 (2H, m), 2.17 (3H, s), 2.59–2.66 (1H, m), 2.86–2.89 (2H, m), 5.43 (1H, s), 7.23 (1H, d, J=7.3 Hz), 7.29 (1H, s), 7.35 (1H, dd, J=7.3 Hz and 7.2 Hz), 7.51 (1H, d, J=7.3 Hz), 9.65 (1H, brs), 12.18 (1H, brs).

Example 1119

5-Cyano-4,7-dihydro-4-(2-fluorophenyl)-6-(piperidin-4-yl)-2H-pyrazolo[3,4-b]pyridine Hydrochloride The title compound was prepared from ethyl nipecotate, 2-fluorobenzaldehyde and 3-aminopyrazole in the same manner as in Examples 1001 and 1002.

MS (EI): 323 (M$^+$).

$^1$H-NMR (400 MHz, DMSO-d$_6$) δ (ppm): 1.85–1.89 (2H, m), 2.12–2.20 (2H, m), 2.90–2.98 (3H, m), 3.33–3.39 (2H, m), 5.20 (1H, s), 7.14–7.28 (5H, m), 8.37 (1H, br), 9.09 (1H, br), 9.66 (1H, brs), 12.23 (1H, brs).

Example 1120

5-Cyano-4-(2,3-difluorophenyl)-4,7-dihydro-6-(piperidin-4-yl)-2H-pyrazolo[3,4-b]pyridine Hydrochloride The title compound was prepared from ethyl nipecotate, 2,3-difluorobenzaldehyde and 3-aminopyrazole in the same manner as in Examples 1001 and 1002.

MS (EI): 341 (M$^+$).

$^1$H-NMR (400 MHz, DMSO-d$_6$) δ (ppm): 1.84–1.88 (2H, m), 2.14–2.19 (2H, m), 2.95–3.00 (3H, m), 3.33–3.38 (2H, m), 5.26 (1H, s), 7.03 (1H, d, J=7.3 Hz), 7.18 (1H, dd, J=7.3 Hz and 7.2 Hz), 7.26–7.31 (2H, m), 8.80 (2H, br), 9.74 (1H, brs), 12.29 (1H, brs).

Example 1121

5-Cyano-4-(2,6-difluorophenyl)-4,7-dihydro-6-(piperidin-4-yl)-2H-pyrazolo[3,4-b]pyridine Hydrochloride The title compound was prepared from ethyl nipecotate, 2,6-difluorobenzaldehyde and 3-aminopyrazole in the same manner as in Examples 1001 and 1002.

MS (EI): 341 (M$^+$).

$^1$H-NMR (400 MHz, DMSO-d$_6$) δ (ppm): 1.76–1.84 (2H, m), 2.13–2.18 (2H, m), 2.91–2.95 (3H, m), 3.28–3.30 (2H, m), 5.35 (1H, s), 7.02–7.07 (2H, m), 7.31. -7.38 (2H, m), 8.77 (2H, br), 9.68 (1H, brs), 12.22 (1H, brs).

Example 1122

5-Cyano-4,7-dihydro-4-(2-methylthiophenyl)-6-(piperidin-4-yl)-2H-pyrazolo[3,4-b]pyridine 2 Hydrochloride The title compound was prepared from ethyl nipecotate, 2-methylthiobenzaldehyde and 3-aminopyrazole in the same manner as in Examples 1001 and 1002.

MS (EI): 351 (M$^+$).

¹H-NMR (400 MHz, DMSO-d₆) δ (ppm): 1.86–1.93 (2H, m), 2.17–2.23 (2H, m), 2.50 (3H, s), 2.95–3.00 (3H, m), 3.36–3.40 (4H, m), 5.36 (1H, s), 7.14–7.33 (5H, m), 8.49 (1H, br), 9.22 (1H, br), 9.63 (1H, brs).

Example 1123

5-Cyano-4-(2,6-dichlorophenyl)-4,7-dihydro-6-(piperidin-4-yl)-2H-pyrazolo[3,4-b]pyridine Hydrochloride The title compound was prepared from ethyl nipecotate, 2,6-dichlorobenzaldehyde and 3-aminopyrazole in the same manner as in Examples 1001 and 1002.

MS (EI): 373 (M⁺).

¹H-NMR (400 MHz, DMSO-d₆) δ (ppm): 1.80–1.84 (2H, m), 2.12–2.20 (2H, m), 2.90–2.98 (3H, m), 3.30–3.33 (2H, m), 5.92 (1H, s), 7.19 (1H, s), 7.29 (1H, dd, J=7.3 Hz and 7.2 Hz), 7.38 (1H, d, J=7.3 Hz), 7.51 (1H, d, J=7.3 Hz), 8.41 (1H, br), 9.16 (1H, br), 9.73 (1H, brs), 12.18 (1H, brs).

Example 1124

5-Cyano-4,7-dihydro-6-(piperidin-4-yl)-4-(2-trifluoromethylphenyl)-2H-pyrazolo[3,4-b]pyridine 2 Hydrochloride The title compound was prepared from ethyl nipecotate, 2-trifluoromethylbenzaldehyde and 3-aminopyrazole in the same manner as in Examples 1001 and 1002.

MS (EI): 373 (M⁺)

¹H-NMR (400 MHz, DMSO-d₆) δ (ppm): 1.83–1.90 (2H, m), 2.18–2.26 (2H, m), 2.92–3.00 (3H, m), 3.38–3.43 (2H, m), 4.16 (2H, br), 5.22 (1H, s), 7.06 (1H, s), 7.42–7.44 (2H, m), 7.63–7.69 (2H, m), 8.57 (1H, br), 9.30 (1H, br), 9.77 (1H, br).

Example 1125

5-Cyano-4,7-dihydro-4-(2-fluorophenyl)-6-(1-methylpiperidin-4-yl)-2H-pyrazolo[3,4-b]pyridine The title compound was prepared from 5-cyano-4,7-dihydro-4-(2-fluorophenyl)-6-(piperidin-4-yl)-2H-pyrazolo[3,4-b]pyridine hydrochloride in the same manner as in Example 1003.

MS (EI): 337 (M⁺).

¹H-NMR (400 MHz, DMSO-d₆) δ (ppm): 1.55–1.59 (2H, m), 1.83–1.88 (2H, m), 1.96–2.00 (2H, m), 2.15 (3H, s), 2.60–2.63 (1H, m), 2.84–2.88 (2H, m), 5.17 (1H, s), 7.13–7.24 (5H, m), 9.60 (1H, brs), 12.18 (1H, brs).

Example 1126

5-Cyano-4-(2,3-difluorophenyl)-4,7-dihydro-6-(1-methylpiperidin-4-yl)-2H-pyrazolo[3,4-b]pyridine The title compound was prepared from 5-cyano-4-(2,3-difluorophenyl)-4,7-dihydro-6-(piperidin-4-yl)-2H-pyrazolo[3,4-b]pyridine hydrochloride in the same manner as in Example 1003.

MS (EI): 355 (M⁺).

¹H-NMR (400 MHz, DMSO-d₆) δ (ppm): 1.55–1.59 (2H, m), 1.82–1.8 (2H, m), 1.99–2.02 (2H, m), 2.15 (3H, s), 2.57–2.60 (1H, m), 2.84–2.88 (2H, m), 5.23 (1H, s), 7.00 (1H, dd, J=7.3 Hz and 7.2 Hz), 7.16 (1H, d, J=7.3 Hz), 7.27–7.30 (2H, m), 9.66 (1H, brs), 12.24 (1H, brs).

Example 1127

5-Cyano-4-(2,6-difluorophenyl)-4,7-dihydro-6-(1-methylpiperidin-4-yl)-2H-pyrazolo[3,4-b]pyridine The title compound was prepared from 5-cyano-4-(2,6-difluorophenyl)-4,7-dihydro-6-(piperidin-4-yl)-2H-pyrazolo[3,4-b]pyridine hydrochloride in the same manner as in Example 1003.

MS (EI): 355 (M⁺).

¹H-NMR (400 MHz, DMSO-d₆) δ (ppm): 1.49–1.53 (2H, m), 1.82–1.86 (2H, m), 1.96–2.01 (2H, m), 2.15 (3H, s), 2.48–2.51 (1H, m), 2.83–2.86 (2H, m), 5.31 (1H, s), 7.00–7.05 (2H, m), 7.29–7.31 (2H, m), 9.60 (1H, brs), 12.15 (1H, brs).

Example 1128

5-Cyano-4,7-dihydro-4-(2-nitrophenyl)-6-(piperidin-4-yl)-2H-pyrazolo[3,4-b]pyridine 2 Hydrochloride The title compound was prepared from ethyl nipecotate, 2-nitrobenzaldehyde and 3-aminopyrazole in the same manner as in Examples 1001 and 1002.

MS (EI): 351 (M⁺).

¹H-NMR (400 MHz, DMSO-d₆) δ (ppm): 1.84–1.93 (2H, m), 2.17–2.23 (2H, m), 2.94–3.00 (3H, m), 3.35–3.38 (2H, m), 4.42 (2H, br), 5.40 (1H, s), 7.30 (1H, s), 7.46–7.51 (2H, m), 7.71 (1H, dd, J=7.3 Hz and 7.2 Hz), 7.90 (1H, d, J=7.3 Hz), 8.61 (1H, br), 9.36 (1H, br), 9.87 (1H, brs).

Example 1129

5-Cyano-4,7-dihydro-4-phenyl-6-(piperidin-4-yl)-2H-pyrazolo[3,4-b]pyridine 2 Hydrochloride The title compound was prepared from ethyl nipecotate, benzaldehyde and 3-aminopyrazole in the same manner as in Examples 1001 and 1002.

MS (EI): 305 (M⁺).

¹H-NMR (400 MHz, DMSO-d₆) δ (ppm): 1.81–1.89 (2H, m), 2.14–2.20 (2H, m), 2.90–2.96 (3H, m), 3.32–3.35 (2H, m), 4.20 (2H, br), 4.89 (1H, s), 7.17–7.22 (4H, m), 7.28–7.31 (2H, m), 8.58 (1H, br), 9.32 (1H, br), 9.65 (1H, brs).

Example 1130

5-Cyano-4,7-dihydro-6-(1-methylpiperidin-4-yl)-4-(2-methylthiophenyl)-2H-pyrazolo[3,4-b]pyridine The title compound was prepared from 5-cyano-4,7-dihydro-4-(2-methylthiophenyl)-6-(piperidin-4-yl)-2H-pyrazolo[3,4-b]pyridine 2 hydrochloride in the same manner as in Example 1003.

MS (EI): 366 (M⁺)

¹H-NMR (400 MHz, DMSO-d₆) δ (ppm): 1.58–1.66 (2H, m), 1.83–1.89 (2H, m), 1.97–2.02 (2H, m), 2.15 (3H, s), 2.50 (3H, s), 2.62–2.65 (1H, m), 2.84–2.87 (2H, m), 5.32 (1H, s), 7.12–7.30 (5H, m), 9.57 (1H, brs), 12.18 (1H, brs).

Example 1131

5-Cyano-4-(2,6-dichlorophenyl)-4,7-dihydro-6-(1-methylpiperidin-4-yl)-2H-pyrazolo[3,4-b]pyridine The title compound was prepared from 5-cyano-4-(2,6-dichlorophenyl)-4,7-dihydro-6-(piperidin-4-yl)-2H-pyrazolo[3,4-b]pyridine hydrochloride in the same manner as in Example 1003.

MS (EI): 387 (M⁺)

¹H-NMR (400 MHz, DMSO-d₆) δ (ppm): 1.52–1.56 (2H, m), 1.83–1.87 (2H, m), 1.99–2.06 (2H, m), 2.15 (3H, s), 2.52–2.55 (1H, s), 2.83–2.87 (2H, m), 5.90 (1H, s), 7.17 (1H, s), 7.28 (1H, dd, J=7.3 Hz and 7.2 Hz), 7.36 (1H, d, J=7.3 Hz), 7.48 (1H, d, J=7.3 Hz), 9.67 (1H, brs), 12.12 (1H, brs).

Example 1132

5-Cyano-4,7-dihydro-6-(1-methylpiperidin-4-yl)-4-(2-trifluoromethylphenyl)-2H-pyrazolo[3,4-b]pyridine The title compound was prepared from 5-cyano-4,7-dihydro-6-(piperidin-4-yl)-4-(2-trifluoromethylphenyl)-2H-pyrazolo[3,4-b]pyridine 2 hydrochloride in the same manner as in Example 1003.

MS (EI): 387 (M⁺).

¹H-NMR (400 MHz, DMSO-d₆) δ (ppm): 1.57–1.62 (2H, m), 1.83–1.86 (2H, m), 1.97–2.03 (2H, m), 2.16 (3H, s), 2.60–2.63 (1H, m), 2.84–2.87 (2H, m), 5.18 (1H, s), 7.05 (1H, s), 7.40–7.42 (2H, m), 7.62–7.68 (2H, m), 9.69 (1H, brs), 12.23 (1H, brs).

Example 1133

5-Cyano-4,7-dihydro-6-(1-methylpiperidin-4-yl)-4-(2-nitrophenyl)-2H-pyrazolo[3,4-b]pyridine The title compound was prepared from 5-cyano-4,7-dihydro-4-(2-nitrophenyl)-6-(piperidin-4-yl)-2H-pyrazolo[3,4-b]pyridine 2 hydrochloride in the same manner as in Example 1003.

MS (EI): 365 (M⁺)

¹H-NMR (400 MHz, DMSO-d₆) δ (ppm): 1.58–1.67 (2H, m), 1.86–1.90 (2H, m), 1.99–2.06 (2H, m), 2.16 (3H, s), 2.58–2.61 (1H, m), 2.86–2.90 (2H, m), 5.36 (1H, s), 7.26 (1H, s), 7.42–7.48 (2H, m), 7.69 (1H, dd, J=7.3 Hz and 7.2 Hz), 7.88 (1H, d, J=7.3 Hz), 9.72 (1H, brs), 12.26 (1H, brs).

Example 1134

5-Cyano-4,7-dihydro-4-phenyl-6-(1-methylpiperidin-4-yl)-2H-pyrazolo[3,4-b]pyridine The title compound was prepared from 5-cyano-4,7-dihydro-4-phenyl-6-(piperidin-4-yl)-2H-pyrazolo[3,4-b]pyridine 2 hydrochloride in the same manner as in Example 1003.

MS (EI): 319 (M⁺).

¹H-NMR (400 MHz, DMSO-d₆) δ (ppm): 1.54–1.57 (2H, m), 1.81–1.87 (2H, m), 1.97–2.03 (2H, m), 2.15 (3H, s), 2.58–2.60 (1H, m), 2.84–2.86 (2H, m), 4.87 (1H, s), 7.17–7.20 (4H, m), 7.27–7.32 (2H, m), 9.52 (1H, brs), 12.13 (1H, brs).

Example 1135

5-Cyano-4-(2,2-difluoro-1,3-benzodioxol-4-yl)-4,7-dihydro-6-propyl-2H-pyrazolo[3,4-b]pyridine The title compound was prepared from ethyl butanoate, 2,2-difluoro-1,3-benzodioxol-4-aldehyde and 3-aminopyrazole in the same manner as in Example 1001.

MS (EI): 322 (M⁺).

¹H-NMR (400 MHz, DMSO-d₆) δ (ppm): 0.93 (3H, t, J=7.3 Hz), 1.63–1.68 (2H, m), 2.34–2.45 (2H, m), 5.16 (1H, s), 7.02 (1H, d, J=7.3 Hz), 7.18 (1H, dd, J=7.3 Hz and 7.2 Hz), 7.28 (1H, d, J=7.2 Hz), 9.88 (1H, brs), 12.22 (1H, brs).

Example 1136

4-(2,1,3-Benzothiadiazol-4-yl)-5-cyano-4,7-dihydro-6-(piperidin-4-yl)-2H-pyrazolo[3,4-b]pyridine 2 Hydrochloride The title compound was prepared from ethyl nipecotate, 2,1,3-benzothiadiazol-4-aldehyde and 3-aminopyrazole in the same manner as in Examples 1001 and 1002.

MS (EI): 363 (M⁺).

¹H-NMR (400 MHz, DMSO-d₆) δ (ppm): 1.89–1.98 (2H, m), 2.22–2.29 (2H, m), 2.98–3.05 (3H, m), 3.37–3.43 (2H, m), 5.20 (2H, br), 5.72 (1H, s), 7.24 (1H, s), 7.48 (1H, d, J=6.6 Hz), 7.72 (1H, dd, J=9.0 Hz and 6.6 Hz), 7.99 (1H, d, J=9.0 Hz), 8.68 (1H, br), 9.43 (1H, br), 9.86 (1H, brs).

Example 1137

5-Cyano-4-(2,2-difluoro-1,3-benzodioxol-4-yl)-4,7-dihydro-6-(piperidin-4-yl)-2H-pyrazolo[3,4-b]pyridine 2 Hydrochloride The title compound was prepared from ethyl nipecotate, 2,2-difluoro-1,3-benzodioxol-4-aldehyde and 3-aminopyrazole in the same manner as in Examples 1001 and 1002.

MS (EI): 385 (M⁺).

¹H-NMR (400 MHz, DMSO-d₆) δ (ppm): 1.82–1.85 (2H, m), 2.16–2.22 (2H, m), 2.95–3.00 (3H, m), 3.34–3.39 (2H, m), 5.17 (1H, s), 5.65 (2H, br), 7.05 (1H, d, J=7.3 Hz), 7.19 (1H, dd, J=7.3 Hz and 7.2 Hz), 7.29 (1H, d, J=7.3 Hz), 7.33 (1H, s), 8.65 (1H, br), 9.43 (1H, br), 9.86 (1H, brs).

Example 1138

4-(2,1,3-Benzothiadiazol-4-yl)-5-cyano-4,7-dihydro-6-(1-methylpiperidin-4-yl)-2H-pyrazolo[3,4-b]pyridine The title compound was prepared from 4-(2,1,3-benzothiadiazol-4-yl)-5-cyano-4,7-dihydro-6-(piperidin-4-yl)-2H-pyrazolo[3,4-b]pyridine 2 hydrochloride in the same manner as in Example 1003.

MS (EI): 377 (M⁺)

¹H-NMR (400 MHz, DMSO-d₆) δ (ppm): 1.64–1.73 (2H, m), 1.91–1.97 (2H, m), 2.05–2.09 (2H, m), 2.419 (3H, s), 2.70–2.72 (1H, m), 2.90–2.93 (2H, m), 5.71 (1H, s), 7.22 (1H, s), 7.45 (1H, d, J=6.6 Hz), 7.72 (1H, dd, J=9.0 Hz and 6.6 Hz), 7.98 (1H, d, J=9.0 Hz), 9.71 (1H, brs), 12.13 (1H, brs).

Example 1139

5-cyano-4-(2,2-difluoro-1,3-benzodioxol-4-yl)-4,7-dihydro-6-(1-methylpiperidin-4-yl)-2H-pyrazolo[3,4-b]pyridine The title compound was prepared from 5-cyano-4-(2,2-difluoro-1,3-benzodioxol-4-yl)-4,7-dihydro-6-(piperidin-4-yl)-2H-pyrazolo[3,4-b]pyridine 2 hydrochloride in the same manner as in Example 1003.

MS (EI): 399 (M⁺).

¹H-NMR (400 MHz, DMSO-d₆) δ (ppm): 1.5–1.58 (2H, m), 1.86–1.90 (2H, m), 1.99–2.03 (2H, m), 2.16 (3H, s), 2.59–2.62 (1H, m), 2.85–2.89 (2H, m), 5.15 (1H, s), 7.03

(1H, d, J=7.3 Hz), 7.17 (1H, dd, J=7.3 Hz and 7.2 Hz), 7.26–7.31 (2H, m), 9.71 (1H, brs), 12.26 (1H, brs).

Example 1140

5-Cyano-4-(2-cyanophenyl)-4,7-dihydro-6-(piperidin-4-yl)-2H-pyrazolo[3,4-b]pyridine 2 hydrochloride The title compound was prepared from ethyl nipecotate, 2-cyanobenzaldehyde and 3-aminopyrazole in the same manner as in Examples 1001 and 1002.

MS (EI): 330 (M$^+$).

$^1$H-NMR (400 MHz, DMSO-d$_6$) δ (ppm): 1.86–1.90 (2H, m), 2.18–2.22 (2H, m), 2.92–2.98 (3H, m), 3.34–3.37 (2H ,m), 5.10 (2H, br), 5.25 (1H, s), 7.27 (1H, s), 7.43–7.47 (2H, m), 7.68 (1H, dd, J=7.3 Hz and 7.2 Hz), 7.82 (1H, d, J=7.3 Hz), 8.61 (1H, br), 9.41 (1H, br), 9. 93 (1H, brs).

Example 1141

5-Cyano-4-(2-cyanophenyl)-4,7-dihydro-6-(1-methylpiperidin-4-yl)-2H-pyrazolo[3,4-b]pyridine The title compound was prepared from 5-cyano-4-(2-cyanophenyl)-4,7-dihydro-6-(piperidin-4-yl)-2H-pyrazolo[3,4-b]pyridine 2 hydrochloride in the same manner as in Example 1003.

MS (EI): 344 (M$^+$)

$^1$H-NMR (400 MHz, DMSO-d$_6$) δ (ppm): 1.58–1.63 (2H, m), 1.82–1.87 (2H, m), 1.98–2.06 (2H, m), 2.16 (3H, s), 2.59–2.61 (1H, m), 2.84–2.88 (2H, m), 5.23 (1H, s), 7.25 (1H, s), 7.39–7.46 (2H, m), 7.6 (1H, dd, J=7.3 Hz and 7.2 Hz), 7.81 (1H, d, J=7.3 Hz), 9.77 (1H, brs), 12.26 (1H, brs).

Example 1142

5-Cyano-4,7-dihydro-6-(piperidin-4-yl)-4-(pyridin-4-yl)-2H-pyrazolo[3,4-b]pyridine 3 Hydrochloride The title compound was prepared from ethyl nipecotate, pyridine-4-aldehyde and 3-aminopyrazole in the same manner as in Examples 1001 and 1002.

MS (EI): 306 (M$^+$).

$^1$H-NMR (400 MHz, DMSO-d$_6$) δ (ppm): 1.86–1.92 (2H, m), 2.18–2.25 (2H, m), 2.93–3.00 (3H, m), 3.35–3.38 (2H, m), 5.41 (1H, s), 6.50 (3H, br), 7.42 (1H, s), 7.97 (2H, d, J=6.8 Hz), 8.90 (1H, br), 8.93 (2H, d, J=6.8 Hz), 9.60 (1H, br), 10.10 (1H, brs).

Example 1143

5-Cyano-4,7-dihydro-6-(piperidin-4-yl)-4-(pyridin-3-yl)-2H-pyrazolo[3,4-b]pyridine 3 Hydrochloride The title compound was prepared from ethyl nipecotate, pyridine-3-aldehyde and 3-aminopyrazole in the same manner as in Examples 1001 and 1002.

MS (EI): 306 (M$^+$)

$^1$H-NMR (400 MHz, DMSO-d$_6$) δ (ppm): 1.86–1.93 (2H, m), 2.19–2.25 (2H, m), 2.90–2.97 (3H, m), 3.35–3.38 (2H, m), 5.39 (1H, s), 6.50 (3H, br), 7.41 (1H, s), 8.09 (1H, dd, J=8.2 Hz and 5.4 Hz), 8.49 (1H, d, J=8.2 Hz), 8.72 (1H, br), 8.88 (1H, d, J=5.4 Hz), 8.92 (1H, s), 9.57 (1H, br), 10.02 (1H, brs).

Example 1144

5-Cyano-4,7-dihydro-6-(1-methylpiperidin-4-yl)-4-(pyridin-4-yl)-2H-pyrazolo[3,4-b]pyridine The title compound was prepared from 5-cyano-4,7-dihydro-6-(piperidin-4-yl)-4-(pyridin-4-yl)-2H-pyrazolo[3,4-b]pyridine 3 hydrochloride in the same manner as in Example 1003.

MS (EI): 320 (M$^+$).

$^1$H-NMR (400 MHz, DMSO-d$_6$) δ (ppm): 1.56–1.64 (2H, m), 1.86–1.90 (2H, m), 1.99–2.03 (2H, m), 2.17 (3H, s), 2.61–2.64 (1H, m), 2.86–2.89 (2H, m), 4.96 (1H, s), 7.23 (2H, d, J=6.8 Hz), 7.31 (1H, s), 8.50 (2H, d, J=6.8 Hz), 9.67 (1H, brs), 12.25 (1H, brs).

Example 1145

5-Cyano-4,7-dihydro-6-(1-methylpiperidin-4-yl)-4-(pyridin-3-yl)-2H-pyrazolo[3,4-b]pyridine The title compound was prepared from 5-cyano-4,7-dihydro-6-(piperidin-4-yl)-4-(pyridin-3-yl)-2H-pyrazolo[3,4-b]pyridine 3 hydrochloride in the same manner as in Example 1003.

MS (EI): 320 (M$^+$).

$^1$H-NMR (400 MHz, DMSO-d$_6$) δ (ppm): 1.57–1.60 (2H, m), 1.84–1.89 (2H, m), 1.99–2.05 (2H, m), 2.17 (3H, s), 2.58–2.61 (1H, m), 2.85–2.8 (2H, m), 4.98 (1H, s), 7.29 (1H, s), 7.35 (1H, dd, J=8.2 Hz and 5.4 Hz), 7.55 (1H, d, J=8.2 Hz), 8.42–8.45 (2H, m), 9.64 (1H, brs), 12.23 (1H, brs).

Example 1146

6-(exo-2-Azabicyclo[2,2,2]octan-6-yl)-4-(2-bromo-3-cyanophenyl)-5-cyano-4,7-dihydro-2H-pyrazolo[3,4-b]pyridine 2 Hydrochloride The title compound was prepared from exo-2-azabicyclo[2,2,2]octane-6-carboxylic acid ethyl ester, 2-bromo-3-cyanobenzaldehyde and 3-aminopyrazole in the same manner as in Examples 1001 and 1002.

MS (EI): 435 (M$^+$).

$^1$H-NMR (400 MHz, DMSO-d$_6$) δ (ppm): 1.52–1.54 (1H, m), 1.74–2.18 (6H, m), 3.06–3.09 (2H, m), 3.50–3.52 (2H, m), 3.87 (2H, br), 5.51 (1H, s), 7.33 (1H, d, J=7.3 Hz), 7.55–7.60 (2H, m), 7.84 (1H, d, J=7.3 Hz), 8.97 (1H, br), 9.73 (1H, br), 9.78 (1H, brs).

Example 1147

6-(endo-2-Azabicyclo[2,2,2]octan-6-yl)-4-(2-bromo-3-cyanophenyl)-5-cyano-4,7-dihydro-2H-pyrazolo[3,4-b]pyridine 2 Hydrochloride The title compound was prepared from endo-2-azabicyclo[2,2,2]octane-6-carboxylic acid ethyl ester, 2-bromo-3-cyanobenzaldehyde and 3-aminopyrazole in the same manner as in Examples 1001 and 1002.

MS (EI): 435 (M$^+$)

$^1$H-NMR (400 MHz, DMSO-d$_6$) δ (ppm): 1.67–1.69 (3H, m), 2.02–2.12 (4H, m), 3.02–3.05 (1H, m), 3.31–3.35 (1H, m), 3.45–3.51 (2H, m), 4.04 (2H, br), 5.50 (1H, s), 7.34 (1H, s), 7.56 (1H, dd, J=7.3 Hz and 7.2 Hz), 7.82 (1H, d, J=7.3 Hz), 8.16 (1H, br), 9.82 (1H, br), 9.93 (1H, brs).

Example 1148

4-(2-Bromo-3-cyanophenyl)-5-cyano-4,7-dihydro-6-(exo-2-methyl-2-azabicyclo[2,2,2]octan-6-yl)-2H-pyrazolo[3,4-b]pyridine The title compound was prepared from 6-(exo-2-azabicyclo[2,2,2]octan-6-yl)-4-(2-bromo-3-cyanophenyl)-5-cyano-4,7-dihydro-2H-pyrazolo[3,4-b]pyridine 2 hydrochloride in the same manner as in Example 1003.

MS (EI): 449 (M$^+$).

¹H-NMR (400 MHz, DMSO-d₆) δ (ppm): 1.42–1.45 (1H, m), 1.72–1.88 (5H, m), 2.06–2.09 (1H, m), 2.46–2.51 (4H, m), 3.04–3.07 (1H, m), 3.45–3.48 (2H, m), 5.48 (1H, s), 7.34 (1H, s), 7.57–7.60 (2H, m), 7.83 (1H, dd, J=7.3 Hz and 7.2 Hz), 9.83 (1H, brs), 12.37 (1H, brs).

Example 1149

Ethyl 4-(2,2-difluoro-1,3-benzodioxol-4-yl)-4,7-dihydro-6-propyl-2H-pyrazolo[3,4-b]pyridine-5-carboxylate A solution of 2,2-difluoro-1,3-benzodioxol-4-aldehyde (2.0 g), Meldrum's acid (1.6 g), ethyl 3-keto-hexanoate (1.7 g) and ammonium acetate (0.91 g) in acetic acid (20 mL) were stirred under reflux for 12 hrs. The reaction mixture was cooled to room temperature, and the solvent was evaporated under reduced pressure to give colorless crystals (2.4 g). To a solution of dimethylformamide (1.9 g) in chloroform (10 mL) were added phosphorus oxychloride (4.0 g) and a solution of the obtained colorless crystals (2.4 g) in chloroforom (10 mL) under ice-cooling, and the mixture was stirred overnight. Under ice-cooling, an aqueous sodium acetate (27 g) solution was added, and the mixture was stirred for one hour. The reaction mixture was extracted with chloroform, and the solvent was evaporated under reduced pressure to give an oil. The obtained oil was purified by silica gel column chromatography (eluent:hexane-ethyl acetate (8:2)) to give colorless crystals. To a solution of the obtained colorless crystals in pyridine (20 mL) was added hydrazine (1.0 g), and the mixture was stirred with heating for 3 hours. The reaction mixture was cooled to room temperature, and the solvent was evaporated under reduced pressure to give an oil. The oil was purified by silica gel column chromatography (eluent:hexane-ethyl acetate (1:1)) to give the title compound (190 mg) as colorless crystals.

MS (EI): 391 (M⁺).

¹H-NMR (400 MHz, DMSO-d₆) δ (ppm): 0.90–0.97 (6H, m), 1.58–1.64 (2H, m), 2.60–2.64 (1H, m), 2.83–2.86 (1H, m), 3.83 (2H, q, J=7.3 Hz), 5.32 (1H, m), 6.86 (1H, d, J=7.3 Hz), 7.03–7.11 (2H, m), 7.24 (1H, s), 9.61 (1H, brs), 12.06 (1H, brs).

Example 1150

Ethyl 4-(2-bromo-3-cyanophenyl)-4,7-dihydro-6-(piperidin-4-yl)-2H-pyrazolo[3,4-b]pyridine-5-carboxylate 2 Hydrobromide The title compound was prepared from 2-bromo-3-cyanobenzaldehyde in the same manner as in Example 1110.

MS (EI): 455 (M⁺)

¹H-NMR (400 MHz, DMSO-d₆) δ (ppm): 0.84 (3H, t, J=7.3 Hz), 1.78–1.81 (1H, m), 1.98–2.14 (3H, m), 2.87–2.90 (2H, m), 3.40–3.42 (2H, m), 3.78 (2H, q, J=7.3 Hz), 3.80–4.25 (3H, m), 5.64 (1H, s), 7.35 (1H, s), 7.40–7.47 (2H, m), 7.70 (1H, d, J=7.3 Hz), 8.10 (1H, br), 8.73 (1H, br), 9.37 (1H, brs).

Example 1151

Ethyl 4-(2-bromo-3-cyanophenyl)-4,7-dihydro-6-(1-methylpiperidin-4-yl)-2H-pyrazolo[3,4-b]pyridine-5-carboxylate The title compound was prepared from ethyl 4-(2-bromo-3-cyanophenyl)-4,7-dihydro-6-(piperidin-4-yl)-2H-pyrazolo[3,4-b]pyridine-5-carboxylate 2 hydrobromide in the same manner as in Example 1003.

MS (EI): 469 (M⁺)

¹H-NMR (400 MHz, DMSO-d₆) δ (ppm): 0.85 (3H, t, J=7.3 Hz), 1.53–1.55 (1H, m), 1.70–1.72 (1H, m), 1.87–2.06 (4H, m), 2.16 (3H, s), 2.84–2.88 (2H, m), 3.78 (2H, q, J=7.3 Hz), 3.94–3.96 (1H, m), 5.63 (1H, s), 7.34–7.48 (3H, m), 7.68 (1H, d, J=7.3 Hz), 9.34 (1H, brs), 12.16 (1H, brs).

Example 1152

4-(2,1,3-Benzoxadiazol-4-yl)-5-cyano-4,7-dihydro-6-(1-methyl-2-oxo-piperidin-4-yl)-2H-pyrazolo[3,4-b]pyridine The title compound was prepared from 1-methyl-2-oxo-piperidine-4-carboxylic acid ethyl ester, 2,1,3-benzoxadiazole-4-aldehyde and 3-aminopyrazole in the same manner as in Example 1001.

MS (EI): 375 (M⁺).

¹H-NMR (400 MHz, DMSO-d₆) δ (ppm): 1.88–1.91 (1H, m), 2.26–2.33 (2H, m), 2.65–2.70 (1H, m), 2.82 (3H, m), 3.17–3.20 (1H, m), 3.31–3.36 (2H, m), 5.40 (1H, s), 7.29 (1H, s), 7.44 (1H, d, J=6.6 Hz), 7.58 (1H, dd, J=9.0 Hz and 6.6 Hz), 7.92 (1H, d, J=9.0 Hz), 9.88 (1H, brs), 12.22 (1H, brs).

Example 1153

4-(2-Bromo-3-cyanophenyl)-5-cyano-4,7-dihydro-6-(1-methyl-2-oxo-piperidin-4-yl)-2H-pyrazolo[3,4-b]pyridine The title compound was prepared from 1-methyl-2-oxo-piperidine-4-carboxylic acid ethyl ester, 2-bromo-3-cyanobenzaldehyde and 3-aminopyrazole in the same manner as in Example 1001.

MS (EI): 437 (M⁺)

¹H-NMR (400 MHz, DMSO-d₆) δ (ppm): 1.88–1.92 (1H, m), 2.25–2.36 (2H, m), 2.69–2.74 (1H, m), 2.84 (3H, s), 3.18–3.36 (3H, m), 5.50 (1H, s), 7.37 (1H, s), 7.59–7.62 (2H, m), 7.85 (1H, d, J=7.3 Hz), 9.90 (1H, brs), 12.33 (1H, brs).

Example 1154

4-(2-Chlorophenyl)-4,7-dihydro-5-(5-methyl-1,3,4-oxadiazol-2-yl)-6-propyl-2H-pyrazolo[3,4-b]pyridine A solution of 2-chlorobenzaldehyde (21 g), Meldrum's acid (21 g), 3-keto-hexanoic acid 2-cyanoethyl ester (27 g) and ammonium acetate (13 g) in acetic acid (150 mL) was heated under reflux overnight. The reaction mixture was cooled to room temperature, and the solvent was evaporated under reduced pressure to give colorless crystals (16 g). A 1N NaOH solution (100 mL) was added, and the mixture was stirred with heating for 3 hours. The reaction mixture was cooled to room temperature, and the solvent was acidified. The reaction mixture was extracted with ethyl acetate, and the solvent was evaporated under reduced pressure to give colorless crystals (9.6 g). Hydrazine (0.22 g) and CDI (0.66 g) were added to the obtained colorless crystals (1.0 g) in DMF (5 mL), and the mixture was stirred for 3 hours. And the precipitated crystals were collected by filtration to give colorless crystals (0.7 g). Orthoacetic acid triethyl ester (3.7 g) was added to the obtained colorless crystals (1.0 g) in DMF (5 mL), and the mixture was heated for 3 hours. And the precipitated crystals were collected by filtration to give colorless crystals (0.6 g). To a solution of dimethylformamide (0.55 g) in chloroform (3 mL) were added phosphorus oxychloride (1.2 g) and a solution of the obtained colorless crystals in chloroform (6 mL) under ice-cooling, and the mixture was stirred overnight. Under ice-cooling, an aqueous sodium acetate (7.7 g) solution was added, and the mixture was stirred for one hour. The reaction mixture was extracted with chloroform, and the solvent was evaporated under reduced pressure to give an oil. The obtained oil was purified by silica gel column chromatography (eluent:hexane-ethyl acetate (8:2)) to give colorless crystals. To a solution of the obtained colorless crystals in pyridine (10 mL) was added hydrazine (0.15 g), and the mixture was stirred with heating for 3 hours. The reaction mixture was cooled to room temperature, and the solvent was evaporated under reduced pressure to give an oil. The oil was purified by silica gel column chromatography (eluent:hexane-ethyl acetate (1:1)) to give the title compound (170 mg) as colorless crystals.

MS (EI): 356 (M$^+$).

$^1$H-NMR (400 MHz, DMSO-d$_6$) δ (ppm): 1.00 (3H, t, J=7.3 Hz), 1.67–1.74 (2H, m), 2.31 (3H, s), 2.70–2.83 (2H, m), 5.71 (1H, s), 7.07–7.12 (3H, m), 7.33–7.40 (2H, m), 9.49 (1H, brs), 12.04 (1H, brs).

Example 1155

4-(2-Bromo-3-cyanophenyl)-5-cyano-4,7-dihydro-6-(1-(methylamino)ethyl)-2H-pyrazolo[3,4-b]pyridine 2 Hydrochloride The title compound was prepared from 2-methylglycine ethyl ester, 2-bromo-3-cyanobenzaldehyde and 3-aminopyrazole in the same manner as in Examples 1015 and 1002.

MS (EI): 384 (M$^+$)

$^1$H-NMR (400 MHz, DMSO-d$_6$) δ (ppm): 1.49 (3H, d, J=7.3 Hz), 3.09 (3H, s), 4.00 (2H, br), 4.60 (1H, q, J=7.3 Hz), 5.53 (1H, s), 7.48–7.53 (2H, m), 7.64 (1H, s), 7.82 (1H, d, J=7.3 Hz), 8.00–8.29 (2H, r), 10.97 (1H, brs).

Example 1156

4-(2-Chlorophenyl)-4,7-dihydro-5-(5-methyl-1,2,4-oxadiazol-3-yl)-6-propyl-2H-pyrazolo[3,4-b]pyridine A solution of 2-chlorobenzaldehyde (21 g), Meldrum's acid (21 g), 3-keto-hexanoic acid 2-cyanoethyl ester (27 g) and ammonium acetate (13 g) in acetic acid (150 mL) was heated under reflux overnight. The reaction mixture was cooled to room temperature, and the solvent was evaporated under reduced pressure to give colorless crystals (16 g). A 1N NaOH solution (100 mL) was added, and the mixture was stirred with heating for 3 hours. The reaction mixture was cooled to room temperature, and the solvent was acidified. The reaction mixture was extracted with ethyl acetate, and the solvent was evaporated under reduced pressure to give colorless crystals (9.6 g). An Ammonia solution (3.0 g) and CDI (2.8 g) were added to the obtained colorless crystals (4.2 g) in DMF (20 mL), and the mixture was stirred overnight. The reaction mixture was extracted with ethyl acetate, and the solvent was evaporated under reduced pressure to give an oil. The residue in N,N-dimethylacetamide dimethyl acetal (30 mL) solution was heated for 2 hours, and the solvent was evaporated under reduced pressure. Hydroxyammonium (1.4 g), 1N NaOH (20 mL), dioxane (20 mL) and acetic acid (28 mL) were added to the residue, and the mixture was heated for one hour. The reaction mixture was extracted with ethyl acetate, and the solvent was evaporated under reduced pressure to give an oil. The oil was purified by silica gel column chromatography (eluent:hexane-ethyl acetate (1:1)) to give the colorless crystals (1.3 g). To a solution of dimethylformamide (1.7 g) in chloroform (10 mL) were added phosphorus oxychloride (3.5 g) and a solution of the obtained colorless crystals in chloroforom (20 mL) under ice-cooling, and the mixture was stirred overnight. Under ice-cooling, an aqueous sodium acetate (23 g) solution was added, and the mixture was stirred for one hour. The reaction mixture was extracted with chloroform, and the solvent was evaporated under reduced pressure to give an oil. The obtained oil was purified by silica gel column chromatography (eluent:hexane-ethyl acetate (8:2)) to give colorless crystals. To a solution of the obtained colorless crystals in pyridine (15 mL) was added hydrazine (0.6 g), and the mixture was stirred with heating for 3 hours. The reaction mixture was cooled to room temperature, and the solvent was evaporated under reduced pressure to give an oil. The oil was purified by silica gel column chromatography (eluent:hexane-ethyl acetate (1:1)) to give the title compound (500 mg) as colorless crystals.

MS (EI): 356 (M$^+$).

$^1$H-NMR (400 MHz, DMSO-d$_6$) δ (ppm): 0.99 (3H, s), 1.62 (3H, t, J=7.3 Hz), 1.66–1.73 (2H, m), 2.13 (3H, s), 2.35–2.38 (2H, m), 2.84–3.05 (2H, m), 5.73 (1H, s), 7.06–7.17 (3H, m), 9.90 (1H, brs), 12.11 (1H, brs).

Example 1157

4-(2,1,3-Benzoxadiazol-4-yl)-4,7-dihydro-5-(5-methyl-1,3,4-oxadiazol-2-yl)-6-propyl-2H-pyrazolo [3,4-b]pyridine The title compound was prepared from 2,1,3-benzoxadiazole-4-aldehyde in the same manner as in Example 1154.

MS (EI): 364 (M$^+$)

$^1$H-NMR (400 MHz, DMSO-d$_6$) δ (ppm): 1.01 (3H, t, J=7.3 Hz), 1.69–1.76 (2H, m), 2.31 (3H, s), 2.72–2.86 (2H, m), 5.82 (1H, s), 7.18 (1H, d, J=6.6 Hz), 7.32 (1H, s), 7.48 (1H, dd, J=9.0 Hz and 6.6 Hz), 7.80 (1H, d, J=9.0 Hz), 9.65 (1H, brs), 12.07 (1H, brs).

Example 1158

4-(2-Bromo-3-cyanophenyl)-4,7-dihydro-5-(5-methyl-1,3,4-oxadiazol-2-yl)-6-propyl-2H-pyrazolo [3,4-b]pyridine The title compound was prepared from 2-bromo-3-cyanobenzaldehyde in the same manner as in Example 1154.

MS (EI): 425 (M$^+$)

$^1$H-NMR (400 MHz, DMSO-d$_6$) δ (ppm): 1.00 (3H, t, J=7.3 Hz), 1.66–1.73 (2H, m), 2.33 (3H, s)., 2.74–2.78 (2H, m), 5.78 (1H, s), 7.40–7.47 (3H, m), 7.69 (1H, dd, J=7.3 Hz and 7.2 Hz), 9.63 (1H, brs), 12.14 (1H, brs).

Example 1159

6-(1-Amino-1-methylethyl)-4-(2-chlorophenyl)-5-cyano-4,7-dihydro-2H-pyrazolo[3,4-b]pyridine Hydrochloride The title compound was prepared from 2,2-dimethylglycine ethyl ester, 2-chlorobenzaldehyde and 3-aminopyrazole in the same manner as in Examples 1015 and 1002.
Example 1001
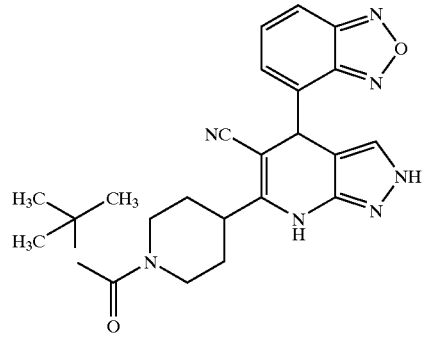
Example 1002
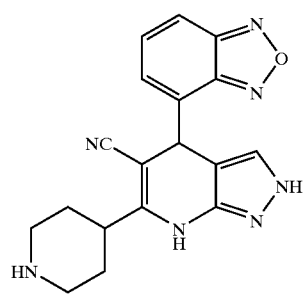
Example 1003
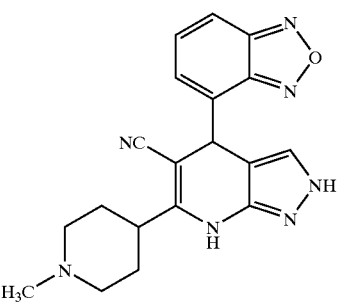
Example 1004
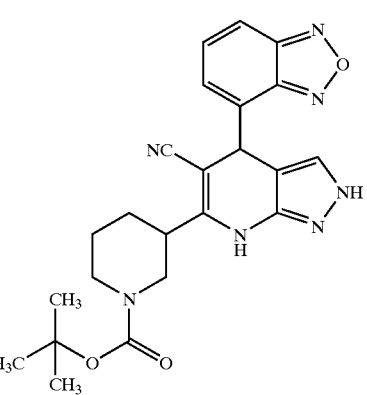
-continued
Example 1005
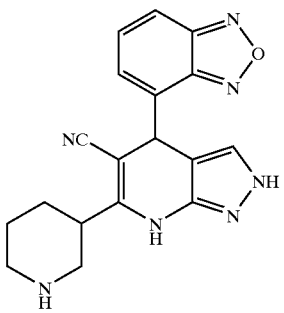
Example 1006
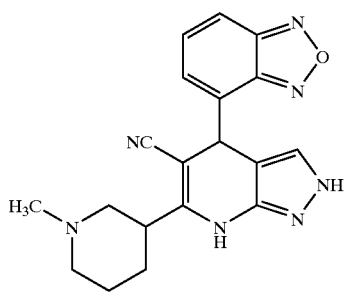
Example 1007
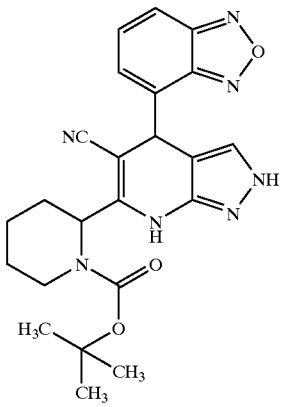
Example 1008
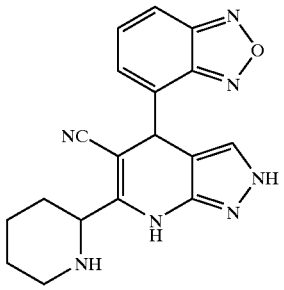
Example 1009
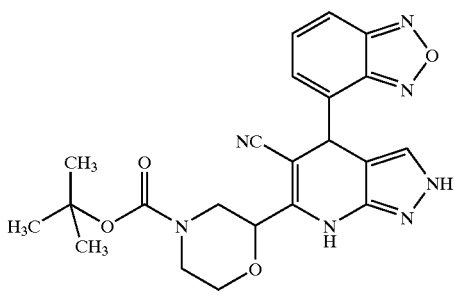

Example 1010
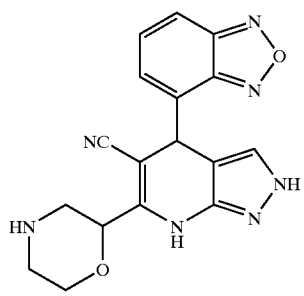
Example 1015
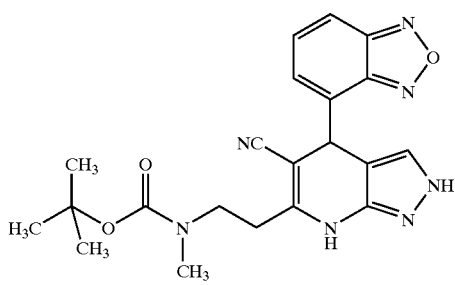
Example 1011
Example 1016
Example 1012
Example 1017
Example 1013
Example 1018
Example 1014
Example 1019

Example 1020
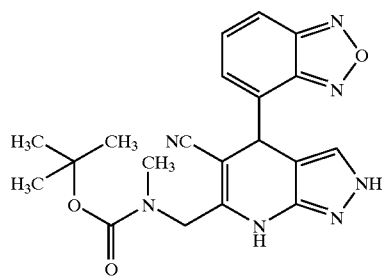
Example 1025
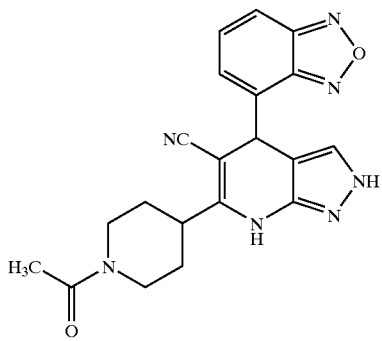
Example 1021
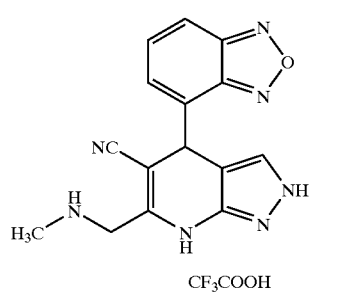
Example 1026
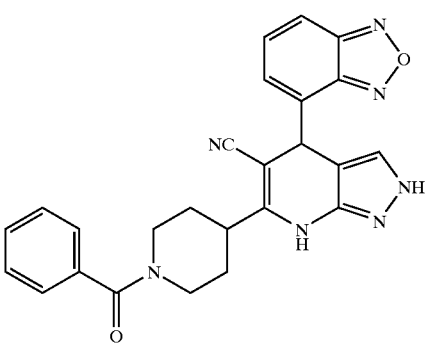
Example 1022
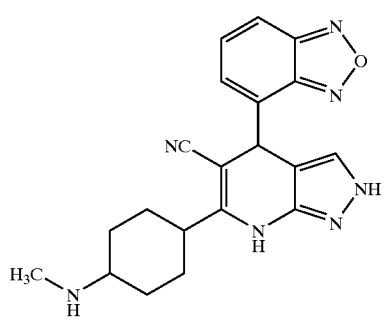
Example 1023
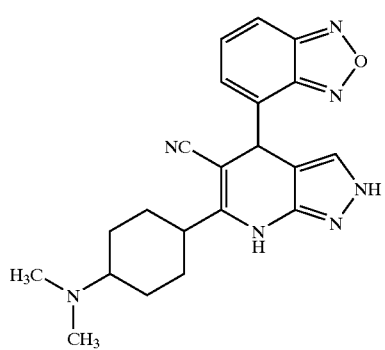
Example 1027
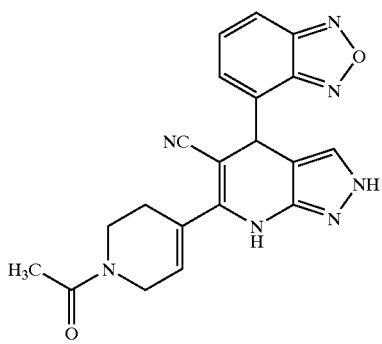
Example 1024
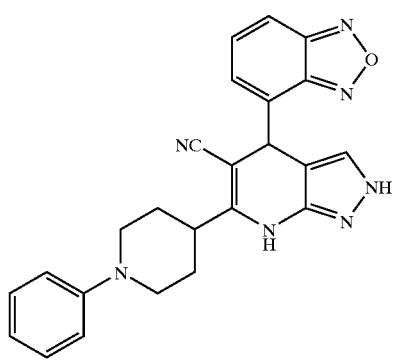
Example 1028
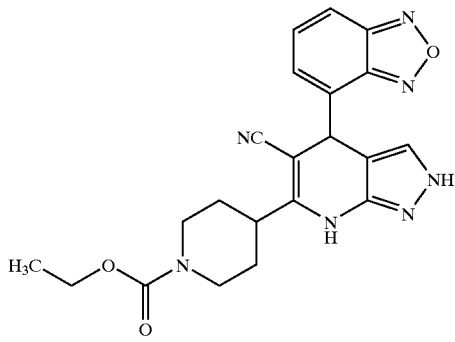

Example 1029
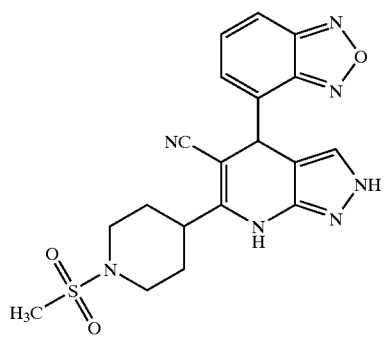
Example 1033
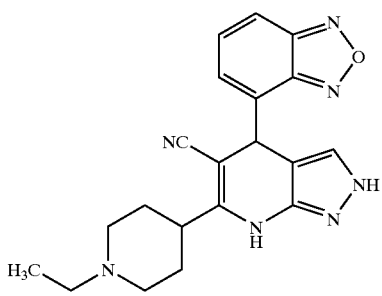
Example 1030
Example 1034
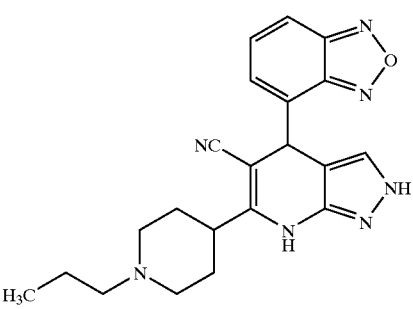
Example 1031
Example 1035
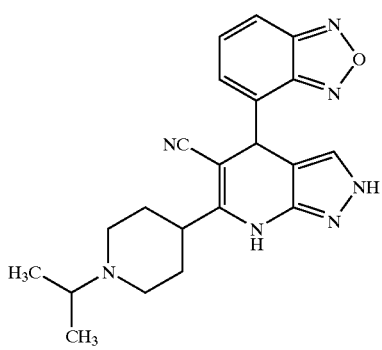
Example 1032
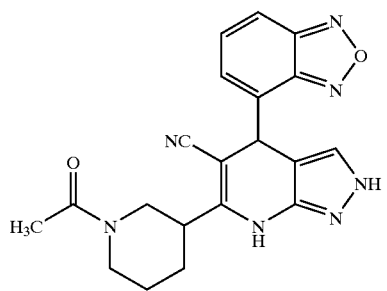
Example 1036
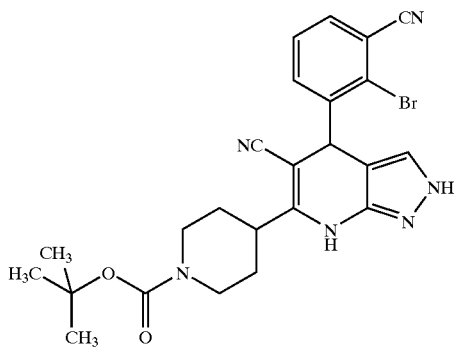

Example 1037
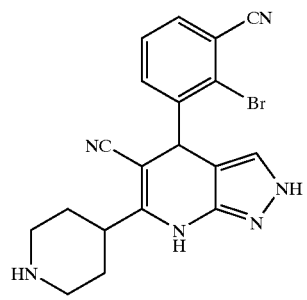
Example 1038
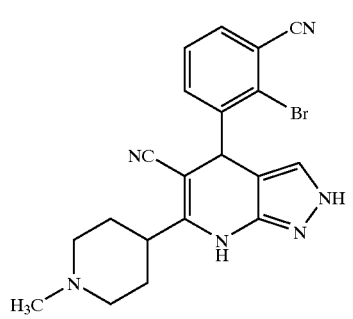
Example 1039
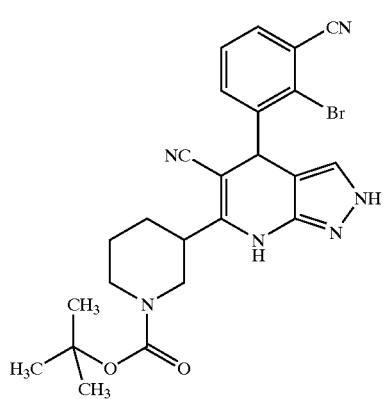
Example 1040
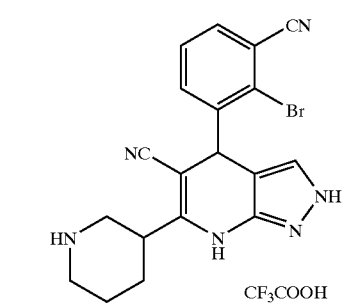
Example 1041
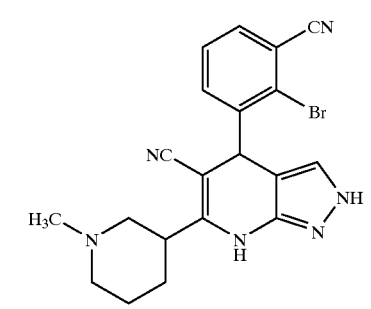
Example 1042
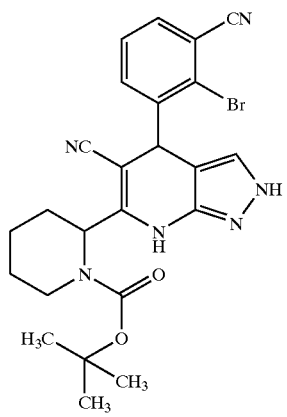
Example 1043
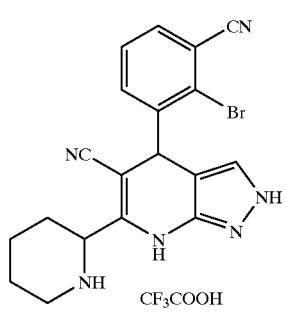
Example 1044
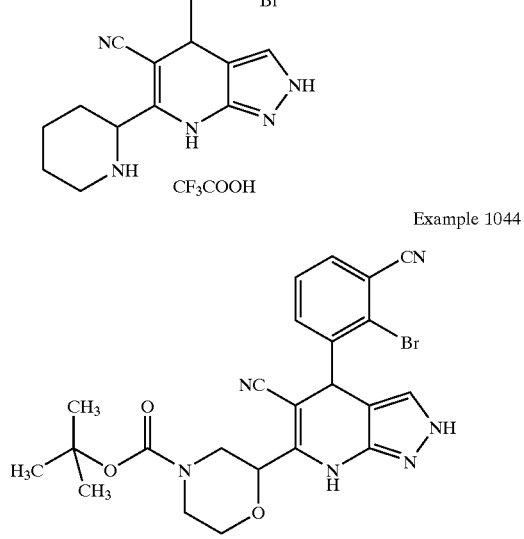
Example 1045
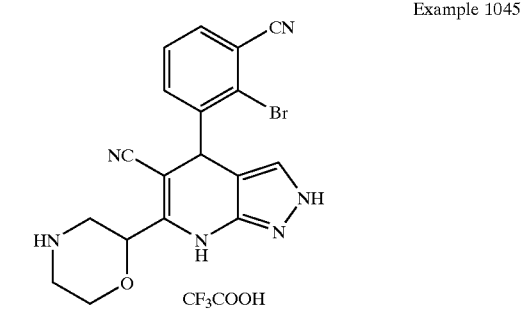
Example 1046
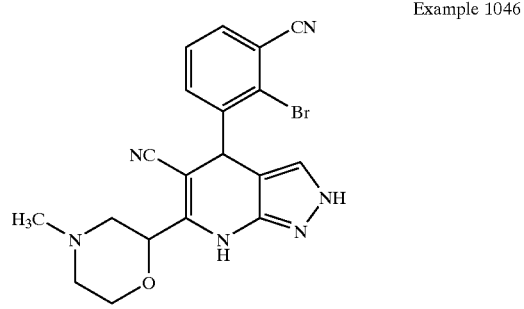

Example 1047

Example 1048

Example 1049

Example 1050

Example 1051

Example 1052

Example 1053

Example 1054

Example 1055

Example 1056

Example 1057
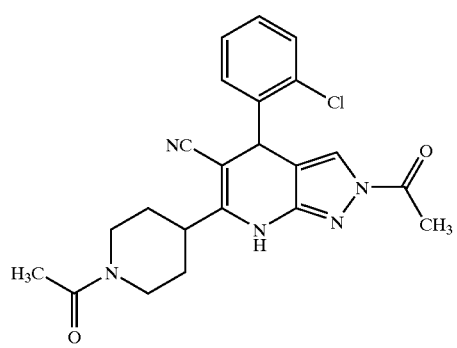
Example 1058
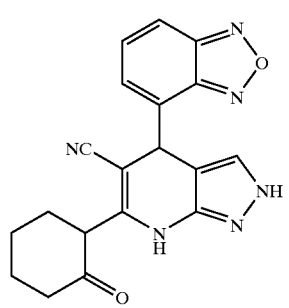
Example 1059
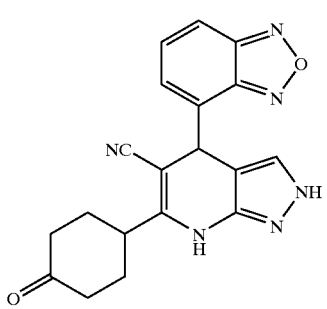
Example 1060
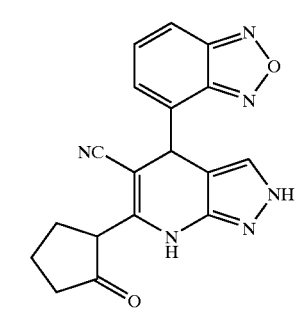
Example 1061
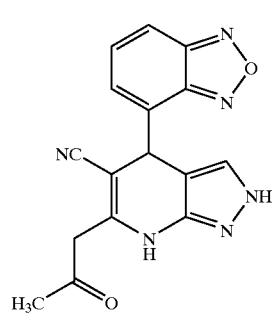
Example 1062
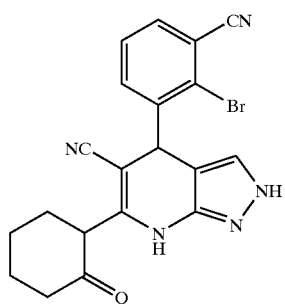
Example 1063
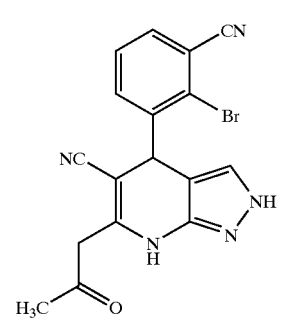
Example 1064
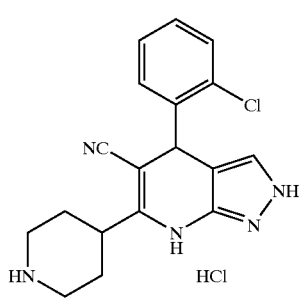
Example 1065
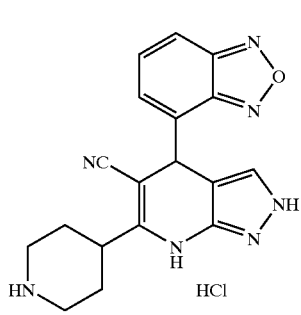
Example 1066
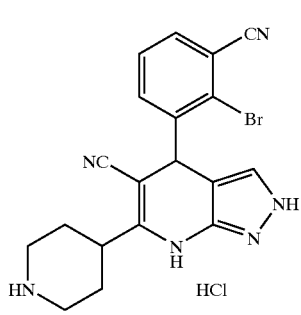

Example 1067
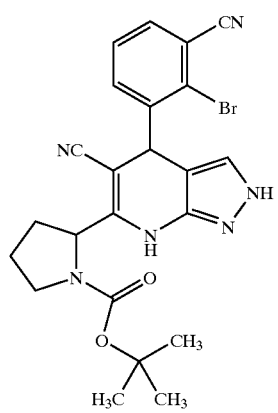
Example 1068
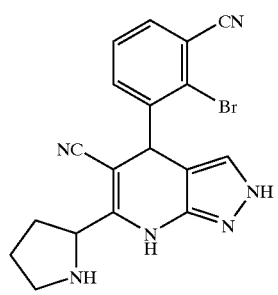
Example 1069
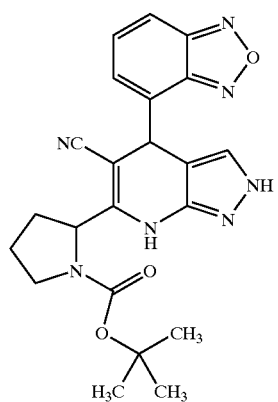
Example 1070
Example 1071
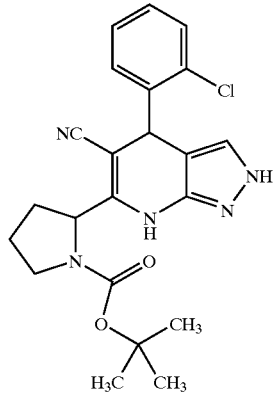
Example 1072
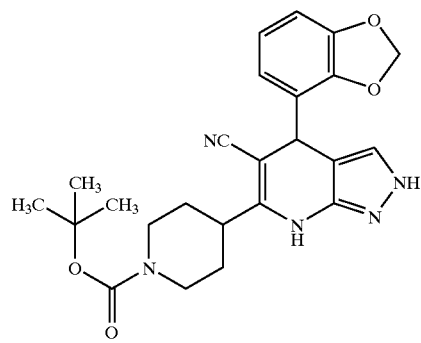
Example 1073
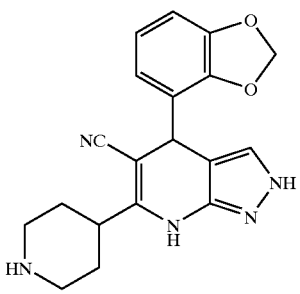
Example 1074
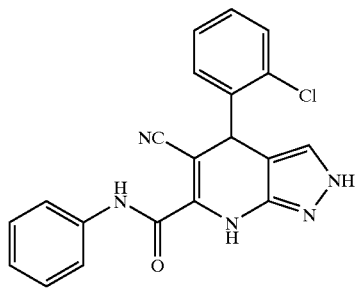
Example 1075
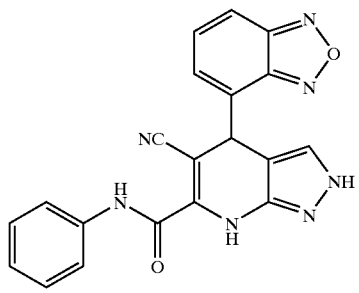

-continued
Example 1076
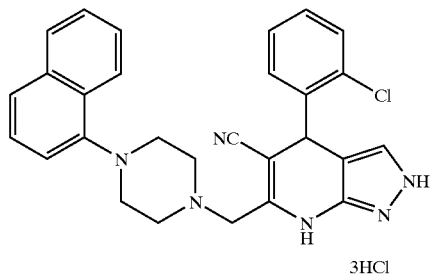
3HCl
Example 1077
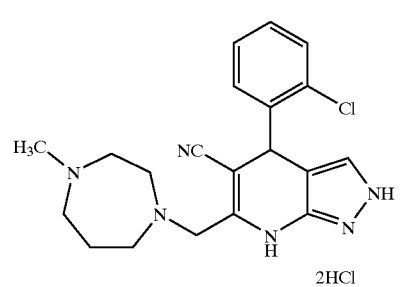
2HCl
Example 1078
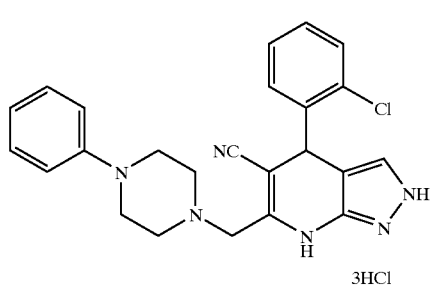
3HCl
Example 1079
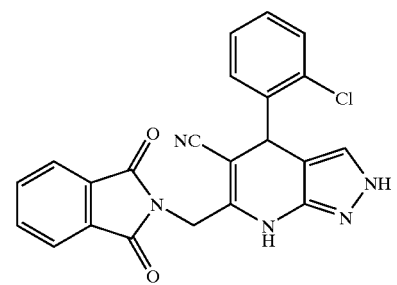
Example 1080
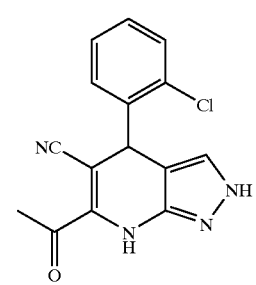
-continued
Example 1081
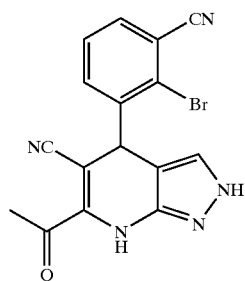
Example 1082
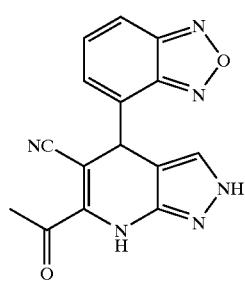
Example 1083
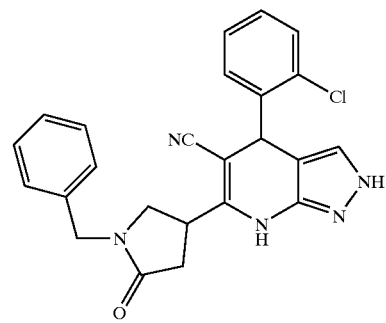
Example 1084
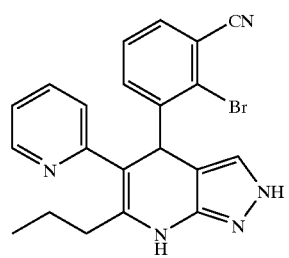
Example 1085
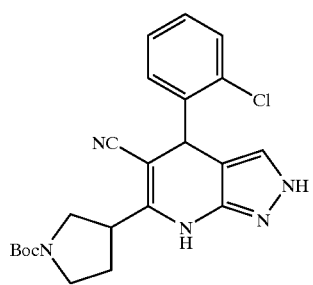

Example 1086
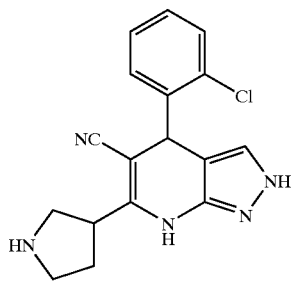
Example 1087
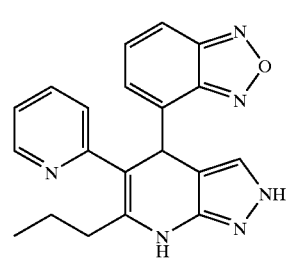
Example 1088
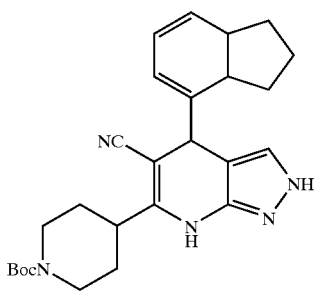
Example 1089
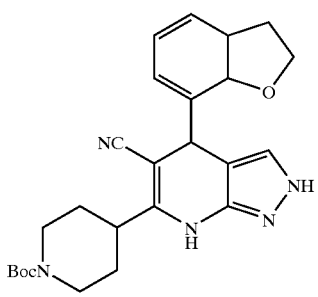
Example 1090
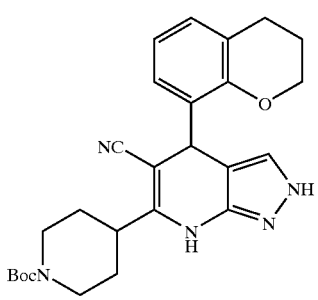
Example 1091
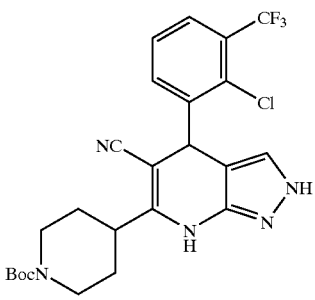
Example 1092
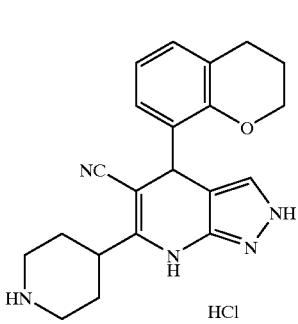
Example 1093
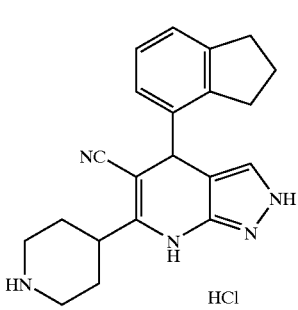
Example 1094
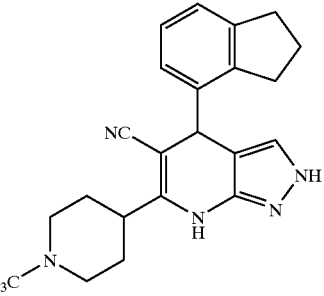
Example 1095
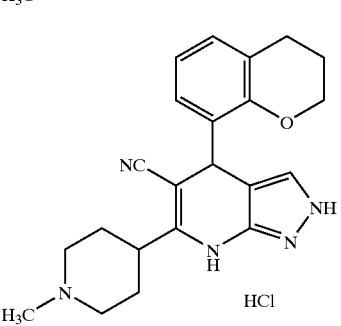

Example 1096

Example 1097

Example 1098

Example 1099

Example 1100

Example 1101

Example 1102

Example 1103

Example 1104

Example 1105

Example 1106
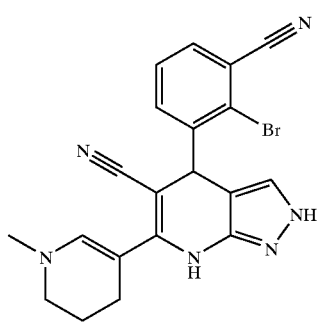
Example 1107
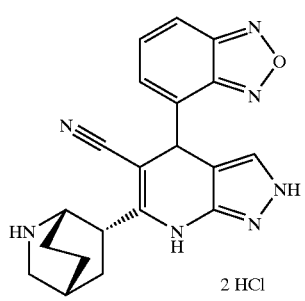
2 HCl
Example 1108
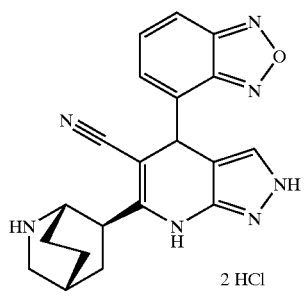
2 HCl
Example 1109
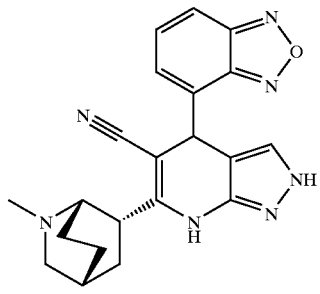
Example 1110
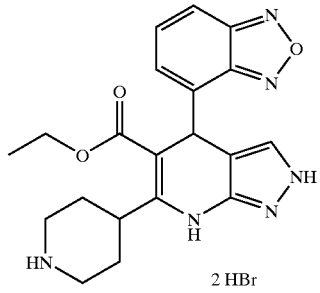
2 HBr
Example 1111
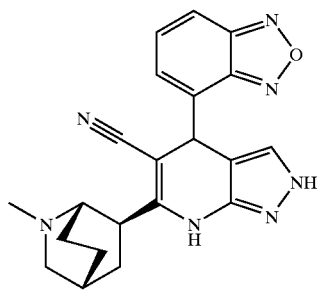
Example 1112
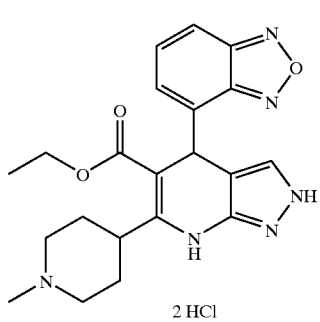
2 HCl
Example 1113
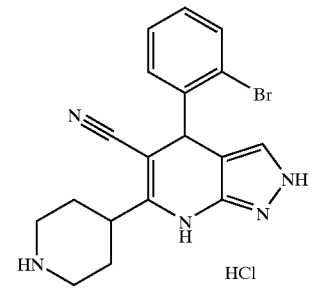
HCl
Example 1114
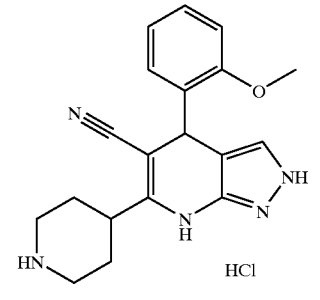
HCl
Example 1115
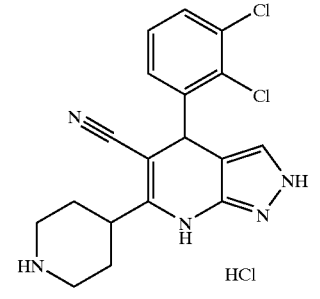
HCl 265
-continued
Example 1116
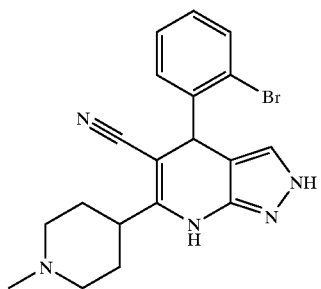
Example 1117
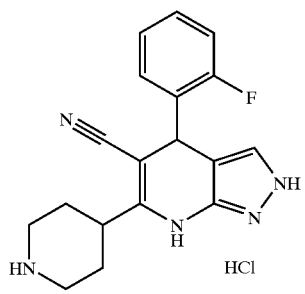
Example 1118
Example 1119
Example 1120
266
-continued
Example 1121
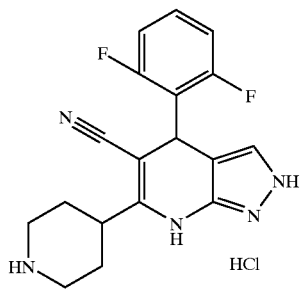
Example 1122
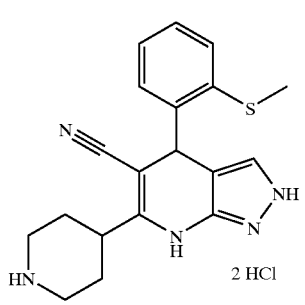
Example 1123
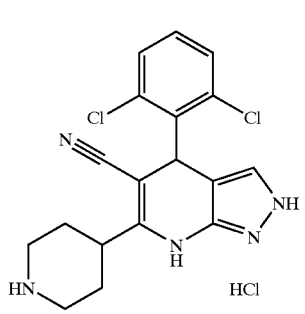
Example 1124
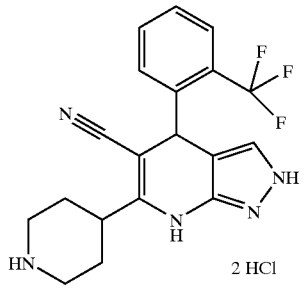
Example 1125
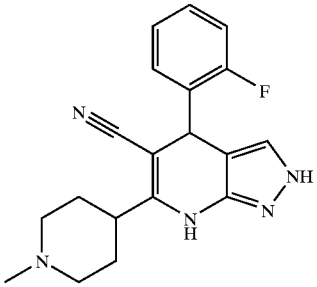

Example 1126
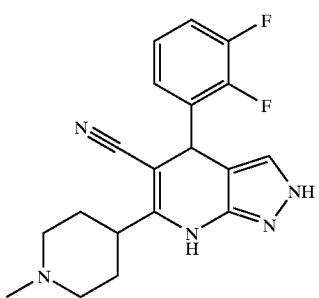
Example 1127
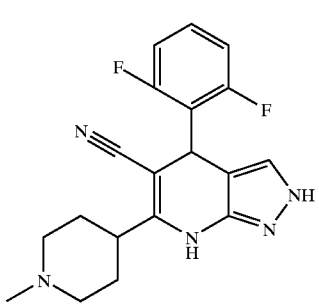
Example 1128
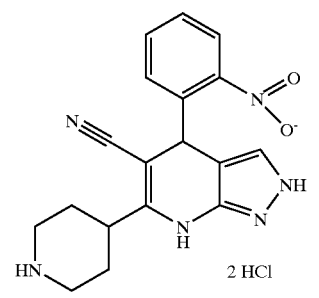
2 HCl
Example 1129
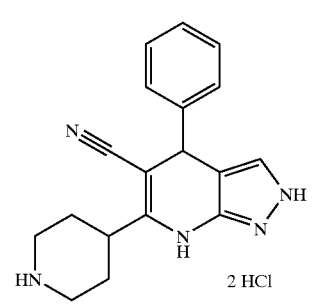
2 HCl
Example 1130
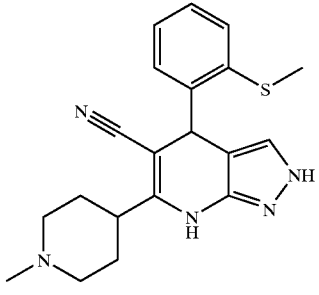
Example 1131
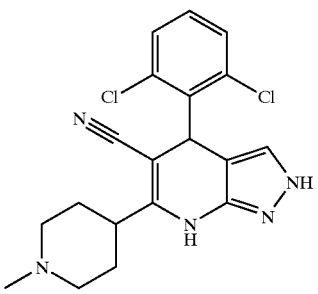
Example 1132
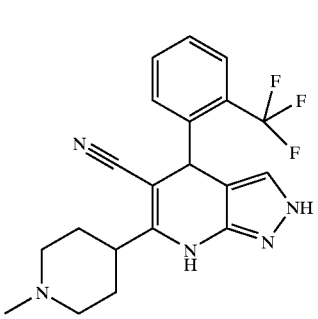
Example 1133
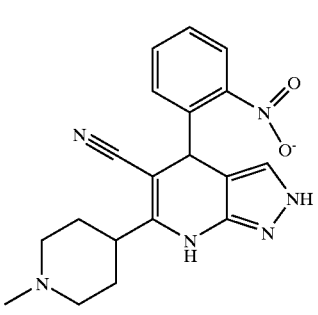
Example 1134
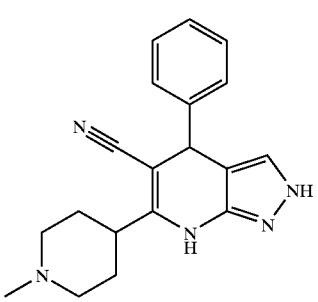
Example 1135
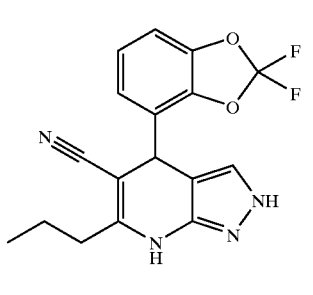

Example 1136
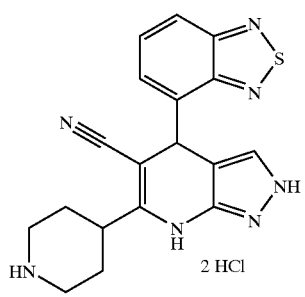
2 HCl
Example 1137
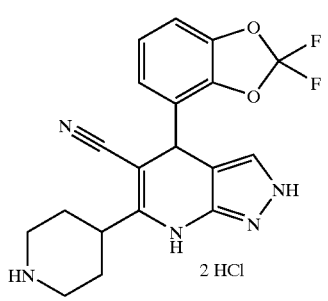
2 HCl
Example 1138
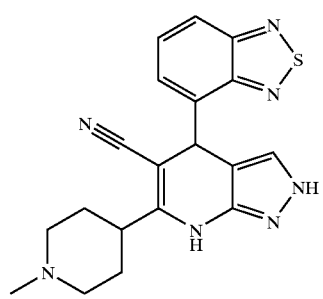
Example 1139
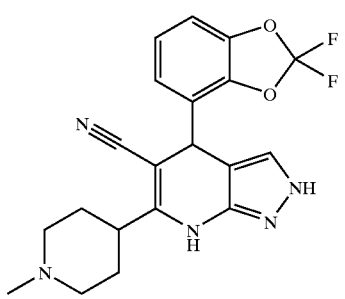
Example 1140
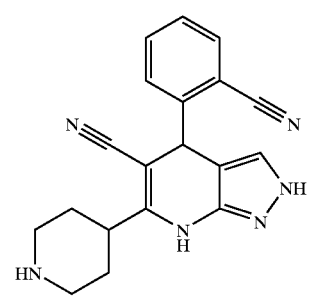
Example 1141
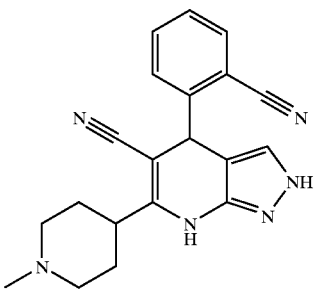
Example 1142
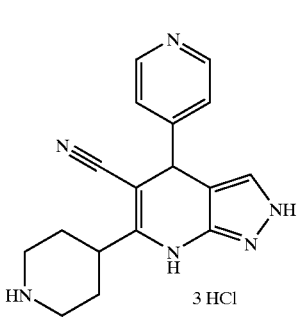
3 HCl
Example 1143
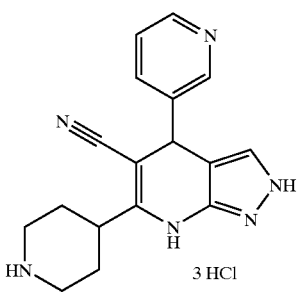
3 HCl
Example 1144
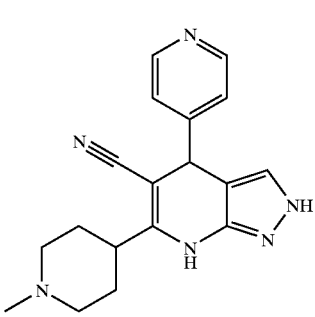
Example 1145
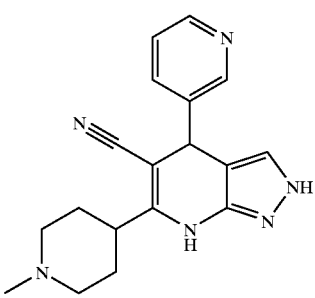

Example 1146
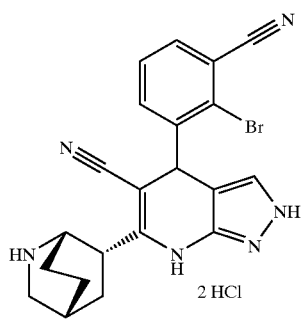
2 HCl
Example 1147
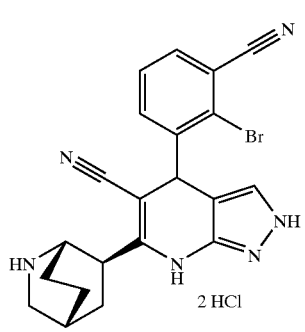
2 HCl
Example 1148
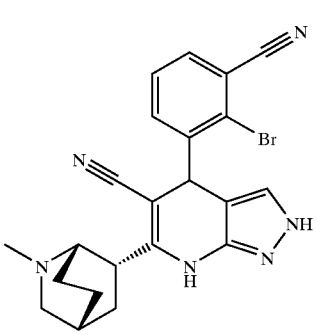
Example 1149
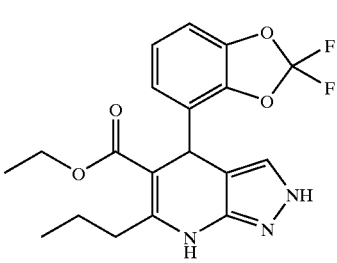
Example 1150
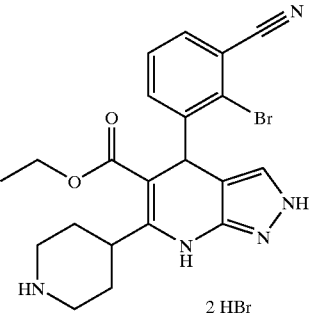
2 HBr
Example 1151
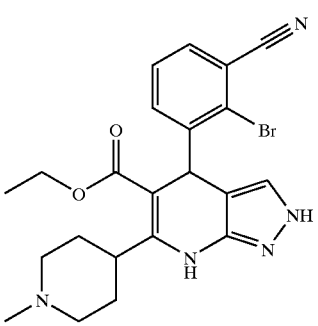
Example 1152
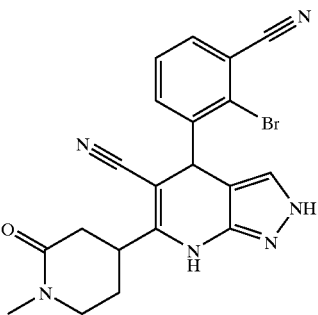
Example 1153
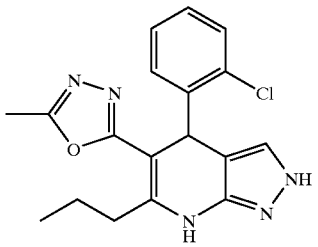
Example 1154
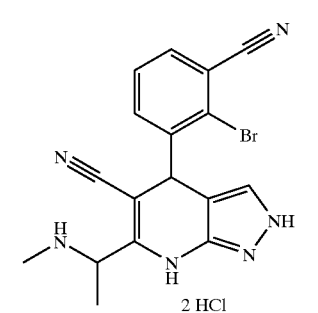
Example 1155
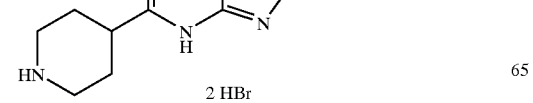
2 HCl -continued Example 1156

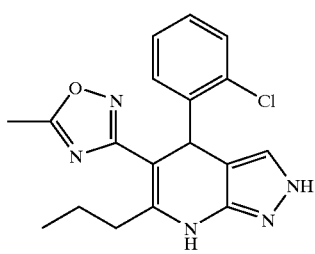

Example 1157

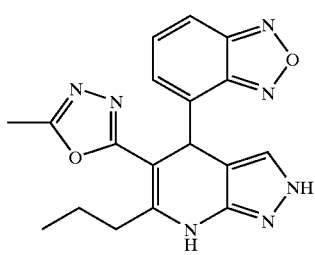

Example 1158

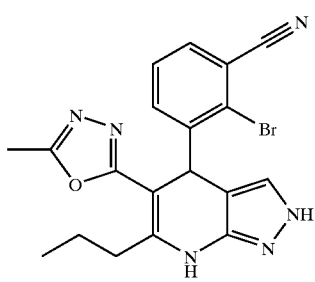

Example 1159

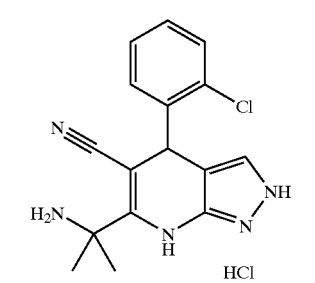

Formulation Example 1

The compound of Example 1 (0.5 part), lactose (25 parts), crystalline cellulose (35 parts) and corn starch (3 parts) were thoroughly mixed and kneaded well with a binder made of corn starch (2 parts). The kneaded product was passed through a 16 mesh sieve, dried in an oven at 50° C. and passed through a 24 mesh sieve. The kneaded powder thus obtained, corn starch (8 parts), crystalline cellulose (11 parts) and talc (9 parts) were thoroughly mixed and compression-punched to give tablets containing 0.5 mg of the active ingredient per tablet.

Formulation Example 2

The compound of Example 1 (1.0 mg) and sodium chloride (9.0 mg) were dissolved in water for injection, and the solution was filtered to remove pyrogen. The filtrate was transferred into an ampoule under sterile conditions. After sterilization, the ampoule was weld-sealed to give injection containing 1.0 mg of the active ingredient.

The effects of the compounds of the present invention on glycogen synthase kinase-3 beta (GSK-3β) were evaluated and confirmed as follows.

Formulation Example 3

The compound of Example 1001 (0.5 part), lactose (25 parts), crystalline cellulose (35 parts) and corn starch (3 parts) were thoroughly mixed and kneaded well with a binder made of corn starch (2 parts). The kneaded product was passed through a 16 mesh sieve, dried in an oven at 50° C. and passed through a 24 mesh sieve. The kneaded powder thus obtained, corn starch (8 parts), crystalline cellulose (11 parts) and talc (9 parts) were thoroughly mixed and compression-punched to give tablets containing 0.5 mg of the active ingredient per tablet.

Formulation Example 4

The compound of Example 1001 (1.0 mg) and sodium chloride (9.0 mg) were dissolved in water for injection, and the solution was filtered to remove pyrogen. The filtrate was transferred into an ampoule under sterile conditions. After sterilization, the ampoule was weld-sealed to give injection containing 1.0 mg of the active ingredient.

The effects of the compounds of the present invention on glycogen synthase kinase-3 beta (GSK-3β) were evaluated and confirmed as follows.

Experimental Example 1

GSK-3β-inhibitory Activity

CREB phosphopeptide (4.6 mmol), rabbit GSK-3β (0.5 unit), ATP (5 mmol), [γ-$^{32}$P]ATP (12.3 kBq) and a test compound were reacted in a GSK-3β buffer solution (25 μL) (20 mmol/L Tris-HCl (pH 7.5), 10 mmol/L magnesium chloride, 5 mmol/L dithiothreitol) containing 1% dimethyl sulfoxide, at 30° C. for 20 minutes. The reaction product (10 μL) was adsorbed on a P81 ion-exchange paper, and the paper was washed with phosphoric acid (100 mmol/L) and measured for cpm on a scintillation counter. As a result, the compounds of the present invention showed the $IC_{50}$ values of 1 to 1000 mmol/L. For example, the $IC_{50}$ values of the compounds of Examples 1, 14, 27, 66 and 140 were 210, 170, 25, 51 and 24 mmol/L, respectively.

CREB Phosphopeptide is Lys-Arg-Arg-Glu-Ile-Leu-Ser-Arg-Arg-Pro-Ser(P)-Tyr-Arg.

Experimental Example 2

GSK-3β-inhibitory Activity in Rat Cultured Hippocampal Neurons

Hippocampal neurons were obtained from rat embryos on the 18th day after conception. After culturing the hippocampal neurons for 7 days, the neurons were treated with amyloid β (25–35) (20 μmol/L) and a test compound (GSK-3β inhibitor), and the culture was continued for 3 hours, whereby phosphorylation of Tau protein was induced. After the completion of culture, the level of phosphorylation of Tau protein was determined by EIA method using phosphorylated Tau-recognizing antibody (phosphorylated site by GSK-3β), and the inhibitory effect of the GSK-3β inhibitor on the neurons was evaluated. FIG. 1 shows the GSK-3β-inhibitory activity of the compounds of Example 47 and Example 137.

Experimental Example 3

Effect on Amyloid β-induced Cytotoxicity in Rat Cultured Hippocampal Neurons

Figure 2:
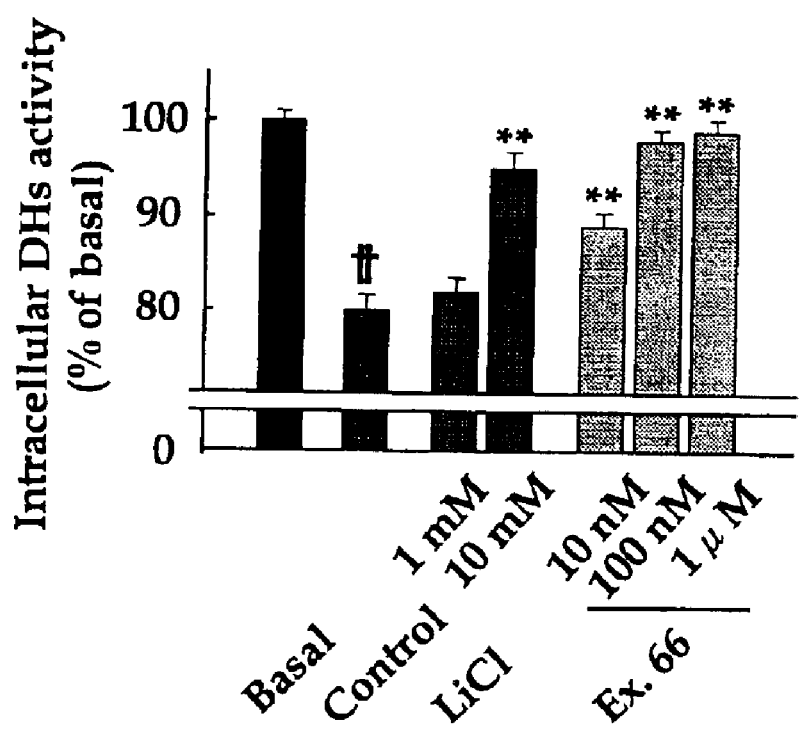
FIG. 2 shows the effect of the compound of Example 66 on amyloid β-induced cytotoxicity.

Hippocampal neurons were obtained from rat embryos on the 18th day after conception. After culturing the hippocampal neurons for 7 days, the neurons were treated with amyloid β (25–35) (20 μmol/L) and a test compound (GSK-3β inhibitor), and the culture was continued for 24 hours, whereby cytotoxicity (decreased activity of intracellular dehydrogenases) was induced. After the completion of culture, activity of intracellular dehydrogenases was determined and the effect of the GSK-3β inhibitor on the amyloid β-induced cytotoxicity was evaluated. FIG. 2 shows the effect of the compounds of Example 66 on amyloid β-induced cytotoxicity.

Experimental Example 4

GSK-3β-inhibitory Effect in Gerbil Brain Ischemia Model

Figure 3:
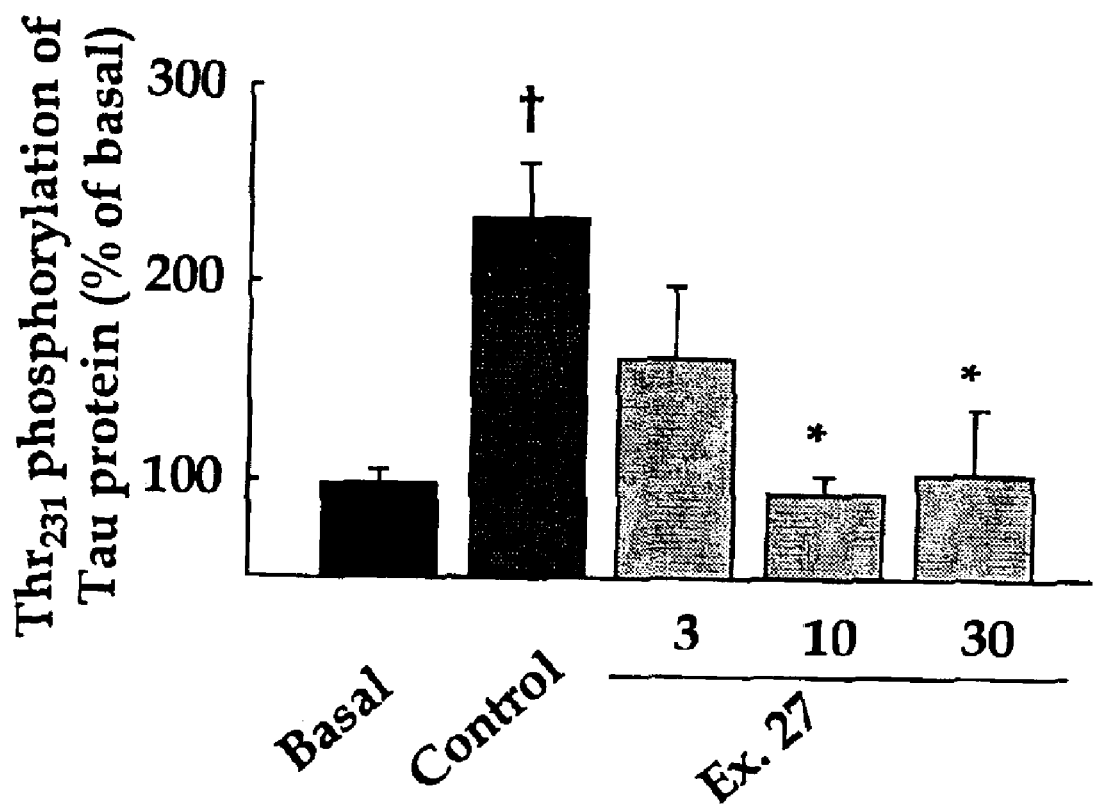
FIG. 3 shows the GSK-3β-inhibitory effect of the compound of Example 27 in a gerbil brain ischemia model.

A test compound (GSK-3β inhibitor) was intraperitoneally administered to gerbils and 30 minutes later, brain ischemia was created by shutting off (for 4 minutes) all carotid arteries, whereby phosphorylation of Tau protein in the brain was induced. Three hours after the brain ischemia, the hippocampus was obtained from the gerbil brain and the level of phosphorylation of Tau protein was determined by Western blot using phosphorylated Tau-recognizing antibody (phosphorylated site by GSK-3β), based on which the GSK-3β-inhibitory effect of the GSK-3β inhibitor in the gerbil brain was evaluated. FIG. 3 shows the GSK-3β-inhibitory effect of the compounds of Example 27 in gerbil brain ischemia model.

Experimental Example 5

GSK-3β-inhibitory Activity

CREB phosphopeptide (4.6 mmol), rabbit GSK-3β (0.5 unit), ATP (5 mmol), [γ-$^{32}$P]ATP (12.3 kBq) and a test compound were reacted in a GSK-3β buffer solution (25 μL) (20 mmol/L Tris-HCl (pH 7.5), 10 mmol/L magnesium chloride, 5 mmol/L dithiothreitol) containing 1% dimethyl sulfoxide, at 30° C. for 20 minutes. The reaction product (10 μL) was adsorbed on a P81 ion-exchange paper, and the paper was washed with phosphoric acid (100 mmol/L) and measured for cpm on a scintillation counter. As a result, the compounds of the present invention showed the IC$_{50}$ values of 1 to 1000 mmol/L. For example, the IC$_{50}$ values of the compounds are shown in the following Table 1.

CREB Phosphopeptide is Lys-Arg-Arg-Glu-Ile-Leu-Ser-Arg-Arg-Pro-Ser(P)-Tyr-Arg.

TABLE 1

| Example No. | IC$_{50}$ (nmol/L) |
|---|---|
| 1002 | 10 |
| 1003 | 2.5 |
| 1008 | 3.7 |
| 1011 | 14 |
| 1023 | 4.1 |
| 1058 | 1.8 |
| 1063 | 3.0 |
| 1146 | 0.61 |
| 1148 | 3.2 |
| 1155 | 2.2 |
| 1158 | 0.65 |

Experimental Example 6

GSK-3β-inhibitory Activity in Rat Cultured Hippocampal Neurons

Hippocampal neurons were obtained from rat embryos on the 18th day after conception. After culturing the hippocampal neurons for 7 days, the neurons were treated with amyloid β (25–35) (20 μmol/L) and a test compound (GSK-3β inhibitor), and the culture was continued for 3 hours, whereby phosphorylation of Tau protein was induced. After the completion of culture, the level of phosphorylation of Tau protein was determined by EIA method using phosphorylated Tau-recognizing antibody (phosphorylated site by GSK-3β), and the inhibitory effect of the GSK-3β inhibitor on the neurons was evaluated.

Experimental Example 7

Effect on Amyloid β-induced Cytotoxicity in Rat Cultured Hippocampal Neurons

Hippocampal neurons were obtained from rat embryos on the 18th day after conception. After culturing the hippocampal neurons for 7 days, the neurons were treated with amyloid β (25–35) (20 μmol/L) and a test compound (GSK-3β inhibitor), and the culture was continued for 24 hours, whereby cytotoxicity (decreased activity of intracellular dehydrogenases) was induced. After the completion of culture, activity of intracellular dehydrogenases was determined, and the effect of the GSK-3β inhibitor on the amyloid β-induced cytotoxicity was evaluated.

Experimental Example 8

GSK-3β-inhibitory Effect in Gerbil Brain Ischemia Model

A test compound (GSK-3β inhibitor) was intraperitoneally administered to gerbils, and 30 minutes later, brain ischemia was created by shutting off (for 4 minutes) all carotid arteries, whereby phosphorylation of Tau protein in the brain was induced. Three hours after the brain ischemia, the hippocampus was obtained from the gerbil brain, and the level of phosphorylation of Tau protein was determined by Western blot using phosphorylated Tau-recognizing antibody (phosphorylated site by GSK-3β), based on which the GSK-3β-inhibitory effect of the GSK-3β inhibitor in the gerbil brain was evaluated.

The compounds of the present invention show a selective and strong inhibitory action on glycogen synthase kinase-3 beta (GSK-3β), and are useful as medicaments for prevention and/or treatment of diabetes, diabetic complications, neurodegenerative diseases (Alzheimer's disease, ischemic cerebrovascular disorders, Down's syndrome, cerebral ischemia due to cerebral amyloid angiopathy, progressive supranuclear paralysis, subacute sclerosing panencephalitic Parkinsonism, postencephalitic Parkinsonism, boxer's encephalopathy, Parkinsonism dementia complex of Guam, Lewy body disease, Pick's disease, corticobasal degeneration, frontotemporal dementia, AIDS encephalopathy, Huntington's disease, manic-depressive psychosis and the like), alopecia, breast cancer, non-small cell lung carcinoma, thyroid cancer, T or B-cell leukemia, and several virus-induced tumors, or as immunopotentiators.

This application is based on patent application Nos. 2001–304707, 2001–26379, 2001–081238 and 2002–230581 filed in Japan, the contents of which are hereby incorporated by reference.

What is claimed is:

1. A dihydropyrazolopyridine compound of the formula (I):

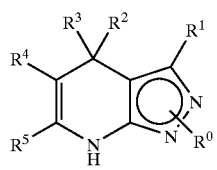

wherein $R^0$ is hydrogen, alkyl, aralkyl, acyl, cycloalkyl, formyl, haloalkyl, aminoalkyl, alkoxyalkyl, phenoxyalkyl, hydroxyalkyl, aminocarbonyl, alkylthiocarbonyl, carboxyalkyl, cycloalkoxyalkyl, alkylsulfinyl, alkylsulfonyl, phenylsulfonyl, phenylsulfinyl, mercaptoalkyl, alkylthioalkyl, acyloxyacetyl, acyloxyalkyl, phenyl optionally having substituent(s), aromatic heterocyclic group optionally having substituent(s), phenylalkyl optionally having substituent(s), or a group of the formula: —COOR$^8$ wherein R$^8$ is hydrogen, alkyl, aryl optionally having substituent(s) or aralkyl optionally having substituent(s);

$R^1$ and $R^2$ are the same or different and each is hydrogen, alkyl, aralkyl, acyl, cycloalkyl, hydroxy, thiol, halogen, amino, formyl, carboxy, cyano, nitro, alkylthio, haloalkyl, aminoalkyl, acylamino, alkoxy, cycloalkoxy, phenoxy, phenylalkoxy, aminoalkoxy, alkoxyalkyl, phenoxyalkyl, hydroxyalkyl, alkoxycarbonyl, aminocarbonyl, alkylthiocarbonyl, carboxyalkyl, cycloalkoxyalkyl, phenylthio, alkylsulfinyl, alkylsulfonyl, phenylsulfonyl, mercaptoalkyl, alkylthioalkyl, phenyl optionally having substituent(s), aromatic heterocyclic group or phenylalkyl;

$R^3$ is
(1) haloalkyl,
(2) cycloalkyl,
(3) phenyl optionally having substituent(s),
(4) aromatic heterocyclic group,
(5) a benzene ring fused with a saturated or unsaturated 5 or 6 membered carbocyclic ring,
(6) a benzene ring fused with a saturated or unsaturated 5 to 7 membered carbocyclic ring containing 1 to 3 heteroatom(s), or
(7) a 5 to 7 membered saturated or unsaturated carbocyclic ring containing 1 to 3 heteroatom(s), which is fused with a benzene ring,
wherein the groups of (2) to (7) may have one or more substituent(s), or
a group selected from the groups represented by the following formulas (II) and (III):

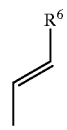

wherein R$^6$ and R$^7$ are each phenyl optionally having substituent(s) or an aromatic heterocyclic group, or R$^2$ and R$^3$ in conjunction form a ring optionally containing heteroatom(s), wherein the ring may be fused with a benzene ring optionally having substituent(s);

$R^4$ is alkoxycarbonyl, alkylcarbonyl, aminocarbonyl, hydrazinocarbonyl, alkylthiocarbonyl, formyl, carbamoyl, alkylthio, phenylthio, alkylsulfinyl, phenylsulfinyl, alkylsulfonyl, phenylsulfonyl, dialkylphosphinyl, dialkylphosphonyl, phenyl optionally having substituent(s), an aromatic heterocyclic group optionally having substituent(s), cyano or nitro; and $R^5$ is hydrogen, cyano, formyl, alkyl, cycloalkyl, alkoxyalkyl, phenoxyalkyl, dialkoxyalkyl, hydroxyalkyl, haloalkyl, carboxyalkyl, cycloalkoxyalkyl, phenylthio, alkylsulfinyl, alkylsulfonyl, phenylsulfonyl, mercaptoalkyl, alkylthioalkyl, alkoxycarbonylalkyl, alkoxycarbonylethenyl, aryl optionally having substituent(s), an aromatic heterocyclic group or phenylalkyl, or a group derived from a 5 to 7 membered saturated or unsaturated carbocyclic ring containing 1 to 3 heteroatom(s), which is fused with a benzene ring; or phenylaminoalkyl,
acyl,
acylalkyl,
aminocarbonyl,
arylaminocarbonyl,
a saturated or unsaturated 4 to 7 membered heterocyclic ring optionally having substituent(s),
a saturated 3 to 7 membered carbocyclic ring having substituent(s),
alkyl substituted by a saturated or unsaturated 4 to 7 membered ring containing 1 or 2 nitrogen atom(s), which optionally has a substituent, or
a group of the formula: —(CR$^a$R$^b$)$_n$NR$^{11}$R$^{12}$ wherein n is an integer of 1 to 4, R$^a$ is hydrogen or alkyl, R$^b$ is hydrogen or alkyl, R$^{11}$ is hydrogen, alkyl, alkylsulfonyl, phenylsulfonyl, phenylalkylsulfonyl, alkylsulfinyl, phenylsulfinyl, phenylalkylsulfinyl, alkoxycarbonyl, phenoxycarbonyl, phenylalkoxycarbonyl, alkylcarbonyl, phenylcarbonyl or phenylalkylcarbonyl, and R$^{12}$ is hydrogen or alkyl, or R$^4$ and R$^5$ in conjunction may form a 5 or 6 membered ring optionally containing heteroatom(s), provided that when R$^0$, R$^1$ and R$^2$ are each hydrogen, R$^4$ is methoxycarbonyl and R$^5$ is methyl, then R$^3$ is not phenyl, 2-chloropheny, 3-nitrophenyl, 4-carboxyphenyl or 4-methoxycarbonylphenyl, and when R$^5$ is alkyl, then R$^4$ is not alkoxycarbonyl, alkylsulfonyl, alkylsulfinyl, phenylsulfinyl, phenylsulfonyl, dialkylphosphinyl, dialkylphosphonyl, cyano or nitro, or an optically active form thereof, a pharmaceutically acceptable salt thereof or a hydrate thereof.

2. The dihydropyrazolopyridine compound of claim 1, wherein $R^0$ is hydrogen, alkyl, acyl, cycloalkyl, formyl, haloalkyl, aminoalkyl, alkoxyalkyl, phenoxyalkyl, hydroxyalkyl, aminocarbonyl, alkylthiocarbonyl, carboxyalkyl, cycloalkoxyalkyl, alkylsulfinyl, alkylsulfonyl, phenylsulfonyl, mercaptoalkyl, alkylthioalkyl, acyloxyacetyl, acyloxyalkyl, phenyl optionally having substituent(s), aromatic heterocyclic group optionally having substituent(s), phenylalkyl optionally having substituent(s), or a group of the formula: —COOR$^8$ wherein R$^8$ is hydrogen, alkyl, aryl optionally having substituent(s) or aralkyl optionally having substituent(s);

$R^1$ and $R^2$ are the same or different and each is hydrogen, alkyl, acyl, cycloalkyl, hydroxy, thiol, halogen, amino, formyl, carboxy, cyano, nitro, alkylthio, haloalkyl, aminoalkyl, acylamino, alkoxy, cycloalkoxy, phenoxy, phenylalkoxy, aminoalkoxy, alkoxyalkyl, phenoxyalkyl, hydroxyalkyl, alkoxycarbonyl, aminocarbonyl, alkylthiocarbonyl, carboxyalkyl, cycloalkoxyalkyl, phenylthio, alkylsulfinyl, alkylsulfonyl, phenylsulfonyl, mercaptoalkyl, alkylthioalkyl, phenyl optionally having substituent(s), aromatic heterocyclic group or phenylalkyl;

$R^3$ is
(1) alkyl or haloalkyl,
(2) cycloalkyl,
(3) phenyl optionally having substituent(s),
(4) aromatic heterocyclic group,
(5) a benzene ring fused with a saturated or unsaturated 5 or 6 membered carbocyclic ring,
(6) a benzene ring fused with a saturated or unsaturated 5 to 7 membered carbocyclic ring containing 1 to 3 heteroatom(s), or
(7) a 5 to 7 membered saturated or unsaturated carbocyclic ring containing 1 to 3 heteroatom(s), which is fused with a benzene ring,
wherein the groups of (2) to (7) may have one or more substituent(s), or
a group selected from the groups represented by the following formulas (II) and (III):

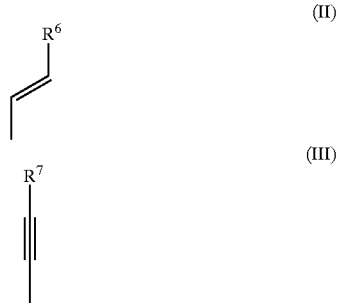

wherein $R^6$ and $R^7$ are each phenyl optionally having substituent(s) or an aromatic heterocyclic group,
or $R^2$ and $R^3$ in conjunction form a ring optionally containing heteroatom(s), wherein the ring may be fused with a benzene ring optionally having substituent(s);

$R^4$ is alkoxycarbonyl, aminocarbonyl, hydrazinocarbonyl, alkylthiocarbonyl, formyl, carbamoyl, alkylthio, phenylthio, alkylsulfinyl, phenylsulfinyl, alkylsulfonyl, phenylsulfonyl, dialkylphosphinyl, dialkylphosphonyl, cyano or nitro; and $R^5$ is hydrogen, cyano, formyl, alkyl, cycloalkyl, alkoxyalkyl, phenoxyalkyl, dialkoxyalkyl, hydroxyalkyl, haloalkyl, carboxyalkyl, cycloalkoxyalkyl, phenylthio, alkylsulfinyl, alkylsulfonyl, phenylsulfonyl, mercaptoalkyl, alkylthioalkyl, alkoxycarbonylalkyl, alkoxycarbonylethenyl, aryl optionally having substituent(s), an aromatic heterocyclic group or phenylalkyl, or a group derived from a 5 to 7 membered saturated or unsaturated carbocyclic ring containing 1 to 3 heteroatom(s), which is fused with a benzene ring, or $R^4$ and $R^5$ in conjunction may form a 5 or 6 membered ring optionally containing heteroatom(s), provided that when $R^0$, $R^1$ and $R^2$ are each hydrogen, $R^4$ is methoxycarbonyl and $R^5$ is methyl, then $R^3$ should not be phenyl, 2-chloropheny, 3-nitrophenyl, 4-carboxyphenyl or 4-methoxycarbonylphenyl, or an optically active form thereof, a pharmaceutically acceptable salt thereof or a hydrate thereof.

3. The dihydropyrazolopyridine compound of claim 2, wherein $R^5$ is alkyl having 2 to 8 carbon atoms, cycloalkyl, alkoxyalkyl, phenoxyalkyl, hydroxyalkyl, phenyl optionally having substituent(s), an aromatic heterocyclic group or phenylalkyl, or an optically active form thereof, a pharmaceutically acceptable salt thereof or a hydrate thereof.

4. The dihydropyrazolopyridine compound of claim 2, wherein $R^1$ is hydrogen, alkyl, phenyl optionally having substituent(s), an aromatic heterocyclic group or phenylalkyl, or an optically active form thereof, a pharmaceutically acceptable salt thereof or a hydrate thereof.

5. The dihydropyrazolopyridine compound of claim 2, wherein $R^2$ is hydrogen or alkyl, or an optically active form thereof, a pharmaceutically acceptable salt thereof or a hydrate thereof.

6. The dihydropyrazolopyridine compound of claim 2, wherein $R^3$ is phenyl optionally having 1 to 3 substituent(s), naphthyl, 2,1,3-benzoxadiazol-4-yl or 3,4-dihydro-2H-benzopyran-8-yl, or an optically active form thereof, a pharmaceutically acceptable salt thereof or a hydrate thereof.

7. The dihydropyrazolopyridine compound of claim 2, wherein $R^4$ is alkoxycarbonyl having 2 to 5 carbon atoms, cyano or nitro, or an optically active form thereof, a pharmaceutically acceptable salt thereof or a hydrate thereof.

8. The dihydropyrazolopyridine compound of claim 2, wherein $R^5$ is alkyl having 2 to 4 carbon atoms, cyclopropyl, phenyl, thienyl or hydroxyalkyl, or an optically active form thereof, a pharmaceutically acceptable salt thereof or a hydrate thereof.

9. The dihydropyrazolopyridine compound of claim 2, wherein $R^2$ and $R^3$ in conjunction form a ring containing sulfur atom and the ring is condensed with a benzene ring optionally having substituent(s), or an optically active form thereof, a pharmaceutically acceptable salt thereof or a hydrate thereof.

10. The dihydropyrazolopyridine compound of claim 2, wherein $R^0$ is hydrogen or a group of the formula: —COOR$^8$ wherein R$^8$ is alkyl, aryl optionally having substituent(s) or aralkyl optionally having substituent(s), or an optically active form thereof, a pharmaceutically acceptable salt thereof or a hydrate thereof.

11. The dihydropyrazolopyridine compound of claim 2, which is selected from the group consisting of
(32) ethyl 4,7-dihydro-4-(2-methoxyphenyl)-6-propyl-2H-pyrazolo[3,4-b]pyridine-5-carboxylate,
(47) ethyl 4-(2-chloro-3-trifluoromethylphenyl)-4,7-dihydro-6-propyl-2H-pyrazolo[3,4-b]pyridine-5-carboxylate,

(66) ethyl 4,7-dihydro-4-(naphthalen-1-yl)-6-propyl-2H-pyrazolo[3,4-b]pyridine-5-carboxylate,
(73) ethyl 4-(3,4-dihydro-2H-benzopyran-8-yl)-4,7-dihydro-6-propyl-2H-pyrazolo[3,4-b]pyridine-5-carboxylate,
(87) ethyl 4-(2-chlorophenyl)-4,7-dihydro-6-(thiophen-2-yl)-2H-pyrazolo[3,4-b]pyridine-5-carboxylate,
(116) ethyl 4-(2,1,3-benzoxadiazol-4-yl)-4,7-dihydro-6-propyl-2H-pyrazolo[3,4-b]pyridine-5-carboxylate,
(122) 4-(2,3-dichlorophenyl)-4,7-dihydro-5-nitro-6-propyl-2H-pyrazolo[3,4-b]pyridine,
(140) 4-(2,1,3-benzoxadiazol-4-yl)-5-cyano-4,7-dihydro-6-propyl-2H-pyrazolo[3,4-b]pyridine,
(147) 4-(2-bromo-3-cyanophenyl)-5-cyano-4,7-dihydro-6-phenyl-2H-pyrazolo[3,4-b]pyridine,
(158) 4-(2,1,3-benzoxadiazol-4-yl)-5-cyano-4,7-dihydro-6-phenyl-2H-pyrazolo[3,4-b]pyridine,
(171) 4-(2,1,3-benzoxadiazol-4-yl)-5-cyano-4,7-dihydro-6-(thiophen-2-yl)-2H-pyrazolo[3,4-b]pyridine,
(182) ethyl 4-(2-bromo-3-nitrophenyl)-4,7-dihydro-6-propyl-2H-pyrazolo[3,4-b]pyridine-5-carboxylate,
(183) ethyl 4-(2-bromo-3-cyanophenyl)-4,7-dihydro-6-propyl-2H-pyrazolo[3,4-b]pyridine-5-carboxylate,
(189) 4-(2-bromo-3-nitrophenyl)-5-cyano-4,7-dihydro-6-propyl-2H-pyrazolo[3,4-b]pyridine,
(205) ethyl 2-tert-butoxycarbonyl-4-(2-chlorophenyl)-4,7-dihydro-6-propyl-2H-pyrazolo[3,4-b]pyridine-5-carboxylate,
(240) ethyl 4-(2,1,3-benzoxadiazol-4-yl)-6-ethyl-4,7-dihydro-2H-pyrazolo[3,4-b]pyridine-5-carboxylate,
(257) 4-(2,1,3-benzoxadiazol-4-yl)-5-cyano-4,7-dihydro-6-hydroxymethyl-2H-pyrazolo[3,4-b]pyridine,
(260) 4-(2-bromo-3-cyanophenyl)-5-cyano-4,7-dihydro-6-isopropyl-2H-pyrazolo[3,4-b]pyridine,
(264) 4-(2,1,3-benzoxadiazol-4-yl)-5-cyano-4,7-dihydro-6-isopropyl-2H-pyrazolo[3,4-b]pyridine, and
(268) 4-(2-bromo-3-cyanophenyl)-5-cyano-6-cyclopropyl-4,7-dihydro-2H-pyrazolo[3,4-b]pyridine,
a tautomer, an optically active form thereof, a pharmaceutically acceptable salt thereof or a hydrate thereof.

12. The dihydropyrazolopyridine compound of claim 1, wherein
$R^0$ is hydrogen, alkyl, aralkyl, acyl, cycloalkyl, formyl, haloalkyl, aminoalkyl, alkoxyalkyl, phenoxyalkyl, hydroxyalkyl, aminocarbonyl, alkylthiocarbonyl, carboxyalkyl, cycloalkoxyalkyl, alkylsulfinyl, alkylsulfonyl, phenylsulfonyl, phenylsulfinyl, mercaptoalkyl, alkylthioalkyl, acyloxyacetyl, acyloxyalkyl, phenyl optionally having substituent(s), aromatic heterocyclic group optionally having substituent(s), phenylalkyl optionally having substituent(s), or a group of the formula: —COOR$^8$ wherein R$^8$ is hydrogen, alkyl, aryl optionally having substituent(s) or aralkyl optionally having substituent(s);
$R^1$ is hydrogen;
$R^2$ is hydrogen, alkyl, aralkyl, acyl, cycloalkyl, hydroxy, thiol, halogen, amino, formyl, carboxy, cyano, nitro, alkylthio, haloalkyl, aminoalkyl, acylamino, alkoxy, cycloalkoxy, phenoxy, phenylalkoxy, aminoalkoxy, alkoxyalkyl, phenoxyalkyl, hydroxyalkyl, alkoxycarbonyl, aminocarbonyl, alkylthiocarbonyl, carboxyalkyl, cycloalkoxyalkyl, phenylthio, alkylsulfinyl, alkylsulfonyl, phenylsulfonyl, mercaptoalkyl, alkylthioalkyl, phenyl optionally having substituent(s), aromatic heterocyclic group or phenylalkyl;
$R^3$ is
(1) alkyl or haloalkyl,
(2) cycloalkyl,
(3) phenyl optionally having substituent(s),
(4) aromatic heterocyclic group,
(5) a benzene ring fused with a saturated or unsaturated 5 or 6 membered carbocyclic ring,
(6) a benzene ring fused with a saturated or unsaturated 5 to 7 membered carbocyclic ring containing 1 to 3 heteroatom(s), or
(7) a 5 to 7 membered saturated or unsaturated carbocyclic ring containing 1 to 3 heteroatom(s), which is fused with a benzene ring,
wherein the groups of (2) to (7) may have one or more substituent(s), or
a group selected from the groups represented by the following formulas (II) and (III):

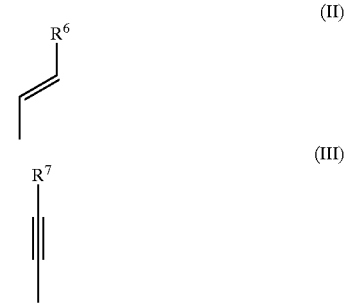

wherein $R^6$ and $R^7$ are each phenyl optionally having substituent(s) or an aromatic heterocyclic group,
or $R^2$ and $R^3$ in conjunction form a ring optionally containing heteroatom(s), wherein the ring may be fused with a benzene ring optionally having substituent(s);
$R^4$ is alkoxycarbonyl,
alkylcarbonyl,
alkylsulfonyl,
alkylsulfinyl,
phenylsulfinyl,
phenylsulfonyl,
dialkylphosphinyl,
dialkylphosphonyl,
phenyl optionally having substituent(s),
an aromatic heterocyclic group optionally having substituent(s),
cyano or
nitro; and
$R^5$ is alkyl,
phenylaminoalkyl,
acyl,
acylalkyl,
aminocarbonyl,
arylaminocarbonyl,
a saturated or unsaturated 4 to 7 membered heterocyclic ring optionally having substituent(s),
a saturated 3 to 7 membered carbocyclic ring having substituent(s),
alkyl substituted by a saturated or unsaturated 4 to 7 membered ring containing 1 or 2 nitrogen atom(s), which optionally has a substituent, or a group of the formula: —(CR$^a$R$^b$)$_n$NR$^{11}$R$^{12}$ wherein n is an integer of 1 to 4, R$^a$ is hydrogen or alkyl, R$^b$ is hydrogen or alkyl, R$^{11}$ is hydrogen, alkyl, alkylsulfonyl, phenylsulfonyl, phenylalkylsulfonyl, alkylsulfinyl, phenylsulfinyl, phenylalkylsulfinyl, alkoxycarbonyl, phenoxycarbonyl, phenylalkoxycarbonyl, alkylcarbonyl, phenylcarbonyl or phenylalkylcarbonyl, and R$^{12}$ is hydrogen or alkyl, provided that when R$^0$, R$^1$ and R$^2$ are each hydrogen, R$^4$ is methoxycarbonyl and R$^5$ is methyl, then R$^3$ is not phenyl, 2-chlorophenyl, 3-mitrophenyl, 4-carboxyphenyl or 4-methoxycarbonylphenyl, and when R$^5$ is alkyl, then R$^4$ is not alkoxycarbonyl, alkylsulfonyl, alkylsulfinyl, phenylsulfinyl, phenylsulfonyl, dialkylphosphinyl, dialkylphosphonyl, cyano or nitro, or an optically active form thereof, or a pharmaceutically acceptable salt thereof.

13. The dihydropyrazolopyridine compound of claim 12, wherein
R$^4$ is alkoxycarbonyl, alkylcarbonyl, alkylsulfonyl, alkylsulfinyl, phenylsulfinyl, phenylsulfonyl, dialkylphosphinyl, dialkylphosphonyl, phenyl optionally having substituent(s), an aromatic heterocyclic group having substituent(s), cyano or nitro, and
R$^5$ is alkyl, phenylaminoalkyl, acyl, acylalkyl, aminocarbonyl, arylaminocarbonyl, a saturated or unsaturated 4 to 7 membered heterocyclic ring optionally having substituent(s), a saturated 3 to 7 membered carbocyclic ring having substituent(s), alkyl substituted by a saturated or unsaturated 4 to 7 membered ring containing 1 or 2 nitrogen atom(s), which optionally has a substituent, or a group of the formula: —(CH$_2$)$_n$NR$^{11}$R$^{12}$ wherein n is an integer of 1 to 4, R$^{11}$ is hydrogen, alkyl, alkylsulfonyl, phenylsulfonyl, phenylalkylsulfonyl, alkylsulfinyl, phenylsulfinyl, phenylalkylsulfinyl, alkoxycarbonyl, phenoxycarbonyl, phenylalkoxycarbonyl, alkylcarbonyl, phenylcarbonyl or phenylalkylcarbonyl, and R$^{12}$ is hydrogen or alkyl,
or an optically active form thereof, or a pharmaceutically acceptable salt thereof.

14. The dihydropyrazolopyridine compound of claim 12 or 13, wherein R$^2$ is hydrogen or alkyl, or an optically active form thereof, or a pharmaceutically acceptable salt thereof.

15. The dihydropyrazolopyridine compound of claim 12 or 13, wherein R$^5$ is phenyl optionally having 1 to 3 substituent(s), naphthyl, 2,1,3-benzoxadiazol-4-yl or 3,4-dihydro-2H-benzopyran-8-yl, or an optically active form thereof, or a pharmaceutically acceptable salt thereof.

16. The dihydropyrazolopyridine compound of claim 12 or 13, wherein R$^4$ is alkoxycarbonyl having 2 to 5 carbon atoms, alkylcarbonyl having 2 to 5 carbon atoms, alkylsulfonyl having 1 to 4 carbon atoms, or alkylsulfinyl having 1 to 4 carbon atoms, or an optically active form thereof, or a pharmaceutically acceptable salt thereof.

17. The dihydropyrazolopyridine compound of claim 12 or 13, wherein R$^5$ is a group of the formula: —(CH$_2$)$_n$NR$^{11}$R$^{12}$ wherein n is an integer of 1 to 4, R$^{11}$ is hydrogen, alkyl or alkoxycarbonyl and R$^{12}$ is hydrogen or alkyl, or an optically active form thereof, or a pharmaceutically acceptable salt thereof.

18. The dihydropyrazolopyridine compound of claim 12 or 13, wherein R$^0$ is hydrogen or a group of the formula: —COOR$^8$ wherein R$^8$ is alkyl, aryl optionally having substituent(s) or aralkyl optionally having substituent(s), or an optically active form thereof, or a pharmaceutically acceptable salt thereof.

19. The dihydropyrazolopyridine compound of claim 12 or 13, which is selected from the group consisting of (1002) 4-(2,1,3-benzoxadiazol-4-yl)-5-cyano-4,7-dihydro-6-(piperidin-4-yl)-2H-pyrazolo[3,4-b]pyridine, (1003) 4-(2,1,3-benzoxadiazol-4-yl)-5-cyano-4,7-dihydro-6-(1-methylpiperidin-4-yl)-2H-pyrazolo[3,4-b]pyridine, (1011) 4-(2,1,3-benzoxadiazol-4-yl)-5-cyano-4,7-dihydro-6-(4-methylmorpholin-2-yl)-2H-pyrazolo[3,4-b]pyridine, (1014) 4-(2,1,3-benzoxadiazol-4-yl)-5-cyano-4,7-dihydro-6-(1-methyl-1,2,3,6-tetrahydropyridin-4-yl)-2H-pyrazolo[3,4-b]-pyridine, (1023) 4-(2,1,3-benzoxadiazol-4-yl)-5-cyano-4,7-dihydro-6-(4-(N,N-dimethylamino)cyclohexyl)-2H-pyrazolo[3,4-b]pyridine, (1027) 6-(1-acetyl-1,2,3,6-tetrahydropyridin-4-yl)-4-(2,1,3-benzoxadiazol-4-yl)-5-cyano-4,7-dihydro-2H-pyrazolo[3,4-b]-pyridine, (1033) 4-(2,1,3-benzoxadiazol-4-yl)-5-cyano-4,7-dihydro-6-(1-ethylpiperidin-4-yl)-2H-pyrazolo[3,4-b] pyridine, (1037) 4-(2-bromo-3-cyanophenyl)-5-cyano-4,7-dihydro-6-(piperidin-4-yl)-2H-pyrazolo[3,4-b]pyridine, (1038) 4-(2-bromo-3-cyanophenyl)-5-cyano-4,7-dihydro-6-(1-methylpiperidin-4-yl)-2H-pyrazolo[3,4-b] pyridine, (1041) 4-(2-bromo-3-cyanophenyl)-5-cyano-4,7-dihydro-6-(1-methylpiperidin-3-yl)-2H-pyrazolo[3,4-b] pyridine, (1046) 4-(2-bromo-3-cyanophenyl)-5-cyano-4,7-dihydro-6-(4-methylmorpholin-2-yl)-2H-pyrazolo[3,4-b] pyridine, (1048) 4-(2-bromo-3-cyanophenyl)-5-cyano-4,7-dihydro-6-(1-methyl-1,2,3,6-tetrahydropyridin-4-yl)-2H-pyrazolo[3,4-b]-pyridine, (1051) 6-(1-acetylpiperidin-4-yl)-4-(2-bromo-3-cyanophenyl)-5-cyano-4,7-dihydro-2H-pyrazolo[3,4-b]pyridine, (1052) 6-(1-benzoylpiperidin-4-yl)-4-(2-bromo-3-cyanophenyl)-5-cyano-4,7-dihydro-2H-pyrazolo[3,4-b]pyridine, (1053) 4-(2-bromo-3-cyanophenyl)-5-cyano-4,7-dihydro-6-(1-methanesulfonylpiperidin-4-yl)-2H-pyrazolo[3,4-b]pyridine, (1059) 4-(2,1,3-benzoxadiazol-4-yl)-5-cyano-4,7-dihydro-6-(4-oxocyclohexan-1-yl)-2H-pyrazolo[3,4-b] pyridine, (1062) 4-(2-bromo-3-cyanophenyl)-5-cyano-4,7-dihydro-6-(2-oxocyclohexan-1-yl)-2H-pyrazolo[3,4-b] pyridine, (1063) 6-acetylmethyl-4-(2-bromo-3-cyanophenyl)-5-cyano-4,7-dihydro-2H-pyrazolo[3,4-b]pyridine, (1073) 5-cyano-4,7-dihydro-4-(2,3-(methylenedioxy)phenyl)-6-(piperidin-4-yl)-2H-pyrazolo[3,4-b] pyridine, (1075) 4-(2,1,3-benzoxadiazol-4-yl)-5-cyano-4,7-dihydro-2H-pyrazolo[3,4-b]pyridine-6-carboxylic acid phenylamide, (1078) 4-(2-chlorophenyl)-5-cyano-4,7-dihydro-6-(4-phenyl-piperazin-1-yl)methyl-2H-pyrazolo[3,4-b] pyridine, (1081) 6-acetyl-4-(2-bromo-3-cyanophenyl)-5-cyano-4,7-dihydro-2H-pyrazolo[3,4-b]pyridine, (1082) 6-acetyl-4-(2,1,3-benzoxadiazol-4-yl)-5-cyano-4,7-dihydro-2H-pyrazolo[3,4-b]pyridine, (1084) 4-(2-bromo-3-cyanophenyl)-5-(pyridin-2-yl)-4,7-dihydro-6-propyl-2H-pyrazolo[3,4-b]pyridine, (1086) 4-(2-chlorophenyl)-5-cyano-4,7-dihydro-6-(pyrrolidin-3-yl)-2H-pyrazolo[3,4-b]pyridine, and (1087) 4-(2,1,3-benzoxadiazol-4-yl)-5-(pyridin-2-yl)-4,7-dihydro-6-propyl-2-pyrazolo[3,4-b]pyridine, a tautomer thereof, an optically active form thereof, or a pharmaceutically acceptable salt thereof.

20. A pharmaceutical composition comprising a dihydropyrazolopyridine compound of claim 1 or 2, an optically active form thereof, a pharmaceutically acceptable salt thereof or a hydrate thereof, and a pharmaceutically acceptable additive.

21. A pharmaceutical composition comprising a dihydropyrazolopyridine compound of claim 12 or 13, an optically active form thereof, or a pharmaceutically acceptable salt thereof, and a pharmaceutically acceptable additive.

22. A glycogen synthase kinase-3 beta inhibitor comprising a compound selected from the group consisting of a dihydropyrazolopyridine compound of claim 1 or 2, an optically active form thereof, a pharmaceutically acceptable salt thereof and a hydrate thereof.

23. A glycogen synthase kinase-3 beta inhibitor comprising a compound selected from the group consisting of a dihydropyrazolopyridine compound of claim 12 or 13, an optically active form thereof and a pharmaceutically acceptable salt thereof.

24. An optically active form at 4-position of a dihydropyrazolopyridine compound of claim 1 or 2, a pharmaceutically acceptable salt thereof or a hydrate thereof.

25. An optically active form at 4-position of a dihydropyrazolopyridine compound of claim 12 or 13, or a pharmaceutically acceptable salt thereof.

26. A pharmaceutical composition comprising a dihydropyrazolopyridine compound of claim 24, a pharmaceutically acceptable salt thereof or a hydrate thereof, and a pharmaceutically acceptable additive.

27. A pharmaceutical composition comprising a dihydropyrazolopyridine compound of claim 25, or a pharmaceutically acceptable salt thereof, and a pharmaceutically acceptable additive.

28. A glycogen synibase kinase-3 beta inhibitor comprising a compound selected from the group consisting of a dihydropyrazolopyridine compound of claim 24, a pharmaceutically acceptable salt thereof and a hydrate thereof.

29. A glycogen synthase kinase-3 beta inhibitor comprising a compound selected from the group consisting of a dihydropyrazolopyridine compound of claim 25 and a pharmaceutically acceptable salt thereof.

30. A method for treatment of Alzheimer's disease or diabetes, which comprises administering an effective amount of the composition of claim 20 or 21 to a patient in need thereof.

31. A method for treatment of Alzheimer's disease or diabetes, which comprises administering an effective amount of the composition of claim 26 or 27 to a patient in need thereof.

* * * * *